US009353174B2

(12) United States Patent
Paszty et al.

(10) Patent No.: US 9,353,174 B2
(45) Date of Patent: May 31, 2016

(54) EPITOPES

(71) Applicant: AMGEN INC., Thousand Oaks, CA (US)

(72) Inventors: Christopher J. Paszty, Ventura, CA (US); Hsieng Sen Lu, Westlake Village, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 14/185,590

(22) Filed: Feb. 20, 2014

(65) Prior Publication Data

US 2014/0248666 A1 Sep. 4, 2014

Related U.S. Application Data

(62) Division of application No. 13/096,263, filed on Apr. 28, 2011, now Pat. No. 8,715,663, which is a division of application No. 11/410,540, filed on Apr. 25, 2006, now Pat. No. 8,003,108.

(60) Provisional application No. 60/792,645, filed on Apr. 17, 2006, provisional application No. 60/782,244, filed on Mar. 13, 2006, provisional application No. 60/776,847, filed on Feb. 24, 2006, provisional application No. 60/677,583, filed on May 3, 2005.

(51) Int. Cl.

| | |
|---|---|
| ***C12N 15/13*** | (2006.01) |
| ***C12N 15/63*** | (2006.01) |
| ***C07K 16/18*** | (2006.01) |
| ***C07K 14/51*** | (2006.01) |
| ***C07K 16/22*** | (2006.01) |
| *A61K 39/00* | (2006.01) |

(52) U.S. Cl.

CPC ................. *C07K 16/18* (2013.01); *C07K 14/51* (2013.01); *C07K 16/22* (2013.01); *C12N 15/63* (2013.01); *A61K 2039/505* (2013.01); *C07K 2317/24* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 4,331,647 | A | 5/1982 | Goldenberg |
| 4,376,110 | A | 3/1983 | David et al. |
| 4,411,993 | A | 10/1983 | Gillis |
| 4,427,115 | A | 1/1984 | Laipply |
| 4,543,439 | A | 9/1985 | Frackelton, Jr. et al. |
| RE32,011 | E | 10/1985 | Zimmerman et al. |
| 4,837,440 | A | 6/1989 | Burtscher et al. |
| 4,902,614 | A | 2/1990 | Wakabayashi et al. |
| 5,070,108 | A | 12/1991 | Margolis |
| 5,145,684 | A | 9/1992 | Liversidge et al. |
| 5,223,409 | A | 6/1993 | Ladner et al. |
| 5,399,363 | A | 3/1995 | Liversidge et al. |
| 5,453,492 | A | 9/1995 | Butzow et al. |
| 5,466,468 | A | 11/1995 | Schneider et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,627,052 | A | 5/1997 | Schrader et al. |
| 5,641,515 | A | 6/1997 | Ramtoola |
| 5,698,426 | A | 12/1997 | Huse |
| 5,738,868 | A | 4/1998 | Shinkarenko et al. |
| 5,780,263 | A | 7/1998 | Hastings et al. |
| 5,795,587 | A | 8/1998 | Gao et al. |
| 5,795,965 | A | 8/1998 | Tsuchiya et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,877,397 | A | 3/1999 | Lonberg et al. |
| 6,054,561 | A | 4/2000 | Ring |
| 6,057,421 | A | 5/2000 | Muller et al. |
| 6,117,911 | A | 9/2000 | Grainger et al. |
| 6,133,426 | A | 10/2000 | Gonzalez et al. |
| 6,180,370 | B1 | 1/2001 | Queen et al. |
| 6,207,153 | B1 | 3/2001 | Dan et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,703,199 | B1 | 3/2004 | Koide |
| 6,803,453 | B1 | 10/2004 | Brunkow et al. |
| 6,806,055 | B2 | 10/2004 | Berman et al. |
| 6,815,201 | B2 | 11/2004 | Pinter |
| 6,818,748 | B2 | 11/2004 | Fulton et al. |
| 7,192,583 | B2 | 3/2007 | Brunkow et al. |
| 7,226,902 | B2 | 6/2007 | Winkler et al. |

(Continued)

FOREIGN PATENT DOCUMENTS

| | | |
|---|---|---|
| JP | 4-141095 | 5/1992 |
| WO | WO-91/13152 | 9/1991 |
| WO | WO-92/02551 | 2/1992 |
| WO | WO-92/06693 | 4/1992 |
| WO | WO-95/30003 | 11/1995 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-02/24888 | 3/2002 |

(Continued)

OTHER PUBLICATIONS

Albertsen et. al., A physical map and candidate genes in the BRCA1 region on chromosome 17q12-21. *Nat. Genet.*, 7:472-9 (1994).

(Continued)

*Primary Examiner* — Xiaozhen Xie

(74) *Attorney, Agent, or Firm* — Marshall, Gerstein & Borun LLP

(57) ABSTRACT

Compositions and methods relating to epitopes of sclerostin protein, and sclerostin binding agents, such as antibodies capable of binding to sclerostin, are provided.

31 Claims, 25 Drawing Sheets

(56) References Cited

U.S. PATENT DOCUMENTS

| | | | | |
|---|---|---|---|---|
| 7,381,409 | B2 | 6/2008 | Winkler et al. | |
| 7,572,899 | B2 | 8/2009 | Brunkow et al. | |
| 7,578,999 | B2 | 8/2009 | Winkler et al. | |
| 7,592,429 | B2 | 9/2009 | Paszty et al. | |
| 7,642,238 | B2 | 1/2010 | Shaughnessy | |
| 7,758,858 | B2 | 7/2010 | Brunkow et al. | |
| 7,868,134 | B2 | 1/2011 | Winkler et al. | |
| 7,872,106 | B2 | 1/2011 | Paszty et al. | |
| 2003/0166247 | A1 | 9/2003 | Brunkow et al. | |
| 2003/0186915 | A1 | 10/2003 | Pan et al. | |
| 2003/0229041 | A1 | 12/2003 | Sutherland et al. | |
| 2004/0009535 | A1 * | 1/2004 | Brunkow et al. | 435/7.1 |
| 2004/0023356 | A1 | 2/2004 | Krumlauf et al. | |
| 2004/0058321 | A1 | 3/2004 | Brunkow et al. | |
| 2004/0141875 | A1 | 7/2004 | Doshi | |
| 2004/0146888 | A1 | 7/2004 | Paszty et al. | |
| 2004/0158045 | A1 | 8/2004 | Brunkow et al. | |
| 2005/0085418 | A1 | 4/2005 | Winkler et al. | |
| 2005/0106683 | A1 | 5/2005 | Winkler et al. | |
| 2005/0238646 | A1 | 10/2005 | Ledbetter et al. | |
| 2006/0233801 | A1 | 10/2006 | Brunkow et al. | |
| 2007/0072797 | A1 | 3/2007 | Robinson et al. | |
| 2007/0110747 | A1 | 5/2007 | Paszty et al. | |
| 2007/0292444 | A1 | 12/2007 | Krumlauf et al. | |
| 2008/0182788 | A1 | 7/2008 | Brunkow et al. | |
| 2008/0234219 | A1 | 9/2008 | Brunkow et al. | |
| 2009/0074763 | A1 | 3/2009 | Padhi et al. | |
| 2009/0117118 | A1 | 5/2009 | Winkler et al. | |
| 2009/0304713 | A1 | 12/2009 | Paszty et al. | |
| 2010/0015665 | A1 | 1/2010 | Latham et al. | |
| 2010/0036091 | A1 | 2/2010 | Robinson et al. | |
| 2010/0151524 | A1 | 6/2010 | Winkler et al. | |
| 2011/0044978 | A1 | 2/2011 | Ke et al. | |
| 2011/0097342 | A1 | 4/2011 | Paszty et al. | |
| 2011/0150866 | A1 | 6/2011 | Brunkow et al. | |

FOREIGN PATENT DOCUMENTS

| | | |
|---|---|---|
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2004/094477 | 11/2004 |
| WO | WO-2004/098491 | 11/2004 |
| WO | WO-2005/003158 | 1/2005 |
| WO | WO-2005/014650 | 2/2005 |
| WO | WO-2006/102070 | 9/2006 |
| WO | WO-2006/119062 | 11/2006 |
| WO | WO-2006/119107 | 11/2006 |
| WO | WO-2008/061013 | 5/2008 |
| WO | WO-2008/092894 | 8/2008 |
| WO | WO-2008/115732 | 9/2008 |
| WO | WO-2008/133722 | 11/2008 |
| WO | WO-2009/039175 | 3/2009 |
| WO | WO-2009/047356 | 4/2009 |
| WO | WO-2009/056634 | 5/2009 |
| WO | WO-2009/079471 | 6/2009 |

OTHER PUBLICATIONS

Alting-Mees et. al., Monoclonal antibody expression libraries: A rapid alternative to hybridomas. *Strat. Molec. Biol.*, 3:1-9 (1990).

Alves et. al., Sclerosteosis: A marker of Dutch ancestry? *Rev. Bras. Genet.*, 4:825-34 (1982).

Angal et. al., A single amino acid substitution abolishes the heterogeneity of chimeric mouse/human (IgG4) antibody. *Mol. Immunol.*, 30(1):105-8 (1993).

Annex regarding the purported relevance of gene/peptides mentioned by Professor Arnett, dated Mar. 18, 2011.

Anonymous, Amgen presents denosumab and sclerostin antibody data at American Society for Bone and Mineral Research Annual Meeting. Amgen Media Press Release. <www.amgen.com/media/media_pr_detail.jsp?releaseID-907028> (2006).

Anonymous, UCB on track. UCB News <http://hugin.info/133973/R/1176122/233395.pdf> (2007).

Avsian-Kretchmer et. al., Comparative genomic analysis of the eight-membered ring cystine knot-containing bone morphogenetic protein antagonists. *Molec. Endocrinol.*, 18(1):1-12 (2004).

Babcook et. al., A novel strategy for generating monoclonal antibodies from single, isolated lymphocytes producing antibodies of defined specificities. *Proc. Natl. Acad. Sci. USA*, 93:7843-8 (1996).

Baines et. al., Purification of immunoglobulin G (IgG). *Meth. Molec. Biol.*, 10:79-104 (1992).

Balemans et. al., Extracellular regulation of BMP signaling in vertebrates: A cocktail of modulators. *Dev. Biol.*, 250:231-50 (2002).

Balemans et. al., Increased bone density in sclerosteosis is due to the deficiency of a novel secreted protein (SOST). *Hum. Mol. Genet.*, 10:537-43 (2001).

Balemans et. al., Localization of the gene for sclerosteosis to the van Buchem disease-gene region on chromosome 17q12-q21. *Am. J. Hum. Genet.*, 64:1661-9 (1999).

Balint et. al., Antibody engineering by parsimonious mutagenesis. *Gene*, 137(1):109-18 (1993).

Baxevanis (Ed.) et. al., Bioinformatics: A practical guide to the analysis of genes and proteins, John Wiley & Sons, Inc. p. 234 (1998).

Beighton et. al., The clinical features of sclerosteosis. *Clin. Genet.*, 25:175-81 (1984).

Beighton et. al., The syndromic status of sclerosteosis and van Buchem disease. *Ann. Intern. Med.*, 84:393-7 (1976).

Bendayan, Possibilities of false immunocytochemical results generated by the use of monoclonal antibodies: The example of the anti-proinsulin antibody. *J. Histochem. Cytochem.*, 43(9):881-6 (1995).

Bendig, Humanization of rodent monoclonal antibodies by CDR grafting. *Methods*, 8:83-93 (1995).

Berman et. al., The protein data bank. *Acta. Cryst.*, 58(1):899-907 (2002).

Bird et. al., Single-chain antigen-binding proteins. *Science*, 242:423-6 (1988).

Birren et. al., EMBL sequence database accession No. AC003098.2, Nov. 14, 1997.

Bishop (Ed.), Guide to Human Genome Computing, Second Edition, Academic Press, Chapter 1: Introduction to human genome computer via the world wide web, pp. 1-14 (2003).

Black et. al., A somatic cell hybrid map of the long arm of human chromosome 17, containing the familial breast cancer ILocus (BRCAI). *Am. J. Hum. Genet.*, 52:702-10 (1993).

Blum et. al., Study plan for German students in the summer of 1998, University Bioinformatik lecture announcement (1998).

Boden et. al., Glucocorticoid-induced differentiation of fetal rat calvarial osteoblasts is mediated by bone morphogenetic protein-6. *Endocrinology*, 138(7):2820-8 (1997).

Boerner et. al., Production of antigen-specific human monoclonal antibodies from in vitro-primed human splenocytes. *J. Immunol.*, 147:86-95 (1991).

Bonaldo et. al., EMBL Sequence Database Accession No. AI113131, Sep. 4, 1998.

Bonaldo et. al., Normalization and subtraction: Two approaches to facilitate gene discovery. *Genome Res.*, 6(9):791-806 (1996).

Bondestam, Ligands & Signaling Components of the Transforming Growth Factor, Helsinki University Biomedical Dissertations (2002).

Bork et. al., Go hunting in sequence databases by watch out for the traps. *Trends Genet.*, 12: 425-7 (1996).

Bost et. al., Antibodies against a peptide sequence within the HIV envelope protein crossreacts with human interleukin-2. *Immunol. Invest.*, 17(6&7):577-86 (1988).

Bostrom et. al., Ligand and signaling components of the transforming growth factor β family. *J. Orth. Res.*, 13:357-67 (1995).

Bottcher et. al., NCBI Sequence database accession No. NM_004329, Aug. 2, 2009.

Bouffard et. al., A physical map of human chromosome 7: An integrated YAC contig map with average STS spacing of 79 kb. *Genome Res.*, 7: 673-92 (1997).

Bowie et. al., A method to identify protein sequences that fold into a known three-dimensional structure. *Science*, 253:164-70 (1991).

(56) References Cited

OTHER PUBLICATIONS

Bowie et. al., Deciphering the message in protein sequences: Tolerance to amino acid substitutions. *Science*, 247(4948):1306-10 (1990).
Bradley et. al., Modifying the mouse: Design and desire. *Bio/Technology*, 10:534-9 (1992).
Brenner et. al., Population statistics of protein structures: Lessons from structural classifications. *Curr. Op. Struct. Biol.*, 7(3):369-76 (1997).
Brown, Hybridization analysis of DNA blots, *Current Protocols in Protein Science*, 13:A.4H.1-A.4H.9 (1990).
Brown, Hybridization analysis of DNA blots, *Current Protocols in Protein Science*, 2.10.1-2.10.16 (2000).
Bruggemann et. al., Production of human antibody repertoires in transgenic mice. *Curr. Opin. Biotechnol.*, 8:455-8 (1997).
Brunkow et. al., Bone dysplasia sclerosteosis results from loss of the SOST gene product, a novel cysteine knot-containing protein. *Am. J. Hum. Genet.*, 68:577-89 (2001).
Burton et. al., Human antibodies from combinatorial libraries. *Adv. Immunol.*, 57:191-280 (1994).
Byrne et. al., CD4+CD45RBHi T cell transfer induced colitis in mice is accompanied by osteopenia which is treatable with recombinant human osteoprotegerin. *Gut.*, 54:78-86 (2005).
Campbell et. al., Totipotency or multipotentiality of cultured cells: Applications and progress. *Theriogenology*, 47:63-72 (1997).
Chan et. al., A new paradigm in the treatment of osteoporosis: Wnt pathway proteins and their antagonists. *Curr. Opin. Invest. Drugs*, 8:293-8 (2007).
Chandran et. al., Recent trends in drug delivery systems: Liposomal drug delivery system—Preparation and characterization. *Indian J. Exp. Biol.*, 35(8):801-9 (1997).
Charlier et. al., A pore mutation in a novel KQT-like potassium channel gene in an idiopathic epilepsy family. *Nat. Genet.*, 18:53-5 (1998).
Chou et. al., Empirical predication of protein conformation. *Ann. Rev. Biochem.*, 47:251-76 (1979).
Chou et. al., Prediction of the secondary structure of proteins from their amino acid sequence. *Adv. Enzymol. Relat. Areas Mol. Biol.*, 47:145-8 (1978).
Clark, Antibody humanization: A case of the 'Emperor's New Clothes'?. *Immunology Today*, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec. Res. Inst.*, 55:33-6 (1994).
Cook et. al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Couvreur et. al., Polyalkylcyanoacrylates as colloidal drug carriers. *Crit. Rev. Ther. Drug Carrier Syst.*, 5(1):1-20 (1988).
Crameri et. al., DNA shuffling of a family of genes from diverse species accelerates directed evolution. *Nature*, 391:288-91 (1998).
Dall'Acqua et. al., Antibody humanization by framework shuffling. *Methods*, 36(1):43-60 (2005).
Davies, et. al., Affinity improvement of single antibody VH domains: Residues in all three hypervariable regions affect antigen binding. *Immunotechnology*, 2(3): 169-79 (1996).
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Dr. Martyn Robinson, submitted in Opposition to European Patent No. 1133558, dated Jan. 13, 2008.
Declaration of Dr. Mary E. Brunkow, submitted in Opposition to European Patent No. 1133558, dated Jan. 9, 2008.
Declaration of Prof. Edgar Wingender filed in connection with that Opposition regarding European Patent EP 1133558 B1, dated Mar. 10, 2011.
Delmas et. al., The use of biochemical markers of bone turnover in osteoporosis. *Osteoporosis International*, Suppl. 6:S2-17 (2000).
Durham et. al., Alterations in insulin-like growth factor (IGF)-dependent IGF-binding protein-4 proteolysis in transformed osteoblastic cells. *Endocrinology*, 136(4):1374-80 (1995).
Ebara et. al., Mechanism for the action of bone morphogenetic proteins and regulation of their activity. *Spine*, 27(165):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, dated Sep. 28, 2009.
Epstein et. al., Endocrine function in sclerosteosis. *S. Afr. Med. J.*, 55:1105-10 (1979).
European Patent Office Communication, Opposition to European Patent No. 1133558, dated Nov. 4, 2008.
Expert Opinion from Dr. Catalina Lopez-Correa, submitted in Opposition to European Patent No. 1133558, dated Mar. 6, 2009.
Frost et. al., On the rat model of human osteopenias and osteoporoses. *Bone and Mineral*, 18:227-36 (1992).
Fujiwara et. al., GenBank Sequence Database Accession No. D79813, Feb. 9, 1996.
Gazzerro et. al., Bone morphogenetic proteins induce the expression of noggin which limits their activity in cultured rat osteoblasts. *J. Clin. Invest.*, 102(12):2106-14 (1998).
Gazzerro et. al., Potential drug targets within bone morphogenetic protein signaling pathways. *Curr. Opin. Pharmacol.*, 7: 325-3 (2007).
Gencic et. al., Conservative amino acid substitution in the myelin proteolipid protein of Jimpymsd mice. *J. Neurosci.*, 10(1):117-24 (1990).
Geysen et. al., Cognitive features of continuous antigenic determinants. *J. Molec. Recog.*, 1(1):32-41 (1988).
Gitelman et. al., Vgr-1/BMP-6 induces osteoblastic differentiation of pluripotential mesenchymal cells. *Cell Growth & Differentiation*, 6:827-36 (1995).
Glasky et. al., Stability of specific immunoglobulin secretion by EBV-transformed lymphoblastoid cells and human-murine heterohybridomas. *Hybridoma*, 8:377-89 (1989).
Green et. al., Antigen-specific human monoclonal antibodies from mice engineered with human Ig heavy and light chain YACs. *Nat. Genet.*, 7:13 (1994).
Greene et. al., Screening Recombinant DNA Libraries. *Current Protocols in Molecular Biology*, Ch. 6(1) (1990).
Gribskov et. al., Profile analysis. *Meth. Enzym.*, 183:146-59 (1990).
Gribskov et. al., Profile analysis: Detection of distantly related proteins. *Proc. Nat. Acad. Sci. USA*, 84(13):4355-8 (1987).
Groeneveld et. al., Bone morphogenetic proteins in human bone regeneration. *Eur. J. Endocrinol.*, 142:9-21 (2000).
Groppe et. al., Structural basis of BMP signaling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection, 8th Ed., pp. 149, 258, 428 (1994).

(56) References Cited

OTHER PUBLICATIONS

Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28 (1996).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunisation: Human antibodies from synthetic repertoires of germline VH gene segments rearranged in vitro. *J. Molec. Biol.*, 227:381-8 (1992).
Hsu et. al., The Xenopus dorsalizing factor gremlin identified a novel family of secreted proteins that antagonize BMP activities. *Molec. Cell*, 1:673-83 (1998).
Huse et. al., Generation of a large combinatorial library of the immunoglobulin repertoire in phage lambda. *Science*, 246:1275-81 (1989).
Hwang et. al., Use of human germline genes in a CDR homology-based approach to antibody humanization. *Methods*, 36(1):35-42 (2005).
Ide et. al., GenBank Sequence Database Accession No. BAA19765, Feb. 7, 1999.
Ide et. al., GenBank Sequence Database Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for site-directed mutagenesis. *Protein Engineering*, 13(12):839-47 (2000).
Jakobovits et. al., Production of antigen-specific human antibodies from mice engineered with human heavy and light chain YACsa. *Ann. N.Y. Acad. Sci.*, 764:525-35 (1995).
Jee et. al., Overview: Animal models of osteopenia and osteoporosis. *J. Musculoskel. Neuron. Interact.*, 1:193-207 (2001).
Jilka et. al., Increased bone formation by prevention of osteoblast apoptosis with parathyroid hormone. *J. Clin. Invest.*, 104:439-46 (1999).
Jones, Progress in protein structure predication. *Curr. Opin. Struct. Biol.*, 7(3):377-387 (1997).
Kabat et. al., Sequences of proteins of immunological interest, U.S. Department of Health and Human Services, *NIH, USA* (1987) (Table of Contents).
Kalu, The ovariectomized rat model of postmenopausal bone loss. *Bone and Mineral*, 15:175-92 (1991).
Kang et. al., Linkage of recognition and replication functions by assembling combinatorial antibody Fab libraries along phage surfaces. *Proc. Natl. Acad. Sci. USA*, 88:4363-6 (1991).
Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et. al., Signal transduction by bone morphogenetic proteins. *Cytokine and Growth Factor Reviews*, 9(1):49-61 (1998).
Keller et. al., Molecular recognition of BMP-2 and BMP receptor IA. *Nat. Struct. Mol. Biol.*, 11(5):481-488 (2004).
Khalil, TGF-β: From latent to active. *Microbes and Infection*, 1(15):1255-63 (1999).
Khosla et. al., Concise review for primary-care physicians. Treatment options for osteoporosis. *Mayo Clin. Proc.*, 70:978-82 (1995).
Kirsch et. al., BMP-2 antagonists emerge from alterations in the low-affinity binding epitope for receptor BMPR-II, *EMBO J.*, 19(13): 3314-24 (2000).
Kohler et. al., Continuous cultures of fused cells secreting antibody of predefined specificity. *Nature*, 256:495 (1975).
Koli et. al., Latency, activation, and binding proteins of TGF-. *Microscopy Res. Tech.*, 52:354-62 (2001).
Koreth et. al., Microsatellites and PCR genomic analysis. *J. Pathology*, 178:239-48 (1996).
Kramer et. al., The gapped duplex DNA approach to oligonucleotide-directed mutation construction. *Nuc. Acids Res.*, 12:9441 (1984).
Kunkel et. al., Rapid and efficient site-specific mutagenesis without phenotypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).
Kurahashi et. al., Regions of genomic instability on 22q11 and 11q23 as the etiology for the recurrent constitutional t (11;22). *Hum. Molec. Genet.*, 9: 1665-70 (2000).
Kusu et. al., Sclerostin is a novel secreted osteoclast-derived bone morphogenetic protein antagonist with unique ligand specificity. *J. Biol. Chem.*, 278:24113-7 (2003).
Lasic, Novel applications of liposomes. *Trends Biotechnol.*, 16(7):307-21 (1998).
Leppert et. al., Benign familial neonatal epilepsy with mutations in two potassium channel genes. *Curr. Opin. Neurol.*, 12: 143-7 (1999).
Li et. al., Sclerostin binds to LRP5/6 and antagonizes canonical Wnt signaling. *J. Biol. Chem.*, 280: 19883-7 (2005).
Li et. al., Treatment with an anti-sclerostin antibody directly stimulates bone formation in a dose-dependent manner in ovariectomized rats with established osteopenia. J. Bone Min. Res., 22(Suppl. S1): S65 (2007).
Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Liu et. al., GenBank Sequence Database Accession No. U25110, Feb. 2, 1996.
Liu et. al., Human type II receptor for bone morphogenic proteins (BMPs): Extension of the two-kinase receptor model to the BMPs. *Molec. Cell. Biol.*, 15(7):3479-86 (1995).
Lonberg et. al., Antigen-specific human antibodies from mice comprising four distinct genetic modifications. *Nature*, 368:856 (1994).
Low et. al., Mimicking somatic hypermutation: Affinity maturation of antibodies displayed on bacteriophage using a bacterial mutator strain. *J. Mol. Biol.*, 250:350-68 (1996).
Lowik et. al., Wnt signaling is involved in the inhibitory action of sclerostin on BMP-stimulated bone formation. *J. Musculoskeleton Neuronal Interact.* 6: 357 (2006).
Malone et. al., Bone anabolism achieved by reducing sclerostin bioavailability with an anti-sclerostin antibody. 37th International Sun Valley Workshop on Skeletal Tissue Biology. Aug. 5-8, 2007.
Margalit, Liposome-mediated drug targeting in topical and regional therapies. *Crit. Rev. Ther. Drug Carrier Syst.*, 12(2-3):233-61 (1995).
Marks et. al., By-passing immunization: Building high affinity human antibodies by chain shuffling. *Bio/Technology*, 10:779-83 (1992).
Mayer et. al., Differentiation of osteogenetic cells: Systems and regulators, Z. Orthop., 130: 276-84 (1992)—Abstract Only.
Minabe-Saegusa et. al., GenBank Sequence Database Accession No. AB011030, Jun. 23, 1998.
Miyazono et. al., Divergence and convergence of TGF-β/BMP signaling. *J. Cell. Physiol.*, 187:265-76 (2001).
Miyazono et. al., TGF-β signaling by Smad proteins. *Adv. Immunology*, 75:115-57 (2000).
Mori et. al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).

(56) References Cited

OTHER PUBLICATIONS

Moult, The current state of the art in protein structure prediction. *Curr. Opin. Biotech.*, 7(4):422-7 (1996).
Mullins et. al., Perspectives series: Molecular medicine in genetically engineered animals; Transgenesis in the rat and larger mammals. *J. Clin. Invest.*, 97(7):1557-60 (1996).
Nagaraja et. al., X chromosome map at 75-kb STS resolution, revealing extremes of recombination and GC content. *Genome Res.*, 7: 210-22 (1997).
Nakase et. al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et. al., The crystal structure of the BMP-2: BMPR-1A complex and the generation of BMP-2 antagonists. *J. Bone Joint Surg.*, 83-A:S1-7-S1-14 (2001).
Nicolas et. al., An age-related decrease in the concentration of insulin-like growth factor binding protein-5 in human cortical bone. *Calcif. Tissue Int.*, 57:206-12 (1995).
Nifuji et. al., Coordinated expression of noggin and bone morphogenetic proteins (BMPs) during early skeletogenesis and induction of noggin expression by BMP-7. *J. Bone Miner. Res.*, 14(12):2057-66 (1999).
Nisonoff et. al., Separation of univalent fragments from the bivalent rabbit antibody molecule by reduction of disulfide bonds. *Arch. Biochem. Biophys.*, 89:230-44 (1960).
Niu et. al., Sclerostin inhibition leads to increased periosteal and endocortical bone formation as well as decreased cortical porosity in aged ovariectomized rats. *J. Bone Min. Res.*, 22(Suppl. S1) S65 (2007).
Notice of Opposition against European Patent No. 1133558, Opponent: Eli Lilly and Company, dated May 31, 2007.
Notice of Opposition to European Patent No. 1 133 558, dated May 29, 2007.
Nygren et. al., Scaffolds for engineering novel binding sites in proteins. *Curr. Opin. Struct. Biol.*, 7:463-9 (1997).
Oelgeschlager et. al., The evolutionarily conserved BMP-binding protein twisted gastrulation promotes BMP signaling. *Nature*, 405:757-63 (2000).
OMIM #607625, Niemann-pick disease, type C2 (2007).
Oreffo et. al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Oshima et. al., TGF-β receptor type II deficiency results in defects of yolk Sac hematopoiesis and vasculogenesis. *Dev. Biol.*, 179:297-302 (1996).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padlan et. al., Structure of an antibody-antigen complex; Crystal structure of the HyHEL-10 Feb-lysozyme complex. *Proc. Natl. Acad. Sci. USA*, 86:5938-42 (1989).
Patel et. al., Current and potential future drug treatments for osteoporosis. *Ann. Rheumatic Dis.*, 55: 700-14 (1996).
Patten et. al., Applications of DNA shuffling to pharmaceuticals and vaccines. *Curr. Opin. Biotechnol.*, 8:724-33 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-Θ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional antibody Fv and Fab fragments in *Escherichia coli. Meth. Enzymol.*, 178:497-515 (1989).
Pockwinse et. al., Expression of cell growth and bone specific genes at single cell resolution during development of bone tissue-like organization in primary osteoblast cultures. *J. Cell. Biol.*, 49:310-23 (1992).
Poole et. al., Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).
Quintanar-Guerrero et. al., Preparation techniques and mechanisms of formation of biodegradable nanoparticles from preformed polymers. *Drug Dev. Ind. Pharm.*, 24(12):1113-28 (1998).
Rawadi et. al., BMP-2 controls alkaline phosphatase expression and osteoblast mineralization by a Wnt autocrine loop. *J. Bone Min. Res.*, 18: 1842-53 (2003).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
Robinson et. al., The sclerostin antibody project. *Hum. Antibodies*, 16: 36 (2007).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Sali et. al., Comparative protein modeling by satisfaction of spatial restraints. *J. Mol. Biol.*, 234(3):779-815 (1993).
Sambrook et. al., Synthetic oligonucleotide probes, molecular cloning—A Laboratory Manual, Ch.11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N.Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Second declaration of Martyn Robinson, citation in Appeal, European Patent No. 1133558, dated Apr. 15, 2010.
Serra et. al., Expression of a truncated, kinase-defective TGF-β type II receptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc. Biol.*, 20:1425-9 (2000).
Silverman et. al., Sclerostin, *J. Osteoporosis*, 2010: 1-3 (2010).
Sivakumar et. al., New insights into extracellular matrix assembly and reorganization from dynamic imaging of extracellular matrix proteins in living osteoblasts. *J. Cell. Sci.*, 119(7):1350-60 (2006).

(56) References Cited

OTHER PUBLICATIONS

Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Staehling-Hampton et. al., A 52-kb deletion in the SOST-MEOX1 intergenic region on 17q12-q21 is associated with van Buchem disease in the Dutch population. *Am. J. Med. Gen.*, 110: 144-52 (2002).
Sudo et. al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Sutherland et. al., Sclerostin promotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.
Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
The Merck Manual—Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
van Bezooijen et. al., Sclerostin is an osteocyte-expressed negative regulator of bone formation, but not a classical BMP antagonist. *J. Exp. Med.*, 199: 805-14 (2004).
van Bezooijen et. al., SOST/sclerostin, an osteocyte-derived negative regulator of bone formation, *Cytokine Growth Factor Rev.*, 16: 319-27 (2005).
van Bezooijen et. al., Wnt but not BMP signaling is involved in the inhibitory action of sclerostin on BMP-stimulated bone formation. *J. Bone. Miner. Res.*, 22:19-28 (2007).
Van Hul et. al., Van Buchem Disease (hyperostosis corticalis generalisata) maps to chromosome 17q12-a21. *Am. J. Hum. Genet.*, 2:391-9 (1998).
Vanier et. al., Recent advances in elucidating Niemann-Pick C disease. *Brain Pathol.*, 8: 163-74 (1998).
Viter et. al., Analysis of antigenic structure of potato virus M Ukrainian strains. *Biopolimery I Kletka, Naukova Dumka, Kiev K*, UK, 16: 312-9 (2000).
Von Bubnoff et. al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang, Bone morphogenetic proteins (BMPs): Therapeutic potential in healing bony defects. *TIBTECH*, 11:379-83 (1993).
Warmington et. al., Sclerostin antagonism in adult rodents, via monoclonal antibody mediated blockade, increases bone mineral density and implicates sclerostin as a key regulator of bone mass during adulthood. *J. Bone Min. Res.*, 19:S56-7 (2004).
Warmington et. al., Sclerostin monoclonal antibody treatment of osteoporotic rats completely reverses one year of ovariectomy-induced systemic bone loss, *J. Bone Min. Res.*, 20:S22 (2005).
Winkler et. al., Osteocyte control of bone formation via sclerostin, a novel BMP antagonist. *EMBO J.* 22: 6267-76 (2003).
Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).
Winter et. al., Making antibodies by phase display technology. *Annu. Rev. Immunol.*, 12:433-55 (1994).
Wolff et. al., Monoclonal antibody homodimers: Enhanced antitumor activity in nude mice. Cancer Res., 53:2560-5 (1993).
Written submission—Observation by a Third Party According to Art.115 EPC, Opposition to European Patent No. 1133558, dated Nov. 25, 2008.
Written Submission of Eli Lilly & Company, Opposition to European Patent No. 1133558, dated Mar. 9, 2009.
Written submission of UCB S.A., Proprietor's Preliminary Response to the Opponent's submission of Mar. 9, 2009, Opposition to European Patent No. 1133558, dated Mar. 20, 2009.
Yanagita et. al., USAG-1: A bone morphogenetic protein antagonist abundantly expressed in the kidney. *Biochem. Biophys. Res. Comm.* ,316: 490-550 (2004).
Yang et. al., CDR walking mutagenesis for the affinity maturation of a potent human Anti-HIV-1 antibody into the picomolar range. *J. Mol. Biol.*, 254:392-403 (1995).
Yerges et. al., NCBI Sequence Database Accession No. NM_001203, Jul. 12, 2009.
Yerges et. al., NCBI Sequence Database Accession No. NP_001194, Jul. 12, 2009.
Zambaux et. al., Influence of experimental parameters on the characteristics of poly(lactic acid) nanoparticles prepared by a double emulsion method. *J. Controlled Rel.*, 50(1-3):31-40 (1998).
Zhang et. al., Humanization of an anti-human TNF-β antibody by variable region resurfacing with the aid of molecular modeling. *Molec. Immunol.*, 42(12):1445-51 (2005).
Zimmerman et. al., The spemann organizer signal noggin binds and inactivates bone morphogenetic protein 4. *Cell*, 86(4):599-606 (1996).
zur Muhlen et. al., Solid lipid nanoparticles (SLN) for controlled drug delivery—Drug release and release mechanism. *Eur. J. Pharm. Biopharm.*, 45(2):149-55 (1998).

* cited by examiner

A.

```
  1 AQVLTQTPAS VSAAVGGTVT INCQSSQSVY DNNWLAWFQQ KPGQPPKLLI
 51 YDASDLASGV PSRFSGSGSG TQFTLTISGV QCADAATYYC QGAYNDVIYA
101 FGGGTEVVVK RTDAAPTVSI FPPSSEQLTS GGASVVCFLN NFYPKDINVK
151 WKIDGSERQN GVLNSWTDQD SKDSTYSMSS TLTLTKDEYE RHNSYTCEAT
201 HKTSTSPIVK SFNRNEC
```

B.

```
  1 QSLEESGGRL VTPGTPLTLT CTASGFSLSS YWMNWVRQAP GEGLEWIGTI
 51 DSGGRTDYAS WAKGRFTISR TSTTMDLKMT SLTTGDTARY FCARNWNLWG
101 QGTLVTVSSA STKGPSVYPL APGSAAQTNS MVTLGCLVKG YFPEPVTVTW
151 NSGSLSSGVH TFPAVLQSDL YTLSSSVTVP SSTWPSETVT CNVAHPASST
201 KVDKKIVPRD CGCKPCICTV PEVSSVFIFP PKPKDVLTIT LTPKVTCVVV
251 DISKDDPEVQ FSWFVDDVEV HTAQTQPREE QFNSTFRSVS ELPIMHQDWL
301 NGKEFKCRVN SAAFPAPIEK TISKTKGRPK APQVYTIPPP KEQMAKDKVS
351 LTCMITDFFP EDITVEWQWN GQPAENYKNT QPIMNTNGSY FVYSKLNVQK
401 SNWEAGNTFT CSVLHEGLHN HHTEKSLSHS PGK
```

```
  1 QIVLTQSPTI VSASPGEKVT LICSASSSVS FVDWFQQKPG TSPKRWIYRT
 51 SNLGFGVPAR FSGGGSGTSH SLTISRMEAE DAATYYCQQR STYPPTFGAG
101 TKLELKRADA APTVSIFPPS SEQLTSGGAS VVCFLNNFYP KDINVKWKID
151 GSERQNGVLN SWTDQDSKDS TYSMSSTLTL TKDEYERHNS YTCEATHKTS
201 TSPIVKSFNR NEC
```

B.

```
  1 QVTLKESGPG ILQPSQTLSL TCSFSGFSLS TSGMGVGWIR HPSGKNLEWL
 51 AHIWWDDVKR YNPVLKSRLT ISKDTSNSQV FLKIANVDTA DTATYYCARI
101 EDFDYDEEYY AMDYWGQGTS VIVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFVYS KLNVQKSNWE AGNTFTCSVL HEGLHNHHTE KSLSHSPGK
```

```
  1 DIVLTQSPAS LTVSLGLRAT ISCKASQSVD YDGDSYMNWY QQKPGQPPKL
 51 LIYAASNLES GIPARFSGNG SGTDFTLNIH PVEEEDAVTY YCQQSNEDPW
101 TFGGGTKLEI KRADAAPTVS IFPPSSEQLT SGGASVVCFL NNFYPKDINV
151 KWKIDGSERQ NGVLNSWTDQ DSKDSTYSMS STLTLTKDEY ERHNSYTCEA
201 THKTSTSPIV KSFNRNEC
```

B.

```
  1 EVQLQQSGPE LVKPGTSVKM SCKASGYTFT DCYMNWVKQS HGKSLEWIGD
 51 INPFNGGTTY NQKFKGKATL TVDKSSSTAY MQLNSLTSDD SAVYYCARSH
101 YYFDGRVPWD AMDYWGQGTS VTVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFIYS KLNVQKSNWE AGNTFTCSVL HEGLHNHHTE KSLSHSPGK
```

```
  1 DVQMIQSPSS LSASLGDIVT MTCQASQGTS INLNWFQQKP GKAPKLLIYG
 51 SSNLEDGVPS RFSGSRYGTD FTLTISSLED EDLATYFCLQ HSYLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

B.

```
  1 EVQLQQSGPE LVTPGASVKI SCKASGYTFT DHYMSWVKQS HGKSLEWIGD
 51 INPYSGETTY NQKFKGTATL TVDKSSSIAY MEIRGLTSED SAVYYCARDD
101 YDASPFAYWG QGTLVTVSAA KTTPPSVYPL APGSAAQTNS MVTLGCLVKG
151 YFPEPVTVTW NSGSLSSGVH TFPAVLQSDL YTLSSSVTVP SSTWPSETVT
201 CNVAHPASST KVDKKIVPRD CGCKPCICTV PEVSSVFIFP PKPKDVLTIT
251 LTPKVTCVVV DISKDDPEVQ FSWFVDDVEV HTAQTQPREE QFNSTFRSVS
301 ELPIMHQDWL NGKEFKCRVN SPAFPAPIEK TISKTKGRPK APQVYTIPPP
351 KEQMAKDKVS LTCMITDFFP EDITVEWQWN GQPAENYKNT QPIMDTDGSY
401 FIYSKLNVQK SNWEAGNTFT CSVLHEGLHN HHTEKSLSHS PGK
```

Figure 4

```
1   QGWQAFKNDA TEIIPELGEY PEPPPELENN KTMNRAENGG RPPHHPFETK

51  DVSEYSCREL HFTRYVTDGP CRSAKPVTEL VCSGQCGPAR LLPNAIGRGK
          C1             C2             C3  C4
101 WWRPSGPDFR CIPDRYRAQR VQLLCPGGEA PRARKVRLVA SCKCKRLTRF
               C5            C6                    C7 C8
151 HNQSELKDFG TEAARPQKGR KPRPRARSAK ANQAELENAY
```

```
1   CAGGGGTGGC AGGCGTTCAA GAATGATGCC ACGGAAATCA TCCCCGAGCT
51  CGGAGAGTAC CCCGAGCCTC CACCGGAGCT GGAGAACAAC AAGACCATGA
101 ACCGGGCGGA GAACGGAGGG CGGCCTCCCC ACCACCCCTT TGAGACCAAA
151 GACGTGTCCG AGTACAGCTG CCGCGAGCTG CACTTCACCC GCTACGTGAC
201 CGATGGGCCG TGCCGCAGCG CCAAGCCGGT CACCGAGCTG GTGTGCTCCG
251 GCCAGTGCGG CCCGGCGCGC CTGCTGCCCA ACGCCATCGG CCGCGGCAAG
301 TGGTGGCGAC CTAGTGGGCC CGACTTCCGC TGCATCCCCG ACCGCTACCG
351 CGCGCAGCGC GTGCAGCTGC TGTGTCCCGG TGGTGAGGCG CCGCGCGCGC
401 GCAAGGTGCG CCTGGTGGCC TCGTGCAAGT GCAAGCGCCT CACCCGCTTC
451 CACAACCAGT CGGAGCTCAA GGACTTCGGG ACCGAGGCCG CTCGGCCGCA
501 GAAGGGCCGG AAGCCGCGGC CCCGCGCCCG GAGCGCCAAA GCCAACCAGG
551 CCGAGCTGGA GAACGCCTAC
```

Figure 8

| Peptides | Seq.pos. | Obs. Mass | Sequence |
|---|---|---|---|
| T19.2 | 65-72 | 2146.34 | 1. YVTDGP CR (910) C2 |
| | 121-132 | (2145.8) | 2. VQLLCPGGEA PR (1239) C6 |
| T20 | | 9620.8 (MALDI); 9638.41 (ESI-MS) | |
| | 51-90 | (4419.1) | 1. DVSEYSCREL HFTRYVTDGP CRSAKPVTEL VCSGQCGPAR |
| | 104-149 | (5226.2) | 2. PSGPDFR CIPDRYRAQR VQLLCPGGEA PRARKVRLVA SCKCKRLT R |
| T20.6 | | 7105.7 (MALDI); 7122.0 (ESI-MS) | |
| | 51-64 | 3944.5 | 1. DVSEYSCREL HFTR (1740.9) C1 |
| | 101-117 | | 2. WWRPSGPPFR CIPDRYR (2206.6) C5 |
| | 73-90 | 3177.0 | 3. SAKPVTELVC SGQCGPAR (1802.2) C3,C4 |
| | 138-149 | | 4. LVASCKCKRL TR (1378.5) C7,C8 |
| T21-22 | | 10,147 (MALDI); 10170.3 (ESI-MS) | |
| | 51-90 | (4419.1) | 1. DVSEYSCREL HFTRYVTDGP CRSAKPVTEL VCSGQCGPAR |
| | 101-149 | (5754.8) | 2. WWRPSGPDFR CIPDRYRAQR VQLLCPGGEA PRARKVRLVA SCKCKRLTR |

Figure 11

| Peptides | Seq.pos. | Obs.Mass | Sequence |
|---|---|---|---|
| AspN14.6 | 34-47 | 1245.5 | ENGGRPPHHPF |
| | 12-25 | 1585.4 | EIIPELGFYP EPPP |
| | 158-184 | 2964.5 | DFGTEAARPQ KGRKPRPRAR SAKANQA |
| AspN18.6 | 9-50 | | DATEIIPELG EYPEPPPELE NNKTMNRAEN GGRPPHHPFE TK (Glycopeptide) |
| AspN22.7-23.5 | 51-154 | 11,740 | DVSEYSCREL HFTRYVTDGP CRSAKPVTEL VCSGQCGPAR LLPNAIGRGK WWRPSGPDFR CIPDRYRAQR VQLLCPGGEA PRARKVRLVA SCKCKRLTRF HNQS |

Figure 12

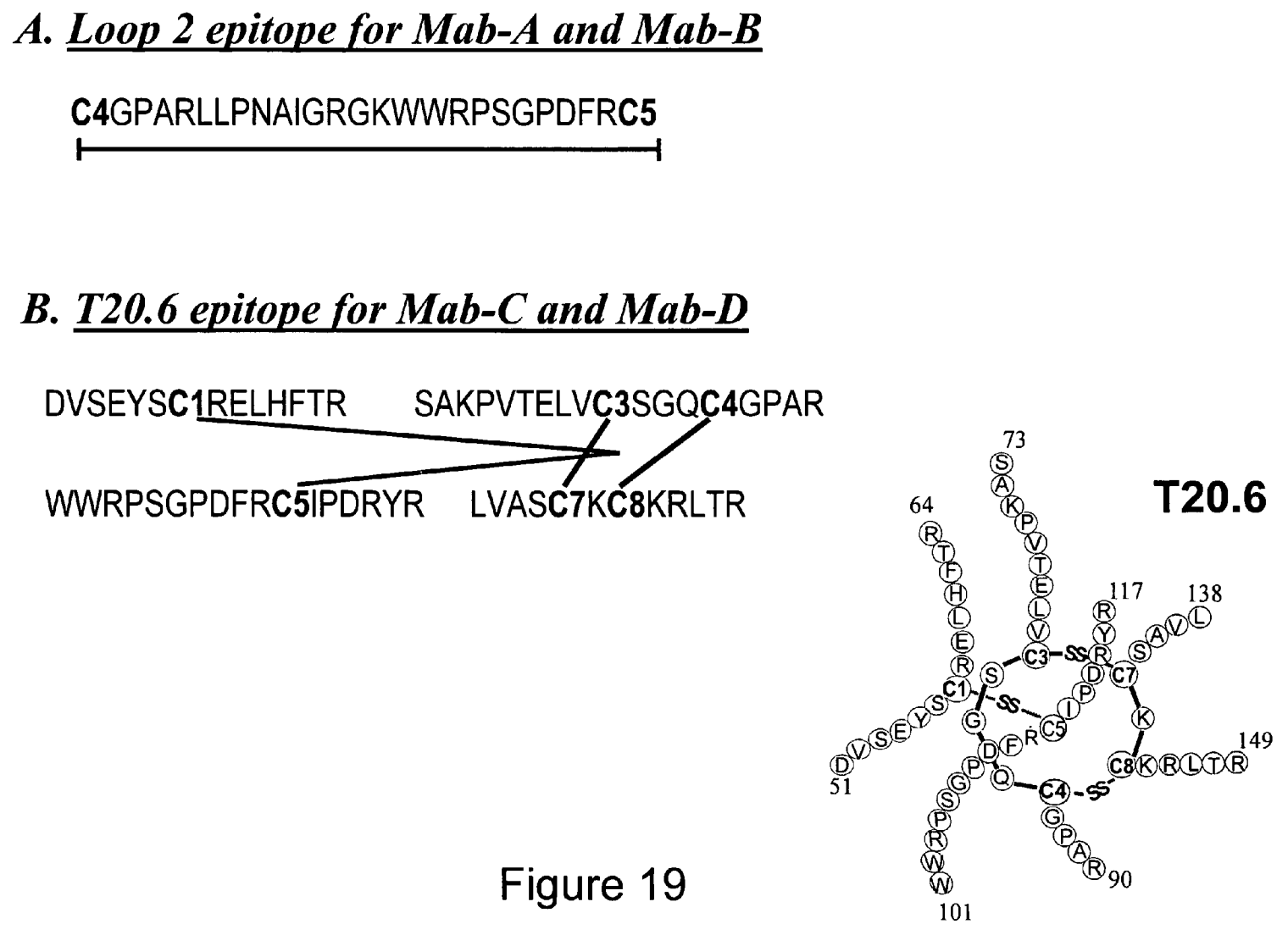

*A. Loop 2 epitope for Mab-A and Mab-B*

C4GPARLLPNAIGRGKWWRPSGPDFRC5

*B. T20.6 epitope for Mab-C and Mab-D*

DVSEYSC1RELHFTR SAKPVTELVC3SGQC4GPAR

WWRPSGPDFRC5IPDRYR LVASC7KC8KRLTR

Figure 19

*"T20.6 derivative 1 (cystine-knot + 4 arms)" epitope for Mab-D*
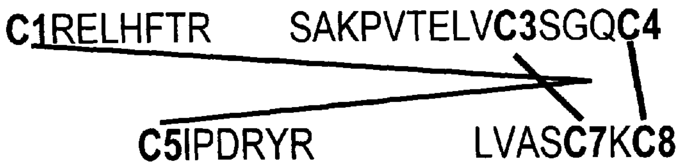
"T20.6 derivative 1 (cystine-knot + 4 arms)"
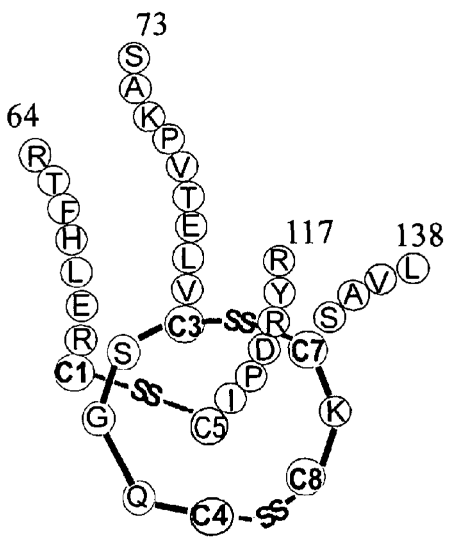
Figure 21

* = statistically significantly different from Mouse Scl group.

Error bars = Mean +/- SEM

* = statistically significantly different from Human Scl group.

Error bars = Mean +/- SEM

EPITOPES

RELATED APPLICATIONS

The present application is a divisional of U.S. patent application Ser. No. 13/096,263 (now U.S. Pat. No. 8,715,663), filed Apr. 28, 2011, which is a divisional of U.S. patent application Ser. No. 11/410,540 (now U.S. Pat. No. 8,003,108), filed Apr. 25, 2006, which claims benefit of priority from U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005, under 35 U.S.C. §119. The foregoing patent applications are incorporated herein by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "42277B_SeqListing.txt," 503,914 bytes, created on Feb. 20, 2014.

TECHNICAL FIELD

The present invention relates generally to epitopes of sclerostin protein, including human sclerostin protein, and binding agents (such as antibodies) capable of binding to sclerostin or fragments thereof.

BACKGROUND OF THE INVENTION

Two or three distinct phases of changes to bone mass occur over the life of an individual (see Riggs, *West J. Med.* 154:63-77 (1991)). The first phase occurs in both men and women and proceeds to attainment of a peak bone mass. This first phase is achieved through linear growth of the endochondral growth plates and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss and occurs in both men and women. In women, a third phase of bone loss also occurs, most likely due to postmenopausal estrogen deficiencies. During this phase alone, women may lose an additional bone mass from the cortical bone and from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long-term benefit and whether estrogen has any effect on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, *Mayo Clin. Proc.* 70:978982, 1995).

Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (see Khosla and Riggs, supra).

Sclerostin, the product of the SOST gene, is absent in sclerosteosis, a skeletal disease characterized by bone overgrowth and strong dense bones (Brunkow et al., *Am. J. Hum. Genet.,* 68:577-589, 2001; Balemans et al., *Hum. Mol. Genet.,* 10:537-543, 2001). The amino acid sequence of human sclerostin is reported by Brunkow et al. ibid and is disclosed herein as SEQ ID NO:1.

BRIEF SUMMARY OF THE INVENTION

Disclosed herein are compositions and methods that can be used to increase at least one of bone formation, bone mineral density, bone mineral content, bone mass, bone quality and bone strength, and that therefore may be used to treat a wide variety of conditions in which an increase in at least one of bone formation, bone mineral density, bone mineral content, bone mass, bone quality and bone strength is desirable. The present invention also offers other related advantages described herein.

The invention relates to regions (epitopes) of human sclerostin recognized by the binding agents disclosed herein, methods of using these epitopes, and methods of making such epitopes.

The invention also relates to epitopes specific to the region of sclerostin identified as Loop 2, and binding agents which specifically bind to that region.

The invention also relates to epitopes specific to the cysteine-knot region of sclerostin, and binding agents such as antibodies specifically binding to that region.

The invention relates to binding agents, such as antibodies, that specifically bind to sclerostin. The binding agents can be characterized by their ability to cross-block the binding of at least one antibody disclosed herein to sclerostin and/or to be cross-blocked from binding sclerostin by at least one antibody disclosed herein. The antibodies and other binding agents can also be characterized by their binding pattern to human sclerostin peptides in a "human sclerostin peptide epitope competition binding assay" as disclosed herein.

The invention relates to binding agents, such as antibodies, that can increase at least one of bone formation, bone mineral density, bone mineral content, bone mass, bone quality and bone strength in a mammal.

The invention relates to binding agents, such as antibodies, that can block the inhibitory effect of sclerostin in a cell based mineralization assay.

The invention further relates to polypeptide constructs comprising two, three, or four polypeptide fragments linked by at least one disulfide bond, representing a core region of the cysteine-knot of sclerostin, and antibodies capable of specifically binding thereto.

The invention relates to methods of obtaining epitopes suitable for use as immunogens for generating, in mammals, binding agents, such as antibodies capable of binding specifically to sclerostin; in certain embodiments the binding agents generated are capable of neutralizing sclerostin activity in vivo.

The invention relates to a composition for eliciting an antibody specific for sclerostin when the composition is administered to an animal, the composition comprising a polypeptide having the amino acid sequence of SEQ ID NO:6, SEQ ID NO:63, SEQ ID NO:64, SEQ ID NO:65, SEQ ID NO:66, SEQ ID NO:67, SEQ ID NO:68, or SEQ ID NO:69.

The invention also relates to a composition for eliciting an antibody specific for sclerostin when the composition is administered to an animal, the composition comprising at least one polypeptide consisting essentially of the amino acid sequence of SEQ ID NO:2, SEQ ID NO:3, SEQ ID NO:4 or SEQ ID NO:5; the composition may comprise at least two or at least three of the amino acid sequences of SEQ ID NO:2, SEQ ID NO:3, SEQ ID NO:4 and SEQ ID NO:5, and the composition may comprise all four of the amino acid sequences of SEQ ID NO:2, SEQ ID NO:3, SEQ ID NO:4 and SEQ ID NO:5.

The invention further relates to a composition for eliciting an antibody specific for sclerostin when the composition is administered to an animal, the composition comprising a polypeptide having the amino acid sequences of SEQ ID NO:2, SEQ ID NO:3, SEQ ID NO:4 and SEQ ID NO:5, wherein SEQ ID NO:2 and 4 are joined by a disulfide bond at amino acid positions 57 and 111 with reference to SEQ ID NO:1, and SEQ ID NO:3 and 5 are joined by at least one of (a) a disulfide bond at amino acid positions 82 and 142 with reference to SEQ ID NO:1, and (b) a disulfide bond at amino acid positions 86 and 144 with reference to SEQ ID NO:1; the polypeptide may retain the tertiary structure of the corresponding polypeptide region of human sclerostin of SEQ ID NO:1.

The invention also relates to polypeptide T20.6 consisting essentially of a multiply truncated human sclerostin protein of SEQ ID NO:1, wherein amino acids 1-50, 65-72, 91-100, 118-137, and 150-190 of SEQ ID NO:1 are absent from the polypeptide; this polypeptide may be obtained by tryptic digestion of human sclerostin, and the protein may be isolated by HPLC fractionation.

The invention further relates to immunogenic portion T20.6 of human sclerostin comprising amino acids 51-64, 73-90, 101-117, and 138-149 of SEQ ID NO:1, wherein the immunogenic portion comprises at least one of:

(a) a disulfide bond between amino acids 57 and 111;
(b) a disulfide bond between amino acids 82 and 142; and
(c) a disulfide bond between amino acids 86 and 144;

the immunogenic portion may have at least two of these disulfide bonds; and the immunogenic portion may have all three disulfide bonds.

The invention further relates to an immunogenic portion T20.6 derivative of human sclerostin comprising amino acids 57-64, 73-86, 111-117, and 138-144 of SEQ ID NO:1, wherein the immunogenic portion comprises at least one of:

(a) a disulfide bond between amino acids 57 and 111;
(b) a disulfide bond between amino acids 82 and 142; and
(c) a disulfide bond between amino acids 86 and 144;

the immunogenic portion may have at least two of these disulfide bonds; and the immunogenic portion may have all three disulfide bonds.

The invention yet further relates to a polypeptide consisting essentially of a human sclerostin protein of SEQ ID NO:1 truncated at the C-terminal and N-terminal ends, wherein amino acids 1-85 and 112-190 of SEQ ID NO:1 are absent from the polypeptide.

The invention also relates to an immunogenic portion of human sclerostin, comprising amino acids 86-111 of SEQ ID NO:1; the immunogenic portion may consist essentially of contiguous amino acids CGPARLLPNAIGRGKWWRPSGPDFRC (SEQ ID NO:6).

The invention further relates to an immunogenic portion of rat sclerostin, comprising amino acids 92-109 of SEQ ID NO:98; the immunogenic portion may consist essentially of contiguous amino acids PNAIGRVKWWRPNGPDFR (SEQ ID NO:96).

The invention still further relates to an immunogenic portion of rat sclerostin, comprising amino acids 99-120 of SEQ ID NO:98; the immunogenic portion may consist essentially of contiguous amino acids KWWRPNGPDFRCIPDRYRAQRV (SEQ ID NO:97).

The invention relates to a method of producing an immunogenic portion of human sclerostin, comprising the steps of:

(a) treating human sclerostin to achieve complete tryptic digestion;
(b) collecting the tryptic digest sample having average molecular weight of 7,122.0 Daltons (theoretical mass 7121.5 Daltons) or retention time of about 20.6 minutes as determined by elution from a reverse-phase HPLC column with linear gradient from 0.05% trifluoroacetic acid to 90% acetonitrile in 0.05% TFA at a flow rate of 0.2 ml/min; and
(c) purifying the immunogenic portion.

The invention relates to a method of generating an antibody capable of specifically binding to sclerostin, comprising:

(a) immunizing an animal with a composition comprising a polypeptide of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97;
(b) collecting sera from the animal; and
(c) isolating from the sera an antibody capable of specifically binding to sclerostin.

The invention also relates to a method of generating an antibody capable of specifically binding to sclerostin, the method comprising:

(a) immunizing an animal with a composition comprising polypeptide T20.6 or a derivative of T20.6;

(b) collecting sera from the animal; and (c) isolating from the sera an antibody capable of specifically binding to sclerostin.

The invention further relates to a method of detecting an anti-sclerostin antibody in a biological sample, comprising the steps of (a) contacting the biological sample with a polypeptide consisting essentially of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97 under conditions allowing a complex to form between the antibody and the polypeptide; and (b) detecting the presence or absence of the complex, wherein the presence of the complex indicates that the biological sample contains an anti-sclerostin antibody.

The invention also relates to a method of detecting an anti-sclerostin antibody in a biological sample, comprising the steps of (a) contacting the biological sample with polypeptide T20.6 or a derivative of T20.6 under conditions allowing a complex to form between the antibody and the polypeptide; and (b) detecting the presence or absence of the complex, wherein the presence of the complex indicates that the biological sample contains an anti-sclerostin antibody.

The invention further relates to a sclerostin binding agent, such as an antibody, that cross-blocks the binding of at least one of antibodies Ab-A, Ab-B, Ab-C, or Ab-D to a sclerostin protein. The sclerostin binding agent may also be cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an antibody, that is cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an isolated antibody, that cross-blocks the binding of at least one of antibodies 1-24 (Ab-1 to Ab-24) to a sclerostin protein. The sclerostin binding agent may also be cross-blocked from binding to sclerostin by at least one of antibodies 1-24 (Ab-1 to Ab-24). The isolated antibody, or an antigen-binding fragment thereof, may be a polyclonal antibody, a monoclonal antibody, a humanized antibody, a human antibody, or a chimeric antibody.

The invention further relates to a sclerostin binding agent, such as an isolated antibody, that is cross-blocked from binding to sclerostin by at least one of antibodies 1-24 (Ab-1 to Ab-24); the isolated antibody, or an antigen-binding fragment thereof, may be a polyclonal antibody, a monoclonal antibody, a humanized antibody, a human antibody, or a chimeric antibody.

The invention further relates to a binding agent, such as an isolated antibody that exhibits a similar binding pattern to human sclerostin peptides in a "human sclerostin peptide epitope competition binding assay" as that exhibited by at least one of the antibodies Ab-A, Ab-B, Ab-C or Ab-D; the isolated antibody, or an antigen-binding fragment thereof, may be a polyclonal antibody, a monoclonal antibody, a humanized antibody, a human antibody, or a chimeric antibody.

The invention still further relates to a method for treating a bone disorder associated with at least one of low bone formation, low bone mineral density, low bone mineral content, low bone mass, low bone quality and low bone strength in a mammalian subject which comprises providing to a subject in need of such treatment an amount of an anti-sclerostin binding agent sufficient to increase at least one of bone formation, bone mineral density, bone mineral content, bone mass, bone quality and bone strength wherein the anti-sclerostin binding agent comprises an antibody, or sclerostin-binding fragment thereof.

The invention also relates to an isolated sclerostin polypeptide or fragments thereof, wherein the polypeptide contains 6 conserved cysteine residues and the fragments thereof comprise from 7 to 14 amino acids of SEQ ID NO:2; 8 to 17 amino acids of SEQ ID NO:3; 8 to 18 residues of SEQ ID NO:4; and 6 to 12 residues of SEQ ID NO:5, and the polypeptide or fragments thereof are stabilized by disulfide bonds between SEQ ID NO:2 and 4, and between SEQ ID NO:3 and 5; the polypeptide or fragments may comprise 10-14 amino acids of SEQ ID NO:2; 14 to 17 amino acids of SEQ ID NO:3; 13 to 18 amino acids of SEQ ID NO:4, and 8 to 12 residues of SEQ ID NO:5; and the polypeptide or fragments may comprise SEQ ID NO:2, SEQ ID NO:3, SEQ ID NO:4, and SEQ ID NO:5.

Provided herein are antibodies that specifically bind to human sclerostin. The antibodies are characterized by their ability to cross-block the binding of at least one antibody disclosed herein to human sclerostin and/or to be cross-blocked from binding human sclerostin by at least one antibody disclosed herein.

Also provided is an isolated antibody, or an antigen-binding fragment thereof, that can increase at least one of bone formation, bone mineral density, bone mineral content, bone mass, bone quality and bone strength in a mammal.

Also provided in an isolated antibody, or an antigen-binding fragment thereof, that can block the inhibitory effect of sclerostin in a cell based mineralization assay.

Also provided is a binding agent, such as an antibody, that specifically binds to human sclerostin and has at least one CDR sequence selected from SEQ ID NOs: 39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof, wherein the antibody or antigen-binding fragment thereof neutralizes sclerostin.

Also provided is a binding agent, such as an antibody, that specifically binds to human sclerostin and has at least one CDR sequence selected from SEQ ID NOs:39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof.

Also provided are regions of human sclerostin which are important for the in vivo activity of the protein.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 1 depicts the amino acid sequences of the mature form (signal peptides cleaved off) of the light chain (FIG. 1A) (SEQ ID NO:23) and heavy chain (FIG. 1B) (SEQ ID NO:27) for the anti-human sclerostin and anti-mouse sclerostin antibody Ab-A.

FIG. 2 depicts the amino acid sequences of the mature form (signal peptides cleaved off) of the light chain (FIG. 2A) (SEQ ID NO:31) and heavy chain (FIG. 2B) (SEQ ID NO:35) for the anti-human sclerostin and anti-mouse sclerostin antibody Ab-B.

FIG. 3 depicts the amino acid sequences of the mature form (signal peptides cleaved off) of the light chain (FIG. 3A) (SEQ ID NO:15) and heavy chain (FIG. 3B) (SEQ ID NO:19) for the anti-human sclerostin and anti-mouse sclerostin antibody Ab-C.

FIG. 4 depicts the amino acid sequences of the mature form (signal peptides cleaved off) of the light chain (FIG. 4A) (SEQ ID NO:7) and heavy chain (FIG. 4B) (SEQ ID NO:11) for the anti-human sclerostin and anti-mouse sclerostin antibody Ab-D.

FIG. 8 depicts the amino acid sequence of the mature form (signal peptide cleaved off) of human sclerostin (SEQ ID NO:1). Also depicted is the nucleotide sequence of the human sclerostin coding region that encodes the mature form of human sclerostin. The eight cysteines are numbered C1 through C8. The cysteine-knot is formed by three disulfide bonds (C1-C5; C3-C7; C4-C8). C2 and C6 also form a disulfide bond, however this disulfide is not part of the cysteine-knot.

FIG. 11 depicts sequence and mass information for the isolated human sclerostin disulfide linked peptides generated by trypsin digestion. Seq. pos.=sequence position. Obs.=observed. Observed mass was determined by ESI-LC-MS analysis.

FIG. 12 depicts sequence and mass information for the isolated human sclerostin peptides generated by AspN digestion. The AspN22.7-23.5 peptide contains the 4 disulfide bonds. Seq. pos.=sequence position. Obs.=observed. Observed mass was determined by ESI-LC-MS analysis.

FIG. 19 shows two Mab binding epitopes of human sclerostin. FIG. 19A shows sequence of the Loop 2 epitope for binding of Ab-A and Ab-B to human sclerostin (SEQ ID NO:6). FIG. 19B shows sequence, disulfide bonding and schematic of the T20.6 epitope for binding of Ab-C and Ab-D to human sclerostin (SEQ ID NO:2-5).

FIG. 20A shows digestion of the human sclerostin Ab-D complex. FIG. 20B shows digestion of human sclerostin alone. The T19.2, T20, T20.6 and T21-22 peptide peaks are indicated.

FIG. 21 shows the sequence, disulfide bonding and schematic of the "T20.6 derivative 1 (cysteine-knot+4 arms)" epitope for binding of Ab-D to human sclerostin. (SEQ ID NO:70-73).

Extent of mineralization (various types of insoluble calcium phosphate) was quantitated by measuring calcium.

Figure 23:
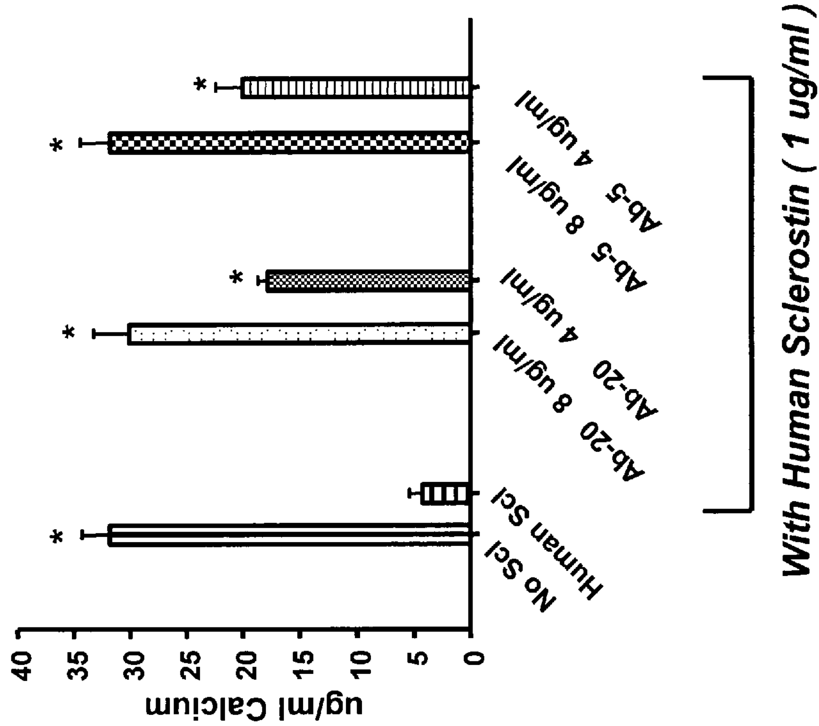

FIG. 23 depicts results from the MC3T3-E1-BF osteoblast cell line mineralization assay used for identifying anti-sclerostin neutralizing Mabs. Human sclerostin (Scl) was used at 1 μg/ml. Monoclonal antibodies were used at 8 and 4 μg/ml. Extent of mineralization (various types of insoluble calcium phosphate) was quantitated by measuring calcium.

Figure 24:
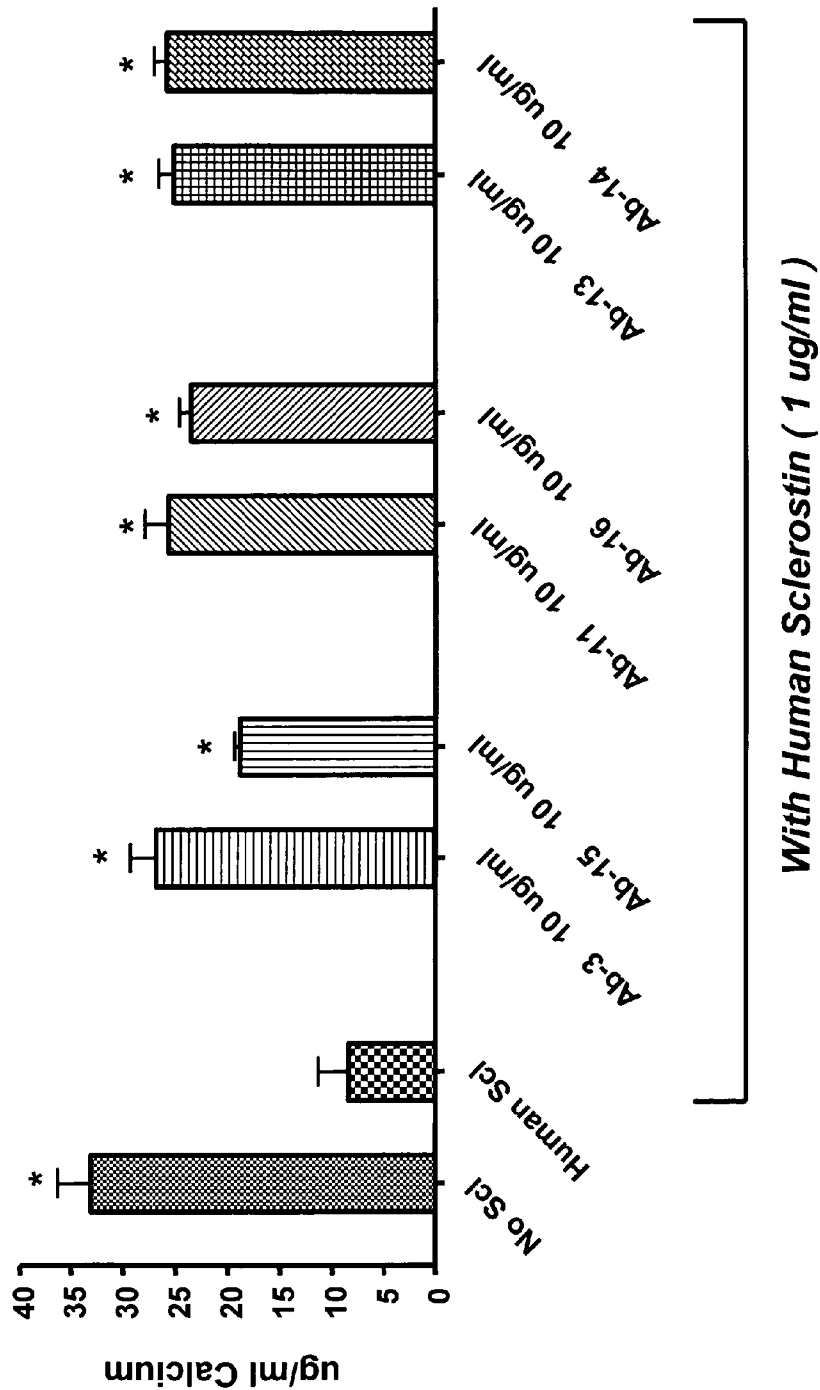

FIG. 24 shows results from the MC3T3-E1-BF osteoblast cell line mineralization assay used for identifying anti-sclerostin neutralizing Mabs. Human sclerostin (Scl) was used at 1 μg/ml. Monoclonal antibodies were used at 10 μg/ml. Extent of mineralization (various types of insoluble calcium phosphate) was quantitated by measuring calcium.

Figure 25:
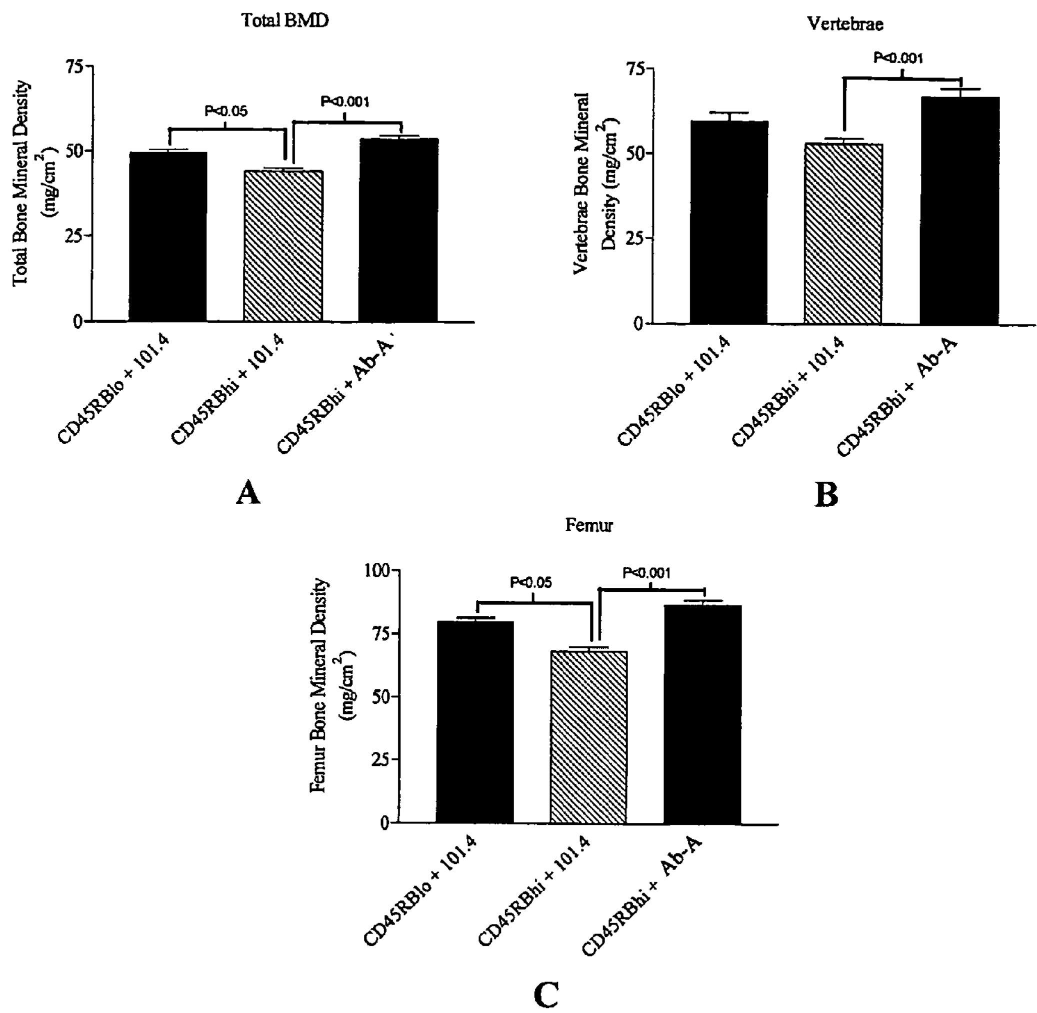

FIG. 25 depicts results from an inflammation-induced bone loss SCID mouse model. Ab-A treatment protected mice from inflammation-related bone loss associated with colitis when measured as total bone mineral density (FIG. 25A), vertebral bone density (FIG. 25B), and femur bone density (FIG. 25C).

DETAILED DESCRIPTION

The present invention relates to regions of the human sclerostin protein that contain epitopes recognized by antibodies that also bind to full-length sclerostin, and methods of making and using these epitopes. The invention also provides binding agents (such as antibodies) that specifically bind to sclerostin or portions of sclerostin, and methods for using such binding agents. The binding agents are useful to block or impair binding of human sclerostin to one or more ligand.

Recombinant human sclerostin/SOST is commercially available from R&D Systems (Minneapolis, Minn., USA; 2006 cat#1406-ST-025). Additionally, recombinant mouse sclerostin/SOST is commercially available from R&D Systems (Minneapolis, Minn., USA; 2006 cat#1589-ST-025). Research grade sclerostin binding monoclonal antibodies are commercially available from R&D Systems (Minneapolis, Minn., USA; mouse monoclonal: 2006 cat#MAB1406; rat monoclonal: 2006 cat#MAB1589). U.S. Pat. Nos. 6,395,511 and 6,803,453, and U.S. Patent Publications 20040009535 and 20050106683 refer to anti-sclerostin antibodies generally.

As used herein, the term human sclerostin is intended to include the protein of SEQ ID NO:1 and allelic variants thereof. Sclerostin can be purified from 293T host cells that have been transfected by a gene encoding sclerostin by elution of filtered supernatant of host cell culture fluid using a Heparin HP column, using a salt gradient. The preparation and further purification using cation exchange chromatography are described in Examples 1 and 2.

Binding agents of the invention are preferably antibodies, as defined herein. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003). pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human sclerostin, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding human sclerostin with an affinity at least equal to $1\times10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_V$). If desired, the chains may be covalently coupled either directly, for example via a disulfide bond between the two variable domains, or through a linker, for example a peptide linker, to form a single chain Fv (sc$F_V$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, binding agents comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain preferred embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative, that do not destroy the sclerostin binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to sclerostin, or to increase or decrease the affinity of the antibodies to sclerostin described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in Certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LAC1-D1, Z domain and tendramisat domains may be used (See e.g., Nygren and Uhlen, 1997, Current Opinion in Structural Biology, 7, 463-469).

In preferred embodiments, it will be appreciated that the binding agents of the invention include the humanized antibodies described herein. Humanized antibodies such as those described herein can be produced using techniques known to those skilled in the art (Zhang, W., et al., *Molecular Immunology.* 42(12):1445-1451, 2005; Hwang W. et al., *Methods.* 36(1):35-42, 2005; Dall'Acqua W F, et al., *Methods* 36(1): 43-60, 2005; and Clark, M., *Immunology Today.* 21(8):397-402, 2000).

Additionally, one skilled in the art will recognize that suitable binding agents include portions of these antibodies, such as one or more of CDR-1-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to sclerostin and/or neutralizes sclerostin. The non-CDR portion of the binding agent may be a non-protein molecule in which the binding agent exhibits a similar binding pattern to human sclerostin peptides in a "human sclerostin peptide epitope competition binding assay" as that exhibited by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin. The non-CDR portion of the binding agent may be composed of amino acids, wherein the binding agent is a recombinant binding protein or a synthetic peptide, and the recombinant binding protein cross-blocks the binding of an antibody disclosed herein to sclerostin and/or neutralizes sclerostin. The non-CDR portion of the binding agent may be composed of amino acids, wherein the binding agent is a recombinant binding protein, and the recombinant binding protein exhibits a similar binding pattern to human sclerostin peptides in the human sclerostin peptide epitope competition binding assay (described hereinbelow) as that exhibited by at least one of the antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®. Each of the above-mentioned CDRs will be typically located in a variable region framework at positions 31-35 (CDR-H1), 50-65 (CDR-H2) and 95-102 (CDR-H3) of the heavy chain and positions 24-34 (CDR-L1), 50-56 (CDR-L2) and 89-97 (CDR-L3) of the light chain according to the Kabat numbering system (Kabat et al., 1987 in *Sequences of Proteins of Immunological Interest*, U.S. Department of Health and Human Services, NIH, USA).

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual,* 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J. Mol. Biol.,* 254, 392-403, 1995), chain shuffling (Marks et al., *Bio/Technology,* 10, 779-783, 1992), use of mutation strains of *E. coli*. (Low et al., *J. Mol. Biol.,* 250, 350-368, 1996), DNA shuffling (Patten et al., *Curr. Opin. Biotechnol.,* 8, 724-733, 1997), phage display (Thompson et al., *J. Mol. Biol.,* 256, 7-88, 1996) and sexual PCR (Crameri, et al., *Nature,* 391, 288-291, 1998). All of these methods of affinity maturation are discussed by Vaughan et al. (*Nature Biotechnology,* 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., *Nature* 256:495, 1975; Coligan et al. (eds.), *Current Protocols in Immunology,* 1:2.5.12.6.7 (John Wiley & Sons 1991); U.S. Pat. No. RE 32,011,U.S. Pat. No. 4,902,614, U.S. Pat. No. 4,543,439, and U.S. Pat. No. 4,411,993; Monoclonal Antibodies, Hybridomas: A New Dimension in Biological Analyses, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human sclerostin of SEQ ID NO:1, or a fragment thereof, according to methods known in the art and described herein. The presence of specific antibody production may be monitored after the initial injection and/or after a booster injection by obtaining a serum sample and detecting the presence of an antibody that binds to human sclerostin or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3×63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human sclerostin, using any one of a variety of immunoassays known in the art and described herein. The hybridomas are cloned (e.g., by limited dilution cloning or by soft agar plaque isolation) and positive clones that produce an antibody specific to sclerostin are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology, Vol.* 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N.Y. Acad. Sci.* 764: 525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for sclerostin. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to sclerostin can be identified by immunodetection methods as provided herein, for example, an ELISA, and then isolated by standard cloning techniques. The stability of the lymphoblastoid cell line producing an anti-sclerostin antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with human sclerostin, followed by fusion of primed B cells with a heterohybrid fusion partner. See, e.g., Boerner et al., 1991 *J. Immunol.* 147:86-95.

In certain embodiments, a B cell that is producing an anti-human sclerostin antibody is selected and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. B cells from an immunized animal may be isolated from the spleen, lymph node, or peripheral blood sample by selecting a cell that is producing an antibody that specifically binds to sclerostin. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human sclerostin. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J Molec. Biol.* 227:381-388; Schlebusch et al., 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZapπ (L) vectors (Stratagene, La Jolla, Calif.). Briefly, mRNA is isolated from a B cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli.*

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{Hl}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents specifically bind to sclerostin. As with all binding agents and binding assays, one of skill in this art recognizes that the various moieties to which a binding agent should not detectably bind in order to be therapeutically effective and suitable would be exhaustive and impractical to list. Therefore, for a binding agent disclosed herein, the term "specifically binds" refers to the ability of a binding agent to bind to sclerostin, preferably human sclerostin, with greater affinity than it binds to an unrelated control protein. Preferably the control protein is hen egg white lysozyme. Preferably the binding agents bind to sclerostin with an affinity that is at least, 50, 100, 250, 500, 1000, or 10,000 times greater than the affinity for a control protein. A binding agent may have a binding affinity for human sclerostin of less than or equal to $1\times10^{-7}$M, less than or equal to $1\times10^{-8}$M, less than or equal to $1\times10^{-9}$M, less than or equal to $1\times10^{-19}$M, less than or equal to $1\times10^{-11}$M, or less than or equal to $1\times10^{-12}$M.

Affinity may be determined by an affinity ELISA assay. In certain embodiments, affinity may be determined by a BIAcore assay. In certain embodiments, affinity may be determined by a kinetic method. In certain embodiments, affinity may be determined by an equilibrium/solution method. Such methods are described in further detail herein or known in the art.

Sclerostin binding agents of the present invention preferably modulate sclerostin function in the cell-based assay described herein and/or the in vivo assay described herein and/or bind to one or more of the epitopes described herein and/or cross-block the binding of one of the antibodies described in this application and/or are cross-blocked from binding sclerostin by one of the antibodies described in this application. Accordingly such binding agents can be identified using the assays described herein.

In certain embodiments, binding agents are generated by first identifying antibodies that bind to one more of the epitopes provided herein and/or neutralize in the cell-based and/or in vivo assays described herein and/or cross-block the antibodies described in this application and/or are cross-blocked from binding sclerostin by one of the antibodies described in this application. The CDR regions from these antibodies are then used to insert into appropriate biocompatible frameworks to generate sclerostin binding agents. The non-CDR portion of the binding agent may be composed of amino acids, or may be a non-protein molecule. The assays described herein allow the characterization of binding agents. Preferably the binding agents of the present invention are antibodies as defined herein.

It will be understood by one skilled in the art that some proteins, such as antibodies, may undergo a variety of post-translational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

Antibodies referred to as Ab-A, Ab-B, Ab-C, Ab-D and Ab-1 are described below. "HC" refers to the heavy chain and "LC" refers to the light chain. For some antibodies below, the CDRs are box shaded and the constant (C) regions are shown in bold italics.

Ab-D

Figure 18:
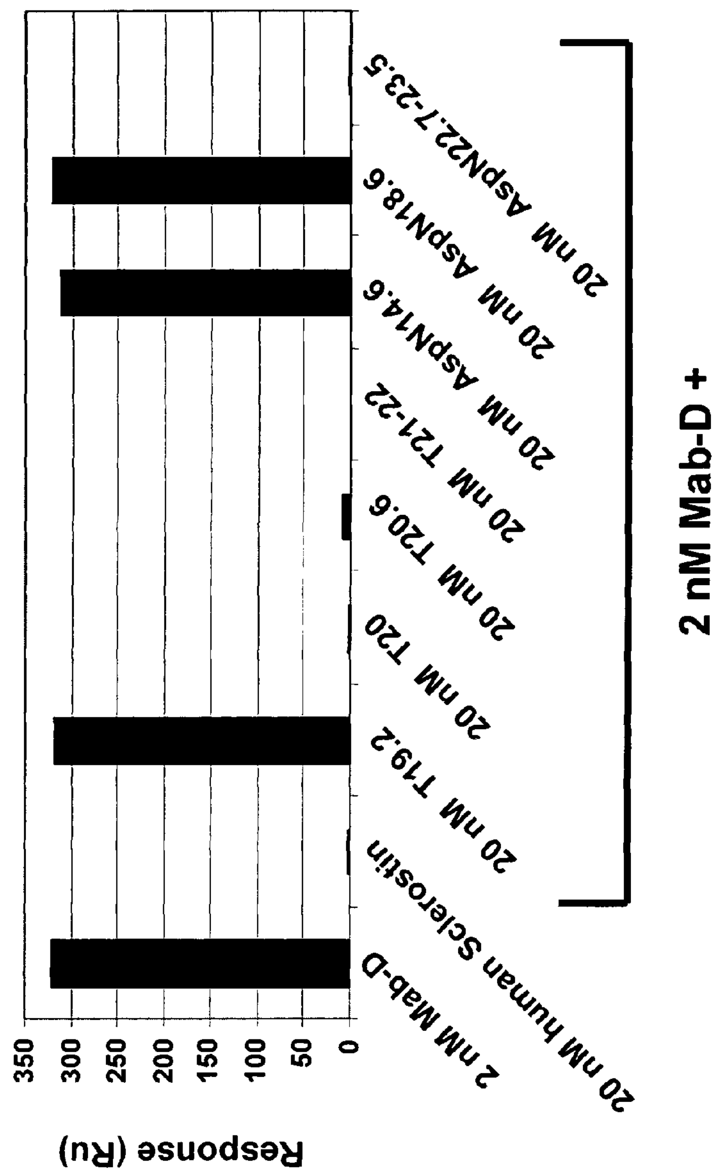
FIG. 18 shows the resonance unit (Ru) signal from Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-D. Human sclerostin peptides used were T19.2, T20, T20.6, T21-22, AspN14.6, AspN18.6 and AspN22.7-23.5.

Antibody D (also referred to herein as Ab-D and Mab-D) is a mouse antibody which exhibits high affinity binding to sclerostin. The BIAcore binding pattern of Ab-D is shown in FIG. 18.

The amino acid sequence of the mature form (signal peptide removed) of Ab-D light chain:

```
                                                 (SEQ ID NO: 7)
  1 DVQMIQSPSS LSASLGDIVT MTCQASQGTS INLNWFQQKP
    GKAPKLLIYG

 51 SSNLEDGVPS RFSGSRYGTD FTLTISSLED EDLATYFCLQ
    HSYLPYTFGG

101 GTKLEIKRAD AAPTVSIFPP SSEQLTSGGA SVVCFLNNFY
    PKDINVKWKI

151 DGSERQNGVL NSWTDQDSKD STYSMSSTLT LTKDEYERHN
    SYTCEATHKT

201 STSPIVKSFN RNEC
```

Nucleic acid sequence encoding the mature form (signal peptide removed) of Ab-D LC is as follows:

```
                                                 (SEQ ID NO: 8)
  1 GATGTCCAGA TGATTCAGTC TCCATCCTCC CTGTCTGCAT
    CTTTGGGAGA

 51 CATAGTCACC ATGACTTGCC AGGCAAGTCA GGGCACTAGC
    ATTAATTTAA

101 ACTGGTTTCA GCAAAAACCA GGGAAGGCTC CTAAGCTCCT
    GATCTATGGT

151 TCAAGCAACT TGGAAGATGG GGTCCCATCA AGGTTCAGTG
    GCAGTAGATA

201 TGGGACAGAT TTCACTCTCA CCATCAGCAG CCTGGAGGAT
    GAAGATCTGG

251 CAACTTATTT CTGTCTACAA CATAGTTATC TCCCGTACAC
    GTTCGGAGGG

301 GGGACCAAGC TGGAAATAAA ACGGGCTGAT GCTGCACCAA
    CTGTATCCAT

351 CTTCCCACCA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT

451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT
    GTTAG
```

The amino acid sequence of Ab-D LC including signal peptide is as follows:

```
                                                 (SEQ ID NO: 9)
  1 MNTRAPAEFL GFLLLWFLGA RCDVQMIQSP SSLSASLGDI
    VTMTCQASQG

 51 TSINLNWFQQ KPGKAPKLLI YGSSNLEDGV PSRFSGSRYG
    TDFTLTISSL

101 EDEDLATYFC LQHSYLPYTF GGGTKLEIKR ADAAPTVSIF
    PPSSEQLTSG
```

-continued

```
151 GASVVCFLNN FYPKDINVKW KIDGSERQNG VLNSWTDQDS
    KDSTYSMSST

201 LTLTKDEYER HNSYTCEATH KTSTSPIVKS FNRNEC
```

Nucleic acid sequence of Ab-D LC including signal peptide encoding sequence:

```
                                                (SEQ ID NO: 10)
  1 ATGAACACGA GGGCCCCTGC TGAGTTCCTT GGGTTCCTGT
    TGCTCTGGTT

 51 TTTAGGTGCC AGATGTGATG TCCAGATGAT TCAGTCTCCA
    TCCTCCCTGT

101 CTGCATCTTT GGGAGACATA GTCACCATGA CTTGCCAGGC
    AAGTCAGGGC

151 ACTAGCATTA ATTTAAACTG GTTTCAGCAA AAACCAGGGA
    AGGCTCCTAA

201 GCTCCTGATC TATGGTTCAA GCAACTTGGA AGATGGGGTC
    CCATCAAGGT

251 TCAGTGGCAG TAGATATGGG ACAGATTTCA CTCTCACCAT
    CAGCAGCCTG

301 GAGGATGAAG ATCTGGCAAC TTATTTCTGT CTACAACATA
    GTTATCTCCC

351 GTACACGTTC GGAGGGGGGA CCAAGCTGGA AATAAAACGG
    GCTGATGCTG

401 CACCAACTGT ATCCATCTTC CCACCATCCA GTGAGCAGTT
    AACATCTGGA

451 GGTGCCTCAG TCGTGTGCTT CTTGAACAAC TTCTACCCCA
    AAGACATCAA

501 TGTCAAGTGG AAGATTGATG GCAGTGAACG ACAAAATGGC
    GTCCTGAACA

551 GTTGGACTGA TCAGGACAGC AAAGACAGCA CCTACAGCAT
    GAGCAGCACC

601 CTCACGTTGA CCAAGGACGA GTATGAACGA CATAACAGCT
    ATACCTGTGA

651 GGCCACTCAC AAGACATCAA CTTCACCCAT TGTCAAGAGC
    TTCAACAGGA

701 ATGAGTGTTA G
```

The amino acid sequence of the mature form (signal peptide removed) of Ab-D HC heavy chain is as follows:

```
                                                (SEQ ID NO: 11)
  1 EVQLQQSGPE LVTPGASVKI SCKASGYTFT DHYMSWVKQS
    HGKSLEWIGD

 51 INPYSGETTY NQKFKGTATL TVDKSSSIAY MEIRGLTSED
    SAVYYCARDD

101 YDASPFAYWG QGTLVTVSAA KTTPPSVYPL APGSAAQTNS
    MVTLGCLVKG

151 YFPEPVTVTW NSGSLSSGVH TFPAVLQSDL YTLSSSVTVP
    SSTWPSETVT

201 CNVAHPASST KVDKKIVPRD CGCKPCICTV PEVSSVFIFP
    PKPKDVLTIT

251 LTPKVTCVVV DISKDDPEVQ FSWFVDDVEV HTAQTQPREE
    QFNSTFRSVS
```

-continued

```
301 ELPIMHQDWL NGKEFKCRVN SPAFPAPIEK TISKTKGRPK
    APQVYTIPPP

351 KEQMAKDKVS LTCMITDFFP EDITVEWQWN GQPAENYKNT
    QPIMDTDGSY

401 FIYSKLNVQK SNWEAGNTFT CSVLHEGLHN HHTEKSLSHS
    PGK
```

The nucleic acid sequence encoding the mature form (signal peptide removed) of Ab-D HC is:

```
                                          (SEQ ID NO: 12)
   1 GAGGTCCAGC TGCAACAGTC TGGACCTGAA CTGGTGACGC
     CTGGGGCTTC

  51 AGTGAAGATA TCTTGTAAGG CTTCTGGATA CACATTCACT
     GACCACTACA

 101 TGAGCTGGGT GAAGCAGAGT CATGGAAAAA GCCTTGAGTG
     GATTGGAGAT

 151 ATTAATCCCT ATTCTGGTGA AACTACCTAC AACCAGAAGT
     TCAAGGGCAC

 201 GGCCACATTG ACTGTAGACA AGTCTTCCAG TATAGCCTAC
     ATGGAGATCC

 251 GCGGCCTGAC ATCTGAGGAC TCTGCAGTCT ATTACTGTGC
     AAGAGATGAT

 301 TACGACGCCT CTCCGTTTGC TTACTGGGGC CAAGGGACTC
     TGGTCACTGT

 351 CTCTGCAGCC AAAACGACAC CCCCATCTGT CTATCCACTG
     GCCCCTGGAT

 401 CTGCTGCCCA AACTAACTCC ATGGTGACCC TGGGATGCCT
     GGTCAAGGGC

 451 TATTTCCCTG AGCCAGTGAC AGTGACCTGG AACTCTGGAT
     CCCTGTCCAG

 501 CGGTGTGCAC ACCTTCCCAG CTGTCCTGCA GTCTGACCTC
     TACACTCTGA

 551 GCAGCTCAGT GACTGTCCCC TCCAGCACCT GGCCCAGCGA
     GACCGTCACC

 601 TGCAACGTTG CCCACCCGGC CAGCAGCACC AAGGTGGACA
     AGAAAATTGT

 651 GCCCAGGGAT TGTGGTTGTA AGCCTTGCAT ATGTACAGTC
     CCAGAAGTAT

 701 CATCTGTCTT CATCTTCCCC CCAAAGCCCA AGGATGTGCT
     CACCATTACT

 751 CTGACTCCTA AGGTCACGTG TGTTGTGGTA GACATCAGCA
     AGGATGATCC

 801 CGAGGTCCAG TTCAGCTGGT TTGTAGATGA TGTGGAGGTG
     CACACAGCTC

 851 AGACGCAACC CCGGGAGGAG CAGTTCAACA GCACTTTCCG
     CTCAGTCAGT

 901 GAACTTCCCA TCATGCACCA GGACTGGCTC AATGGCAAGG
     AGTTCAAATG

 951 CAGGGTCAAC AGTCCAGCTT TCCCTGCCCC CATCGAGAAA
     ACCATCTCCA

1001 AAACCAAAGG CAGACCGAAG GCTCCACAGG TGTACACCAT
     TCCACCTCCC
```

-continued

```
1051 AAGGAGCAGA TGGCCAAGGA TAAAGTCAGT CTGACCTGCA
     TGATAACAGA

1101 CTTCTTCCCT GAAGACATTA CTGTGGAGTG GCAGTGGAAT
     GGGCAGCCAG

1151 CGGAGAACTA CAAGAACACT CAGCCCATCA TGGACACAGA
     TGGCTCTTAC

1201 TTCATCTACA GCAAGCTCAA TGTGCAGAAG AGCAACTGGG
     AGGCAGGAAA

1251 TACTTTCACC TGCTCTGTGT TACATGAGGG CCTGCACAAC
     CACCATACTG

1301 AGAAGAGCCT CTCCCACTCT CCTGGTAAAT GA
```

The amino acid sequence of Ab-D HC including signal peptide is:

```
                                          (SEQ ID NO: 13)
  1 MRCRWIFLFL LSGTAGVLSE VQLQQSGPEL VTPGASVKIS
    CKASGYTFTD

 51 HYMSWVKQSH GKSLEWIGDI NPYSGETTYN QKFKGTATLT
    VDKSSSIAYM

101 EIRGLTSEDS AVYYCARDDY DASPFAYWGQ GTLVTVSAAK
    TTPPSVYPLA

151 PGSAAQTNSM VTLGCLVKGY FPEPVTVTWN SGSLSSGVHT
    FPAVLQSDLY

201 TLSSSVTVPS STWPSETVTC NVAHPASSTK VDKKIVPRDC
    GCKPCICTVP

251 EVSSVFIFPP KPKDVLTITL TPKVTCVVVD ISKDDPEVQF
    SWFVDDVEVH

301 TAQTQPREEQ FNSTFRSVSE LPIMHQDWLN GKEFKCRVNS
    PAFPAPIEKT

351 ISKTKGRPKA PQVYTIPPPK EQMAKDKVSL TCMITDFFPE
    DITVEWQWNG

401 QPAENYKNTQ PIMDTDGSYF IYSKLNVQKS NWEAGNTFTC
    SVLHEGLHNH

451 HTEKSLSHSP GK
```

The nucleic acid sequence of Ab-D HC including signal peptide encoding sequence is:

```
                                          (SEQ ID NO: 14)
   1 ATGAGATGCA GGTGGATCTT TCTCTTTCTC CTGTCAGGAA
     CTGCAGGTGT

  51 CCTCTCTGAG GTCCAGCTGC AACAGTCTGG ACCTGAACTG
     GTGACGCCTG

 101 GGGCTTCAGT GAAGATATCT TGTAAGGCTT CTGGATACAC
     ATTCACTGAC

 151 CACTACATGA GCTGGGTGAA GCAGAGTCAT GGAAAAAGCC
     TTGAGTGGAT

 201 TGGAGATATT AATCCCTATT CTGGTGAAAC TACCTACAAC
     CAGAAGTTCA

 251 AGGGCACGGC CACATTGACT GTAGACAAGT CTTCCAGTAT
     AGCCTACATG

 301 GAGATCCGCG GCCTGACATC TGAGGACTCT GCAGTCTATT
     ACTGTGCAAG

 351 AGATGATTAC GACGCCTCTC CGTTTGCTTA CTGGGGCCAA
     GGGACTCTGG
```

-continued

```
 401 TCACTGTCTC TGCAGCCAAA ACGACACCCC CATCTGTCTA
     TCCACTGGCC

 451 CCTGGATCTG CTGCCCAAAC TAACTCCATG GTGACCCTGG
     GATGCCTGGT

 501 CAAGGGCTAT TTCCCTGAGC CAGTGACAGT GACCTGGAAC
     TCTGGATCCC

 551 TGTCCAGCGG TGTGCACACC TTCCCAGCTG TCCTGCAGTC
     TGACCTCTAC

 601 ACTCTGAGCA GCTCAGTGAC TGTCCCCTCC AGCACCTGGC
     CCAGCGAGAC

 651 CGTCACCTGC AACGTTGCCC ACCCGGCCAG CAGCACCAAG
     GTGGACAAGA

 701 AAATTGTGCC CAGGGATTGT GGTTGTAAGC CTTGCATATG
     TACAGTCCCA

 751 GAAGTATCAT CTGTCTTCAT CTTCCCCCCA AAGCCCAAGG
     ATGTGCTCAC

 801 CATTACTCTG ACTCCTAAGG TCACGTGTGT TGTGGTAGAC
     ATCAGCAAGG

 851 ATGATCCCGA GGTCCAGTTC AGCTGGTTTG TAGATGATGT
     GGAGGTGCAC

 901 ACAGCTCAGA CGCAACCCCG GGAGGAGCAG TTCAACAGCA
     CTTTCCGCTC

 951 AGTCAGTGAA CTTCCCATCA TGCACCAGGA CTGGCTCAAT
     GGCAAGGAGT

1001 TCAAATGCAG GGTCAACAGT CCAGCTTTCC CTGCCCCCAT
     CGAGAAAACC

1051 ATCTCCAAAA CCAAAGGCAG ACCGAAGGCT CCACAGGTGT
     ACACCATTCC

1101 ACCTCCCAAG GAGCAGATGG CCAAGGATAA AGTCAGTCTG
     ACCTGCATGA

1151 TAACAGACTT CTTCCCTGAA GACATTACTG TGGAGTGGCA
     GTGGAATGGG

1201 CAGCCAGCGG AGAACTACAA GAACACTCAG CCCATCATGG
     ACACAGATGG

1251 CTCTTACTTC ATCTACAGCA AGCTCAATGT GCAGAAGAGC
     AACTGGGAGG

1301 CAGGAAATAC TTTCACCTGC TCTGTGTTAC ATGAGGGCCT
     GCACAACCAC

1351 CATACTGAGA AGAGCCTCTC CCACTCTCCT GGTAAATGA
```

The CDR (complementarity determining region) sequences in the variable region of the heavy chain of Ab-D are as follows:

```
CDR-H1:   DHYMS (SEQ ID NO: 39)

CDR-H2:   DINPYSGETTYNQKFKG (SEQ ID NO: 40)

CDR-H3:   DDYDASPFAY (SEQ ID NO: 41)
```

The light chain variable region CDR sequences of Ab-D are:

```
CDR-L1:   QASQGTSINLN (SEQ ID NO: 42)

CDR-L2:   GSSNLED (SEQ ID NO: 43)

CDR-L3:   LQHSYLPYT (SEQ ID NO: 44)
```

Ab-C

Figure 17:
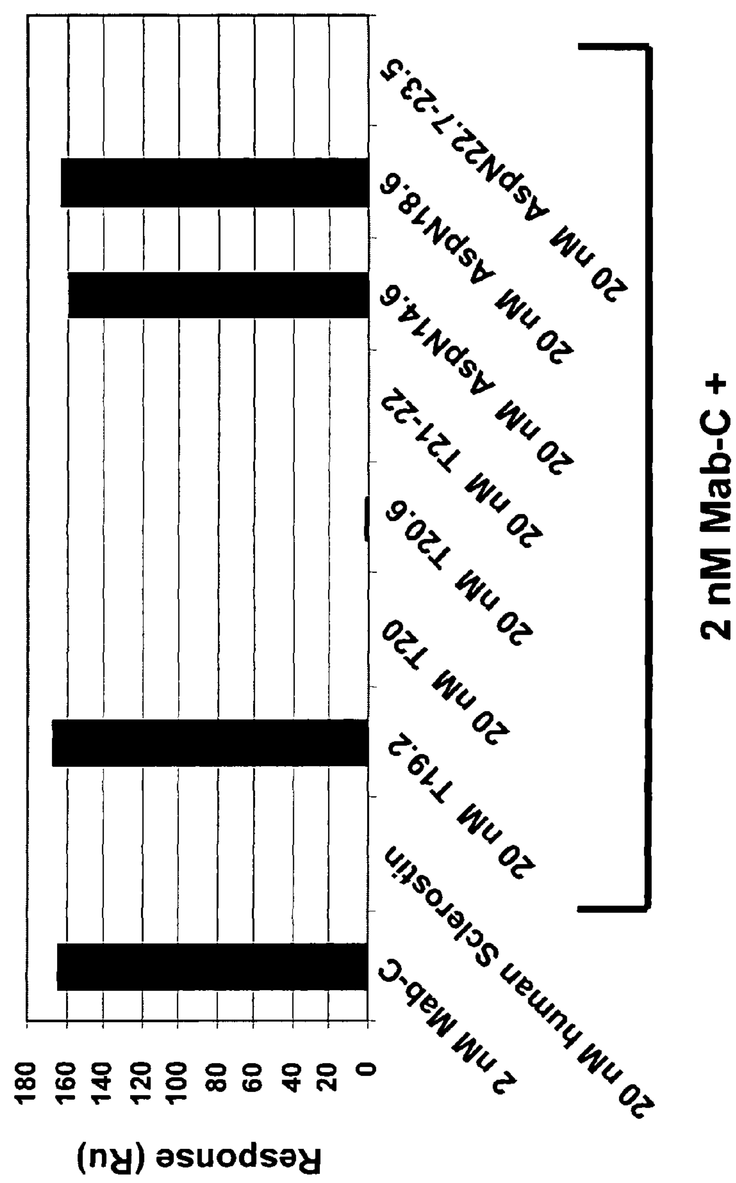
FIG. 17 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-C. Human sclerostin peptides used were T19.2, T20, T20.6, T21-22, AspN14.6, AspN18.6 and AspN22.7-23.5.

Antibody C (also referred to herein as Ab-C and Mab-C) is a mouse antibody which exhibits high affinity binding to sclerostin. The BIAcore binding pattern of Ab-C is shown in FIG. 17. The amino acid sequence of the mature form (signal peptide removed) of Ab-C Light Chain is as follows:

```
                                        (SEQ ID NO: 15)
  1 DIVLTQSPAS LTVSLGLRAT ISCKASQSVD YDGDSYMNWY
    QQKPGQPPKL

 51 LIYAASNLES GIPARFSGNG SGTDFTLNIH PVEEEDAVTY
    YCQQSNEDPW

101 TFGGGTKLEI KRADAAPTVS IFPPSSEQLT SGGASVVCFL
    NNFYPKDINV

151 KWKIDGSERQ NGVLNSWTDQ DSKDSTYSMS STLTLTKDEY
    ERHNSYTCEA

201 THKTSTSPIV KSFNRNEC
```

The nucleic acid sequence encoding the mature form (signal peptide removed) of Ab-C LC is:

```
                                        (SEQ ID NO: 16)
  1 GACATTGTGC TGACCCAATC TCCAGCTTCT TTGACTGTGT
    CTCTAGGCCT

 51 GAGGGCCACC ATCTCCTGCA AGGCCAGCCA AAGTGTTGAT
    TATGATGGTG

101 ATAGTTATAT GAACTGGTAC CAGCAGAAAC CAGGACAGCC
    ACCCAAACTC

151 CTCATCTATG CTGCATCCAA TCTAGAATCT GGGATCCCAG
    CCAGGTTTAG

201 TGGCAATGGG TCTGGGACAG ACTTCACCCT CAACATCCAT
    CCTGTGGAGG

251 AGGAGGATGC TGTAACCTAT TACTGTCAAC AAAGTAATGA
    GGATCCGTGG

301 ACGTTCGGTG GAGGCACCAA GCTGGAAATC AAACGGGCTG
    ATGCTGCACC

351 AACTGTATCC ATCTTCCCAC CATCCAGTGA GCAGTTAACA
    TCTGGAGGTG

401 CCTCAGTCGT GTGCTTCTTG AACAACTTCT ACCCCAAAGA
    CATCAATGTC

451 AAGTGGAAGA TTGATGGCAG TGAACGACAA AATGGCGTCC
    TGAACAGTTG

501 GACTGATCAG GACAGCAAAG ACAGCACCTA CAGCATGAGC
    AGCACCCTCA

551 CGTTGACCAA GGACGAGTAT GAACGACATA ACAGCTATAC
    CTGTGAGGCC

601 ACTCACAAGA CATCAACTTC ACCCATTGTC AAGAGCTTCA
    ACAGGAATGA

651 GTGTTAG
```

The amino acid sequence of Ab-C LC including signal peptide is:

```
                                        (SEQ ID NO: 17)
  1 METDTILLWV LLLWVPGSTG DIVLTQSPAS LTVSLGLRAT
    ISCKASQSVD
```

-continued

```
51 YDGDSYMNWY QQKPGQPPKL LIYAASNLES GIPARFSGNG
   SGTDFTLNIH

101 PVEEEDAVTY YCQQSNEDPW TFGGGTKLEI KRADAAPTVS
    IFPPSSEQLT

151 SGGASVVCFL NNFYPKDINV KWKIDGSERQ NGVLNSWTDQ
    DSKDSTYSMS

201 STLTLTKDEY ERHNSYTCEA THKTSTSPIV KSFNRNEC
```

The nucleic acid sequence of Ab-C LC including signal peptide encoding sequence is:

```
                                       (SEQ ID NO: 18)
1 ATGGAGACAG ACACAATCCT GCTATGGGTG CTGCTGCTCT
  GGGTTCCAGG

51 CTCCACTGGT GACATTGTGC TGACCCAATC TCCAGCTTCT
   TTGACTGTGT

101 CTCTAGGCCT GAGGGCCACC ATCTCCTGCA AGGCCAGCCA
    AAGTGTTGAT

151 TATGATGGTG ATAGTTATAT GAACTGGTAC CAGCAGAAAC
    CAGGACAGCC

201 ACCCAAACTC CTCATCTATG CTGCATCCAA TCTAGAATCT
    GGGATCCCAG

251 CCAGGTTTAG TGGCAATGGG TCTGGGACAG ACTTCACCCT
    CAACATCCAT

301 CCTGTGGAGG AGGAGGATGC TGTAACCTAT TACTGTCAAC
    AAAGTAATGA

351 GGATCCGTGG ACGTTCGGTG GAGGCACCAA GCTGGAAATC
    AAACGGGCTG

401 ATGCTGCACC AACTGTATCC ATCTTCCCAC CATCCAGTGA
    GCAGTTAACA

451 TCTGGAGGTG CCTCAGTCGT GTGCTTCTTG AACAACTTCT
    ACCCCAAAGA

501 CATCAATGTC AAGTGGAAGA TTGATGGCAG TGAACGACAA
    AATGGCGTCC

551 TGAACAGTTG GACTGATCAG GACAGCAAAG ACAGCACCTA
    CAGCATGAGC

601 AGCACCCTCA CGTTGACCAA GGACGAGTAT GAACGACATA
    ACAGCTATAC

651 CTGTGAGGCC ACTCACAAGA CATCAACTTC ACCCATTGTC
    AAGAGCTTCA

701 ACAGGAATGA GTGTTAG
```

Ab-C Heavy Chain

The amino acid sequence of the mature form (signal peptide removed) of Ab-C HC is (SEQ ID NO: 19)

1 EVQLQQSGPE LVKPGTSVKM SCKASGYTFT DCYMNWVKQS HGKSLEWIGD

51 INPFNGGTTY NQKFKGKATL TVDKSSSTAY MQLNSLTSDD SAVYYCARSH

101 YYFDGRVPWD AMDYWGQGTS VTVSS*AKTTP PSVYPLAPGS AAQTNSMVTL*

151 *GCLVKGYFPE PVTVTWNSGS LSSGVHTFPA VLQSDLYTLS SSVTVPSSTW*

201 *PSETVTCNVA HPASSTKVDK KIVPRDCGCK PCICTVPEVS SVFIFPPKPK*

251 *DVLTITLTPK VTCVVVDISK DDPEVQFSWF VDDVEVHTAQ TQPREEQFNS*

301 *TFRSVSELPI MHQDWLNGKE FKCRVNSAAF PAPIEKTISK TKGRPKAPQV*

351 *YTIPPPKEQM AKDKVSLTCM ITDFFPEDIT VEWQWNGQPA ENYKNTQPIM*

401 *DTDGSYFIYS KLNVQKSNWE AGNTFTCSVL HEGLHNHHTE KSLSHSPGK*

The nucleic acid sequence encoding the mature form (signal peptide removed) of Ab-C HC is as follows:

```
                                       (SEQ ID NO: 20)
1 GAGGTCCAGC TGCAACAATC TGGACCTGAG CTGGTGAAGC
  CTGGGACTTC

51 AGTGAAGATG TCCTGTAAGG CTTCTGGATA CACATTCACT
   GACTGCTACA

101 TGAACTGGGT GAAGCAGAGC CATGGGAAGA GCCTTGAATG
    GATTGGAGAT

151 ATTAATCCTT TCAACGGTGG TACTACCTAC AACCAGAAGT
    TCAAGGGCAA

201 GGCCACATTG ACTGTAGACA AATCCTCCAG CACAGCCTAC
    ATGCAGCTCA

251 ACAGCCTGAC ATCTGACGAC TCTGCAGTCT ATTACTGTGC
    AAGATCCCAT

301 TATTACTTCG ATGGTAGAGT CCCTTGGGAT GCTATGGACT
    ACTGGGGTCA

351 AGGAACCTCA GTCACCGTCT CCTCAGCCAA AACGACACCC
    CCATCTGTCT

401 ATCCACTGGC CCCTGGATCT GCTGCCCAAA CTAACTCCAT
    GGTGACCCTG

451 GGATGCCTGG TCAAGGGCTA TTTCCCTGAG CCAGTGACAG
    TGACCTGGAA

501 CTCTGGATCC CTGTCCAGCG GTGTGCACAC CTTCCCAGCT
    GTCCTGCAGT

551 CTGACCTCTA CACTCTGAGC AGCTCAGTGA CTGTCCCCTC
    CAGCACCTGG

601 CCCAGCGAGA CCGTCACCTG CAACGTTGCC CACCCGGCCA
    GCAGCACCAA

651 GGTGGACAAG AAAATTGTGC CCAGGGATTG TGGTTGTAAG
    CCTTGCATAT

701 GTACAGTCCC AGAAGTATCA TCTGTCTTCA TCTTCCCCCC
    AAAGCCCAAG

751 GATGTGCTCA CCATTACTCT GACTCCTAAG GTCACGTGTG
    TTGTGGTAGA

801 CATCAGCAAG GATGATCCCG AGGTCCAGTT CAGCTGGTTT
    GTAGATGATG

851 TGGAGGTGCA CACAGCTCAG ACGCAACCCC GGGAGGAGCA
    GTTCAACAGC
```

-continued

```
 901 ACTTTCCGCT CAGTCAGTGA ACTTCCCATC ATGCACCAGG
     ACTGGCTCAA

 951 TGGCAAGGAG TTCAAATGCA GGGTCAACAG TGCAGCTTTC
     CCTGCCCCCA

1001 TCGAGAAAAC CATCTCCAAA ACCAAAGGCA GACCGAAGGC
     TCCACAGGTG

1051 TACACCATTC CACCTCCCAA GGAGCAGATG GCCAAGGATA
     AAGTCAGTCT

1101 GACCTGCATG ATAACAGACT TCTTCCCTGA AGACATTACT
     GTGGAGTGGC

1151 AGTGGAATGG GCAGCCAGCG GAGAACTACA AGAACACTCA
     GCCCATCATG

1201 GACACAGATG GCTCTTACTT CATCTACAGC AAGCTCAATG
     TGCAGAAGAG

1251 CAACTGGGAG GCAGGAAATA CTTTCACCTG CTCTGTGTTA
     CATGAGGGCC

1301 TGCACAACCA CCATACTGAG AAGAGCCTCT CCCACTCTCC
     TGGTAAATGA
```

The amino acid sequence of Ab-C HC including signal peptide is:

```
                                    (SEQ ID NO: 21)
  1 MGWNWIFLFL LSGTAGVYSE VQLQQSGPEL VKPGTSVKMS
    CKASGYTFTD

 51 CYMNWVKQSH GKSLEWIGDI NPFNGGTTYN QKFKGKATLT
    VDKSSSTAYM

101 QLNSLTSDDS AVYYCARSHY YFDGRVPWDA MDYWGQGTSV
    TVSSAKTTPP

151 SVYPLAPGSA AQTNSMVTLG CLVKGYFPEP VTVTWNSGSL
    SSGVHTFPAV

201 LQSDLYTLSS SVTVPSSTWP SETVTCNVAH PASSTKVDKK
    IVPRDCGCKP

251 CICTVPEVSS VFIFPPKPKD VLTITLTPKV TCVVVDISKD
    DPEVQFSWFV

301 DDVEVHTAQT QPREEQFNST FRSVSELPIM HQDWLNGKEF
    KCRVNSAAFP

351 APIEKTISKT KGRPKAPQVY TIPPPKEQMA KDKVSLTCMI
    TDFFPEDITV

401 EWQWNGQPAE NYKNTQPIMD TDGSYFIYSK LNVQKSNWEA
    GNTFTCSVLH

451 EGLHNHHTEK SLSHSPGK
```

The nucleic acid sequence of Ab-C HC including signal peptide encoding sequence is:

```
                                    (SEQ ID NO: 22)
   1 ATGGGATGGA ACTGGATCTT TCTCTTCCTC TTGTCAGGAA
     CTGCAGGTGT

  51 CTACTCTGAG GTCCAGCTGC AACAATCTGG ACCTGAGCTG
     GTGAAGCCTG

 101 GGACTTCAGT GAAGATGTCC TGTAAGGCTT CTGGATACAC
     ATTCACTGAC

 151 TGCTACATGA ACTGGGTGAA GCAGAGCCAT GGGAAGAGCC
     TTGAATGGAT
```

-continued

```
 201 TGGAGATATT AATCCTTTCA ACGGTGGTAC TACCTACAAC
     CAGAAGTTCA

 251 AGGGCAAGGC CACATTGACT GTAGACAAAT CCTCCAGCAC
     AGCCTACATG

 301 CAGCTCAACA GCCTGACATC TGACGACTCT GCAGTCTATT
     ACTGTGCAAG

 351 ATCCCATTAT TACTTCGATG GTAGAGTCCC TTGGGATGCT
     ATGGACTACT

 401 GGGGTCAAGG AACCTCAGTC ACCGTCTCCT CAGCCAAAAC
     GACACCCCCA

 451 TCTGTCTATC CACTGGCCCC TGGATCTGCT GCCCAAACTA
     ACTCCATGGT

 501 GACCCTGGGA TGCCTGGTCA AGGGCTATTT CCCTGAGCCA
     GTGACAGTGA

 551 CCTGGAACTC TGGATCCCTG TCCAGCGGTG TGCACACCTT
     CCCAGCTGTC

 601 CTGCAGTCTG ACCTCTACAC TCTGAGCAGC TCAGTGACTG
     TCCCCTCCAG

 651 CACCTGGCCC AGCGAGACCG TCACCTGCAA CGTTGCCCAC
     CCGGCCAGCA

 701 GCACCAAGGT GGACAAGAAA ATTGTGCCCA GGGATTGTGG
     TTGTAAGCCT

 751 TGCATATGTA CAGTCCCAGA AGTATCATCT GTCTTCATCT
     TCCCCCCAAA

 801 GCCCAAGGAT GTGCTCACCA TTACTCTGAC TCCTAAGGTC
     ACGTGTGTTG

 851 TGGTAGACAT CAGCAAGGAT GATCCCGAGG TCCAGTTCAG
     CTGGTTTGTA

 901 GATGATGTGG AGGTGCACAC AGCTCAGACG CAACCCCGGG
     AGGAGCAGTT

 951 CAACAGCACT TTCCGCTCAG TCAGTGAACT TCCCATCATG
     CACCAGGACT

1001 GGCTCAATGG CAAGGAGTTC AAATGCAGGG TCAACAGTGC
     AGCTTTCCCT

1051 GCCCCCATCG AGAAAACCAT CTCCAAAACC AAAGGCAGAC
     CGAAGGCTCC

1101 ACAGGTGTAC ACCATTCCAC CTCCCAAGGA GCAGATGGCC
     AAGGATAAAG

1151 TCAGTCTGAC CTGCATGATA ACAGACTTCT TCCCTGAAGA
     CATTACTGTG

1201 GAGTGGCAGT GGAATGGGCA GCCAGCGGAG AACTACAAGA
     ACACTCAGCC

1251 CATCATGGAC ACAGATGGCT CTTACTTCAT CTACAGCAAG
     CTCAATGTGC

1301 AGAAGAGCAA CTGGGAGGCA GGAAATACTT TCACCTGCTC
     TGTGTTACAT

1351 GAGGGCCTGC ACAACCACCA TACTGAGAAG AGCCTCTCCC
     ACTCTCCTGG

1401 TAAATGA
```

The CDR (complementarity determining region) sequences in the variable region of the heavy chain of Ab-C are as follows:

CDR-H1: DCYMN (SEQ ID NO: 45)

CDR-H2: DINPFNGGTTYNQKFKG (SEQ ID NO: 46)

CDR-H3: SHYYFDGRVPWDAMDY (SEQ ID NO: 47)

The light chain variable region CDR sequences of Ab-C are:

CDR-L1: KASQSVDYDGDSYMN (SEQ ID NO: 48)

CDR-L2: AASNLES (SEQ ID NO: 49)

CDR-L3: QQSNEDPWT (SEQ ID NO: 50)

Ab-A

Figure 15:
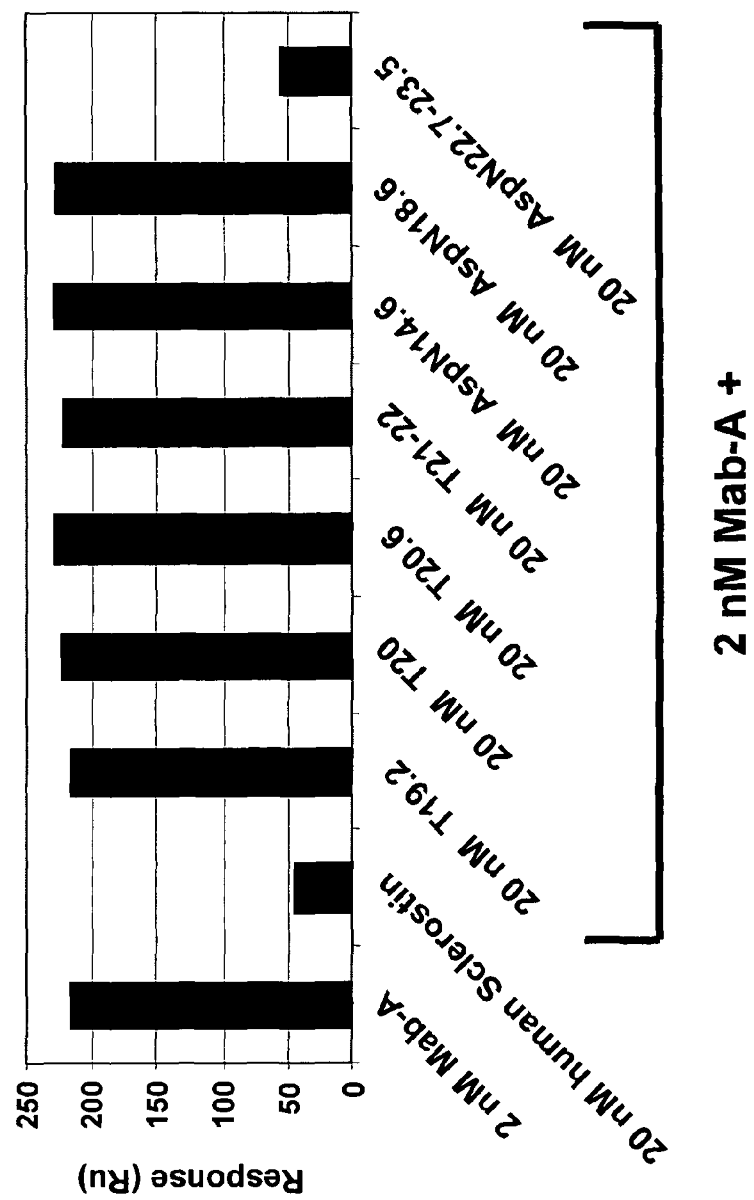
FIG. 15 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-A. Human sclerostin peptides used were T19.2, T20, T20.6, T21-22, AspN14.6, AspN18.6 and AspN22.7-23.5.

Antibody A (also referred to herein as Ab-A and Mab-A) is a rabbit-mouse chimeric antibody which exhibits high affinity binding to sclerostin. The BIAcore binding pattern of Ab-A is shown in FIG. 15.

Ab-A Light Chain

The amino acid sequence of the mature form (signal peptide removed) of Ab-A LC:

```
                                          (SEQ ID NO: 23)
  1 AQVLTQTPAS VSAAVGGTVT INCQSSQSVY DNNWLAWFQQ
    KPGQPPKLLI

 51 YDASDLASGV PSRFSGSGSG TQFTLTISGV QCADAATYYC
    QGAYNDVIYA

101 FGGGTEVVVK RTDAAPTVSI FPPSSEQLTS GGASVVCFLN
    NFYPKDINVK

151
    WKIDGSERQN GVLNSWTDQD SKDSTYSMSS TLTLTKDEYE
    RHNSYTCEAT

201 HKTSTSPIVK SFNRNEC
```

The nucleic acid sequence encoding the mature form (signal peptide removed) of Ab-A LC:

```
                                          (SEQ ID NO: 24)
  1 GCGCAAGTGC TGACCCAGAC TCCAGCCTCC GTGTCTGCAG
    CTGTGGGAGG

 51 CACAGTCACC ATCAATTGCC AGTCCAGTCA GAGTGTTTAT
    GATAACAACT

101 GGTTAGCCTG GTTTCAGCAG AAACCAGGGC AGCCTCCCAA
    GCTCCTGATT

151 TATGATGCAT CCGATCTGGC ATCTGGGGTC CCATCGCGGT
    TCAGTGGCAG

201 TGGATCTGGG ACACAGTTCA CTCTCACCAT CAGCGGCGTG
    CAGTGTGCCG

251 ATGCTGCCAC TTACTACTGT CAAGGCGCTT ATAATGATGT
    TATTTATGCT

301 TTCGGCGGAG GGACCGAGGT GGTGGTCAAA CGTACGGATG
    CTGCACCAAC

351 TGTATCCATC TTCCCACCAT CCAGTGAGCA GTTAACATCT
    GGAGGTGCCT

401 CAGTCGTGTG CTTCTTGAAC AACTTCTACC CCAAAGACAT
    CAATGTCAAG
```

-continued

```
451 TGGAAGATTG ATGGCAGTGA ACGACAAAAT GGCGTCCTGA
    ACAGTTGGAC

501 TGATCAGGAC AGCAAAGACA GCACCTACAG CATGAGCAGC
    ACCCTCACGT

551 TGACCAAGGA CGAGTATGAA CGACATAACA GCTATACCTG
    TGAGGCCACT

601 CACAAGACAT CAACTTCACC CATTGTCAAG AGCTTCAACA
    GGAATGAGTG

651 TTAG
```

The amino acid sequence of Ab-A LC including signal peptide is:

```
                                          (SEQ ID NO: 25)
  1 MDTRAPTQLL GLLLLWLPGA TFAQVLTQTP ASVSAAVGGT
    VTINCQSSQS

 51 VYDNNWLAWF QQKPGQPPKL LIYDASDLAS GVPSRFSGSG
    SGTQFTLTIS

101 GVQCADAATY YCQGAYNDVI YAFGGGTEVV VKRTDAAPTV
    SIFPPSSEQL

151 TSGGASVVCF LNNFYPKDIN VKWKIDGSER QNGVLNSWTD
    QDSKDSTYSM

201 SSTLTLTKDE YERHNSYTCE ATHKTSTSPI VKSFNRNEC
```

The nucleic acid sequence of Ab-A LC including signal peptide encoding sequence is:

```
                                          (SEQ ID NO: 26)
  1 ATGGACACGA GGGCCCCCAC TCAGCTGCTG GGGCTCCTGC
    TGCTCTGGCT

 51 CCCAGGTGCC ACATTTGCGC AAGTGCTGAC CCAGACTCCA
    GCCTCCGTGT

101 CTGCAGCTGT GGGAGGCACA GTCACCATCA ATTGCCAGTC
    CAGTCAGAGT

151 GTTTATGATA ACAACTGGTT AGCCTGGTTT CAGCAGAAAC
    CAGGGCAGCC

201 TCCCAAGCTC CTGATTTATG ATGCATCCGA TCTGGCATCT
    GGGGTCCCAT

251 CGCGGTTCAG TGGCAGTGGA TCTGGGACAC AGTTCACTCT
    CACCATCAGC

301 GGCGTGCAGT GTGCCGATGC TGCCACTTAC TACTGTCAAG
    GCGCTTATAA

351 TGATGTTATT TATGCTTTCG GCGGAGGGAC CGAGGTGGTG
    GTCAAACGTA

401 CGGATGCTGC ACCAACTGTA TCCATCTTCC CACCATCCAG
    TGAGCAGTTA

451 ACATCTGGAG GTGCCTCAGT CGTGTGCTTC TTGAACAACT
    TCTACCCCAA

501 AGACATCAAT GTCAAGTGGA AGATTGATGG CAGTGAACGA
    CAAAATGGCG

551 TCCTGAACAG TTGGACTGAT CAGGACAGCA AAGACAGCAC
    CTACAGCATG

601 AGCAGCACCC TCACGTTGAC CAAGGACGAG TATGAACGAC
    ATAACAGCTA
```

-continued

```
651 TACCTGTGAG GCCACTCACA AGACATCAAC TTCACCCATT
    GTCAAGAGCT

701 TCAACAGGAA TGAGTGTTAG
```

The amino acid sequence of the mature form (signal peptide removed) of Ab-A HC is:

```
                                        (SEQ ID NO: 27)
  1 QSLEESGGRL VTPGTPLTLT CTASGFSLSS YWMNWVRQAP
    GEGLEWIGTI

 51 DSGGRTDYAS WAKGRFTISR TSTTMDLKMT SLTTGDTARY
    FCARNWNLWG

101 QGTLVTVSSA STKGPSVYPL APGSAAQTNS MVTLGCLVKG
    YFPEPVTVTW

151 NSGSLSSGVH TFPAVLQSDL YTLSSSVTVP SSTWPSETVT
    CNVAHPASST

201 KVDKKIVPRD CGCKPCICTV PEVSSVFIFP PKPKDVLTIT
    LTPKVTCVVV

251 DISKDDPEVQ FSWFVDDVEV HTAQTQPREE QFNSTFRSVS
    ELPIMHQDWL

301 NGKEFKCRVN SAAFPAPIEK TISKTKGRPK APQVYTIPPP
    KEQMAKDKVS

351 LTCMITDFFP EDITVEWQWN GQPAENYKNT QPIMNTNGSY
    FVYSKLNVQK

401 SNWEAGNTFT CSVLHEGLHN HHTEKSLSHS PGK
```

The nucleic acid sequence encoding the mature form (signal peptide removed) of Ab-A HC:

```
                                        (SEQ ID NO: 28)
   1 CAGTCGCTGG AGGAGTCCGG GGGTCGCCTG GTCACGCCTG
     GGACACCCCT

  51 GACACTCACC TGCACAGCCT CTGGATTCTC CCTCAGTAGT
     TATTGGATGA

 101 ACTGGGTCCG CCAGGCTCCA GGGGAGGGGC TGGAATGGAT
     CGGAACCATT

 151 GATTCTGGTG GTAGGACGGA CTACGCGAGC TGGGCAAAAG
     GCCGATTCAC

 201 CATCTCCAGA ACCTCGACTA CGATGGATCT GAAAATGACC
     AGTCTGACGA

 251 CCGGGGACAC GGCCCGTTAT TTCTGTGCCA GAAATTGGAA
     CTTGTGGGGC

 301 CAAGGCACCC TCGTCACCGT CTCGAGCGCT TCTACAAAGG
     GCCCATCTGT

 351 CTATCCACTG GCCCCTGGAT CTGCTGCCCA AACTAACTCC
     ATGGTGACCC

 401 TGGGATGCCT GGTCAAGGGC TATTTCCCTG AGCCAGTGAC
     AGTGACCTGG

 451 AACTCTGGAT CCCTGTCCAG CGGTGTGCAC ACCTTCCCAG
     CTGTCCTGCA

 501 GTCTGACCTC TACACTCTGA GCAGCTCAGT GACTGTCCCC
     TCCAGCACCT

 551 GGCCCAGCGA GACCGTCACC TGCAACGTTG CCCACCCGGC
     CAGCAGCACC

 601 AAGGTGGACA AGAAAATTGT GCCCAGGGAT TGTGGTTGTA
     AGCCTTGCAT

 651 ATGTACAGTC CCAGAAGTAT CATCTGTCTT CATCTTCCCC
     CCAAAGCCCA

 701 AGGATGTGCT CACCATTACT CTGACTCCTA AGGTCACGTG
     TGTTGTGGTA

 751 GACATCAGCA AGGATGATCC CGAGGTCCAG TTCAGCTGGT
     TTGTAGATGA

 801 TGTGGAGGTG CACACAGCTC AGACGCAACC CCGGGAGGAG
     CAGTTCAACA

 851 GCACTTTCCG CTCAGTCAGT GAACTTCCCA TCATGCACCA
     GGACTGGCTC

 901 AATGGCAAGG AGTTCAAATG CAGGGTCAAC AGTGCAGCTT
     TCCCTGCCCC

 951 CATCGAGAAA ACCATCTCCA AAACCAAAGG CAGACCGAAG
     GCTCCACAGG

1001 TGTACACCAT TCCACCTCCC AAGGAGCAGA TGGCCAAGGA
     TAAAGTCAGT

1051 CTGACCTGCA TGATAACAGA CTTCTTCCCT GAAGACATTA
     CTGTGGAGTG

1101 GCAGTGGAAT GGGCAGCCAG CGGAGAACTA CAAGAACACT
     CAGCCCATCA

1151 TGGACACAGA TGGCTCTTAC TTCGTCTACA GCAAGCTCAA
     TGTGCAGAAG

1201 AGCAACTGGG AGGCAGGAAA TACTTTCACC TGCTCTGTGT
     TACATGAGGG

1251 CCTGCACAAC CACCATACTG AGAAGAGCCT CTCCCACTCT
     CCTGGTAAAT

1301 GA
```

The amino acid sequence of the Ab-A HC including signal peptide is:

```
                                        (SEQ ID NO: 29)
  1 METGLRWLLL VAVLKGVHCQ SLEESGGRLV TPGTPLTLTC
    TASGFSLSSY

 51 WMNWVRQAPG EGLEWIGTID SGGRTDYASW AKGRFTISRT
    STTMDLKMTS

101 LTTGDTARYF CARNWNLWGQ GTLVTVSSAS TKGPSVYPLA
    PGSAAQTNSM

151 VTLGCLVKGY FPEPVTVTWN SGSLSSGVHT FPAVLQSDLY
    TLSSSVTVPS

201 STWPSETVTC NVAHPASSTK VDKKIVPRDC GCKPCICTVP
    EVSSVFIFPP

251 KPKDVLTITL TPKVTCVVVD ISKDDPEVQF SWFVDDVEVH
    TAQTQPREEQ

301 FNSTFRSVSE LPIMHQDWLN GKEFKCRVNS AAFPAPIEKT
    ISKTKGRPKA
```

-continued

```
351 PQVYTIPPPK EQMAKDKVSL TCMITDFFPE DITVEWQWNG
    QPAENYKNTQ

401 PIMNTNGSYF VYSKLNVQKS NWEAGNTFTC SVLHEGLHNH
    HTEKSLSHSP

451 GK
```

The nucleic acid sequence of Ab-A HC including signal peptide encoding sequence:

```
                                    (SEQ ID NO: 30)
   1 ATGGAGACTG GGCTGCGCTG GCTTCTCCTG GTCGCTGTGC
     TCAAAGGTGT

  51 CCACTGTCAG TCGCTGGAGG AGTCCGGGGG TCGCCTGGTC
     ACGCCTGGGA

 101 CACCCCTGAC ACTCACCTGC ACAGCCTCTG GATTCTCCCT
     CAGTAGTTAT

 151 TGGATGAACT GGGTCCGCCA GGCTCCAGGG GAGGGGCTGG
     AATGGATCGG

 201 AACCATTGAT TCTGGTGGTA GGACGGACTA CGCGAGCTGG
     GCAAAAGGCC

 251 GATTCACCAT CTCCAGAACC TCGACTACGA TGGATCTGAA
     AATGACCAGT

 301 CTGACGACCG GGGACACGGC CCGTTATTTC TGTGCCAGAA
     ATTGGAACTT

 351 GTGGGGCCAA GGCACCCTCG TCACCGTCTC GAGCGCTTCT
     ACAAAGGGCC

 401 CATCTGTCTA TCCACTGGCC CCTGGATCTG CTGCCCAAAC
     TAACTCCATG

 451 GTGACCCTGG GATGCCTGGT CAAGGGCTAT TTCCCTGAGC
     CAGTGACAGT

 501 GACCTGGAAC TCTGGATCCC TGTCCAGCGG TGTGCACACC
     TTCCCAGCTG

 551 TCCTGCAGTC TGACCTCTAC ACTCTGAGCA GCTCAGTGAC
     TGTCCCCTCC

 601 AGCACCTGGC CCAGCGAGAC CGTCACCTGC AACGTTGCCC
     ACCCGGCCAG

 651 CAGCACCAAG GTGGACAAGA AAATTGTGCC CAGGGATTGT
     GGTTGTAAGC

 701 CTTGCATATG TACAGTCCCA GAAGTATCAT CTGTCTTCAT
     CTTCCCCCCA

 751 AAGCCCAAGG ATGTGCTCAC CATTACTCTG ACTCCTAAGG
     TCACGTGTGT

 801 TGTGGTAGAC ATCAGCAAGG ATGATCCCGA GGTCCAGTTC
     AGCTGGTTTG

 851 TAGATGATGT GGAGGTGCAC ACAGCTCAGA CGCAACCCCG
     GGAGGAGCAG

 901 TTCAACAGCA CTTTCCGCTC AGTCAGTGAA CTTCCCATCA
     TGCACCAGGA

 951 CTGGCTCAAT GGCAAGGAGT TCAAATGCAG GGTCAACAGT
     GCAGCTTTCC

1001 CTGCCCCCAT CGAGAAAACC ATCTCCAAAA CCAAAGGCAG
     ACCGAAGGCT

1051 CCACAGGTGT ACACCATTCC ACCTCCCAAG GAGCAGATGG
     CCAAGGATAA

1101 AGTCAGTCTG ACCTGCATGA TAACAGACTT CTTCCCTGAA
     GACATTACTG

1151 TGGAGTGGCA GTGGAATGGG CAGCCAGCGG AGAACTACAA
     GAACACTCAG

1201 CCCATCATGG ACACAGATGG CTCTTACTTC GTCTACAGCA
     AGCTCAATGT

1251 GCAGAAGAGC AACTGGGAGG CAGGAAATAC TTTCACCTGC
     TCTGTGTTAC

1301 ATGAGGGCCT GCACAACCAC CATACTGAGA AGAGCCTCTC
     CCACTCTCCT

1351 GGTAAATGA
```

The CDR (complementarity determining region) sequences in the variable region of the heavy chain of Ab-A are as follows:

```
CDR-H1:   SYWMN (SEQ ID NO: 51)

CDR-H2:   TIDSGGRTDYASWAKG (SEQ ID NO: 52)

CDR-H3:   NWNL (SEQ ID NO: 53)
```

The light chain variable region CDR sequences of Ab-A are:

```
CDR-L1:   QSSQSVYDNNWLA (SEQ ID NO: 54)

CDR-L2:   DASDLAS (SEQ ID NO: 55)

CDR-L3:   QGAYNDVIYA (SEQ ID NO: 56)
```

Ab-A was humanized, and is referred to as Antibody 1 (also referred to herein as Ab-1), having the following sequences:

The nucleic acid sequence of the Ab-1 LC variable region including signal peptide encoding sequence is

```
                                                  (SEQ ID NO: 74)
ATGGACACGAGGGCCCCCACTCAGCTGCTGGGGCTCCTGCTGCTCTGGC

TCCCAGGTGCCACATTTGCTCAAGTTCTGACCCAGAGTCCAAGCAGTCT

CTCCGCCAGCGTAGGCGATCGTGTGACTATTACCTGTCAATCTAGTCAG

AGCGTGTATGATAACAATTGGCTGGCGTGGTACCAGCAAAAACCGGGCA

AAGCCCCGAAGCTGCTCATCTATGACGCGTCCGATCTGGCTAGCGGTGT

GCCAAGCCGTTTCAGTGGCAGTGGCAGCGGTACTGACTTTACCCTCACA

ATTTCGTCTCTCCAGCCGGAAGATTTCGCCACTTACTATTGTCAAGGTG

CTTACAACGATGTGATTTATGCCTTCGGTCAGGGCACTAAAGTAGAAAT

CAAACGT
```

The amino acid sequence of Ab-1 LC variable region including signal peptide is:

```
                                                  (SEQ ID NO: 75)
MDTRAPTQLLGLLLLWLPGATFAQVLTQSPSSLSASVGDRVTITCQSSQS

VYDNNWLAWYQQKPGKAPKLLIYDASDLASGVPSRFSGSGSGTDFTLTIS

SLQPEDFATYYCQGAYNDVIYAFGQGTKVEIKR
```

The nucleic acid sequence of Ab-1 HC variable region including signal peptide encoding sequence is:

```
                                        (SEQ ID NO: 76)
ATGGAGACTGGGCTGCGCTGGCTTCTCCTGGTCGCTGTGCTCAAAGGTG

TCCACTGTGAGGTGCAGCTGTTGGAGTCTGGAGGCGGGCTTGTCCAGCC

TGGAGGGAGCCTGCGTCTCTCTTGTGCAGCAAGCGGCTTCAGCTTATCC

TCTTACTGGATGAATTGGGTGCGGCAGGCACCTGGGAAGGGCCTGGAGT

GGGTGGGCACCATTGATTCCGGAGGCCGTACAGACTACGCGTCTTGGGC

AAAGGGCCGTTTCACCATTTCCCGCGACAACTCCAAAAATACCATGTAC

CTCCAGATGAACTCTCTCCGCGCAGAGGACACAGCACGTTATTACTGTG

CACGCAACTGGAATCTGTGGGGTCAAGGTACTCTTGTAACAGTCT

CGAGC
```

Amino acid sequence of Ab-1 HC variable region including signal peptide

```
                                        (SEQ ID NO: 77)
METGLRWLLLVAVLKGVHCEVQLLESGGGLVQPGGSLRLSCAASGFSLSS

YWMNWVRQAPGKGLEWVGTIDSGGRTDYASWAKGRFTISRDNSKNTMYLQ

MNSLRAEDTARYYCARNWNLWGQGTLVTVSS
```

The CDR (complementarity determining region) sequences in the variable region of the heavy chain of Ab-1 are as follows:

```
CDR-H1:    SYWMN (SEQ ID NO: 51)

CDR-H2:    TIDSGGRTDYASWAKG (SEQ ID NO: 52)

CDR-H3:    NWNL (SEQ ID NO: 53)
```

The light chain variable region CDR sequences of Ab-1 are:

```
CDR-L1:    QSSQSVYDNNWLA (SEQ ID NO: 54)

CDR-L2:    DASDLAS (SEQ ID NO: 55)

CDR-L3:    QGAYNDVIYA (SEQ ID NO: 56)
```

Ab-B

Figure 16:
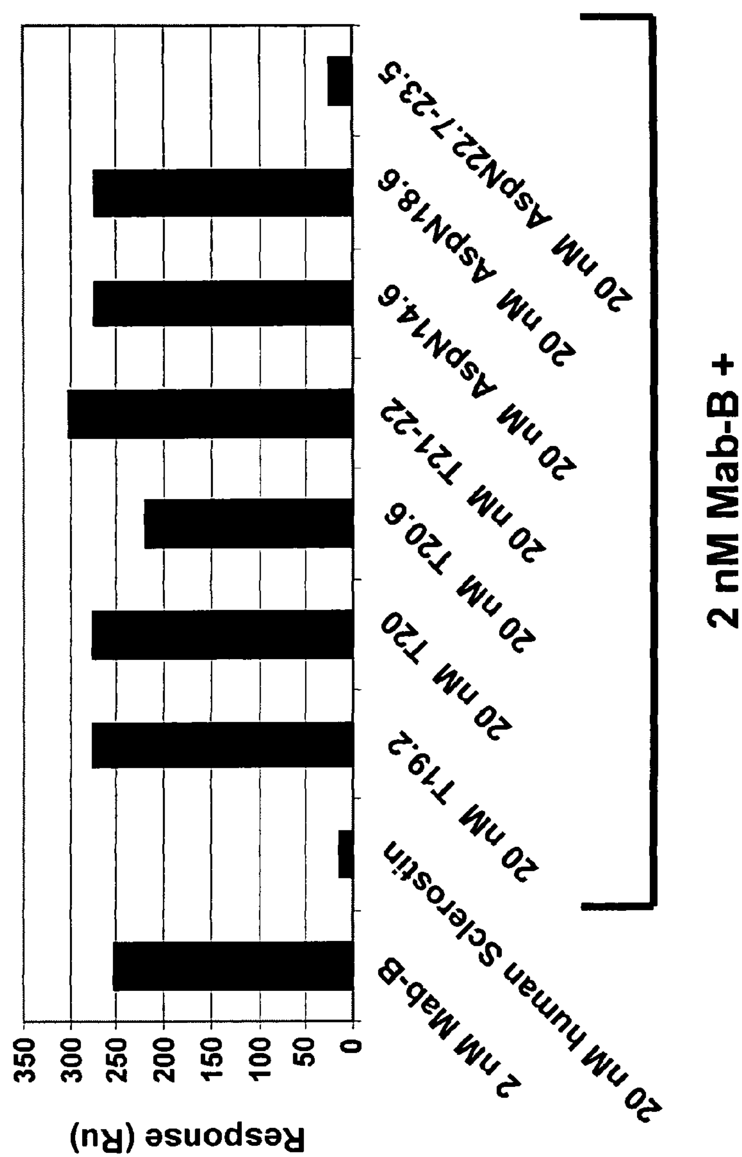
FIG. 16 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-B. Human sclerostin peptides used were T19.2, T20, T20.6, T21-22, AspN14.6, AspN18.6 and AspN22.7-23.5.

Antibody B (also referred to herein as Ab-B and Mab-B) is a mouse antibody which exhibits high affinity binding to sclerostin. The BIAcore binding pattern of Ab-B is shown in FIG. 16.

Ab-B Light Chain

The amino acid sequence of the mature form (signal peptide removed) of the Ab-B LC is:

```
                                        (SEQ ID NO: 31)
  1 QIVLTQSPTI VSASPGEKVT LICSASSSVS FVDWFQQKPG
    TSPKRWIYRT

 51 SNLGFGVPAR FSGGGSGTSH SLTISRMEAE DAATYYCQQR
    STYPPTFGAG
```

-continued

```
101 TKLELKRADA APTVSIFPPS SEQLTSGGAS VVCFLNNFYP
    KDINVKWKID

151
    GSERQNGVLN SWTDQDSKDS TYSMSSTLTL TKDEYERHNS
    YTCEATHKTS

201 TSPIVKSFNR NEC
```

The nucleic acid sequence encoding the mature form (signal peptide removed) of Ab-B LC is:

```
                                        (SEQ ID NO: 32)
  1 CAAATTGTTC TCACCCAGTC TCCAACAATC GTGTCTGCAT
    CTCCAGGGGA

 51 GAAGGTCACC CTAATCTGCA GTGCCAGTTC AAGTGTAAGT
    TTCGTGGACT

101 GGTTCCAGCA GAAGGCAGGC ACTTCTCCCA AACGCTGGAT
    TTACAGAACA

151 TCCAACCTGG GTTTTGGAGT CCCTGCTCGC TTCAGTGGCG
    GTGGATCTGG

201 GACCTCTCAC TCTCTCACAA TCAGCCGAAT GGAGGCTGAA
    GATGCTGCCA

251 CTTATTACTG CCAGCAAAGG AGTACTTACC CACCCACGTT
    CGGTGCTGGG

301 ACCAAGCTGG AACTGAAACG GGCTGATGCT GCACCAACTG
    TATCCATCTT

351 CCCACCATCC AGTGAGCAGT TAACATCTGG AGGTGCCTCA
    GTCGTGTGCT

401 TCTTGAACAA CTTCTACCCC AAAGACATCA ATGTCAAGTG
    GAAGATTGAT

451 GGCAGTGAAC GACAAAATGG CGTCCTGAAC AGTTGGACTG
    ATCAGGACAG

501 CAAAGACAGC ACCTACAGCA TGAGCAGCAC CCTCACGTTG
    ACCAAGGACG

551 AGTATGAACG ACATAACAGC TATACCTGTG AGGCCACTCA
    CAAGAGATCA

601 ACTTCACCCA TTGTCAAGAG CTTCAACAGG AATGAGTGTT
    AG
```

The amino acid sequence of Ab-B LC including signal peptide is:

```
                                        (SEQ ID NO: 33)
  1 MHFQVQIFSF LLISASVIVS RGQIVLTQSP TIVSASPGEK
    VTLICSASSS

 51 VSFVDWFQQK PGTSPKRWIY RTSNLGFGVP ARFSGGGSGT
    SHSLTISRME

101 AEDAATYYCQ QRSTYPPTFG AGTKLELKRA DAAPTVSIFP
    PSSEQLTSGG

151 ASVVCFLNNF YPKDINVKWK IDGSERQNGV LNSWTDQDSK
    DSTYSMSSTL

201 TLTKDEYERH NSYTCEATHK TSTSPIVKSF NRNEC
```

The nucleic acid sequence of Ab-B LC including signal peptide encoding sequence is:

(SEQ ID NO: 34)

```
1   ATGCATTTTC AAGTGCAGAT TTTCAGCTTC CTGCTAATCA
    GTGCCTCAGT

51  CATAGTGTCC AGAGGGCAAA TTGTTCTCAC CCAGTCTCCA
    ACAATCGTGT

101 CTGCATCTCC AGGGGAGAAG GTCACCCTAA TCTGCAGTGC
    CAGTTCAAGT

151 GTAAGTTTCG TGGACTGGTT CCAGCAGAAG CCAGGCACTT
    CTCCCAAACG

201 CTGGATTTAC AGAACATCCA ACCTGGGTTT TGGAGTCCCT
    GCTCGCTTCA

251 GTGGCGGTGG ATCTGGGACC TCTCACTCTC TCACAATCAG
    CCGAATGGAG

301 GCTGAAGATG CTGCCACTTA TTACTGCCAG CAAAGGAGTA
    CTTACCCACC

351 CACGTTCGGT GCTGGGACCA AGCTGGAACT GAAACGGGCT
    GATGCTGCAC

401 CAACTGTATC CATCTTCCCA CCATCCAGTG AGCAGTTAAC
    ATCTGGAGGT

451 GCCTCAGTCG TGTGCTTCTT GAACAACTTC TACCCCAAAG
    ACATCAATGT

501 CAAGTGGAAG ATTGATGGCA GTGAACGACA AAATGGCGTC
    CTGAACAGTT

551 GGACTGATCA GGACAGCAAA GACAGCACCT ACAGCATGAG
    CAGCACCCTC

601 ACGTTGACCA AGGACGAGTA TGAACGACAT AACAGCTATA
    CCTGTGAGGC

651 CACTCACAAG ACATCAACTT CACCCATTGT CAAGAGCTTC
    AACAGGAATG

701 AGTGTTAG
```

Ab-B Heavy Chain

The amino acid sequence of the mature form (signal peptide removed) of Ab-B HC:

(SEQ ID NO: 35)

```
1   QVTLKESGPG ILQPSQTLSL TCSFSGFSLS TSGMGVGWIR
    HPSGKNLEWL

51  AHIWWDDVKR YNPVLKSRLT ISKDTSNSQV FLKIANVDTA
    DTATYYCARI

101 EDFDYDEEYY AMDYWGQGTS VIVSSAKTTP PSVYPLAPGS
    AAQTNSMVTL

151
    GCLVKGYFPE PVTVTWNSGS LSSGVHTFPA VLQSDLYTLS
    SSVTVPSSTW

201
    PSETVTCNVA HPASSTKVDK KIVPRDCGCK PCICTVPEVS
    SVFIFPPKPK

251
    DVLTITLTPK VTCVVVDISK DDPEVQFSWF VDDVEVHTAQ
    TQPREEQFNS
```

-continued

```
301
    TFRSVSELPI MHQDWINGKE FKCRVNSAAF PAPIEKTISK
    TKGRPKAPQV

351
    YTIPPRKEQM AKDKVSLTCM ITDFFPEDIT VEWQWNGQPA
    ENYKNTQPIM

401
    DTDGSYFVYS KLNVQKSNWE AGNTFTCSVL HEGLHNHHTE
    KSLSHSPGK
```

The nucleic acid sequence encoding the mature form (signal peptide removed) of Ab-B HC:

(SEQ ID NO: 36)

```
1   CAGGTTACTC TGAAAGAGTC TGGCCCTGGG ATATTGCAGC
    CCTCCCAGAC

51  CCTCAGTCTG ACTTGTTCTT TCTCTGGGTT TTCACTGAGC
    ACTTCTGGTA

101 TGGGTGTAGG CTGGATTCGT CACCCATCAG GGAAGAATCT
    GGAGTGGCTG

151 GCACACATTT GGTGGGATGA TGTCAAGCGC TATAACCCAG
    TCCTGAAGAG

201 CCGACTGACT ATCTCCAAGG ATACCTCCAA CAGCCAGGTA
    TTCCTCAAGA

251 TCGCCAATGT GGACACTGCA GATACTGCCA CATACTACTG
    TGCTCGAATA

301 GAGGACTTTG ATTACGACGA GGAGTATTAT GCTATGGACT
    ACTGGGGTCA

351 AGGAACCTCA GTCATCGTCT CCTCAGCCAA AACGACACCC
    CCATCTGTCT

401 ATCCACTGGC CCCTGGATCT GCTGCCCAAA CTAACTCCAT
    GGTGACCCTG

451 GGATGCCTGG TCAAGGGCTA TTTCCCTGAG CCAGTGACAG
    TGACCTGGAA

501 CTCTGGATCC CTGTCCAGCG GTGTGCACAC CTTCCCAGCT
    GTCCTGCAGT

551 CTGACCTCTA CACTCTGAGC AGCTCAGTGA CTGTCCCCTC
    CAGCACCTGG

601 CCCAGCGAGA CCGTCACCTG CAACGTTGCC CACCCGGCCA
    GCAGCACCAA

651 GGTGGACAAG AAAATTGTGC CCAGGGATTG TGGTTGTAAG
    CCTTGCATAT

701 GTACAGTCCC AGAAGTATCA TCTGTCTTCA TCTTCCCCCC
    AAAGCCCAAG

751 GATGTGCTCA CCATTACTCT GACTCCTAAG GTCACGTGTG
    TTGTGGTAGA

801 CATCAGCAAG GATGATCCCG AGGTCCAGTT CAGCTGGTTT
    GTAGATGATG

851 TGGAGGTGCA CACAGCTCAG ACGCAACCCC GGGAGGAGCA
    GTTCAACAGC

901 ACTTTCCGCT CAGTCAGTGA ACTTCCCATC ATGCACCAGG
    ACTGGCTCAA
```

-continued

```
 951 TGGCAAGGAG TTCAAATGCA GGGTCAACAG TGCAGCTTTC
     CCTGCCCCCA

1001 TCGAGAAAAC CATCTCCAAA ACCAAAGGCA GACCGAAGGC
     TCCACAGGTG

1051 TACACCATTC CACCTCCCAA GGAGCAGATG GCCAAGGATA
     AAGTCAGTCT

1101 GACCTGCATG ATAACAGACT TCTTCCCTGA AGACATTACT
     GTGGAGTGGC

1151 AGTGGAATGG GCAGCCAGCG GAGAACTACA AGAACACTCA
     GCCCATCATG

1201 GACACAGATG GCTCTTACTT CGTCTACAGC AAGCTCAATG
     TGCAGAAGAG

1251 CAACTGGGAG GCAGGAAATA CTTTCACCTG CTCTGTGTTA
     CATGAGGGCC

1301 TGCACAACCA CCATACTGAG AAGAGCCTCT CCCACTCTCC
     TGGTAAATGA
```

The amino acid sequence of Ab-B HC including signal peptide:

```
                                    (SEQ ID NO: 37)
  1 MGRLTSSFLL LIVPAYVLSQ VTLKESGPGI LQPSQTLSLT
    CSFSGFSLST

 51 SGMGVGWIRH PSGKNLEWLA HIWWDDVKRY NPVLKSRLTI
    SKDTSNSQVF

101 LKIANVDTAD TATYYCARIE DFDYDEEYYA MDYWGQGTSV
    IVSSAKTTPP

151 SVYPLAPGSA AQTNSMVTLG CLVKGYFPEP VTVTWNSGSL
    SSGVHTFPAV

201 LQSDLYTLSS SVTVPSSTWP SETVTCNVAH PASSTKVDKK
    IVPRDCGCKP

251 CICTVPEVSS VFIFPPKPKD VLTITLTPKV TCVVVDISKD
    DPEVQFSWFV

301 DDVEVHTAQT QPREEQFNST FRSVSELPIM HQDWLNGKEF
    KCRVNSAAFP

351 APIEKTISKT KGRPKAPQVY TIPPPKEQMA KDKVSLTCMI
    TDFFPEDITV

401 EWQWNGQPAE NYKNTQPIMD TDGSYFVYSK LNVQKSNWEA
    GNTFTCSVLH

451 EGLHNHHTEK SLSHSPGK
```

The nucleic acid sequence of Ab-B HC including signal peptide encoding sequence:

```
                                    (SEQ ID NO: 38)
   1 ATGGGCAGGC TTACTTCTTC ATTCCTGCTA CTGATTGTCC
     CTGCATATGT

  51 CCTGTCCCAG GTTACTCTGA AAGAGTCTGG CCCTGGGATA
     TTGCAGCCCT

 101 CCCAGACCCT CAGTCTGACT TGTTCTTTCT CTGGGTTTTC
     ACTGAGCACT

 151 TCTGGTATGG GTGTAGGCTG GATTCGTCAC CCATCAGGGA
     AGAATCTGGA

 201 GTGGCTGGCA CACATTTGGT GGGATGATGT CAAGCGCTAT
     AACCCAGTCC
```

-continued

```
 251 TGAAGAGCCG ACTGACTATC TCCAAGGATA CCTCCAACAG
     CCAGGTATTC

 301 CTCAAGATCG CCAATGTGGA CACTGCAGAT ACTGCCACAT
     ACTACTGTGC

 351 TCGAATAGAG GACTTTGATT ACGACGAGGA GTATTATGCT
     ATGGACTACT

 401 GGGGTCAAGG AACCTCAGTC ATCGTCTCCT CAGCCAAAAC
     GACACCCCCA

 451 TCTGTCTATC CACTGGCCCC TGGATCTGCT GCCCAAACTA
     ACTCCATGGT

 501 GACCCTGGGA TGCCTGGTCA AGGGCTATTT CCCTGAGCCA
     GTGACAGTGA

 551 CCTGGAACTC TGGATCCCTG TCCAGCGGTG TGCACACCTT
     CCCAGCTGTC

 601 CTGCAGTCTG ACCTCTACAC TCTGAGCAGC TCAGTGACTG
     TCCCCTCCAG

 651 CACCTGGCCC AGCGAGACCG TCACCTGCAA CGTTGCCCAC
     CCGGCCAGCA

 701 GCACCAAGGT GGACAAGAAA ATTGTGCCCA GGGATTGTGG
     TTGTAAGCCT

 751 TGCATATGTA CAGTCCCAGA AGTATCATCT GTCTTCATCT
     TCCCCCCAAA

 801 GCCCAAGGAT GTGCTCACCA TTACTCTGAC TCCTAAGGTC
     ACGTGTGTTG

 851 TGGTAGACAT CAGCAAGGAT GATCCCGAGG TCCAGTTCAG
     CTGGTTTGTA

 901 GATGATGTGG AGGTGCACAC AGCTCAGACG CAACCCCGGG
     AGGAGCAGTT

 951 CAACAGCACT TTCCGCTCAG TCAGTGAACT TCCCATCATG
     CACCAGGACT

1001 GGCTCAATGG CAAGGAGTTC AAATGCAGGG TCAACAGTGC
     AGCTTTCCCT

1051 GCCCCCATCG AGAAAACCAT CTCCAAAACC AAAGGCAGAC
     CGAAGGCTCC

1101 ACAGGTGTAC ACCATTCCAC CTCCCAAGGA GCAGATGGCC
     AAGGATAAAG

1151 TCAGTCTGAC CTGCATGATA ACAGACTTCT TCCCTGAAGA
     CATTACTGTG

1201 GAGTGGCAGT GGAATGGGCA GCCAGCGGAG AACTACAAGA
     ACACTCAGCC

1251 CATCATGGAC ACAGATGGCT CTTACTTCGT CTACAGCAAG
     CTCAATGTGC

1301 AGAAGAGCAA CTGGGAGGCA GGAAATACTT TCACCTGCTC
     TGTGTTACAT

1351 GAGGGCCTGC ACAACCACCA TACTGAGAAG AGCCTCTCCC
     ACTCTCCTGG

1401 TAAATGA
```

The CDR (complementarity determining region) sequences in the variable region of the heavy chain of Ab-B are as follows:

```
CDR-H1: TSGMGVG (SEQ ID NO: 57)

CDR-H2: HIWWDDVKRYNPVLKS (SEQ ID NO: 58)

CDR-H3: EDFDYDEEYYAMDY (SEQ ID NO: 59)
```

The light chain variable region CDR sequences of Ab-B are:

```
CDR-L1:      SASSSVSFVD (SEQ ID NO: 60)

CDR-L2:      RTSNLGF (SEQ ID NO: 61)

CDR-L3:      QQRSTYPPT (SEQ ID NO: 62)
```

Antibodies disclosed herein bind to regions of human sclerostin which are important for the in vivo activity of the protein. Binding of an antibody to sclerostin can be correlated with increases in, for example, the bone mineral density achieved by use of the antibody in vivo such as described in Examples 5 and 9 (mice) and Example 12 (monkey). Increases in at least one of bone formation, bone mineral content, bone mass, bone quality and bone strength can also be achieved by use of the antibody in vivo such as described in Examples 5 and 9 (mice) and Example 12 (monkey). Since the binding of an antibody to sclerostin is primarily determined by its CDR sequences, an antibody for practicing the invention may be generated with all or some of the disclosed CDR sequences in an appropriate framework, wherein the antibody retains the ability to bind specifically to sclerostin, and can be expected to achieve increases in, for example, bone mineral density. Such antibodies are useful in the treatment of human or animal conditions that are caused by, associated with, or result in at least one of low bone formation, low bone mineral density, low bone mineral content, low bone mass, low bone quality and low bone strength. Methods of constructing and expressing antibodies and fragments thereof comprising CDR's of the present invention are known to those of skill in the art.

The present invention therefore relates in one embodiment to an isolated antibody, including Ab-A, or an antigen binding fragment thereof, which specifically binds to sclerostin and wherein the variable domain of the heavy chain comprises at least one CDR having the sequences given in SEQ ID NO:51 for CDR-H1, SEQ ID NO:52 for CDR-H2 and SEQ ID NO:53 for CDR-H3. The antibody or antigen binding fragment thereof may comprise a heavy chain variable domain in which the CDRs consist of at least one of the peptides of SEQ ID NO:51 for CDR-H1, SEQ ID NO:52 for CDR-H2 and SEQ ID NO:53 for CDR-H3.

When in antibodies of the invention a light chain is present the light chain may be any suitable complementary chain and may in particular be selected from a light chain wherein the variable domain comprises at least one CDR having the sequences given in SEQ ID NO:54 for CDR-L1, SEQ ID NO:55 for CDR-L2 and SEQ ID NO:56 for CDR-L3. The antibody or antigen binding fragment thereof may comprise a light chain variable domain in which the CDRs consist of at least one of the peptides of SEQ ID NO:54 for CDR-L1, SEQ ID NO:55 for CDR-L2 and SEQ ID NO:56 for CDR-L3.

The present invention further relates to an isolated antibody, including Ab-B, or an antigen binding fragment hereof, which specifically binds to sclerostin and wherein the variable domain of the heavy chain comprises at least one CDR having the sequences given in SEQ ID NO:57 for CDR-H1, SEQ ID NO:58 for CDR-H2 and SEQ ID NO:59 for CDR-H3. The antibody or antigen binding fragment thereof may comprise a heavy chain variable domain in which the CDRs consist of at least one of the peptides of SEQ ID NO:57 for CDR-H1, SEQ ID NO:58 for CDR-H2 and SEQ ID NO:59 for CDR-H3.

When in antibodies of the invention a light chain is present the light chain may be any suitable complementary chain and may in particular be selected from a light chain wherein the variable domain comprises at least one CDR having the sequences given in SEQ ID NO:60 for CDR-L1, SEQ ID NO:61 for CDR-L2 and SEQ ID NO:62 for CDR-L3. The antibody or antigen binding fragment thereof may comprise a light chain variable domain in which the CDRs consist of at least one of the peptides of SEQ ID NO:60 for CDR-L1, SEQ ID NO:61 for CDR-L2 and SEQ ID NO:62 for CDR-L3.

The present invention still further relates to an isolated antibody, including Ab-C, or an antigen binding fragment hereof, which specifically binds to sclerostin and wherein the variable domain of the heavy chain comprises at least one CDR having the sequences given in SEQ ID NO:45 for CDR-H1, SEQ ID NO:46 for CDR-H2 and SEQ ID NO:47 for CDR-H3. The antibody or antigen binding fragment thereof may comprise a heavy chain variable domain in which the CDRs consist of at least one of the peptides of SEQ ID NO:45 for CDR-H1, SEQ ID NO:46 for CDR-H2 and SEQ ID NO:47 for CDR-H3.

When in antibodies of the invention a light chain is present the light chain may be any suitable complementary chain and may in particular be selected from a light chain wherein the variable domain comprises at least one CDR having the sequences given in SEQ ID NO:48 for CDR-L1, SEQ ID NO:49 for CDR-L2 and SEQ ID NO:50 for CDR-L3. The antibody or antigen binding fragment thereof may comprise a light chain variable domain in which the CDRs consist of at least one of the peptides of SEQ ID NO:48 for CDR-L1, SEQ ID NO:49 for CDR-L2 and SEQ ID NO:50 for CDR-L3.

The present invention also relates to an isolated antibody, including Ab-D, or an antigen binding fragment hereof, which specifically binds to sclerostin and wherein the variable domain of the heavy chain comprises at least one CDR having the sequences given in SEQ ID NO:39 for CDR-H1, SEQ ID NO:40 for CDR-H2 and SEQ ID NO:41 for CDR-H3. The antibody or antigen binding fragment thereof may comprise a heavy chain variable domain in which the CDRs consist of at least one of the peptides of SEQ ID NO:39 for CDR-H1, SEQ ID NO:40 for CDR-H2 and SEQ ID NO:41 for CDR-H3.

When in antibodies of the invention a light chain is present the light chain may be any suitable complementary chain and may in particular be selected from a light chain wherein the variable domain comprises at least one CDR having the sequences given in SEQ ID NO:42 for CDR-L1, SEQ ID NO:43 for CDR-L2 and SEQ ID NO:44 for CDR-L3. The antibody or antigen binding fragment thereof may comprise a light chain variable domain in which the CDRs consist of at least one of the peptides of SEQ ID NO:42 for CDR-L1, SEQ ID NO:43 for CDR-L2 and SEQ NO:44 for CDR-L3.

Additional anti-sclerostin antibodies are described below. For some of the amino acid sequences the complementarity-determining regions (CDRs) are boxed-shaded and the constant regions are in bold-italics.

Ab-2

The sequences of the Antibody 2 (also referred to as Ab-2) LC and HC are as follows:

Ab-2 Light Chain:

Amino acid sequence of the mature form (signal peptide removed) of the Ab-2 LC:

```
                                        (SEQ ID NO: 117)
1 QIVLSQSPAI LSTSPGEKVT MTCRASSSVY YMHWYQQKPG
  SSPKPWIYAT
```

-continued

```
 51 SNLASGVPVR FSGSGSGTSY SLTITRVEAE DAATYYCQQW
    SSDPLTFGAG

101 TKLELKRADA APTVSIFPPS SEQLTSGGAS VVCFLNNFYP
    KDINVKWKID

151
    GSERQNGVLN SWTDQDSKDS TYSMSSTLTL TKDEYERHNS
    YTCEATHKTS

201 TSPIVKSFNR NEC
```

Nucleic acid sequence encoding the mature form (signal peptide removed) of the Ab-2 LC:

```
                                             (SEQ ID NO: 118)
  1 CAAATTGTTC TCTCCCAGTC TCCAGCAATC CTGTCTACAT
    CTCCAGGGGA

 51 GAAGGTCACA ATGACTTGCA GGGCCAGCTC AAGTGTATAT
    TACATGCACT

101 GGTACCAGCA GAAGCCAGGA TCCTCCCCCA AACCCTGGAT
    TTATGCCACA

151 TCCAACCTGG CTTCTGGAGT CCCTGTTCGC TTCAGTGGCA
    GTGGGTCTGG

201 GACCTCTTAC TCTCTCACAA TCACCAGAGT GGAGGCTGAA
    GATGCTGCCA

251 CTTATTACTG CCAGCAGTGG AGTAGTGACC CACTCACGTT
    CGGTGCTGGG

301 ACCAAGCTGG AGCTGAAACG GGCTGATGCT GCACCAACTG
    TATCCATCTT

351 CCCACCATCC AGTGAGCAGT TAACATCTGG AGGTGCCTCA
    GTCGTGTGCT

401 TCTTGAACAA CTTCTACCCC AAAGACATCA ATGTCAAGTG
    GAAGATTGAT

451 GGCAGTGAAC GACAAAATGG CGTCCTGAAC AGTTGGACTG
    ATCAGGACAG

501 CAAAGACAGC ACCTACAGCA TGAGCAGCAC CCTCACGTTG
    ACCAAGGACG

551 AGTATGAACG ACATAACAGC TATACCTGTG AGGCCACTCA
    CAAGACATCA

601 ACTTCACCCA TTGTCAAGAG CTTCAACAGG AATGAGTGTT
    AG
```

Amino acid sequence of the Ab-2 LC including signal peptide:

```
                                             (SEQ ID NO: 119)
  1 MDFQVQIFSF LLISASVIMS RGQIVLSQSP AILSTSPGEK
    VTMTCRASSS

 51 VYYMHWYQQK PGSSPKPWIY ATSNLASGVP VRFSGSGSGT
    SYSLTITRVE

101 AEDAATYYCQ QWSSDPLTFG AGTKLELKRA DAAPTVSIFP
    PSSEQLTSGG

151 ASVVCFLNNF YPKDINVKWK IDGSERQNGV LNSWTDQDSK
    DSTYSMSSTL

201 TLTKDEYERH NSYTCEATHK TSTSPIVKSF NRNEC
```

Nucleic acid sequence of the Ab-2 LC including signal peptide encoding sequence:

```
                                             (SEQ ID NO: 120)
  1 ATGGATTTTC AAGTGCAGAT TTTCAGCTTC CTGCTAATCA
    GTGCTTCAGT

 51 CATTATGTCC AGGGGACAAA TTGTTCTCTC CCAGTCTCCA
    GCAATCCTGT

101 CTACATCTCC AGGGGAGAAG GTCACAATGA CTTGCAGGGC
    CAGCTCAAGT

151 GTATATTACA TGCACTGGTA CCAGCAGAAG CCAGGATCCT
    CCCCCAAACC

201 CTGGATTTAT GCCACATCCA ACCTGGCTTC TGGAGTCCCT
    GTTCGCTTCA

251 GTGGCAGTGG GTCTGGGACC TCTTACTCTC TCACAATCAC
    CAGAGTGGAG

301 GCTGAAGATG CTGCCACTTA TTACTGCCAG CAGTGGAGTA
    GTGACCCACT

351 CACGTTCGGT GCTGGGACCA AGCTGGAGCT GAAACGGGCT
    GATGCTGCAC

401 CAACTGTATC CATCTTCCCA CCATCCAGTG AGCAGTTAAC
    ATCTGGAGGT

451 GCCTCAGTCG TGTGCTTCTT GAACAACTTC TACCCCAAAG
    ACATCAATGT

501 CAAGTGGAAG ATTGATGGCA GTGAACGACA AAATGGCGTC
    CTGAACAGTT

551 GGACTGATCA GGACAGCAAA GACAGCACCT ACAGCATGAG
    CAGCACCCTC

601 ACGTTGACCA AGGACGAGTA TGAACGACAT AACAGCTATA
    CCTGTGAGGC

651 CACTCACAAG ACATCAACTT CACCCATTGT CAAGAGCTTC
    AACAGGAATG

701 AGTGTTAG
```

Ab-2 Heavy Chain

Amino acid sequence of the mature form (signal peptide removed) of the Ab-2 HC:

```
                                             (SEQ ID NO: 121)
  1 EVQVQQSGPE LVKPGASVKL SCTASGFNIK DYFIHWVKQR
    PEQGLEWIGR

 51 LDPEDGESDY APKFQDKAIM TADTSSNTAY LQLRSLTSED
    TAIYYCERED

101 YDGTYTFFPY WGQGTLVTVS AAKTTPPSVY PLAPGSAAQT
    NSMVTLGCLV

151
    KGYFPEPVTV TWNSGSLSSG VHTFPAVLQS DLYTLSSSVT
    VPSSTWPSET

201
    VTCNVAHPAS STKVDKKIVP RDCGCKPCIC TVPEVSSVFI
    FPPKPKDVLT

251
    ITLTPKVTCV VVDISKDDPE VQFSWFVDDV EVHTAQTQPR
    EEQFNSTFRS

301
    VSELPIMHQD WLNGKEFKCR VNSAAFPAPI EKTISKTKGR
    PKAPQVYTIP
```

-continued

351
*PPKEQMAKDK VSLTCMITDF FPEDITVEWQ WNGQPAENYK NTQPIMDTDG*

401
*SYFIYSKLNV QKSNWEAGNT FTCSVLHEGL HNHHTEKSLS HSPGK*

Nucleic acid sequence encoding the mature form (signal peptide removed) of the Ab-2 HC:

(SEQ ID NO: 122)

```
   1 GAGGTTCAGG TGCAGCAGTC TGGGCCAGAA CTTGTGAAGC CAGGGGCCTC
  51 AGTCAAGTTG TCCTGCACAG CTTCTGGCTT CAACATTAAA GACTACTTTA
 101 TACACTGGGT GAAGCAGAGG CCTGAACAGG GCCTGGAGTG GATTGGAAGG
 151 CTTGATCCTG AGGATGGTGA AAGTGATTAT GCCCCGAAGT TCCAGGACAA
 201 GGCCATTATG ACAGCAGACA CATCATCCAA CACAGCCTAT CTTCAGCTCA
 251 GAAGCCTGAC ATCTGAGGAC ACTGCCATCT ATTATTGTGA GAGAGAGGAC
 301 TACGATGGTA CCTACACCTT TTTTCCTTAC TGGGGCCAAG GGACTCTGGT
 351 CACTGTCTCT GCAGCCAAAA CGACACCCCC ATCTGTCTAT CCACTGGCCC
 401 CTGGATCTGC TGCCCAAACT AACTCCATGG TGACCCTGGG ATGCCTGGTC
 451 AAGGGCTATT TCCCTGAGCC AGTGACAGTG ACCTGGAACT CTGGATCCCT
 501 GTCCAGCGGT GTGCACACCT TCCCAGCTGT CCTGCAGTCT GACCTCTACA
 551 CTCTGAGCAG CTCAGTGACT GTCCCCTCCA GCACCTGGCC CAGCGAGACC
 601 GTCACCTGCA ACGTTGCCCA CCCGGCCAGC AGCACCAAGG TGGACAAGAA
 651 AATTGTGCCC AGGGATTGTG GTTGTAAGCC TTGCATATGT ACAGTCCCAG
 701 AAGTATCATC TGTCTTCATC TTCCCCCCAA AGCCCAAGGA TGTGCTCACC
 751 ATTACTCTGA CTCCTAAGGT CACGTGTGTT GTGGTAGACA TCAGCAAGGA
 801 TGATCCCGAG GTCCAGTTCA GCTGGTTTGT AGATGATGTG GAGGTGCACA
 851 CAGCTCAGAC GCAACCCCGG GAGGAGCAGT TCAACAGCAC TTTCCGCTCA
 901 GTCAGTGAAC TTCCCATCAT GCACCAGGAC TGGCTCAATG GCAAGGAGTT
 951 CAAATGCAGG GTCAACAGTG CAGCTTTCCC TGCCCCCATC GAGAAAACCA
1001 TCTCCAAAAC CAAAGGCAGA CCGAAGGCTC CACAGGTGTA CACCATTCCA
1051 CCTCCCAAGG AGCAGATGGC CAAGGATAAA GTCAGTCTGA CCTGCATGAT
1101 AACAGACTTC TTCCCTGAAG ACATTACTGT GGAGTGGCAG TGGAATGGGC
1151 AGCCAGCGGA GAACTACAAG AACACTCAGC CCATCATGGA CACAGATGGC
1201 TCTTACTTCA TCTACAGCAA GCTCAATGTG CAGAAGAGCA ACTGGGAGGC
1251 AGGAAATACT TTCACCTGCT CTGTGTTACA TGAGGGCCTG CACAACCACC
1301 ATACTGAGAA GAGCCTCTCC CACTCTCCTG GTAAATGA
```

Amino acid sequence of the Ab-2 HC including signal peptide:

(SEQ ID NO: 123)

```
  1 MKCSWVIFFL MAVVTGVNSE VQVQQSGPEL VKPGASVKLS CTASGFNIKD
 51 YFIHWVKQRP EQGLEWIGRL DPEDGESDYA PKFQDKAIMT ADTSSNTAYL
101 QLRSLTSEDT AIYYCEREDY DGTYTFFPYW GQGTLVTVSA AKTTPPSVYP
151 LAPGSAAQTN SMVTLGCLVK GYFPEPVTVT WNSGSLSSGV HTFPAVLQSD
201 LYTLSSSVTV PSSTWPSETV TCNVAHPASS TKVDKKIVPR DCGCKPCICT
251 VPEVSSVFIF PPKPKDVLTI TLTPKVTCVV VDISKDDPEV QFSWFVDDVE
301 VHTAQTQPRE EQFNSTFRSV SELPIMHQDW LNGKEFKCRV NSAAFPAPIE
351 KTISKTKGRP KAPQVYTIPP PKEQMAKDKV SLTCMITDFF PEDITVEWQW
401 NGQPAENYKN TQPIMDTDGS YFIYSKLNVQ KSNWEAGNTF TCSVLHEGLH
451 NHHTEKSLSH SPGK
```

Nucleic acid sequence of the Ab-2 HC including signal peptide encoding sequence:

(SEQ ID NO: 124)

```
  1 ATGAAATGCA GCTGGGTCAT CTTCTTCCTG ATGGCAGTGG TTACAGGGGT
 51 CAATTCAGAG GTTCAGGTGC AGCAGTCTGG GCCAGAACTT GTGAAGCCAG
101 GGGCCTCAGT CAAGTTGTCC TGCACAGCTT CTGGCTTCAA CATTAAAGAC
151 TACTTTATAC ACTGGGTGAA GCAGAGGCCT GAACAGGGCC TGGAGTGGAT
201 TGGAAGGCTT GATCCTGAGG ATGGTGAAAG TGATTATGCC CCGAAGTTCC
251 AGGACAAGGC CATTATGACA GCAGACACAT CATCCAACAC AGCCTATCTT
301 CAGCTCAGAA GCCTGACATC TGAGGACACT GCCATCTATT ATTGTGAGAG
```

-continued

```
351 AGAGGACTAC GATGGTACCT ACACCTTTTT TCCTTACTGG
    GGCCAAGGGA

401 CTCTGGTCAC TGTCTCTGCA GCCAAAACGA CACCCCCATC
    TGTCTATCCA

451 CTGGCCCCTG GATCTGCTGC CCAAACTAAC TCCATGGTGA
    CCCTGGGATG

501 CCTGGTCAAG GGCTATTTCC CTGAGCCAGT GACAGTGACC
    TGGAACTCTG

551 GATCCCTGTC CAGCGGTGTG CACACCTTCC CAGCTGTCCT
    GCAGTCTGAC

601 CTCTACACTC TGAGCAGCTC AGTGACTGTC CCCTCCAGCA
    CCTGGCCCAG

651 CGAGACCGTC ACCTGCAACG TTGCCCACCC GGCCAGCAGC
    ACCAAGGTGG

701 ACAAGAAAAT TGTGCCCAGG GATTGTGGTT GTAAGCCTTG
    CATATGTACA

751 GTCCCAGAAG TATCATCTGT CTTCATCTTC CCCCCAAAGC
    CCAAGGATGT

801 GCTCACCATT ACTCTGACTC CTAAGGTCAC GTGTGTTGTG
    GTAGACATCA

851 GCAAGGATGA TCCCGAGGTC CAGTTCAGCT GGTTTGTAGA
    TGATGTGGAG

901 GTGCACACAG CTCAGACGCA ACCCCGGGAG GAGCAGTTCA
    ACAGCACTTT

951 CCGCTCAGTC AGTGAACTTC CCATCATGCA CCAGGACTGG
    CTCAATGGCA

1001 AGGAGTTCAA ATGCAGGGTC AACAGTGCAG CTTTCCCTGC
     CCCCATCGAG

1051 AAAACCATCT CCAAAACCAA AGGCAGACCG AAGGCTCCAC
     AGGTGTACAC

1101 CATTCCACCT CCCAAGGAGC AGATGGCCAA GGATAAAGTC
     AGTCTGACCT

1151 GCATGATAAC AGACTTCTTC CCTGAAGACA TTACTGTGGA
     GTGGCAGTGG

1201 AATGGGCAGC CAGCGGAGAA CTACAAGAAC ACTCAGCCCA
     TCATGGACAC

1251 AGATGGCTCT TACTTCATCT ACAGCAAGCT CAATGTGCAG
     AAGAGCAACT

1301 GGGAGGCAGG AAATACTTTC ACCTGCTCTG TGTTACATGA
     GGGCCTGCAC

1351 AACCACCATA CTGAGAAGAG CCTCTCCCAC TCTCCTGGTA
     AATGA
```

Ab-3

The sequences of the Antibody 3 (also referred to herein as Ab-3) LC and HC are as follows:

Ab-3 Light Chain

Amino acid sequence of the mature form (signal peptide removed) of the Ab-3 LC:

(SEQ ID NO: 125)

```
1  EIVLTQSPAL MAASPGEKVT ITCSVSSTIS SNHLHWFQQK
   SDTSPKPWIY

51 GTSNLASGVP VRFSGSGSGT SYSLTISSME AEDAATYYCQ
   QWSSYPLTFG
```

-continued

101 AGTKLELR*RA DAAPTVSIFP PSSEQLTSGG ASVVCFLNNF YPKDINVKWK*

151 *IDGSERQNGV LNSWTDQDSK DSTYSMSSTL TLTKDEYERH NSYTCEATHK*

201 *TSTSPIVKSF NRNEC*

Nucleic acid sequence encoding the mature form (signal peptide removed) of the Ab-3 LC:

(SEQ ID NO: 126)

```
1   GAAATTGTGC TCACCCAGTC TCCAGCACTC ATGGCTGCAT
    CTCCGGGGGA

51  GAAGGTCACC ATCACCTGCA GTGTCAGTTC AACTATAAGT
    TCCAACCACT

101 TGCACTGGTT CCAGCAGAAG TCAGACACCT CCCCCAAACC
    CTGGATTTAT

151 GGCACATCCA ACCTGGCTTC TGGAGTCCCT GTTCGCTTCA
    GTGGCAGTGG

201 ATCTGGGACC TCTTATTCTC TCACAATCAG CAGCATGGAG
    GCTGAGGATG

251 CTGCCACTTA TTACTGTCAA CAGTGGAGTA GTTACCCACT
    CACGTTCGGC

301 GCTGGGACCA AGCTGGAGCT GAGACGGGCT GATGCTGCAC
    CAACTGTATC

351 CATCTTCCCA CCATCCAGTG AGCAGTTAAC ATCTGGAGGT
    GCCTCAGTCG

401 TGTGCTTCTT GAACAACTTC TACCCCAAAG ACATCAATGT
    CAAGTGGAAG

451 ATTGATGGCA GTGAACGACA AAATGGCGTC CTGAACAGTT
    GGACTGATCA

501 GGACAGCAAA GACAGCACCT ACAGCATGAG CAGCACCCTC
    ACGTTGACCA

551 AGGACGAGTA TGAACGACAT AACAGCTATA CCTGTGAGGC
    CACTCACAAG

601 ACATCAACTT CACCCATTGT CAAGAGCTTC AACAGGAATG
    AGTGTTAG
```

Amino acid sequence of the Ab-3 LC including signal peptide:

(SEQ ID NO: 127)

```
1   MDFHVQIFSF MLISVTVILS SGEIVLTQSP ALMAASPGEK
    VTITCSVSST

51  ISSNHLHWFQ QKSDTSPKPW IYGTSNLASG VPVRFSGSGS
    GTSYSLTISS

101 MEAEDAATYY CQQWSSYPLT FGAGTKLELR RADAAPTVSI
    FPPSSEQLTS

151 GGASVVCFLN NFYPKDINVK WKIDGSERQN GVLNSWTDQD
    SKDSTYSMSS

201 TLTLTKDEYE RHNSYTCEAT HKTSTSPIVK SFNRNEC
```

Nucleic acid sequence of the Ab-3 LC including signal peptide encoding sequence:

```
                                          (SEQ ID NO: 128)
  1 ATGGATTTTC ATGTGCAGAT TTTCAGCTTC ATGCTAATCA
    GTGTCACAGT

 51 CATTTTGTCC AGTGGAGAAA TTGTGCTCAC CCAGTCTCCA
    GCACTCATGG

101 CTGCATCTCC GGGGGAGAAG GTCACCATCA CCTGCAGTGT
    CAGTTCAACT

151 ATAAGTTCCA ACCACTTGCA CTGGTTCCAG CAGAAGTCAG
    ACACCTCCCC

201 CAAACCCTGG ATTTATGGCA CATCCAACCT GGCTTCTGGA
    GTCCCTGTTC

251 GCTTCAGTGG CAGTGGATCT GGGACCTCTT ATTCTCTCAC
    AATCAGCAGC

301 ATGGAGGCTG AGGATGCTGC CACTTATTAC TGTCAACAGT
    GGAGTAGTTA

351 CCCACTCACG TTCGGCGCTG GGACCAAGCT GGAGCTGAGA
    CGGGCTGATG

401 CTGCACCAAC TGTATCCATC TTCCCACCAT CCAGTGAGCA
    GTTAACATCT

451 GGAGGTGCCT CAGTCGTGTG CTTCTTGAAC AACTTCTACC
    CCAAAGACAT

501 CAATGTCAAG TGGAAGATTG ATGGCAGTGA ACGACAAAAT
    GGCGTCCTGA

551 ACAGTTGGAC TGATCAGGAC AGCAAAGACA GCACCTACAG
    CATGAGCAGC

601 ACCCTCACGT TGACCAAGGA CGAGTATGAA CGACATAACA
    GCTATACCTG

651 TGAGGCCACT CACAAGACAT CAACTTCACC CATTGTCAAG
    AGCTTCAACA

701 GGAATGAGTG TTAG
```

Ab-3 Heavy Chain

Amino acid sequence of the mature form (signal peptide removed) of the Ab-3 HC:

```
                                          (SEQ ID NO: 129)
  1 EVQLQQSGAE LVRPGALVKL SCTASDFNIK DFYLHWMRQR
    PEQGLDWIGR

 51 IDPENGDTLY DPKFQDKATL TTDTSSNTAY LQLSGLTSET
    TAVYYCSREA

101 DYFHDGTSYW YFDVWGAGTT ITVSSAKTTP PSVYPLAPGS
    AAQTNSMVTL

151 GCLVKGYFPE PVTVTWNSGS LSSGVHTFPA VLQSDLYTLS
    SSVTVPSSTW

201 PSETVTCNVA HPASSTKVDK KIVPRDCGCK PCICTVPEVS
    SVFIFPPKPK

251 DVLTITLTPK VTCVVVDISK DDPEVQFSWF VDDVEVHTAQ
    TQPREEQFNS

301 TFRSVSELPI MHQDWLNGKE FKCRVNSAAF PAPIEKTISK
    TKGRPKAPQV

351 YTIPPPKEQM AKDKVSLTCM ITDFFPEDIT VEWQWNGQPA
    ENYKNTQPIM
```

-continued

```
401 DTDGSYFIYS KLNVQKSNWE AGNTFTCSVL HEGLHNHHTE
    KSLSHSPGK
```

Nucleic acid sequence encoding the mature form (signal peptide removed) of the Ab-3 HC:

```
                                           (SEQ ID NO: 130)
   1 GAGGTTCAGC TGCAGCAGTC TGGGGCTGAA CTTGTGAGGC
     CAGGGGCCTT

  51 AGTCAAGTTG TCCTGCACAG CTTCTGACTT CAACATTAAA
     GACTTCTATC

 101 TACACTGGAT GAGGCAGCGG CCTGAACAGG GCCTGGACTG
     GATTGGAAGG

 151 ATTGATCCTG AGAATGGTGA TACTTTATAT GACCCGAAGT
     TCCAGGACAA

 201 GGCCACTCTT ACAACAGACA CATCCTCCAA CACAGCCTAC
     CTGCAGCTCA

 251 GCGGCCTGAC ATCTGAGACC ACTGCCGTCT ATTACTGTTC
     TAGAGAGGCG

 301 GATTATTTCC ACGATGGTAC CTCCTACTGG TACTTCGATG
     TCTGGGGCGC

 351 AGGGACCACA ATCACCGTCT CCTCAGCCAA AACGACACCC
     CCATCTGTCT

 401 ATCCACTGGC CCCTGGATCT GCTGCCCAAA CTAACTCCAT
     GGTGACCCTG

 451 GGATGCCTGG TCAAGGGCTA TTTCCCTGAG CCAGTGACAG
     TGACCTGGAA

 501 CTCTGGATCC CTGTCCAGCG GTGTGCACAC CTTCCCAGCT
     GTCCTGCAGT

 551 CTGACCTCTA CACTCTGAGC AGCTCAGTGA CTGTCCCCTC
     CAGCACCTGG

 601 CCCAGCGAGA CCGTCACCTG CAACGTTGCC CACCCGGCCA
     GCAGCACCAA

 651 GGTGGACAAG AAAATTGTGC CCAGGGATTG TGGTTGTAAG
     CCTTGCATAT

 701 GTACAGTCCC AGAAGTATCA TCTGTCTTCA TCTTCCCCCC
     AAAGCCCAAG

 751 GATGTGCTCA CCATTACTCT GACTCCTAAG GTCACGTGTG
     TTGTGGTAGA

 801 CATCAGCAAG GATGATCCCG AGGTCCAGTT CAGCTGGTTT
     GTAGATGATG

 851 TGGAGGTGCA CACAGCTCAG ACGCAACCCC GGGAGGAGCA
     GTTCAACAGC

 901 ACTTTCCGCT CAGTCAGTGA ACTTCCCATC ATGCACCAGG
     ACTGGCTCAA

 951 TGGCAAGGAG TTCAAATGCA GGGTCAACAG TGCAGCTTTC
     CCTGCCCCCA

1001 TCGAGAAAAC CATCTCCAAA ACCAAAGGCA GACCGAAGGC
     TCCACAGGTG

1051 TACACCATTC CACCTCCCAA GGAGCAGATG GCCAAGGATA
     AAGTCAGTCT

1101 GACCTGCATG ATAACAGACT TCTTCCCTGA AGACATTACT
     GTGGAGTGGC

1151 AGTGGAATGG GCAGCCAGCG GAGAACTACA AGAACACTCA
     GCCCATCATG
```

-continued

```
1201 GACACAGATG GCTCTTACTT CATCTACAGC AAGCTCAATG
     TGCAGAAGAG

1251 CAACTGGGAG GCAGGAAATA CTTTCACCTG CTCTGTGTTA
     CATGAGGGCC

1301 TGCACAACCA CCATACTGAG AAGAGCCTCT CCCACTCTCC
     TGGTAAATGA
```

Amino acid sequence of the Ab-3 HC including signal peptide:

```
                                          (SEQ ID NO: 131)
   1 MKCSWVIFFL MAVVTGVNSE VQLQQSGAEL VRPGALVKLS
     CTASDFNIKD

  51 FYLHWMRQRP EQGLDWIGRI DPENGDTLYD PKFQDKATLT
     TDTSSNTAYL

 101 QLSGLTSETT AVYYCSREAD YFHDGTSYWY FDVWGAGTTI
     TVSSAKTTPP

 151 SVYPLAPGSA AQTNSMVTLG CLVKGYFPEP VTVTWNSGSL
     SSGVHTFPAV

 201 LQSDLYTLSS SVTVPSSTWP SETVTCNVAH PASSTKVDKK
     IVPRDCGCKP

 251 CICTVPEVSS VFIFPPKPKD VLTITLTPKV TCVVVDISKD
     DPEVQFSWFV

 301 DDVEVHTAQT QPREEQFNST FRSVSELPIM HQDWLNGKEF
     KCRVNSAAFP

 351 APIEKTISKT KGRPKAPQVY TIPPPKEQMA KDKVSLTCMI
     TDFFPEDITV

 401 EWQWNGQPAE NYKNTQPIMD TDGSYFIYSK LNVQKSNWEA
     GNTFTCSVLH

 451 EGLHNHHTEK SLSHSPGK
```

Nucleic acid sequence of the Ab-3 HC including signal peptide encoding sequence:

```
                                          (SEQ ID NO: 132)
   1 ATGAAATGCA GCTGGGTCAT CTTCTTCCTG ATGGCAGTGG
     TTACAGGGGT

  51 CAATTCAGAG GTTCAGCTGC AGCAGTCTGG GGCTGAACTT
     GTGAGGCCAG

 101 GGGCCTTAGT CAAGTTGTCC TGCACAGCTT CTGACTTCAA
     CATTAAAGAC

 151 TTCTATCTAC ACTGGATGAG GCAGCGGCCT GAACAGGGCC
     TGGACTGGAT

 201 TGGAAGGATT GATCCTGAGA ATGGTGATAC TTTATATGAC
     CCGAAGTTCC

 251 AGGACAAGGC CACTCTTACA ACAGACACAT CCTCCAACAC
     AGCCTACCTG

 301 CAGCTCAGCG GCCTGACATC TGAGACCACT GCCGTCTATT
     ACTGTTCTAG

 351 AGAGGCGGAT TATTTCCACG ATGGTACCTC CTACTGGTAC
     TTCGATGTCT

 401 GGGGCGCAGG GACCACAATC ACCGTCTCCT CAGCCAAAAC
     GACACCCCCA

 451 TCTGTCTATC CACTGGCCCC TGGATCTGCT GCCCAAACTA
     ACTCCATGGT
```

-continued

```
 501 GACCCTGGGA TGCCTGGTCA AGGGCTATTT CCCTGAGCCA
     GTGACAGTGA

 551 CCTGGAACTC TGGATCCCTG TCCAGCGGTG TGCACACCTT
     CCCAGCTGTC

 601 CTGCAGTCTG ACCTCTACAC TCTGAGCAGC TCAGTGACTG
     TCCCCTCCAG

 651 CACCTGGCCC AGCGAGACCG TCACCTGCAA CGTTGCCCAC
     CCGGCCAGCA

 701 GCACCAAGGT GGACAAGAAA ATTGTGCCCA GGGATTGTGG
     TTGTAAGCCT

 751 TGCATATGTA CAGTCCCAGA AGTATCATCT GTCTTCATCT
     TCCCCCCAAA

 801 GCCCAAGGAT GTGCTCACCA TTACTCTGAC TCCTAAGGTC
     ACGTGTGTTG

 851 TGGTAGACAT CAGCAAGGAT GATCCCGAGG TCCAGTTCAG
     CTGGTTTGTA

 901 GATGATGTGG AGGTGCACAC AGCTCAGACG CAACCCCGGG
     AGGAGCAGTT

 951 CAACAGCACT TTCCGCTCAG TCAGTGAACT TCCCATCATG
     CACCAGGACT

1001 GGCTCAATGG CAAGGAGTTC AAATGCAGGG TCAACAGTGC
     AGCTTTCCCT

1051 GCCCCCATCG AGAAAACCAT CTCCAAAACC AAAGGCAGAC
     CGAAGGCTCC

1101 ACAGGTGTAC ACCATTCCAC CTCCCAAGGA GCAGATGGCC
     AAGGATAAAG

1151 TCAGTCTGAC CTGCATGATA ACAGACTTCT TCCCTGAAGA
     CATTACTGTG

1201 GAGTGGCAGT GGAATGGGCA GCCAGCGGAG AACTACAAGA
     ACACTCAGCC

1251 CATCATGGAC ACAGATGGCT CTTACTTCAT CTACAGCAAG
     CTCAATGTGC

1301 AGAAGAGCAA CTGGGAGGCA GGAAATACTT TCACCTGCTC
     TGTGTTACAT

1351 GAGGGCCTGC ACAACCACCA TACTGAGAAG AGCCTCTCCC
     ACTCTCCTGG

1401 TAAATGA
```

Ab-4

The sequences of the Antibody 4 (also referred to herein as Ab-4) LC and HC are as follows:

Ab-4 Light Chain:

Amino acid sequence of the mature form (signal peptide removed) of the Ab-4 LC:

```
                                          (SEQ ID NO: 133)
   1 DIQMTQITSS LSASLGDRVS ISCRASQDIS NYLNWYQQKP
     DGTFKLLIFY

  51 TSRLLSGVPS RFSGSGSGTD YSLTIYNLEQ EDFATYFCQQ
     GDTLPYTFGG
```

-continued

```
101 GTKLEIK***RAD AAPTVSIFPP SSEQLTSGGA SVVCFLNNFY
    PKDINVKWKI***

151
    ***DGSERQNGVL NSWTDQDSKD STYSMSSTLT LTKDEYERHN
    SYTCEATHKT***

201 ***STSPIVKSFN RNEC***
```

Nucleic acid sequence encoding the mature form (signal peptide removed) of the Ab-4 LC:

```
                                       (SEQ ID NO: 134)
  1  GATATCCAGA TGACACAGAT TACATCCTCC CTGTCTGCCT
     CTCTGGGAGA

 51  CAGGGTCTCC ATCAGTTGCA GGGCAAGTCA AGACATTAGC
     AATTATTTAA

101  ACTGGTATCA GCAGAAACCA GATGGAACTT TTAAACTCCT
     TATCTTCTAC

151  ACATCAAGAT TACTCTCAGG AGTCCCATCA AGGTTCAGTG
     GCAGTGGGTC

201  TGGAACAGAT TATTCTCTCA CCATTTACAA CCTGGAGCAA
     GAAGATTTTG

251  CCACTTACTT TTGCCAACAG GGAGATACGC TTCCGTACAC
     TTTCGGAGGG

301  GGGACCAAGC TGGAAATAAA ACGGGCTGAT GCTGCACCAA
     CTGTATCCAT

351  CTTCCCACCA TCCAGTGAGC AGTTAACATC TGGAGGTGCC
     TCAGTCGTGT

401  GCTTCTTGAA CAACTTCTAC CCCAAAGACA TCAATGTCAA
     GTGGAAGATT

451  GATGGCAGTG AACGACAAAA TGGCGTCCTG AACAGTTGGA
     CTGATCAGGA

501  CAGCAAAGAC AGCACCTACA GCATGAGCAG CACCCTCACG
     TTGACCAAGG

551  ACGAGTATGA ACGACATAAC AGCTATACCT GTGAGGCCAC
     TCACAAGACA

601  TCAACTTCAC CCATTGTCAA GAGCTTCAAC AGGAATGAGT
     GTTAG
```

Amino acid sequence of the Ab-4 LC including signal peptide:

```
                                       (SEQ ID NO: 135)
  1  MMSSAQFLGL LLLCFQGTRC DIQMTQITSS LSASLGDRVS
     ISCRASQDIS

 51  NYLNWYQQKP DGTFKLLIFY TSRLLSGVPS RFSGSGSGTD
     YSLTIYNLEQ

101  EDFATYFCQQ GDTLPYTFGG GTKLEIKRAD AAPTVSIFPP
     SSEQLTSGGA

151  SVVCFLNNFY PKDINVKWKI DGSERQNGVL NSWTDQDSKD
     STYSMSSTLT

201  LTKDEYERHN SYTCEATHKT STSPIVKSFN RNEC
```

Nucleic acid sequence of the Ab-4 LC including signal peptide encoding sequence:

```
                                       (SEQ ID NO: 136)
  1  ATGATGTCCT CTGCTCAGTT CCTTGGTCTC CTGTTGCTCT
     GTTTTCAAGG

 51  TACCAGATGT GATATCCAGA TGACACAGAT TACATCCTCC
     CTGTCTGCCT

101  CTCTGGGAGA CAGGGTCTCC ATCAGTTGCA GGGCAAGTCA
     AGACATTAGC

151  AATTATTTAA ACTGGTATCA GCAGAAACCA GATGGAACTT
     TTAAACTCCT

201  TATCTTCTAC ACATCAAGAT TACTCTCAGG AGTCCCATCA
     AGGTTCAGTG

251  GCAGTGGGTC TGGAACAGAT TATTCTCTCA CCATTTACAA
     CCTGGAGCAA

301  GAAGATTTTG CCACTTACTT TTGCCAACAG GGAGATACGC
     TTCCGTACAC

351  TTTCGGAGGG GGGACCAAGC TGGAAATAAA ACGGGCTGAT
     GCTGCACCAA

401  CTGTATCCAT CTTCCCACCA TCCAGTGAGC AGTTAACATC
     TGGAGGTGCC

451  TCAGTCGTGT GCTTCTTGAA CAACTTCTAC CCCAAAGACA
     TCAATGTCAA

501  GTGGAAGATT GATGGCAGTG AACGACAAAA TGGCGTCCTG
     AACAGTTGGA

551  CTGATCAGGA CAGCAAAGAC AGCACCTACA GCATGAGCAG
     CACCCTCACG

601  TTGACCAAGG ACGAGTATGA ACGACATAAC AGCTATACCT
     GTGAGGCCAC

651  TCACAAGACA TCAACTTCAC CCATTGTCAA GAGCTTCAAC
     AGGAATGAGT

701  GTTAG
```

Ab-4 Heavy Chain:

Amino acid sequence of the mature form (signal peptide removed) of the Ab-4 HC:

```
                                       (SEQ ID NO: 137)
  1  EVQLQQSGPE LMKPGASVKM SCKASGYTFT DYNMHWVKQN
     QGKTLEWIGE

 51  INPNSGGAGY NQKFKGKATL TVDKSSTTAY MELRSLTSED
     SAVYYCARLG

101  YDDIYDDWYF DVWGAGTTVT VSS***AKTTPPS VYPLAPGSAA
     QTNSMVTLGC***

151
     ***LVKGYFPEPV TVTWNSGSLS SGVHTFPAVL QSDLYTLSSS
     VTVPSSTWPS***

201
     ***ETVTCNVAHP ASSTKVDKKI VPRDCGCKPC ICTVPEVSSV
     FIFPPKPKDV***

251
     ***LTITLTPKVT CVVVDISKDD PEVQFSWFVD DVEVHTAQTQ
     PREEQFNSTF***

301
     ***RSVSELPIMH QDWLNGKEFK CRVNSAAFPA PIEKTISKTK
     GRPKAPQVYT***
```

-continued

351
*IPPPKEQMAK DKVSLTCMIT DFFPEDITVE WQWNGQPAEN YKNTQPIMDT*

401
*DGSYFIYSKL NVQKSNWEAG NTFTCSVLHE GLHNHHTEKS LSHSPGK*

Nucleic acid sequence encoding the mature form (signal peptide removed) of the Ab-4 HC:

(SEQ ID NO: 138)

```
   1 GAGGTCCAAC TGCAACAGTC TGGACCTGAA CTAATGAAGC
     CTGGGGCTTC

  51 AGTGAAGATG TCCTGCAAGG CTTCTGGATA TACATTCACT
     GACTACAACA

 101 TGCACTGGGT GAAGCAGAAC CAAGGAAAGA CCCTAGAGTG
     GATAGGAGAA

 151 ATTAATCCTA ACAGTGGTGG TGCTGGCTAC AACCAGAAGT
     TCAAGGGCAA

 201 GGCCACATTG ACTGTAGACA AGTCCTCCAC CACAGCCTAC
     ATGGAGCTCC

 251 GCAGCCTGAC ATCTGAGGAC TCTGCAGTCT ATTACTGTGC
     AAGATTGGGC

 301 TACGATGATA TCTACGACGA CTGGTACTTC GATGTCTGGG
     GCGCAGGGAC

 351 CACGGTCACC GTCTCCTCAG CCAAAACGAC ACCCCCATCT
     GTCTATCCAC

 401 TGGCCCCTGG ATCTGCTGCC CAAACTAACT CCATGGTGAC
     CCTGGGATGC

 451 CTGGTCAAGG GCTATTTCCC TGAGCCAGTG ACAGTGACCT
     GGAACTCTGG

 501 ATCCCTGTCC AGCGGTGTGC ACACCTTCCC AGCTGTCCTG
     CAGTCTGACC

 551 TCTACACTCT GAGCAGCTCA GTGACTGTCC CCTCCAGCAC
     CTGGCCCAGC

 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA
     ATGA
```

Amino acid sequence of the Ab-4 HC including signal peptide:

(SEQ ID NO: 139)

```
  1 MGWSWTFLFL LSGTAGVLSE VQLQQSGPEL MKPGASVKMS
    CKASGYTFTD

 51 YNMHWVKQNQ GKTLEWIGEI NPNSGGAGYN QKFKGKATLT
    VDKSSTTAYM

101 ELRSLTSEDS AVYYCARLGY DDIYDDWYFD VWGAGTTVTV
    SSAKTTPPSV

151 YPLAPGSAAQ TNSMVTLGCL VKGYFPEPVT VTWNSGSLSS
    GVHTFPAVLQ

201 SDLYTLSSSV TVPSSTWPSE TVTCNVAHPA SSTKVDKKIV
    PRDCGCKPCI

251 CTVPEVSSVF IFPPKPKDVL TITLTPKVTC VVVDISKDDP
    EVQFSWFVDD

301 VEVHTAQTQP REEQFNSTFR SVSELPIMHQ DWLNGKEFKC
    RVNSAAFPAP

351 IEKTISKTKG RPKAPQVYTI PPPKEQMAKD KVSLTCMITD
    FFPEDITVEW

401 QWNGQPAENY KNTQPIMDTD GSYFIYSKLN VQKSNWEAGN
    TFTCSVLHEG

451 LHNHHTEKSL SHSPGK
```

Nucleic acid sequence of the Ab-4 HC including signal peptide encoding sequence:

(SEQ ID NO: 140)

```
  1 ATGGGATGGA GCTGGACCTT TCTCTTCCTC CTGTCAGGAA
    CTGCAGGTGT

 51 CCTCTCTGAG GTCCAACTGC AACAGTCTGG ACCTGAACTA
    ATGAAGCCTG

101 GGGCTTCAGT GAAGATGTCC TGCAAGGCTT CTGGATATAC
    ATTCACTGAC

151 TACAACATGC ACTGGGTGAA GCAGAACCAA GGAAAGACCC
    TAGAGTGGAT

201 AGGAGAAATT AATCCTAACA GTGGTGGTGC TGGCTACAAC
    CAGAAGTTCA

251 AGGGCAAGGC CACATTGACT GTAGACAAGT CCTCCACCAC
    AGCCTACATG

301 GAGCTCCGCA GCCTGACATC TGAGGACTCT GCAGTCTATT
    ACTGTGCAAG

351 ATTGGGCTAC GATGATATCT ACGACGACTG GTACTTCGAT
    GTCTGGGGCG
```

-continued

```
401  CAGGGACCAC GGTCACCGTC TCCTCAGCCA AAACGACACC
     CCCATCTGTC

451  TATCCACTGG CCCCTGGATC TGCTGCCCAA ACTAACTCCA
     TGGTGACCCT

501  GGGATGCCTG GTCAAGGGCT ATTTCCCTGA GCCAGTGACA
     GTGACCTGGA

551  ACTCTGGATC CCTGTCCAGC GGTGTGCACA CCTTCCCAGC
     TGTCCTGCAG

601  TCTGACCTCT ACACTCTGAG CAGCTCAGTG ACTGTCCCCT
     CCAGCACCTG

651  GCCCAGCGAG ACCGTCACCT GCAACGTTGC CCACCCGGCC
     AGCAGCACCA

701  AGGTGGACAA GAAAATTGTG CCCAGGGATT GTGGTTGTAA
     GCCTTGCATA

751  TGTACAGTCC CAGAAGTATC ATCTGTCTTC ATCTTCCCCC
     CAAAGCCCAA

801  GGATGTGCTC ACCATTACTC TGACTCCTAA GGTCACGTGT
     GTTGTGGTAG

851  ACATCAGCAA GGATGATCCC GAGGTCCAGT TCAGCTGGTT
     TGTAGATGAT

901  GTGGAGGTGC ACACAGCTCA GACGCAACCC CGGGAGGAGC
     AGTTCAACAG

951  CACTTTCCGC TCAGTCAGTG AACTTCCCAT CATGCACCAG
     GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG

1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAATG

1401 A
```

Ab-4 was humanized to generate Ab-5.

Ab-5

The sequences of the Antibody 5 (also referred to herein as Ab-5) LC and HC are as follows:

Ab-5 Light Chain:

Amino acid sequence of the mature form (signal peptide removed) of the Ab-5 LC:

```
                                   (SEQ ID NO: 141)
 1  DIQMTQSPSS LSASVGDRVT ITCRASQDIS NYLNWYQQKP
    GKAPKLLIYY

51  TSRLLSGVPS RFSGSGSGTD FTLTISSLQP EDFATYYCQQ
    GDTLPYTFGG
```

-continued

```
101  GTKVEIKRTV AAPSVFIFPP SDEQLKSGTA SVVCLLNNFY
     PREAKVQWKV

151
    DNALQSGNSQ ESVTEQDSKD STYSLSSTLT LSKADYEKHK
    VYACEVTHQG

201  LSSPVTKSFN RGEC
```

Nucleic acid sequence encoding the mature form (signal peptide removed) of the Ab-5 LC:

```
                                    (SEQ ID NO: 142)
  1  GACATCCAGA TGACCCAGTC TCCATCCTCC CTCTCCGCAT
     CCGTAGGCGA

 51  CCGCGTAACC ATAACATGTA GAGCATCTCA AGATATTTCC
     AACTATTTGA

101  ATTGGTACCA ACAAAAACCC GGCAAAGCAC CTAAACTCCT
     CATTTACTAT

151  ACATCAAGAC TCCTCTCCGG CGTTCCATCA CGATTCTCAG
     GCTCCGGCTC

201  CGGCACAGAT TTCACACTCA CTATTTCCTC CCTCCAACCA
     GAAGATTTTG

251  CAACCTATTA CTGTCAACAA GGCGATACAC TCCCATACAC
     ATTCGGCGGC

301  GGCACAAAAG TTGAAATTAA ACGTACGGTG GCTGCACCAT
     CTGTCTTCAT

351  CTTCCCGCCA TCTGATGAGC AGTTGAAATC TGGAACTGCC
     TCTGTTGTGT

401  GCCTGCTGAA TAACTTCTAT CCCAGAGAGG CCAAAGTACA
     GTGGAAGGTG

451  GATAACGCCC TCCAATCGGG TAACTCCCAG GAGAGTGTCA
     CAGAGCAGGA

501  CAGCAAGGAC AGCACCTACA GCCTCAGCAG CACCCTGACG
     CTGAGCAAAG

551  CAGACTACGA GAAACACAAA GTCTACGCCT GCGAAGTCAC
     CCATCAGGGC

601  CTGAGCTCGC CCGTCACAAA GAGCTTCAAC AGGGGAGAGT
     GT
```

Amino acid sequence of the Ab-5 LC including signal peptide:

```
                                    (SEQ ID NO: 143)
  1  MDMRVPAQLL GLLLLWLRGA RCDIQMTQSP SSLSASVGDR
     VTITCRASQD

 51  ISNYLNWYQQ KPGKAPKLLI YYTSRLLSGV PSRFSGSGSG
     TDFTLTISSL

101  QPEDFATYYC QQGDTLPYTF GGGTKVEIKR TVAAPSVFIF
     PPSDEQLKSG

151  TASVVCLLNN FYPREAKVQW KVDNALQSGN SQESVTEQDS
     KDSTYSLSST

201  LTLSKADYEK HKVYACEVTH QGLSSPVTKS FNRGEC
```

Nucleic acid sequence of the Ab-5 LC including signal peptide encoding sequence:

```
                                    (SEQ ID NO: 144)
  1  ATGGACATGA GGGTCCCCGC TCAGCTCCTG GGGCTCCTGC
     TACTCTGGCT

 51  CCGAGGTGCC AGATGTGACA TCCAGATGAC CCAGTCTCCA
     TCCTCCCTCT

101  CCGCATCCGT AGGCGACCGC GTAACCATAA CATGTAGAGC
     ATCTCAAGAT

151  ATTTCCAACT ATTTGAATTG GTACCAACAA AAACCCGGCA
     AAGCACCTAA

201  ACTCCTCATT TACTATACAT CAAGACTCCT CTCCGGCGTT
     CCATCACGAT

251  TCTCAGGCTC CGGCTCCGGC ACAGATTTCA CACTCACTAT
     TTCCTCCCTC

301  CAACCAGAAG ATTTTGCAAC CTATTACTGT CAACAAGGCG
     ATACACTCCC

351  ATACACATTC GGCGGCGGCA CAAAAGTTGA AATTAAACGT
     ACGGTGGCTG

401  CACCATCTGT CTTCATCTTC CCGCCATCTG ATGAGCAGTT
     GAAATCTGGA

451  ACTGCCTCTG TTGTGTGCCT GCTGAATAAC TTCTATCCCA
     GAGAGGCCAA

501  AGTACAGTGG AAGGTGGATA ACGCCCTCCA ATCGGGTAAC
     TCCCAGGAGA

551  GTGTCACAGA GCAGGACAGC AAGGACAGCA CCTACAGCCT
     CAGCAGCACC

601  CTGACGCTGA GCAAAGCAGA CTACGAGAAA CACAAAGTCT
     ACGCCTGCGA

651  AGTCACCCAT CAGGGCCTGA GCTCGCCCGT CACAAAGAGC
     TTCAACAGGG

701  GAGAGTGT
```

Ab-5 Heavy Chain:

Amino acid sequence of the mature form (signal peptide removed) of the Ab-5 HC:

```
                                    (SEQ ID NO: 145)
  1  EVQLVQSGAE VKKPGASVKV SCKASGYTFT DYNMHWVRQA
     PGQGLEWMGE

 51  INPNSGGAGY NQKFKGRVTM TTDTSTSTAY MELRSLRSDD
     TAVYYCARLG

101  YDDIYDDWYF DVWGQGTTVT VSSASTKGPS VFPLAPCSRS
     TSESTAALGC

151
     LVKDYFPEPV TVSWNSGALT SGVHTFPAVL QSSGLYSLSS
     VVTVPSSNFG

201
     TQTYTCNVDH KPSNTKVDKT VERKCCVECP PCPAPPVAGP
     SVFLFPPKPK

251
     DTLMISRTPE VTCVVVDVSH EDPEVQFNWY VDGVEVHNAK
     TKPREEQFNS
```

-continued

```
301
     TFRVVSVLTV VHQDWLNGKE YKCKVSNKGL PAPIEKTISK
     TKGQPREPQV

351
     YTLPPSREEM TKNQVSLTCL VKGFYPSDIA VEWESNGQPE
     NNYKTTPPML

401
     DSDGSFFLYS KLTVDKSRWQ QGNVFSCSVM HEALHNHYTQ
     KSLSLSPGK
```

Amino acid sequence of the mature form (signal peptide removed) of the Ab-5 HC without carboxy-terminal lysine:

```
                                    (SEQ ID NO: 392)
  1  EVQLVQSGAE VKKPGASVKV SCKASGYTFT DYNMHWVRQA
     PGQGLEWMGE

 51  INPNSGGAGY NQKFKGRVTM TTDTSTSTAY MELRSLRSDD
     TAVYYCARLG

101  YDDIYDDWYF DVWGQGTTVT VSSASTKGPS VFPLAPCSRS
     TSESTAALGC

151
     LVKDYFPEPV TVSWNSGALT SGVHTFPAVL QSSGLYSLSS
     VVTVPSSNFG

201
     TQTYTCNVDH KPSNTKVDKT VERKCCVECP PCPAPPVAGP
     SVFLFPPKPK

251
     DTLMISRTPE VTCVVVDVSH EDPEVQFNWY VDGVEVHNAK
     TKPREEQFNS

301
     TFRVVSVLTV VHQDWLNGKE YKCKVSNKGL PAPIEKTISK
     TKGQPREPQV

351
     YTLPPSREEM TKNQVSLTCL VKGFYPSDLA VEWESNGQPE
     NNYKTTPPML

401
     DSDGSFFLYS KLTVDKSRWQ QGNVFSCSVM HEALHNHYTQ
     KSLSLSPG
```

Nucleic acid sequence encoding the mature form (signal peptide removed) of the Ab-5 HC:

```
                                    (SEQ ID NO: 146)
  1  GAGGTGCAGC TGGTGCAGAG CGGCGCCGAG GTAAAAAAAC
     CAGGAGCAAG

 51  CGTTAAAGTT TCTTGTAAAG CAAGCGGATA TACATTTACA
     GATTACAACA

101  TGCATTGGGT AAGACAAGCG CCAGGACAAG GATTGGAATG
     GATGGGCGAA

151  ATTAACCCTA ATAGTGGAGG AGCAGGCTAC AATCAAAAAT
     TCAAAGGGAG

201  AGTTACAATG ACAACAGACA CAAGCACTTC AACAGCATAT
     ATGGAACTGC

251  GATCACTTAG AAGCGACGAT ACAGCTGTAT ACTATTGCGC
     ACGACTTGGG

301  TATGATGATA TATATGATGA CTGGTATTTC GATGTTTGGG
     GCCAGGGAAC
```

-continued

```
351 AACAGTTACC GTCTCTAGTG CCTCCACCAA GGGCCCATCG
    GTCTTCCCCC

401 TGGCGCCCTG CTCCAGGAGC ACCTCCGAGA GCACAGCGGC
    CCTGGGCTGC

451 CTGGTCAAGG ACTACTTCCC CGAACCGGTG ACGGTGTCGT
    GGAACTCAGG

501 CGCTCTGACC AGCGGCGTGC ACACCTTCCC AGCTGTCCTA
    CAGTCCTCAG

551 GACTCTACTC CCTCAGCAGC GTGGTGACCG TGCCCTCCAG
    CAACTTCGGC

601 ACCCAGACCT ACACCTGCAA CGTAGATCAC AAGCCCAGCA
    ACACCAAGGT

651 GGACAAGACA GTTGAGCGCA AATGTTGTGT CGAGTGCCCA
    CCGTGCCCAG

701 CACCACCTGT GGCAGGACCG TCAGTCTTCC TCTTCCCCCC
    AAAACCCAAG

751 GACACCCTCA TGATCTCCCG GACCCCTGAG GTCACGTGCG
    TGGTGGTGGA

801 CGTGAGCCAC GAAGACCCCG AGGTCCAGTT CAACTGGTAC
    GTGGACGGCG

851 TGGAGGTGCA TAATGCCAAG ACAAAGCCAC GGGAGGAGCA
    GTTCAACAGC

901 ACGTTCCGTG TGGTCAGCGT CCTCACCGTT GTGCACCAGG
    ACTGGCTGAA

951 CGGCAAGGAG TACAAGTGCA AGGTCTCCAA CAAAGGCCTC
    CCAGCCCCCA

1001 TCGAGAAAAC CATCTCCAAA ACCAAAGGGC AGCCCCGAGA
     ACCACAGGTG

1051 TACACCCTGC CCCCATCCCG GGAGGAGATG ACCAAGAACC
     AGGTCAGCCT

1101 GACCTGCCTG GTCAAAGGCT TCTACCCCAG CGACATCGCC
     GTGGAGTGGG

1151 AGAGCAATGG GCAGCCGGAG AACAACTACA AGACCACACC
     TCCCATGCTG

1201 GACTCCGACG GCTCCTTCTT CCTCTACAGC AAGCTCACCG
     TGGACAAGAG

1251 CAGGTGGCAG CAGGGGAACG TCTTCTCATG CTCCGTGATG
     CATGAGGCTC

1301 TGCACAACCA CTACACGCAG AAGAGCCTCT CCCTGTCTCC
     GGGTAAA
```

Amino acid sequence of the Ab-5 HC including signal peptide:

```
                                        (SEQ ID NO: 147)
  1 MDWTWRILFL VAAATGAHSE VQLVQSGAEV KKPGASVKVS
    CKASGYTFTD

 51 YNMHWVRQAP GQGLEWMGEI NPNSGGAGYN QKFKGRVTMT
    TDTSTSTAYM

101 ELRSLRSDDT AVYYCARLGY DDIYDDWYFD VWGQGTTVTV
    SSASTKGPSV

151 FPLAPCSRST SESTAALGCL VKDYFPEPVT VSWNSGALTS
    GVHTFPAVLQ

201 SSGLYSLSSV VTVPSSNFGT QTYTCNVDHK PSNTKVDKTV
    ERKCCVECPP
```

-continued

```
251 CPAPPVAGPS VFLFPPKPKD TLMISRTPEV TCVVVDVSHE
    DPEVQFNWYV

301 DGVEVHNAKT KPREEQFNST FRVVSVLTVV HQDWLNGKEY
    KCKVSNKGLP

351 APIEKTISKT KGQPREPQVY TLPPSREEMT KNQVSLTCLV
    KGFYPSDIAV

401 EWESNGQPEN NYKTTPPMLD SDGSFFLYSK LTVDKSRWQQ
    GNVFSCSVMH

451 EALHNHYTQK SLSLSPGK
```

Nucleic acid sequence of the Ab-5 HC including signal peptide encoding sequence:

```
                                        (SEQ ID NO: 148)
  1 ATGGACTGGA CCTGGAGGAT CCTCTTCTTG GTGGCAGCAG
    CCACAGGAGC

 51 CCACTCCGAG GTGCAGCTGG TGCAGAGCGG CGCCGAGGTA
    AAAAAACCAG

101 GAGCAAGCGT TAAAGTTTCT TGTAAAGCAA GCGGATATAC
    ATTTACAGAT

151 TACAACATGC ATTGGGTAAG ACAAGCGCCA GGACAAGGAT
    TGGAATGGAT

201 GGGCGAAATT AACCCTAATA GTGGAGGAGC AGGCTACAAT
    CAAAAATTCA

251 AAGGGAGAGT TACAATGACA ACAGACACAA GCACTTCAAC
    AGCATATATG

301 GAACTGCGAT CACTTAGAAG CGACGATACA GCTGTATACT
    ATTGCGCACG

351 ACTTGGGTAT GATGATATAT ATGATGACTG GTATTTCGAT
    GTTTGGGGCC

401 AGGGAACAAC AGTTACCGTC TCTAGTGCCT CCACCAAGGG
    CCCATCGGTC

451 TTCCCCCTGG CGCCCTGCTC CAGGAGCACC TCCGAGAGCA
    CAGCGGCCCT

501 GGGCTGCCTG GTCAAGGACT ACTTCCCCGA ACCGGTGACG
    GTGTCGTGGA

551 ACTCAGGCGC TCTGACCAGC GGCGTGCACA CCTTCCCAGC
    TGTCCTACAG

601 TCCTCAGGAC TCTACTCCCT CAGCAGCGTG GTGACCGTGC
    CCTCCAGCAA

651 CTTCGGCACC CAGACCTACA CCTGCAACGT AGATCACAAG
    CCCAGCAACA

701 CCAAGGTGGA CAAGACAGTT GAGCGCAAAT GTTGTGTCGA
    GTGCCCACCG

751 TGCCCAGCAC CACCTGTGGC AGGACCGTCA GTCTTCCTCT
    TCCCCCCAAA

801 ACCCAAGGAC ACCCTCATGA TCTCCCGGAC CCCTGAGGTC
    ACGTGCGTGG

851 TGGTGGACGT GAGCCACGAA GACCCCGAGG TCCAGTTCAA
    CTGGTACGTG

901 GACGGCGTGG AGGTGCATAA TGCCAAGACA AAGCCACGGG
    AGGAGCAGTT

951 CAACAGCACG TTCCGTGTGG TCAGCGTCCT CACCGTTGTG
    CACCAGGACT
```

-continued

```
1001 GGCTGAACGG CAAGGAGTAC AAGTGCAAGG TCTCCAACAA
     AGGCCTCCCA

1051 GCCCCCATCG AGAAAACCAT CTCCAAAACC AAAGGGCAGC
     CCCGAGAACC

1101 ACAGGTGTAC ACCCTGCCCC CATCCCGGGA GGAGATGACC
     AAGAACCAGG

1151 TCAGCCTGAC CTGCCTGGTC AAAGGCTTCT ACCCCAGCGA
     CATCGCCGTG

1201 GAGTGGGAGA GCAATGGGCA GCCGGAGAAC AACTACAAGA
     CCACACCTCC

1251 CATGCTGGAC TCCGACGGCT CCTTCTTCCT CTACAGCAAG
     CTCACCGTGG

1301 ACAAGAGCAG GTGGCAGCAG GGGAACGTCT TCTCATGCTC
     CGTGATGCAT

1351 GAGGCTCTGC ACAACCACTA CACGCAGAAG AGCCTCTCCC
     TGTCTCCGGG

1401 TAAA
```

Ab-5 Variable domains:

Ab-5 light chain variable domain amino acid sequence (without signal sequence):

```
                                    (SEQ ID NO: 376)
  1 DIQMTQSPSS LSASVGDRVT ITCRASQDIS NYLNWYQQKP
    GKAPKLLIYY

 51 TSRLLSGVPS RFSGSGSGTD FTLTISSLQP EDFATYYCQQ
    GDTLPYTFGG

101 GTKVEIK
```

Ab-5 light chain variable domain DNA sequence (without signal sequence):

```
                                    (SEQ ID NO: 377)
  1 GACATCCAGA TGACCCAGTC TCCATCCTCC CTCTCCGCAT
    CCGTAGGCGA

 51 CCGCGTAACC ATAACATGTA GAGCATCTCA AGATATTTCC
    AACTATTTGA

101 ATTGGTACCA ACAAAAACCC GGCAAAGCAC CTAAACTCCT
    CATTTACTAT

151 ACATCAAGAC TCCTCTCCGG CGTTCCATCA CGATTCTCAG
    GCTCCGGCTC

201 CGGCACAGAT TTCACACTCA CTATTTCCTC CCTCCAACCA
    GAAGATTTTG

251 CAACCTATTA CTGTCAACAA GGCGATACAC TCCCATACAC
    ATTCGGCGGC

301 GGCACAAAAG TTGAAATTAA A
```

Ab-5 heavy chain variable domain amino acid sequence (without signal sequence):

```
                                    (SEQ ID NO: 378)
  1 EVQLVQSGAE VKKPGASVKV SCKASGYTFT DYNMHWVRQA
    PGQGLEWMGE

 51 INPNSGGAGY NQKFKGRVTM TTDTSTSTAY MELRSLRSDD
    TAVYYCARLG

101 YDDIYDDWYF DVWGQGTTVT VSS
```

Ab-5 heavy chain variable domain DNA sequence (without signal sequence):

```
                                    (SEQ ID NO: 379)
  1 GAGGTGCAGC TGGTGCAGAG CGGCGCCGAG GTAAAAAAAC
    CAGGAGCAAG

 51 CGTTAAAGTT TCTTGTAAAG CAAGCGGATA TACATTTACA
    GATTACAACA

101 TGCATTGGGT AAGACAAGCG CCAGGACAAG GATTGGAATG
    GATGGGCGAA

151 ATTAACCCTA ATAGTGGAGG AGCAGGCTAC AATCAAAAAT
    TCAAAGGGAG

201 AGTTACAATG ACAACAGACA CAAGCACTTC AACAGCATAT
    ATGGAACTGC

251 GATCACTTAG AAGCGACGAT ACAGCTGTAT ACTATTGCGC
    ACGACTTGGG

301 TATGATGATA TATATGATGA CTGGTATTTC GATGTTTGGG
    GCCAGGGAAC

351 AACAGTTACC GTCTCTAGT
```

The CDR (complementarity determining region) sequences in the variable region of the heavy chain of Ab-5 are as follows:

```
CDR-H1:  DYNMH (SEQ ID NO: 245)

CDR-H2:  EINPNSGGAGYNQKFKG (SEQ ID NO: 246)

CDR-H3:  LGYDDIYDDWYFDV (SEQ ID NO: 247)
```

The light chain variable region CDR sequences of Ab-5 are:

```
CDR-L1:  RASQDISNYLN (SEQ ID NO: 78)

CDR-L2:  YTSRLLS (SEQ ID NO: 79)

CDR-L3:  QQGDTLPYT (SEQ ID NO: 80)
```

Ab-6

The sequences of the Antibody 6 (also referred to herein as Ab-6) LC and HC are as follows:

Ab-6 Light Chain:

Amino acid sequence of the mature form (signal peptide removed) of the Ab-6 LC:

```
                                    (SEQ ID NO: 149)
  1 DIQMTQTTSS LSASLGDRVT ISCRASQDIS NYLNWFQQKP
    DGTLKLLIFY

 51 TSRLHSGVPS RFSGSGSGTD YSLTISNLEQ EDIATYFCQQ
    GDTLPYTFGG

101 GTKLEIRRAD AAPTVSIFPP SSEQLTSGGA SVVCFLNNFY
    PKDINVKWKI

151 DGSERQNGVL NSWTDQDSKD STYSMSSTLT LTKDEYERHN
    SYTCEATHKT

201 STSPIVKSFN RNEC
```

Nucleic acid sequence encoding the mature form (signal peptide removed) of the Ab-6 LC:

```
                                        (SEQ ID NO: 150)
  1 GATATCCAGA TGACACAGAC TACATCCTCC CTGTCTGCCT
    CTCTGGGAGA

 51 CAGAGTCACC ATCAGTTGCA GGGCAAGTCA GGACATTAGC
    AATTATTTAA

101 ACTGGTTTCA GCAGAAACCA GATGGAACTC TTAAACTCCT
    GATCTTCTAC

151 ACATCAAGAT TACACTCAGG AGTTCCATCA AGGTTCAGTG
    GCAGTGGGTC

201 TGGAACAGAT TATTCTCTCA CCATTAGCAA CCTGGAGCAA
    GAAGATATTG

251 CCACTTACTT TTGCCAACAG GGTGATACGC TTCCGTACAC
    GTTCGGGGGG

301 GGGACCAAGC TGGAAATAAG ACGGGCTGAT GCTGCACCAA
    CTGTATCCAT

351 CTTCCCACCA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT

451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT
    GTTAG
```

Amino acid sequence of the Ab-6 LC including signal peptide:

```
                                        (SEQ ID NO: 151)
  1 MMSSAQFLGL LLLCFQGTRC DIQMTQTTSS LSASLGDRVT
    ISCRASQDIS

 51 NYLNWFQQKP DGTLKLLIFY TSRLHSGVPS RFSGSGSGTD
    YSLTISNLEQ

101 EDIATYFCQQ GDTLPYTFGG GTKLEIRRAD AAPTVSIFPP
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-6 LC including signal peptide encoding sequence:

```
                                        (SEQ ID NO: 152)
  1 ATGATGTCCT CTGCTCAGTT CCTTGGTCTC CTGTTGCTCT
    GTTTTCAAGG

 51 TACCAGATGT GATATCCAGA TGACACAGAC TACATCCTCC
    CTGTCTGCCT

101 CTCTGGGAGA CAGAGTCACC ATCAGTTGCA GGGCAAGTCA
    GGACATTAGC

151 AATTATTTAA ACTGGTTTCA GCAGAAACCA GATGGAACTC
    TTAAACTCCT
```

-continued

```
201 GATCTTCTAC ACATCAAGAT TACACTCAGG AGTTCCATCA
    AGGTTCAGTG

251 GCAGTGGGTC TGGAACAGAT TATTCTCTCA CCATTAGCAA
    CCTGGAGCAA

301 GAAGATATTG CCACTTACTT TTGCCAACAG GGTGATACGC
    TTCCGTACAC

351 GTTCGGGGGG GGGACCAAGC TGGAAATAAG ACGGGCTGAT
    GCTGCACCAA

401 CTGTATCCAT CTTCCCACCA TCCAGTGAGC AGTTAACATC
    TGGAGGTGCC

451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG

601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GTTAG
```

Ab-6 Heavy Chain:

Amino acid sequence of the mature form (signal peptide removed) of the Ab-6 HC:

```
                                        (SEQ ID NO: 153)
  1 EVQLQQSGPE LMKPGASVKM SCKASGYTFT DYNMHWVKQN
    QGKSLEWIGE

 51 INPNSGGSGY NQKFKGKATL TVDKSSSTAY MELRSLTSED
    SAVYYCARLV

101 YDGSYEDWYF DVWGAGTTVT VSSAKTTPPS VYPLAPGSAA
    QTNSMVTLGC

151 LVKGYFPEPV TVTWNSGSLS SGVHTFPAVL QSDLYTLSSS
    VTVPSSTWPS

201 ETVTCNVAHP ASSTKVDKKI VPRDCGCKPC ICTVPEVSSV
    FIFPPKPKDV

251 LTITLTPKVT CVVVDISKDD PEVQFSWFVD DVEVHTAQTQ
    PREEQFNSTF

301 RSVSELPIMH QDWLNGKEFK CRVNSAAFPA PIEKTISKTK
    GRPKAPQVYT

351 IPPPKEQMAK DKVSLTCMIT DFFPEDITVE WQWNGQPAEN
    YKNTQPIMDT

401 DGSYFIYSKL NVQKSNWEAG NTFTCSVLHE GLHNHHTEKS
    LSHSPGK
```

Nucleic acid sequence encoding the mature form (signal peptide removed) of the Ab-6 HC:

```
                                        (SEQ ID NO: 154)
  1 GAGGTCCAGC TGCAACAGTC TGGACCTGAA CTAATGAAGC
    CTGGGGCTTC

 51 AGTGAAGATG TCCTGCAAGG CTTCTGGATA CACATTCACT
    GACTACAACA
```

-continued

```
 101 TGCACTGGGT GAAACAGAAC CAAGGAAAGA GCCTAGAGTG
     GATAGGAGAA

 151 ATTAATCCTA ACAGTGGTGG TAGTGGCTAC AACCAAAAGT
     TCAAAGGCAA

 201 GGCCACATTG ACTGTAGACA AGTCTTCCAG CACAGCCTAC
     ATGGAGCTCC

 251 GCAGCCTGAC ATCTGAGGAC TCTGCAGTCT ATTACTGTGC
     AAGATTGGTC

 301 TACGATGGCA GCTACGAGGA CTGGTACTTC GATGTCTGGG
     GCGCAGGGAC

 351 CACGGTCACC GTCTCCTCAG CCAAAACGAC ACCCCCATCT
     GTCTATCCAC

 401 TGGCCCCTGG ATCTGCTGCC CAAACTAACT CCATGGTGAC
     CCTGGGATGC

 451 CTGGTCAAGG GCTATTTCCC TGAGCCAGTG ACAGTGACCT
     GGAACTCTGG

 501 ATCCCTGTCC AGCGGTGTGC ACACCTTCCC AGCTGTCCTG
     CAGTCTGACC

 551 TCTACACTCT GAGCAGCTCA GTGACTGTCC CCTCCAGCAC
     CTGGCCCAGC

 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA
     ATGA
```

Amino acid sequence of the Ab-6 HC including signal peptide:

```
                                      (SEQ ID NO: 155)
  1 MGWSWTFLFL LSGTAGVLSE VQLQQSGPEL MKPGASVKMS
    CKASGYTFTD

 51 YNMHWVKQNQ GKSLEWIGEI NPNSGGSGYN QKFKGKATLT
    VDKSSSTAYM

101 ELRSLTSEDS AVYYCARLVY DGSYEDWYFD VWGAGTTVTV
    SSAKTTPPSV

151 YPLAPGSAAQ TNSMVTLGCL VKGYFPEPVT VTWNSGSLSS
    GVHTFPAVLQ

201 SDLYTLSSSV TVPSSTWPSE TVTCNVAHPA SSTKVDKKIV
    PRDCGCKPCI

251 CTVPEVSSVF IFPPKPKDVL TITLTPKVTC VVVDISKDDP
    EVQFSWFVDD

301 VEVHTAQTQP REEQFNSTFR SVSELPIMHQ DWLNGKEFKC
    RVNSAAFPAP

351 IEKTISKTKG RPKAPQVYTI PPPKEQMAKD KVSLTCMITD
    FFPEDITVEW

401 QWNGQPAENY KNTQPIMDTD GSYFIYSKLN VQKSNWEAGN
    TFTCSVLHEG

451 LHNHHTEKSL SHSPGK
```

Nucleic acid sequence of the Ab-6 HC including signal peptide encoding sequence:

```
                                      (SEQ ID NO: 156)
  1 ATGGGATGGA GCTGGACCTT TCTCTTCCTC CTGTCAGGAA
    CTGCAGGTGT

 51 CCTCTCTGAG GTCCAGCTGC AACAGTCTGG ACCTGAACTA
    ATGAAGCCTG

101 GGGCTTCAGT GAAGATGTCC TGCAAGGCTT CTGGATACAC
    ATTCACTGAC

151 TACAACATGC ACTGGGTGAA ACAGAACCAA GGAAAGAGCC
    TAGAGTGGAT

201 AGGAGAAATT AATCCTAACA GTGGTGGTAG TGGCTACAAC
    CAAAAGTTCA

251 AAGGCAAGGC CACATTGACT GTAGACAAGT CTTCCAGCAC
    AGCCTACATG

301 GAGCTCCGCA GCCTGACATC TGAGGACTCT GCAGTCTATT
    ACTGTGCAAG

351 ATTGGTCTAC GATGGCAGCT ACGAGGACTG GTACTTCGAT
    GTCTGGGGCG

401 CAGGGACCAC GGTCACCGTC TCCTCAGCCA AAACGACACC
    CCCATCTGTC

451 TATCCACTGG CCCCTGGATC TGCTGCCCAA ACTAACTCCA
    TGGTGACCCT

501 GGGATGCCTG GTCAAGGGCT ATTTCCCTGA GCCAGTGACA
    GTGACCTGGA

551 ACTCTGGATC CCTGTCCAGC GGTGTGCACA CCTTCCCAGC
    TGTCCTGCAG

601 TCTGACCTCT ACACTCTGAG CAGCTCAGTG ACTGTCCCCT
    CCAGCACCTG

651 GCCCAGCGAG ACCGTCACCT GCAACGTTGC CCACCCGGCC
    AGCAGCACCA
```

-continued

```
 701 AGGTGGACAA GAAAATTGTG CCCAGGGATT GTGGTTGTAA
     GCCTTGCATA

 751 TGTACAGTCC CAGAAGTATC ATCTGTCTTC ATCTTCCCCC
     CAAAGCCCAA

 801 GGATGTGCTC ACCATTACTC TGACTCCTAA GGTCACGTGT
     GTTGTGGTAG

 851 ACATCAGCAA GGATGATCCC GAGGTCCAGT TCAGCTGGTT
     TGTAGATGAT

 901 GTGGAGGTGC ACACAGCTCA GACGCAACCC CGGGAGGAGC
     AGTTCAACAG

 951 CACTTTCCGC TCAGTCAGTG AACTTCCCAT CATGCACCAG
     GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG

1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAATG

1401 A
```

Ab-7

The sequences of the Antibody 7 (also referred to herein as Ab-7) LC and HC are as follows:

Ab-7 Light Chain:

Amino acid sequence of the mature form (signal peptide removed) of the Ab-7 LC:

(SEQ ID NO: 157)

1 DIQMTQTTSS LSASLGDRVT ICCRASQVIT NYLYWYQQKP DGTFKLLIYY

51 TSRLHSGVPS RFSGSGSGTD YSLTISNLEQ EDIATYFCQQ GDTLPYTFGG

101 GTKLEIK*RAD AAPTVSIFPP SSEQLTSGGA SVVCFLNNFY PKDINVKWKI*

151 *DGSERQNGVL NSWTDQDSKD STYSMSSTLT LTKDEYERHN SYTCEATHKT*

201 *STSPIVKSFN RNEC*

Nucleic acid sequence encoding the mature form (signal peptide removed) of the Ab-7 LC:

```
                                     (SEQ ID NO: 158)
  1 GATATCCAGA TGACACAGAC TACATCCTCC CTGTCTGCCT
    CTCTGGGAGA
```

-continued

```
 51 CAGAGTCACC ATCTGTTGCA GGGCAAGTCA GGTCATTACC
    AATTATTTAT

101 ACTGGTATCA GCAGAAACCA GATGGAACTT TTAAACTCCT
    GATCTACTAC

151 ACATCAAGAT TACACTCAGG AGTCCCATCA AGGTTCAGTG
    GCAGTGGGTC

201 TGGAACAGAT TATTCTCTCA CCATTAGCAA CCTGGAACAG
    GAAGATATTG

251 CCACTTACTT TTGCCAACAG GGTGATACGC TTCCGTACAC
    GTTCGGAGGG

301 GGGACCAAGC TGGAAATAAA ACGGGCTGAT GCTGCACCAA
    CTGTATCCAT

351 CTTCCCACCA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT

451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT GT
```

Amino acid sequence of the Ab-7 LC including signal peptide:

```
                                     (SEQ ID NO: 159)
  1 MMSSAQFLGL LLLCFQGTRC DIQMTQTTSS LSASLGDRVT
    ICCRASQVIT

 51 NYLYWYQQKP DGTFKLLIYY TSRLHSGVPS RFSGSGSGTD
    YSLTISNLEQ

101 EDIATYFCQQ GDTLPYTFGG GTKLEIKRAD AAPTVSIFPP
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-7 LC including signal peptide encoding sequence:

```
                                     (SEQ ID NO: 160)
  1 ATGATGTCCT CTGCTCAGTT CCTTGGTCTC CTGTTGCTCT
    GTTTTCAAGG

 51 TACCAGATGT GATATCCAGA TGACACAGAC TACATCCTCC
    CTGTCTGCCT

101 CTCTGGGAGA CAGAGTCACC ATCTGTTGCA GGGCAAGTCA
    GGTCATTACC

151 AATTATTTAT ACTGGTATCA GCAGAAACCA GATGGAACTT
    TTAAACTCCT

201 GATCTACTAC ACATCAAGAT TACACTCAGG AGTCCCATCA
    AGGTTCAGTG
```

-continued

```
251 GCAGTGGGTC TGGAACAGAT TATTCTCTCA CCATTAGCAA
    CCTGGAACAG

301 GAAGATATTG CCACTTACTT TTGCCAACAG GGTGATACGC
    TTCCGTACAC

351 GTTCGGAGGG GGGACCAAGC TGGAAATAAA ACGGGCTGAT
    GCTGCACCAA

401 CTGTATCCAT CTTCCCACCA TCCAGTGAGC AGTTAACATC
    TGGAGGTGCC

451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG

601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GT
```

Ab-7 Heavy Chain:

Amino acid sequence of the mature form (signal peptide removed) of the Ab-7 HC:

(SEQ ID NO: 161)

1 EVQLQQSGPE LMKPGASVKM SCKASGYTFT DYNMHWMKQN QGKSLEWIGE

51 INPNSGGAGY NQQFKGKATL TVDKSSRTAY MELRSLTSED SAVYYCARLG

101 YVGNYEDWYF DVWGAGTTVT VSS*AKTTPPS VYPLAPGSAA QTNSMVTLGC*

151 *LVKGYFPEPV TVTWNSGSLS SGVHTFPAVL QSDLYTLSSS VTVPSSTWPS*

201 *ETVTCNVAHP ASSTKVDKKI VPRDCGCKPC ICTVPEVSSV FIFPPKPKDV*

251 *LTITLTPKVT CVVVDISKDD PEVQFSWFVD DVEVHTAQTQ PREEQFNSTF*

301 *RSVSELPIMH QDWLNGKEFK CRVNSAAFPA PIEKTISKTK GRPKAPQVYT*

351 *IPPPKEQMAK DKVSLTCMIT DFFPEDITVE WQWNGQPAEN YKNTQPIMDT*

401 *DGSYFIYSKL NVQKSNWEAG NTFTCSVLHE GLHNHHTEKS LSHSPGK*

Nucleic acid sequence encoding the mature form (signal peptide removed) of the Ab-7 HC:

(SEQ ID NO: 162)

```
   1 GAGGTCCAGC TGCAACAGTC TGGACCTGAA CTAATGAAGC
     CTGGGGCTTC

  51 AGTGAAGATG TCCTGCAAGG CTTCTGGATA CACATTCACT
     GACTACAACA

 101 TGCACTGGAT GAAGCAGAAC CAAGGAAAGA GCCTAGAATG
     GATAGGAGAA

 151 ATTAATCCTA ACAGTGGTGG TGCTGGCTAC AACCAGCAGT
     TCAAAGGCAA

 201 GGCCACATTG ACTGTAGACA AGTCCTCCAG GACAGCCTAC
     ATGGAGCTCC

 251 GCAGCCTGAC ATCTGAGGAC TCTGCAGTCT ATTACTGTGC
     AAGATTGGGC

 301 TACGTTGGTA ATTACGAGGA CTGGTACTTC GATGTCTGGG
     GCGCAGGGAC

 351 CACGGTCACC GTCTCCTCAG CCAAAACGAC ACCCCCATCT
     GTCTATCCAC

 401 TGGCCCCTGG ATCTGCTGCC CAAACTAACT CCATGGTGAC
     CCTGGGATGC

 451 CTGGTCAAGG GCTATTTCCC TGAGCCAGTG ACAGTGACCT
     GGAACTCTGG

 501 ATCCCTGTCC AGCGGTGTGC ACACCTTCCC AGCTGTCCTG
     CAGTCTGACC

 551 TCTACACTCT GAGCAGCTCA GTGACTGTCC CCTCCAGCAC
     CTGGCCCAGC

 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA A
```

Amino acid sequence of the Ab-7 HC including signal peptide:

(SEQ ID NO: 163)

1 MGWSWTFLFL LSGTAGVLSE VQLQQSGPEL MKPGASVKMS CKASGYTFTD

51 YNMHWMKQNQ GKSLEWIGEI NPNSGGAGYN QQFKGKATLT VDKSSRTAYM

-continued

```
101 ELRSLTSEDS AVYYCARLGY VGNYEDWYFD VWGAGTTVTV
    SSAKTTPPSV

151 YPLAPGSAAQ TNSMVTLGCL VKGYFPEPVT VTWNSGSLSS
    GVHTFPAVLQ

201 SDLYTLSSSV TVPSSTWPSE TVTCNVAHPA SSTKVDKKIV
    PRDCGCKPCI

251 CTVPEVSSVF IFPPKPKDVL TITLTPKVTC VVVDISKDDP
    EVQFSWFVDD

301 VEVHTAQTQP REEQFNSTFR SVSELPIMHQ DWLNGKEFKC
    RVNSAAFPAP

351 IEKTISKTKG RPKAPQVYTI PPPKEQMAKD KVSLTCMITD
    FFPEDITVEW

401 QWNGQPAENY KNTQPIMDTD GSYFIYSKLN VQKSNWEAGN
    TFTCSVLHEG

451 LHNHHTEKSL SHSPGK
```

Nucleic acid sequence of the Ab-7 HC including signal peptide encoding sequence:

```
                                        (SEQ ID NO: 164)
   1 ATGGGATGGA GCTGGACCTT TCTCTTCCTC CTGTCAGGAA
     CTGCAGGTGT

  51 CCTCTCTGAG GTCCAGCTGC AACAGTCTGG ACCTGAACTA
     ATGAAGCCTG

 101 GGGCTTCAGT GAAGATGTCC TGCAAGGCTT CTGGATACAC
     ATTCACTGAC

 151 TACAACATGC ACTGGATGAA GCAGAACCAA GGAAAGAGCC
     TAGAATGGAT

 201 AGGAGAAATT AATCCTAACA GTGGTGGTGC TGGCTACAAC
     CAGCAGTTCA

 251 AAGGCAAGGC CACATTGACT GTAGACAAGT CCTCCAGGAC
     AGCCTACATG

 301 GAGCTCCGCA GCCTGACATC TGAGGACTCT GCAGTCTATT
     ACTGTGCAAG

 351 ATTGGGCTAC GTTGGTAATT ACGAGGACTG GTACTTCGAT
     GTCTGGGGCG

 401 CAGGGACCAC GGTCACCGTC TCCTCAGCCA AAACGACACC
     CCCATCTGTC

 451 TATCCACTGG CCCCTGGATC TGCTGCCCAA ACTAACTCCA
     TGGTGACCCT

 501 GGGATGCCTG GTCAAGGGCT ATTTCCCTGA GCCAGTGACA
     GTGACCTGGA

 551 ACTCTGGATC CCTGTCCAGC GGTGTGCACA CCTTCCCAGC
     TGTCCTGCAG

 601 TCTGACCTCT ACACTCTGAG CAGCTCAGTG ACTGTCCCCT
     CCAGCACCTG

 651 GCCCAGCGAG ACCGTCACCT GCAACGTTGC CCACCCGGCC
     AGCAGCACCA

 701 AGGTGGACAA GAAAATTGTG CCCAGGGATT GTGGTTGTAA
     GCCTTGCATA

 751 TGTACAGTCC CAGAAGTATC ATCTGTCTTC ATCTTCCCCC
     CAAAGCCCAA

 801 GGATGTGCTC ACCATTACTC TGACTCCTAA GGTCACGTGT
     GTTGTGGTAG
```

-continued

```
 851 ACATCAGCAA GGATGATCCC GAGGTCCAGT TCAGCTGGTT
     TGTAGATGAT

 901 GTGGAGGTGC ACACAGCTCA GACGCAACCC CGGGAGGAGC
     AGTTCAACAG

 951 CACTTTCCGC TCAGTCAGTG AACTTCCCAT CATGCACCAG
     GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG

1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAA
```

Ab-8

The sequences of the Antibody 8 (also referred to herein as Ab-8) LC and HC are as follows:

Ab-8 Light Chain:

Amino acid sequence of the mature form (signal peptide removed) of the Ab-8 LC:

(SEQ ID NO: 165)

1 DIQMTQTTSS LSASLGDRVS ISCRASQDIS NYLNWYQQKP DGTFKLLIFY

51 TSRLLSGVPS RFSGSGSGTD YSLTIYNLEQ EDFATYFCQQ GDTLPYTFGG

101 GTKLEIK*RAD AAPTVSIFPP SSEQLTSGGA SVVCFLNNFY PKDINVKWKI*

151 *DGSERQNGVL NSWTDQDSKD STYSMSSTLT LTKDEYERHN SYTCEATHKT*

201 *STSPIVKSFN RNEC*

Nucleic acid sequence encoding the mature form (signal peptide removed) of the Ab-8 LC:

```
                                        (SEQ ID NO: 166)
   1 GATATCCAGA TGACACAGAC TACATCCTCC CTGTCTGCCT
     CTCTGGGAGA

  51 CAGGGTCTCC ATCAGTTGCA GGGCAAGTCA AGACATTAGC
     AATTATTTAA

 101 ACTGGTATCA GCAGAAACCA GATGGAACTT TTAAACTCCT
     TATCTTCTAC

 151 ACATCAAGAT TACTCTCAGG AGTCCCATCA AGGTTCAGTG
     GCAGTGGGTC

 201 TGGAACAGAT TATTCTCTCA CCATTTACAA CCTGGAGCAA
     GAAGATTTTG
```

-continued

```
251 CCACTTACTT TTGCCAACAG GGAGATACGC TTCCGTACAC
    TTTCGGAGGG

301 GGGACCAAAC TGGAAATAAA ACGGGCTGAT GCTGCACCAA
    CTGTATCCAT

351 CTTCCCACCA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT

451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT
    GTTAG
```

Amino acid sequence of the Ab-8 LC including signal peptide:

```
                                           (SEQ ID NO: 167)
  1 MMSSAQFLGL LLLCFQGTRC DIQMTQTTSS LSASLGDRVS
    ISCRASQDIS

 51 NYLNWYQQKP DGTFKLLIFY TSRLLSGVPS RFSGSGSGTD
    YSLTIYNLEQ

101 EDFATYFCQQ GDTLPYTFGG GTKLEIKRAD AAPTVSIFPP
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-8 LC including signal peptide encoding sequence:

```
                                           (SEQ ID NO: 168)
  1 ATGATGTCCT CTGCTCAGTT CCTTGGTCTC CTGTTGCTCT
    GTTTTCAAGG

 51 TACCAGATGT GATATCCAGA TGACACAGAC TACATCCTCC
    CTGTCTGCCT

101 CTCTGGGAGA CAGGGTCTCC ATCAGTTGCA GGGCAAGTCA
    AGACATTAGC

151 AATTATTTAA ACTGGTATCA GCAGAAACCA GATGGAACTT
    TTAAACTCCT

201 TATCTTCTAC ACATCAAGAT TACTCTCAGG AGTCCCATCA
    AGGTTCAGTG

251 GCAGTGGGTC TGGAACAGAT TATTCTCTCA CCATTTACAA
    CCTGGAGCAA

301 GAAGATTTTG CCACTTACTT TTGCCAACAG GGAGATACGC
    TTCCGTACAC

351 TTTCGGAGGG GGGACCAAAC TGGAAATAAA ACGGGCTGAT
    GCTGCACCAA

401 CTGTATCCAT CTTCCCACCA TCCAGTGAGC AGTTAACATC
    TGGAGGTGCC
```

-continued

```
451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG

601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GTTAG
```

Ab-8 Heavy Chain:

Amino acid sequence of the mature form (signal peptide removed) of the Ab-8 HC:

```
                                           (SEQ ID NO: 169)
  1 EVQLQQSGPE LMKPGASVKM SCKASGYTFT DYNMHWVKQN
    QGKTLDWIGE

 51 INPNSGGAGY NQKFKGKATL TVDKSSTTAY MELRSLTSED
    SAVYYCARLG

101 YDDIYDDWYF DVWGAGTTVT VSSAKTTPPS VYPLAPGSAA
    QTNSMVTLGC

151 LVKGYFPEPV TVTWNSGSLS SGVHTFPAVL QSDLYTLSSS
    VTVPSSTWPS

201 ETVTCNVAHP ASSTKVDKKI VPRDCGCKPC ICTVPEVSSV
    FIFPPKPKDV

251 LTITLTPKVT CVVVDISKDD PEVQFSWFVD DVEVHTAQTQ
    PREEQFNSTF

301 RSVSELPIMH QDWLNGKEFK CRVNSAAFPA PIEKTISKTK
    GRPKAPQVYT

351 IPPPKEQMAK DKVSLTCMIT DFFPEDITVE WQWNGQPAEN
    YKNTQPIMDT

401 DGSYFIYSKL NVQKSNWEAG NTFTCSVLHE GLHNHHTEKS
    LSHSPGK
```

Nucleic acid sequence encoding the mature form (signal peptide removed) of the Ab-8 HC:

```
                                           (SEQ ID NO: 170)
  1 GAGGTCCAAC TGCAACAGTC TGGACCTGAA CTAATGAAGC
    CTGGGGCTTC

 51 AGTGAAGATG TCCTGCAAGG CTTCTGGATA TACATTCACT
    GACTACAACA

101 TGCACTGGGT GAAGCAGAAC CAAGGAAAGA CCCTAGACTG
    GATAGGAGAA

151 ATTAATCCTA ACAGTGGTGG TGCTGGCTAC AACCAGAAGT
    TCAAGGGCAA

201 GGCCACATTG ACTGTAGACA AGTCCTCCAC CACAGCCTAC
    ATGGAGCTCC

251 GCAGCCTGAC ATCTGAGGAC TCTGCAGTCT ATTACTGTGC
    AAGATTGGGC

301 TACGATGATA TCTACGACGA CTGGTACTTC GATGTCTGGG
    GCGCAGGGAC
```

-continued

```
 351 CACGGTCACC GTCTCCTCAG CCAAAACGAC ACCCCCATCT
     GTCTATCCAC

 401 TGGCCCCTGG ATCTGCTGCC CAAACTAACT CCATGGTGAC
     CCTGGGATGC

 451 CTGGTCAAGG GCTATTTCCC TGAGCCAGTG ACAGTGACCT
     GGAACTCTGG

 501 ATCCCTGTCC AGCGGTGTGC ACACCTTCCC AGCTGTCCTG
     CAGTCTGACC

 551 TCTACACTCT GAGCAGCTCA GTGACTGTCC CCTCCAGCAC
     CTGGCCCAGC

 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA
     ATGA
```

Amino acid sequence of the Ab-8 HC including signal peptide:

```
                                           (SEQ ID NO: 171)
  1 MGWSWTFLFL LSGTAGVLSE VQLQQSGPEL MKPGASVKMS
    CKASGYTFTD

 51 YNMHWVKQNQ GKTLDWIGEI NPNSGGAGYN QKFKGKATLT
    VDKSSTTAYM

101 ELRSLTSEDS AVYYCARLGY DDIYDDWYFD VWGAGTTVTV
    SSAKTTPPSV

151 YPLAPGSAAQ TNSMVTLGCL VKGYFPEPVT VTWNSGSLSS
    GVHTFPAVLQ

201 SDLYTLSSSV TVPSSTWPSE TVTCNVAHPA SSTKVDKKIV
    PRDCGCKPCI
```

-continued

```
251 CTVPEVSSVF IFPPKPKDVL TITLTPKVTC VVVDISKDDP
    EVQFSWFVDD

301 VEVHTAQTQP REEQFNSTFR SVSELPIMHQ DWLNGKEFKC
    RVNSAAFPAP

351 IEKTISKTKG RPKAPQVYTI PPPKEQMAKD KVSLTCMITD
    FFPEDITVEW

401 QWNGQPAENY KNTQPIMDTD GSYFIYSKLN VQKSNWEAGN
    TFTCSVLHEG

451 LHNHHTEKSL SHSPGK
```

Nucleic acid sequence of the Ab-8 HC including signal peptide encoding sequence:

```
                                            (SEQ ID NO: 172)
  1 ATGGGATGGA GCTGGACCTT TCTCTTCCTC CTGTCAGGAA
    CTGCAGGTGT

 51 CCTCTCTGAG GTCCAACTGC AACAGTCTGG ACCTGAACTA
    ATGAAGCCTG

101 GGGCTTCAGT GAAGATGTCC TGCAAGGCTT CTGGATATAC
    ATTCACTGAC

151 TACAACATGC ACTGGGTGAA GCAGAACCAA GGAAAGACCC
    TAGACTGGAT

201 AGGAGAAATT AATCCTAACA GTGGTGGTGC TGGCTACAAC
    CAGAAGTTCA

251 AGGGCAAGGC CACATTGACT GTAGACAAGT CCTCCACCAC
    AGCCTACATG

301 GAGCTCCGCA GCCTGACATC TGAGGACTCT GCAGTCTATT
    ACTGTGCAAG

351 ATTGGGCTAC GATGATATCT ACGACGACTG GTACTTCGAT
    GTCTGGGGCG

401 CAGGGACCAC GGTCACCGTC TCCTCAGCCA AAACGACACC
    CCCATCTGTC

451 TATCCACTGG CCCCTGGATC TGCTGCCCAA ACTAACTCCA
    TGGTGACCCT

501 GGGATGCCTG GTCAAGGGCT ATTTCCCTGA GCCAGTGACA
    GTGACCTGGA

551 ACTCTGGATC CCTGTCCAGC GGTGTGCACA CCTTCCCAGC
    TGTCCTGCAG

601 TCTGACCTCT ACACTCTGAG CAGCTCAGTG ACTGTCCCCT
    CCAGCACCTG

651 GCCCAGCGAG ACCGTCACCT GCAACGTTGC CCACCCGGCC
    AGCAGCACCA

701 AGGTGGACAA GAAAATTGTG CCCAGGGATT GTGGTTGTAA
    GCCTTGCATA

751 TGTACAGTCC CAGAAGTATC ATCTGTCTTC ATCTTCCCCC
    CAAAGCCCAA

801 GGATGTGCTC ACCATTACTC TGACTCCTAA GGTCACGTGT
    GTTGTGGTAG

851 ACATCAGCAA GGATGATCCC GAGGTCCAGT TCAGCTGGTT
    TGTAGATGAT

901 GTGGAGGTGC ACACAGCTCA GACGCAACCC CGGGAGGAGC
    AGTTCAACAG
```

-continued

```
951 CACTTTCCGC TCAGTCAGTG AACTTCCCAT CATGCACCAG
    GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG

1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAATG

1401 A
```

Ab-9

The sequences of the Antibody 9 (also referred to herein as Ab-9) LC and HC are as follows:

Ab-9 Light Chain:

Amino acid sequence of the mature form (signal peptide removed) of the Ab-9 LC:

```
                                             (SEQ ID NO: 173)
1 DIQMTQITSS LSASLGDRVS ISCRASQDIS NYLNWYQQKP
  DGTFKLLIFY

51 TSRLFSGVPS RFSGSGSGTD YSLTIYNLEQ EDFATYFCQQ
   GDTLPYTFGG

101 GTKVEIKRAD AAPTVSIFPP SSEQLTSGGA SVVCFLNNFY
    PKDINVKWKI

151 DGSERQNGVL NSWTDQDSKD STYSMSSTLT LTKDEYERHN
    SYTCEATHKT

201 STSPIVKSFN RNEC
```

Nucleic acid sequence encoding the mature form (signal peptide removed) of the Ab-9 LC:

```
                                             (SEQ ID NO: 174)
1 GATATCCAGA TGACACAGAT TACATCCTCC CTGTCTGCCT
  CTCTGGGAGA

51 CAGGGTCTCC ATCAGTTGCA GGGCAAGTCA AGACATTAGC
   AATTATTTAA

101 ATTGGTATCA GCAGAAACCA GATGGAACTT TTAAACTCCT
    TATCTTCTAC

151 ACATCAAGAT TATTTTCAGG AGTCCCATCA AGGTTCAGTG
    GCAGTGGGTC

201 TGGAACAGAT TATTCTCTCA CCATTTACAA CCTGGAGCAA
    GAAGATTTTG

251 CCACTTACTT TTGCCAACAG GGAGATACGC TTCCGTACAC
    TTTCGGAGGG

301 GGGACCAAGG TGGAAATAAA ACGGGCTGAT GCTGCACCAA
    CTGTATCCAT

351 CTTCCCACCA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT

451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT GT
```

Amino acid sequence of the Ab-9 LC including signal peptide:

```
                                             (SEQ ID NO: 175)
1 MMSSAQFLGL LLLCFQGTRC DIQMTQITSS LSASLGDRVS
  ISCRASQDIS

51 NYLNWYQQKP DGTFKLLIFY TSRLFSGVPS RFSGSGSGTD
   YSLTIYNLEQ

101 EDFATYFCQQ GDTLPYTFGG GTKVEIKRAD AAPTVSIFPP
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-9 LC including signal peptide encoding sequence:

```
                                             (SEQ ID NO: 176)
1 ATGATGTCCT CTGCTCAGTT CCTTGGTCTC CTGTTGCTCT
  GTTTTCAAGG

51 TACCAGATGT GATATCCAGA TGACACAGAT TACATCCTCC
   CTGTCTGCCT

101 CTCTGGGAGA CAGGGTCTCC ATCAGTTGCA GGGCAAGTCA
    AGACATTAGC

151 AATTATTTAA ATTGGTATCA GCAGAAACCA GATGGAACTT
    TTAAACTCCT

201 TATCTTCTAC ACATCAAGAT TATTTTCAGG AGTCCCATCA
    AGGTTCAGTG

251 GCAGTGGGTC TGGAACAGAT TATTCTCTCA CCATTTACAA
    CCTGGAGCAA

301 GAAGATTTTG CCACTTACTT TTGCCAACAG GGAGATACGC
    TTCCGTACAC

351 TTTCGGAGGG GGGACCAAGG TGGAAATAAA ACGGGCTGAT
    GCTGCACCAA

401 CTGTATCCAT CTTCCCACCA TCCAGTGAGC AGTTAACATC
    TGGAGGTGCC

451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG
```

-continued

```
601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GT
```

Ab-9 Heavy Chain:

Amino acid sequence of the mature form (signal peptide removed) of the Ab-9 HC:

```
                                    (SEQ ID NO: 177)
  1 EVQLQQSGPE LMKPGTSVKM SCKASGYTFT DYNMHWVKQT
    QGKTLEWIGE

 51 INPNSGGAGY NQKFKGKATL TVDKSSTTAY MELRSLTSED
    SAVYYCAKLG

101 YDDIYDDWYF DVWGAGTTVT VSSAKTTAPS VYPLAPVCGD
    TTGSSVTLGC

151 LVKGYFPEPV TLTWNSGSLS SDVHTFPALL QSGLYTLSSS
    VTVTTWPSQT

201 ITCNVAHPAS STKVDKKIEP RGSPTHKPCP PCPAPNLLGG
    PSVFIFPPKI

251 KDVLMISLSP MVTCVVVDVS EDDPDVHVSW FVNNVEVHTA
    QTQTHREDYN

301 STIRVVSALP IQHQDWMSGK EFKCKVNNKA LPAPIERTIS
    KPKGPVRAPQ

351 VYVLPPPEEE MTKKQVTLTC MITDFMPEDI YVEWTNNGQT
    ELNYKNTEPV

401 LDSDGSYFMY SKLRVEKKNW VERNSYSCSV VHEGLHNHHT
    TKSFSRTPGK
```

Nucleic acid sequence encoding the mature form (signal peptide removed) of the Ab-9 HC:

```
                                    (SEQ ID NO: 178)
   1 GAGGTCCAAC TGCAACAGTC TGGACCTGAA CTAATGAAGC
     CTGGGACTTC

  51 AGTGAAGATG TCCTGCAAGG CTTCTGGATA TACATTCACT
     GACTACAACA

 101 TGCACTGGGT GAAGCAGACC CAAGGAAAGA CCCTAGAGTG
     GATAGGAGAA

 151 ATTAATCCTA ACAGTGGTGG TGCTGGCTAC AACCAGAAGT
     TCAAGGGCAA

 201 GGCCACATTG ACTGTAGACA AGTCCTCCAC CACAGCCTAC
     ATGGAGCTCC

 251 GCAGCCTGAC ATCTGAGGAC TCTGCAGTCT ATTACTGTGC
     AAAATTGGGC

 301 TACGATGATA TCTACGACGA CTGGTATTTC GATGTCTGGG
     GCGCAGGGAC

 351 CACGGTCACC GTCTCCTCAG CCAAAACAAC AGCCCCATCG
     GTCTATCCAC

 401 TGGCCCCTGT GTGTGGAGAT ACAACTGGCT CCTCGGTGAC
     TCTAGGATGC
```

-continued

```
 451 CTGGTCAAGG GTTATTTCCC TGAGCCAGTG ACCTTGACCT
     GGAACTCTGG

 501 ATCCCTGTCC AGTGATGTGC ACACCTTCCC AGCTCTCCTG
     CAGTCTGGCC

 551 TCTACACCCT CAGCAGCTCA GTGACTGTAA CCACCTGGCC
     CAGCCAGACC

 601 ATCACCTGCA ATGTGGCCCA CCCGGCAAGC AGCACCAAAG
     TGGACAAGAA

 651 AATTGAGCCC AGAGGGTCCC CAACACATAA ACCCTGTCCT
     CCATGCCCAG

 701 CTCCTAACCT CTTGGGTGGA CCATCCGTCT TCATCTTCCC
     TCCAAAGATC

 751 AAGGATGTAC TCATGATCTC CCTGAGCCCC ATGGTCACGT
     GTGTGGTGGT

 801 GGATGTGAGC GAGGATGACC CAGATGTCCA TGTCAGCTGG
     TTCGTGAACA

 851 ACGTGGAAGT ACACACAGCT CAGACACAAA CCCATAGAGA
     GGATTACAAC

 901 AGTACTATCC GGGTGGTCAG TGCCCTCCCC ATCCAGCACC
     AGGACTGGAT

 951 GAGTGGCAAG GAGTTCAAAT GCAAGGTCAA CAACAAAGCC
     CTCCCAGCGC

1001 CCATCGAGAG AACCATCTCA AAACCCAAAG GGCCAGTAAG
     AGCTCCACAG

1051 GTATATGTCT TGCCTCCACC AGAAGAAGAG ATGACTAAGA
     AACAGGTCAC

1101 TCTGACCTGC ATGATCACAG ACTTCATGCC TGAAGACATT
     TACGTGGAGT

1151 GGACCAACAA CGGGCAAACA GAGCTAAACT ACAAGAACAC
     TGAACCAGTC

1201 CTGGACTCTG ATGGTTCTTA CTTCATGTAC AGCAAGCTGA
     GAGTGGAAAA

1251 GAAGAACTGG GTGGAAAGAA ATAGCTACTC CTGTTCAGTG
     GTCCACGAGG

1301 GTCTGCACAA TCACCACACG ACTAAGAGCT TCTCCCGGAC
     TCCGGGTAAA
```

Amino acid sequence of the Ab-9 HC including signal peptide:

```
                                    (SEQ ID NO: 179)
  1 MGWSWTFLFL LSGTAGVLSE VQLQQSGPEL MKPGTSVKMS
    CKASGYTFTD

 51 YNMHWVKQTQ GKTLEWIGEI NPNSGGAGYN QKFKGKATLT
    VDKSSTTAYM

101 ELRSLTSEDS AVYYCAKLGY DDIYDDWYFD VWGAGTTVTV
    SSAKTTAPSV

151 YPLAPVCGDT TGSSVTLGCL VKGYFPEPVT LTWNSGSLSS
    DVHTFPALLQ

201 SGLYTLSSSV TVTTWPSQTI TCNVAHPASS TKVDKKIEPR
    GSPTHKPCPP

251 CPAPNLLGGP SVFIFPPKIK DVLMISLSPM VTCVVVDVSE
    DDPDVHVSWF

301 VNNVEVHTAQ TQTHREDYNS TIRVVSALPI QHQDWMSGKE
    FKCKVNNKAL
```

-continued

```
351 PAPIERTISK PKGPVRAPQV YVLPPPEEEM TKKQVTLTCM
    ITDFMPEDIY

401 VEWTNNGQTE LNYKNTEPVL DSDGSYFMYS KLRVEKKNWV
    ERNSYSCSVV

451 HEGLHNHHTT KSFSRTPGK
```

Nucleic acid sequence of the Ab-9 HC including signal peptide encoding sequence:

```
                                        (SEQ ID NO: 180)
   1 ATGGGATGGA GCTGGACCTT TCTCTTCCTC CTGTCAGGAA
     CTGCAGGTGT

  51 CCTCTCTGAG GTCCAACTGC AACAGTCTGG ACCTGAACTA
     ATGAAGCCTG

 101 GGACTTCAGT GAAGATGTCC TGCAAGGCTT CTGGATATAC
     ATTCACTGAC

 151 TACAACATGC ACTGGGTGAA GCAGACCCAA GGAAAGACCC
     TAGAGTGGAT

 201 AGGAGAAATT AATCCTAACA GTGGTGGTGC TGGCTACAAC
     CAGAAGTTCA

 251 AGGGCAAGGC CACATTGACT GTAGACAAGT CCTCCACCAC
     AGCCTACATG

 301 GAGCTCCGCA GCCTGACATC TGAGGACTCT GCAGTCTATT
     ACTGTGCAAA

 351 ATTGGGCTAC GATGATATCT ACGACGACTG GTATTTCGAT
     GTCTGGGGCG

 401 CAGGGACCAC GGTCACCGTC TCCTCAGCCA AAACAACAGC
     CCCATCGGTC

 451 TATCCACTGG CCCCTGTGTG TGGAGATACA ACTGGCTCCT
     CGGTGACTCT

 501 AGGATGCCTG GTCAAGGGTT ATTTCCCTGA GCCAGTGACC
     TTGACCTGGA

 551 ACTCTGGATC CCTGTCCAGT GATGTGCACA CCTTCCCAGC
     TCTCCTGCAG

 601 TCTGGCCTCT ACACCCTCAG CAGCTCAGTG ACTGTAACCA
     CCTGGCCCAG

 651 CCAGACCATC ACCTGCAATG TGGCCCACCC GGCAAGCAGC
     ACCAAAGTGG

 701 ACAAGAAAAT TGAGCCCAGA GGGTCCCCAA CACATAAACC
     CTGTCCTCCA

 751 TGCCCAGCTC CTAACCTCTT GGGTGGACCA TCCGTCTTCA
     TCTTCCCTCC

 801 AAAGATCAAG GATGTACTCA TGATCTCCCT GAGCCCCATG
     GTCACGTGTG

 851 TGGTGGTGGA TGTGAGCGAG GATGACCCAG ATGTCCATGT
     CAGCTGGTTC

 901 GTGAACAACG TGGAAGTACA CACAGCTCAG ACACAAACCC
     ATAGAGAGGA

 951 TTACAACAGT ACTATCCGGG TGGTCAGTGC CCTCCCCATC
     CAGCACCAGG

1001 ACTGGATGAG TGGCAAGGAG TTCAAATGCA AGGTCAACAA
     CAAAGCCCTC

1051 CCAGCGCCCA TCGAGAGAAC CATCTCAAAA CCCAAAGGGC
     CAGTAAGAGC

1101 TCCACAGGTA TATGTCTTGC CTCCACCAGA AGAAGAGATG
     ACTAAGAAAC

1151 AGGTCACTCT GACCTGCATG ATCACAGACT TCATGCCTGA
     AGACATTTAC

1201 GTGGAGTGGA CCAACAACGG GCAAACAGAG CTAAACTACA
     AGAACACTGA

1251 ACCAGTCCTG GACTCTGATG GTTCTTACTT CATGTACAGC
     AAGCTGAGAG

1301 TGGAAAAGAA GAACTGGGTG GAAAGAAATA GCTACTCCTG
     TTCAGTGGTC

1351 CACGAGGGTC TGCACAATCA CCACACGACT AAGAGCTTCT
     CCCGGACTCC

1401 GGGTAAA
```

Ab-10

The sequences of the Antibody 10 (also referred to herein as Ab-10) LC and HC are as follows:

Ab-10 Light Chain:

Amino acid sequence of the mature form (signal peptide removed) of the Ab-10 LC:

```
                                        (SEQ ID NO: 181)
  1 DIQMTQTTSS LSASLGDRVS ISCRASQDIS NYLNWYQQKP
    DGTFKLLIFY

 51 TSRLLSGVPS RFSGSGSGTD YSLTIYNLEQ EDFATYFCQQ
    GDTLPYTFGG

101 GTKLEIKRAD AAPTVSIFPL SSEQLTSGGA SVVCFLNNFY
    PKDINVKWKI

151 DGSERQNGVL NSWTDQDSKD STYSMSSTLT LTKDEYERHN
    SYTCEATHKT

201 STSPIVKSFN RNEC
```

Nucleic acid sequence encoding the mature form (signal peptide removed) of the Ab-10 LC:

```
                                        (SEQ ID NO: 182)
  1 GATATCCAGA TGACACAGAC TACATCCTCC CTGTCTGCCT
    CTCTGGGAGA

 51 CAGGGTCTCC ATCAGTTGCA GGGCAAGTCA AGACATTAGC
    AATTATTTAA

101 ACTGGTATCA GCAGAAACCA GATGGAACTT TTAAACTCCT
    TATCTTCTAC

151 ACATCAAGAT TACTCTCAGG AGTCCCATCA AGGTTCAGTG
    GCAGTGGGTC

201 TGGAACAGAT TATTCTCTCA CCATTTACAA CCTGGAGCAA
    GAAGATTTTG

251 CCACTTACTT TTGCCAACAG GGAGATACGC TTCCGTACAC
    TTTCGGAGGG

301 GGGACCAAAC TGGAAATAAA ACGGGCTGAT GCTGCACCAA
    CTGTATCCAT

351 CTTCCCACTA TCCAGTGAGC AGTTAACATC TGGAGGTGCC
    TCAGTCGTGT

401 GCTTCTTGAA CAACTTCTAC CCCAAAGACA TCAATGTCAA
    GTGGAAGATT
```

-continued

```
451 GATGGCAGTG AACGACAAAA TGGCGTCCTG AACAGTTGGA
    CTGATCAGGA

501 CAGCAAAGAC AGCACCTACA GCATGAGCAG CACCCTCACG
    TTGACCAAGG

551 ACGAGTATGA ACGACATAAC AGCTATACCT GTGAGGCCAC
    TCACAAGACA

601 TCAACTTCAC CCATTGTCAA GAGCTTCAAC AGGAATGAGT
    GTTAG
```

Amino acid sequence of the Ab-10 LC including signal peptide:

```
                                     (SEQ ID NO: 183)
  1 MMSSAQFLGL LLLCFQGTRC DIQMTQTTSS LSASLGDRVS
    ISCRASQDIS

 51 NYLNWYQQKP DGTFKLLIFY TSRLLSGVPS RFSGSGSGTD
    YSLTIYNLEQ

101 EDFATYFCQQ GDTLPYTFGG GTKLEIKRAD AAPTVSIFPL
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-10 LC including signal peptide encoding sequence:

```
                                     (SEQ ID NO: 184)
  1 ATGATGTCCT CTGCTCAGTT CCTTGGTCTC CTGTTGCTCT
    GTTTTCAAGG

 51 TACCAGATGT GATATCCAGA TGACACAGAC TACATCCTCC
    CTGTCTGCCT

101 CTCTGGGAGA CAGGGTCTCC ATCAGTTGCA GGGCAAGTCA
    AGACATTAGC

151 AATTATTTAA ACTGGTATCA GCAGAAACCA GATGGAACTT
    TTAAACTCCT

201 TATCTTCTAC ACATCAAGAT TACTCTCAGG AGTCCCATCA
    AGGTTCAGTG

251 GCAGTGGGTC TGGAACAGAT TATTCTCTCA CCATTTACAA
    CCTGGAGCAA

301 GAAGATTTTG CCACTTACTT TTGCCAACAG GGAGATACGC
    TTCCGTACAC

351 TTTCGGAGGG GGGACCAAAC TGGAAATAAA ACGGGCTGAT
    GCTGCACCAA

401 CTGTATCCAT CTTCCCACTA TCCAGTGAGC AGTTAACATC
    TGGAGGTGCC

451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG

601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GTTAG
```

Ab-10 Heavy Chain:

Amino acid sequence of the mature form (signal peptide removed) of the Ab-10 HC:

```
                                     (SEQ ID NO: 185)
  1 EVQLQQSGPE LMKPGASVKM SCKASGYTFT DYNMHWVKQN
    QGKTLEWIGE

 51 INPNSGGAGY NQKFKGKATL TVDKSSTTAY MELRSLTSED
    SAVYYCARLG

101 YDDIYDDWYF DVWGAGTTVT VSSAKTTPPS VYPLAPGSAA
    QTNSMVTLGC

151 LVKGYFPEPV TVTWNSGSLS SGVHTFPAVL QSDLYTLSSS
    VTVPSSTWPS

201 ETVTCNVAHP ASSTKVDKKI VPRDCGCKPC ICTVPEVSSV
    FIFPPKPKDV

251 LTITLTPKVT CVVVDISKDD PEVQFSWFVD DVEVHTAQTQ
    PREEQFNSTF

301 RSVSELPIMH QDWLNGKEFK CRVNSAAFPA PIEKTISKTK
    GRPKAPQVYT

351 IPPPKEQMAK DKVSLTCMIT DFFPEDITVE WQWNGQPAEN
    YKNTQPIMDT

401 DGSYFIYSKL NVQKSNWEAG NTFTCSVLHE GLHNHHTEKS
    LSHSPGK
```

Nucleic acid sequence encoding the mature form (signal peptide removed) of the Ab-10 HC:

```
                                     (SEQ ID NO: 186)
  1 GAGGTCCAAC TGCAACAGTC TGGACCTGAA CTAATGAAGC
    CTGGGGCTTC

 51 AGTGAAGATG TCCTGCAAGG CTTCTGGATA TACATTCACT
    GACTACAACA

101 TGCACTGGGT GAAGCAGAAC CAAGGAAAGA CCCTAGAATG
    GATAGGAGAA

151 ATTAATCCTA ACAGTGGTGG TGCTGGCTAC AACCAGAAGT
    TCAAGGGCAA

201 GGCCACATTG ACTGTAGACA AGTCCTCCAC CACAGCCTAC
    ATGGAGCTCC

251 GCAGCCTGAC ATCTGAGGAC TCTGCAGTCT ATTACTGTGC
    AAGATTGGGC

301 TACGATGATA TCTACGACGA CTGGTACTTC GATGTCTGGG
    GCGCAGGGAC

351 CACGGTCACC GTCTCCTCAG CCAAAACGAC ACCCCCATCT
    GTCTATCCAC

401 TGGCCCCTGG ATCTGCTGCC CAAACTAACT CCATGGTGAC
    CCTGGGATGC

451 CTGGTCAAGG GCTATTTCCC TGAGCCAGTG ACAGTGACCT
    GGAACTCTGG

501 ATCCCTGTCC AGCGGTGTGC ACACCTTCCC AGCTGTCCTG
    CAGTCTGACC

551 TCTACACTCT GAGCAGCTCA GTGACTGTCC CCTCCAGCAC
    CTGGCCCAGC
```

-continued

```
 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA
     ATGA
```

Amino acid sequence of the Ab-10 HC including signal peptide:

```
                                          (SEQ ID NO: 187)
  1 MGWSWTFLFL LSGTAGVLSE VQLQQSGPEL MKPGASVKMS
    CKASGYTFTD

 51 YNMHWVKQNQ GKTLEWIGEI NPNSGGAGYN QKFKGKATLT
    VDKSSTTAYM

101 ELRSLTSEDS AVYYCARLGY DDIYDDWYFD VWGAGTTVTV
    SSAKTTPPSV

151 YPLAPGSAAQ TNSMVTLGCL VKGYFPEPVT VTWNSGSLSS
    GVHTFPAVLQ

201 SDLYTLSSSV TVPSSTWPSE TVTCNVAHPA SSTKVDKKIV
    PRDCGCKPCI

251 CTVPEVSSVF IFPPKPKDVL TITLTPKVTC VVVDISKDDP
    EVQFSWFVDD

301 VEVHTAQTQP REEQFNSTFR SVSELPIMHQ DWLNGKEFKC
    RVNSAAFPAP

351 IEKTISKTKG RPKAPQVYTI PPPKEQMAKD KVSLTCMITD
    FFPEDITVEW

401 QWNGQPAENY KNTQPIMDTD GSYFIYSKLN VQKSNWEAGN
    TFTCSVLHEG

451 LHNHHTEKSL SHSPGK
```

Nucleic acid sequence of the Ab-10 HC including signal peptide encoding sequence:

```
                                           (SEQ ID NO: 188)
   1 ATGGGATGGA GCTGGACCTT TCTCTTCCTC CTGTCAGGAA
     CTGCAGGTGT

  51 CCTCTCTGAG GTCCAACTGC AACAGTCTGG ACCTGAACTA
     ATGAAGCCTG

 101 GGGCTTCAGT GAAGATGTCC TGCAAGGCTT CTGGATATAC
     ATTCACTGAC

 151 TACAACATGC ACTGGGTGAA GCAGAACCAA GGAAAGACCC
     TAGAATGGAT

 201 AGGAGAAATT AATCCTAACA GTGGTGGTGC TGGCTACAAC
     CAGAAGTTCA

 251 AGGGCAAGGC CACATTGACT GTAGACAAGT CCTCCACCAC
     AGCCTACATG

 301 GAGCTCCGCA GCCTGACATC TGAGGACTCT GCAGTCTATT
     ACTGTGCAAG

 351 ATTGGGCTAC GATGATATCT ACGACGACTG GTACTTCGAT
     GTCTGGGGCG

 401 CAGGGACCAC GGTCACCGTC TCCTCAGCCA AAACGACACC
     CCCATCTGTC

 451 TATCCACTGG CCCCTGGATC TGCTGCCCAA ACTAACTCCA
     TGGTGACCCT

 501 GGGATGCCTG GTCAAGGGCT ATTTCCCTGA GCCAGTGACA
     GTGACCTGGA

 551 ACTCTGGATC CCTGTCCAGC GGTGTGCACA CCTTCCCAGC
     TGTCCTGCAG

 601 TCTGACCTCT ACACTCTGAG CAGCTCAGTG ACTGTCCCCT
     CCAGCACCTG

 651 GCCCAGCGAG ACCGTCACCT GCAACGTTGC CCACCCGGCC
     AGCAGCACCA

 701 AGGTGGACAA GAAAATTGTG CCCAGGGATT GTGGTTGTAA
     GCCTTGCATA

 751 TGTACAGTCC CAGAAGTATC ATCTGTCTTC ATCTTCCCCC
     CAAAGCCCAA

 801 GGATGTGCTC ACCATTACTC TGACTCCTAA GGTCACGTGT
     GTTGTGGTAG

 851 ACATCAGCAA GGATGATCCC GAGGTCCAGT TCAGCTGGTT
     TGTAGATGAT

 901 GTGGAGGTGC ACACAGCTCA GACGCAACCC CGGGAGGAGC
     AGTTCAACAG

 951 CACTTTCCGC TCAGTCAGTG AACTTCCCAT CATGCACCAG
     GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG
```

-continued

```
1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAATG

1401 A
```

Ab-11

The sequences of the Antibody 11 (also referred to herein as Ab-11) LC and HC are as follows:

Ab-11 Light Chain:

Amino acid sequence of the mature form (signal peptide removed) of the Ab-11 LC:

```
                                        (SEQ ID NO: 189)
  1 QIVLSQSPAF LSVSPGDKVT MTCRASSSIS YIHWFQQKPG
    SSPRSWIYAT

 51 SNLASGVPGR FSGSGSGTSY SLTISRVEAE DAATYYCQQW
    SSDPLTFGAG

101 TKLELKRADA APTVSIFPPS SEQLTSGGAS VVCFLNNFYP
    KDINVKWKID

151 GSERQNGVLN SWTDQDSKDS TYSMSSTLTL TKDEYERHNS
    YTCEATHKTS

201 TSPIVKSFNR NEC
```

Nucleic acid sequence encoding the mature form (signal peptide removed) of the Ab-11 LC:

```
                                        (SEQ ID NO: 190)
  1 CAAATTGTTC TCTCCCAGTC TCCAGCATTC CTGTCTGTAT
    CTCCAGGGGA

 51 TAAGGTCACA ATGACTTGCA GGGCCAGCTC AAGTATAAGT
    TACATACACT

101 GGTTTCAGCA GAAGCCAGGA TCCTCCCCCA GATCCTGGAT
    TTATGCCACA

151 TCCAACCTGG CTTCTGGAGT CCCTGGTCGC TTCAGTGGCA
    GTGGGTCTGG

201 GACCTCTTAC TCTCTCACAA TCAGCAGAGT GGAGGCTGAG
    GATGCTGCCA

251 CTTATTACTG CCAGCAGTGG AGTAGTGACC CACTCACGTT
    CGGTGCTGGG

301 ACCAAGCTGG AGCTGAAACG GGCTGATGCT GCACCAACTG
    TATCCATCTT

351 CCCACCATCC AGTGAGCAGT TAACATCTGG AGGTGCCTCA
    GTCGTGTGCT

401 TCTTGAACAA CTTCTACCCC AAAGACATCA ATGTCAAGTG
    GAAGATTGAT

451 GGCAGTGAAC GACAAAATGG CGTCCTGAAC AGTTGGACTG
    ATCAGGACAG

501 CAAAGACAGC ACCTACAGCA TGAGCAGCAC CCTCACGTTG
    ACCAAGGACG
```

-continued

```
551 AGTATGAACG ACATAACAGC TATACCTGTG AGGCCACTCA
    CAAGACATCA

601 ACTTCACCCA TTGTCAAGAG CTTCAACAGG AATGAGTGTT
    AG
```

Amino acid sequence of the Ab-11 LC including signal peptide:

```
                                        (SEQ ID NO: 191)
  1 MDFQVQIFSF LLISASVIMS RGQIVLSQSP AFLSVSPGDK
    VTMTCRASSS

 51 ISYIHWFQQK PGSSPRSWIY ATSNLASGVP GRFSGSGSGT
    SYSLTISRVE

101 AEDAATYYCQ QWSSDPLTFG AGTKLELKRA DAAPTVSIFP
    PSSEQLTSGG

151 ASVVCFLNNF YPKDINVKWK IDGSERQNGV LNSWTDQDSK
    DSTYSMSSTL

201 TLTKDEYERH NSYTCEATHK TSTSPIVKSF NRNEC
```

Nucleic acid sequence of the Ab-11 LC including signal peptide encoding sequence:

```
                                        (SEQ ID NO: 192)
  1 ATGGATTTTC AAGTGCAGAT TTTCAGCTTC CTGCTAATCA
    GTGCTTCAGT

 51 CATAATGTCC AGAGGACAAA TTGTTCTCTC CCAGTCTCCA
    GCATTCCTGT

101 CTGTATCTCC AGGGGATAAG GTCACAATGA CTTGCAGGGC
    CAGCTCAAGT

151 ATAAGTTACA TACACTGGTT TCAGCAGAAG CCAGGATCCT
    CCCCCAGATC

201 CTGGATTTAT GCCACATCCA ACCTGGCTTC TGGAGTCCCT
    GGTCGCTTCA

251 GTGGCAGTGG GTCTGGGACC TCTTACTCTC TCACAATCAG
    CAGAGTGGAG

301 GCTGAGGATG CTGCCACTTA TTACTGCCAG CAGTGGAGTA
    GTGACCCACT

351 CACGTTCGGT GCTGGGACCA AGCTGGAGCT GAAACGGGCT
    GATGCTGCAC

401 CAACTGTATC CATCTTCCCA CCATCCAGTG AGCAGTTAAC
    ATCTGGAGGT

451 GCCTCAGTCG TGTGCTTCTT GAACAACTTC TACCCCAAAG
    ACATCAATGT

501 CAAGTGGAAG ATTGATGGCA GTGAACGACA AAATGGCGTC
    CTGAACAGTT

551 GGACTGATCA GGACAGCAAA GACAGCACCT ACAGCATGAG
    CAGCACCCTC

601 ACGTTGACCA AGGACGAGTA TGAACGACAT AACAGCTATA
    CCTGTGAGGC

651 CACTCACAAG ACATCAACTT CACCCATTGT CAAGAGCTTC
    AACAGGAATG

701 AGTGTTAG
```

Ab-11 Heavy Chain:

Amino acid sequence of the mature form (signal peptide removed) of the Ab-11 HC:

(SEQ ID NO: 193)

```
1 EVQLQQSGAD LVQPGASVKV SCTASGFDIK DYYIHWMKQR
  PDQGLEWIGR

51 VDPDNGETEF APKFPGKATF TTDTSSNTAY LQLRGLTSED
  TAIYYCGRED

101 YDGTYTWFPY WGQGTLVTVS AAKTTPPSVY PLAPGSAAQT
  NSMVTLGCLV

151 KGYFPEPVTV TWNSGSLSSG VHTFPAVLQS DLYTLSSSVT
  VPSSTWPSET

201 VTCNVAHPAS STKVDKKIVP RDCGCKPCIC TVPEVSSVFI
  FPPKPKDVLT

251 ITLTPKVTCV VVDISKDDPE VQFSWFVDDV EVHTAQTQPR
  EEQFNSTFRS

301 VSELPIMHQD WLNGKEFKCR VNSAAFPAPI EKTISKTKGR
  PKAPQVYTIP

351 PPKEQMAKDK VSLTCMITDF FPEDITVEWQ WNGQPAENYK
  NTQPIMDTDG

401 SYFIYSKLNV QKSNWEAGNT FTCSVLHEGL HNHHTEKSLS
  HSPGK
```

Nucleic acid sequence encoding the mature form (signal peptide removed) of the Ab-11 HC:

(SEQ ID NO: 194)

```
1 GAAGTTCAGC TGCAACAGTC TGGGGCAGAC CTTGTGCAGC
  CAGGGGCCTC

51 AGTCAAGGTG TCCTGCACAG CTTCTGGCTT CGACATTAAG
  GACTACTATA

101 TACACTGGAT GAAACAGAGG CCTGACCAGG GCCTGGAGTG
  GATTGGAAGG

151 GTTGATCCTG ACAATGGTGA GACTGAATTT GCCCCGAAGT
  TCCCGGGCAA

201 GGCCACTTTT ACAACAGACA CATCCTCCAA CACAGCCTAC
  CTACAACTCA

251 GAGGCCTGAC ATCTGAGGAC ACTGCCATCT ATTACTGTGG
  GAGAGAAGAC

301 TACGATGGTA CCTACACCTG GTTTCCTTAT TGGGGCCAAG
  GGACTCTGGT

351 CACTGTCTCT GCAGCCAAAA CGACACCCCC ATCTGTCTAT
  CCACTGGCCC

401 CTGGATCTGC TGCCCAAACT AACTCCATGG TGACCCTGGG
  ATGCCTGGTC

451 AAGGGCTATT TCCCTGAGCC AGTGACAGTG ACCTGGAACT
  CTGGATCCCT

501 GTCCAGCGGT GTGCACACCT TCCCAGCTGT CCTGCAGTCT
  GACCTCTACA

551 CTCTGAGCAG CTCAGTGACT GTCCCCTCCA GCACCTGGCC
  CAGCGAGACC

601 GTCACCTGCA ACGTTGCCCA CCCGGCCAGC AGCACCAAGG
  TGGACAAGAA
```

-continued

```
651 AATTGTGCCC AGGGATTGTG GTTGTAAGCC TTGCATATGT
  ACAGTCCCAG

701 AAGTATCATC TGTCTTCATC TTCCCCCCAA AGCCCAAGGA
  TGTGCTCACC

751 ATTACTCTGA CTCCTAAGGT CACGTGTGTT GTGGTAGACA
  TCAGCAAGGA

801 TGATCCCGAG GTCCAGTTCA GCTGGTTTGT AGATGATGTG
  GAGGTGCACA

851 CAGCTCAGAC GCAACCCCGG GAGGAGCAGT TCAACAGCAC
  TTTCCGCTCA

901 GTCAGTGAAC TTCCCATCAT GCACCAGGAC TGGCTCAATG
  GCAAGGAGTT

951 CAAATGCAGG GTCAACAGTG CAGCTTTCCC TGCCCCCATC
  GAGAAAACCA

1001 TCTCCAAAAC CAAAGGCAGA CCGAAGGCTC CACAGGTGTA
  CACCATTCCA

1051 CCTCCCAAGG AGCAGATGGC CAAGGATAAA GTCAGTCTGA
  CCTGCATGAT

1101 AACAGACTTC TTCCCTGAAG ACATTACTGT GGAGTGGCAG
  TGGAATGGGC

1151 AGCCAGCGGA GAACTACAAG AACACTCAGC CCATCATGGA
  CACAGATGGC

1201 TCTTACTTCA TCTACAGCAA GCTCAATGTG CAGAAGAGCA
  ACTGGGAGGC

1251 AGGAAATACT TTCACCTGCT CTGTGTTACA TGAGGGCCTG
  CACAACCACC

1301 ATACTGAGAA GAGCCTCTCC CACTCTCCTG GTAAATGA
```

Amino acid sequence of the Ab-11 HC including signal peptide:

(SEQ ID NO: 195)

```
1 MKCSWVIFFL MAVVTGVNSE VQLQQSGADL VQPGASVKVS
  CTASGFDIKD

51 YYIHWMKQRP DQGLEWIGRV DPDNGETEFA PKFPGKATFT
  TDTSSNTAYL

101 QLRGLTSEDT AIYYCGREDY DGTYTWFPYW GQGTLVTVSA
  AKTTPPSVYP

151 LAPGSAAQTN SMVTLGCLVK GYFPEPVTVT WNSGSLSSGV
  HTFPAVLQSD

201 LYTLSSSVTV PSSTWPSETV TCNVAHPASS TKVDKKIVPR
  DCGCKPCICT

251 VPEVSSVFIF PPKPKDVLTI TLTPKVTCVV VDISKDDPEV
  QFSWFVDDVE

301 VHTAQTQPRE EQFNSTFRSV SELPIMHQDW LNGKEFKCRV
  NSAAFPAPIE

351 KTISKTKGRP KAPQVYTIPP PKEQMAKDKV SLTCMITDFF
  PEDITVEWQW

401 NGQPAENYKN TQPIMDTDGS YFIYSKLNVQ KSNWEAGNTF
  TCSVLHEGLH

451 NHHTEKSLSH SPGK
```

Nucleic acid sequence of the Ab-11 HC including signal peptide encoding sequence:

```
                                        (SEQ ID NO: 196)
   1 ATGAAATGCA GCTGGGTCAT CTTCTTCCTG ATGGCAGTGG
     TTACAGGGGT

  51 CAATTCAGAA GTTCAGCTGC AACAGTCTGG GGCAGACCTT
     GTGCAGCCAG

 101 GGGCCTCAGT CAAGGTGTCC TGCACAGCTT CTGGCTTCGA
     CATTAAGGAC

 151 TACTATATAC ACTGGATGAA ACAGAGGCCT GACCAGGGCC
     TGGAGTGGAT

 201 TGGAAGGGTT GATCCTGACA ATGGTGAGAC TGAATTTGCC
     CCGAAGTTCC

 251 CGGGCAAGGC CACTTTTACA ACAGACACAT CCTCCAACAC
     AGCCTACCTA

 301 CAACTCAGAG GCCTGACATC TGAGGACACT GCCATCTATT
     ACTGTGGGAG

 351 AGAAGACTAC GATGGTACCT ACACCTGGTT TCCTTATTGG
     GGCCAAGGGA

 401 CTCTGGTCAC TGTCTCTGCA GCCAAAACGA CACCCCCATC
     TGTCTATCCA

 451 CTGGCCCCTG GATCTGCTGC CCAAACTAAC TCCATGGTGA
     CCCTGGGATG

 501 CCTGGTCAAG GGCTATTTCC CTGAGCCAGT GACAGTGACC
     TGGAACTCTG

 551 GATCCCTGTC CAGCGGTGTG CACACCTTCC CAGCTGTCCT
     GCAGTCTGAC

 601 CTCTACACTC TGAGCAGCTC AGTGACTGTC CCCTCCAGCA
     CCTGGCCCAG

 651 CGAGACCGTC ACCTGCAACG TTGCCCACCC GGCCAGCAGC
     ACCAAGGTGG

 701 ACAAGAAAAT TGTGCCCAGG GATTGTGGTT GTAAGCCTTG
     CATATGTACA

 751 GTCCCAGAAG TATCATCTGT CTTCATCTTC CCCCCAAAGC
     CCAAGGATGT

 801 GCTCACCATT ACTCTGACTC CTAAGGTCAC GTGTGTTGTG
     GTAGACATCA

 851 GCAAGGATGA TCCCGAGGTC CAGTTCAGCT GGTTTGTAGA
     TGATGTGGAG

 901 GTGCACACAG CTCAGACGCA ACCCCGGGAG GAGCAGTTCA
     ACAGCACTTT

 951 CCGCTCAGTC AGTGAACTTC CCATCATGCA CCAGGACTGG
     CTCAATGGCA

1001 AGGAGTTCAA ATGCAGGGTC AACAGTGCAG CTTTCCCTGC
     CCCCATCGAG

1051 AAAACCATCT CCAAAACCAA AGGCAGACCG AAGGCTCCAC
     AGGTGTACAC

1101 CATTCCACCT CCCAAGGAGC AGATGGCCAA GGATAAAGTC
     AGTCTGACCT

1151 GCATGATAAC AGACTTCTTC CCTGAAGACA TTACTGTGGA
     GTGGCAGTGG
```

-continued

```
1201 AATGGGCAGC CAGCGGAGAA CTACAAGAAC ACTCAGCCCA
     TCATGGACAC

1251 AGATGGCTCT TACTTCATCT ACAGCAAGCT CAATGTGCAG
     AAGAGCAACT

1301 GGGAGGCAGG AAATACTTTC ACCTGCTCTG TGTTACATGA
     GGGCCTGCAC

1351 AACCACCATA CTGAGAAGAG CCTCTCCCAC TCTCCTGGTA
     AATGA
```

Ab-12

The sequences of the Antibody 12 (also referred to herein as Ab-12) LC and HC are as follows:

Ab-12 Light Chain:

Amino acid sequence of the mature form (signal peptide removed) of the Ab-12 LC:

(SEQ ID NO: 197)

1 DLQMTQTTSS LSASLGDRVT ISCRASQDIS NYLNWYQQKP DGTVKLLIFY

51 TSTLQSGVPS RFSGSGSGTN YSLTITNLEQ DDAATYFCQQ GDTLPYTFGG

101 GTKLEIK*RAD AAPTVSIFPP SSEQLTSGGA SVVCFLNNFY PKDINVKWKI*

151 *DGSERQNGVL NSWTDQDSKD STYSMSSTLT LTKDEYERHN SYTCEATHKT*

201 *STSPIVKSFN RNEC*

Nucleic acid sequence encoding the mature form (signal peptide removed) of the Ab-12 LC:

```
                                        (SEQ ID NO: 198)
   1 GATCTCCAGA TGACACAGAC TACTTCCTCC CTGTCTGCCT
     CTCTGGGAGA

  51 CAGAGTCACC ATCAGTTGCA GGGCAAGTCA GGACATTAGC
     AATTATTTAA

 101 ACTGGTATCA GCAGAAACCA GATGGAACTG TTAAGCTCCT
     GATCTTCTAC

 151 ACATCAACAT TACAGTCAGG AGTCCCATCG AGGTTCAGTG
     GCAGTGGGTC

 201 TGGAACAAAT TATTCTCTCA CCATTACCAA CCTGGAGCAA
     GATGATGCTG

 251 CCACTTACTT TTGCCAACAG GGTGATACGC TTCCGTACAC
     GTTCGGAGGG

 301 GGGACCAAGC TGGAAATAAA ACGGGCTGAT GCTGCACCAA
     CTGTATCCAT

 351 CTTCCCACCA TCCAGTGAGC AGTTAACATC TGGAGGTGCC
     TCAGTCGTGT

 401 GCTTCTTGAA CAACTTCTAC CCCAAAGACA TCAATGTCAA
     GTGGAAGATT

 451 GATGGCAGTG AACGACAAAA TGGCGTCCTG AACAGTTGGA
     CTGATCAGGA

 501 CAGCAAAGAC AGCACCTACA GCATGAGCAG CACCCTCACG
     TTGACCAAGG
```

-continued

```
551 ACGAGTATGA ACGACATAAC AGCTATACCT GTGAGGCCAC
    TCACAAGACA

601 TCAACTTCAC CCATTGTCAA GAGCTTCAAC AGGAATGAGT
    GTTAG
```

Amino acid sequence of the Ab-12 LC including signal peptide:

```
                                    (SEQ ID NO: 199)
  1 MMSSAQFLGL LLLCFQGSRC DLQMTQTTSS LSASLGDRVT
    ISCRASQDIS

 51 NYLNWYQQKP DGTVKLLIFY TSTLQSGVPS RFSGSGSGTN
    YSLTITNLEQ

101 DDAATYFCQQ GDTLPYTFGG GTKLEIKRAD AAPTVSIFPP
    SSEQLTSGGA

151 SVVCFLNNFY PKDINVKWKI DGSERQNGVL NSWTDQDSKD
    STYSMSSTLT

201 LTKDEYERHN SYTCEATHKT STSPIVKSFN RNEC
```

Nucleic acid sequence of the Ab-12 LC including signal peptide encoding sequence:

```
                                    (SEQ ID NO: 200)
  1 ATGATGTCCT CTGCTCAGTT CCTTGGTCTC CTGTTGCTCT
    GTTTTCAAGG

 51 TTCCAGATGT GATCTCCAGA TGACACAGAC TACTTCCTCC
    CTGTCTGCCT

101 CTCTGGGAGA CAGAGTCACC ATCAGTTGCA GGGCAAGTCA
    GGACATTAGC

151 AATTATTTAA ACTGGTATCA GCAGAAACCA GATGGAACTG
    TTAAGCTCCT

201 GATCTTCTAC ACATCAACAT TACAGTCAGG AGTCCCATCG
    AGGTTCAGTG

251 GCAGTGGGTC TGGAACAAAT TATTCTCTCA CCATTACCAA
    CCTGGAGCAA

301 GATGATGCTG CCACTTACTT TTGCCAACAG GGTGATACGC
    TTCCGTACAC

351 GTTCGGAGGG GGGACCAAGC TGGAAATAAA ACGGGCTGAT
    GCTGCACCAA

401 CTGTATCCAT CTTCCCACCA TCCAGTGAGC AGTTAACATC
    TGGAGGTGCC

451 TCAGTCGTGT GCTTCTTGAA CAACTTCTAC CCCAAAGACA
    TCAATGTCAA

501 GTGGAAGATT GATGGCAGTG AACGACAAAA TGGCGTCCTG
    AACAGTTGGA

551 CTGATCAGGA CAGCAAAGAC AGCACCTACA GCATGAGCAG
    CACCCTCACG

601 TTGACCAAGG ACGAGTATGA ACGACATAAC AGCTATACCT
    GTGAGGCCAC

651 TCACAAGACA TCAACTTCAC CCATTGTCAA GAGCTTCAAC
    AGGAATGAGT

701 GTTAG
```

Ab-12 Heavy Chain:

Amino acid sequence of the mature form (signal peptide removed) of the Ab-12 HC:

```
                                    (SEQ ID NO: 201)
  1 EVQLQQSGPE LMKPGASVKM SCKASGYTFT DYNMHWMKQN
    QGKSLEWIGE

 51 INPNSGGSGY NQKFKGKATL TVDKSSSTAY MELRSLTSED
    SAVYYCARLG

101 YYGNYEDWYF DVWGAGTTVT VSSAKTTPPS VYPLAPGSAA
    QTNSMVTLGC

151 LVKGYFPEPV TVTWNSGSLS SGVHTFPAVL QSDLYTLSSS
    VTVPSSTWPS

201 ETVTCNVAHP ASSTKVDKKI VPRDCGCKPC ICTVPEVSSV
    FIFPPKPKDV

251 LTITLTPKVT CVVVDISKDD PEVQFSWFVD DVEVHTAQTQ
    PREEQFNSTF

301 RSVSELPIMH QDWLNGKEFK CRVNSAAFPA PIEKTISKTK
    GRPKAPQVYT

351 IPPPKEQMAK DKVSLTCMIT DFFPEDITVE WQWNGQPAEN
    YKNTQPIMDT

401 DGSYFIYSKL NVQKSNWEAG NTFTCSVLHE GLHNHHTEKS
    LSHSPGK
```

Nucleic acid sequence encoding the mature form (signal peptide removed) of the Ab-12 HC:

```
                                    (SEQ ID NO: 202)
  1 GAGGTCCAGT TGCAACAGTC TGGACCTGAA CTAATGAAGC
    CTGGGGCTTC

 51 AGTGAAGATG TCCTGCAAGG CTTCTGGATA CACATTCACT
    GACTACAACA

101 TGCACTGGAT GAAGCAGAAC CAAGGAAAGA GCCTAGAGTG
    GATAGGAGAG

151 ATTAATCCTA ACAGTGGTGG TTCTGGTTAC AACCAGAAGT
    TCAAAGGCAA

201 GGCCACATTG ACTGTAGACA AGTCCTCCAG CACAGCCTAC
    ATGGAGCTCC

251 GCAGCCTGAC ATCTGAGGAC TCTGCAGTCT ATTACTGTGC
    AAGATTGGGC

301 TACTATGGTA ACTACGAGGA CTGGTATTTC GATGTCTGGG
    GCGCAGGGAC

351 CACGGTCACC GTCTCCTCTG CCAAAACGAC ACCCCCATCT
    GTCTATCCAC

401 TGGCCCCTGG ATCTGCTGCC CAAACTAACT CCATGGTGAC
    CCTGGGATGC

451 CTGGTCAAGG GCTATTTCCC TGAGCCAGTG ACAGTGACCT
    GGAACTCTGG

501 ATCCCTGTCC AGCGGTGTGC ACACCTTCCC AGCTGTCCTG
    CAGTCTGACC

551 TCTACACTCT GAGCAGCTCA GTGACTGTCC CCTCCAGCAC
    CTGGCCCAGC
```

-continued

```
 601 GAGACCGTCA CCTGCAACGT TGCCCACCCG GCCAGCAGCA
     CCAAGGTGGA

 651 CAAGAAAATT GTGCCCAGGG ATTGTGGTTG TAAGCCTTGC
     ATATGTACAG

 701 TCCCAGAAGT ATCATCTGTC TTCATCTTCC CCCCAAAGCC
     CAAGGATGTG

 751 CTCACCATTA CTCTGACTCC TAAGGTCACG TGTGTTGTGG
     TAGACATCAG

 801 CAAGGATGAT CCCGAGGTCC AGTTCAGCTG GTTTGTAGAT
     GATGTGGAGG

 851 TGCACACAGC TCAGACGCAA CCCCGGGAGG AGCAGTTCAA
     CAGCACTTTC

 901 CGCTCAGTCA GTGAACTTCC CATCATGCAC CAGGACTGGC
     TCAATGGCAA

 951 GGAGTTCAAA TGCAGGGTCA ACAGTGCAGC TTTCCCTGCC
     CCCATCGAGA

1001 AAACCATCTC CAAAACCAAA GGCAGACCGA AGGCTCCACA
     GGTGTACACC

1051 ATTCCACCTC CCAAGGAGCA GATGGCCAAG GATAAAGTCA
     GTCTGACCTG

1101 CATGATAACA GACTTCTTCC CTGAAGACAT TACTGTGGAG
     TGGCAGTGGA

1151 ATGGGCAGCC AGCGGAGAAC TACAAGAACA CTCAGCCCAT
     CATGGACACA

1201 GATGGCTCTT ACTTCATCTA CAGCAAGCTC AATGTGCAGA
     AGAGCAACTG

1251 GGAGGCAGGA AATACTTTCA CCTGCTCTGT GTTACATGAG
     GGCCTGCACA

1301 ACCACCATAC TGAGAAGAGC CTCTCCCACT CTCCTGGTAA
     ATGA
```

Amino acid sequence of the Ab-12 HC including signal peptide:

```
                                      (SEQ ID NO: 203)
   1 MGWSWTFLFL LSGTSGVLSE VQLQQSGPEL MKPGASVKMS
     CKASGYTFTD

  51 YNMHWMKQNQ GKSLEWIGEI NPNSGGSGYN QKFKGKATLT
     VDKSSSTAYM

 101 ELRSLTSEDS AVYYCARLGY YGNYEDWYFD VWGAGTTVTV
     SSAKTTPPSV

 151 YPLAPGSAAQ TNSMVTLGCL VKGYFPEPVT VTWNSGSLSS
     GVHTFPAVLQ

 201 SDLYTLSSSV TVPSSTWPSE TVTCNVAHPA SSTKVDKKIV
     PRDCGCKPCI

 251 CTVPEVSSVF IFPPKPKDVL TITLTPKVTC VVVDISKDDP
     EVQFSWFVDD

 301 VEVHTAQTQP REEQFNSTFR SVSELPIMHQ DWLNGKEFKC
     RVNSAAFPAP

 351 IEKTISKTKG RPKAPQVYTI PPPKEQMAKD KVSLTCMITD
     FFPEDITVEW

 401 QWNGQPAENY KNTQPIMDTD GSYFIYSKLN VQKSNWEAGN
     TFTCSVLHEG

 451 LHNHHTEKSL SHSPGK
```

Nucleic acid sequence of the Ab-12 HC including signal peptide encoding sequence:

```
                                      (SEQ ID NO: 204)
   1 ATGGGATGGA GCTGGACCTT TCTCTTCCTC CTGTCAGGAA
     CTTCGGGTGT

  51 CCTCTCTGAG GTCCAGTTGC AACAGTCTGG ACCTGAACTA
     ATGAAGCCTG

 101 GGGCTTCAGT GAAGATGTCC TGCAAGGCTT CTGGATACAC
     ATTCACTGAC

 151 TACAACATGC ACTGGATGAA GCAGAACCAA GGAAAGAGCC
     TAGAGTGGAT

 201 AGGAGAGATT AATCCTAACA GTGGTGGTTC TGGTTACAAC
     CAGAAGTTCA

 251 AAGGCAAGGC CACATTGACT GTAGACAAGT CCTCCAGCAC
     AGCCTACATG

 301 GAGCTCCGCA GCCTGACATC TGAGGACTCT GCAGTCTATT
     ACTGTGCAAG

 351 ATTGGGCTAC TATGGTAACT ACGAGGACTG GTATTTCGAT
     GTCTGGGGCG

 401 CAGGGACCAC GGTCACCGTC TCCTCTGCCA AAACGACACC
     CCCATCTGTC

 451 TATCCACTGG CCCCTGGATC TGCTGCCCAA ACTAACTCCA
     TGGTGACCCT

 501 GGGATGCCTG GTCAAGGGCT ATTTCCCTGA GCCAGTGACA
     GTGACCTGGA

 551 ACTCTGGATC CCTGTCCAGC GGTGTGCACA CCTTCCCAGC
     TGTCCTGCAG

 601 TCTGACCTCT ACACTCTGAG CAGCTCAGTG ACTGTCCCCT
     CCAGCACCTG

 651 GCCCAGCGAG ACCGTCACCT GCAACGTTGC CCACCCGGCC
     AGCAGCACCA

 701 AGGTGGACAA GAAAATTGTG CCCAGGGATT GTGGTTGTAA
     GCCTTGCATA

 751 TGTACAGTCC CAGAAGTATC ATCTGTCTTC ATCTTCCCCC
     CAAAGCCCAA

 801 GGATGTGCTC ACCATTACTC TGACTCCTAA GGTCACGTGT
     GTTGTGGTAG

 851 ACATCAGCAA GGATGATCCC GAGGTCCAGT TCAGCTGGTT
     TGTAGATGAT

 901 GTGGAGGTGC ACACAGCTCA GACGCAACCC CGGGAGGAGC
     AGTTCAACAG

 951 CACTTTCCGC TCAGTCAGTG AACTTCCCAT CATGCACCAG
     GACTGGCTCA

1001 ATGGCAAGGA GTTCAAATGC AGGGTCAACA GTGCAGCTTT
     CCCTGCCCCC

1051 ATCGAGAAAA CCATCTCCAA AACCAAAGGC AGACCGAAGG
     CTCCACAGGT

1101 GTACACCATT CCACCTCCCA AGGAGCAGAT GGCCAAGGAT
     AAAGTCAGTC

1151 TGACCTGCAT GATAACAGAC TTCTTCCCTG AAGACATTAC
     TGTGGAGTGG
```

-continued

```
1201 CAGTGGAATG GGCAGCCAGC GGAGAACTAC AAGAACACTC
     AGCCCATCAT

1251 GGACACAGAT GGCTCTTACT TCATCTACAG CAAGCTCAAT
     GTGCAGAAGA

1301 GCAACTGGGA GGCAGGAAAT ACTTTCACCT GCTCTGTGTT
     ACATGAGGGC

1351 CTGCACAACC ACCATACTGA GAAGAGCCTC TCCCACTCTC
     CTGGTAAATG

1401 A
```

Ab-13

The sequences of the Antibody 13 (also referred to herein as Ab-13) LC and HC are as follows:

Ab-13 Light Chain:

Amino acid sequence of the mature form (signal peptide removed) of the Ab-13 LC:

(SEQ ID NO: 205)

1 QIVLTQSPAI MSASPGEKVT MTCRASSSVT SSYLNWYQQK PGSSPKLWIY

51 STSNLASGVP ARFSGSGSGT SYSLTISSVE AEDAATYYCQ QYDFFPSTFG

101 GGTKLEIK*RA DAAPTVSIFP PSSEQLTSGG ASVVCFLNNF YPKDINVKWK*

151 *IDGSERQNGV LNSWTDQDSK DSTYSMSSTL TLTKDEYERH NSYTCEATHK*

201 *TSTSPIVKSF NRNEC*

Nucleic acid sequence encoding the mature form (signal peptide removed) of the Ab-13 LC:

(SEQ ID NO: 206)

```
  1 CAGATTGTTC TCACCCAGTC TCCAGCAATC ATGTCTGCAT
    CTCCAGGGGA

 51 GAAGGTCACC ATGACCTGCA GGGCCAGCTC AAGTGTAACT
    TCCAGTTACT

101 TGAACTGGTA CCAGCAGAAG CCAGGATCTT CCCCCAAACT
    CTGGATTTAT

151 AGCACATCCA ACCTGGCTTC AGGAGTCCCA GCTCGCTTCA
    GTGGCAGTGG

201 GTCTGGGACC TCTTACTCTC TCACAATCAG CAGTGTGGAG
    GCTGAGGATG

251 CTGCCACTTA TTACTGCCAG CAGTATGATT TTTTCCCATC
    GACGTTCGGT

301 GGAGGCACCA AGCTGGAAAT CAAGCGGGCT GATGCTGCAC
    CAACTGTATC

351 CATCTTCCCA CCATCCAGTG AGCAGTTAAC ATCTGGAGGT
    GCCTCAGTCG

401 TGTGCTTCTT GAACAACTTC TACCCCAAAG ACATCAATGT
    CAAGTGGAAG

451 ATTGATGGCA GTGAACGACA AAATGGCGTC CTGAACAGTT
    GGACTGATCA

501 GGACAGCAAA GACAGCACCT ACAGCATGAG CAGCACCCTC
    ACGTTGACCA
```

-continued

```
551 AGGACGAGTA TGAACGACAT AACAGCTATA CCTGTGAGGC
    CACTCACAAG

601 ACATCAACTT CACCCATCGT CAAGAGCTTC AACAGGAATG
    AGTGT
```

Amino acid sequence of the Ab-13 LC including signal peptide:

(SEQ ID NO: 207)

```
  1 MDSQVQIFSF LLISALVKMS RGQIVLTQSP AIMSASPGEK
    VTMTCRASSS

 51 VTSSYLNWYQ QKPGSSPKLW IYSTSNLASG VPARFSGSGS
    GTSYSLTISS

101 VEAEDAATYY CQQYDFFPST FGGGTKLEIK RADAAPTVSI
    FPPSSEQLTS

151 GGASVVCFLN NFYPKDINVK WKIDGSERQN GVLNSWTDQD
    SKDSTYSMSS

201 TLTLTKDEYE RHNSYTCEAT HKTSTSPIVK SFNRNEC
```

Nucleic acid sequence of the Ab-13 LC including signal peptide encoding sequence:

(SEQ ID NO: 208)

```
  1 ATGGATTCTC AAGTGCAGAT TTTCAGCTTC CTTCTAATCA
    GTGCCTTAGT

 51 CAAAATGTCC AGAGGACAGA TTGTTCTCAC CCAGTCTCCA
    GCAATCATGT

101 CTGCATCTCC AGGGGAGAAG GTCACCATGA CCTGCAGGGC
    CAGCTCAAGT

151 GTAACTTCCA GTTACTTGAA CTGGTACCAG CAGAAGCCAG
    GATCTTCCCC

201 CAAACTCTGG ATTTATAGCA CATCCAACCT GGCTTCAGGA
    GTCCCAGCTC

251 GCTTCAGTGG CAGTGGGTCT GGGACCTCTT ACTCTCTCAC
    AATCAGCAGT

301 GTGGAGGCTG AGGATGCTGC CACTTATTAC TGCCAGCAGT
    ATGATTTTTT

351 CCCATCGACG TTCGGTGGAG GCACCAAGCT GGAAATCAAG
    CGGGCTGATG

401 CTGCACCAAC TGTATCCATC TTCCCACCAT CCAGTGAGCA
    GTTAACATCT

451 GGAGGTGCCT CAGTCGTGTG CTTCTTGAAC AACTTCTACC
    CCAAAGACAT

501 CAATGTCAAG TGGAAGATTG ATGGCAGTGA ACGACAAAAT
    GGCGTCCTGA

551 ACAGTTGGAC TGATCAGGAC AGCAAAGACA GCACCTACAG
    CATGAGCAGC

601 ACCCTCACGT TGACCAAGGA CGAGTATGAA CGACATAACA
    GCTATACCTG

651 TGAGGCCACT CACAAGACAT CAACTTCACC CATCGTCAAG
    AGCTTCAACA

701 GGAATGAGTG T
```

Ab-13 Heavy Chain:

Amino acid sequence of the mature form (signal peptide removed) of the Ab-13 HC:

```
                                        (SEQ ID NO: 209)
  1 EVQLQQSGPE LVKPGASVKM SCKASGYTFT DYYMNWVKQS
    HGESLEWIGD

 51 INPYNDDTTY NHKFKGKATL TVDKSSNTAY MQLNSLTSED
    SAVYYCARET

101 AVITTNAMDY WGQGTSVTVS SAKTTPPSVY PLAPGSAAQT
    NSMVTLGCLV

151 KGYFPEPVTV TWNSGSLSSG VHTFPAVLQS DLYTLSSSVT
    VPSSTWPSET

201 VTCNVAHPAS STKVDKKIVP RDCGCKPCIC TVPEVSSVFI
    FPPKPKDVLT

251 ITLTPKVTCV VVDISKDDPE VQFSWFVDDV EVHTAQTQPR
    EEQFNSTFRS

301 VSELPIMHQD WLNGKEFKCR VNSAAFPAPI EKTISKTKGR
    PKAPQVYTIP

351 PPKEQMAKDK VSLTCMITDF FPEDITVEWQ WNGQPAENYK
    NTQPIMDTDG

401 SYFIYSKLNV QKSNWEAGNT FTCSVLHEGL HNHHTEKSLS
    HSPGK
```

Nucleic acid sequence encoding the mature form (signal peptide removed) of the Ab-13 HC:

```
                                        (SEQ ID NO: 210)
   1 GAGGTCCAGC TGCAACAATC TGGACCTGAG CTGGTGAAGC
     CTGGGGCTTC

  51 AGTGAAGATG TCCTGTAAGG CTTCTGGATA CACATTCACT
     GACTACTACA

 101 TGAACTGGGT GAAGCAGAGC CATGGAGAGA GCCTTGAGTG
     GATTGGAGAT

 151 ATTAATCCTT ACAACGATGA TACTACCTAC AACCACAAGT
     TCAAGGGCAA

 201 GGCCACATTG ACTGTAGACA AATCCTCCAA CACAGCCTAC
     ATGCAGCTCA

 251 ACAGCCTGAC ATCTGAGGAC TCTGCAGTCT ATTACTGTGC
     AAGAGAGACG

 301 GCCGTTATTA CTACGAATGC TATGGACTAC TGGGGTCAAG
     GAACCTCAGT

 351 CACCGTCTCC TCAGCCAAAA CGACACCCCC ATCTGTCTAT
     CCACTGGCCC

 401 CTGGATCTGC TGCCCAAACT AACTCCATGG TGACCCTGGG
     ATGCCTGGTC

 451 AAGGGCTATT TCCCTGAGCC AGTGACAGTG ACCTGGAACT
     CTGGATCCCT

 501 GTCCAGCGGT GTGCACACCT TCCCAGCTGT CCTGCAGTCT
     GACCTCTACA

 551 CTCTGAGCAG CTCAGTGACT GTCCCCTCCA GCACCTGGCC
     CAGCGAGACC
```

-continued

```
 601 GTCACCTGCA ACGTTGCCCA CCCGGCCAGC AGCACCAAGG
     TGGACAAGAA

 651 AATTGTGCCC AGGGATTGTG GTTGTAAGCC TTGCATATGT
     ACAGTCCCAG

 701 AAGTATCATC TGTCTTCATC TTCCCCCCAA AGCCCAAGGA
     TGTGCTCACC

 751 ATTACTCTGA CTCCTAAGGT CACGTGTGTT GTGGTAGACA
     TCAGCAAGGA

 801 TGATCCCGAG GTCCAGTTCA GCTGGTTTGT AGATGATGTG
     GAGGTGCACA

 851 CAGCTCAGAC GCAACCCCGG GAGGAGCAGT TCAACAGCAC
     TTTCCGCTCA

 901 GTCAGTGAAC TTCCCATCAT GCACCAGGAC TGGCTCAATG
     GCAAGGAGTT

 951 CAAATGCAGG GTCAACAGTG CAGCTTTCCC TGCCCCCATC
     GAGAAAACCA

1001 TCTCCAAAAC CAAAGGCAGA CCGAAGGCTC CACAGGTGTA
     CACCATTCCA

1051 CCTCCCAAGG AGCAGATGGC CAAGGATAAA GTCAGTCTGA
     CCTGCATGAT

1101 AACAGACTTC TTCCCTGAAG ACATTACTGT GGAGTGGCAG
     TGGAATGGGC

1151 AGCCAGCGGA GAACTACAAG AACACTCAGC CCATCATGGA
     CACAGATGGC

1201 TCTTACTTCA TCTACAGCAA GCTCAATGTG CAGAAGAGCA
     ACTGGGAGGC

1251 AGGAAATACT TTCACCTGCT CTGTGTTACA TGAGGGCCTG
     CACAACCACC

1301 ATACTGAGAA GAGCCTCTCC CACTCTCCTG GTAAA
```

Amino acid sequence of the Ab-13 HC including signal peptide:

```
                                        (SEQ ID NO: 211)
  1 MGWNWIFLFL LSGTAGVYSE VQLQQSGPEL VKPGASVKMS
    CKASGYTFTD

 51 YYMNWVKQSH GESLEWIGDI NPYNDDTTYN HKFKGKATLT
    VDKSSNTAYM

101 QLNSLTSEDS AVYYCARETA VITTNAMDYW GQGTSVTVSS
    AKTTPPSVYP

151 LAPGSAAQTN SMVTLGCLVK GYFPEPVTVT WNSGSLSSGV
    HTFPAVLQSD

201 LYTLSSSVTV PSSTWPSETV TCNVAHPASS TKVDKKIVPR
    DCGCKPCICT

251 VPEVSSVFIF PPKPKDVLTI TLTPKVTCVV VDISKDDPEV
    QFSWFVDDVE

301 VHTAQTQPRE EQFNSTFRSV SELPIMHQDW LNGKEFKCRV
    NSAAFPAPIE

351 KTISKTKGRP KAPQVYTIPP PKEQMAKDKV SLTCMITDFF
    PEDITVEWQW
```

-continued

```
401 NGQPAENYKN TQPIMDTDGS YFIYSKLNVQ KSNWEAGNTF
    TCSVLHEGLH

451 NHHTEKSLSH SPGK
```

Nucleic acid sequence of the Ab-13 HC including signal peptide encoding sequence:

```
                                        (SEQ ID NO: 212)
   1 ATGGGATGGA ACTGGATCTT TCTCTTCCTC TTGTCAGGAA
     CTGCAGGTGT

  51 CTACTCTGAG GTCCAGCTGC AACAATCTGG ACCTGAGCTG
     GTGAAGCCTG

 101 GGGCTTCAGT GAAGATGTCC TGTAAGGCTT CTGGATACAC
     ATTCACTGAC

 151 TACTACATGA ACTGGGTGAA GCAGAGCCAT GGAGAGAGCC
     TTGAGTGGAT

 201 TGGAGATATT AATCCTTACA ACGATGATAC TACCTACAAC
     CACAAGTTCA

 251 AGGGCAAGGC CACATTGACT GTAGACAAAT CCTCCAACAC
     AGCCTACATG

 301 CAGCTCAACA GCCTGACATC TGAGGACTCT GCAGTCTATT
     ACTGTGCAAG

 351 AGAGACGGCC GTTATTACTA CGAATGCTAT GGACTACTGG
     GGTCAAGGAA

 401 CCTCAGTCAC CGTCTCCTCA GCCAAAACGA CACCCCCATC
     TGTCTATCCA

 451 CTGGCCCCTG GATCTGCTGC CCAAACTAAC TCCATGGTGA
     CCCTGGGATG

 501 CCTGGTCAAG GGCTATTTCC CTGAGCCAGT GACAGTGACC
     TGGAACTCTG

 551 GATCCCTGTC CAGCGGTGTG CACACCTTCC CAGCTGTCCT
     GCAGTCTGAC

 601 CTCTACACTC TGAGCAGCTC AGTGACTGTC CCCTCCAGCA
     CCTGGCCCAG

 651 CGAGACCGTC ACCTGCAACG TTGCCCACCC GGCCAGCAGC
     ACCAAGGTGG

 701 ACAAGAAAAT TGTGCCCAGG GATTGTGGTT GTAAGCCTTG
     CATATGTACA

 751 GTCCCAGAAG TATCATCTGT CTTCATCTTC CCCCCAAAGC
     CCAAGGATGT

 801 GCTCACCATT ACTCTGACTC CTAAGGTCAC GTGTGTTGTG
     GTAGACATCA

 851 GCAAGGATGA TCCCGAGGTC CAGTTCAGCT GGTTTGTAGA
     TGATGTGGAG

 901 GTGCACACAG CTCAGACGCA ACCCCGGGAG GAGCAGTTCA
     ACAGCACTTT

 951 CCGCTCAGTC AGTGAACTTC CCATCATGCA CCAGGACTGG
     CTCAATGGCA

1001 AGGAGTTCAA ATGCAGGGTC AACAGTGCAG CTTTCCCTGC
     CCCCATCGAG

1051 AAAACCATCT CCAAAACCAA AGGCAGACCG AAGGCTCCAC
     AGGTGTACAC
```

-continued

```
1101 CATTCCACCT CCCAAGGAGC AGATGGCCAA GGATAAAGTC
     AGTCTGACCT

1151 GCATGATAAC AGACTTCTTC CCTGAAGACA TTACTGTGGA
     GTGGCAGTGG

1201 AATGGGCAGC CAGCGGAGAA CTACAAGAAC ACTCAGCCCA
     TCATGGACAC

1251 AGATGGCTCT TACTTCATCT ACAGCAAGCT CAATGTGCAG
     AAGAGCAACT

1301 GGGAGGCAGG AAATACTTTC ACCTGCTCTG TGTTACATGA
     GGGCCTGCAC

1351 AACCACCATA CTGAGAAGAG CCTCTCCCAC TCTCCTGGTA
     AA
```

Ab-13 was humanized to generate Ab-14.

The sequences of the Antibody 14 (also referred to herein as Ab-14) LC and HC are as follows:

Ab-14 Light Chain:

Amino acid sequence of the mature form (signal peptide removed) of the Ab-14 LC:

(SEQ ID NO: 213)

1 DIQLTQSPSF LSASVGDRVT ITCRASSSVT SSYLNWYQQK PGKAPKLLIY

51 STSNLASGVP SRFSGSGSGT EFTLTISSLQ PEDFATYYCQ QYDFFPSTFG

101 GGTKVEIK*RT VAAPSVFIFP PSDEQLKSGT ASVVCLLNNF YPREAKVQWK*

151 *VDNALQSGNS QESVTEQDSK DSTYSLSSTL TLSKADYEKH KVYACEVTHQ*

201 *GLSSPVTKSF NRGEC*

Nucleic acid sequence encoding the mature form (signal peptide removed) of the Ab-14 LC:

```
                                        (SEQ ID NO: 214)
  1 GACATCCAGC TGACCCAGAG CCCCAGCTTC CTTTCCGCAT
    CCGTTGGTGA

 51 CCGAGTAACA ATCACATGCC GCGCCTCATC TTCAGTTACA
    TCTTCTTATC

101 TTAATTGGTA TCAACAAAAA CCAGGAAAAG CACCTAAACT
    TCTTATATAC

151 TCTACATCTA ATCTCGCATC AGGAGTTCCC TCTCGATTTT
    CAGGATCTGG

201 ATCAGGCACA GAATTTACAC TTACTATATC ATCACTCCAA
    CCAGAAGACT

251 TCGCCACTTA TTACTGCCAA CAATACGATT TTTTTCCAAG
    CACATTCGGA

301 GGAGGTACAA AAGTAGAAAT CAAGCGTACG GTGGCTGCAC
    CATCTGTCTT

351 CATCTTCCCG CCATCTGATG AGCAGTTGAA ATCTGGAACT
    GCCTCTGTTG

401 TGTGCCTGCT GAATAACTTC TATCCCAGAG AGGCCAAAGT
    ACAGTGGAAG

451 GTGGATAACG CCCTCCAATC GGGTAACTCC CAGGAGAGTG
    TCACAGAGCA
```

-continued

```
501 GGACAGCAAG GACAGCACCT ACAGCCTCAG CAGCACCCTG
    ACGCTGAGCA

551 AAGCAGACTA CGAGAAACAC AAAGTCTACG CCTGCGAAGT
    CACCCATCAG

601 GGCCTGAGCT CGCCCGTCAC AAAGAGCTTC AACAGGGGAG
    AGTGT
```

Amino acid sequence of the Ab-14 LC including signal peptide:

```
                                          (SEQ ID NO: 215)
  1 MDMRVPAQLL GLLLLWLPGA RCDIQLTQSP SFLSASVGDR
    VTITCRASSS

 51 VTSSYLNWYQ QKPGKAPKLL IYSTSNLASG VPSRFSGSGS
    GTEFTLTISS

101 LQPEDFATYY CQQYDFFPST FGGGTKVEIK RTVAAPSVFI
    FPPSDEQLKS

151 GTASVVCLLN NFYPREAKVQ WKVDNALQSG NSQESVTEQD
    SKDSTYSLSS

201 TLTLSKADYE KHKVYACEVT HQGLSSPVTK SFNRGEC
```

Nucleic acid sequence of the Ab-14 LC including signal peptide encoding sequence:

```
                                          (SEQ ID NO: 216)
  1 ATGGACATGA GGGTCCCCGC TCAGCTCCTG GGGCTCCTGC
    TACTCTGGCT

 51 CCCAGGTGCC AGATGTGACA TCCAGCTGAC CCAGAGCCCC
    AGCTTCCTTT

101 CCGCATCCGT TGGTGACCGA GTAACAATCA CATGCCGCGC
    CTCATCTTCA

151 GTTACATCTT CTTATCTTAA TTGGTATCAA CAAAAACCAG
    GAAAAGCACC

201 TAAACTTCTT ATATACTCTA CATCTAATCT CGCATCAGGA
    GTTCCCTCTC

251 GATTTTCAGG ATCTGGATCA GGCACAGAAT TTACACTTAC
    TATATCATCA

301 CTCCAACCAG AAGACTTCGC CACTTATTAC TGCCAACAAT
    ACGATTTTTT

351 TCCAAGCACA TTCGGAGGAG GTACAAAAGT AGAAATCAAG
    CGTACGGTGG

401 CTGCACCATC TGTCTTCATC TTCCCGCCAT CTGATGAGCA
    GTTGAAATCT

451 GGAACTGCCT CTGTTGTGTG CCTGCTGAAT AACTTCTATC
    CCAGAGAGGC

501 CAAAGTACAG TGGAAGGTGG ATAACGCCCT CCAATCGGGT
    AACTCCCAGG

551 AGAGTGTCAC AGAGCAGGAC AGCAAGGACA GCACCTACAG
    CCTCAGCAGC

601 ACCCTGACGC TGAGCAAAGC AGACTACGAG AAACACAAAG
    TCTACGCCTG

651 CGAAGTCACC CATCAGGGCC TGAGCTCGCC CGTCACAAAG
    AGCTTCAACA

701 GGGGAGAGTG T
```

Ab-14 Heavy Chain:

Amino acid sequence of the mature form (signal peptide removed) of the Ab-14 HC:

```
                                          (SEQ ID NO: 217)
  1 EVQLVQSGAE VKKPGASVKV SCKASGYTFT DYYMNWVRQA
    PGQRLEWMGD

 51 INPYNDDTTY NHKFKGRVTI TRDTSASTAY MELSSLRSED
    TAVYYCARET

101 AVITTNAMDY WGQGTTVTVS SASTKGPSVF PLAPCSRSTS
    ESTAALGCLV

151 KDYFPEPVTV SWNSGALTSG VHTFPAVLQS SGLYSLSSVV
    TVPSSNFGTQ

201 TYTCNVDHKP SNTKVDKTVE RKCCVECPPC PAPPVAGPSV
    FLFPPKPKDT

251 LMISRTPEVT CVVVDVSHED PEVQFNWYVD GVEVHNAKTK
    PREEQFNSTF

301 RVVSVLTVVH QDWLNGKEYK CKVSNKGLPA PIEKTISKTK
    GQPREPQVYT

351 LPPSREEMTK NQVSLTCLVK GFYPSDIAVE WESNGQPENN
    YKTTPPMLDS

401 DGSFFLYSKL TVDKSRWQQG NVFSCSVMHE ALHNHYTQKS
    LSLSPGK
```

Amino acid sequence of the mature form (signal peptide removed) of the Ab-14 HC without carboxy-terminal lysine:

```
                                          (SEQ ID NO: 393)
  1 EVQLVQSGAE VKKPGASVKV SCKASGYTFT DYYMNWVRQA
    PGQRLEWMGD

 51 INPYNDDTTY NHKFKGRVTI TRDTSASTAY MELSSLRSED
    TAVYYCARET

101 AVITTNAMDY WGQGTTVTVS SASTKGPSVF PLAPCSRSTS
    ESTAALGCLV

151 KDYFPEPVTV SWNSGALTSG VHTFPAVLQS SGLYSLSSVV
    TVPSSNFGTQ

201 TYTCNVDHKP SNTKVDKTVE RKCCVECPPC PAPPVAGPSV
    FLFPPKPKDT

251 LMISRTPEVT CVVVDVSHED PEVQFNWYVD GVEVHNAKTK
    PREEQFNSTF

301 RVVSVLTVVH QDWLNGKEYK CKVSNKGLPA PIEKTISKTK
    GQPREPQVYT

351 LPPSREEMTK NQVSLTCLVK GFYPSDIAVE WESNGQPENN
    YKTTPPMLDS

401 DGSFFLYSKL TVDKSRWQQG NVFSCSVMHE ALHNHYTQKS
    LSLSPG
```

Nucleic acid sequence encoding the mature form (signal peptide removed) of the Ab-14 HC:

(SEQ ID NO: 218)

```
   1 GAGGTGCAGC TGGTGCAGAG CGGCGCCGAG GTCAAGAAAC
     CTGGAGCAAG

  51 CGTAAAGGTT AGTTGCAAAG CATCTGGATA CACATTTACC
     GACTACTACA

 101 TGAATTGGGT ACGACAAGCC CCTGGACAAA GACTTGAATG
     GATGGGAGAC

 151 ATTAACCCTT ATAACGACGA CACTACATAC AATCATAAAT
     TTAAAGGAAG

 201 AGTTACAATT ACAAGAGATA CATCCGCATC AACCGCCTAT
     ATGGAACTTT

 251 CCTCATTGAG ATCTGAAGAC ACTGCTGTTT ATTACTGTGC
     AAGAGAAACT

 301 GCCGTTATTA CTACTAACGC TATGGATTAC TGGGGTCAAG
     GAACCACTGT

 351 TACCGTCTCT AGTGCCTCCA CCAAGGGCCC ATCGGTCTTC
     CCCCTGGCGC

 401 CCTGCTCCAG GAGCACCTCC GAGAGCACAG CGGCCCTGGG
     CTGCCTGGTC

 451 AAGGACTACT TCCCCGAACC GGTGACGGTG TCGTGGAACT
     CAGGCGCTCT

 501 GACCAGCGGC GTGCACACCT TCCCAGCTGT CCTACAGTCC
     TCAGGACTCT

 551 ACTCCCTCAG CAGCGTGGTG ACCGTGCCCT CCAGCAACTT
     CGGCACCCAG

 601 ACCTACACCT GCAACGTAGA TCACAAGCCC AGCAACACCA
     AGGTGGACAA

 651 GACAGTTGAG CGCAAATGTT GTGTCGAGTG CCCACCGTGC
     CCAGCACCAC

 701 CTGTGGCAGG ACCGTCAGTC TTCCTCTTCC CCCCAAAACC
     CAAGGACACC

 751 CTCATGATCT CCCGGACCCC TGAGGTCACG TGCGTGGTGG
     TGGACGTGAG

 801 CCACGAAGAC CCCGAGGTCC AGTTCAACTG GTACGTGGAC
     GGCGTGGAGG

 851 TGCATAATGC CAAGACAAAG CCACGGGAGG AGCAGTTCAA
     CAGCACGTTC

 901 CGTGTGGTCA GCGTCCTCAC CGTTGTGCAC CAGGACTGGC
     TGAACGGCAA

 951 GGAGTACAAG TGCAAGGTCT CCAACAAAGG CCTCCCAGCC
     CCCATCGAGA

1001 AAACCATCTC CAAAACCAAA GGGCAGCCCC GAGAACCACA
     GGTGTACACC

1051 CTGCCCCCAT CCCGGGAGGA GATGACCAAG AACCAGGTCA
     GCCTGACCTG

1101 CCTGGTCAAA GGCTTCTACC CCAGCGACAT CGCCGTGGAG
     TGGGAGAGCA

1151 ATGGGCAGCC GGAGAACAAC TACAAGACCA CACCTCCCAT
     GCTGGACTCC

1201 GACGGCTCCT TCTTCCTCTA CAGCAAGCTC ACCGTGGACA
     AGAGCAGGTG
```

-continued

```
1251 GCAGCAGGGG AACGTCTTCT CATGCTCCGT GATGCATGAG
     GCTCTGCACA

1301 ACCACTACAC GCAGAAGAGC CTCTCCCTGT CTCCGGGTAA A
```

Amino acid sequence of the Ab-14 HC including signal peptide:

(SEQ ID NO: 219)

```
  1 MDWTWRILFL VAAATGAHSE VQLVQSGAEV KKPGASVKVS
    CKASGYTFTD

 51 YYMNWVRQAP GQRLEWMGDI NPYNDDTTYN HKFKGRVTIT
    RDTSASTAYM

101 ELSSLRSEDT AVYYCARETA VITTNAMDYW GQGTTVTVSS
    ASTKGPSVFP

151 LAPCSRSTSE STAALGCLVK DYFPEPVTVS WNSGALTSGV
    HTFPAVLQSS

201 GLYSLSSVVT VPSSNFGTQT YTCNVDHKPS NTKVDKTVER
    KCCVECPPCP

251 APPVAGPSVF LFPPKPKDTL MISRTPEVTC VVVDVSHEDP
    EVQFNWYVDG

301 VEVHNAKTKP REEQFNSTFR VVSVLTVVHQ DWLNGKEYKC
    KVSNKGLPAP

351 IEKTISKTKG QPREPQVYTL PPSREEMTKN QVSLTCLVKG
    FYPSDIAVEW

401 ESNGQPENNY KTTPPMLDSD GSFFLYSKLT VDKSRWQQGN
    VFSCSVMHEA

451 LHNHYTQKSL SLSPGK
```

Nucleic acid sequence of the Ab-14 HC including signal peptide encoding sequence:

(SEQ ID NO: 220)

```
  1 ATGGACTGGA CCTGGAGGAT CCTCTTCTTG GTGGCAGCAG
    CCACAGGAGC

 51 CCACTCCGAG GTGCAGCTGG TGCAGAGCGG CGCCGAGGTC
    AAGAAACCTG

101 GAGCAAGCGT AAAGGTTAGT TGCAAAGCAT CTGGATACAC
    ATTTACCGAC

151 TACTACATGA ATTGGGTACG ACAAGCCCCT GGACAAAGAC
    TTGAATGGAT

201 GGGAGACATT AACCCTTATA ACGACGACAC TACATACAAT
    CATAAATTTA

251 AAGGAAGAGT TACAATTACA AGAGATACAT CCGCATCAAC
    CGCCTATATG

301 GAACTTTCCT CATTGAGATC TGAAGACACT GCTGTTTATT
    ACTGTGCAAG

351 AGAAACTGCC GTTATTACTA CTAACGCTAT GGATTACTGG
    GGTCAAGGAA

401 CCACTGTTAC CGTCTCTAGT GCCTCCACCA AGGGCCCATC
    GGTCTTCCCC

451 CTGGCGCCCT GCTCCAGGAG CACCTCCGAG AGCACAGCGG
    CCCTGGGCTG

501 CCTGGTCAAG GACTACTTCC CCGAACCGGT GACGGTGTCG
    TGGAACTCAG

551 GCGCTCTGAC CAGCGGCGTG CACACCTTCC CAGCTGTCCT
    ACAGTCCTCA
```

-continued

```
 601 GGACTCTACT CCCTCAGCAG CGTGGTGACC GTGCCCTCCA
     GCAACTTCGG

 651 CACCCAGACC TACACCTGCA ACGTAGATCA CAAGCCCAGC
     AACACCAAGG

 701 TGGACAAGAC AGTTGAGCGC AAATGTTGTG TCGAGTGCCC
     ACCGTGCCCA

 751 GCACCACCTG TGGCAGGACC GTCAGTCTTC CTCTTCCCCC
     CAAAACCCAA

 801 GGACACCCTC ATGATCTCCC GGACCCCTGA GGTCACGTGC
     GTGGTGGTGG

 851 ACGTGAGCCA CGAAGACCCC GAGGTCCAGT TCAACTGGTA
     CGTGGACGGC

 901 GTGGAGGTGC ATAATGCCAA GACAAAGCCA CGGGAGGAGC
     AGTTCAACAG

 951 CACGTTCCGT GTGGTCAGCG TCCTCACCGT TGTGCACCAG
     GACTGGCTGA

1001 ACGGCAAGGA GTACAAGTGC AAGGTCTCCA ACAAAGGCCT
     CCCAGCCCCC

1051 ATCGAGAAAA CCATCTCCAA AACCAAAGGG CAGCCCCGAG
     AACCACAGGT

1101 GTACACCCTG CCCCCATCCC GGGAGGAGAT GACCAAGAAC
     CAGGTCAGCC

1151 TGACCTGCCT GGTCAAAGGC TTCTACCCCA GCGACATCGC
     CGTGGAGTGG

1201 GAGAGCAATG GGCAGCCGGA GAACAACTAC AAGACCACAC
     CTCCCATGCT

1251 GGACTCCGAC GGCTCCTTCT TCCTCTACAG CAAGCTCACC
     GTGGACAAGA

1301 GCAGGTGGCA GCAGGGGAAC GTCTTCTCAT GCTCCGTGAT
     GCATGAGGCT

1351 CTGCACAACC ACTACACGCA GAAGAGCCTC TCCCTGTCTC
     CGGGTAAA
```

The CDR sequences in the variable region of the heavy chain of Ab-14 are:

```
CDR-H1:  DYYMN (SEQ ID NO: 296)

CDR-H2:  DINPYNDDTTYNHKFKG (SEQ ID NO: 297)

CDR-H3:  ETAVITTNAMD (SEQ ID NO: 298)
```

The light chain variable region CDR sequences of Ab-14 are:

```
CDR-L1:  RASSSVTSSYLN (SEQ ID NO: 284)

CDR-L2:  STSNLAS (SEQ ID NO: 285)

CDR-L3:  QQYDFFPST (SEQ ID NO: 286)
```

Ab-14 Variable domains:

Ab-14 light chain variable domain amino acid sequence (without signal sequence):

```
                                    (SEQ ID NO: 380)
  1 DIQLTQSPSF LSASVGDRVT ITCRASSSVT SSYLNWYQQK
    PGKAPKLLIY
```

-continued

```
 51 STSNLASGVP SRFSGSGSGT EFTLTISSLQ PEDFATYYCQ
    QYDFFPSTFG

101 GGTKVEIK
```

Ab-14 light chain variable domain DNA sequence (without signal sequence):

```
                                    (SEQ ID NO: 381)
  1 GACATCCAGC TGACCCAGAG CCCCAGCTTC CTTTCCGCAT
    CCGTTGGTGA

 51 CCGAGTAACA ATCACATGCC GCGCCTCATC TTCAGTTACA
    TCTTCTTATC

101 TTAATTGGTA TCAACAAAAA CCAGGAAAAG CACCTAAACT
    TCTTATATAC

151 TCTACATCTA ATCTCGCATC AGGAGTTCCC TCTCGATTTT
    CAGGATCTGG

201 ATCAGGCACA GAATTTACAC TTACTATATC ATCACTCCAA
    CCAGAAGACT

251 TCGCCACTTA TTACTGCCAA CAATACGATT TTTTTCCAAG
    CACATTCGGA

301 GGAGGTACAA AAGTAGAAAT CAAG
```

Ab-14 heavy chain variable domain amino acid sequence (without signal sequence):

```
                                    (SEQ ID NO: 382)
  1 EVQLVQSGAE VKKPGASVKV SCKASGYTFT DYYMNWVRQA
    PGQRLEWMGD

 51 INPYNDDTTY NHKFKGRVTI TRDTSASTAY MELSSLRSED
    TAVYYCARET

101 AVITTNAMDY WGQGTTVTVS S
```

Ab-14 heavy chain variable domain DNA sequence (without signal sequence):

```
                                    (SEQ ID NO: 383)
  1 GAGGTGCAGC TGGTGCAGAG CGGCGCCGAG GTCAAGAAAC
    CTGGAGCAAG

 51 CGTAAAGGTT AGTTGCAAAG CATCTGGATA CACATTTACC
    GACTACTACA

101 TGAATTGGGT ACGACAAGCC CCTGGACAAA GACTTGAATG
    GATGGGAGAC

151 ATTAACCCTT ATAACGACGA CACTACATAC AATCATAAAT
    TTAAAGGAAG

201 AGTTACAATT ACAAGAGATA CATCCGCATC AACCGCCTAT
    ATGGAACTTT

251 CCTCATTGAG ATCTGAAGAC ACTGCTGTTT ATTACTGTGC
    AAGAGAAACT

301 GCCGTTATTA CTACTAACGC TATGGATTAC TGGGGTCAAG
    GAACCACTGT

351 TACCGTCTCT AGT
```

Ab-3 was humanized to generate Ab-15.

Ab-15

The sequences of the Antibody 15 (also referred to herein as Ab-15) LC and HC are as follows:

Ab-15 Light Chain:

Amino acid sequence of the mature form (signal peptide removed) of the Ab-15 LC:

```
                                    (SEQ ID NO: 221)
  1 DIQMTQSPSS LSASVGDRVT ITCSVSSTIS SNHLHWFQQK
    PGKAPKSLIY

 51 GTSNLASGVP SRFSGSGSGT DFTLTISSLQ PEDFATYYCQ
    QWSSYPLTFG

101 GGTKVEIKRT VAAPSVFIFP PSDEQLKSGT ASVVCLLNNF
    YPREAKVQWK

151 VDNALQSGNS QESVTEQDSK DSTYSLSSTL TLSKADYEKH
    KVYACEVTHQ

201 GLSSPVTKSF NRGEC
```

Nucleic acid sequence encoding the mature form (signal peptide removed) of the Ab-15 LC:

```
                                    (SEQ ID NO: 222)
  1 GACATCCAGA TGACCCAGTC TCCATCCTCC CTCTCAGCAT
    CCGTAGGCGA

 51 TAGAGTTACA ATAACATGCA GCGTATCATC AACTATATCA
    TCAAATCATC

101 TTCATTGGTT CCAACAGAAA CCCGGCAAAG CACCTAAATC
    ACTTATATAC

151 GGCACATCAA ATCTCGCATC AGGCGTTCCT TCAAGATTTT
    CAGGCTCTGG

201 CTCAGGCACC GACTTTACTC TTACAATATC CTCCCTCCAA
    CCCGAAGACT

251 TCGCAACCTA TTACTGTCAA CAATGGTCCT CATATCCACT
    CACATTTGGC

301 GGCGGCACAA AAGTAGAAAT TAAACGTACG GTGGCTGCAC
    CATCTGTCTT

351 CATCTTCCCG CCATCTGATG AGCAGTTGAA ATCTGGAACT
    GCCTCTGTTG

401 TGTGCCTGCT GAATAACTTC TATCCCAGAG AGGCCAAAGT
    ACAGTGGAAG

451 GTGGATAACG CCCTCCAATC GGGTAACTCC CAGGAGAGTG
    TCACAGAGCA

501 GGACAGCAAG GACAGCACCT ACAGCCTCAG CAGCACCCTG
    ACGCTGAGCA

551 AAGCAGACTA CGAGAAACAC AAAGTCTACG CCTGCGAAGT
    CACCCATCAG

601 GGCCTGAGCT CGCCCGTCAC AAAGAGCTTC AACAGGGGAG
    AGTGT
```

Amino acid sequence of the Ab-15 LC including signal peptide:

```
                                    (SEQ ID NO: 223)
  1 MDMRVPAQLL GLLLLWLRGA RCDIQMTQSP SSLSASVGDR
    VTITCSVSST

 51 ISSNHLHWFQ QKPGKAPKSL IYGTSNLASG VPSRFSGSGS
    GTDFTLTISS

101 LQPEDFATYY CQQWSSYPLT FGGGTKVEIK RTVAAPSVFI
    FPPSDEQLKS

151 GTASVVCLLN NFYPREAKVQ WKVDNALQSG NSQESVTEQD
    SKDSTYSLSS

201 TLTLSKADYE KHKVYACEVT HQGLSSPVTK SFNRGEC
```

Nucleic acid sequence of the Ab-15 LC including signal peptide encoding sequence:

```
                                    (SEQ ID NO: 224)
  1 ATGGACATGA GGGTCCCCGC TCAGCTCCTG GGGCTCCTGC
    TACTCTGGCT

 51 CCGAGGTGCC AGATGTGACA TCCAGATGAC CCAGTCTCCA
    TCCTCCCTCT

101 CAGCATCCGT AGGCGATAGA GTTACAATAA CATGCAGCGT
    ATCATCAACT

151 ATATCATCAA ATCATCTTCA TTGGTTCCAA CAGAAACCCG
    GCAAAGCACC

201 TAAATCACTT ATATACGGCA CATCAAATCT CGCATCAGGC
    GTTCCTTCAA

251 GATTTTCAGG CTCTGGCTCA GGCACCGACT TTACTCTTAC
    AATATCCTCC

301 CTCCAACCCG AAGACTTCGC AACCTATTAC TGTCAACAAT
    GGTCCTCATA

351 TCCACTCACA TTTGGCGGCG GCACAAAAGT AGAAATTAAA
    CGTACGGTGG

401 CTGCACCATC TGTCTTCATC TTCCCGCCAT CTGATGAGCA
    GTTGAAATCT

451 GGAACTGCCT CTGTTGTGTG CCTGCTGAAT AACTTCTATC
    CCAGAGAGGC

501 CAAAGTACAG TGGAAGGTGG ATAACGCCCT CCAATCGGGT
    AACTCCCAGG

551 AGAGTGTCAC AGAGCAGGAC AGCAAGGACA GCACCTACAG
    CCTCAGCAGC

601 ACCCTGACGC TGAGCAAAGC AGACTACGAG AAACACAAAG
    TCTACGCCTG

651 CGAAGTCACC CATCAGGGCC TGAGCTCGCC CGTCACAAAG
    AGCTTCAACA

701 GGGGAGAGTG T
```

Ab-15 Heavy Chain

Amino acid sequence of the mature form (signal peptide removed) of Ab-15 HC.

```
                                    (SEQ ID NO: 225)
  1 EVQLVQSGAE VKKPGASVKV SCKASDFNIK DFYLHWVRQA
    PGQGLEWIGR

 51 IDPENGDTLY DPKFQDKVTM TTDTSTSTAY MELRSLRSDD
    TAVYYCAREA

101 DYFHDGTSYW YFDVWGRGTL VTVSSASTKG PSVFPLAPCS
    RSTSESTAAL

151 GCLVKDYFPE PVTVSWNSGA LTSGVHTFPA VLQSSGLYSL
    SSVVTVPSSN
```

-continued

```
201 FGTQTYTCNV DHKPSNTKVD KTVERKCCVE CPPCPAPPVA
    GPSVFLFPPK

251 PKDTLMISRT PEVTCVVVDV SHEDPEVQFN WYVDGVEVHN
    AKTKPREEQF

301 NSTFRVVSVL TVVHQDWLNG KEYKCKVSNK GLPAPIEKTI
    SKTKGQPREP

351 QVYTLPPSRE EMTKNQVSLT CLVKGFYPSD IAVEWESNGQ
    PENNYKTTPP

401 MLDSDGSFFL YSKLTVDKSR WQQGNVFSCS VMHEALHNHY
    TQKSLSLSPG

451 K
```

Amino acid sequence of the mature form (signal peptide removed) of Ab-15 HC without carboxy-terminal lysine:

```
                                            (SEQ ID NO: 394)
  1 EVQLVQSGAE VKKPGASVKV SCKASDFNIK DFYLHWVRQA
    PGQGLEWIGR

 51 IDPENGDTLY DPKFQDKVTM TTDTSTSTAY MELRSLRSDD
    TAVYYCAREA

101 DYFHDGTSYW YFDVWGRGTL VTVSSASTKG PSVFPLAPCS
    RSTSESTAAL

151 GCLVKDYFPE PVTVSWNSGA LTSGVHTFPA VLQSSGLYSL
    SSVVTVPSSN

201 FGTQTYTCNV DHKPSNTKVD KTVERKCCVE CPPCPAPPVA
    GPSVFLFPPK

251 PKDTLMISRT PEVTCVVVDV SHEDPEVQFN WYVDGVEVHN
    AKTKPREEQF

301 NSTFRVVSVL TVVHQDWLNG KEYKCKVSNK GLPAPIEKTI
    SKTKGQPREP

351 QVYTLPPSRE EMTKNQVSLT CLVKGFYPSD IAVEWESNGQ
    PENNYKTTPP

401 MLDSDGSFFL YSKLTVDKSR WQQGNVFSCS VMHEALHNHY
    TQKSLSLSPG

451
```

Nucleic acid sequence encoding the mature form (signal peptide removed) of the Ab-15 HC:

```
                                            (SEQ ID NO: 226)
   1 GAGGTGCAGC TGGTGCAGTC TGGGGCTGAG GTGAAGAAGC
     CTGGGGCCTC

  51 AGTGAAGGTC TCCTGCAAGG CTTCTGACTT CAACATTAAA
     GACTTCTATC

 101 TACACTGGGT GCGACAGGCC CCTGGACAAG GGCTTGAGTG
     GATTGGAAGG

 151 ATTGATCCTG AGAATGGTGA TACTTTATAT GACCCGAAGT
     TCCAGGACAA

 201 GGTCACCATG ACCACAGACA CGTCCACCAG CACAGCCTAC
     ATGGAGCTGA

 251 GGAGCCTGAG ATCTGACGAC ACGGCCGTGT ATTACTGTGC
     GAGAGAGGCG
```

-continued

```
 301 GATTATTTCC ACGATGGTAC CTCCTACTGG TACTTCGATG
     TCTGGGGCCG

 351 TGGCACCCTG GTCACCGTCT CTAGTGCCTC CACCAAGGGC
     CCATCGGTCT

 401 TCCCCCTGGC GCCCTGCTCC AGGAGCACCT CCGAGAGCAC
     AGCGGCCCTG

 451 GGCTGCCTGG TCAAGGACTA CTTCCCCGAA CCGGTGACGG
     TGTCGTGGAA

 501 CTCAGGCGCT CTGACCAGCG GCGTGCACAC CTTCCCAGCT
     GTCCTACAGT

 551 CCTCAGGACT CTACTCCCTC AGCAGCGTGG TGACCGTGCC
     CTCCAGCAAC

 601 TTCGGCACCC AGACCTACAC CTGCAACGTA GATCACAAGC
     CCAGCAACAC

 651 CAAGGTGGAC AAGACAGTTG AGCGCAAATG TTGTGTCGAG
     TGCCCACCGT

 701 GCCCAGCACC ACCTGTGGCA GGACCGTCAG TCTTCCTCTT
     CCCCCCAAAA

 751 CCCAAGGACA CCCTCATGAT CTCCCGGACC CCTGAGGTCA
     CGTGCGTGGT

 801 GGTGGACGTG AGCCACGAAG ACCCCGAGGT CCAGTTCAAC
     TGGTACGTGG

 851 ACGGCGTGGA GGTGCATAAT GCCAAGACAA AGCCACGGGA
     GGAGCAGTTC

 901 AACAGCACGT TCCGTGTGGT CAGCGTCCTC ACCGTTGTGC
     ACCAGGACTG

 951 GCTGAACGGC AAGGAGTACA AGTGCAAGGT CTCCAACAAA
     GGCCTCCCAG

1001 CCCCCATCGA GAAAACCATC TCCAAAACCA AAGGGCAGCC
     CCGAGAACCA

1051 CAGGTGTACA CCCTGCCCCC ATCCCGGGAG GAGATGACCA
     AGAACCAGGT

1101 CAGCCTGACC TGCCTGGTCA AAGGCTTCTA CCCCAGCGAC
     ATCGCCGTGG

1151 AGTGGGAGAG CAATGGGCAG CCGGAGAACA ACTACAAGAC
     CACACCTCCC

1201 ATGCTGGACT CCGACGGCTC CTTCTTCCTC TACAGCAAGC
     TCACCGTGGA

1251 CAAGAGCAGG TGGCAGCAGG GGAACGTCTT CTCATGCTCC
     GTGATGCATG

1301 AGGCTCTGCA CAACCACTAC ACGCAGAAGA GCCTCTCCCT
     GTCTCCGGGT

1351 AAA
```

Amino acid sequence of the Ab-15 HC including signal peptide:

```
                                            (SEQ ID NO: 227)
  1 MDWTWRILFL VAAATGAHSE VQLVQSGAEV KKPGASVKVS
    CKASDFNIKD

 51 FYLHWVRQAP GQGLEWIGRI DPENGDTLYD PKFQDKVTMT
    TDTSTSTAYM

101 ELRSLRSDDT AVYYCAREAD YFHDGTSYWY FDVWGRGTLV
    TVSSASTKGP
```

-continued

```
151 SVFPLAPCSR STSESTAALG CLVKDYFPEP VTVSWNSGAL
    TSGVHTFPAV

201 LQSSGLYSLS SVVTVPSSNF GTQTYTCNVD HKPSNTKVDK
    TVERKCCVEC

251 PPCPAPPVAG PSVFLFPPKP KDTLMISRTP EVTCVVVDVS
    HEDPEVQFNW

301 YVDGVEVHNA KTKPREEQFN STFRVVSVLT VVHQDWLNGK
    EYKCKVSNKG

351 LPAPIEKTIS KTKGQPREPQ VYTLPPSREE MTKNQVSLTC
    LVKGFYPSDI

401 AVEWESNGQP ENNYKTTPPM LDSDGSFFLY SKLTVDKSRW
    QQGNVFSCSV

451 MHEALHNHYT QKSLSLSPGK
```

Nucleic acid sequence of the Ab-15 HC including signal peptide encoding sequence:

```
                                      (SEQ ID NO: 228)
   1 ATGGACTGGA CCTGGAGGAT CCTCTTCTTG GTGGCAGCAG
     CCACAGGAGC

  51 CCACTCCGAG GTGCAGCTGG TGCAGTCTGG GGCTGAGGTG
     AAGAAGCCTG

 101 GGGCCTCAGT GAAGGTCTCC TGCAAGGCTT CTGACTTCAA
     CATTAAAGAC

 151 TTCTATCTAC ACTGGGTGCG ACAGGCCCCT GGACAAGGGC
     TTGAGTGGAT

 201 TGGAAGGATT GATCCTGAGA ATGGTGATAC TTTATATGAC
     CCGAAGTTCC

 251 AGGACAAGGT CACCATGACC ACAGACACGT CCACCAGCAC
     AGCCTACATG

 301 GAGCTGAGGA GCCTGAGATC TGACGACACG GCCGTGTATT
     ACTGTGCGAG

 351 AGAGGCGGAT TATTTCCACG ATGGTACCTC CTACTGGTAC
     TTCGATGTCT

 401 GGGGCCGTGG CACCCTGGTC ACCGTCTCTA GTGCCTCCAC
     CAAGGGCCCA

 451 TCGGTCTTCC CCCTGGCGCC CTGCTCCAGG AGCACCTCCG
     AGAGCACAGC

 501 GGCCCTGGGC TGCCTGGTCA AGGACTACTT CCCCGAACCG
     GTGACGGTGT

 551 CGTGGAACTC AGGCGCTCTG ACCAGCGGCG TGCACACCTT
     CCCAGCTGTC

 601 CTACAGTCCT CAGGACTCTA CTCCCTCAGC AGCGTGGTGA
     CCGTGCCCTC

 651 CAGCAACTTC GGCACCCAGA CCTACACCTG CAACGTAGAT
     CACAAGCCCA

 701 GCAACACCAA GGTGGACAAG ACAGTTGAGC GCAAATGTTG
     TGTCGAGTGC

 751 CCACCGTGCC CAGCACCACC TGTGGCAGGA CCGTCAGTCT
     TCCTCTTCCC

 801 CCCAAAACCC AAGGACACCC TCATGATCTC CCGGACCCCT
     GAGGTCACGT

 851 GCGTGGTGGT GGACGTGAGC CACGAAGACC CCGAGGTCCA
     GTTCAACTGG
```

-continued

```
 901 TACGTGGACG GCGTGGAGGT GCATAATGCC AAGACAAAGC
     CACGGGAGGA

 951 GCAGTTCAAC AGCACGTTCC GTGTGGTCAG CGTCCTCACC
     GTTGTGCACC

1001 AGGACTGGCT GAACGGCAAG GAGTACAAGT GCAAGGTCTC
     CAACAAAGGC

1051 CTCCCAGCCC CCATCGAGAA AACCATCTCC AAAACCAAAG
     GGCAGCCCCG

1101 AGAACCACAG GTGTACACCC TGCCCCCATC CCGGGAGGAG
     ATGACCAAGA

1151 ACCAGGTCAG CCTGACCTGC CTGGTCAAAG GCTTCTACCC
     CAGCGACATC

1201 GCCGTGGAGT GGGAGAGCAA TGGGCAGCCG GAGAACAACT
     ACAAGACCAC

1251 ACCTCCCATG CTGGACTCCG ACGGCTCCTT CTTCCTCTAC
     AGCAAGCTCA

1301 CCGTGGACAA GAGCAGGTGG CAGCAGGGGA ACGTCTTCTC
     ATGCTCCGTG

1351 ATGCATGAGG CTCTGCACAA CCACTACACG CAGAAGAGCC
     TCTCCCTGTC

1401 TCCGGGTAAA
```

The CDR sequences in the variable region of the heavy chain of Ab-15 are:

```
CDR-H1:    DFYLH (SEQ ID NO: 290)

CDR-H2:    RIDPENGDTLYDPKFQD (SEQ ID NO: 291)

CDR-H3:    EADYFHDGTSYWYFDV (SEQ ID NO: 292)
```

The light chain variable region CDR sequences of Ab-15 are:

```
CDR-L1:    SVSSTISSNHLH (SEQ ID NO: 278)

CDR-L2:    GTSNLAS (SEQ ID NO: 279)

CDR-L3:    QQWSSYPLT (SEQ ID NO: 280)
```

Ab-15 Variable domains:

Ab-15 light chain variable domain amino acid sequence (without signal sequence):

```
                                      (SEQ ID NO: 384)
  1 DIQMTQSPSS LSASVGDRVT ITCSVSSTIS SNHLHWFQQK
    PGKAPKSLIY

 51 GTSNLASGVP SRFSGSGSGT DFTLTISSLQ PEDFATYYCQ
    QWSSYPLTFG

101 GGTKVEIK
```

Ab-15 light chain variable domain DNA sequence (without signal sequence):

```
                                      (SEQ ID NO: 385)
  1 GACATCCAGA TGACCCAGTC TCCATCCTCC CTCTCAGCAT
    CCGTAGGCGA

 51 TAGAGTTACA ATAACATGCA GCGTATCATC AACTATATCA
    TCAAATCATC
```

```
101 TTCATTGGTT CCAACAGAAA CCCGGCAAAG CACCTAAATC
    ACTTATATAC

151 GGCACATCAA ATCTCGCATC AGGCGTTCCT TCAAGATTTT
    CAGGCTCTGG

201 CTCAGGCACC GACTTTACTC TTACAATATC CTCCCTCCAA
    CCCGAAGACT

251 TCGCAACCTA TTACTGTCAA CAATGGTCCT CATATCCACT
    CACATTTGGC

301 GGCGGCACAA AAGTAGAAAT TAAA
```

Ab-15 heavy chain variable domain amino acid sequence (without signal sequence):

```
                                        (SEQ ID NO: 386)
  1 EVQLVQSGAE VKKPGASVKV SCKASDFNIK DFYLHWVRQA
    PGQGLEWIGR

 51 IDPENGDTLY DPKFQDKVTM TTDTSTSTAY MELRSLRSDD
    TAVYYCAREA

101 DYFHDGTSYW YFDVWGRGTL VTVSS
```

Ab-15 heavy chain variable domain DNA sequence (without signal sequence):

```
                                        (SEQ ID NO: 387)
  1 GAGGTGCAGC TGGTGCAGTC TGGGGCTGAG GTGAAGAAGC
    CTGGGGCCTC

 51 AGTGAAGGTC TCCTGCAAGG CTTCTGACTT CAACATTAAA
    GACTTCTATC

101 TACACTGGGT GCGACAGGCC CCTGGACAAG GGCTTGAGTG
    GATTGGAAGG

151 ATTGATCCTG AGAATGGTGA TACTTTATAT GACCCGAAGT
    TCCAGGACAA

201 GGTCACCATG ACCACAGACA CGTCCACCAG CACAGCCTAC
    ATGGAGCTGA

251 GGAGCCTGAG ATCTGACGAC ACGGCCGTGT ATTACTGTGC
    GAGAGAGGCG

301 GATTATTTCC ACGATGGTAC CTCCTACTGG TACTTCGATG
    TCTGGGGCCG

351 TGGCACCCTG GTCACCGTCT CTAGT
```

Ab-11 was humanized to generate Ab-16.

Ab-16

The sequences of the Antibody 16 (also referred to herein as Ab-16) LC and HC are as follows:

Ab-16 Light Chain:

Amino acid sequence of the mature form (signal peptide removed) of the Ab-16 LC:

```
                                        (SEQ ID NO: 229)
  1 DIQLTQSPSF LSASVGDRVT ITCRASSSIS YIHWYQQKPG
    KAPKLLIYAT

 51 SNLASGVPSR FSGSGSGTEF TLTISSLQPE DFATYYCQQW
    SSDPLTFGGG

101 TKVEIKRTVA APSVFIFPPS DEQLKSGTAS VVCLLNNFYP
    REAKVQWKVD

151 NALQSGNSQE SVTEQDSKDS TYSLSSTLTL SKADYEKHKV
    YACEVTHQGL

201 SSPVTKSFNR GEC
```

Nucleic acid sequence encoding the mature form (signal peptide removed) of the Ab-16 LC:

```
                                        (SEQ ID NO: 230)
  1 GACATCCAGT TGACCCAGTC TCCATCCTTC CTGTCTGCAT
    CTGTAGGAGA

 51 CAGAGTCACC ATCACTTGCA GGGCCAGCTC AAGTATAAGT
    TACATACACT

101 GGTATCAGCA AAAACCAGGG AAAGCCCCTA AGCTCCTGAT
    CTATGCCACA

151 TCCAACCTGG CTTCTGGGGT CCCATCAAGG TTCAGCGGCA
    GTGGATCTGG

201 GACAGAATTC ACTCTCACAA TCAGCAGCCT GCAGCCTGAA
    GATTTTGCAA

251 CTTATTACTG TCAGCAGTGG AGTAGTGACC CACTCACGTT
    CGGCGGAGGG

301 ACCAAGGTGG AGATCAAACG TACGGTGGCT GCACCATCTG
    TCTTCATCTT

351 CCCGCCATCT GATGAGCAGT TGAAATCTGG AACTGCCTCT
    GTTGTGTGCC

401 TGCTGAATAA CTTCTATCCC AGAGAGGCCA AAGTACAGTG
    GAAGGTGGAT

451 AACGCCCTCC AATCGGGTAA CTCCCAGGAG AGTGTCACAG
    AGCAGGACAG

501 CAAGGACAGC ACCTACAGCC TCAGCAGCAC CCTGACGCTG
    AGCAAAGCAG

551 ACTACGAGAA ACACAAAGTC TACGCCTGCG AAGTCACCCA
    TCAGGGCCTG

601 AGCTCGCCCG TCACAAAGAG CTTCAACAGG GGAGAGTGT
```

Amino acid sequence of the Ab-16 LC including signal peptide:

```
                                        (SEQ ID NO: 231)
  1 MDMRVPAQLL GLLLLWLPGA RCDIQLTQSP SFLSASVGDR
    VTITCRASSS

 51 ISYIHWYQQK PGKAPKLLIY ATSNLASGVP SRFSGSGSGT
    EFTLTISSLQ

101 PEDFATYYCQ QWSSDPLTFG GGTKVEIKRT VAAPSVFIFP
    PSDEQLKSGT

151 ASVVCLLNNF YPREAKVQWK VDNALQSGNS QESVTEQDSK
    DSTYSLSSTL

201 TLSKADYEKH KVYACEVTHQ GLSSPVTKSF NRGEC
```

Nucleic acid sequence of the Ab-16 LC including signal peptide encoding sequence:

```
                                        (SEQ ID NO: 232)
  1 ATGGACATGA GGGTCCCCGC TCAGCTCCTG GGGCTCCTGC
    TGCTCTGGCT

 51 CCCAGGTGCC AGATGTGACA TCCAGTTGAC CCAGTCTCCA
    TCCTTCCTGT
```

-continued

```
101 CTGCATCTGT AGGAGACAGA GTCACCATCA CTTGCAGGGC
    CAGCTCAAGT

151 ATAAGTTACA TACACTGGTA TCAGCAAAAA CCAGGGAAAG
    CCCCTAAGCT

201 CCTGATCTAT GCCACATCCA ACCTGGCTTC TGGGGTCCCA
    TCAAGGTTCA

251 GCGGCAGTGG ATCTGGGACA GAATTCACTC TCACAATCAG
    CAGCCTGCAG

301 CCTGAAGATT TTGCAACTTA TTACTGTCAG CAGTGGAGTA
    GTGACCCACT

351 CACGTTCGGC GGAGGGACCA AGGTGGAGAT CAAACGTACG
    GTGGCTGCAC

401 CATCTGTCTT CATCTTCCCG CCATCTGATG AGCAGTTGAA
    ATCTGGAACT

451 GCCTCTGTTG TGTGCCTGCT GAATAACTTC TATCCCAGAG
    AGGCCAAAGT

501 ACAGTGGAAG GTGGATAACG CCCTCCAATC GGGTAACTCC
    CAGGAGAGTG

551 TCACAGAGCA GGACAGCAAG GACAGCACCT ACAGCCTCAG
    CAGCACCCTG

601 ACGCTGAGCA AAGCAGACTA CGAGAAACAC AAAGTCTACG
    CCTGCGAAGT

651 CACCCATCAG GGCCTGAGCT CGCCCGTCAC AAAGAGCTTC
    AACAGGGGAG

701 AGTGT
```

Ab-16 Heavy Chain:

Amino acid sequence of the mature form (signal peptide removed) of the Ab-16 HC:

```
                                        (SEQ ID NO: 233)
  1 EVQLVQSGAE VKKPGASVKV SCKASGFDIKDYYIHWVRQA
    PGQGLEWIGR

 51 VDPDNGETEF APKFPGKVTM TTDTSISTAY MELSRLRSDD
    TAVYYCARED

101 YDGTYTWFPY WGQGTLVTVS SASTKGPSVF PLAPCSRSTS
    ESTAALGCLV

151 KDYFPEPVTV SWNSGALTSG VHTFPAVLQS SGLYSLSSVV
    TVPSSNFGTQ

201 TYTCNVDHKP SNTKVDKTVE RKCCVECPPC PAPPVAGPSV
    FLFPPKPKDT

251 LMISRTPEVT CVVVDVSHED PEVQFNWYVD GVEVHNAKTK
    PREEQFNSTF

301 RVVSVLTVVH QDWLNGKEYK CKVSNKGLPA PIEKTISKTK
    GQPREPQVYT

351 LPPSREEMTK NQVSLTCLVK GFYPSDIAVE WESNGQPENN
    YKTTPPMLDS

401 DGSFFLYSKL TVDKSRWQQG NVFSCSVMHE ALHNHYTQKS
    LSLSPGK
```

Amino acid sequence of the mature form (signal peptide removed) of the Ab-16 HC without carboxy-terminal lysine:

```
                                        (SEQ ID NO: 395)
  1 EVQLVQSGAE VKKPGASVKV SCKASGFDIKDYYIHWVRQA
    PGQGLEWIGR

 51 VDPDNGETEF APKFPGKVTM TTDTSISTAY MELSRLRSDD
    TAVYYCARED

101 YDGTYTWFPY WGQGTLVTVS SASTKGPSVF PLAPCSRSTS
    ESTAALGCLV

151 KDYFPEPVTV SWNSGALTSG VHTFPAVLQS SGLYSLSSVV
    TVPSSNFGTQ

201 TYTCNVDHKP SNTKVDKTVE RKCCVECPPC PAPPVAGPSV
    FLFPPKPKDT

251 LMISRTPEVT CVVVDVSHED PEVQFNWYVD GVEVHNAKTK
    PREEQFNSTF

301 RVVSVLTVVH QDWLNGKEYK CKVSNKGLPA PIEKTISKTK
    GQPREPQVYT

351 LPPSREEMTK NQVSLTCLVK GFYPSDLAVE WESNGQPENN
    YKTTPPMLDS

401 DGSFFLYSKL TVDKSRWQQG NVFSCSVMHE ALHNHYTQKS
    LSLSPG
```

Nucleic acid sequence encoding the mature form (signal peptide removed) of the Ab-16 HC:

```
                                        (SEQ ID NO: 234)
  1 GAGGTGCAGC TGGTGCAGTC TGGGGCTGAG GTGAAGAAGC
    CTGGGGCCTC

 51 AGTGAAGGTC TCCTGCAAGG CTTCTGGATT CGACATTAAG
    GACTACTATA

101 TACACTGGGT GCGACAGGCC CCTGGACAAG GGCTTGAGTG
    GATCGGAAGG

151 GTTGATCCTG ACAATGGTGA GACTGAATTT GCCCCGAAGT
    TCCCGGGCAA

201 GGTCACCATG ACCACAGACA CGTCCATCAG CACAGCCTAC
    ATGGAGCTGA

251 GCAGGCTGAG ATCTGACGAC ACGGCCGTGT ATTACTGTGC
    GAGAGAAGAC

301 TACGATGGTA CCTACACCTG GTTTCCTTAT TGGGGCCAAG
    GGACTCTGGT

351 CACCGTCTCT AGTGCCTCCA CCAAGGGCCC ATCGGTCTTC
    CCCCTGGCGC

401 CCTGCTCCAG GAGCACCTCC GAGAGCACAG CGGCCCTGGG
    CTGCCTGGTC

451 AAGGACTACT TCCCCGAACC GGTGACGGTG TCGTGGAACT
    CAGGCGCTCT

501 GACCAGCGGC GTGCACACCT TCCCAGCTGT CCTACAGTCC
    TCAGGACTCT

551 ACTCCCTCAG CAGCGTGGTG ACCGTGCCCT CCAGCAACTT
    CGGCACCCAG

601 ACCTACACCT GCAACGTAGA TCACAAGCCC AGCAACACCA
    AGGTGGACAA
```

-continued

```
 651 GACAGTTGAG CGCAAATGTT GTGTCGAGTG CCCACCGTGC
     CCAGCACCAC

 701 CTGTGGCAGG ACCGTCAGTC TTCCTCTTCC CCCCAAAACC
     CAAGGACACC

 751 CTCATGATCT CCCGGACCCC TGAGGTCACG TGCGTGGTGG
     TGGACGTGAG

 801 CCACGAAGAC CCCGAGGTCC AGTTCAACTG GTACGTGGAC
     GGCGTGGAGG

 851 TGCATAATGC CAAGACAAAG CCACGGGAGG AGCAGTTCAA
     CAGCACGTTC

 901 CGTGTGGTCA GCGTCCTCAC CGTTGTGCAC CAGGACTGGC
     TGAACGGCAA

 951 GGAGTACAAG TGCAAGGTCT CCAACAAAGG CCTCCCAGCC
     CCCATCGAGA

1001 AAACCATCTC CAAAACCAAA GGGCAGCCCC GAGAACCACA
     GGTGTACACC

1051 CTGCCCCCAT CCCGGGAGGA GATGACCAAG AACCAGGTCA
     GCCTGACCTG

1101 CCTGGTCAAA GGCTTCTACC CCAGCGACAT CGCCGTGGAG
     TGGGAGAGCA

1151 ATGGGCAGCC GGAGAACAAC TACAAGACCA CACCTCCCAT
     GCTGGACTCC

1201 GACGGCTCCT TCTTCCTCTA CAGCAAGCTC ACCGTGGACA
     AGAGCAGGTG

1251 GCAGCAGGGG AACGTCTTCT CATGCTCCGT GATGCATGAG
     GCTCTGCACA

1301 ACCACTACAC GCAGAAGAGC CTCTCCCTGT CTCCGGGTAA A
```

Amino acid sequence of the Ab-16 HC including signal peptide:

```
                                        (SEQ ID NO: 235)
  1 MDWTWRILFL VAAATGAHSE VQLVQSGAEV KKPGASVKVS
    CKASGFDIKD

 51 YYIHWVRQAP GQGLEWIGRV DPDNGETEFA PKFPGKVTMT
    TDTSISTAYM

101 ELSRLRSDDT AVYYCAREDY DGTYTWFPYW GQGTLVTVSS
    ASTKGPSVFP

151 LAPCSRSTSE STAALGCLVK DYFPEPVTVS WNSGALTSGV
    HTFPAVLQSS

201 GLYSLSSVVT VPSSNFGTQT YTCNVDHKPS NTKVDKTVER
    KCCVECPPCP

251 APPVAGPSVF LFPPKPKDTL MISRTPEVTC VVVDVSHEDP
    EVQFNWYVDG

301 VEVHNAKTKP REEQFNSTFR VVSVLTVVHQ DWLNGKEYKC
    KVSNKGLPAP

351 IEKTISKTKG QPREPQVYTL PPSREEMTKN QVSLTCLVKG
    FYPSDIAVEW

401 ESNGQPENNY KTTPPMLDSD GSFFLYSKLT VDKSRWQQGN
    VFSCSVMHEA

451 LHNHYTQKSL SLSPGK
```

Nucleic acid sequence of the Ab-16 HC including signal peptide encoding sequence:

```
                                        (SEQ ID NO: 236)
   1 ATGGACTGGA CCTGGAGGAT CCTCTTCTTG GTGGCAGCAG
     CCACAGGAGC

  51 CCACTCCGAG GTGCAGCTGG TGCAGTCTGG GGCTGAGGTG
     AAGAAGCCTG

 101 GGGCCTCAGT GAAGGTCTCC TGCAAGGCTT CTGGATTCGA
     CATTAAGGAC

 151 TACTATATAC ACTGGGTGCG ACAGGCCCCT GGACAAGGGC
     TTGAGTGGAT

 201 CGGAAGGGTT GATCCTGACA ATGGTGAGAC TGAATTTGCC
     CCGAAGTTCC

 251 CGGGCAAGGT CACCATGACC ACAGACACGT CCATCAGCAC
     AGCCTACATG

 301 GAGCTGAGCA GGCTGAGATC TGACGACACG GCCGTGTATT
     ACTGTGCGAG

 351 AGAAGACTAC GATGGTACCT ACACCTGGTT TCCTTATTGG
     GGCCAAGGGA

 401 CTCTGGTCAC CGTCTCTAGT GCCTCCACCA AGGGCCCATC
     GGTCTTCCCC

 451 CTGGCGCCCT GCTCCAGGAG CACCTCCGAG AGCACAGCGG
     CCCTGGGCTG

 501 CCTGGTCAAG GACTACTTCC CCGAACCGGT GACGGTGTCG
     TGGAACTCAG

 551 GCGCTCTGAC CAGCGGCGTG CACACCTTCC CAGCTGTCCT
     ACAGTCCTCA

 601 GGACTCTACT CCCTCAGCAG CGTGGTGACC GTGCCCTCCA
     GCAACTTCGG

 651 CACCCAGACC TACACCTGCA ACGTAGATCA CAAGCCCAGC
     AACACCAAGG

 701 TGGACAAGAC AGTTGAGCGC AAATGTTGTG TCGAGTGCCC
     ACCGTGCCCA

 751 GCACCACCTG TGGCAGGACC GTCAGTCTTC CTCTTCCCCC
     CAAAACCCAA

 801 GGACACCCTC ATGATCTCCC GGACCCCTGA GGTCACGTGC
     GTGGTGGTGG

 851 ACGTGAGCCA CGAAGACCCC GAGGTCCAGT TCAACTGGTA
     CGTGGACGGC

 901 GTGGAGGTGC ATAATGCCAA GACAAAGCCA CGGGAGGAGC
     AGTTCAACAG

 951 CACGTTCCGT GTGGTCAGCG TCCTCACCGT TGTGCACCAG
     GACTGGCTGA

1001 ACGGCAAGGA GTACAAGTGC AAGGTCTCCA ACAAAGGCCT
     CCCAGCCCCC

1051 ATCGAGAAAA CCATCTCCAA AACCAAAGGG CAGCCCCGAG
     AACCACAGGT

1101 GTACACCCTG CCCCCATCCC GGGAGGAGAT GACCAAGAAC
     CAGGTCAGCC

1151 TGACCTGCCT GGTCAAAGGC TTCTACCCCA GCGACATCGC
     CGTGGAGTGG

1201 GAGAGCAATG GGCAGCCGGA GAACAACTAC AAGACCACAC
     CTCCCATGCT
```

-continued

```
1251 GGACTCCGAC GGCTCCTTCT TCCTCTACAG CAAGCTCACC
     GTGGACAAGA

1301 GCAGGTGGCA GCAGGGGAAC GTCTTCTCAT GCTCCGTGAT
     GCATGAGGCT

1351 CTGCACAACC ACTACACGCA GAAGAGCCTC TCCCTGTCTC
     CGGGTAAA
```

The CDR sequences in the variable region of the heavy chain of Ab-16 are:

```
CDR-H1:   DYYIH (SEQ ID NO: 293)

CDR-H2:   RVDPDNGETEFAPKFPG (SEQ ID NO: 294)

CDR-H3:   EDYDGTYTWFPY (SEQ ID NO: 295)
```

The light chain variable region CDR sequences of Ab-16 are:

```
CDR-L1:      RASSSISYIH (SEQ ID NO: 281)

CDR-L2:      ATSNLAS (SEQ ID NO: 282)

CDR-L3:      QQWSSDPLT (SEQ ID NO: 283)
```

Ab-16 Variable domains:

Ab-16 light chain variable domain amino acid sequence (without signal sequence):

```
                                        (SEQ ID NO: 388)
  1 DIQLTQSPSF LSASVGDRVT ITCRASSSIS YIHWYQQKPG
    KAPKLLIYAT

 51 SNLASGVPSR FSGSGSGTEF TLTISSLQPE DFATYYCQQW
    SSDPLTFGGG

101 TKVEIK
```

Ab-16 light chain variable domain DNA sequence (without signal sequence):

```
                                        (SEQ ID NO: 389)
  1 GACATCCAGT TGACCCAGTC TCCATCCTTC CTGTCTGCAT
    CTGTAGGAGA

 51 CAGAGTCACC ATCACTTGCA GGGCCAGCTC AAGTATAAGT
    TACATACACT

101 GGTATCAGCA AAAACCAGGG AAAGCCCCTA AGCTCCTGAT
    CTATGCCACA

151 TCCAACCTGG CTTCTGGGGT CCCATCAAGG TTCAGCGGCA
    GTGGATCTGG

201 GACAGAATTC ACTCTCACAA TCAGCAGCCT GCAGCCTGAA
    GATTTTGCAA

251 CTTATTACTG TCAGCAGTGG AGTAGTGACC CACTCACGTT
    CGGCGGAGGG

301 ACCAAGGTGG AGATCAAA
```

Ab-16 heavy chain variable domain amino acid sequence (without signal sequence):

```
                                        (SEQ ID NO: 390)
  1 EVQLVQSGAE VKKPGASVKV SCKASGFDIK DYYIHWVRQA
    PGQGLEWIGR

 51 VDPDNGETEF APKFPGKVTM TTDTSISTAY MELSRLRSDD
    TAVYYCARED

101 YDGTYTWFPY WGQGTLVTVS S
```

Ab-16 heavy chain variable domain DNA sequence (without signal sequence):

```
                                        (SEQ ID NO: 391)
  1 GAGGTGCAGC TGGTGCAGTC TGGGGCTGAG GTGAAGAAGC
    CTGGGGCCTC

 51 AGTGAAGGTC TCCTGCAAGG CTTCTGGATT CGACATTAAG
    GACTACTATA

101 TACACTGGGT GCGACAGGCC CCTGGACAAG GGCTTGAGTG
    GATCGGAAGG

151 GTTGATCCTG ACAATGGTGA GACTGAATTT GCCCCGAAGT
    TCCCGGGCAA

201 GGTCACCATG ACCACAGACA CGTCCATCAG CACAGCCTAC
    ATGGAGCTGA

251 GCAGGCTGAG ATCTGACGAC ACGGCCGTGT ATTACTGTGC
    GAGAGAAGAC

301 TACGATGGTA CCTACACCTG GTTTCCTTAT TGGGGCCAAG
    GGACTCTGGT

351 CACCGTCTCT AGT
```

Additional antibodies are referred to herein as Antibodies 17-22 (also referred to herein as Ab-17, Ab-18, Ab-19, Ab-20, Ab-21, and Ab-22). The Kappa Constant region for all VK regions of Ab-17, Ab-19, and Ab-21 is as follows:

```
                                        (SEQ ID NO: 323)
TDAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKS

FNRNEC
```

The Heavy Constant Region for all VH regions of antibodies 17, 19 and 21 is as follows:

```
                                        (SEQ ID NO: 324)
AKTTPPSVYPLAPGSAAQTNSMVTLGCLVKGYFPEPVTVTWNSGSLSSGV

HTFPAVLQSDLYTLSSSVTVPSSTWPSETVTCNVAHPASSTKVDKKIVPR

DCGCKPCICTVPEVSSVFIFPPKPKDVLTITLTPKVTCVVVDISKDDPEV

QFSWFVDDVEVHTAQTQPREEQFNSTFRSVSELPIMHQDWLNGKEFKCRV

NSAAFPAPIEKTISKTKGRPKAPQVYTIPPPKEQMAKDKVSLTCMITDFF

PEDITVEWQWNGQPAENYKNTQPIMDTDGSYFVYSKLNVQKSNWEAGNTF

TCSVLHEGLHNHHTEKSLSHSPGK
```

In the following antibody amino acid sequences, the boxed-shaded amino acids represent complement-determining regions (CDRs) and the underlined amino acids represent signal peptide.

Ab-17

Amino acid sequence of the Ab-17 LC including signal peptide:

(SEQ ID NO: 299)
MDFQVQIFSFMLISVTVILSSGEIVLTQSPALMAASPGEKVTITCSVSS
SISSSNLHWSQQKSGTSPKLWIYGTSNLASGVPVRFSGSGSGTSYSLTI
SSMEAEDAATYYCQQWTTTYTFGSGTKLELKR

Nucleic acid sequence of the Ab-17 LC including signal peptide:

(SEQ ID NO: 300)
ATGGATTTTCAGGTGCAGATTTTCAGCTTCATGCTAATCAGTGTCACAGT
CATATTGTCCAGTGGAGAAATTGTGCTCACCCAGTCTCCAGCACTCATGG
CTGCATCTCCAGGGGAGAAGGTCACCATCACCTGCAGTGTCAGCTCGAGT
ATAAGTTCCAGCAACTTACACTGGTCCCAGCAGAAGTCAGGAACCTCCCC
CAAACTCTGGATTTATGGCACATCCAACCTTGCTTCTGGAGTCCCTGTTC
GCTTCAGTGGCAGTGGATCTGGGACCTCTTATTCTCTCACAATCAGCAGC
ATGGAGGCTGAAGATGCTGCCACTTATTACTGTCAACAGTGGACTACTAC
GTATACGTTCGGATCGGGGACCAAGCTGGAGCTGAAACGT

Amino acid sequence of the Ab-17 HC including signal peptide:

(SEQ ID NO: 301)
MGWNWIIFFLMAVVTGVNSEVQLRQSGADLVKPGASVKLSCTASGFNIK
DYYIHWVKQRPEQGLEWIGRIDPDNGESTYVPKFQGKATITADTSSNTA
YLQLRSLTSEDTAIYYCGREGLDYGDYYAVDYWGQGTSVTVSS

Nucleic acid sequence of the Ab-17 HC including signal peptide:

(SEQ ID NO: 302)
ATGGGATGGAACTGGATCATCTTCTTCCTGATGGCAGTGGTTACAGGGGT
CAATTCAGAGGTGCAGTTGCGGCAGTCTGGGGCAGACCTTGTGAAGCCAG
GGGCCTCAGTCAAGTTGTCCTGCACAGCTTCTGGCTTCAACATTAAAGAC
TACTATATACACTGGGTGAAGCAGAGGCCTGAACAGGGCCTGGAGTGGAT
TGGAAGGATTGATCCTGATAATGGTGAAAGTACATATGTCCCGAAGTTCC
AGGGCAAGGCCACTATAACAGCAGACACATCATCCAACACAGCCTACCTA
CAACTCAGAAGCCTGACATCTGAGGACACTGCCATCTATTATTGTGGGAG
AGAGGGGCTCGACTATGGTGACTACTATGCTGTGGACTACTGGGGTCAAG
GAACCTCGGTCACAGTCTCGAGC

Ab-17 was humanized to generate Ab-18.

Ab-18

Amino acid sequence of the Ab-18 LC including signal peptide:

(SEQ ID NO: 303)
MDMRVPAQLLGLLLLWLPGARCDIQLTQSPSFLSASVGDRVTITCSVSS
SISSSNLHWYQQKPGKAPKLLIYGTSNLASGVPSRFSGSGSGTEFTLTI
SSLQPEDFATYYCQQWTTTYTFGQGTKLEIKR

Nucleic acid sequence of the Ab-18 LC including signal peptide:

(SEQ ID NO: 304)
ATGGATATGCGCGTGCCGGCGCAGCTGCTGGGCCTGCTGCTGCTGTGGCT
GCCGGGCGCGCGCTGCGATATTCAGCTGACCCAGAGCCCGAGCTTTCTGA
GCGCGAGCGTGGGCGATCGCGTGACCATTACCTGCAGCGTGAGCAGCAGC
ATTAGCAGCAGCAACCTGCATTGGTATCAGCAGAAACCGGGCAAAGCGCC
GAAACTGCTGATTTATGGCACCAGCAACCTGGCGAGCGGCGTGCCGAGCC
GCTTTAGCGGCAGCGGCAGCGGCACCGAATTTACCCTGACCATTAGCAGC
CTGCAGCCGGAAGATTTTGCGACCTATTATTGCCAGCAGTGGACCACCAC
CTATACCTTTGGCCAGGGCACCAAACTGGAAATTAAACGT

Amino acid sequence of the Ab-18 HC including signal peptide:

(SEQ ID NO: 305)
MDWTWSILFLVAAPTGAHSEVQLVQSGAEVICKPGASVKVSCKASGFNI
KDYYIHWVRQAPGQGLEWMGRIDPDNGESTYVPKFQGRVTMTTDTSTST
AYMELRSLRSDDTAVYYCAREGLDYGDYYAVDYNGQGTLVTVSS

Nucleic acid sequence of the Ab-18 HC including signal peptide:

(SEQ ID NO: 306)
ATGGATTGGACCTGGAGCATTCTGTTTCTGGTGGCGGCGCCGACCGGCGC
GCATAGCGAAGTGCAGCTGGTGCAGAGCGGCGCGGAAGTGAAAAAACCGG
GCGCGAGCGTGAAAGTGAGCTGCAAAGCGAGCGGCTTTAACATTAAAGAT
TATTATATTCATTGGGTGCGCCAGGCGCCGGGCCAGGGCCTGGAATGGAT
GGGCCGCATTGATCCGGATAACGGCGAAAGCACCTATGTGCCGAAATTTC
AGGGCCGCGTGACCATGACCACCGATACCAGCACCAGCACCGCGTATATG
GAACTGCGCAGCCTGCGCAGCGATGATACCGCGGTGTATTATTGCGCGCG
CGAAGGCCTGGATTATGGCGATTATTATGCGGTGGATTATTGGGGCCAGG
GCACCCTGGTGACCGTCTCGAGC

Ab-18 light chain variable domain amino acid sequence (without signal sequence):

(SEQ ID NO: 368)

DIQLTQSPSFLSASVGDRVTITCSVSSSISSSNLHWYQQKPGKAPKLLIY

GTSNLASGVPSRFSGSGSGTEFTLTISSLQPEDFATYYCQQWTTTYTFGQ

GTKLEIKR

Ab-18 light chain variable domain DNA sequence (without signal sequence):

(SEQ ID NO: 369)

GATATTCAGCTGACCCAGAGCCCGAGCTTTCTGAGCGCGAGCGTGGGCGA

TCGCGTGACCATTACCTGCAGCGTGAGCAGCAGCATTAGCAGCAGCAACC

TGCATTGGTATCAGCAGAAACCGGGCAAAGCGCCGAAACTGCTGATTTAT

GGCACCAGCAACCTGGCGAGCGGCGTGCCGAGCCGCTTTAGCGGCAGCGG

CAGCGGCACCGAATTTACCCTGACCATTAGCAGCCTGCAGCCGGAAGATT

TTGCGACCTATTATTGCCAGCAGTGGACCACCACCTATACCTTTGGCCAG

GGCACCAAACTGGAAATTAAACGT

Ab-18 heavy chain variable domain amino acid sequence (without signal sequence):

(SEQ ID NO: 370)

EVQLVQSGAEVKKPGASVKVSCKASGFNIKDYYIHWVRQAPGQGLEWMG

RIDPDNGESTYVPKFQGRVTMTTDTSTSTAYMELRSLRSDDTAVYYCAR

EGLDYGDYYAVDYWGQGTLVTVSS

Ab-18 heavy chain variable domain DNA sequence (without signal sequence):

(SEQ ID NO: 371)

GAAGTGCAGCTGGTGCAGAGCGGCGCGGAAGTGAAAAAACCGGGCGCGAG

CGTGAAAGTGAGCTGCAAAGCGAGCGGCTTTAACATTAAAGATTATTATA

TTCATTGGGTGCGCCAGGCGCCGGGCCAGGGCCTGGAATGGATGGGCCGC

ATTGATCCGGATAACGGCGAAAGCACCTATGTGCCGAAATTTCAGGGCCG

CGTGACCATGACCACCGATACCAGCACCAGCACCGCGTATATGGAACTGC

GCAGCCTGCGCAGCGATGATACCGCGGTGTATTATTGCGCGCGCGAAGGC

CTGGATTATGGCGATTATTATGCGGTGGATTATTGGGGCCAGGGCACCCT

GGTGACCGTCTCGAGC

Ab-19

Amino acid sequence of the Ab-19 LC including signal peptide:

(SEQ ID NO: 307)

MMSSAQFLGLLLLCFQGTRCDIQMTQTTSSLSASLGDRVNISCRASQDI

SSYLNWYQQKPDGTVKLLIYSTSRLNSGVPSRFSGSGSGTDYSLTISNL

AQEDIATYFCQQDIKHPTFGGGTKLELKR

Nucleic acid sequence of the Ab-19 LC including signal peptide:

(SEQ ID NO: 308)

ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTGGGAGACAGAGTCAACATCAGCTGCAGGGCAAGTCAGGACATTAGC

AGTTATTTAAACTGGTATCAGCAGAAACCAGATGGAACTGTTAAACTCCT

GATCTACTCCACATCAAGATTAAACTCAGGAGTCCCATCAAGGTTCAGTG

GCAGTGGGTCTGGGACAGATTATTCTCTCACTATTAGCAACCTGGCACAA

GAAGATATTGCCACTTACTTTTGCCAACAGGATATTAAGCATCCGACGTT

CGGTGGAGGCACCAAGTTGGAGCTGAAACGT

Amino acid sequence of the Ab-19 HC including signal peptide:

(SEQ ID NO: 309)

MEWIWIFLFLLSGTAGVHSEVQLQQSGPELVKPGASVKMSCKASGFTFT

DYIMHWVKQKPGQGLEWIGYINPYNDDTEYNEKFKGKATLTSDKSSSTA

YMDLSSLTSEGSAVYYCARSIYYYDAPFAYWGQGTLVTVSS

Nucleic acid sequence of the Ab-19 HC including signal peptide:

(SEQ ID NO: 310)

ATGGAATGGATCTGGATATTTCTCTTCCCTCCTGTCAGGAACTGCAGGTG

TCCACTCTGAGGTCCAGCTGCAGCAGTCTGGACCTGAGCTGGTAAAGCCT

GGGGCTTCAGTGAAGATGTCCTGCAAGGCTTCTGGGTTCACATTCACTGA

CTACATTATGCACTGGGTGAAGCAGAAGCCTGGGCAGGGCCTTGAGTGGA

TTGGATATATTAATCCTTACAATGATGATACTGAATACAATGAGAAGTTC

AAAGGCAAGGCCACACTGACTTCAGACAAATCCTCCAGCACAGCCTACAT

GGATCTCAGCAGTCTGACCTCTGAGGGCTCTGCGGTCTATTACTGTGCAA

GATCGATTTATTACTACGATGCCCCGTTTGCTTACTGGGGCCAAGGGACT

CTGGTCACAGTCTCGAGC

Ab-19 was humanized to generate Antibody 20 (also referred to herein as Ab-20) and Antibody 23 (also referred to herein as Ab-23).

Ab-20

IgG4 version

Amino acid sequence of the Ab-20 LC including signal peptide:

(SEQ ID NO: 311)

MMSSAQFLGLLLLCFQGTRCDIQMTQSPSSLSASVGDRVTITCRASQDIS

SYLNWYQQKPGKAPKLLIYSTSRLNSGVPSRFSGSGSGTDFTLTISSLQP

EDFATYYCQQDIKHPTFGQGTKVEIKR

Nucleic acid sequence of the Ab-20 LC including signal peptide:

(SEQ ID NO: 312)

ATGATGTCCTCTGCTCAGTTCCTTGGTCTCCTGTTGCTCTGTTTTCAAGG

TACCAGATGTGATATCCAGATGACCCAGTCTCCATCCTCCCTGTCTGCAT

CTGTAGGTGACCGTGTCACCATCACTTGCCGCGCAAGTCAGGATATTAGC

AGCTATTTAAATTGGTATCAGCAGAAACCAGGGAAAGCCCCTAAGCTCCT

GATCTATTCTACTTCCCGTTTGAATAGTGGGGTCCCATCACGCTTCAGTG

GCAGTGGCTCTGGGACAGATTTCACTCTCACCATCAGCAGTCTGCAACCT

GAAGATTTTGCAACTTACTACTGTCAACAGGATATTAAACACCCTACGTT

CGGTCAAGGCACCAAGGTGGAGATCAAACGT

Amino acid sequence of the Ab-20 HC including signal peptide:

(SEQ ID NO: 313)

MEWIWIFLFLLSGTAGVHSEVQLVQSGAEVKKPGSSVKVSCKASGFTFTD

YIMHWVRQAPGQGLEWMGYINPYNDDTEYNEKFKGRVTITADKSTSTAYM

ELSSLRSEDTAVYYCARSIYYYDAPFAYWGQGTLVTVSS

Nucleic acid sequence of the Ab-20 HC including signal peptide:

(SEQ ID NO: 349)

ATGGAATGGATCTGGATATTTCTCTTCCTCCTGTCAGGAACTGCAGGTGT

CCACTCTGAGGTGCAGCTGGTGCAGTCTGGGGCTGAGGTGAAGAAGCCTG

GGTCCTCGGTGAAGGTCTCCTGCAAGGCTTCTGGTTTTACCTTCACCGAC

TATATTATGCACTGGGTGCGTCAGGCCCCTGGTCAAGGGCTTGAGTGGAT

GGGCTATATCAACCCTTATAATGATGACACCGAATACAACGAGAAGTTCA

AGGGCCGTGTCACGATTACCGCGGACAAATCCACGAGCACAGCCTACATG

GAGCTGAGCAGCCTGCGCTCTGAGGACACGGCCGTGTATTACTGTGCGCG

TTCGATTTATTACTACGATGCCCCGTTTGCTTACTGGGGCCAAGGGACTC

TGGTCACAGTCTCGAGC

Ab-23

IgG2 version

Light Chain:

Amino acid sequence of the mature form (signal peptide removed) of the Ab-23 LC:

(SEQ ID NO: 341)

1 DIQMTQSPSS LSASVGDRVT ITCRASQDIS SYLNWYQQKP GKAPKLLIYS

51 TSRLNSGVPS RFSGSGSGTD FTLTISSLQP EDFATYYCQQ DIKHPTFGQG

101 TKVEIK*RTVA APSVFIFPPS DEQLKSGTAS VVCLLNNFYP REAKVQWKVD*

-continued

*151 NALQSGNSQE SVTEQDSKDS TYSLSSTLTL SKADYEKHKV YACEVTHQGL*

*201 SSPVTKSFNR GEC*

Nucleic acid sequence encoding the mature form (signal peptide removed) of the Ab-23 LC:

(SEQ ID NO: 342)

1 GACATCCAGA TGACCCAGTC TCCATCCTCC CTGTCTGCAT CTGTAGGTGA

51 CCGTGTCACC ATCAGTTGCC GCGCAAGTCA GGATATTAGC AGCTATTTAA

101 ATTGGTATCA GCAGAAACCA GGGAAAGCCC CTAAGCTCCT GATCTATTCT

151 ACTTCCCGTT TGAATAGTGG GGTCCCATCA CGCTTCAGTG GCAGTGGCTC

201 TGGGACAGAT TTCACTCTCA CCATCAGCAG TCTGCAACCT GAAGATTTTG

251 CAACTTACTA CTGTCAACAG GATATTAAAC ACCCTACGTT CGGTCAAGGC

301 ACCAAGGTGG AGATCAAACG TACGGTGGCT GCACCATCTG TCTTCATCTT

351 CCCGCCATCT GATGAGCAGT TGAAATCTGG AACTGCCTCT GTTGTGTGCC

401 TGCTGAATAA CTTCTATCCC AGAGAGGCCA AAGTACAGTG GAAGGTGGAT

451 AACGCCCTCC AATCGGGTAA CTCCCAGGAG AGTGTCACAG AGGAGGACAG

501 CAAGGACAGC ACCTACAGCC TCAGCAGCAC CCTGACGCTG AGCAAAGCAG

551 ACTACGAGAA ACACAAAGTC TACGCCTGCG AAGTCACCCA TCAGGGCCTG

601 AGCTCGCCCG TCACAAAGAG CTTCAACAGG GGAGAGTGT

Amino acid sequence of the Ab-23 LC including signal peptide:

(SEQ ID NO: 343)

1 MDMRVPAQLL GLLLLWLRGA RCDIQMTQSP SSLSASVGDR VTITCRASQD

51 ISSYLNWYQQ KPGKAPKLLI YSTSRLNSGV PSRFSGSGSG TDFTLTISSL

101 QPEDFATYYC QQDIKHPTFG QGTKVEIKRT VAAPSVFIFP PSDEQLKSGT

151 ASVVCLLNNF YPREAKVQWK VDNALQSGNS QESVTEQDSK DSTYSLSSTL

201 TLSKADYEKH KVYACEVTHQ GLSSPVTKSF NRGEC

Nucleic acid sequence of the Ab-23 LC including signal peptide encoding sequence:

(SEQ ID NO: 344)

1 ATGGACATGA GGGTGCCCGC TCAGCTCCTG GGGCTCCTGC TGCTGTGGCT

51 GAGAGGTGCC AGATGTGACA TCCAGATGAC CCAGTCTCCA TCCTCCCTGT

-continued

```
101 CTGCATCTGT AGGTGACCGT GTCACCATCA CTTGCCGCGC
    AAGTCAGGAT

151 ATTAGCAGCT ATTTAAATTG GTATCAGCAG AAACCAGGGA
    AAGCCCCTAA

201 GCTCCTGATC TATTCTACTT CCCGTTTGAA TAGTGGGGTC
    CCATCACGCT

251 TCAGTGGCAG TGGCTCTGGG ACAGATTTCA CTCTCACCAT
    CAGCAGTCTG

301 CAACCTGAAG ATTTTGCAAC TTACTACTGT CAACAGGATA
    TTAAACACCC

351 TACGTTCGGT CAAGGCACCA AGGTGGAGAT CAAACGTACG
    GTGGCTGCAC

401 CATCTGTCTT CATCTTCCCG CCATCTGATG AGCAGTTGAA
    ATCTGGAACT

451 GCCTCTGTTG TGTGCCTGCT GAATAACTTC TATCCCAGAG
    AGGCCAAAGT

501 ACAGTGGAAG GTGGATAACG CCCTCCAATC GGGTAACTCC
    CAGGAGAGTG

551 TCACAGAGCA GGACAGCAAG GACAGCACCT ACAGCCTCAG
    CAGCACCCTG

601 ACGCTGAGCA AAGCAGACTA CGAGAAACAC AAAGTCTACG
    CCTGCGAAGT

651 CACCCATCAG GGCCTGAGCT CGCCCGTCAC AAAGAGCTTC
    AACAGGGGAG

701 AGTGT
```

Heavy Chain:

Amino acid sequence of the mature form (signal peptide removed) of the Ab-23 HC:

```
                                              (SEQ ID NO: 345)
  1 EVQLVQSGAE VKKPGSSVKV SCKASGFTFT DYIMHWVRQA
    PGQGLEWMGY

 51 INPYNDDTEY NEKFKGRVTI TADKSTSTAY MELSSLRSED
    TAVYYCARSI

101 YYYDAPFAYW GQGTLVTVSS ASTKGPSVFP LAPCSRSTSE
    STAALGCLVK

151 DYFPEPVTVS WNSGALTSGV HTFPAVLQSS GLYSLSSVVT
    VPSSNFGTQT

201 YTCNVDHKPS NTKVDKTVER KCCVECPPCP APPVAGPSVF
    LFPPKPKDTL

251 MISRTPEVTC VVVDVSHEDP EVQFNWYVDG VEVHNAKTKP
    REEQFNSTFR

301 VVSVLTVVHQ DWLNGKEYKC KVSNKGLPAP IEKTISKTKG
    QPREPQVYTL

351 PPSREEMTKN QVSLTCLVKG FYPSDIAVEW ESNGQPENNY
    KTTPPMLDSD

401 GSFFLYSKLT VDKSRWQQGN VFSCSVMHEA LHNHYTQKSL
    SLSPGK
```

Amino acid sequence of the mature form (signal peptide removed) of the Ab-23 HC without carboxy-terminal lysine:

```
                                              (SEQ ID NO: 396)
  1 EVQLVQSGAE VKKPGSSVKV SCKASGFTFT DYIMHWVRQA
    PGQGLEWMGY

 51 INPYNDDTEY NEKFKGRVTI TADKSTSTAY MELSSLRSED
    TAVYYCARSI

101 YYYDAPFAYW GQGTLVTVSS ASTKGPSVFP LAPCSRSTSE
    STAALGCLVK

151 DYFPEPVTVS WNSGALTSGV HTFPAVLQSS GLYSLSSVVT
    VPSSNFGTQT

201 YTCNVDHKPS NTKVDKTVER KCCVECPPCP APPVAGPSVF
    LFPPKPKDTL

251 MISRTPEVTC VVVDVSHEDP EVQFNWYVDG VEVHNAKTKP
    REEQFNSTFR

301 VVSVLTVVHQ DWLNGKEYKC KVSNKGLPAP IEKTISKTKG
    QPREPQVYTL

351 PPSREEMTKN QVSLTCLVKG FYPSDIAVEW ESNGQPENNY
    KTTPPMLDSD

401 GSFFLYSKLT VDKSRWQQGN VFSCSVMHEA LHNHYTQKSL
    SLSPG
```

Nucleic acid sequence encoding the mature form (signal peptide removed) of the Ab-23 HC:

```
                                              (SEQ ID NO: 346)
  1 GAGGTGCAGC TGGTGCAGTC TGGGGCTGAG GTGAAGAAGC
    CTGGGTCCTC

 51 GGTGAAGGTC TCCTGCAAGG CTTCTGGTTT TACCTTCACC
    GACTATATTA

101 TGCACTGGGT GCGTCAGGCC CCTGGTCAAG GGCTTGAGTG
    GATGGGCTAT

151 ATCAACCCTT ATAATGATGA CACCGAATAC AACGAGAAGT
    TCAAGGGCCG

201 TGTCACGATT ACCGCGGACA AATCCACGAG CACAGCCTAC
    ATGGAGCTGA

251 GCAGCCTGCG CTCTGAGGAC ACGGCCGTGT ATTACTGTGC
    GCGTTCGATT

301 TATTACTACG ATGCCCCGTT TGCTTACTGG GGCCAAGGGA
    CTCTGGTCAC

351 CGTCTCTAGT GCCTCCACCA AGGGCCCATC GGTCTTCCCC
    CTGGCGCCCT

401 GCTCCAGGAG CACCTCCGAG AGCACAGCGG CCCTGGGCTG
    CCTGGTCAAG

451 GACTACTTCC CCGAACCGGT GACGGTGTCG TGGAACTCAG
    GCGCTCTGAC

501 CAGCGGCGTG CACACCTTCC CAGCTGTCCT ACAGTCCTCA
    GGACTCTACT

551 CCCTCAGCAG CGTGGTGACC GTGCCCTCCA GCAACTTCGG
    CACCCAGACC

601 TACACCTGCA ACGTAGATCA CAAGCCCAGC AACACCAAGG
    TGGACAAGAC
```

-continued

```
651 AGTTGAGCGC AAATGTTGTG TCGAGTGCCC ACCGTGCCCA
    GCACCACCTG

701 TGGCAGGACC GTCAGTCTTC CTCTTCCCCC CAAAACCCAA
    GGACACCCTC

751 ATGATCTCCC GGACCCCTGA GGTCACGTGC GTGGTGGTGG
    ACGTGAGCCA

801 CGAAGACCCC GAGGTCCAGT TCAACTGGTA CGTGGACGGC
    GTGGAGGTGC

851 ATAATGCCAA GACAAAGCCA CGGGAGGAGC AGTTCAACAG
    CACGTTCCGT

901 GTGGTCAGCG TCCTCACCGT TGTGCACCAG GACTGGCTGA
    ACGGCAAGGA

951 GTACAAGTGC AAGGTCTCCA ACAAAGGCCT CCCAGCCCCC
    ATCGAGAAAA

1001 CCATCTCCAA AACCAAAGGG CAGCCCCGAG AACCACAGGT
     GTACACCCTG

1051 CCCCCATCCC GGGAGGAGAT GACCAAGAAC CAGGTCAGCC
     TGACCTGCCT

1101 GGTCAAAGGC TTCTACCCCA GCGACATCGC CGTGGAGTGG
     GAGAGCAATG

1151 GGCAGCCGGA GAACAACTAC AAGACCACAC CTCCCATGCT
     GGACTCCGAC

1201 GGCTCCTTCT TCCTCTACAG CAAGCTCACC GTGGACAAGA
     GCAGGTGGCA

1251 GCAGGGGAAC GTCTTCTCAT GCTCCGTGAT GCATGAGGCT
     CTGCACAACC

1301 ACTACACGCA GAAGAGCCTC TCCCTGTCTC CGGGTAAA
```

Amino acid sequence of the Ab-23 HC including signal peptide:

```
                                     (SEQ ID NO: 347)
  1 MDWTWRILFL VAAATGAHSE VQLVQSGAEV KKPGSSVKVS
    CKASGFTFTD

 51 YIMHWVRQAP GQGLEWMGYI NPYNDDTEYN EKFKGRVTIT
    ADKSTSTAYM

101 ELSSLRSEDT AVYYCARSIY YYDAPFAYWG QGTLVTVSSA
    STKGPSVFPL

151 APCSRSTSES TAALGCLVKD YFPEPVTVSW NSGALTSGVH
    TFPAVLQSSG

201 LYSLSSVVTV PSSNFGTQTY TCNVDHKPSN TKVDKTVERK
    CCVECPPCPA

251 PPVAGPSVFL FPPKPKDTLM ISRTPEVTCV VVDVSHEDPE
    VQFNWYVDGV

301 EVHNAKTKPR EEQFNSTFRV VSVLTVVHQD WLNGKEYKCK
    VSNKGLPAPI

351 EKTISKTKGQ PREPQVYTLP PSREEMTKNQ VSLTCLVKGF
    YPSDIAVEWE

401 SNGQPENNYK TTPPMLDSDG SFFLYSKLTV DKSRWQQGNV
    FSCSVMHEAL

451 HNHYTQKSLS LSPGK
```

Nucleic acid sequence of the Ab-23 HC including signal peptide encoding sequence:

```
                                      (SEQ ID NO: 348)
   1 ATGGACTGGA CCTGGAGGAT CCTCTTCTTG GTGGCAGCAG
     CCACAGGAGC

  51 CCACTCCGAG GTGCAGCTGG TGCAGTCTGG GGCTGAGGTG
     AAGAAGCCTG

 101 GGTCCTCGGT GAAGGTCTCC TGCAAGGCTT CTGGTTTTAC
     CTTCACCGAC

 151 TATATTATGC ACTGGGTGCG TCAGGCCCCT GGTCAAGGGC
     TTGAGTGGAT

 201 GGGCTATATC AACCCTTATA ATGATGACAC CGAATACAAC
     GAGAAGTTCA

 251 AGGGCCGTGT CACGATTACC GCGGACAAAT CCACGAGCAC
     AGCCTACATG

 301 GAGCTGAGCA GCCTGCGCTC TGAGGACACG GCCGTGTATT
     ACTGTGCGCG

 351 TTCGATTTAT TACTACGATG CCCCGTTTGC TTACTGGGGC
     CAAGGGACTC

 401 TGGTCACCGT CTCTAGTGCC TCCACCAAGG GCCCATCGGT
     CTTCCCCCTG

 451 GCGCCCTGCT CCAGGAGCAC CTCCGAGAGC ACAGCGGCCC
     TGGGCTGCCT

 501 GGTCAAGGAC TACTTCCCCG AACCGGTGAC GGTGTCGTGG
     AACTCAGGCG

 551 CTCTGACCAG CGGCGTGCAC ACCTTCCCAG CTGTCCTACA
     GTCCTCAGGA

 601 CTCTACTCCC TCAGCAGCGT GGTGACCGTG CCCTCCAGCA
     ACTTCGGCAC

 651 CCAGACCTAC ACCTGCAACG TAGATCACAA GCCCAGCAAC
     ACCAAGGTGG

 701 ACAAGACAGT TGAGCGCAAA TGTTGTGTCG AGTGCCCACC
     GTGCCCAGCA

 751 CCACCTGTGG CAGGACCGTC AGTCTTCCTC TTCCCCCCAA
     AACCCAAGGA

 801 CACCCTCATG ATCTCCCGGA CCCCTGAGGT CACGTGCGTG
     GTGGTGGACG

 851 TGAGCCACGA AGACCCCGAG GTCCAGTTCA ACTGGTACGT
     GGACGGCGTG

 901 GAGGTGCATA ATGCCAAGAC AAAGCCACGG GAGGAGCAGT
     TCAACAGCAC

 951 GTTCCGTGTG GTCAGCGTCC TCACCGTTGT GCACCAGGAC
     TGGCTGAACG

1001 GCAAGGAGTA CAAGTGCAAG GTCTCCAACA AAGGCCTCCC
     AGCCCCCATC

1051 GAGAAAACCA TCTCCAAAAC CAAAGGGCAG CCCCGAGAAC
     CACAGGTGTA

1101 CACCCTGCCC CCATCCCGGG AGGAGATGAC CAAGAACCAG
     GTCAGCCTGA

1151 CCTGCCTGGT CAAAGGCTTC TACCCCAGCG ACATCGCCGT
     GGAGTGGGAG
```

-continued

```
1201 AGCAATGGGC AGCCGGAGAA CAACTACAAG ACCACACCTC
     CCATGCTGGA

1251 CTCCGACGGC TCCTTCTTCC TCTACAGCAA GCTCACCGTG
     GACAAGAGCA

1301 GGTGGCAGCA GGGGAACGTC TTCTCATGCT CCGTGATGCA
     TGAGGCTCTG

1351 CACAACCACT ACACGCAGAA GAGCCTCTCC CTGTCTCCGG
     GTAAA
```

The CDR (complementarity determining region) sequences in the variable region of the heavy chain of Ab-23 are as follows:

```
CDR-H1:  DYIMH (SEQ ID NO: 269)

CDR-H2:  YINPYNDDTEYNEKFKG (SEQ ID NO: 270)

CDR-H3:  SIYYYDAPFAY (SEQ ID NO: 271)
```

The light chain variable region CDR sequences of Ab-23 are:

```
CDR-L1:  RASQDISSYLN (SEQ ID NO: 239)

CDR-L2:  STSRLNS (SEQ ID NO: 240)

CDR-L3:  QQDIKHPT (SEQ ID NO: 241)
```

Ab-23 Variable domains:

Ab-23 light chain variable domain amino acid sequence (without signal sequence):

```
                                   (SEQ ID NO: 364)
DIQMTQSPSS LSASVGDRVT ITCRASQDIS SYLNWYQQKP

GKAPKLLIYS TSRLNSGVPS RFSGSGSGTD FTLTISSLQP

EDFATYYCQQ DIKHPTFGQG TKVEIK
```

Ab-23 light chain variable domain DNA sequence (without signal sequence):

```
                                   (SEQ ID NO: 365)
GACATCCAGATGACCCAGTCTCCATCCTCCCTGTCTGCATCTGTAGGTG

ACCGTGTCACCATCACTTGCC GCGCAAGTCA GGATATTAGC AGCTA

TTTAAATTGGTATCAGCAGAAACCA GGGAAAGCCC CTAAGCTCCT G

ATCTATTCTACTTCCCGTTTGAATAGTGG GGTCCCATCA CGCTTCAG

TG GCAGTGGCTCTGGGACAGATTTCACTCTCA CCATCAGCAG TCTG

CAACCT GAAGATTTTGCAACTTACTACTGTCAACAG GATATTAAAC

ACCCTACGTT CGGTCAAGGCACCAAGGTGGAGATCAAA
```

Ab-23 heavy chain variable domain amino acid sequence (without signal sequence):

```
                                   (SEQ ID NO: 366)
EVQLVQSGAE VKKPGSSVKV SCKASGFTFT DYIMHWVRQA

PGQGLEWMGYINPYNDDTEY NEKFKGRVTI TADKSTSTAY

MELSSLRSED TAVYYCARSIYYYDAPFAYW GQGTLVTVSS
```

Ab-23 heavy chain variable domain DNA sequence (without signal sequence):

```
                                   (SEQ ID NO: 367)
GAGGTGCAGCTGGTGCAGTCTGGGGCTGAGGTGAAGAAGCCTGGGTCCT

CGGTGAAGGTC TCCTGCAAGG CTTCTGGTTT TACCTTCACC GACT

ATATTATGCACTGGGTGCGTCAGGCC CCTGGTCAAG GGCTTGAGTG

GATGGGCTATATCAACCCTT ATAATGATGA CACCGAATAC AACGAG

AAGT TCAAGGGCCGTGTCACGATT ACCGCGGACA AATCCACGAG

CACAGCCTAC ATGGAGCTGAGCAGCCTGCG CTCTGAGGAC ACGGCC

GTGT ATTACTGTGC GCGTTCGATTTATTACTACG ATGCCCCGTT

TGCTTACTGG GGCCAAGGGACTCTGGTCACCGTCTCTAGT
```

Ab-21

Amino acid sequence of the Ab-21 LC including signal peptide:

```
                                   (SEQ ID NO: 315)
MKSQTQVFVYMLLWLSGVEGDIVMTQSHKFMSTSVGDRVTITCKASQDV

FTAVAWYQQKPGQSPKLLIYWASTRRHTGVPDRFTGSGSGTDFTLTISN

VQSEDLADYFCQQYSSYPLTFGAGTKLELKR
```

Nucleic acid sequence of the Ab-21 LC including signal peptide:

```
                                   (SEQ ID NO: 316)
ATGAAGTCACAGACCCAGGTCTTTGTATACATGTTGCTGTGGTTGTCTG

GTGTTGAAGGAGACATTGTGATGACCCAGTCTCACAAATTCATGTCCAC

GTCAGTAGGAGACAGGGTCACCATCACCTGCAAGGCCAGTCAGGATGTC

TTTACTGCTGTAGCCTGGTATCAACAGAAACCAGGACAATCTCCTAAAC

TACTGATTTACTGGGCATCCACCCGGCACACTGGAGTCCCTGATCGCTT

CACAGGCAGTGGATCTGGGACAGATTTCACTCTCACCATTAGCAATGTG

CAGTCTGAAGACTTGGCAGATTATTTCTGTCAACAATATAGCAGCT

ATCCTCTCACGTTCGGTGCTGGGACCAAGTTGGAGCTGAAACGT
```

Amino acid sequence of the Ab-21 HC including signal peptide:

```
                                   (SEQ ID NO: 317)
MGWNWIIFFLMAVVTGVNSEVQLQQSGAELVRPGALVKLSCKASGFNIK

DYYMHWVKQRPEQGLEWIGRIDPENGDIIYDPKFQGKASITTDTSSNTA

YLQLSSLTSEDTAVYYCAYDAGDPAWFTYWGQGTLVTVSS
```

Nucleic acid sequence of the Ab-21 HC including signal peptide:

```
                                   (SEQ ID NO: 318)
ATGGGATGGAACTGGATCATCTTCTTCCTGATGGCAGTGGTTACAGGGG

TCAATTCAGAGGTTCAGCTGCAGCAGTCTGGGGCTGAGCTTGTGAGGCC
```

-continued

AGGGGCCTTAGTCAAGTTGTCCTGCAAAGCTTCTGGCTTCAATATTAAA

GACTACTATATGCACTGGGTGAAGCAGAGGCCTGAACAGGGCCTGGAGT

GGATTGGAAGGATTGATCCTGAGAATGGTGATATTATATATGACCCGAA

GTTCCAGGGCAAGGCCAGTATAACAACAGACACATCCTCCAACACAGCC

TACCTGCAGCTCAGCAGCCTGACGTCTGAGGACACTGCCGTCTATTACT

GTGCTTACGATGCTGGTGACCCCGCCTGGTTTACTTACTGGGGCCAAGG

GACTCTGGTCACCGTCTCGAGC

Ab-21 was humanized to yield Ab-22.

Ab-22

Amino acid sequence of the Ab-22 LC including signal peptide:

(SEQ ID NO: 319)

MDMRVPAQLLGLLLLWLRGARCDIQMTQSPSSLSASVGDRVTITCKASQ

DVFTAVAWYQQKPGKAPKLLIYWASTRHTGVPSRFSGSGSGTDFTLTIS

SLQPEDFATYYCQQYSSYPLTFGGGTKVEIKR

Nucleic acid sequence of the Ab-22 LC including signal peptide:

(SEQ ID NO: 320)

ATGGATATGCGCGTGCCGGCGCAGCTGCTGGGCCTGCTGCTGCTGTGGC

TGCGCGGCGCGCGCTGCGATATCCAGATGACCCAGAGCCCGAGCAGCCT

GAGCGCGAGCGTGGGCGATCGCGTGACCATTACCTGCAAAGCGAGCCAG

GATGTGTTTACCGCGGTGGCGTGGTATCAGCAGAAACCGGGCAAAGCGC

CGAAACTGCTGATTTATTGGGCGAGCACCCGCCATACCGGCGTGCCGAG

TCGCTTTAGCGGCAGCGGCAGCGGCACCGATTTTACCCTGACCATTAGC

AGCCTGCAGCCGGAAGATTTTGCGACCTATTATTGCCAGCAGTATAG

CAGCTATCCGCTGACCTTTGGCGGCGGCACCAAAGTGGAAATTAAACGT

Amino acid sequence of the Ab-22 HC including signal peptide:

(SEQ ID NO: 321)

MDWTWSILFLVAAPTGAHSEVQLVQSGAEVKKPGASVKVSCKASGFNIK

DYYMHWVRQAPGQGLEWIGRIDPENGDIIYDPKFQGRVTMTTDTSTSTA

YMELRSLRSDDTAVYYCAYDAGDPAWFTYWGQGTLVTVSS

Nucleic acid sequence of the Ab-22 HC including signal peptide:

(SEQ ID NO: 322)

ATGGATTGGACCTGGAGCATTCTGTTTCTGGTGGCGGCGCCGACCGGCG

CGCATAGCGAAGTGCAGCTGGTGCAGAGCGGCGCGGAAGTGAAAAAACC

GGGCGCGAGCGTGAAAGTGAGCTGCAAAGCGAGCGGCTTTAACATTAAA

GATTATTATATGCATTGGGTGCGCCAGGCGCCGGGCCAGGGCCTGGAAT

-continued

GGATCGGCCGCATTGATCCGGAAAACGGCGATATTATTTATGATCCGAA

ATTTCAGGGCCGCGTGACCATGACCACCGATACCAGCACCAGCACCGCG

TATATGGAACTGCGCAGCCTGCGCAGCGATGATACCGCGGTGTATTATT

GCGCGTATGATGCGGGCGATCCGGCGTGGTTTACCTATTGGGGCCAGGG

CACCCTGGTGACCGTCTCGAGC

Ab-22 light chain variable domain amino acid sequence (without signal sequence):

(SEQ ID NO: 336)

DIQMTQSPSS LSASVGDRVT ITCKASQDVF TAVAWYQQKP

GKAPKLLIYW ASTRHTGVPS RFSGSGSGTD FTLTISSLQP

EDFATYYCQQ YSSYPLTFGG GTKVEIKR

Ab-22 light chain variable domain DNA sequence (without signal sequence):

(SEQ ID NO: 337)

GATATCCAGATGACCCAGAGCCCGAGCAGCCTGAGCGCGAGCGTGGGCGA

TCGCGTGACCATTACCTGCAAAGCGAGCCAGGATGTGTTTACCGCGGTGG

CGTGGTATCAGCAGAAACCGGGCAAAGCGCCGAAACTGCTGATTTATTGG

GCGAGCACCCGCCATACCGGCGTGCCGAGTCGCTTTAGCGGCAGCGGCAG

CGGCACCGATTTTACCCTGACCATTAGCAGCCTGCAGCCGGAAGATTTTG

CGACCTATTATTGCCAGCAGTATAGCAGCTATCCGCTGACCTTTGGCGGC

GGCACCAAAGTGGAAATTAAACGT

Ab-22 heavy chain variable domain amino acid sequence (without signal sequence):

(SEQ ID NO: 338)

EVQLVQSGAE VKKPGASVKV SCKASGFNIK DYYMHWVRQA

PGQGLEWIGR IDPENGDIIY DPKFQGRVTM TTDTSTSTAY

MELRSLRSDD TAVYYCAYDA GDPAWFTYWG QGTLVTVSS

Ab-22 heavy chain variable domain DNA sequence (without signal sequence):

(SEQ ID NO: 339)

GAAGTGCAGCTGGTGCAGAGCGGCGCGGAAGTGAAAAAACCGGGCGCGAG

CGTGAAAGTGAGCTGCAAAGCGAGCGGCTTTAACATTAAAGATTATTATA

TGCATTGGGTGCGCCAGGCGCCGGGCCAGGGCCTGGAATGGATCGGCCGC

ATTGATCCGGAAAACGGCGATATTATTTATGATCCGAAATTTCAGGGCCG

CGTGACCATGACCACCGATACCAGCACCAGCACCGCGTATATGGAACTGC

GCAGCCTGCGCAGCGATGATACCGCGGTGTATTATTGCGCGTATGATGCG

GGCGATCCGGCGTGGTTTACCTATTGGGGCCAGGGCACCCTGGTGACCGT

CTCGAGC.

For Ab-18, Ab-20, and Ab-22, the light chain human kappa constant region is as follows:

```
                                        (SEQ ID NO: 325)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC*
```

and the heavy chain human gamma-4 constant region is as follows:

```
                                        (SEQ ID NO: 326)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK*
```

The hinge region contains the Ser-241-Pro mutation to improve hinge stability (Angal S et al, (1993), Mol Immunol, 30(1), 105-108).

Ab-24

The sequences of Antibody 24 (also referred to herein as Ab-24) LC and HC are as follows:

Light Chain:

Amino acid sequence of the mature form (signal peptide removed) of the Ab-24 LC:

```
                                        (SEQ ID NO: 350)
  1 DIVLTQSPAS LAVSLGQRAT IACKASQSVD YDGTSYMNWY
    QQKPGQPPKL

 51 LIYAASNLES EIPARFSGTG SGTDFTLNIH PVEEEDITTY
    YCQQSNEDPF

101 TFGGGTKLEI KRADAAPTVS IFPPSSEQLT SGGASVVCFL
    NNFYPKDINV

151 KWKIDGSERQ NGVLNSWTDQ DSKDSTYSMS STLTLTKDEY
    ERHNSYTCEA

201 THKTSTSPIV
    KSFNRNEC
```

Nucleic acid sequence encoding the mature form (signal peptide removed) of the Ab-24 LC:

```
                                        (SEQ ID NO: 354)
  1 GACATTGTGT TGACCCAGTC TCCAGCTTCT TTGGCTGTGT
    CTCTAGGGCA

 51 GAGGGCCACC ATCGCCTGCA AGGCCAGCCA AAGTGTTGAT
    TATGATGGTA

101 CTAGTTATAT GAATTGGTAC CAACAGAAAC CAGGACAGCC
    ACCCAAACTC

151 CTCATCTATG CTGCATCCAA TCTAGAATCT GAGATCCCAG
    CCAGGTTTAG
```

-continued

```
201 TGGCACTGGG TCTGGGACAG ACTTCACCCT CAACATCCAT
    CCTGTGGAGG

251 AGGAGGATAT CACAACCTAT TACTGTCAGC AAAGTAATGA
    GGATCCGTTC

301 ACGTTCGGAG GGGGGACCAA GTTGGAAATA AAACGGGCTG
    ATGCTGCACC

351 AACTGTATCC ATCTTCCCAC CATCCAGTGA GCAGTTAACA
    TCTGGAGGTG

401 CCTCAGTCGT GTGCTTCTTG AACAACTTCT ACCCCAAAGA
    CATCAATGTC

451 AAGTGGAAGA TTGATGGCAG TGAACGACAA AATGGCGTCC
    TGAACAGTTG

501 GACTGATCAG GACAGCAAAG ACAGCACCTA CAGCATGAGC
    AGCACCCTCA

551 CGTTGACCAA GGACGAGTAT GAACGACATA ACAGCTATAC
    CTGTGAGGCC

601 ACTCACAAGA CATCAACTTC ACCCATTGTC AAGAGCTTCA
    ACAGGAATGA

651 GTGTTAG
```

Amino acid sequence of the Ab-24 LC including signal peptide:

```
                                        (SEQ ID NO: 355)
  1 METDTILLWV LLLWVPGSTG DIVLTQSPAS LAVSLGQRAT
    IACKASQSVD

 51 YDGTSYMNWY QQKPGQPPKL LIYAASNLES EIPARFSGTG
    SGTDFTLNIH

101 PVEEEDITTY YCQQSNEDPF TFGGGTKLEI KRADAAPTVS
    IFPPSSEQLT

151 SGGASVVCFL NNFYPKDINV KWKIDGSERQ NGVLNSWTDQ
    DSKDSTYSMS

201 STLTLTKDEY ERHNSYTCEA THKTSTSPIV KSFNRNEC
```

Nucleic acid sequence of the Ab-24 LC including signal peptide encoding sequence:

```
                                        (SEQ ID NO: 356)
  1 ATGGAGACAG ACACAATCCT GCTATGGGTG CTGCTGCTCT
    GGGTTCCAGG

 51 CTCCACTGGT GACATTGTGT TGACCCAGTC TCCAGCTTCT
    TTGGCTGTGT

101 CTCTAGGGCA GAGGGCCACC ATCGCCTGCA AGGCCAGCCA
    AAGTGTTGAT

151 TATGATGGTA CTAGTTATAT GAATTGGTAC CAACAGAAAC
    CAGGACAGCC

201 ACCCAAACTC CTCATCTATG CTGCATCCAA TCTAGAATCT
    GAGATCCCAG

251 CCAGGTTTAG TGGCACTGGG TCTGGGACAG ACTTCACCCT
    CAACATCCAT

301 CCTGTGGAGG AGGAGGATAT CACAACCTAT TACTGTCAGC
    AAAGTAATGA

351 GGATCCGTTC ACGTTCGGAG GGGGGACCAA GTTGGAAATA
    AAACGGGCTG

401 ATGCTGCACC AACTGTATCC ATCTTCCCAC CATCCAGTGA
    GCAGTTAACA
```

-continued

```
451 TCTGGAGGTG CCTCAGTCGT GTGCTTCTTG AACAACTTCT
    ACCCCAAAGA

501 CATCAATGTC AAGTGGAAGA TTGATGGCAG TGAACGACAA
    AATGGCGTCC

551 TGAACAGTTG GACTGATCAG GACAGCAAAG ACAGCACCTA
    CAGCATGAGC

601 AGCACCCTCA CGTTGACCAA GGACGAGTAT GAACGACATA
    ACAGCTATAC

651 CTGTGAGGCC ACTCACAAGA CATCAACTTC ACCCATTGTC
    AAGAGCTTCA

701 ACAGGAATGA GTGTTAG
```

Ab-24 Heavy Chain:

Amino acid sequence of the mature form (signal peptide removed) of the Ab-24 HC:

```
                                           (SEQ ID NO: 357)
  1 QVQLQQPGTE LVRPGTSVKL SCKASGYIFT TYWMNWVKQR
    PGQGLEWIGM

 51 IHPSASEIRL DQKFKDKATL TLDKSSSTAY MHLSGPTSVD
    SAVYYCARSG

101 EWGSMDYWGQ GTSVTVSSAK TTPPSVYPLA PGSAAQTNSM
    VTLGCLVKGY

151 FPEPVTVTWN SGSLSSGVHT FPAVLQSDLY TLSSSVTVPS
    STWPSETVTC

201 NVAHPASSTK VDKKIVPRDC GCKPCICTVP EVSSVFIFPP
    KPKDVLTITL

251 TPKVTCVVVD ISKDDPEVQF SWFVDDVEVH TAQTQPREEQ
    FNSTFRSVSE

301 LPIMHQDWLN GKEFKCRVNS AAFPAPIEKT ISKTKGRPKA
    PQVYTIPPPK

351 EQMAKDKVSL TCMITDFFPE DITVEWQWNG QPAENYKNTQ
    PIMDTDGSYF

401 IYSKLNVQKS NWEAGNTFTC SVLHEGLHNH HTEKSLSHSP
    GK
```

Nucleic acid sequence encoding the mature form (signal peptide removed) of the Ab-24 HC:

```
                                           (SEQ ID NO: 361)
  1 CAGGTCCAAC TACAGCAGCC TGGGACTGAG CTGGTGAGGC
    CTGGAACTTC

 51 AGTGAAGTTG TCCTGTAAGG CTTCTGGCTA CATCTTCACC
    ACCTACTGGA

101 TGAACTGGGT GAAACAGAGG CCTGGACAAG GCCTTGAGTG
    GATTGGCATG

151 ATTCATCCTT CCGCAAGTGA AATTAGGTTG GATCAGAAAT
    TCAAGGACAA

201 GGCCACATTG ACTCTTGACA AATCCTCCAG CACAGCCTAT
    ATGCACCTCA

251 GCGGCCCGAC ATCTGTGGAT TCTGCGGTCT ATTACTGTGC
    AAGATCAGGG

301 GAATGGGGGT CTATGGACTA CTGGGGTCAA GGAACCTCAG
    TCACCGTCTC
```

-continued

```
 351 CTCAGCCAAA ACGACACCCC CATCTGTCTA TCCACTGGCC
     CCTGGATCTG

 401 CTGCCCAAAC TAACTCCATG GTGACCCTGG GATGCCTGGT
     CAAGGGCTAT

 451 TTCCCTGAGC CAGTGACAGT GACCTGGAAC TCTGGATCCC
     TGTCCAGCGG

 501 TGTGCACACC TTCCCAGCTG TCCTGCAGTC TGACCTCTAC
     ACTCTGAGCA

 551 GCTCAGTGAC TGTCCCCTCC AGCACCTGGC CCAGCGAGAC
     CGTCACCTGC

 601 AACGTTGCCC ACCCGGCCAG CAGCACCAAG GTGGACAAGA
     AAATTGTGCC

 651 CAGGGATTGT GGTTGTAAGC CTTGCATATG TACAGTCCCA
     GAAGTATCAT

 701 CTGTCTTCAT CTTCCCCCCA AAGCCCAAGG ATGTGCTCAC
     CATTACTCTG

 751 ACTCCTAAGG TCACGTGTGT TGTGGTAGAC ATCAGCAAGG
     ATGATCCCGA

 801 GGTCCAGTTC AGCTGGTTTG TAGATGATGT GGAGGTGCAC
     ACAGCTCAGA

 851 CGCAACCCCG GGAGGAGCAG TTCAACAGCA CTTTCCGCTC
     AGTCAGTGAA

 901 CTTCCCATCA TGCACCAGGA CTGGCTCAAT GGCAAGGAGT
     TCAAATGCAG

 951 GGTCAACAGT GCAGCTTTCC CTGCCCCCAT CGAGAAAACC
     ATCTCCAAAA

1001 CCAAAGGCAG ACCGAAGGCT CCACAGGTGT ACACCATTCC
     ACCTCCCAAG

1051 GAGCAGATGG CCAAGGATAA AGTCAGTCTG ACCTGCATGA
     TAACAGACTT

1101 CTTCCCTGAA GACATTACTG TGGAGTGGCA GTGGAATGGG
     CAGCCAGCGG

1151 AGAACTACAA GAACACTCAG CCCATCATGG ACACAGATGG
     CTCTTACTTC

1201 ATCTACAGCA AGCTCAATGT GCAGAAGAGC AACTGGGAGG
     CAGGAAATAC

1251 TTTCACCTGC TCTGTGTTAC ATGAGGGCCT GCACAACCAC
     CATACTGAGA

1301 AGAGCCTCTC CCACTCTCCT GGTAAATGA
```

Amino acid sequence of the Ab-24 HC including signal peptide:

```
                                           (SEQ ID NO: 362)
  1 MGWSSIILFL VATATGVHSQ VQLQQPGTEL VRPGTSVKLS
    CKASGYIFTT

 51 YWMNWVKQRP GQGLEWIGMI HPSASEIRLD QKFKDKATLT
    LDKSSSTAYM

101 HLSGPTSVDS AVYYCARSGE WGSMDYWGQG TSVTVSSAKT
    TPPSVYPLAP

151 GSAAQTNSMV TLGCLVKGYF PEPVTVTWNS GSLSSGVHTF
    PAVLQSDLYT

201 LSSSVTVPSS TWPSETVTCN VAHPASSTKV DKKIVPRDCG
    CKPCICTVPE
```

-continued

```
251 VSSVFIFPPK PKDVLTITLT PKVTCVVVDI SKDDPEVQFS
    WFVDDVEVHT

301 AQTQPREEQF NSTFRSVSEL PIMHQDWLNG KEFKCRVNSA
    AFPAPIEKTI

351 SKTKGRPKAP QVYTIPPPKE QMAKDKVSLT CMITDFFPED
    ITVEWQWNGQ

401 PAENYKNTQP IMDTDGSYFI YSKLNVQKSN WEAGNTFTCS
    VLHEGLHNHH

451 TEKSLSHSPG K
```

Nucleic acid sequence of the Ab-24 HC including signal peptide encoding sequence:

```
                                              (SEQ ID NO: 363)
   1 ATGGGATGGA GCTCTATCAT CCTCTTCTTG GTAGCAACAG
     CTACAGGTGT

  51 CCACTCCCAG GTCCAACTAC AGCAGCCTGG GACTGAGCTG
     GTGAGGCCTG

 101 GAACTTCAGT GAAGTTGTCC TGTAAGGCTT CTGGCTACAT
     CTTCACCACC

 151 TACTGGATGA ACTGGGTGAA ACAGAGGCCT GGACAAGGCC
     TTGAGTGGAT

 201 TGGCATGATT CATCCTTCCG CAAGTGAAAT TAGGTTGGAT
     CAGAAATTCA

 251 AGGACAAGGC CACATTGACT CTTGACAAAT CCTCCAGCAC
     AGCCTATATG

 301 CACCTCAGCG GCCCGACATC TGTGGATTCT GCGGTCTATT
     ACTGTGCAAG

 351 ATCAGGGGAA TGGGGGTCTA TGGACTACTG GGGTCAAGGA
     ACCTCAGTCA

 401 CCGTCTCCTC AGCCAAAACG ACACCCCCAT CTGTCTATCC
     ACTGGCCCCT

 451 GGATCTGCTG CCCAAACTAA CTCCATGGTG ACCCTGGGAT
     GCCTGGTCAA

 501 GGGCTATTTC CCTGAGCCAG TGACAGTGAC CTGGAACTCT
     GGATCCCTGT

 551 CCAGCGGTGT GCACACCTTC CCAGCTGTCC TGCAGTCTGA
     CCTCTACACT

 601 CTGAGCAGCT CAGTGACTGT CCCCTCCAGC ACCTGGCCCA
     GCGAGACCGT

 651 CACCTGCAAC GTTGCCCACC CGGCCAGCAG CACCAAGGTG
     GACAAGAAAA

 701 TTGTGCCCAG GGATTGTGGT TGTAAGCCTT GCATATGTAC
     AGTCCCAGAA

 751 GTATCATCTG TCTTCATCTT CCCCCCAAAG CCCAAGGATG
     TGCTCACCAT
```

-continued

```
 801 TACTCTGACT CCTAAGGTCA CGTGTGTTGT GGTAGACATC
     AGCAAGGATG

 851 ATCCCGAGGT CCAGTTCAGC TGGTTTGTAG ATGATGTGGA
     GGTGCACACA

 901 GCTCAGACGC AACCCCGGGA GGAGCAGTTC AACAGCACTT
     TCCGCTCAGT

 951 CAGTGAACTT CCCATCATGC ACCAGGACTG GCTCAATGGC
     AAGGAGTTCA

1001 AATGCAGGGT CAACAGTGCA GCTTTCCCTG CCCCCATCGA
     GAAAACCATC

1051 TCCAAAACCA AAGGCAGACC GAAGGCTCCA CAGGTGTACA
     CCATTCCACC

1101 TCCCAAGGAG CAGATGGCCA AGGATAAAGT CAGTCTGACC
     TGCATGATAA

1151 CAGACTTCTT CCCTGAAGAC ATTACTGTGG AGTGGCAGTG
     GAATGGGCAG

1201 CCAGCGGAGA ACTACAAGAA CACTCAGCCC ATCATGGACA
     CAGATGGCTC

1251 TTACTTCATC TACAGCAAGC TCAATGTGCA GAAGAGCAAC
     TGGGAGGCAG

1301 GAAATACTTT CACCTGCTCT GTGTTACATG AGGGCCTGCA
     CAACCACCAT

1351 ACTGAGAAGA GCCTCTCCCA CTCTCCTGGT AAATGA
```

The CDR sequences in the variable region of the light chain of Ab-24 are as follows:

```
CDR-L1:     KASQSVDYDGTSYMN (SEQ ID NO: 351)

CDR-L2:     AASNLES (SEQ ID NO: 352)

CDR-L3:     QQSNEDPFT (SEQ ID NO: 353)
```

The CDR sequences in the variable region of the heavy chain of Ab-24 are as follows:

```
CDR-H1:   TYWMN (SEQ ID NO: 358)

CDR-H2:   MIHPSASEIRLDQKFKD (SEQ ID NO: 359)

CDR-H3:   SGEWGSMDY (SEQ ID NO: 360)
```

Table 1 below provides the SEQ ID NOs and amino acid sequences of the CDR's of Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24. L1, L2, and L3 refer to light chain CDR's 1, 2, and 3, and H1, H2, and H3 refer to heavy chain CDR's 1, 2, and 3 according to the Kabat numbering system (Kabat et al., 1987 in *Sequences of Proteins of Immunological Interest*, U.S. Department of Health and Human Services, NIH, USA).

TABLE 1

| SEQ ID NO | DESCRIPTION | AMINO ACID SEQUENCE |
|---|---|---|
| 54 | Ab-A and Ab-1 CDR-L1 | QSSQSVYDNNWLA |
| 55 | Ab-A and Ab-1 CDR-L2 | DASDLAS |
| 56 | Ab-A and Ab-1 CDR-L3 | QGAYNDVIYA |
| 51 | Ab-A and Ab-1 CDR-H1 | SYWMN |

TABLE 1-continued

| SEQ ID NO | DESCRIPTION | AMINO ACID SEQUENCE |
|---|---|---|
| 52 | Ab-A and Ab-1 CDR-H2 | TIDSGGRTDYASWAKG |
| 53 | Ab-A and Ab-1 CDR-H3 | NWNL |
| 60 | Ab-B CDR-L1 | SASSSVSFVD |
| 61 | Ab-B CDR-L2 | RTSNLGF |
| 62 | Ab-B CDR-L3 | QQRSTYPPT |
| 57 | Ab-B CDR-H1 | TSGMGVG |
| 58 | Ab-B CDR-H2 | HIWWDDVKRYNPVLKS |
| 59 | Ab-B CDR-H3 | EDFDYDEEYYAMDY |
| 48 | Ab-C CDR-L1 | KASQSVDYDGDSYMN |
| 49 | Ab-C CDR-L2 | AASNLES |
| 50 | Ab-C CDR-L3 | QQSNEDPWT |
| 45 | Ab-C CDR-H1 | DCYMN |
| 46 | Ab-C CDR-H2 | DINPPNGGTTYNQKFKG |
| 47 | Ab-C CDR-H3 | SHYYFDGRVPWDAMDY |
| 42 | Ab-D CDR-L1 | QASQGTSINLN |
| 43 | Ab-D CDR-L2 | GSSNLED |
| 44 | Ab-D CDR-L3 | LQHSYLPYT |
| 39 | Ab-D CDR-H1 | DHYMS |
| 40 | Ab-D CDR-H2 | DINPYSGETTYNQKFKG |
| 41 | Ab-D CDR-H3 | DDYDASPFAY |
| 275 | Ab-2 CDR-L1 | RASSSVYYYMH |
| 276 | Ab-2 CDR-L2 | ATSNLAS |
| 277 | Ab-2 CDR-L3 | QQWSSDPLT |
| 287 | Ab-2 CDR-H1 | DYFIH |
| 288 | Ab-2 CDR-H2 | RLDPEDGESDYAPKFQD |
| 289 | Ab-2 CDR-H3 | EDYDGTYTFFPY |
| 278 | Ab-3 and Ab-15 CDR-L1 | SVSSTISSNHLH |
| 279 | Ab-3 and Ab-15 CDR-L2 | GTSNLAS |
| 280 | Ab-3 and Ab-15 CDR-L3 | QQWSSYPLT |
| 290 | Ab-3 and Ab-15 CDR-H1 | DFYLH |
| 291 | Ab-3 and Ab-15 CDR-H2 | RIDPENGDTLYDPKFQD |
| 292 | Ab-3 and Ab-15 CDR-H3 | EADYFHDGTSYWYFDV |
| 78 | Ab-4 and Ab-5 CDR-L1 | RASQDISNYLN |
| 79 | Ab-4 and Ab-5 CDR-L2 | YTSRLLS |
| 80 | Ab-4 and Ab-5 CDR-L3 | QQGDTLPYT |
| 245 | Ab-4 and Ab-5 CDR-H1 | DYNMH |
| 246 | Ab-4 and Ab-5 CDR-H2 | EINPNSGGAGYNQKFKG |
| 247 | Ab-4 and Ab-5 CDR-H3 | LGYDDIYDDWYFDV |
| 81 | Ab-6 CDR-L1 | RASQDISNYLN |

TABLE 1-continued

| SEQ ID NO | DESCRIPTION | AMINO ACID SEQUENCE |
|---|---|---|
| 99 | Ab-6 CDR-L2 | YTSRLHS |
| 100 | Ab-6 CDR-L3 | QQGDTLPYT |
| 248 | Ab-6 CDR-H1 | DYNMH |
| 249 | Ab-6 CDR-H2 | EINPNSGGSGYNQKFKG |
| 250 | Ab-6 CDR-H3 | LVYDGSYEDWYFDV |
| 101 | Ab-7 CDR-L1 | RASQVITNYLY |
| 102 | Ab-7 CDR-L2 | YTSRLHS |
| 103 | Ab-7 CDR-L3 | QQGDTLPYT |
| 251 | Ab-7 CDR-H1 | DYNMH |
| 252 | Ab-7 CDR-H2 | EINPNSGGAGYNQQFKG |
| 253 | Ab-7 CDR-H3 | LGYVGNYEDWYFDV |
| 104 | Ab-8 CDR-L1 | RASQDISNYLN |
| 105 | Ab-8 CDR-L2 | YTSRLLS |
| 106 | Ab-8 CDR-L3 | QQGDTLPYT |
| 254 | Ab-8 CDR-H1 | DYNMH |
| 255 | Ab-8 CDR-H2 | EINPNSGGAGYNQKFKG |
| 256 | Ab-8 CDR-H3 | LGYDDIYDDWYFDV |
| 107 | Ab-9 CDR-L1 | RASQDISNYLN |
| 108 | Ab-9 CDR-L2 | YTSRLFS |
| 109 | Ab-9 CDR-L3 | QQGDTLPYT |
| 257 | Ab-9 CDR-H1 | DYNMH |
| 258 | Ab-9 CDR-H2 | EINPNSGGAGYNQKFKG |
| 259 | Ab-9 CDR-H3 | LGYDDIYDDWYFDV |
| 110 | Ab-10 CDR-L1 | RASQDISNYLN |
| 111 | Ab-10 CDR-L2 | YTSRLLS |
| 112 | Ab-10 CDR-L3 | QQGDTLPYT |
| 260 | Ab-10 CDR-H1 | DYNMH |
| 261 | Ab-10 CDR-H2 | EINPNSGGAGYNQKFKG |
| 262 | Ab-10 CDR-H3 | LGYDDIYDDWYFDV |
| 281 | Ab-11 and Ab-16 CDR-L1 | RASSSISYIH |
| 282 | Ab-11 and Ab-16 CDR-L2 | ATSNLAS |
| 283 | Ab-11 and Ab-16 CDR-L3 | QQWSSDPLT |
| 293 | Ab-11 and Ab-16 CDR-H1 | DYYIH |
| 294 | Ab-11 and Ab-16 CDR-H2 | RVDPDNGETEFAPKFPG |
| 295 | Ab-11 and Ab-16 CDR-H3 | EDYDGTYTWFPY |
| 113 | Ab-12 CDR-L1 | RASQDISNYLN |
| 114 | Ab-12 CDR-L2 | YTSTLQS |
| 115 | Ab-12 CDR-L3 | QQGDTLPYT |
| 263 | Ab-12 CDR-H1 | DYNMH |

TABLE 1-continued

| SEQ ID NO | DESCRIPTION | AMINO ACID SEQUENCE |
|---|---|---|
| 264 | Ab-12 CDR-H2 | EINPNSGGSGYNQKFKG |
| 265 | Ab-12 CDR-H3 | LGYYGNYEDWYFDV |
| 284 | Ab-13 and Ab-14 CDR-L1 | RASSSVTSSYLN |
| 285 | Ab-13 and Ab-14 CDR-L2 | STSNLAS |
| 286 | Ab-13 and Ab-14 CDR-L3 | QQYDFFPST |
| 296 | Ab-13 and Ab-14 CDR-H1 | DYYMN |
| 297 | Ab-13 and Ab-14 CDR-H2 | DINPYNDDTTYNHKFKG |
| 298 | Ab-13 and Ab-14 CDR-H3 | ETAVITTNAMD |
| 116 | Ab-17 and Ab-18 CDR-L1 | SVSSSISSSNLH |
| 237 | Ab-17 and Ab-18 CDR-L2 | GTSNLAS |
| 238 | Ab-17 and Ab-18 CDR-L3 | QQWTTTYT |
| 266 | Ab-17 and Ab-18 CDR-H1 | DYYIH |
| 267 | Ab-17 and Ab-18 CDR-H2 | RIDPDNGESTYVPKFQG |
| 268 | Ab-17 and Ab-18 CDR-H3 | EGLDYGDYYAVDY |
| 239 | Ab-19, Ab-20 and Ab-23 CDR-L1 | RASQDISSYLN |
| 240 | Ab-19, Ab-20 and Ab-23 CDR-L2 | STSRLNS |
| 241 | Ab-19, Ab-20 and Ab-23 CDR-L3 | QQDIKHPT |
| 269 | Ab-19, Ab-20 and Ab-23 CDR-H1 | DYIMH |
| 270 | Ab-19, Ab-20 and Ab-23 CDR-H2 | YINPYNDDTEYNEKFKG |
| 271 | Ab-19, Ab-20 and Ab-23 CDR-H3 | SIYYYDAPFAY |
| 242 | Ab-21 and Ab-22 CDR-L1 | KASQDVFTAVA |
| 243 | Ab-21 and Ab-22 CDR-L2 | WASTRHT |
| 244 | Ab-21 and Ab-22 CDR-L3 | QQYSSYPLT |
| 272 | Ab-21 and Ab-22 CDR-H1 | DYYMH |
| 273 | Ab-21 and Ab-22 CDR-H2 | RIDPENGDIIYDPKFQG |
| 274 | Ab-21 and Ab-22 CDR-H3 | DAGDPAWFTY |
| 351 | Ab-24 CDR-L1 | KASQSVDYDGTSYMN |
| 352 | Ab-24 CDR-L2 | AASNLES |
| 353 | Ab-24 CDR-L3 | QQSNEDPFT |
| 358 | Ab-24 CDR-H1 | TYWMN |
| 359 | Ab-24 CDR-H2 | MIHPSASEIRLDQKFKD |
| 360 | Ab-24 CDR-H3 | SGEWGSMDY |

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDR's of Table 1 above; and/or to a CDR of a sclerostin binding agent that cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or to a CDR of a sclerostin binding agent wherein the binding agent can block the inhibitory effect of sclerostin in a cell based mineralization assay (i.e. a sclerostin neutralizing binding agent); and/or to a CDR of a sclerostin binding agent that binds to a Loop 2 epitope;

and/or to a CDR of a sclerostin binding agent that binds to a T20.6 epitope; and/or to a CDR of a sclerostin binding agent that binds to a "T20.6 derivative (cysteine-knot+4 arms)" epitope.

Sclerostin binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cysteine-knot+4 arms)" epitope.

Polynucleotides encoding sclerostin binding agents are within the scope of the invention if they have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and wherein the encoded sclerostin binding agents cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cysteine-knot+4 arms)" epitope.

Antibodies according to the invention may have a binding affinity for human sclerostin of less than or equal to $1\times10^{-7}$M, less than or equal to $1\times10^{-8}$M, less than or equal to $1\times10^{-9}$M, less than or equal to $1\times10^{-10}$ M, less than or equal to $1\times10^{-11}$M, or less than or equal to $1\times10^{-12}$M.

The affinity of a binding agent such as an antibody or binding partner, as well as the extent to which a binding agent (such as an antibody) inhibits binding, can be determined by one of ordinary skill in the art using conventional techniques, for example those described by Scatchard et al. (*Ann. N.Y. Acad. Sci.* 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. Patent Publication No. 2004/0146888 A1.

Characterization Assays

In the methods described above to generate antibodies according to the invention, including the manipulation of the specific Ab-A, Ab-B, Ab-C, Ab-D, and Antibody 1-24 (Ab-1 to Ab-24) CDRs into new frameworks and/or constant regions, appropriate assays are available to select the desired antibodies or binding agents (i.e. assays for determining binding affinity to sclerostin; cross-blocking assays; Biacore-based "human sclerostin peptide epitope competition binding assay;" MC3T3-E1 cell based assay; in vivo assays).

Epitope Binding Assays

Figure 9:
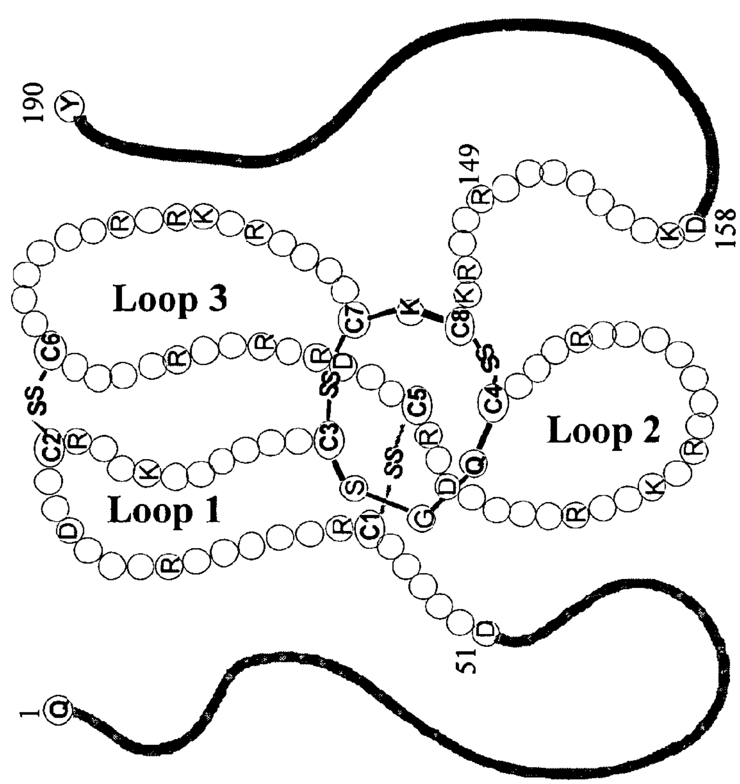
FIG. 9 depicts a schematic of the basic structure of human sclerostin. There is an N-terminal arm (from the first Q to C1) and a C-terminal arm (from C8 to the terminal Y). In between these arms there is the cysteine-knot structure (formed by three disulfides: C1-C5; C3-C7; C4-C8) and three loops which are designated Loop1, Loop 2 and Loop 3. The distal regions of Loop 1 and Loop 3 are linked by the C2-C6 disulfide. Potential trypsin cleavage sites are indicated (arginine=R and lysine=K). Some of the potential AspN cleavage sites are indicated (only aspartic acid (D) residues are shown).

Mature form human sclerostin is a 190 amino acid glycoprotein with a cysteine-knot structure (FIGS. 8 and 9). In addition to the cysteine-knot structure, the protein is characterized as having three loops designated as Loop 1, Loop 2 and Loop 3. Human sclerostin was subjected to proteolytic digestion to produce fragments. Briefly, using different proteases, including trypsin, aspN, and lysC, fragments with various cleavage sites and sizes were generated. The sequences and mass for various human sclerostin peptides were determined. Antibody protection was evaluated to determine the effect on accessibility for proteolysis, including clipped site masking and peptide shifting. Finally, a BIAcore-based "human sclerostin peptide epitope competition assay" was performed.

Figure 13:
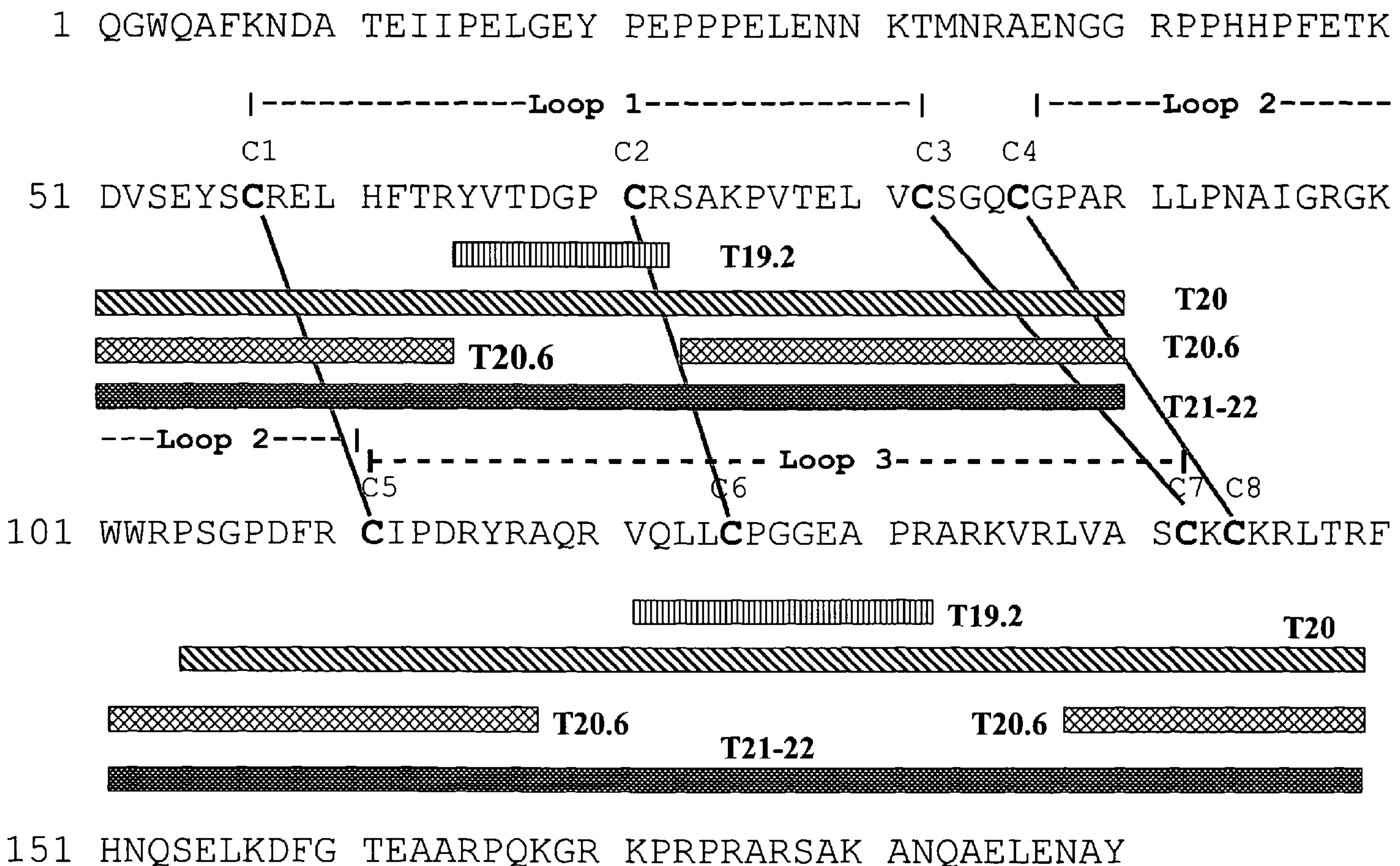
FIG. 13 shows a linear schematic of four human sclerostin peptides (T19.2, T20, T20.6 and T21-22) generated by trypsin digestion.

Exposure of sclerostin to trypsin cleavage resulted in a pattern of peptide fragments as summarized in FIG. 13. The fragments are referred to as T19.2, T20, T20.6, and T21-22. As shown schematically in FIG. 19B, the T20.6 epitope is a complex of four separate peptide sequences which are joined by the three disulfide bonds of the cysteine-knot region. Two of the peptides are joined by two disulfide bonds. The other two peptides are linked by one disulfide bond that, schematically, bisects the first two polypeptides.

The T20.6 epitope that was generated by trypsin digestion retains the cysteine-knot structure of the native polypeptide and is recognized by antibodies Ab-C and Ab-D. A derivative of epitope T20.6 consists of the cysteine-knot region and amino acids 58-64, 73-81, 112-117 and 138-141 in sequence position with reference to SEQ ID NO:1. This derivative epitope is shown in FIG. 21. An epitope comprising the cysteine-knot region may have one or more amino acids that is present in the T20.6 epitope (FIG. 19B) but not present in the T20.6 derivative epitope (FIG. 21).

Another epitope-containing region was identified in the Loop 2 region of human sclerostin (FIG. 19A) and is recognized by antibodies Ab-A and Ab-B. A Loop 2 epitope comprises amino acids 86-111 of SEQ ID NO:1 (C4 GPARLLPNAIGRGKWWRPSGPDFRC5, SEQ ID NO:6). Sterically, with reference to full-length sclerostin of SEQ ID NO:1, the Loop 2-containing structure is defined at one end by a disulfide bond between cysteine at position 86 (C4) and cysteine at position 144 (C8), and at the other end by a disulfide bond between cysteine at position 111 (C5) and cysteine at position 57 (C1).

The peptides generated by aspN cleavage of human sclerostin are shown in FIG. 12. In the Figure, these peptides are designated as AspN14.6, AspN18.6, and AspN22.7-23.5, and are also referred to herein as N14.6, N18.6, and N22.7-23.5, respectively.

One group of antibodies exhibits a specific pattern of binding to certain epitopes as evidenced by a Biacore-based "human sclerostin peptide epitope competition binding assay." Briefly, the antibody is preincubated with the epitope to be tested, at concentrations that will saturate the epitope-binding sites on the antibody. The antibody is then exposed to sclerostin bound to a chip surface. After the appropriate incubation and washing procedures, a pattern of competitive binding is established. As shown in FIG. 18, exemplary antibody Ab-D bound to sclerostin molecules attached to the surface of the chip. Preincubation of antibody Ab-D with sclerostin decreased the binding of the antibody to the sclerostin on the chip to close to zero. Preincubation with a peptide consisting of epitope T19.2 showed that T19.2 did not compete with sclerostin for antibody binding. However, preincubation with any one of the epitopes designated T20, T20.6, T21-22, or N22.7-23.5 abolished a large proportion of the binding of antibody to sclerostin on the chip. In contrast, preincubation of the antibody with any one of the epitopes designated T19.2, N14.6 or N18.6 did not abolish the ability of the antibody to bind to sclerostin. A second exemplary antibody with this binding profile (FIG. 17) is Ab-C.

Antibody Ab-D therefore is exemplary and representative of a group of antibodies that bind to the epitopes T20, T20.6, T21-22, and N22.7-23.5, and have minimal detectable binding to epitopes T19.2, N14.6 and N18.6, as measured by the ability to block antibody binding to sclerostin. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-D are included in the invention. By "similar to" is meant, for example, the antibody will exhibit binding to each of the polypeptides T20, T20.6, T21-22 and N22.7-23.5 whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 18 suggests that the epitope space to which antibody Ab-D and other antibodies having the epitope binding pattern of Ab-D bind consists of a polypeptide comprising the cysteine-knot region of sclerostin.

Thus, as disclosed herein and with reference to FIG. 19B, an exemplary T20.6 epitope comprises four peptide chains attached via three separate disulfide bonds. Peptide chain SAKPVTELVC3SGQC4GPAR (SEQ ID NO:3) is attached to peptide chain LVASC7KC8KRLTR (SEQ ID NO:5) by disulfide bonds from C3 to C7, and from C4 to C8. Peptide chain DVSEYSC1RELHFTR (SEQ ID NO:2) is attached to peptide chain WWRPSGPDFRC5IPDRYR (SEQ ID NO:4) by a disulfide bond from C1 to C5. The polypeptides of SEQ ID NOs:3 and 5 remain associated with the polypeptides of SEQ ID NOs:2 and 4 through a steric construct whereby the C1-C5 bond crosses the plane of the C4-C8 and C3-C7 bonds and is located between them, as illustrated in FIG. 19B.

As disclosed herein and with reference to FIG. 21, an exemplary derivative epitope of T20.6 comprises four peptide chains attached via three separate disulfide bonds. Peptide chain SAKPVTELVC3SGQC4 (SEQ ID NO:70) is attached to peptide chain LVASC7KC8 (SEQ ID NO:71) by disulfide bonds from C3 to C7, and from C4 to C8. Peptide chain C1RELHFTR (SEQ ID NO:72) is attached to peptide chain C5IPDRYR (SEQ ID NO:73) by a disulfide bond from C1 to C5. The polypeptides of SEQ ID NOs:70 and 71 remain associated with the polypeptides of SEQ ID NOs:72 and 73 through a steric construct whereby the C1-C5 bond crosses the plane of the C4-C8 and C3-C7 bonds and is located between them, as illustrated in FIG. 21.

Antibody Ab-A is exemplary and representative of a second group of antibodies that have a characteristic binding pattern to human sclerostin peptides that is distinct from that obtained for antibodies Ab-C and Ab-D. Ab-A and the group of antibodies it represents bind to the N22.7-23.5 epitope and have minimal detectable binding to epitopes T19.2, T20, T20.6, T21-22, N14.6 or N18.6, as measured by the ability to block antibody binding to sclerostin (FIG. 15). A second exemplary antibody with this binding profile (FIG. 16) is Ab-B. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-A are included in the invention. By "similar to" is meant, for example, the antibody will exhibit binding to the N22.7-23.5 polypeptide whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, T20, T20.6, T21-22, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 15 suggests that the epitope space to which antibody Ab-A and other antibodies having the epitope binding pattern of Ab-A bind consists of a polypeptide comprising the Loop 2 region of sclerostin. Thus, as disclosed herein and with reference to FIG. 19A, the Loop 2 region can be described as a linear peptide, but it acquires a tertiary structure when it is present in native sclerostin or a cysteine-knot-containing portion of sclerostin in which the native disulfide bond structure is maintained. The linear or tertiary structure of the Loop 2 epitope can affect antibody binding thereto, as discussed in the Examples. A Loop 2 region can comprise the following amino acid sequence: C4 GPARLLPNAIGRGKWWRPSGPDFRC5 (SEQ ID NO:6). "C4" refers to a cysteine residue located at position 86 with reference to SEQ ID NO:1. "C5" refers to a cysteine residue located at position 111 with reference to SEQ ID NO:1. In native sclerostin protein, C4 is linked to a cysteine at position 144 (C8) by a disulfide bond, and C5 is linked to a cysteine at position 57 (C1) by a disulfide bond. Epitopes derived from the Loop 2 region include CGPARLLPNAIGRGKWWRPS (SEQ ID NO:63); GPARLLPNAIGRGKWWRPSG (SEQ ID NO:64); PARLLPNAIGRGKWWRPSGP (SEQ ID NO:65);

ARLLPNAIGRGKWWRPSGPD (SEQ ID NO:66); RLLPNAIGRGKWWRPSGPDF (SEQ ID NO:67); LLPNAIGRGKWWRPSGPDFR (SEQ ID NO:68); and LPNAIGRGKWWRPSGPDFRC (SEQ ID NO:69)

Cross-Blocking Assays

The terms "cross-block", "cross-blocked" and "cross-blocking" are used interchangeably herein to mean the ability of an antibody or other binding agent to interfere with the binding of other antibodies or binding agents to sclerostin.

The extent to which an antibody or other binding agent is able to interfere with the binding of another to sclerostin, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between antibodies or other binding agents in terms of their binding to sclerostin.

Biacore Cross-Blocking Assay

The following generally describes a suitable Biacore assay for determining whether an antibody or other binding agent cross-blocks or is capable of cross-blocking according to the invention. For convenience reference is made to two antibodies, but it will be appreciated that the assay can be used with any of the sclerostin binding agents described herein. The Biacore machine (for example the Biacore 3000) is operated in line with the manufacturer's recommendations.

Thus in one cross-blocking assay, sclerostin is coupled to a CM5 Biacore chip using standard amine coupling chemistry to generate a sclerostin-coated surface. Typically 200-800 resonance units of sclerostin would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of sclerostin binding sites on that antibody.

The concentration of each antibody in the test mix should be high enough to readily saturate the binding sites for that antibody on the sclerostin molecules captured on the Biacore chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the sclerostin-coated Biacore chip and the total amount of binding recorded. The chip is then treated in such a way as to remove the bound antibodies without damaging the chip-bound sclerostin. Typically this is done by treating the chip with 30 mM HCl for 60 seconds.

The solution of antibody A* alone is then passed over the sclerostin-coated surface and the amount of binding recorded. The chip is again treated to remove all of the bound antibody without damaging the chip-bound sclerostin.

The solution of antibody B* alone is then passed over the sclerostin-coated surface and the amount of binding recorded.

The maximum theoretical binding of the mixture of antibody A* and antibody B* is next calculated, and is the sum of the binding of each antibody when passed over the sclerostin surface alone. If the actual recorded binding of the mixture is less than this theoretical maximum then the two antibodies are cross-blocking each other.

Thus, in general, a cross-blocking antibody or other binding agent according to the invention is one which will bind to sclerostin in the above Biacore cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The Biacore assay described above is a primary assay used to determine if antibodies or other binding agents cross-block each other according to the invention. On rare occasions particular antibodies or other binding agents may not bind to sclerostin coupled via amine chemistry to a CM5 Biacore chip (this usually occurs when the relevant binding site on sclerostin is masked or destroyed by the coupling to the chip). In such cases cross-blocking can be determined using a tagged version of Sclerostin, for example N-terminal His-tagged Sclerostin (R & D Systems, Minneapolis, Minn., USA; 2005 cat#1406-ST-025). In this particular format, an anti-His antibody would be coupled to the Biacore chip and then the His-tagged Sclerostin would be passed over the surface of the chip and captured by the anti-His antibody. The cross blocking analysis would be carried out essentially as described above, except that after each chip regeneration cycle, new His-tagged sclerostin would be loaded back onto the anti-His antibody coated surface. In addition to the example given using N-terminal His-tagged Sclerostin, C-terminal His-tagged sclerostin could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

ELISA-Based Cross-Blocking Assay

The following generally describes an ELISA assay for determining whether an anti-sclerostin antibody or other sclerostin binding agent cross-blocks or is capable of cross-blocking according to the invention. For convenience, reference is made to two antibodies (Ab-X and Ab-Y), but it will be appreciated that the assay can be used with any of the sclerostin binding agents described herein.

The general principal of the assay is to have an anti-sclerostin antibody coated onto the wells of an ELISA plate. An excess amount of a second, potentially cross-blocking, anti-sclerostin antibody is added in solution (i.e. not bound to the ELISA plate). A limited amount of sclerostin is then added to the wells. The coated antibody and the antibody in solution compete for binding of the limited number of sclerostin molecules. The plate is washed to remove sclerostin that has not been bound by the coated antibody and to also remove the second, solution phase antibody as well as any complexes formed between the second, solution phase antibody and sclerostin. The amount of bound sclerostin is then measured using an appropriate sclerostin detection reagent. An antibody in solution that is able to cross-block the coated antibody will be able to cause a decrease in the number of sclerostin molecules that the coated antibody can bind relative to the number of sclerostin molecules that the coated antibody can bind in the absence of the second, solution phase, antibody.

This assay is described in more detail further below for Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y sclerostin binding sites per well are at least 10 fold higher than the moles of Ab-X sclerostin binding sites that were used, per well, during the coating of the ELISA plate. Sclerostin is then added such that the moles of sclerostin added per well are at least 25-fold lower than the moles of Ab-X sclerostin binding sites that were used for coating each well. Following a suitable incubation period the ELISA plate is washed and a sclerostin detection reagent is added to measure the amount of sclerostin specifically bound by the coated anti-sclerostin antibody (in this case Ab-X). The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

An example of such an ELISA-based cross blocking assay can be found in Example 7 ("ELISA-based cross-blocking assay").

Cell Based Neutralization Assay

Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J. Cell Biol. 96:191-198) and subclones of the original cell line can form mineral in culture upon growth in the presence of differentiating agents. Such subclones include MC3T3-E1-BF (Smith E, Redman R, Logg C, Coetzee G, Kasahara N, Frenkel B. 2000. *Glucocorticoids inhibit developmental stage-specific osteoblast cell cycle*. J. Biol. Chem. 275:19992-20001). For both the MC3T3-E1-BF subclone as well as the original MC3T3-E1 cells, sclerostin can inhibit one or more of the sequence of events leading up to and including mineral deposition (i.e. sclerostin inhibits mineralization). Anti-sclerostin antibodies that are able to neutralize sclerostin's inhibitory activity allow for mineralization of the culture in the presence of sclerostin such that there is a statistically significant increase in deposition of calcium phosphate (measured as calcium) as compared to the amount of calcium measured in the sclerostin-only (i.e. no antibody) treatment group. The antibodies used in the cell based mineralization assay experiments shown in FIGS. 22, 23 and 24 have molecular weights of about 145 Kd and have 2 sclerostin binding sites per antibody molecule.

When running the assay with the goal of determining whether a particular anti-sclerostin antibody or anti-sclerostin binding agent can neutralize sclerostin (i.e., is a sclerostin neutralizing antibody or derivative thereof, or is a sclerostin neutralizing binding agent), the amount of sclerostin used in the assay needs to be the minimum amount of sclerostin that causes at least a 70%, statistically significant, reduction in deposition of calcium phosphate (measured as calcium) in the sclerostin-only group, as compared to the amount of calcium measured in the no sclerostin group. An anti-sclerostin neutralizing antibody or an anti-sclerostin neutralizing binding agent is defined as one that causes a statistically significant increase in deposition of calcium phosphate (measured as calcium) as compared to the amount of calcium measured in the sclerostin-only (i.e. no antibody, no binding agent) treatment group. To determine whether an anti-sclerostin antibody or an anti-sclerostin binding agent is neutralizing or not, the amount of anti-sclerostin antibody or anti-sclerostin binding agent used in the assay needs to be such that there is an excess of moles of sclerostin binding sites per well as compared to the number of moles of sclerostin per well. Depending on the potency of the antibody, the fold excess that may be required can be 24, 18, 12, 6, 3, or 1.5, and one of skill is familiar with the routine practice of testing more than one concentration of binding agent. For example, a very potent anti-sclerostin neutralizing antibody or anti-sclerostin neutralizing binding agent will be able to neutralize sclerostin even when there is less than a 6-fold excess of moles of sclerostin binding sites per well as compared to the number of moles of sclerostin per well. A less potent anti-sclerostin neutralizing antibody or anti-sclerostin neutralizing binding agent will be able to neutralize sclerostin only at a 12, 18 or 24 fold excess. Sclerostin binding agents within this full range of potencies are suitable as neutralizing sclerostin binding agents. Exemplary cell based mineralization assays are described in detail in Example 8.

Anti-sclerostin antibodies and derivatives thereof that can neutralize human sclerostin, and sclerostin binding agents that can neutralize human sclerostin may be of use in the treatment of human conditions/disorders that are caused by, associated with, or result in at least one of low bone formation, low bone mineral density, low bone mineral content, low bone mass, low bone quality and low bone strength.

In Vivo Neutralization Assay

Increases in various parameters associated with, or that result from, the stimulation of new bone formation can be measured as an output from in vivo testing of sclerostin binding agents in order to identify those binding agents that are able to neutralize sclerostin and thus able to cause stimulation of new bone formation. Such parameters include various serum anabolic markers [e.g. osteocalcin, P1NP (n-terminal propeptide of type 1 procollagen)], histomorphometric markers of bone formation (e.g. osteoblast surface/bone surface; bone formation rate/bone surface; trabecular thickness), bone mineral density, bone mineral content, bone mass, bone quality and bone strength. A sclerostin neutralizing binding agent is defined as one capable of causing a statistically significant increase, as compared to vehicle treated animals, in any parameter associated with, or that results from, the stimulation of new bone formation. Such in vivo testing can be performed in any suitable mammal (e.g. mouse, rat, monkey). An example of such in vivo testing can be found in Example 5 ("In vivo testing of anti-sclerostin monoclonal antibodies").

Although the amino acid sequence of sclerostin is not 100% identical across mammalian species (e.g. mouse sclerostin is not 100% identical to human sclerostin), it will be appreciated by one skilled in the art that a sclerostin binding agent that can neutralize, in vivo, the sclerostin of a certain species (e.g. mouse) and that also can bind human sclerostin in vitro is very likely to be able to neutralize human sclerostin in vivo. Thus, such a human sclerostin binding agent (e.g. anti-human sclerostin antibody) may be of use in the treatment of human conditions/disorders that are caused by, associated with, or result in at least one of low bone formation, low bone mineral density, low bone mineral content, low bone mass, low bone quality and low bone strength. Mice in which homologous recombination had been used to delete the mouse sclerostin gene and insert the human sclerostin gene in its place (i.e. human sclerostin gene knock-in mice or human SOST knock-in mice) would be an example of an additional in vivo system.

Pharmaceutical compositions are provided, comprising one of the above-described binding agents such as at least one of antibody Ab-A, Ab-B, Ab-C, Ab-D and Ab-1 to Ab-24 to human sclerostin, along with a pharmaceutically or physiologically acceptable carrier, excipient, or diluent. Pharmaceutical compositions and methods of treatment are disclosed in copending application Ser. No. 10/868,497, filed Jun. 16, 2004, which claims priority to Ser. No. 60/478,977, both of which are incorporated by reference herein.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences,* 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3): 691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 μm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 100 mg/kg of body weight. As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Increases in bone mineral content and/or bone mineral density may be determined directly through the use of X-rays (e.g., Dual Energy X-ray Absorptometry or "DEXA"), or by inference through the measurement of 1) markers of bone formation and/or osteoblast activity, such as, but not limited to, osteoblast specific alkaline phosphatase, osteocalcin, type 1 procollagen C' propeptide (PICP), total alkaline phosphatase (see Comier, *Curr. Opin. in Rheu.* 7:243 (1995)) and serum procollagen 1N-terminal propeptide (P1NP) and/or 2) markers of bone resorption and/or osteoclast activity including, but not limited to, pyridinoline, deoxypryridinoline, N-telopeptide, urinary hydroxyproline, plasma tartrate-resistant acid phosphatases, and galactosyl hydroxylysine; (see Cornier, id), serum TRAP 5b (tartrate-resistant acid phosphatase isoform 5b) and serum cross-linked C-telopeptide (sCTXI). The amount of bone mass may also be calculated from body weights or by using other methods (see Guinness-Hey, Metab. *Bone Dis. Relat. Res.* 5:177-181, 1984). Animals and particular animal models are used in the art for testing the effect of the compositions and methods of the invention on, for example, parameters of bone loss, bone resorption, bone formation, bone strength or bone mineralization that mimic conditions of human disease such as osteoporosis and osteopenias. Examples of such models include the ovariectomized rat model (Kalu, D. N., *The ovariectomized rat model of postmenopausal bone loss. Bone and Mineral* 15:175-192 (1991); Frost, H. M. and Jee, W. S. S. *On the rat model of human osteopenias and osteoporosis. Bone and Mineral* 18:227-236 (1992); and Jee, W. S. S, and Yao, W., *Overview: animal models of osteopenia and osteoporosis. J. Musculoskel. Neuron. Interact.* 1:193-207 (2001)).

Particular conditions which may be treated by the compositions of the present invention include dysplasias, wherein growth or development of bone is abnormal and a wide variety of causes of osteopenia, osteoporosis and bone loss. Representative examples of such conditions include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, and pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, fabry disease, turner syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, idiopathic osteopenia or osteoporosis, congenital osteopenia or osteoporosis, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, fibrous dysplasia, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, and bone loss associated with space travel. Further conditions relate to bone loss associated with aging, including facial bone loss associated with aging, cranial bone loss associated with aging, jaw bone loss associated with aging, and skull bone loss associated with aging.

Compositions of the present invention may also be useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

The invention also provides a diagnostic kit comprising at least one anti-sclerostin binding agent according to the present invention. The binding agent may be an antibody. In addition, such a kit may optionally comprise one or more of the following:

(1) instructions for using the one or more binding agent(s) for screening, diagnosis, prognosis, therapeutic monitoring or any combination of these applications;
(2) a labeled binding partner to the anti-sclerostin binding agent(s);
(3) a solid phase (such as a reagent strip) upon which the anti-sclerostin binding agent(s) is immobilized; and
(4) a label or insert indicating regulatory approval for screening, diagnostic, prognostic or therapeutic use or any combination thereof.

If no labeled binding partner to the binding agent(s) is provided, the binding agent(s) itself can be labeled with one or more of a detectable marker(s), e.g. a chemiluminescent, enzymatic, fluorescent, or radioactive moiety.

The following examples are offered by way of illustration, and not by way of limitation.

EXAMPLES

Example 1

Recombinant Expression of Sclerostin

Recombinant human sclerostin/SOST is commercially available from R&D Systems (Minneapolis, Minn., USA; 2006 cat#1406-ST-025). Additionally, recombinant mouse sclerostin/SOST is commercially available from R&D Systems (Minneapolis, Minn., USA; 2006 cat#1589-ST-025).

Alternatively, the different species of sclerostin can be expressed transiently in serum-free suspension adapted 293T or 293EBNA cells. Transfections can be performed as 500 mL or 1 L cultures. The following reagents and materials are available from Gibco BRL (now Invitrogen, Carlsbad, Calif.). Catalog numbers are listed in parentheses: serum-free DMEM (21068-028); DMEM/F12 (3:1) (21068/11765); 1× Insulin-Transferrin-Selenium Supplement (51500-056); 1× Pen Strep Glut (10378-016); 2 mM 1-Glutamine (25030-081); 20 mM HEPES (15630-080); 0.01% Pluronic F68 (24040-032). Briefly, the cell inoculum ($5.0-10.0\times10^5$ cells/mL×culture volume) is centrifuged at 2,500 RPM for 10 minutes at 4° C. to remove the conditioned medium.

The cells are resuspended in serum-free DMEM and centrifuged again at 2,500 RPM for 10 minutes at 4° C. After aspirating the wash solution, the cells are resuspended in growth medium [DMEM/F12 (3:1)+1× Insulin-Transferrin-Selenium Supplement+1× Pen Strep Glut+2 mM L-Glutamine+20 mM HEPES+0.01% Pluronic F68] in a 1 L or 3 L spinner flask culture. The spinner flask culture is maintained on magnetic stir plate at 125 RPM which is placed in a humidified incubator maintained at 37° C. and 5% $CO_2$. The mammalian expression plasmid DNA (e.g. pcDNA3.1, pCEP4, Invitrogen Life Technologies, Carlsbad, Calif.), containing the complete coding region (and stop codon) of sclerostin with a Kozak consensus sequence (e.g., CCACC) directly 5' of the start site ATG, is complexed to the transfection reagent in a 50 mL conical tube.

The DNA-transfection reagent complex can be prepared in 5-10% of the final culture volume in serum-free DMEM or OPTI-MEM. The transfection reagents that can be used for this purpose include X-tremeGene RO-1539 (Roche Applied Science, Indianapolis, Ind.), FuGene6 (Roche Applied Science, Indianapolis, Ind.), Lipofectamine 2000 (Invitrogen, Carlsbad, Calif.) and 293fectin (Invitrogen, Carlsbad, Calif.). 1-5 μg plasmid DNA/mL culture is first added to serum-free DMEM, followed by 1-5 μl transfection reagent/mL culture. The complexes can be incubated at room temperature for approximately 10-30 minutes and then added to the cells in the spinner flask. The transfection/expression can be performed for 4-7 days, after which the conditioned medium (CM) is harvested by centrifugation at 4,000 RPM for 60 minutes at 4° C.

Example 2

Purification of Recombinant Sclerostin

Recombinant sclerostin was purified from mammalian host cells as follows. All purification processes were carried out at room temperature. One purification scheme was used to purify various species of sclerostin, including murine and human sclerostin. The purification scheme used affinity chromatography followed by cation exchange chromatography.

Heparin Chromatography

The mammalian host cell conditioned medium (CM) was centrifuged in a Beckman J6-M1 centrifuge at 4000 rpm for 1 hour at 4° C. to remove cell debris. The CM supernatant was then filtered through a sterile 0.2 μm filter. (At this point the sterile filtered CM may be optionally stored frozen until purification.) If the CM was frozen, it was thawed at the following temperatures, or combination thereof: 4° C., room temperature or warm water. Following thawing the CM was filtered through a sterile 0.2 μm filter and optionally concentrated by tangential flow ultrafiltration (TFF) using a 10 kD molecular weight cut-off membrane. The CM concentrate was filtered through a sterile 0.2 μm filter and then loaded onto a Heparin High Performance (Heparin HP) column (GE Healthcare, formerly Amersham Biosciences) equilibrated in PBS. Alternatively, the filtered CM supernatant may be loaded directly onto the Heparin HP column equilibrated in PBS.

After loading, the Heparin HP column was washed with PBS until the absorbance at 280 nm of the flow-through returned to baseline (i.e., absorbance measured before loading CM supernatant). The sclerostin was then eluted from the column using a linear gradient from 150 mM to 2M sodium chloride in PBS. The absorbance at 280 nm of the eluate was monitored and fractions containing protein were collected. The fractions were then assayed by Coomassie-stained SDS-PAGE to identify fractions containing a polypeptide that migrates at the size of glycosylated sclerostin. The appropriate fractions from the column were combined to make the Heparin HP pool.

Cation Exchange Chromatography

The sclerostin eluted from the Heparin HP column was further purified by cation exchange chromatography using SP High Performance (SPHP) chromatography media (GE Healthcare, formerly Amersham Biosciences). The Heparin HP pool was buffer exchanged into PBS by dialysis using 10,000 MWCO membranes (Pierce Slide-A-Lyzer). The dialyzed Heparin HP pool was then loaded onto an SPHP column equilibrated in PBS. After loading, the column was washed with PBS until the absorbance at 280 nm of the flow-through returned to baseline. The sclerostin was then eluted from the SPHP column using a linear gradient from 150 mM to 1M sodium chloride in PBS. The absorbance at 280 nm of the eluate was monitored and the eluted sclerostin was collected in fractions. The fractions were then assayed by Coomassie-stained SDS-PAGE to identify fractions containing a polypeptide that migrates at the size of glycosylated sclerostin. The appropriate fractions from the column were combined to make the SPHP pool.

Formulation

Following purification, the SPHP pool was formulated in PBS by dialysis using 10,000 MWCO membranes (Pierce Slide-A-Lyzer). If concentration of sclerostin was necessary, a centrifugal device (Amicon Centricon or Centriprep) with a 10,000 MWCO membrane was used. Following formulation the sclerostin was filtered through a sterile 0.2 μm filter and stored at 4° C. or frozen.

Example 3

Peptide Binding ELISA

A series of overlapping peptides (each peptide being approximately 20-25 amino acids long) were synthesized based on the known amino acid sequence of rat sclerostin (SEQ ID NO:98). The peptides were designed such that they all contained a reduced cysteine residue; an additional cysteine was included at the C-terminus of each peptide which did not already contain one in its sequence. This enabled the peptides to be bound to the assay plates by covalent coupling, using commercially available sulfhydryl binding plates (Costar), at a concentration of 1 μg/ml, in phosphate buffered saline (PBS: pH 6.5) containing 1 mM EDTA. Following incubation for 1 hour at room temperature, the plates were washed three times with PBS containing 0.5% Tween 20. The plates were blocked by incubation with a PBS solution containing 0.5% fish skin gelatin (Sigma) for 30 minutes at room temperature and then washed three times in PBS containing 0.5% Tween 20.

Antibodies to be tested were diluted to 1 μg/ml in PBS containing 0.5% fish skin gelatin and incubated with the peptide-coated plates for 1 hour at room temperature. Excess antibody was removed by three washes with PBS, 0.5% Tween 20. The plates were then incubated with an appropriate secondary antibody conjugated to horseradish peroxidase (diluted appropriately in PBS containing 0.5% Tween 20) and capable of binding to the antibody of interest. The plates were then washed three times: once with PBS containing 0.5% Tween 20, and twice with PBS. Finally the plates were incubated with a horseradish peroxidase chromogenic substrate (TMB-Stable Stop, RDI) for 5 minutes at room temperature, the color development was stopped with acid, and the plates' optical density measured at 450 nm.

Materials

Costar's Sulfhydryl Binding Plates (VWR #29442-278)

Coating Buffer: 1×PBS PH 6.5+1 mM EDTA

Blocking Buffer: 1×PBS+0.5% Fish Skin Gelatin (PBS from CS; FSG from Sigma#G 7765)

Wash Buffer: 1×PBS+0.5% Tween 20

Rat Sclerostin peptides

Antibody Samples Transient Ab, Purified recombinant Ab, rabbit Serum, etc.

Appropriate secondary Ab: Goat-anti-Rabbit/Mouse-HRP (Jackson Immuno Research, 115-036-072)

TMB-Stable Stop (RDI#RDI-TMBSX-1L)

0.5M HCl

Methods were as follows:

1. Coat plates with 100 μl/well of rat sclerostin peptide diluted in 1×PBS PH 6.5+1 mM EDTA at 1 μg/ml. Incubate plates 1 hour at room temperature. (Plates should be used within 30 minutes of opening).
2. Wash plates 3× with wash buffer.
3. Block plates with 200 ul/well blocking buffer. Incubate plates 30 minutes at room temp.
4. Repeat washing as described in (2).
5. Incubate plates with 50 ul/well of samples diluted in blocking buffer—Serum titers starting at 1:100; Transient Recombinant Ab use neat; Purified recombinant Ab use at 1 μg/ml (all samples run in duplicates). Incubate plates 1 h at room temp.
6. Wash plates as described in (2).
7. Incubate plates with 50 μl/well of appropriate Secondary Antibody (HRP labeled) diluted 1:1600 in Blocking Buffer. Incubate plates 1 hour at room temperature.
8. Wash plates 1× wash buffer, 2×PBS
9. Incubate plates with 50 μl/well of TMB, 5 minutes at room temp.
10. Stop reaction with 50 μl/well 0.5M HCl.
11. Read plates at 450 nm wavelength.

The following peptides sequences were screened as described above:

```
                                    (SEQ ID NO: 82)
QGWQAFKNDATEIIPGLREYPEPP

                                    (SEQ ID NO: 83)
TEIIPGLREYPEPPQELENN

                                    (SEQ ID NO: 84)
PEPPQELENNQTMNRAENGG

                                    (SEQ ID NO: 85)
ENGGRPPHHPYDTKDVSEYS

                                    (SEQ ID NO: 86)
CRELHYTRFVTDGP

                                    (SEQ ID NO: 87)
CRELHYTRFVTDGPSRSAKPVTELV

                                    (SEQ ID NO: 88)
CRSAKPVTELVSSGQSGPRARLL

                                    (SEQ ID NO: 89)
CGPARLLPNAIGRVKWWRPNGPDFR

                                    (SEQ ID NO: 90)
RAQRVQLLCPGGAAPRSRKV
```

-continued

```
                                    (SEQ ID NO: 91)
PGGAAPRSRKVRLVAS

                                    (SEQ ID NO: 92)
KRLTRFHNQSELKDFGPETARPQ

                                    (SEQ ID NO: 93)
IPDRYAQRVQLLSPGG

                                    (SEQ ID NO: 94)
SELKDFGPETARPQKGRKPRPRAR

                                    (SEQ ID NO: 95)
KGRKPRPRARGAKANQAELENAY

                                    (SEQ ID NO: 96)
PNAIGRVKWWRPNGPDFR

                                    (SEQ ID NO: 97)
KWWRPNGPDFRCIPDRYRAQRV.
```

A high-affinity neutralizing antibody (Ab-19) bound to two overlapping peptide sequences: PNAIGRVKWWRPNGPDFR (SEQ ID NO:96) and KWWRPNGPDFRCIPDRYRAQRV (SEQ ID NO:97).

This procedure allows the recognition of epitopes for antibodies that react with apparent linear epitopes. Peptides that contain all or part of the antibody binding site will bind antibody and thus be detected.

Example 4

Identification of Human Sclerostin Epitopes

Sclerostin Structure

Mature form (signal peptide removed) human sclerostin is a 190 amino acid protein (FIG. 8). FIG. 9 shows a schematic of the general structure of sclerostin with an N-terminal arm (from the N-terminal Q to Cysteine 1) and a C-terminal arm (from Cysteine-8 to the terminal Y). Sandwiched in between these two arms there is the cysteine-knot structure and three loops which are designated Loop1, Loop2 and Loop 3. The four disulfide bonds in sclerostin are Cys1 at sequence position 57 linked to Cys5 at sequence position 111 (referred to as C1-C5), Cys2 at sequence position 71 linked to Cys6 at sequence position 125 (referred to as C2-C6), Cys3 at sequence position 82 linked to Cys7 at sequence position 142 (referred to as C3-C7), Cys4 at sequence position 86 linked to Cys8 at sequence position 144 (referred to as C4-C8). The eight-membered ring structure is formed via C3-C7 and C4-C8 disulfide bonding. This ring structure, together with the C1-C5 disulfide bond penetrating through the ring, forms a typical cysteine-knot. C2-C6, which is not part of the cysteine-knot, brings two large loop structures, loop 1 (residues 57 to 82) and loop 3 (residues 111 to 142) close together. Loop 2 goes from C4 (residue 86) to C5 (residue 111).

Experimental

The general approach for characterizing the epitopes bound by anti-sclerostin monoclonal antibodies involved fragmenting human Sclerostin into peptides with different proteases, determining the sequence of the various human sclerostin peptides, isolating these peptides and testing each of them for their ability to bind to a particular monoclonal antibody using a Biacore-based "human sclerostin peptide epitope competition binding assay.". The resulting data permitted the location of the binding epitope to be determined.

The peptide digests were subjected to HPLC peptide mapping; the individual peaks were collected, and the peptides identified and mapped by matrix assisted laser desorption mass spectrometry (MALDI-MS) and electrospray ionization LC-MS (ESI-LC-MS) analyses and/or by N-terminal sequencing. All HPLC analyses for these studies were performed using a reverse-phase C8 column (2.1 mm i.d.×15 cm length). HPLC peptide mapping was performed with a linear gradient from 0.05% trifloroacetic acid (mobile phase A) to 90% acetonitrile in 0.05% trifluoroacetic acid. Columns were developed over 50 minutes at a flow rate of 0.2 ml/min.

Trypsin and AspN Endoproteinase Digestions

Mature form human sclerostin was digested with trypsin, which cleaves after arginine and lysine, or with AspN. About 200 μg of sclerostin at 0.5-1.0 mg/ml was incubated in PBS (pH 7.2) for 20 hrs at 37° C. with 8 μg of either trypsin or AspN.

Trypsin Digestion

Figure 10:
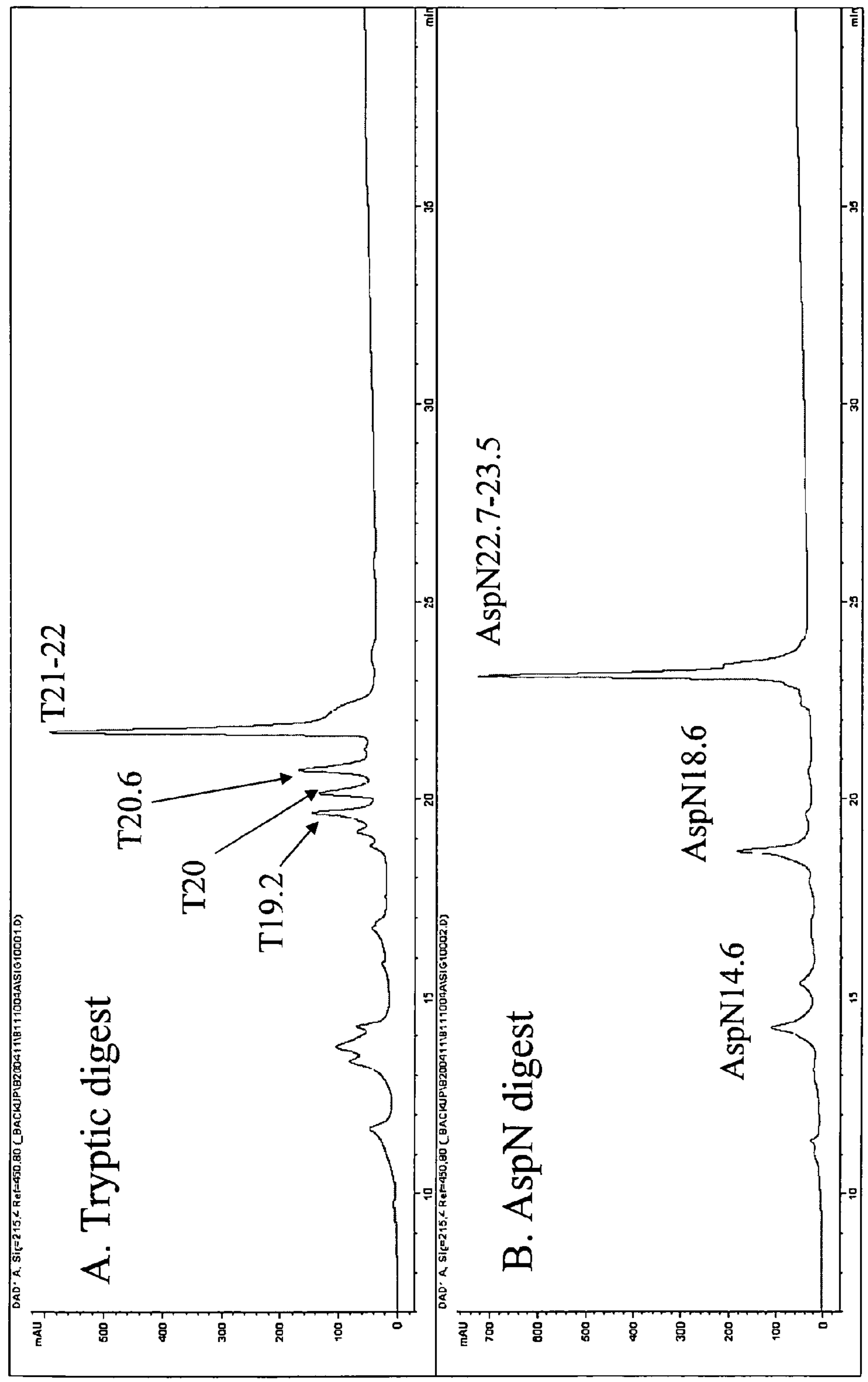
FIG. 10 depicts the HPLC peptide maps of human sclerostin after digestion with either trypsin or AspN. The human sclerostin peptides generated by trypsin digestion are indicated (T19.2, T20, T20.6 and T21-22) as are the human sclerostin peptides generated by AspN digestion (AspN14.6, AspN18.6 and AspN22.7-23.5).

HPLC chromatography of the trypsin digests yielded several major peaks (FIG. 10A). Sequence analysis was conducted on the peptide peaks recovered from HPLC after trypsin digestion. On-line ESI LC-MS analysis of the peptide digest was also performed to determine the precise mass of the peptides that were separated by HPLC. The identity of the peptides present in the peptide peaks was thus determined (FIG. 11). FIG. 13 shows the alignment of various peptide sequences (T19.2, T20, T20.6, T21-22) along the sclerostin sequence. The number following each T (e.g., T19.2) reflects the retention time. T19.2 contains two peptides (one from loop 1 and one from loop 3) linked by the C2-C6 disulfide bond. T20 contains two peptides held together by the cysteine-knot structure, with intact loops 1 and 3 held together by the C2-C6 disulfide and with most of loop 2 absent. T20.6 contains four sequences held together by the cysteine-knot structure, but is missing part of loop 1 and 3 (the T19.2 part) and is missing most of loop 2. T21-22 is almost identical to T20 but has 3 additional amino acids in the loop 2 region.

AspN Digestion

Figure 14:
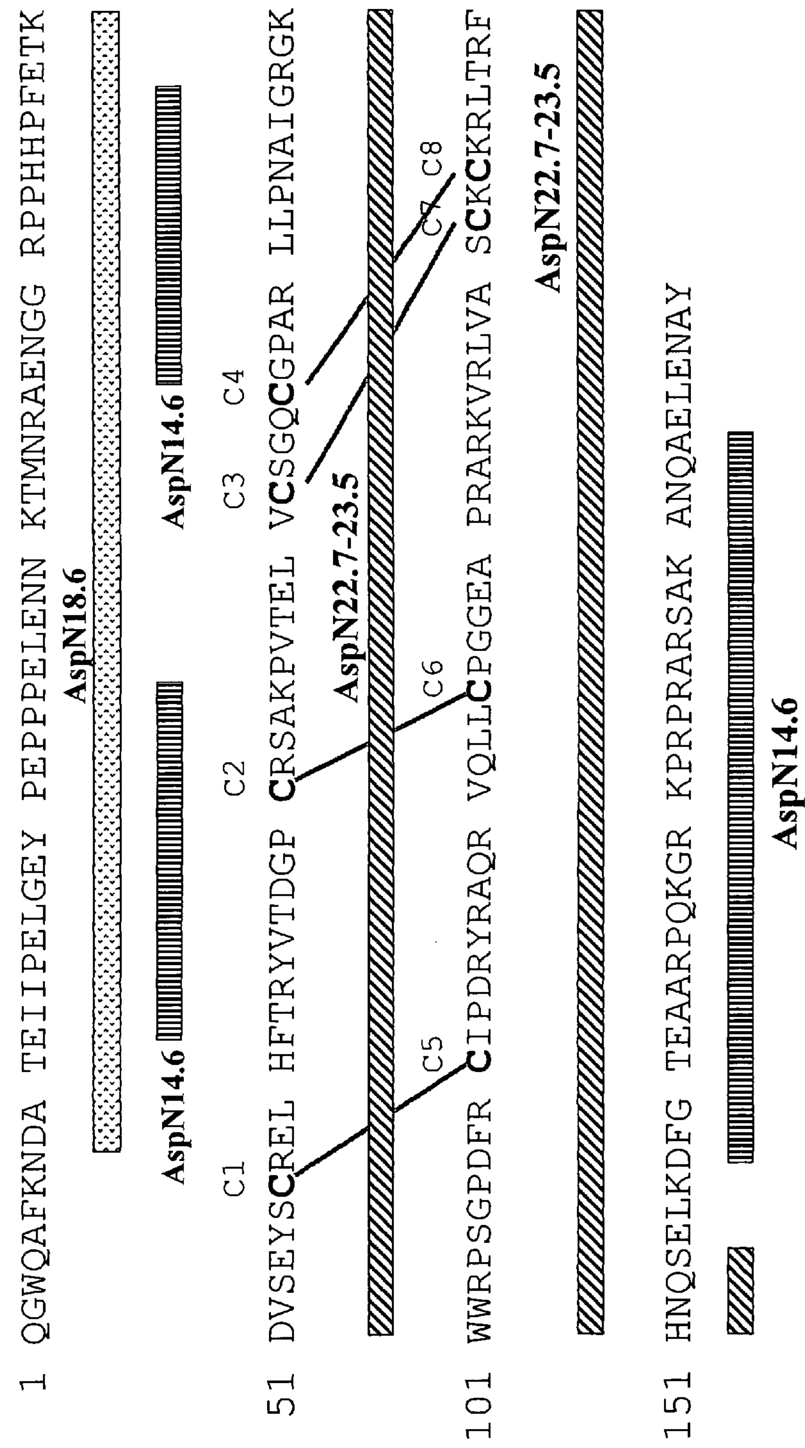
FIG. 14 shows a linear schematic of five human sclerostin peptides (AspN14.6, AspN18.6 and AspN22.7-23.5) generated by AspN digestion. The AspN14.6 HPLC peak is composed of three peptides not linked by any disulfide bonds.

HPLC chromatography of the AspN digests yielded several major peaks (FIG. 10B). Sequence analysis was conducted on the peptide peaks recovered from HPLC. On-line ESI LC-MS analysis of the peptide digest was also performed to determine the precise mass of the peptides that were separated by HPLC. The identity of the peptides present in the peptide peaks from the AspN digestion was thus determined (FIG. 12). FIG. 14 shows the alignment of various peptide sequences (AspN14.6, AspN18.6, AspN22.7-23.5) along the sclerostin sequence. The number following each AspN (e.g. AspN18.6) reflects the retention time. AspN14.6 contains three short peptides from both the N- and C-terminal arms of sclerostin, while AspN18.6 is a larger peptide from the N-terminal arm of sclerostin. AspN22.7-23.5 contains a single peptide fragment of 104 amino acids the encompasses all eight cysteines (the four disulfide bonds), the cysteine-knot and all of loops 1, 2 and 3.

The strategy for characterizing the epitopes was to use these various trypsin and AspN generated human sclerostin peptides and determine which peptides could still be bound by the various Antibodies (Ab-A, Ab-B, Ab-C and Ab-D). Specifically this was tested in a Biacore-based "human sclerostin peptide epitope competition binding assay" where the binding of a particular monoclonal antibody to human sclerostin immobilized on the Biacore chip was determine in the presence or absence of each of the various isolated trypsin and AspN HPLC peptide fractions. In the absence of any competing peptides, the particular monoclonal antibody was able to bind the human sclerostin on the chip and produce a resonance unit, RU, response. Preincubation of the particular monoclonal antibody with intact human sclerostin in solution, followed by testing of binding to the chip, demonstrated that the binding of the Mab to human sclerostin in solution prevented the binding of the Mab to the human sclerostin on the chip, thus validating the general principal of this competition assay.

This general procedure was repeated individually for each peptide. A robust RU response was taken to indicate that the particular peptide being tested could not bind the Mab in solution (hence the Mab was free to bind the human sclerostin that had been immobilized on the chip). Conversely, the absence of a robust RU response indicated that the Mab was able to bind the sclerostin peptide in solution. These binding patterns, couple with the known identity of the various sclerostin peptides, were used to determine the epitopes of sclerostin that were bound by anti-sclerostin antibodies Ab-A, Ab-B, Ab-C and Ab-D.

Biacore-Based Human Sclerostin Peptide Epitope Competition Binding Assay

Preparation of Human Sclerostin Surface:

Immobilization of mature form human sclerostin to a BIAcore sensor chip (CM5) surface was performed according to manufacturer's instructions. Briefly, carboxyl groups on the sensor chip surfaces were activated by injecting 60 μL of a mixture containing 0.2 M N-ethyl-N'-(dimethylaminopropyl) carbodiimide (EDC) and 0.05 M N-hydroxysuccinimide (NHS). Human sclerostin was diluted in 10 mM sodium acetate, pH 4.0 at a concentration of 20 μg/mL followed by injecting over the activated CM5 surface. Excess reactive groups on the surfaces were deactivated by injecting 60 μL of 1M ethanolamine. Final immobilized levels were ~5000 resonance units (RU) for the human sclerostin surface. A blank, mock-coupled reference surface was also prepared on the sensor chips.

Binding Specificity Analysis:

1× Phosphate-buffered saline without calcium chloride or magnesium chloride was from Gibco/Invitrogen, Carlsbad, Calif. Bovine serum albumin, fraction V, IgG-free was from Sigma-Aldrich, St. Louis, Mo. Each Mab (2 nM) was separately incubated with 20 nM human sclerostin or a particular human sclerostin peptide (note: there are 3 unlinked peptides in AspN14.6) in sample buffer (1×PBS+0.005% P-20+0.1 mg/mL BSA) before injection over the immobilized human sclerostin surface. The flow rate for sample injection was 5 μL/min followed by surface regeneration using 1M NaCl in 8 mM Glycine, pH 2.0 at 30 μL/min for 30 seconds. The data was analyzed using BIAevaluation 3.2, and is presented in FIG. 15 (Ab-A), FIG. 16 (Ab-B), FIG. 17 (Ab-C) and FIG. 18 (Ab-D).

Loop 2 and T20.6 Epitopes:

The sclerostin peptide binding pattern for two representative antibodies (Ab-A and Ab-B) were virtually identical (FIG. 15 and FIG. 16) and showed that both of these Antibodies could only bind the AspN22.7-23.5 peptide. The unique difference between AspN22.7-23.5 and all the other sclerostin peptides is that AspN22.7-23.5 contains an intact loop 2. This shows that Ab-A and Ab-B bind the loop 2 region of sclerostin thus defining the loop 2 epitope (FIG. 19A). The sclerostin peptide binding pattern for Ab-C and Ab-D were virtually identical to each other (FIG. 17 and FIG. 18) but completely distinct from that found for Ab-A and Ab-B. Of the peptides tested in this Example, the most diminutive peptide that Ab-C and Ab-D could bind to was the T20.6 peptide. This result defines the T20.6 epitope (FIG. 19B).

Protease Protection Assay:

The general principle of this assay is that binding of a Mab to sclerostin can result in protection of certain specific protease cleavage sites and this information can be used to determine the region of sclerostin to where the Mab binds.

Figure 20:
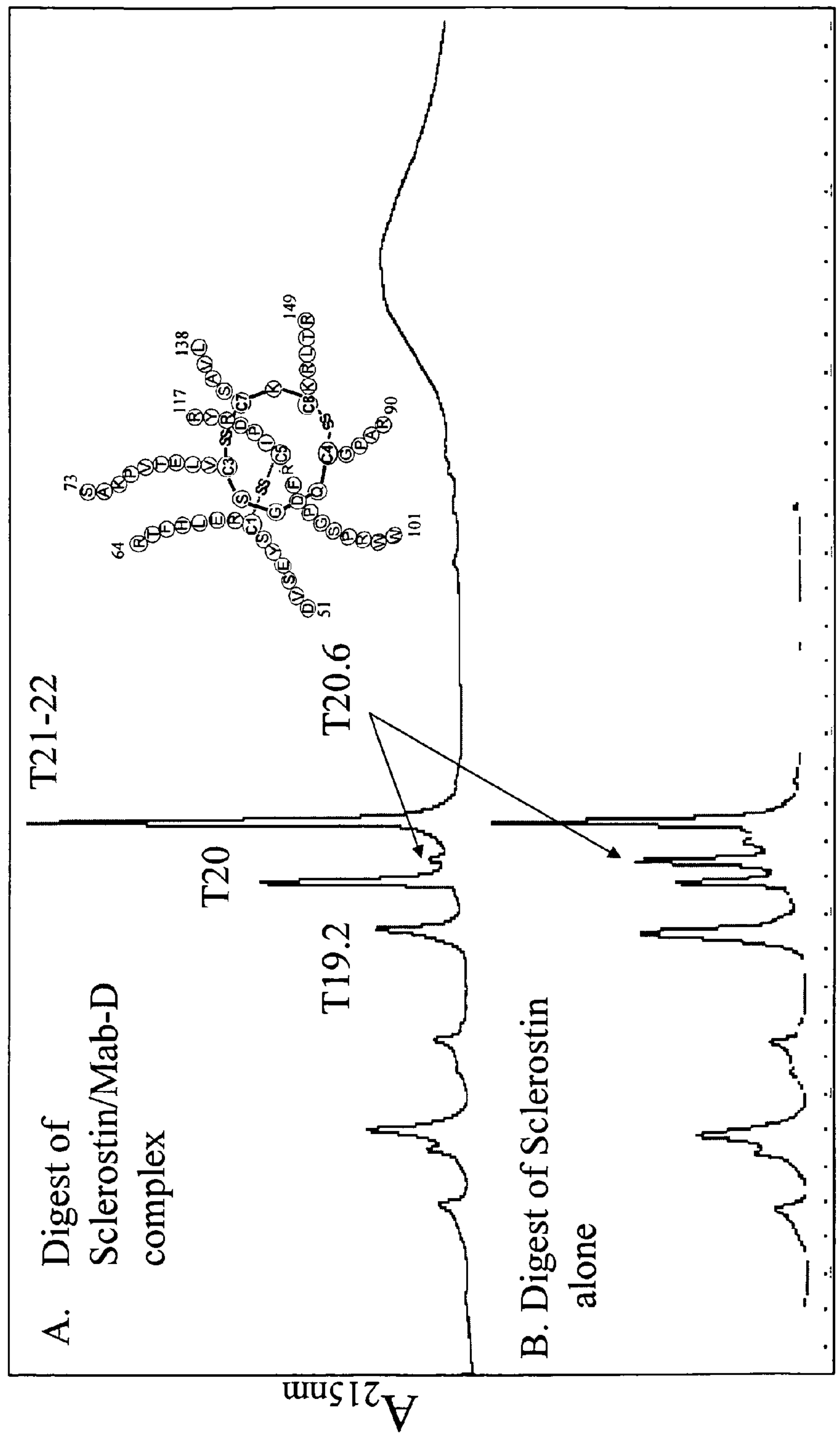
FIG. 20 depicts the HPLC peptide maps of human sclerostin after digestion with trypsin.

"T20.6 Derivative 1 (Cysteine-Knot+4 Arms)" Epitope:

FIG. 20 shows the HPLC peptide maps for a human sclerostin Ab-D complex (FIG. 20A: human sclerostin was preincubated at a 1:1 molar ratio with Ab-D prior to digestion with trypsin as described above) and human sclerostin alone (FIG. 20B: human sclerostin was digested with trypsin as described above). The peptide peaks of T19.2 and T20.6 in FIG. 20A showed a clear reduction in their respective peak height, as compared to FIG. 20B. This reduction in peak heights was accompanied by an increase in peak height for peptides T20 and T21-22. These data indicate that basic amino acid residues in loop 1 and loop 3, which in the absence of Ab-D were cleaved by trypsin to generate peptides T19.2 and T20.6, were resistant to cleavage by trypsin when Ab-D was prebound to sclerostin. The presence of T20, T20.6 and T21-22 indicates that loop 2 was still cleaved efficiently when Ab-D was prebound to sclerostin. These data indicate that Ab-D bound on the loop 1 and loop 3 side of the T20.6 epitope thus defining the smaller "T20.6 derivative 1 (cysteine-knot+4 arms)" epitope shown in FIG. 21.

Example 5

In Vivo Testing of Anti-Sclerostin Monoclonal Antibodies in Mice

Four week-old BDF1 male mice were obtained from Charles River Laboratories (Raleigh, N.C.) and housed in clean caging, five animals per cage. Room temperature was maintained between 68 and 72° F., and relative humidity was maintained between 34 and 73%. The laboratory housing the cages had a 12-hour light/dark cycle and met all AAALAC specifications. Clinical observations of all mice on study occurred once daily.

Figure 5:
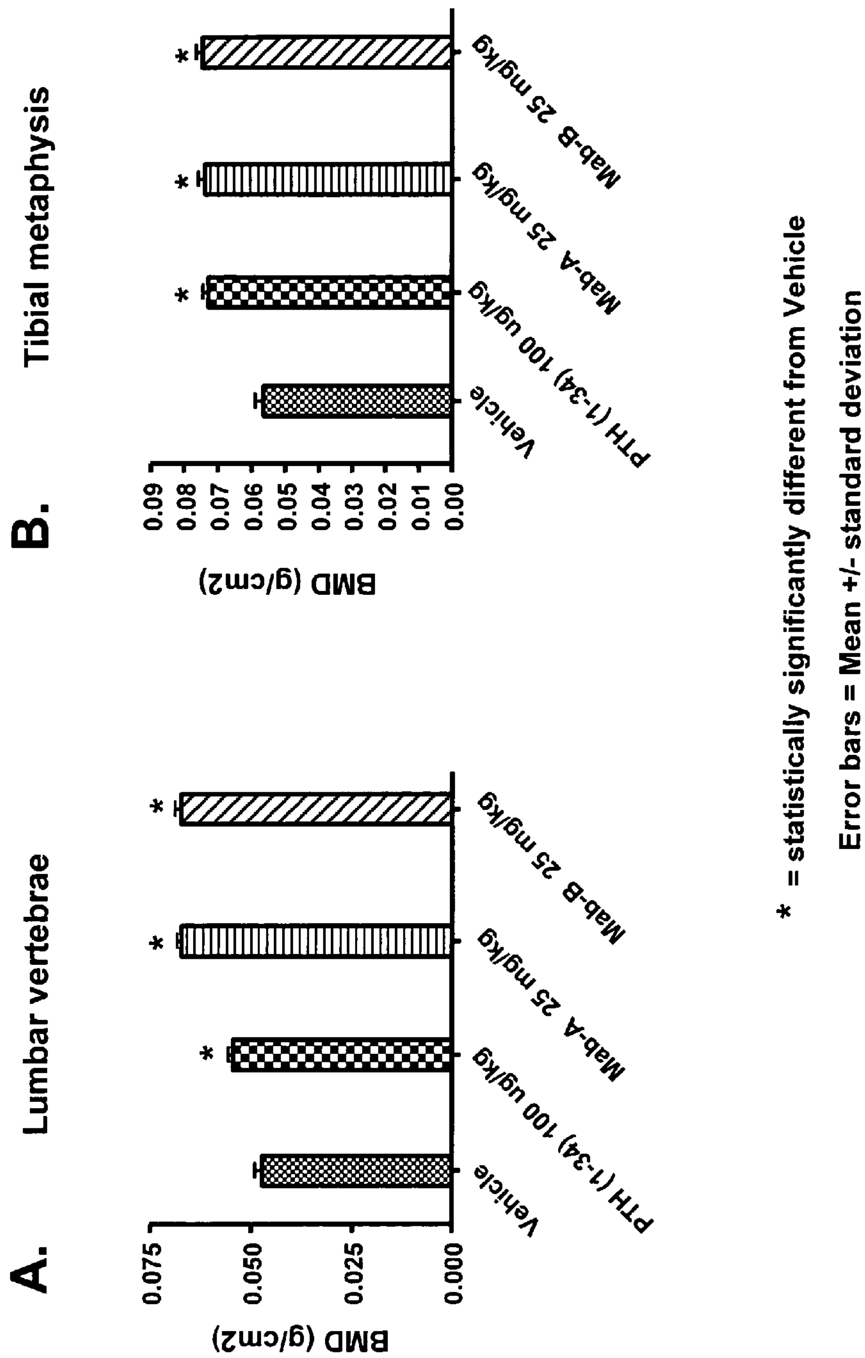
FIG. 5 depicts bone mineral density in mice measured at two skeletal sites (lumbar vertebrae and tibial metaphysis) after 3 weeks of treatment with vehicle, PTH (1-34), Ab-A or Ab-B.
Figure 6:
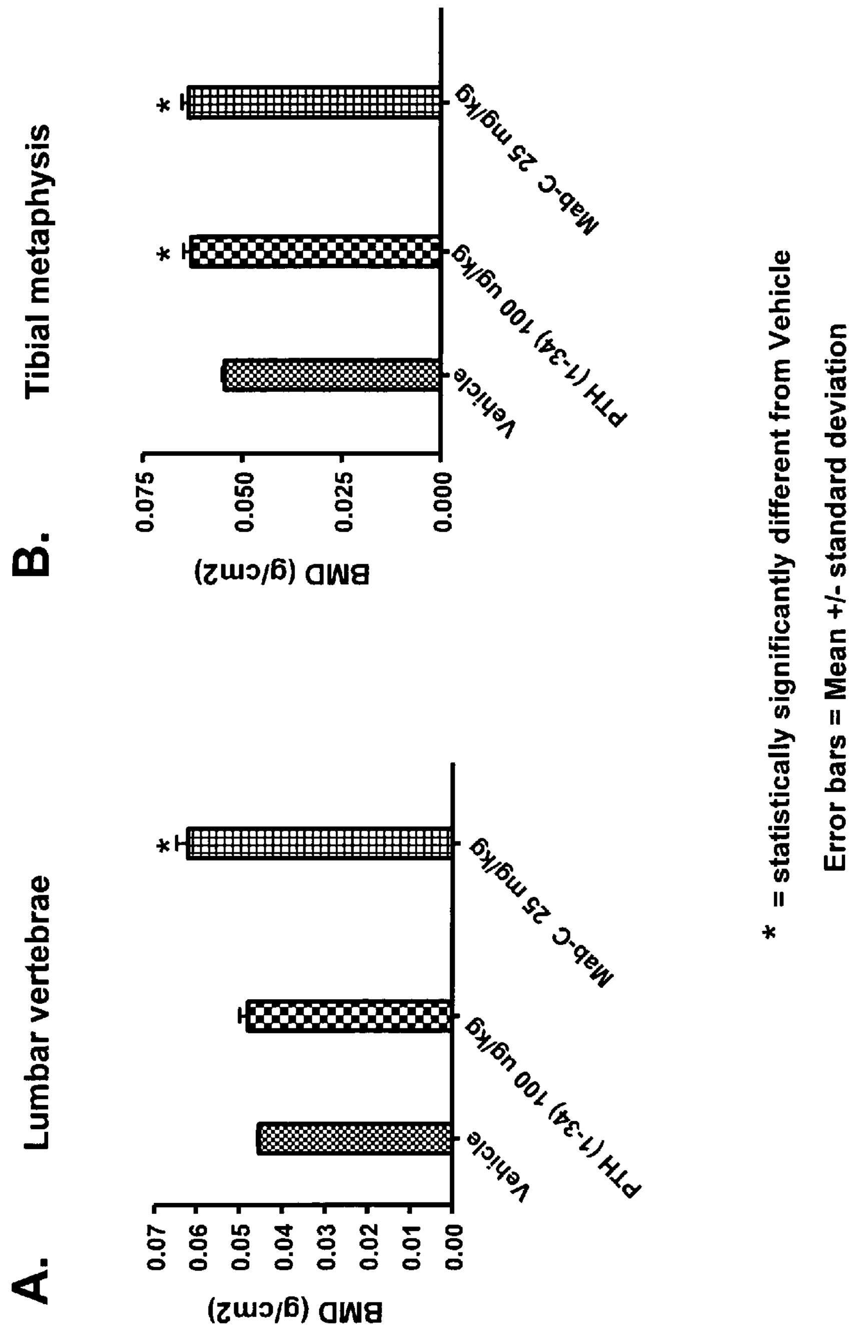
FIG. 6 shows bone mineral density in mice measured at two skeletal sites (lumbar vertebrae and tibial metaphysis) after 2 weeks of treatment with vehicle, PTH (1-34) or Ab-C.
Figure 7:
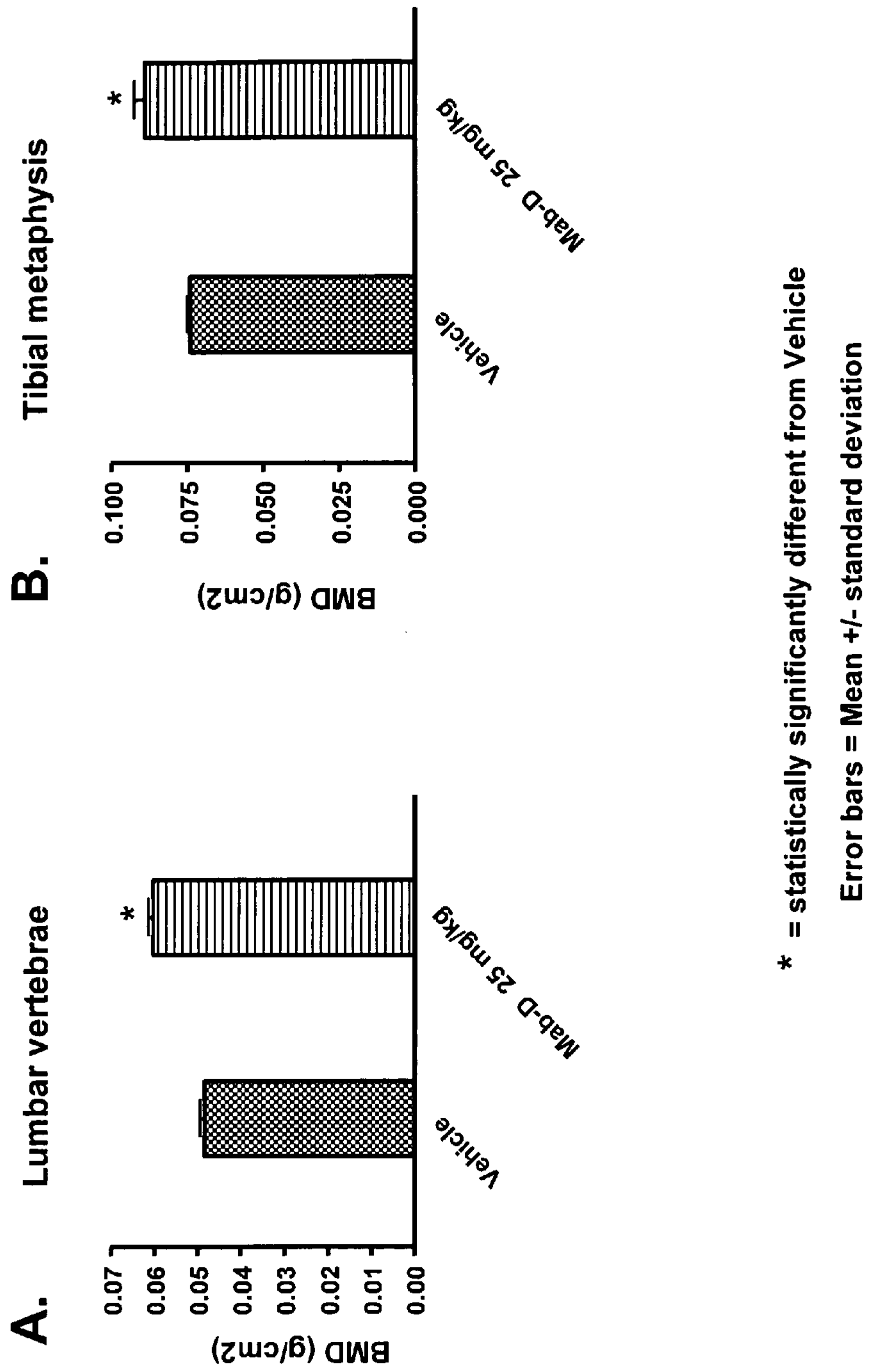
FIG. 7 depicts bone mineral density in mice measured at two skeletal sites (lumbar vertebrae and tibial metaphysis) after 3 weeks of treatment with vehicle or Ab-D.

Purified anti-sclerostin monoclonal antibodies (Ab-A FIG. 1; Ab-B FIG. 2; Ab-C FIG. 3; Ab-D FIG. 4) were diluted in sterile Dulbecco's phosphate buffered saline. Mice were injected with anti-sclerostin Antibodies or PBS vehicle subcutaneously at 21 μl per gram body weight, two times per week (Monday and Thursday) at 25 mg/kg. Human PTH (1-34) was diluted in PTH buffer (0.001N HCl, 0.15 M NaCl, 2% BSA), and dosed subcutaneously at 21 μl per gram body weight five times per week (Monday, Tuesday, Wednesday, Thursday, Friday) at 100 μg/kg as a positive control (FIGS. 5 and 6). Number of mice per group was N=5 in FIGS. 5 and 6, and N=6 in FIG. 7.

PIXImus In Vivo Bone Densitometry

Bone mineral density (BMD) was determined weekly at the proximal tibial metaphysis and lumbar vertebrae by peripheral Dual Energy X-ray Absorptometry (pDEXA) with the PIXImus2 system from GE/Lunar Medical Systems, Madison, Wis. A 25 $mm^2$ region of interest (ROI) was placed to include the proximal articular surface, the epiphysis, and the proximal end on the metaphysis of the tibia. A region of interest (ROI) was placed to include the lumbar vertebrae (L1-L5). The proximal tibia and lumbar regions were analyzed to determine total bone mineral density. Group means were reported±Standard Deviation and compared to the vehicle treatment group for statistical analysis.

Statistical Analysis

Statistical analysis was performed with a Dunnett's and Tukey-Kramer (using MS Excel and JMP v. 5.0. for the BMD data). Group means for each data set were considered significantly different when the P value was less than 0.05 (P<0.05).

Sclerostin Neutralizing Activity of Antibodies

The statistically significant increases in BMD as compared to vehicle seen for each of Ab-A (FIG. 5), Ab-B (FIG. 5), Ab-C (FIG. 6) and Ab-D (FIG. 7) demonstrates that these four antibodies are sclerostin neutralizing antibodies. Furthermore this data shows that, for anti-sclerostin antibodies that bind mouse sclerostin, treatment and analysis of mice as described above can be used to identify sclerostin neutralizing antibodies.

Example 6

Screening Assay for Antibodies that Block Binding of an Antibody to Human Sclerostin Human sclerostin was coupled to a CM5 Biacore chip using standard amine coupling chemistry to generate a sclerostin coated surface. 300 resonance units of sclerostin were coupled to the surface.

The antibodies to be tested were diluted to a concentration of 200 ug/ml in HBS-EP buffer (being 10 mM HEPES pH 7.4, 150 mM NaCl, 3 mM EDTA, 0.005% (v/v) Surfactant P20) and then mixed in a one to one molar ratio (on a binding site basis) to generate the test mixture. This test mixture thus contained each antibody at a concentration of 100 ug/ml (1.3 um on a binding site basis). Separate solutions containing each of the antibodies in the test mix alone were also prepared. These solutions contained the individual antibodies in HBS-EP buffer at a concentration of 100 ug/ml (1.3 um on a binding site basis).

20 μL of the test mixture was passed over the sclerostin-coated chip at a flow rate of 10 μL/min and the amount of binding recorded. The chip was then treated with two 60 second pulses of 30 mM HCl to remove all of the bound antibody. A solution containing only one of the antibodies of the test mixture (at 1.3 μM in the same buffer as the test mixture on a binding site basis) was then passed over the chip in the same manner as the test mixture and the amount of binding recorded. The chip was again treated to remove all of the bound antibody and finally a solution containing the other antibody from the test mixture alone (at 1.3 μM in the same buffer as the test mixture on a binding site basis) was passed over the chip and the amount of binding recorded.

The table below show the results from cross-blocking assays on a range of different antibodies. The values in each square of the table represent the amount of binding (in RU) seen when the antibodies (at 1.3 μM on a binding site basis) or buffer indicated in the top row of the table were mixed with the antibodies (at 1.3 uM on a binding site basis) or buffer indicated in the first column of the table.

| | Buffer | Ab-4 | Ab-13 | Ab-A | Ab-3 | Ab-19 |
|---|---|---|---|---|---|---|
| Buffer | −0.5 | 693 | 428.5 | 707.3 | 316.1 | 649.9 |
| Ab-4 | 687.7 | 795.1 | 1018.2 | 860.5 | 869.3 | 822.5 |
| Ab-13 | 425.6 | 1011.3 | 442.7 | 1108.4 | 431.9 | 1042.4 |
| Ab-A | 692.4 | 833.1 | 1080.4 | 738.5 | 946.2 | 868.1 |
| Ab-3 | 305.5 | 845.1 | 428.2 | 952.2 | 344.4 | 895.7 |
| Ab-19 | 618.1 | 788.6 | 1022.5 | 863.3 | 891.5 | 658.7 |

Using the mean binding value (in RU) for each combination of antibodies in the above table (since each combination appears twice) it is possible to calculate the percentage of the theoretical binding shown by each combination of antibodies. The theoretical binding being calculated as the sum of the average values for the components of each test mixture when assayed alone (i.e., antibody and buffer).

| | Buffer | Ab-4 | Ab-13 | Ab-A | Ab-3 | Ab-19 |
|---|---|---|---|---|---|---|
| Buffer | | | | | | |
| Ab-4 | | | 90.75 | 60.45 | 85.4 | 60.75 |
| Ab-13 | | | | 96.9 | 58.0 | 97.0 |
| Ab-A | | | | | 93.5 | 65.0 |
| Ab-3 | | | | | | 94.4 |
| Ab-19 | | | | | | |

From the above data it is clear that Ab-4, Ab-A and Ab-19 cross-block each other. Similarly Ab-13 and Ab-3 cross block each other.

Example 7

ELISA-Based Cross-Blocking Assay

Liquid volumes used in this example would be those typically used in 96-well plate ELISAs (e.g. 50-200 μl/well). Ab-X and Ab-Y, in this example are assumed to have molecular weights of about 145 Kd and to have 2 sclerostin binding sites per antibody molecule. An anti-sclerostin antibody (Ab-X) is coated (e.g. 50μ of 1 μg/ml) onto a 96-well ELISA plate [e.g. Corning 96 Well EIA/RIA Flat Bottom Microplate (Product #3590); Corning Inc., Acton, Mass.] for at least one hour. After this coating step the antibody solution is removed, the plate is washed once or twice with wash solution (e.g., PBS and 0.05% Tween 20) and is then blocked using an appropriate blocking solution (e.g., PBS, 1% BSA, 1% goat serum and 0.5% Tween 20) and procedures known in the art. Blocking solution is then removed from the ELISA plate and a second anti-sclerostin antibody (Ab-Y), which is being tested for it's ability to cross-block the coated antibody, is added in excess (e.g. 50 μl of 10 μg/ml) in blocking solution to the appropriate wells of the ELISA plate. Following this, a limited amount (e.g. 50 μl of 10 ng/ml) of sclerostin in blocking solution is then added to the appropriate wells and the plate is incubated for at least one hour at room temperature while shaking. The plate is then washed 2-4 times with wash solution. An appropriate amount of a sclerostin detection reagent [e.g., biotinylated anti-sclerostin polyclonal antibody that has been pre-complexed with an appropriate amount of a streptavidin-horseradish peroxidase (HRP) conjugate] in blocking solution is added to the ELISA plate and incubated for at least one hour at room temperature. The plate is then washed at least 4 times with wash solution and is developed with an appropriate reagent [e.g. HRP substrates such as TMB (colorimetric) or various HRP luminescent substrates]. The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

In the event that a tagged version of sclerostin is used in the ELISA, such as a N-terminal His-tagged Sclerostin (R&D Systems, Minneapolis, Minn., USA; 2005 cat#1406-ST-025) then an appropriate type of sclerostin detection reagent would include an HRP labeled anti-His antibody. In addition to using N-terminal His-tagged Sclerostin, one could also use C-terminal His-tagged Sclerostin. Furthermore, various other tags and tag binding protein combinations that are known in the art could be used in this ELISA-based cross-blocking assay (e.g., HA tag with anti-HA antibodies; FLAG tag with anti-FLAG antibodies; biotin tag with streptavidin).

Example 8

Cell Based Mineralization Assay for Identifying Agents Able to Antagonize Sclerostin Activity Introduction Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

Deposition of mineral has a strong biophysical characteristic, in that once mineral "seeds" begin to form, the total amount of mineral that will be deposited in the entire culture can sometimes be deposited quite rapidly, such as within a few days thereafter. The timing and extent of mineral deposition in culture is influenced, in part, by the particular osteoblast-lineage cells/cell-line being used, the growth conditions, the choice of differentiation agents and the particular lot number of serum used in the cell culture media. For osteoblast-lineage cell/cell-line mineralization cultures, at least eight to fifteen serum lots from more than one supplier should be tested in order to identify a particular serum lot that allows for mineralization to take place.

MC3T3-E1 cells (Sudo H et al., *In vitro differentiation and calcification in a new clonal osteogenic cell line derived from newborn mouse calvaria*. J. Cell Biol. 96:191-198) and subclones of the original cell line can form mineral in culture upon growth in the presence of differentiating agents. Such subclones include MC3T3-E1-BF (Smith E, Redman R, Logg C, Coetzee G, Kasahara N, Frenkel B. 2000. *Glucocorticoids inhibit developmental stage-specific osteoblast cell cycle*. J Biol Chem 275:19992-20001).

Identification of Sclerostin Neutralizing Antibodies

MC3T3-E1-BF cells were used for the mineralization assay. Ascorbic acid and B-glycerophosphate were used to induce MC3T3-E1-BF cell differentiation leading to mineral deposition. The specific screening protocol, in 96-well format, involved plating cells on a Wednesday, followed by seven media changes (as described further below) over a 12-day period with most of the mineral deposition taking place in the final approximately eighteen hours (e.g. Sunday night through Monday). For any given treatment, 3 wells were used (N=3). The specific timing, and extent, of mineral deposition may vary depending, in part, on the particular serum lot number being used. Control experiments will allow such variables to be accounted for, as is well know in the art of cell culture experimentation generally.

Figure 22:
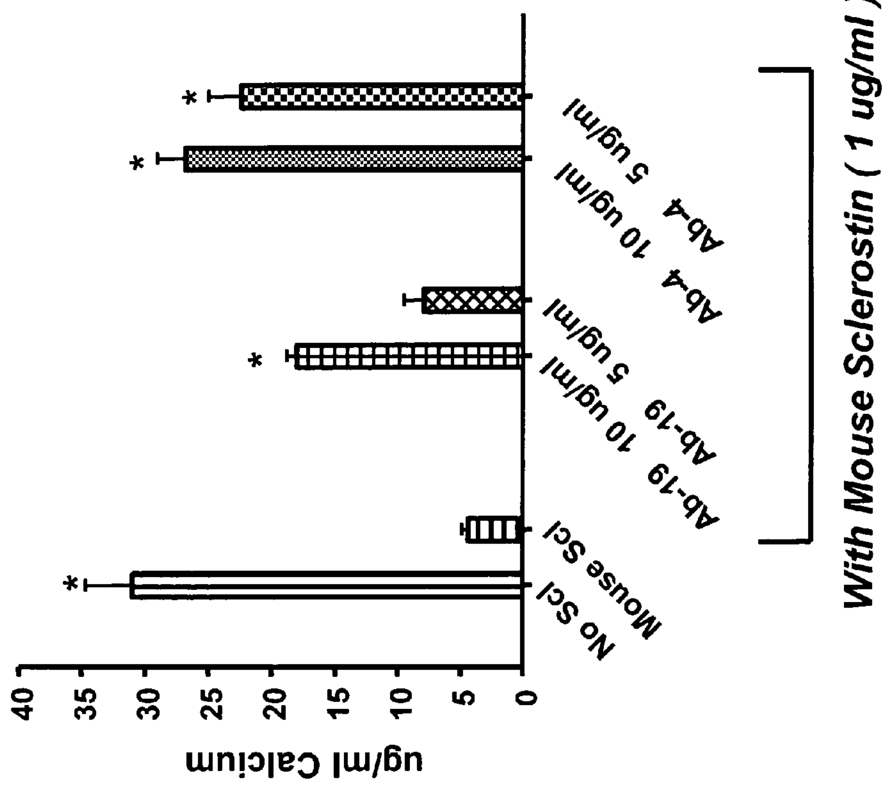
FIG. 22 shows results from the MC3T3-E1-BF osteoblast cell line mineralization assay used for identifying anti-sclerostin neutralizing Mabs. Mouse sclerostin (Scl) was used at 1 μg/ml. Monoclonal antibodies were used at 10 and 5 μg/ml.

In this assay system sclerostin inhibited one or more of the sequence of events leading up to and including mineral deposition (i.e., sclerostin inhibited mineralization). Anti-sclerostin antibodies that were able to neutralize sclerostin's inhibitory activity allowed for mineralization of the culture in the presence of sclerostin such that there was a statistically significant increase in deposition of calcium phosphate (measured as calcium) as compared to the amount of calcium measured in the sclerostin-only (i.e., no antibody) treatment group. For statistical analysis (using MS Excel and JMP) a 1-way-ANOVA followed by Dunnett's comparison was used to determine differences between groups. Group means for each data set were considered significantly different when the P value was less than 0.05 ($P<0.05$). A representative result from running this assay is shown in FIG. 22. In the absence of recombinant mouse sclerostin, the sequence of events leading up to and including mineral deposition proceeded normally. Calcium levels in each treatment group are shown as means±Standard Error of the Mean (SEM). In this exemplary experiment calcium levels from the calcium assay were ~31 μg/ml. However, addition of recombinant mouse sclerostin caused inhibition of mineralization, and calcium was reduced by ~85%. Addition of anti-sclerostin monoclonal antibody Ab-19 or Ab-4 along with the recombinant sclerostin resulted in a statistically significant increase in mineral deposition, as compared to the sclerostin-only group, because the inhibitory activity of sclerostin was neutralized by either antibody. The results from this experiment indicate that Ab-19 and Ab-4 are sclerostin neutralizing monoclonal antibodies (Mabs).

FIG. 23 shows a very similar result using recombinant human sclerostin and two humanized anti-sclerostin Mabs. FIG. 24 also shows a very similar result using recombinant human sclerostin and mouse and humanized anti-sclerostin Mabs as indicated.

The antibodies used for the experiments shown in FIGS. 22, 23 and 24 have molecular weights of about 145 Kd and have 2 sclerostin binding sites per antibody molecule.

A detailed MC3T3-E1-BF cell culture protocol is described below.

Reagents and Medias

| Reagents | Company | Catalog # |
|---|---|---|
| Alpha-MEM | Gibco-Invitrogen | 12571-048 |
| Ascorbic acid | Sigma | A4544 |
| Beta-glycerophosphate | Sigma | G6376 |
| 100X PenStrepGlutamine | Gibco-Invitrogen | 10378-016 |
| Dimethylsulphoxide (DMSO) | Sigma | D5879 or D2650 |
| Fetal bovine serum (FBS) | Cansera | CS-C08-500 (lot # SF50310) |
| or Fetal bovine serum (FBS) | TerraCell Int. | CS-C08-1000A (lot # SF-20308) |

Alpha-MEM is usually manufactured with a 1 year expiration date. Alpha-MEM that was not older than 6-months post-manufacture date was used for the cell culture.

Expansion Medium (Alpha-MEM/10% FBS/PenStrepGlu) was prepared as follows:

A 500 ml bottle of FBS was thawed and filter sterilized through a 0.22 micron filter.

100 mls of this FBS was added to 1 liter of Alpha-MEM followed by the addition of 10 mls of 100× PenStrep-Glutamine. Unused FBS was aliquoted and refrozen for later use.

Differentiation Medium (Alpha-MEM/10% FBS/PenStrepGlu, +50 μg/ml ascorbic acid, +10 mM beta-glycerophosphate) was prepared as follows:

100 mls of Differentiation Medium was prepared by supplementing 100 mls of Expansion Medium with ascorbic acid and beta-glycerophosphate as follows:

| | Stock conc (see below) | Volume | Final Conc. |
|---|---|---|---|
| Ascorbic acid | 10 mg/ml | 0.5 mls | 100 μg/ml (50 ug/ml + 50 μg/ml) |
| β-glycerophosphate | 1M | 1.0 mls | 10 mM |

Differentiation Medium was made by supplementing Expansion Medium only on the day that the Differentiation media was going to be used for cell culture. The final concentration of ascorbic acid in Differentiation medium is 100 μg/ml because Alpha-MEM already contains 50 μg/ml ascorbic acid. Ascorbic acid stock solution (10 mg/ml) was made and aliquoted for freezing at −80° C. Each aliquot was only used once (i.e. not refrozen). Beta-glycerophosphate stock solution (1M) was made and aliquoted for freezing at −20° C. Each aliquot was frozen and thawed a maximum of 5 times before being discarded.

Cell Culture for Expansion of MC3T3-E1-BF Cells.

Cell culture was performed at 37° C. and 5% $CO_2$. A cell bank was generated for the purposes of screening for sclerostin neutralizing antibodies. The cell bank was created as follows:

One vial of frozen MC3T3-E1-BF cells was thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrepGlu. After determining the number of cells using trypan blue and hemacytometer, $1\times10^6$ cells were plated in 50 mls Alpha-MEM/10% FBS/PenStrepGlu media in one T175 flask.

When this passage was confluent (at approximately 7 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, the cells were frozen down at $1-2\times10^6$ live cells/ml in 90% FBS/10% DMSO. This "final passage" of frozen cells was the passage that was used for the screening assay.

Cell Culture for Mineralizing MC3T3-E1-BF Cells.

Cell culture was performed at 37° C. and 5% $CO_2$. It is desirable to minimize temperature and % $CO_2$ fluctuations during the mineralization cell culture procedure. This can be achieved by minimizing the time that plates spend out of the incubator during feeding and also by minimizing the number of times the incubator door is opened and closed during the mineralization cell culture procedure. In this regard having a tissue culture incubator that is dedicated exclusively for the mineralization cell culture (and thus not opened and closed more than is necessary) can be helpful.

An appropriate number of "final passage" vials prepared as described above were thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrep-Glu. After determining the number of cells by trypan blue and hemacytometer, 2500 cells were plated in 200 microliters of Expansion media per well on collagen I coated 96-well plates (Becton Dickinson Labware, cat #354407).

To avoid a mineralization plate-edge effect, cells were not plated in the outermost row/column all the way around the plate. Instead 200 microliters of PBS was added to these wells.

Exemplary Cell Culture Procedure

In the following procedure, the starting day for plating the cells is indicated to be a Wednesday. If a different day of the week is used as the starting day for plating the cells, that day will trigger the daily schedule for removing and adding media during the entire process as indicated below. For example, if the cells are plated on a Tuesday, media should not be removed and added on the first Friday and Saturday, nor on the second Friday and Saturday. With a Tuesday start, the plates would be prepared for the calcium assay on the final Sunday.

Cells were plated on a Wednesday at 2500 cells in 200 μl of Expansion media.

On Thursday all of the Expansion media was removed and 200 μl of Differentiation Media was added.

On Friday 100 μl of media was removed and 100 μl of fresh Differentiation Media was added.

On Monday 100 μl of media was removed and 100 μl of fresh Differentiation Media was added.

On Tuesday 100 μl of media was removed and 100 μl of fresh Differentiation Media was added.

On Wednesday 100 μl of media was removed and 100 μl of fresh Differentiation Media was added.

On Thursday 100 μl of media was removed and 100 μl of fresh Differentiation Media was added.

On Friday 100 μl of media was removed and 100 μl of fresh Differentiation Media was added.

On the following Monday plates were prepared for the calcium assay as follows:

Plates were washed once with 10 mM Tris, HCl pH 7-8.

Working under a fume hood, 200 μl of 0.5N HCl was added per well. Plates were then frozen at −80° C.

Just prior to measuring calcium, the plates were freeze-thawed twice, and then trituration with a multichannel pipette was used to disperse the contents of the plate. The contents of the plate was then allowed to settle at 4° C. for 30 minutes at which point an appropriate amount of supernatant was removed for measuring calcium using a commercially available calcium kit. An exemplary and not-limiting kit is Calcium (CPC) Liquicolor, Cat. No. 0150-250, Stanbio Laboratory, Boerne, Tex.

In this cell based assay, sclerostin inhibits one or more of the sequence of events leading up to and including mineral deposition (i.e. sclerostin inhibits mineralization). Thus, in experiments where sclerostin was included in the particular cell culture experiment, the recombinant sclerostin was added to the media starting on the first Thursday and every feeding day thereafter. In cases where an anti-sclerostin monoclonal antibody (Mab) was being tested for the ability to neutralize sclerostin, i.e. allow for mineralization by neutralizing sclerostin's ability to inhibit mineralization, the Mab was added to the media starting on the first Thursday and every feeding day thereafter. According to the protocol, this was accomplished as follows: the Mab was preincubated with the recombinant sclerostin in Differentiation media for 45-60 minutes at 37° C. and then this media was used for feeding the cells.

Described above is a 12-day mineralization protocol for MC3T3-E1-BF cells. Using the same reagents and feeding protocol, the original MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J Cell Biol 96:191-198) which we obtained from the RIKEN Cell Bank (RCB 1126, RIKEN BioResource Center 3-1-1 Koyadai, Tsukuba-shi, Ibaraki 305-0074 Japan) took longer to mineralize (20 days total for mineralization) than the MC3T3-E1-BF cells. Mineralization of the original MC3T3-E1 cells was inhibited by recombinant sclerostin and this inhibition was blocked using a sclerostin neutralizing antibody.

Example 9

Anti-Sclerostin Antibody Protects from Inflammation-Induced Bone Loss in the CD4 CD45RB$^{HI}$ Transfer Model of Colitis in SCID Mice Summary of Model Injection of the CD45RB$^{high}$ subset of CD4+ T cells into C.B-17 scid mice results in chronic intestinal inflammation with characteristics similar to those of human inflammatory bowel disease (IBD). Diarrhea and wasting disease is noted 3-5 weeks after cell transfer with severe leukocyte infiltration into the colon accompanied by epithelial cell hyperplasia and granuloma formation. C.B-17 scid mice which receive the reciprocal subset of CD4+ cells, those which express CD45R$^{low}$, do not exhibit colitis and have a weight gain indistinguishable from =injected scid mice. In addition to colitis symptoms, the CD4+ CD45RB$^{high}$ T cell transfer model of colitis is accompanied by a reduction in bone mineral density (BMD), thought to be primarily through inflammatory mechanisms rather than dietary malabsorption (Byrne, F. R. et al., Gut 54:78-86, 2005).

Induction of Colitis and Inflammation-Induced Bone Loss

Spleens were taken from female balb/c mice and disrupted through a 70 μm cell strainer. The CD4+ population was then enriched by negative selection with Dynabeads using antibodies against B220, MAC-1, CD8 and I-A$^{d}$. The enriched population was then stained with FITC conjugated anti-CD4 and PE conjugated anti-CD45RB and fractionated into CD4+ CD45RB$^{high}$ and CD4+ CD45RB$^{low}$ populations by two-color sorting on a Moflo (Dakocytomation). The CD45RB$^{high}$ and CD45RB$^{low}$ populations were defined as the brightest staining 40% and the dullest staining 20% of CD4+ cells respectively. 5×10$^{5}$ cells were then injected i.p. into C.B-17 scid mice on day 0 and the development of colitis was monitored through the appearance of soft stools or diarrhea and weight loss. Bone mineral density measurements were taken at the termination of the study (day 88).

Effect of Anti-Sclerostin Treatment on Colitis Symptoms and BMD

Ab-A IgG was dosed at 10 mg/kg s.c. from the day prior to CD4+ CD45RB$^{high}$ cell transfer and compared with mice which received the negative control antibody 101.4 also dosed at 10 mg/kg s.c. The antibodies were dosed weekly thereafter. A group of mice which received non-pathogenic CD4+ CD45RB$^{low}$ cells and were dosed with 10 mg/kg 101.4 was studied as a control. At the termination of the study (day 88) the bone mineral density was measured and sections of the colon taken for analysis of cell infiltration and assessment of histological damage.

a) No Effect on Colitis Symptoms

Typical colitis symptoms such as weight loss and infiltration of inflammatory cells into the colon were unaffected by treatment with Ab-A. Similarly there was no improvement of histological damage to the colon after treatment with Ab-A.

b) Inhibition of Inflammation-Induced Loss of Bone Mineral Density.

On day 88 after transfer of cells into C.B-17 scid mice, the bone mineral density was measured (total BMD, vertebrae BMD and femur BMD). In comparison to control mice which received CD4+ CD45RB$^{low}$ non-pathogenic cells, mice which received CD4+ CD45RB$^{high}$ T cells and the negative control antibody 101.4 had reduced bone mineral density, as shown in FIG. 25. In contrast, no reduction in BMD was noted after treatment with Ab-A. Total, vertebrae and femur measurements of BMD were significantly higher in mice receiving CD4+CD45RB$^{high}$ T cells and treated with Ab-A than mice receiving CD4+ CD45RB$^{high}$ T cells and treated with 101.4 (P<0.001 by Bonferroni multiple comparison test).

Example 10

Kinexa-Based Determination of Affinity ($K_D$) of Anti-Sclerostin Antibodies for Human Sclerostin The affinity of several anti-sclerostin antibodies to human sclerostin was assessed by a solution equilibrium binding analysis using KinExA® 3000 (Sapidyne Instruments Inc., Boise, Id.). For these measurements, Reacti-Gel 6× beads (Pierce, Rockford, Ill.) were pre-coated with 40 μg/ml human sclerostin in 50 mM Na2CO3, pH 9.6 at 4° C. overnight. The beads were then blocked with 1 mg/ml BSA in 1M Tris-HCl, pH 7.5 at 4° C. for two hours. 10 pM, 30 pM, or 100 pM of the antibody was mixed with various concentrations of human sclerostin, ranging in concentration from 0.1 pM to 1 nM, and equilibrated at room temperature for over 8 hours in PBS with 0.1 mg/ml BSA and 0.005% P20. The mixtures were then passed over the human sclerostin coated beads. The amount of bead-bound anti-sclerostin antibody was quantified using fluorescent Cy5-labeled goat anti-mouse-IgG or fluorescent Cy5-labeled goat anti-human-IgG antibodies (Jackson Immuno Research, West Grove, Pa.) for the mouse or human antibody samples, respectively. The amount of fluorescent signal measured was proportional to the concentration of free anti-sclerostin antibody in each reaction mixture at equilibrium. The dissociation equilibrium constant ($K_D$) was obtained from nonlinear regression of the competition curves using a n-curve one-site homogeneous binding model provided in the KinExA Pro software. Results of the KinExA assays for the selected antibodies are summarized in the table below.

| Antibodies | Antigen | $K_D$ (pM) | 95% confidence interval |
|---|---|---|---|
| Ab-13 | Human Sclerostin | 0.6 | 0.4~0.8 pM |
| Ab-4 | Human Sclerostin | 3 | 1.8~4 pM |
| Ab-19 | Human Sclerostin | 3 | 1.7~4 pM |
| Ab-14 | Human Sclerostin | 1 | 0.5~2 pM |
| Ab-5 | Human Sclerostin | 6 | 4.3~8 pM |
| Ab-23 | Human Sclerostin | 4 | 2.1~8 pM |

Example 11

Biacore Method for Determining the Affinity of Humanised Anti-Sclerostin Antibodies for Human Sclerostin The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation process is monitored when the analyte is replaced by buffer. In the affinity BIAcore assay, the ligand is the anti-sclerostin antibody and the analyte is sclerostin.

Instrument

Biacore 3000, Biacore AB, Uppsala, Sweden

Sensor Chip

CM5 (research grade) Catalogue Number: BR-1001-14, Biacore AB, Uppsala, Sweden. Chips were stored at 4° C.

BIAnormalising Solution

70% (w/w) Glycerol. Part of BIAmaintenance Kit Catalogue Number: BR-1002-51, Biacore AB, Uppsala, Sweden. The BIAmaintenance kit was stored at 4° C.

Amine Coupling Kit

Catalogue Number: BR-1000-50, Biacore AB, Uppsala, Sweden.

Ethyl-3-(3-dimethylaminopropyl) carbodiimide hydrochloride (EDC). Made up to 75 mg/mL in distilled water and stored in 200 μL aliquots at −70° C.

N-Hydroxysuccinimide (NHS). Made up to 11.5 mg/mL in distilled water and stored in 200 μL aliquots at −70° C.

1M Ethanolamine hydrochloride-NaOH pH 8.5. Stored in 200 μL aliquots at −70° C.

Buffers

Running buffer for immobilising capture antibody: HBS-EP (being 0.01M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.

Immobilisation buffer: Acetate 5.0 (being 10 mM sodium acetate pH 5.0). Catalogue number: BR-1003-51, Biacore AB, Uppsala, Sweden. Buffer stored at 4° C.

Running buffer for binding assay: HBS-EP (being 0.01M HEPES pH 7.4, 0.15 M NaCl, 3 mM EDTA, 0.005% Surfactant P20, Catalogue Number: BR-1001-88, Biacore AB, Uppsala, Sweden) with CM-Dextran added at 1 mg/mL (Catalogue Number 27560, Fluka BioChemika, Buchs, Switzerland). Buffer stored at 4° C.

Ligand Capture

Affinipure F(ab')$_2$ fragment goat anti-human IgG, Fc fragment specific. Jackson ImmunoResearch Inc (Pennsylvania, USA) Catalogue number: 109-006-098. Reagent stored at 4° C.

Ligand

Humanised anti-human sclerostin antibodies Abs, Ab14 and Ab20.

Analyte

Recombinant human sclerostin. Aliquots stored at −70° C. and thawed once for each assay.

Regeneration Solution 40 mM HCl prepared by dilution with distilled water from an 11.6 M stock solution (BDH, Poole, England. Catalogue number: 101254H).

5 mM NaOH prepared by dilution with distilled water from a 50 mM stock solution. Catalogue number: BR-1003-58, Biacore AB, Uppsala, Sweden.

Assay Method

The assay format was capture of the anti-sclerostin antibody by immobilised anti-human IgG-Fc then titration of the sclerostin over the captured surface.

An example of the procedure is given below:

BIA (Biamolecular Interaction Analysis) was performed using a BIAcore 3000 (BIAcore AB). Affinipure F(ab')$_2$ Fragment goat anti-human IgG, Fc fragment specific (Jackson ImmunoResearch) was immobilised on a CM5 Sensor Chip via amine coupling chemistry to a capture level of ≈4000 response units (RUs). HBS-EP buffer (10 mM HEPES pH 7.4, 0.15 M NaCl, 3 mM EDTA, 0.005% Surfactant P20, BIAcore AB) containing 1 mg/mL CM-Dextran was used as the running buffer with a flow rate of 10 μl/min. A 10 μl injection of the anti-sclerostin antibody at ~5 μg/mL was used for capture by the immobilised anti-human IgG-Fc. Antibody capture levels were typically 100-200 RU. Sclerostin was titrated over the captured anti-sclerostin antibody at various concentrations at a flow rate of 30 μL/min. The surface was regenerated by two 10 μL injections of 40 mM HCl, followed by a 5 μL injection of 5 mM NaOH at a flowrate of 10 μL/min.

Background subtraction binding curves were analysed using the BIAevaluation software (version 3.2) following standard procedures. Kinetic parameters were determined from the fitting algorithm.

The kinetic data and calculated dissociation constants are given in Table 2.

TABLE 2

| Affinity of anti-sclerostin antibodies for sclerostin | | | |
|---|---|---|---|
| Antibody | ka (1/Ms) | kd (1/s) | Kd (pM) |
| Ab-5 | 1.78E+06 | 1.74E−04 | 97.8 |
| Ab-14 | 3.30E+06 | 4.87E−06 | 1.48 |
| Ab-20 | 2.62E+06 | 4.16E−05 | 15.8 |

Example 12

In Vivo Testing of Anti-Sclerostin Monoclonal Antibodies in Cynomolgous Monkeys

Thirty-three, approximately 3-5 year old, female cynomolgus monkeys (*Macaca fascicularis*) were used in this 2-month study. The study contained 11 groups:

Group 1: vehicle (N=4)
Group 2: Ab-23 (N=2, dose 3 mg/kg)
Group 3: Ab-23 (N=3, dose 10 mg/kg)
Group 4: Ab-23 (N=3, dose 30 mg/kg)
Group 5: Ab-5 (N=3, dose 3 mg/kg)
Group 6: Ab-5 (N=3, dose 10 mg/kg)
Group 7: Ab-5 (N=3, dose 30 mg/kg)
Group 8: Ab-14 (N=3, dose 3 mg/kg)
Group 9: Ab-14 (N=3, dose 10 mg/kg)
Group 10: Ab-14 (N=3, dose 30 mg/kg)
Group 11: Parathyroid Hormone (1-34) [PTH (1-34)] (N=3, dose 10 ug/kg)

All dosing was subcutaneous. PTH (1-34) was dosed everyday, monoclonal antibodies (Mabs) were dosed twice (first dose at the beginning of the study and second dose at the one month time point). For assessment of bone parameters (e.g. bone mineral density) pQCT (peripheral quantitative computed tomography) and DXA (dual energy X-ray absorptiometry) scans were performed prior to the beginning of the study (to obtain baseline values) and after a month (prior to the second dose of Mab) and finally at the end of the study (2-month time point) at which point the monkeys were necropsied for further analysis (e.g. histomorphometric analysis). Animals were fluorochrome labeled (days 14, 24, 47, and 57) for dynamic histomorphometry. Serum was collected at various time points during the study [day 1 pre-dose (the day of the first Mab dose), day 1 twelve hours post-dose, day 2, day 3, day 5, day 7, day 14, day 21, day 28, day 29 twelve hours post-dose (day 29 was the day of the second and final Mab dose), day 30, day 31, day 33, day 35, day 42, day 49 and day 56].

Three bone-related serum biomarkers were measured using commercially available kits:

Osteocalcin (OC) (DSL Osteocalcin Radioimmunoassay Kit; Diagnostic Systems Laboratories, Inc., Webster, Tex., USA)

N-terminal Propeptide of Type I Procollagen (P1NP) (P1NP Radioimmunoassay Kit; Orion Diagnostica, Espoo, Finland)

C-telopeptide fragments of collagen type I a1 chains (sCTXI) (Serum CrossLaps® ELISA; Nordic Bioscience Diagnostics A/S, Herlev, Denmark).

pQCT and DXA scans yielded data on various bone parameters (including bone mineral density (BMD) and bone mineral content) across numerous skeletal sites (including tibial metaphysis and diaphysis, radial metaphysis and diaphysis, femur neck, lumbar vertebrae). Analysis of this bone data (percent change from baseline for each animal) and the anabolic (OC, P1NP) serum biomarker data (percent change from baseline for each animal) revealed statistically significant increases, versus the vehicle group, in some parameters at some of the time points and doses for each Mab. This bone parameter data, serum biomarker data, as well as the histomorphometric data, indicated that each of the 3 Mabs (Ab-23, Ab-5 and Ab-14) was able to neutralize sclerostin in cynomolgous monkeys. This activity was most robust for Ab-23 and Ab-5, particularly at the highest dose (30 mg/kg), with a clear increase in bone formation (anabolic effect) as well as net gains in bone (e.g. BMD). Statistically significant increases in bone parameters and anabolic histomorphometric parameters were also found for the positive control group (PTH (1-34)).

Serum bone formation markers (P1NP, osteocalcin) were increased ($p<0.05$ vs vehicle (VEH)) at various time points and doses, but particularly in the 30 mg/kg groups for Ab-23 and Ab-5. Histomorphometric analysis revealed dramatic increases ($p<0.05$ vs VEH) in bone formation rates in cancellous bone at lumbar vertebra and proximal tibia (up to 5-fold increase), as well as at the endocortical surface of the femur midshaft (up to 10-fold increase) at the higher doses of Ab-23 and Ab-5. Trabecular thickness was increased with high dose Ab-23 and Ab-5 in lumbar vertebrae (>60%, $p<0.05$ vs VEH). By study end (2 months), areal BMD, as percent change from baseline, was increased ($p<0.05$ vs VEH) at the femur neck, ultra-distal radius (Ab-23, 30 mg/kg), and lumbar vertebrae (Ab-5, 30 mg/kg). The increases in areal BMD at the lumbar vertebrae were accompanied by increases in vertebral strength (97% increase in vertebral maximal load for Ab-23, 30 mg/kg; $p<0.05$ vs VEH); baseline values for lumbar areal BMD prior to Mab dosing were statistically similar across all groups. In summary, short-term administration of sclerostin-neutralizing Mabs in cynomolgous monkeys resulted, in part, in increases in bone formation, BMD and vertebral bone strength.

From the foregoing, although specific embodiments of the invention have been described herein for purposes of illustration, various modifications may be made without deviating from the spirit and scope of the invention. Accordingly, the invention is not limited except as by the appended claims. All publications, published patent applications, and patent documents disclosed herein are hereby incorporated by reference.

What is claimed is:

1. An isolated polynucleotide encoding a monoclonal antibody that binds to amino acids 138-149 of SEQ ID NO:1 with a binding affinity (Kd) of less than or equal to $1\times10^{-6}$ M.

2. The polynucleotide of claim 1, wherein the antibody is a humanized antibody or a chimeric antibody.

3. The polynucleotide of claim 1, wherein the antibody is a human antibody.

4. The polynucleotide of claim 1, wherein the antibody is an immunoglobulin comprising heavy chains and light chains.

5. The polynucleotide of claim 1, wherein the antibody comprises a non-native constant region.

6. The polynucleotide of claim 1, wherein the antibody is an IgG.

7. The polynucleotide of claim 1, wherein the antibody is an $F(ab')_2$, Fab, Fab', Fv, Fc, or Fd fragment.

8. An isolated polynucleotide encoding a monoclonal antibody that binds to a fragment of a human sclerostin polypeptide of SEQ ID NO: 1, wherein the fragment consists of the amino acid sequences set forth in SEQ ID NOs: 70-73, wherein SEQ ID NO: 70 and 71 are joined by a disulfide bond, and SEQ ID NO: 72 and SEQ ID NO: 73 are joined by a disulfide bond.

9. An isolated polynucleotide encoding a monoclonal antibody that binds to a fragment of a human sclerostin polypeptide of SEQ ID NO: 1, produced by proteolytic digestion of SEQ ID NO: 1, and consisting of the amino acid sequences set forth in SEQ ID NOs: 2-5, wherein SEQ ID NO: 2 and 4 are joined by a disulfide bond at amino acid positions 57 and 111 with reference to SEQ ID NO: 1, and SEQ ID NO: 3 and 5 are joined by at least one of (a) a disulfide bond at amino acid positions 82 and 142 with reference to SEQ ID NO: 1, and (b) a disulfide bond at amino acid positions 86 and 144 with reference to SEQ ID NO: 1.

10. The polynucleotide of claim 9, wherein the fragment of said human sclerostin polypeptide retains the tertiary structure of the corresponding polypeptide region of human sclerostin of SEQ ID NO:1.

11. The polynucleotide thereof of claim 9, wherein the antibody is a humanized antibody or a chimeric antibody.

12. The polynucleotide thereof of claim 9, wherein the antibody is a human antibody.

13. The polynucleotide of claim 9, wherein the antibody is an immunoglobulin comprising heavy chains and light chains.

14. The polynucleotide of claim 9, wherein the antibody is an IgG.

15. The polynucleotide of claim 9, wherein the antibody is an $F(ab')_2$, Fab, Fab', Fv, Fc, or Fd fragment.

16. The polynucleotide of claim 9, wherein the antibody binds to human sclerostin with a binding affinity (Kd) of less than or equal to $1\times10^{-6}$ M.

17. The polynucleotide of claim 9, wherein the antibody binds to human sclerostin with a binding affinity (Kd) of less than or equal to $1\times10^{-7}$M.

18. An isolated polynucleotide encoding a heavy chain of a monoclonal antibody that binds to an epitope of amino acids 138-149 of SEQ ID NO:1 with a binding affinity (Kd) of less than or equal to $1\times10^{-6}$ M.

19. An isolated polynucleotide encoding a light chain of a monoclonal antibody that binds to an epitope of amino acids 138-149 of SEQ ID NO:1 with a binding affinity (Kd) of less than or equal to $1\times10^{-6}$ M.

20. An isolated polynucleotide encoding a heavy chain of a monoclonal antibody that binds to a peptide consisting of amino acids 138-149 of SEQ ID NO:1 with a binding affinity (Kd) of less than or equal to $1\times10^{-6}$ M.

21. An isolated polynucleotide encoding a light chain of a monoclonal antibody that binds to a peptide consisting of amino acids 138-149 of SEQ ID NO:1 with a binding affinity (Kd) of less than or equal to $1\times10^{-6}$ M.

22. An isolated polynucleotide encoding a heavy chain of a monoclonal antibody that binds to a fragment of a human sclerostin polypeptide of SEQ ID NO: 1, wherein the fragment consists of the amino acid sequences set forth in SEQ ID NOs: 70-73, wherein SEQ ID NO: 70 and 71 are joined by a disulfide bond, and SEQ ID NO: 72 and SEQ ID NO: 73 are joined by a disulfide bond.

23. An isolated polynucleotide encoding a light chain of a monoclonal antibody that binds to a fragment of a human sclerostin polypeptide of SEQ ID NO: 1, wherein the fragment consists of the amino acid sequences set forth in SEQ ID NOs: 70-73, wherein SEQ ID NO: 70 and 71 are joined by a disulfide bond, and SEQ ID NO: 72 and SEQ ID NO: 73 are joined by a disulfide bond.

24. A vector comprising the polynucleotide of claim 1.

25. A vector comprising the polynucleotide of claim 9.

26. An isolated host cell comprising a polynucleotide encoding a heavy chain of a monoclonal antibody that binds to an epitope of amino acids 138-149 of SEQ ID NO: 1 with a binding affinity (Kd) of less than or equal to $1\times10^{-6}$ M and a polynucleotide encoding a light chain of a monoclonal antibody that binds to an epitope of amino acids 138-149 of SEQ ID NO: 1 with a binding affinity (Kd) of less than or equal to $1\times10^{-6}$ M.

27. An isolated host cell comprising a polynucleotide encoding a heavy chain of a monoclonal antibody that binds to a peptide consisting of amino acids 138-149 of SEQ ID NO:1 with a binding affinity (Kd) of less than or equal to $1\times10^{-6}$ M and a polynucleotide encoding a light chain of a monoclonal antibody that binds to a peptide consisting of amino acids 138-149 of SEQ ID NO:1 with a binding affinity (Kd) of less than or equal to $1\times10^{-6}$ M.

28. An isolated host cell comprising a polynucleotide encoding a heavy chain of a monoclonal antibody that binds to a fragment of a human sclerostin polypeptide of SEQ ID NO: 1 and a light chain of a monoclonal antibody that binds to a fragment of a human sclerostin polypeptide of SEQ ID NO: 1, wherein the fragment consists of the amino acid sequences set forth in SEQ ID NOs: 70-73, wherein SEQ ID NO: 70 and 71 are joined by a disulfide bond, and SEQ ID NO: 72 and SEQ ID NO: 73 are joined by a disulfide bond.

29. A method of producing an antibody comprising the step of culturing the host cell of claim 26 and isolating the antibody produced therefrom.

30. A method of producing an antibody comprising the step of culturing the host cell of claim 27 and isolating the antibody produced therefrom.

31. A method of producing an antibody comprising the step of culturing the host cell of claim 28 and isolating the antibody produced therefrom.

* * * * *

SEQUENCE LISTING

```
<160> NUMBER OF SEQ ID NOS: 396

<210> SEQ ID NO 1
<211> LENGTH: 190
<212> TYPE: PRT
<213> ORGANISM: Homo sapiens
```

<400> SEQUENCE: 1

```
Gln Gly Trp Gln Ala Phe Lys Asn Asp Ala Thr Glu Ile Ile Pro Glu
1               5                   10                  15

Leu Gly Glu Tyr Pro Glu Pro Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190
```

<210> SEQ ID NO 2
<211> LENGTH: 14
<212> TYPE: PRT
<213> ORGANISM: Homo sapiens

<400> SEQUENCE: 2

```
Asp Val Ser Glu Tyr Ser Cys Arg Glu Leu His Phe Thr Arg
1               5                   10
```

<210> SEQ ID NO 3
<211> LENGTH: 18
<212> TYPE: PRT
<213> ORGANISM: Homo sapiens

<400> SEQUENCE: 3

```
Ser Ala Lys Pro Val Thr Glu Leu Val Cys Ser Gly Gln Cys Gly Pro
1               5                   10                  15

Ala Arg
```

<210> SEQ ID NO 4
<211> LENGTH: 17
<212> TYPE: PRT
<213> ORGANISM: Homo sapiens

<400> SEQUENCE: 4

```
Trp Trp Arg Pro Ser Gly Pro Asp Phe Arg Cys Ile Pro Asp Arg Tyr
1               5                   10                  15

Arg
```

<210> SEQ ID NO 5
<211> LENGTH: 12
<212> TYPE: PRT

<213> ORGANISM: Homo sapiens

<400> SEQUENCE: 5

Leu Val Ala Ser Cys Lys Cys Lys Arg Leu Thr Arg
1 5 10

<210> SEQ ID NO 6
<211> LENGTH: 26
<212> TYPE: PRT
<213> ORGANISM: Homo sapiens

<400> SEQUENCE: 6

Cys Gly Pro Ala Arg Leu Leu Pro Asn Ala Ile Gly Arg Gly Lys Trp
1 5 10 15

Trp Arg Pro Ser Gly Pro Asp Phe Arg Cys
20 25

<210> SEQ ID NO 7
<211> LENGTH: 214
<212> TYPE: PRT
<213> ORGANISM: Mus musculus

<400> SEQUENCE: 7

Asp Val Gln Met Ile Gln Ser Pro Ser Ser Leu Ser Ala Ser Leu Gly
1 5 10 15

Asp Ile Val Thr Met Thr Cys Gln Ala Ser Gln Gly Thr Ser Ile Asn
20 25 30

Leu Asn Trp Phe Gln Gln Lys Pro Gly Lys Ala Pro Lys Leu Leu Ile
35 40 45

Tyr Gly Ser Ser Asn Leu Glu Asp Gly Val Pro Ser Arg Phe Ser Gly
50 55 60

Ser Arg Tyr Gly Thr Asp Phe Thr Leu Thr Ile Ser Ser Leu Glu Asp
65 70 75 80

Glu Asp Leu Ala Thr Tyr Phe Cys Leu Gln His Ser Tyr Leu Pro Tyr
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 8
<211> LENGTH: 645
<212> TYPE: DNA
<213> ORGANISM: Mus musculus

<400> SEQUENCE: 8

```
gatgtccaga tgattcagtc tccatcctcc ctgtctgcat ctttgggaga catagtcacc     60

atgacttgcc aggcaagtca gggcactagc attaatttaa actggtttca gcaaaaacca    120

gggaaggctc ctaagctcct gatctatggt tcaagcaact tggaagatgg ggtcccatca    180

aggttcagtg gcagtagata tgggacagat ttcactctca ccatcagcag cctggaggat    240

gaagatctgg caacttattt ctgtctacaa catagttatc tcccgtacac gttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                     645


<210> SEQ ID NO 9
<211> LENGTH: 236
<212> TYPE: PRT
<213> ORGANISM: Mus musculus

<400> SEQUENCE: 9

Met Asn Thr Arg Ala Pro Ala Glu Phe Leu Gly Phe Leu Leu Leu Trp
1               5                   10                  15

Phe Leu Gly Ala Arg Cys Asp Val Gln Met Ile Gln Ser Pro Ser Ser
            20                  25                  30

Leu Ser Ala Ser Leu Gly Asp Ile Val Thr Met Thr Cys Gln Ala Ser
        35                  40                  45

Gln Gly Thr Ser Ile Asn Leu Asn Trp Phe Gln Gln Lys Pro Gly Lys
    50                  55                  60

Ala Pro Lys Leu Leu Ile Tyr Gly Ser Ser Asn Leu Glu Asp Gly Val
65                  70                  75                  80

Pro Ser Arg Phe Ser Gly Ser Arg Tyr Gly Thr Asp Phe Thr Leu Thr
                85                  90                  95

Ile Ser Ser Leu Glu Asp Glu Asp Leu Ala Thr Tyr Phe Cys Leu Gln
            100                 105                 110

His Ser Tyr Leu Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235


<210> SEQ ID NO 10
<211> LENGTH: 711
<212> TYPE: DNA
```

<213> ORGANISM: Mus musculus

<400> SEQUENCE: 10

```
atgaacacga gggcccctgc tgagttcctt gggttcctgt tgctctggtt tttaggtgcc     60

agatgtgatg tccagatgat tcagtctcca tcctccctgt ctgcatcttt gggagacata    120

gtcaccatga cttgccaggc aagtcagggc actagcatta atttaaactg gtttcagcaa    180

aaaccaggga aggctcctaa gctcctgatc tatggttcaa gcaacttgga agatggggtc    240

ccatcaaggt tcagtggcag tagatatggg acagatttca ctctcaccat cagcagcctg    300

gaggatgaag atctggcaac ttatttctgt ctacaacata gttatctccc gtacacgttc    360

ggagggggga ccaagctgga aataaaacgg gctgatgctg caccaactgt atccatcttc    420

ccaccatcca gtgagcagtt aacatctgga ggtgcctcag tcgtgtgctt cttgaacaac    480

ttctacccca aagacatcaa tgtcaagtgg aagattgatg gcagtgaacg acaaaatggc    540

gtcctgaaca gttggactga tcaggacagc aaagacagca cctacagcat gagcagcacc    600

ctcacgttga ccaaggacga gtatgaacga cataacagct atacctgtga ggccactcac    660

aagacatcaa cttcacccat tgtcaagagc ttcaacagga atgagtgtta g             711
```

<210> SEQ ID NO 11
<211> LENGTH: 443
<212> TYPE: PRT
<213> ORGANISM: Mus musculus

<400> SEQUENCE: 11

```
Glu Val Gln Leu Gln Gln Ser Gly Pro Glu Leu Val Thr Pro Gly Ala
1               5                   10                  15

Ser Val Lys Ile Ser Cys Lys Ala Ser Gly Tyr Thr Phe Thr Asp His
            20                  25                  30

Tyr Met Ser Trp Val Lys Gln Ser His Gly Lys Ser Leu Glu Trp Ile
        35                  40                  45

Gly Asp Ile Asn Pro Tyr Ser Gly Glu Thr Thr Tyr Asn Gln Lys Phe
    50                  55                  60

Lys Gly Thr Ala Thr Leu Thr Val Asp Lys Ser Ser Ser Ile Ala Tyr
65                  70                  75                  80

Met Glu Ile Arg Gly Leu Thr Ser Glu Asp Ser Ala Val Tyr Tyr Cys
                85                  90                  95

Ala Arg Asp Asp Tyr Asp Ala Ser Pro Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
```

```
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Pro Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440


<210> SEQ ID NO 12
<211> LENGTH: 1332
<212> TYPE: DNA
<213> ORGANISM: Mus musculus

<400> SEQUENCE: 12

gaggtccagc tgcaacagtc tggacctgaa ctggtgacgc ctggggcttc agtgaagata      60

tcttgtaagg cttctggata cacattcact gaccactaca tgagctgggt gaagcagagt     120

catggaaaaa gccttgagtg gattggagat attaatccct attctggtga aactacctac     180

aaccagaagt tcaagggcac ggccacattg actgtagaca agtcttccag tatagcctac     240

atggagatcc gcggcctgac atctgaggac tctgcagtct attactgtgc aagagatgat     300

tacgacgcct ctccgtttgc ttactggggc caagggactc tggtcactgt ctctgcagcc     360

aaaacgacac ccccatctgt ctatccactg gcccctggat ctgctgccca aactaactcc     420

atggtgaccc tgggatgcct ggtcaagggc tatttccctg agccagtgac agtgacctgg     480

aactctggat ccctgtccag cggtgtgcac accttcccag ctgtcctgca gtctgacctc     540

tacactctga gcagctcagt gactgtcccc tccagcacct ggcccagcga gaccgtcacc     600

tgcaacgttg cccacccggc cagcagcacc aaggtggaca agaaaattgt gcccagggat     660

tgtggttgta agccttgcat atgtacagtc ccagaagtat catctgtctt catcttcccc     720

ccaaagccca aggatgtgct caccattact ctgactccta aggtcacgtg tgttgtggta     780

gacatcagca aggatgatcc cgaggtccag ttcagctggt ttgtagatga tgtggaggtg     840

cacacagctc agacgcaacc ccgggaggag cagttcaaca gcactttccg ctcagtcagt     900
```

```
gaacttccca tcatgcacca ggactggctc aatggcaagg agttcaaatg cagggtcaac    960

agtccagctt tccctgcccc catcgagaaa accatctcca aaaccaaagg cagaccgaag   1020

gctccacagg tgtacaccat tccacctccc aaggagcaga tggccaagga taaagtcagt   1080

ctgacctgca tgataacaga cttcttccct gaagacatta ctgtggagtg gcagtggaat   1140

gggcagccag cggagaacta caagaacact cagcccatca tggacacaga tggctcttac   1200

ttcatctaca gcaagctcaa tgtgcagaag agcaactggg aggcaggaaa tactttcacc   1260

tgctctgtgt tacatgaggg cctgcacaac caccatactg agaagagcct ctcccactct   1320

cctggtaaat ga                                                       1332


<210> SEQ ID NO 13
<211> LENGTH: 462
<212> TYPE: PRT
<213> ORGANISM: Mus musculus

<400> SEQUENCE: 13

Met Arg Cys Arg Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Thr
            20                  25                  30

Pro Gly Ala Ser Val Lys Ile Ser Cys Lys Ala Ser Gly Tyr Thr Phe
        35                  40                  45

Thr Asp His Tyr Met Ser Trp Val Lys Gln Ser His Gly Lys Ser Leu
    50                  55                  60

Glu Trp Ile Gly Asp Ile Asn Pro Tyr Ser Gly Glu Thr Thr Tyr Asn
65                  70                  75                  80

Gln Lys Phe Lys Gly Thr Ala Thr Leu Thr Val Asp Lys Ser Ser Ser
                85                  90                  95

Ile Ala Tyr Met Glu Ile Arg Gly Leu Thr Ser Glu Asp Ser Ala Val
            100                 105                 110

Tyr Tyr Cys Ala Arg Asp Asp Tyr Asp Ala Ser Pro Phe Ala Tyr Trp
        115                 120                 125

Gly Gln Gly Thr Leu Val Thr Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
```

```
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Pro Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Ile Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460


<210> SEQ ID NO 14
<211> LENGTH: 1389
<212> TYPE: DNA
<213> ORGANISM: Mus musculus

<400> SEQUENCE: 14

atgagatgca ggtggatctt tctctttctc ctgtcaggaa ctgcaggtgt cctctctgag      60

gtccagctgc aacagtctgg acctgaactg gtgacgcctg ggcttcagt gaagatatct      120

tgtaaggctt ctggatacac attcactgac cactacatga gctgggtgaa gcagagtcat     180

ggaaaaagcc ttgagtggat tggagatatt aatccctatt ctggtgaaac tacctacaac     240

cagaagttca agggcacggc cacattgact gtagacaagt cttccagtat agcctacatg     300

gagatccgcg gcctgacatc tgaggactct gcagtctatt actgtgcaag agatgattac     360

gacgcctctc cgtttgctta ctggggccaa gggactctgg tcactgtctc tgcagccaaa     420

acgacacccc catctgtcta tccactggcc cctggatctg ctgcccaaac taactccatg     480

gtgaccctgg gatgcctggt caagggctat ttccctgagc cagtgacagt gacctggaac     540

tctggatccc tgtccagcgg tgtgcacacc ttcccagctg tcctgcagtc tgacctctac     600

actctgagca gctcagtgac tgtcccctcc agcacctggc ccagcgagac cgtcacctgc     660

aacgttgccc acccggccag cagcaccaag gtggacaaga aaattgtgcc cagggattgt     720

ggttgtaagc cttgcatatg tacagtccca gaagtatcat ctgtcttcat cttcccccca     780

aagcccaagg atgtgctcac cattactctg actcctaagg tcacgtgtgt tgtggtagac     840

atcagcaagg atgatcccga ggtccagttc agctggtttg tagatgatgt ggaggtgcac     900

acagctcaga cgcaaccccg ggaggagcag ttcaacagca ctttccgctc agtcagtgaa     960

cttcccatca tgcaccagga ctggctcaat ggcaaggagt tcaaatgcag ggtcaacagt    1020

ccagctttcc ctgcccccat cgagaaaacc atctccaaaa ccaaaggcag accgaaggct    1080

ccacaggtgt acaccattcc acctcccaag gagcagatgg ccaaggataa agtcagtctg    1140

acctgcatga taacagactt cttccctgaa gacattactg tggagtggca gtggaatggg    1200
```

cagccagcgg agaactacaa gaacactcag cccatcatgg acacagatgg ctcttacttc 1260
atctacagca agctcaatgt gcagaagagc aactgggagg caggaaatac tttcacctgc 1320
tctgtgttac atgagggcct gcacaaccac catactgaga agagcctctc ccactctcct 1380
ggtaaatga 1389

<210> SEQ ID NO 15
<211> LENGTH: 218
<212> TYPE: PRT
<213> ORGANISM: Mus musculus

<400> SEQUENCE: 15

```
Asp Ile Val Leu Thr Gln Ser Pro Ala Ser Leu Thr Val Ser Leu Gly
1               5                   10                  15

Leu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Asn Gly Ser Gly Thr Asp Phe Thr Leu Asn Ile His
65                  70                  75                  80

Pro Val Glu Glu Glu Asp Ala Val Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 16
<211> LENGTH: 657
<212> TYPE: DNA
<213> ORGANISM: Mus musculus

<400> SEQUENCE: 16
gacattgtgc tgacccaatc tccagcttct ttgactgtgt ctctaggcct gagggccacc 60
atctcctgca aggccagcca aagtgttgat tatgatggtg atagttatat gaactggtac 120
cagcagaaac caggacagcc acccaaactc ctcatctatg ctgcatccaa tctagaatct 180
gggatcccag ccaggtttag tggcaatggg tctgggacag acttcaccct caacatccat 240
cctgtggagg aggaggatgc tgtaacctat tactgtcaac aaagtaatga ggatccgtgg 300
acgttcggtg gaggcaccaa gctggaaatc aaacgggctg atgctgcacc aactgtatcc 360

```
atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgttag       657


<210> SEQ ID NO 17
<211> LENGTH: 238
<212> TYPE: PRT
<213> ORGANISM: Mus musculus

<400> SEQUENCE: 17

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Leu Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Asn Gly Ser Gly Thr Asp Phe Thr
                85                  90                  95

Leu Asn Ile His Pro Val Glu Glu Glu Asp Ala Val Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 18
<211> LENGTH: 717
<212> TYPE: DNA
<213> ORGANISM: Mus musculus

<400> SEQUENCE: 18

atggagacag acacaatcct gctatgggtg ctgctgctct gggttccagg ctccactggt     60

gacattgtgc tgacccaatc tccagcttct ttgactgtgt ctctaggcct gagggccacc    120

atctcctgca aggccagcca aagtgttgat tatgatggtg atagttatat gaactggtac    180

cagcagaaac caggacagcc acccaaactc ctcatctatg ctgcatccaa tctagaatct    240
```

```
gggatcccag ccaggtttag tggcaatggg tctgggacag acttcaccct caacatccat    300

cctgtggagg aggaggatgc tgtaacctat tactgtcaac aaagtaatga ggatccgtgg    360

acgttcggtg gaggcaccaa gctggaaatc aaacgggctg atgctgcacc aactgtatcc    420

atcttcccac catccagtga gcagttaaca tctggaggtg cctcagtcgt gtgcttcttg    480

aacaacttct accccaaaga catcaatgtc aagtggaaga ttgatggcag tgaacgacaa    540

aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttag       717


<210> SEQ ID NO 19
<211> LENGTH: 449
<212> TYPE: PRT
<213> ORGANISM: Mus musculus

<400> SEQUENCE: 19

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Cys
            20                  25                  30

Tyr Met Asn Trp Val Lys Gln Ser His Gly Lys Ser Leu Glu Trp Ile
        35                  40                  45

Gly Asp Ile Asn Pro Phe Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Ser His Tyr Tyr Phe Asp Gly Arg Val Pro Trp Asp Ala Met
            100                 105                 110

Asp Tyr Trp Gly Gln Gly Thr Ser Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
```

```
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys
```

<210> SEQ ID NO 20
<211> LENGTH: 1350
<212> TYPE: DNA
<213> ORGANISM: Mus musculus

<400> SEQUENCE: 20

```
gaggtccagc tgcaacaatc tggacctgag ctggtgaagc ctgggacttc agtgaagatg     60

tcctgtaagg cttctggata cacattcact gactgctaca tgaactgggt gaagcagagc    120

catgggaaga gccttgaatg gattggagat attaatcctt tcaacggtgg tactacctac    180

aaccagaagt tcaagggcaa ggccacattg actgtagaca aatcctccag cacagcctac    240

atgcagctca acagcctgac atctgacgac tctgcagtct attactgtgc aagatcccat    300

tattacttcg atggtagagt cccttgggat gctatggact actggggtca aggaacctca    360

gtcaccgtct cctcagccaa aacgacaccc ccatctgtct atccactggc ccctggatct    420

gctgcccaaa ctaactccat ggtgaccctg ggatgcctgg tcaagggcta tttccctgag    480

ccagtgacag tgacctggaa ctctggatcc ctgtccagcg gtgtgcacac cttcccagct    540

gtcctgcagt ctgacctcta cactctgagc agctcagtga ctgtcccctc cagcacctgg    600

cccagcgaga ccgtcacctg caacgttgcc cacccggcca gcagcaccaa ggtggacaag    660

aaaattgtgc ccagggattg tggttgtaag ccttgcatat gtacagtccc agaagtatca    720

tctgtcttca tcttcccccc aaagcccaag gatgtgctca ccattactct gactcctaag    780

gtcacgtgtg ttgtggtaga catcagcaag gatgatcccg aggtccagtt cagctggttt    840

gtagatgatg tggaggtgca cacagctcag acgcaacccc gggaggagca gttcaacagc    900

actttccgct cagtcagtga acttcccatc atgcaccagg actggctcaa tggcaaggag    960

ttcaaatgca gggtcaacag tgcagctttc cctgccccca tcgagaaaac catctccaaa   1020

accaaaggca gaccgaaggc tccacaggtg tacaccattc cacctcccaa ggagcagatg   1080

gccaaggata aagtcagtct gacctgcatg ataacagact tcttccctga agacattact   1140

gtggagtggc agtggaatgg gcagccagcg gagaactaca agaacactca gcccatcatg   1200
```

```
gacacagatg gctcttactt catctacagc aagctcaatg tgcagaagag caactgggag   1260

gcaggaaata ctttcacctg ctctgtgtta catgagggcc tgcacaacca ccatactgag   1320

aagagcctct cccactctcc tggtaaatga                                    1350


<210> SEQ ID NO 21
<211> LENGTH: 468
<212> TYPE: PRT
<213> ORGANISM: Mus musculus

<400> SEQUENCE: 21

Met Gly Trp Asn Trp Ile Phe Leu Phe Leu Leu Ser Gly Thr Ala Gly
1               5                   10                  15

Val Tyr Ser Glu Val Gln Leu Gln Gln Ser Gly Pro Glu Leu Val Lys
            20                  25                  30

Pro Gly Thr Ser Val Lys Met Ser Cys Lys Ala Ser Gly Tyr Thr Phe
        35                  40                  45

Thr Asp Cys Tyr Met Asn Trp Val Lys Gln Ser His Gly Lys Ser Leu
    50                  55                  60

Glu Trp Ile Gly Asp Ile Asn Pro Phe Asn Gly Gly Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Asp Asp Ser Ala Val
            100                 105                 110

Tyr Tyr Cys Ala Arg Ser His Tyr Tyr Phe Asp Gly Arg Val Pro Trp
        115                 120                 125

Asp Ala Met Asp Tyr Trp Gly Gln Gly Thr Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350
```

```
Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465


<210> SEQ ID NO 22
<211> LENGTH: 1407
<212> TYPE: DNA
<213> ORGANISM: Mus musculus

<400> SEQUENCE: 22

atgggatgga actggatctt tctcttcctc ttgtcaggaa ctgcaggtgt ctactctgag     60

gtccagctgc aacaatctgg acctgagctg gtgaagcctg ggacttcagt gaagatgtcc    120

tgtaaggctt ctggatacac attcactgac tgctacatga actgggtgaa gcagagccat    180

gggaagagcc ttgaatggat tggagatatt aatcctttca acggtggtac tacctacaac    240

cagaagttca agggcaaggc cacattgact gtagacaaat cctccagcac agcctacatg    300

cagctcaaca gcctgacatc tgacgactct gcagtctatt actgtgcaag atcccattat    360

tacttcgatg gtagagtccc ttgggatgct atggactact ggggtcaagg aacctcagtc    420

accgtctcct cagccaaaac gacaccccca tctgtctatc cactggcccc tggatctgct    480

gcccaaacta actccatggt gaccctggga tgcctggtca agggctattt ccctgagcca    540

gtgacagtga cctggaactc tggatccctg tccagcggtg tgcacacctt cccagctgtc    600

ctgcagtctg acctctacac tctgagcagc tcagtgactg tcccctccag cacctggccc    660

agcgagaccg tcacctgcaa cgttgcccac ccggccagca gcaccaaggt ggacaagaaa    720

attgtgccca gggattgtgg ttgtaagcct tgcatatgta cagtcccaga agtatcatct    780

gtcttcatct tccccccaaa gcccaaggat gtgctcacca ttactctgac tcctaaggtc    840

acgtgtgttg tggtagacat cagcaaggat gatcccgagg tccagttcag ctggtttgta    900

gatgatgtgg aggtgcacac agctcagacg caaccccggg aggagcagtt caacagcact    960

ttccgctcag tcagtgaact tcccatcatg caccaggact ggctcaatgg caaggagttc   1020

aaatgcaggg tcaacagtgc agctttccct gcccccatcg agaaaaccat ctccaaaacc   1080

aaaggcagac cgaaggctcc acaggtgtac accattccac ctcccaagga gcagatggcc   1140

aaggataaag tcagtctgac ctgcatgata acagacttct tccctgaaga cattactgtg   1200

gagtggcagt ggaatgggca gccagcggag aactacaaga acactcagcc catcatggac   1260

acagatggct cttacttcat ctacagcaag ctcaatgtgc agaagagcaa ctgggaggca   1320

ggaaatactt tcacctgctc tgtgttacat gagggcctgc acaaccacca tactgagaag   1380
```

agcctctccc actctcctgg taaatga 1407

<210> SEQ ID NO 23
<211> LENGTH: 217
<212> TYPE: PRT
<213> ORGANISM: Artificial Sequence
<220> FEATURE:
<223> OTHER INFORMATION: Rabbit-Mouse Chimera

<400> SEQUENCE: 23

Ala Gln Val Leu Thr Gln Thr Pro Ala Ser Val Ser Ala Ala Val Gly
1 5 10 15

Gly Thr Val Thr Ile Asn Cys Gln Ser Ser Gln Ser Val Tyr Asp Asn
20 25 30

Asn Trp Leu Ala Trp Phe Gln Gln Lys Pro Gly Gln Pro Pro Lys Leu
35 40 45

Leu Ile Tyr Asp Ala Ser Asp Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Ala Asp Ala Ala Thr Tyr Tyr Cys Gln Gly Ala Tyr Asn Asp
85 90 95

Val Ile Tyr Ala Phe Gly Gly Gly Thr Glu Val Val Val Lys Arg Thr
100 105 110

Asp Ala Ala Pro Thr Val Ser Ile Phe Pro Pro Ser Ser Glu Gln Leu
115 120 125

Thr Ser Gly Gly Ala Ser Val Val Cys Phe Leu Asn Asn Phe Tyr Pro
130 135 140

Lys Asp Ile Asn Val Lys Trp Lys Ile Asp Gly Ser Glu Arg Gln Asn
145 150 155 160

Gly Val Leu Asn Ser Trp Thr Asp Gln Asp Ser Lys Asp Ser Thr Tyr
165 170 175

Ser Met Ser Ser Thr Leu Thr Leu Thr Lys Asp Glu Tyr Glu Arg His
180 185 190

Asn Ser Tyr Thr Cys Glu Ala Thr His Lys Thr Ser Thr Ser Pro Ile
195 200 205

Val Lys Ser Phe Asn Arg Asn Glu Cys
210 215

<210> SEQ ID NO 24
<211> LENGTH: 654
<212> TYPE: DNA
<213> ORGANISM: Artificial Sequence
<220> FEATURE:
<223> OTHER INFORMATION: Rabbit-Mouse Chimera

<400> SEQUENCE: 24
gcgcaagtgc tgacccagac tccagcctcc gtgtctgcag ctgtgggagg cacagtcacc 60
atcaattgcc agtccagtca gagtgtttat gataacaact ggttagcctg gtttcagcag 120
aaaccagggc agcctcccaa gctcctgatt tatgatgcat ccgatctggc atctggggtc 180
ccatcgcggt tcagtggcag tggatctggg acacagttca ctctcaccat cagcggcgtg 240
cagtgtgccg atgctgccac ttactactgt caaggcgctt ataatgatgt tatttatgct 300
ttcggcggag ggaccgaggt ggtggtcaaa cgtacggatg ctgcaccaac tgtatccatc 360
ttcccaccat ccagtgagca gttaacatct ggaggtgcct cagtcgtgtg cttcttgaac 420
aacttctacc ccaaagacat caatgtcaag tggaagattg atggcagtga acgacaaaat 480
ggcgtcctga acagttggac tgatcaggac agcaaagaca gcacctacag catgagcagc 540
accctcacgt tgaccaagga cgagtatgaa cgacataaca gctatacctg tgaggccact 600
cacaagacat caacttcacc cattgtcaag agcttcaaca ggaatgagtg ttag 654

<210> SEQ ID NO 25
<211> LENGTH: 239
<212> TYPE: PRT
<213> ORGANISM: Artificial Sequence
<220> FEATURE:
<223> OTHER INFORMATION: Rabbit-Mouse Chimera

<400> SEQUENCE: 25

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ser Ser
        35                  40                  45

Gln Ser Val Tyr Asp Asn Asn Trp Leu Ala Trp Phe Gln Gln Lys Pro
    50                  55                  60

Gly Gln Pro Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Ala Asp Ala Ala Thr Tyr Tyr Cys
            100                 105                 110

Gln Gly Ala Tyr Asn Asp Val Ile Tyr Ala Phe Gly Gly Gly Thr Glu
        115                 120                 125

Val Val Val Lys Arg Thr Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 26
<211> LENGTH: 720
<212> TYPE: DNA
<213> ORGANISM: Artificial Sequence
<220> FEATURE:
<223> OTHER INFORMATION: Rabbit-Mouse Chimera

<400> SEQUENCE: 26
atggacacga gggcccccac tcagctgctg gggctcctgc tgctctggct cccaggtgcc 60
acatttgcgc aagtgctgac ccagactcca gcctccgtgt ctgcagctgt gggaggcaca 120
gtcaccatca attgccagtc cagtcagagt gtttatgata acaactggtt agcctggttt 180
cagcagaaac cagggcagcc tcccaagctc ctgatttatg atgcatccga tctggcatct 240

```
ggggtcccat cgcggttcag tggcagtgga tctgggacac agttcactct caccatcagc    300

ggcgtgcagt gtgccgatgc tgccacttac tactgtcaag gcgcttataa tgatgttatt    360

tatgctttcg gcggagggac cgaggtggtg gtcaaacgta cggatgctgc accaactgta    420

tccatcttcc caccatccag tgagcagtta acatctggag gtgcctcagt cgtgtgcttc    480

ttgaacaact tctaccccaa agacatcaat gtcaagtgga agattgatgg cagtgaacga    540

caaaatggcg tcctgaacag ttggactgat caggacagca aagacagcac ctacagcatg    600

agcagcaccc tcacgttgac caaggacgag tatgaacgac ataacagcta tacctgtgag    660

gccactcaca agacatcaac ttcacccatt gtcaagagct tcaacaggaa tgagtgttag    720
```

<210> SEQ ID NO 27
<211> LENGTH: 433
<212> TYPE: PRT
<213> ORGANISM: Artificial Sequence
<220> FEATURE:
<223> OTHER INFORMATION: Humanized antibody

<400> SEQUENCE: 27

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Asn Trp Val Arg Gln Ala Pro Gly Glu Gly Leu Glu Trp Ile Gly
        35                  40                  45

Thr Ile Asp Ser Gly Gly Arg Thr Asp Tyr Ala Ser Trp Ala Lys Gly
    50                  55                  60

Arg Phe Thr Ile Ser Arg Thr Ser Thr Thr Met Asp Leu Lys Met Thr
65                  70                  75                  80

Ser Leu Thr Thr Gly Asp Thr Ala Arg Tyr Phe Cys Ala Arg Asn Trp
                85                  90                  95

Asn Leu Trp Gly Gln Gly Thr Leu Val Thr Val Ser Ser Ala Ser Thr
            100                 105                 110

Lys Gly Pro Ser Val Tyr Pro Leu Ala Pro Gly Ser Ala Ala Gln Thr
        115                 120                 125

Asn Ser Met Val Thr Leu Gly Cys Leu Val Lys Gly Tyr Phe Pro Glu
    130                 135                 140

Pro Val Thr Val Thr Trp Asn Ser Gly Ser Leu Ser Ser Gly Val His
145                 150                 155                 160

Thr Phe Pro Ala Val Leu Gln Ser Asp Leu Tyr Thr Leu Ser Ser Ser
                165                 170                 175

Val Thr Val Pro Ser Ser Thr Trp Pro Ser Glu Thr Val Thr Cys Asn
            180                 185                 190

Val Ala His Pro Ala Ser Ser Thr Lys Val Asp Lys Lys Ile Val Pro
        195                 200                 205

Arg Asp Cys Gly Cys Lys Pro Cys Ile Cys Thr Val Pro Glu Val Ser
    210                 215                 220

Ser Val Phe Ile Phe Pro Pro Lys Pro Lys Asp Val Leu Thr Ile Thr
225                 230                 235                 240

Leu Thr Pro Lys Val Thr Cys Val Val Val Asp Ile Ser Lys Asp Asp
                245                 250                 255

Pro Glu Val Gln Phe Ser Trp Phe Val Asp Asp Val Glu Val His Thr
            260                 265                 270

Ala Gln Thr Gln Pro Arg Glu Glu Gln Phe Asn Ser Thr Phe Arg Ser
```

```
        275                 280                 285

Val Ser Glu Leu Pro Ile Met His Gln Asp Trp Leu Asn Gly Lys Glu
    290                 295                 300

Phe Lys Cys Arg Val Asn Ser Ala Ala Phe Pro Ala Pro Ile Glu Lys
305                 310                 315                 320

Thr Ile Ser Lys Thr Lys Gly Arg Pro Lys Ala Pro Gln Val Tyr Thr
                325                 330                 335

Ile Pro Pro Pro Lys Glu Gln Met Ala Lys Asp Lys Val Ser Leu Thr
            340                 345                 350

Cys Met Ile Thr Asp Phe Phe Pro Glu Asp Ile Thr Val Glu Trp Gln
        355                 360                 365

Trp Asn Gly Gln Pro Ala Glu Asn Tyr Lys Asn Thr Gln Pro Ile Met
    370                 375                 380

Asn Thr Asn Gly Ser Tyr Phe Val Tyr Ser Lys Leu Asn Val Gln Lys
385                 390                 395                 400

Ser Asn Trp Glu Ala Gly Asn Thr Phe Thr Cys Ser Val Leu His Glu
                405                 410                 415

Gly Leu His Asn His His Thr Glu Lys Ser Leu Ser His Ser Pro Gly
            420                 425                 430

Lys
```

<210> SEQ ID NO 28
<211> LENGTH: 1302
<212> TYPE: DNA
<213> ORGANISM: Artificial Sequence
<220> FEATURE:
<223> OTHER INFORMATION: Humanized antibody

<400> SEQUENCE: 28

```
cagtcgctgg aggagtccgg gggtcgcctg gtcacgcctg ggacacccct gacactcacc     60

tgcacagcct ctggattctc cctcagtagt tattggatga actgggtccg ccaggctcca    120

ggggaggggc tggaatggat cggaaccatt gattctggtg gtaggacgga ctacgcgagc    180

tgggcaaaag gccgattcac catctccaga acctcgacta cgatggatct gaaaatgacc    240

agtctgacga ccggggacac ggcccgttat ttctgtgcca gaaattggaa cttgtggggc    300

caaggcaccc tcgtcaccgt ctcgagcgct tctacaaagg gcccatctgt ctatccactg    360

gcccctggat ctgctgccca aactaactcc atggtgaccc tgggatgcct ggtcaagggc    420

tatttccctg agccagtgac agtgacctgg aactctggat ccctgtccag cggtgtgcac    480

accttcccag ctgtcctgca gtctgacctc tacactctga gcagctcagt gactgtcccc    540

tccagcacct ggcccagcga gaccgtcacc tgcaacgttg cccacccggc cagcagcacc    600

aaggtggaca agaaaattgt gcccagggat tgtggttgta agccttgcat atgtacagtc    660

ccagaagtat catctgtctt catcttcccc ccaaagccca aggatgtgct caccattact    720

ctgactccta aggtcacgtg tgttgtggta gacatcagca aggatgatcc cgaggtccag    780

ttcagctggt ttgtagatga tgtggaggtg cacacagctc agacgcaacc ccgggaggag    840

cagttcaaca gcactttccg ctcagtcagt gaacttccca tcatgcacca ggactggctc    900

aatggcaagg agttcaaatg cagggtcaac agtgcagctt tccctgcccc catcgagaaa    960

accatctcca aaaccaaagg cagaccgaag gctccacagg tgtacaccat tccacctccc   1020

aaggagcaga tggccaagga taaagtcagt ctgacctgca tgataacaga cttcttccct   1080

gaagacatta ctgtggagtg gcagtggaat gggcagccag cggagaacta caagaacact   1140
```

```
cagcccatca tggacacaga tggctcttac ttcgtctaca gcaagctcaa tgtgcagaag   1200

agcaactggg aggcaggaaa tactttcacc tgctctgtgt tacatgaggg cctgcacaac   1260

caccatactg agaagagcct ctcccactct cctggtaaat ga                      1302


<210> SEQ ID NO 29
<211> LENGTH: 452
<212> TYPE: PRT
<213> ORGANISM: Artificial Sequence
<220> FEATURE:
<223> OTHER INFORMATION: Humanized antibody

<400> SEQUENCE: 29

Met Glu Thr Gly Leu Arg Trp Leu Leu Leu Val Ala Val Leu Lys Gly
1               5                   10                  15

Val His Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Trp Met Asn Trp Val Arg Gln Ala Pro Gly Glu Gly Leu Glu
    50                  55                  60

Trp Ile Gly Thr Ile Asp Ser Gly Gly Arg Thr Asp Tyr Ala Ser Trp
65                  70                  75                  80

Ala Lys Gly Arg Phe Thr Ile Ser Arg Thr Ser Thr Thr Met Asp Leu
                85                  90                  95

Lys Met Thr Ser Leu Thr Thr Gly Asp Thr Ala Arg Tyr Phe Cys Ala
            100                 105                 110

Arg Asn Trp Asn Leu Trp Gly Gln Gly Thr Leu Val Thr Val Ser Ser
        115                 120                 125

Ala Ser Thr Lys Gly Pro Ser Val Tyr Pro Leu Ala Pro Gly Ser Ala
    130                 135                 140

Ala Gln Thr Asn Ser Met Val Thr Leu Gly Cys Leu Val Lys Gly Tyr
145                 150                 155                 160

Phe Pro Glu Pro Val Thr Val Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Pro Ser Ser Thr Trp Pro Ser Glu Thr Val
        195                 200                 205

Thr Cys Asn Val Ala His Pro Ala Ser Ser Thr Lys Val Asp Lys Lys
    210                 215                 220

Ile Val Pro Arg Asp Cys Gly Cys Lys Pro Cys Ile Cys Thr Val Pro
225                 230                 235                 240

Glu Val Ser Ser Val Phe Ile Phe Pro Pro Lys Pro Lys Asp Val Leu
                245                 250                 255

Thr Ile Thr Leu Thr Pro Lys Val Thr Cys Val Val Val Asp Ile Ser
            260                 265                 270

Lys Asp Asp Pro Glu Val Gln Phe Ser Trp Phe Val Asp Asp Val Glu
        275                 280                 285

Val His Thr Ala Gln Thr Gln Pro Arg Glu Glu Gln Phe Asn Ser Thr
    290                 295                 300

Phe Arg Ser Val Ser Glu Leu Pro Ile Met His Gln Asp Trp Leu Asn
305                 310                 315                 320

Gly Lys Glu Phe Lys Cys Arg Val Asn Ser Ala Ala Phe Pro Ala Pro
                325                 330                 335
```

```
Ile Glu Lys Thr Ile Ser Lys Thr Lys Gly Arg Pro Lys Ala Pro Gln
            340                 345                 350

Val Tyr Thr Ile Pro Pro Pro Lys Glu Gln Met Ala Lys Asp Lys Val
        355                 360                 365

Ser Leu Thr Cys Met Ile Thr Asp Phe Phe Pro Glu Asp Ile Thr Val
    370                 375                 380

Glu Trp Gln Trp Asn Gly Gln Pro Ala Glu Asn Tyr Lys Asn Thr Gln
385                 390                 395                 400

Pro Ile Met Asn Thr Asn Gly Ser Tyr Phe Val Tyr Ser Lys Leu Asn
                405                 410                 415

Val Gln Lys Ser Asn Trp Glu Ala Gly Asn Thr Phe Thr Cys Ser Val
            420                 425                 430

Leu His Glu Gly Leu His Asn His His Thr Glu Lys Ser Leu Ser His
        435                 440                 445

Ser Pro Gly Lys
    450


<210> SEQ ID NO 30
<211> LENGTH: 1359
<212> TYPE: DNA
<213> ORGANISM: Artificial Sequence
<220> FEATURE:
<223> OTHER INFORMATION: Humanized antibody

<400> SEQUENCE: 30

atggagactg ggctgcgctg gcttctcctg gtcgctgtgc tcaaaggtgt ccactgtcag      60

tcgctggagg agtccggggg tcgcctggtc acgcctggga cacccctgac actcacctgc     120

acagcctctg gattctccct cagtagttat tggatgaact gggtccgcca ggctccaggg     180

gaggggctgg aatggatcgg aaccattgat tctggtggta ggacggacta cgcgagctgg     240

gcaaaaggcc gattcaccat ctccagaacc tcgactacga tggatctgaa aatgaccagt     300

ctgacgaccg gggacacggc ccgttatttc tgtgccagaa attggaactt gtggggccaa     360

ggcaccctcg tcaccgtctc gagcgcttct acaaagggcc catctgtcta tccactggcc     420

cctggatctg ctgcccaaac taactccatg gtgaccctgg gatgcctggt caagggctat     480

ttccctgagc cagtgacagt gacctggaac tctggatccc tgtccagcgg tgtgcacacc     540

ttcccagctg tcctgcagtc tgacctctac actctgagca gctcagtgac tgtcccctcc     600

agcacctggc ccagcgagac cgtcacctgc aacgttgccc acccggccag cagcaccaag     660

gtggacaaga aaattgtgcc cagggattgt ggttgtaagc cttgcatatg tacagtccca     720

gaagtatcat ctgtcttcat cttcccccca aagcccaagg atgtgctcac cattactctg     780

actcctaagg tcacgtgtgt tgtggtagac atcagcaagg atgatcccga ggtccagttc     840

agctggtttg tagatgatgt ggaggtgcac acagctcaga cgcaaccccg ggaggagcag     900

ttcaacagca ctttccgctc agtcagtgaa cttcccatca tgcaccagga ctggctcaat     960

ggcaaggagt tcaaatgcag ggtcaacagt gcagctttcc ctgcccccat cgagaaaacc    1020

atctccaaaa ccaaaggcag accgaaggct ccacaggtgt acaccattcc acctcccaag    1080

gagcagatgg ccaaggataa agtcagtctg acctgcatga taacagactt cttccctgaa    1140

gacattactg tggagtggca gtggaatggg cagccagcgg agaactacaa gaacactcag    1200

cccatcatgg acacagatgg ctcttacttc gtctacagca agctcaatgt gcagaagagc    1260

aactgggagg caggaaatac tttcacctgc tctgtgttac atgagggcct gcacaaccac    1320

catactgaga agagcctctc ccactctcct ggtaaatga                           1359
```

<210> SEQ ID NO 31
<211> LENGTH: 213
<212> TYPE: PRT
<213> ORGANISM: Mus musculus

<400> SEQUENCE: 31

```
Gln Ile Val Leu Thr Gln Ser Pro Thr Ile Val Ser Ala Ser Pro Gly
1               5                   10                  15

Glu Lys Val Thr Leu Ile Cys Ser Ala Ser Ser Ser Val Ser Phe Val
            20                  25                  30

Asp Trp Phe Gln Gln Lys Pro Gly Thr Ser Pro Lys Arg Trp Ile Tyr
        35                  40                  45

Arg Thr Ser Asn Leu Gly Phe Gly Val Pro Ala Arg Phe Ser Gly Gly
    50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Arg Ser Thr Tyr Pro Pro Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 32
<211> LENGTH: 642
<212> TYPE: DNA
<213> ORGANISM: Mus musculus

<400> SEQUENCE: 32

```
caaattgttc tcacccagtc tccaacaatc gtgtctgcat ctccagggga gaaggtcacc     60

ctaatctgca gtgccagttc aagtgtaagt ttcgtggact ggttccagca gaagccaggc    120

acttctccca aacgctggat ttacagaaca tccaacctgg gttttggagt ccctgctcgc    180

ttcagtggcg gtggatctgg gacctctcac tctctcacaa tcagccgaat ggaggctgaa    240

gatgctgcca cttattactg ccagcaaagg agtacttacc cacccacgtt cggtgctggg    300

accaagctgg aactgaaacg ggctgatgct gcaccaactg tatccatctt cccaccatcc    360

agtgagcagt taacatctgg aggtgcctca gtcgtgtgct tcttgaacaa cttctacccc    420

aaagacatca atgtcaagtg gaagattgat ggcagtgaac gacaaaatgg cgtcctgaac    480

agttggactg atcaggacag caaagacagc acctacagca tgagcagcac cctcacgttg    540

accaaggacg agtatgaacg acataacagc tatacctgtg aggccactca caagacatca    600
```

```
acttcaccca ttgtcaagag cttcaacagg aatgagtgtt ag                  642


<210> SEQ ID NO 33
<211> LENGTH: 235
<212> TYPE: PRT
<213> ORGANISM: Mus musculus

<400> SEQUENCE: 33

Met His Phe Gln Val Gln Ile Phe Ser Phe Leu Leu Ile Ser Ala Ser
1               5                   10                  15

Val Ile Val Ser Arg Gly Gln Ile Val Leu Thr Gln Ser Pro Thr Ile
            20                  25                  30

Val Ser Ala Ser Pro Gly Glu Lys Val Thr Leu Ile Cys Ser Ala Ser
        35                  40                  45

Ser Ser Val Ser Phe Val Asp Trp Phe Gln Gln Lys Pro Gly Thr Ser
    50                  55                  60

Pro Lys Arg Trp Ile Tyr Arg Thr Ser Asn Leu Gly Phe Gly Val Pro
65                  70                  75                  80

Ala Arg Phe Ser Gly Gly Gly Ser Gly Thr Ser His Ser Leu Thr Ile
                85                  90                  95

Ser Arg Met Glu Ala Glu Asp Ala Ala Thr Tyr Tyr Cys Gln Gln Arg
            100                 105                 110

Ser Thr Tyr Pro Pro Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 34
<211> LENGTH: 708
<212> TYPE: DNA
<213> ORGANISM: Mus musculus

<400> SEQUENCE: 34

atgcattttc aagtgcagat tttcagcttc ctgctaatca gtgcctcagt catagtgtcc     60

agagggcaaa ttgttctcac ccagtctcca acaatcgtgt ctgcatctcc aggggagaag    120

gtcaccctaa tctgcagtgc cagttcaagt gtaagtttcg tggactggtt ccagcagaag    180

ccaggcactt ctcccaaacg ctggatttac agaacatcca acctgggttt tggagtccct    240

gctcgcttca gtggcggtgg atctgggacc tctcactctc tcacaatcag ccgaatggag    300

gctgaagatg ctgccactta ttactgccag caaaggagta cttacccacc cacgttcggt    360

gctgggacca agctggaact gaaacgggct gatgctgcac caactgtatc catcttccca    420

ccatccagtg agcagttaac atctggaggt gcctcagtcg tgtgcttctt gaacaacttc    480
```

```
taccccaaag acatcaatgt caagtggaag attgatggca gtgaacgaca aaatggcgtc    540

ctgaacagtt ggactgatca ggacagcaaa gacagcacct acagcatgag cagcaccctc    600

acgttgacca aggacgagta tgaacgacat aacagctata cctgtgaggc cactcacaag    660

acatcaactt cacccattgt caagagcttc aacaggaatg agtgttag                 708


<210> SEQ ID NO 35
<211> LENGTH: 449
<212> TYPE: PRT
<213> ORGANISM: Mus musculus

<400> SEQUENCE: 35

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg His Pro Ser Gly Lys Asn Leu Glu
        35                  40                  45

Trp Leu Ala His Ile Trp Trp Asp Asp Val Lys Arg Tyr Asn Pro Val
    50                  55                  60

Leu Lys Ser Arg Leu Thr Ile Ser Lys Asp Thr Ser Asn Ser Gln Val
65                  70                  75                  80

Phe Leu Lys Ile Ala Asn Val Asp Thr Ala Asp Thr Ala Thr Tyr Tyr
                85                  90                  95

Cys Ala Arg Ile Glu Asp Phe Asp Tyr Asp Glu Glu Tyr Tyr Ala Met
            100                 105                 110

Asp Tyr Trp Gly Gln Gly Thr Ser Val Ile Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335
```

```
Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys


<210> SEQ ID NO 36
<211> LENGTH: 1350
<212> TYPE: DNA
<213> ORGANISM: Mus musculus

<400> SEQUENCE: 36

caggttactc tgaaagagtc tggccctggg atattgcagc cctcccagac cctcagtctg      60

acttgttctt tctctgggtt ttcactgagc acttctggta tgggtgtagg ctggattcgt     120

cacccatcag ggaagaatct ggagtggctg gcacacattt ggtgggatga tgtcaagcgc     180

tataacccag tcctgaagag ccgactgact atctccaagg atacctccaa cagccaggta     240

ttcctcaaga tcgccaatgt ggacactgca gatactgcca catactactg tgctcgaata     300

gaggactttg attacgacga ggagtattat gctatggact actggggtca aggaacctca     360

gtcatcgtct cctcagccaa aacgacaccc ccatctgtct atccactggc ccctggatct     420

gctgcccaaa ctaactccat ggtgaccctg ggatgcctgg tcaagggcta tttccctgag     480

ccagtgacag tgacctggaa ctctggatcc ctgtccagcg gtgtgcacac cttcccagct     540

gtcctgcagt ctgacctcta cactctgagc agctcagtga ctgtcccctc cagcacctgg     600

cccagcgaga ccgtcacctg caacgttgcc cacccggcca gcagcaccaa ggtggacaag     660

aaaattgtgc ccagggattg tggttgtaag ccttgcatat gtacagtccc agaagtatca     720

tctgtcttca tcttcccccc aaagcccaag gatgtgctca ccattactct gactcctaag     780

gtcacgtgtg ttgtggtaga catcagcaag gatgatcccg aggtccagtt cagctggttt     840

gtagatgatg tggaggtgca cacagctcag acgcaacccc gggaggagca gttcaacagc     900

actttccgct cagtcagtga acttcccatc atgcaccagg actggctcaa tggcaaggag     960

ttcaaatgca gggtcaacag tgcagctttc cctgccccca tcgagaaaac catctccaaa    1020

accaaaggca gaccgaaggc tccacaggtg tacaccattc cacctcccaa ggagcagatg    1080

gccaaggata aagtcagtct gacctgcatg ataacagact tcttccctga agacattact    1140

gtggagtggc agtggaatgg gcagccagcg gagaactaca agaacactca gcccatcatg    1200

gacacagatg gctcttactt cgtctacagc aagctcaatg tgcagaagag caactgggag    1260

gcaggaaata ctttcacctg ctctgtgtta catgagggcc tgcacaacca ccatactgag    1320

aagagcctct cccactctcc tggtaaatga                                     1350


<210> SEQ ID NO 37
```

```
<211> LENGTH: 468
<212> TYPE: PRT
<213> ORGANISM: Mus musculus

<400> SEQUENCE: 37

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg His Pro Ser Gly Lys
    50                  55                  60

Asn Leu Glu Trp Leu Ala His Ile Trp Trp Asp Asp Val Lys Arg Tyr
65                  70                  75                  80

Asn Pro Val Leu Lys Ser Arg Leu Thr Ile Ser Lys Asp Thr Ser Asn
                85                  90                  95

Ser Gln Val Phe Leu Lys Ile Ala Asn Val Asp Thr Ala Asp Thr Ala
            100                 105                 110

Thr Tyr Tyr Cys Ala Arg Ile Glu Asp Phe Asp Tyr Asp Glu Glu Tyr
        115                 120                 125

Tyr Ala Met Asp Tyr Trp Gly Gln Gly Thr Ser Val Ile Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
```

```
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465
```

<210> SEQ ID NO 38
<211> LENGTH: 1407
<212> TYPE: DNA
<213> ORGANISM: Mus musculus

<400> SEQUENCE: 38

```
atgggcaggc ttacttcttc attcctgcta ctgattgtcc ctgcatatgt cctgtcccag     60

gttactctga aagagtctgg ccctgggata ttgcagccct cccagaccct cagtctgact    120

tgttctttct ctgggttttc actgagcact tctggtatgg gtgtaggctg gattcgtcac    180

ccatcaggga agaatctgga gtggctggca cacatttggt gggatgatgt caagcgctat    240

aacccagtcc tgaagagccg actgactatc tccaaggata cctccaacag ccaggtattc    300

ctcaagatcg ccaatgtgga cactgcagat actgccacat actactgtgc tcgaatagag    360

gactttgatt acgacgagga gtattatgct atggactact ggggtcaagg aacctcagtc    420

atcgtctcct cagccaaaac gacaccccca tctgtctatc cactggcccc tggatctgct    480

gcccaaacta actccatggt gaccctggga tgcctggtca agggctattt ccctgagcca    540

gtgacagtga cctggaactc tggatccctg tccagcggtg tgcacacctt cccagctgtc    600

ctgcagtctg acctctacac tctgagcagc tcagtgactg tcccctccag cacctggccc    660

agcgagaccg tcacctgcaa cgttgcccac ccggccagca gcaccaaggt ggacaagaaa    720

attgtgccca gggattgtgg ttgtaagcct tgcatatgta cagtcccaga agtatcatct    780

gtcttcatct tccccccaaa gcccaaggat gtgctcacca ttactctgac tcctaaggtc    840

acgtgtgttg tggtagacat cagcaaggat gatcccgagg tccagttcag ctggtttgta    900

gatgatgtgg aggtgcacac agctcagacg caaccccggg aggagcagtt caacagcact    960

ttccgctcag tcagtgaact tcccatcatg caccaggact ggctcaatgg caaggagttc   1020

aaatgcaggg tcaacagtgc agctttccct gcccccatcg agaaaaccat ctccaaaacc   1080

aaaggcagac cgaaggctcc acaggtgtac accattccac ctcccaagga gcagatggcc   1140

aaggataaag tcagtctgac ctgcatgata acagacttct tccctgaaga cattactgtg   1200

gagtggcagt ggaatgggca gccagcggag aactacaaga acactcagcc catcatggac   1260

acagatggct cttacttcgt ctacagcaag ctcaatgtgc agaagagcaa ctgggaggca   1320

ggaaatactt tcacctgctc tgtgttacat gagggcctgc acaaccacca tactgagaag   1380

agcctctccc actctcctgg taaatga                                         1407
```

<210> SEQ ID NO 39
<211> LENGTH: 5
<212> TYPE: PRT
<213> ORGANISM: Mus musculus

<400> SEQUENCE: 39

Asp His Tyr Met Ser
1 5

<210> SEQ ID NO 40
<211> LENGTH: 17
<212> TYPE: PRT
<213> ORGANISM: Mus musculus

<400> SEQUENCE: 40

Asp Ile Asn Pro Tyr Ser Gly Glu Thr Thr Tyr Asn Gln Lys Phe Lys
1 5 10 15

Gly

<210> SEQ ID NO 41
<211> LENGTH: 10
<212> TYPE: PRT
<213> ORGANISM: Mus musculus

<400> SEQUENCE: 41

Asp Asp Tyr Asp Ala Ser Pro Phe Ala Tyr
1 5 10

<210> SEQ ID NO 42
<211> LENGTH: 11
<212> TYPE: PRT
<213> ORGANISM: Mus musculus

<400> SEQUENCE: 42

Gln Ala Ser Gln Gly Thr Ser Ile Asn Leu Asn
1 5 10

<210> SEQ ID NO 43
<211> LENGTH: 7
<212> TYPE: PRT
<213> ORGANISM: Mus musculus

<400> SEQUENCE: 43

Gly Ser Ser Asn Leu Glu Asp
1 5

<210> SEQ ID NO 44
<211> LENGTH: 9
<212> TYPE: PRT
<213> ORGANISM: Mus musculus

<400> SEQUENCE: 44

Leu Gln His Ser Tyr Leu Pro Tyr Thr
1 5

<210> SEQ ID NO 45
<211> LENGTH: 5
<212> TYPE: PRT
<213> ORGANISM: Mus musculus

<400> SEQUENCE: 45

Asp Cys Tyr Met Asn
1 5

<210> SEQ ID NO 46
<211> LENGTH: 17
<212> TYPE: PRT
<213> ORGANISM: Mus musculus

<400> SEQUENCE: 46

Asp Ile Asn Pro Phe Asn Gly Gly Thr Thr Tyr Asn Gln Lys Phe Lys
1               5                   10                  15

Gly

<210> SEQ ID NO 47
<211> LENGTH: 16
<212> TYPE: PRT
<213> ORGANISM: Mus musculus

<400> SEQUENCE: 47

Ser His Tyr Tyr Phe Asp Gly Arg Val Pro Trp Asp Ala Met Asp Tyr
1               5                   10                  15

<210> SEQ ID NO 48
<211> LENGTH: 15
<212> TYPE: PRT
<213> ORGANISM: Mus musculus

<400> SEQUENCE: 48

Lys Ala Ser Gln Ser Val Asp Tyr Asp Gly Asp Ser Tyr Met Asn
1               5                   10                  15

<210> SEQ ID NO 49
<211> LENGTH: 7
<212> TYPE: PRT
<213> ORGANISM: Mus musculus

<400> SEQUENCE: 49

Ala Ala Ser Asn Leu Glu Ser
1               5

<210> SEQ ID NO 50
<211> LENGTH: 9
<212> TYPE: PRT
<213> ORGANISM: Mus musculus

<400> SEQUENCE: 50

Gln Gln Ser Asn Glu Asp Pro Trp Thr
1               5

<210> SEQ ID NO 51
<211> LENGTH: 5
<212> TYPE: PRT
<213> ORGANISM: Artificial Sequence
<220> FEATURE:
<223> OTHER INFORMATION: Rabbit-Mouse Chimera

<400> SEQUENCE: 51

Ser Tyr Trp Met Asn
1               5

<210> SEQ ID NO 52
<211> LENGTH: 16
<212> TYPE: PRT
<213> ORGANISM: Artificial Sequence
<220> FEATURE:
<223> OTHER INFORMATION: Rabbit-Mouse Chimera

<400> SEQUENCE: 52

Thr Ile Asp Ser Gly Gly Arg Thr Asp Tyr Ala Ser Trp Ala Lys Gly
1               5                   10                  15

<210> SEQ ID NO 53

<211> LENGTH: 4
<212> TYPE: PRT
<213> ORGANISM: Artificial Sequence
<220> FEATURE:
<223> OTHER INFORMATION: Rabbit-Mouse Chimera

<400> SEQUENCE: 53

Asn Trp Asn Leu
1

<210> SEQ ID NO 54
<211> LENGTH: 13
<212> TYPE: PRT
<213> ORGANISM: Artificial Sequence
<220> FEATURE:
<223> OTHER INFORMATION: Rabbit-Mouse Chimera

<400> SEQUENCE: 54

Gln Ser Ser Gln Ser Val Tyr Asp Asn Asn Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Rabbit-Mouse Chimera

<400> SEQUENCE: 55

Asp Ala Ser Asp Leu Ala Ser
1               5

<210> SEQ ID NO 56
<211> LENGTH: 10
<212> TYPE: PRT
<213> ORGANISM: Artificial Sequence
<220> FEATURE:
<223> OTHER INFORMATION: Rabbit-Mouse Chimera

<400> SEQUENCE: 56

Gln Gly Ala Tyr Asn Asp Val Ile Tyr Ala
1               5                   10

<210> SEQ ID NO 57
<211> LENGTH: 7
<212> TYPE: PRT
<213> ORGANISM: Mus musculus

<400> SEQUENCE: 57

Thr Ser Gly Met Gly Val Gly
1               5

<210> SEQ ID NO 58
<211> LENGTH: 16
<212> TYPE: PRT
<213> ORGANISM: Mus musculus

<400> SEQUENCE: 58

His Ile Trp Trp Asp Asp Val Lys Arg Tyr Asn Pro Val Leu Lys Ser
1               5                   10                  15

<210> SEQ ID NO 59
<211> LENGTH: 14
<212> TYPE: PRT
<213> ORGANISM: Mus musculus

<400> SEQUENCE: 59

Glu Asp Phe Asp Tyr Asp Glu Glu Tyr Tyr Ala Met Asp Tyr
1 5 10

<210> SEQ ID NO 60
<211> LENGTH: 10
<212> TYPE: PRT
<213> ORGANISM: Mus musculus

<400> SEQUENCE: 60

Ser Ala Ser Ser Ser Val Ser Phe Val Asp
1 5 10

<210> SEQ ID NO 61
<211> LENGTH: 7
<212> TYPE: PRT
<213> ORGANISM: Mus musculus

<400> SEQUENCE: 61

Arg Thr Ser Asn Leu Gly Phe
1 5

<210> SEQ ID NO 62
<211> LENGTH: 9
<212> TYPE: PRT
<213> ORGANISM: Mus musculus

<400> SEQUENCE: 62

Gln Gln Arg Ser Thr Tyr Pro Pro Thr
1 5

<210> SEQ ID NO 63
<211> LENGTH: 20
<212> TYPE: PRT
<213> ORGANISM: Homo sapiens

<400> SEQUENCE: 63

Cys Gly Pro Ala Arg Leu Leu Pro Asn Ala Ile Gly Arg Gly Lys Trp
1 5 10 15

Trp Arg Pro Ser
20

<210> SEQ ID NO 64
<211> LENGTH: 20
<212> TYPE: PRT
<213> ORGANISM: Homo sapiens

<400> SEQUENCE: 64

Gly Pro Ala Arg Leu Leu Pro Asn Ala Ile Gly Arg Gly Lys Trp Trp
1 5 10 15

Arg Pro Ser Gly
20

<210> SEQ ID NO 65
<211> LENGTH: 20
<212> TYPE: PRT
<213> ORGANISM: Homo sapiens

<400> SEQUENCE: 65

Pro Ala Arg Leu Leu Pro Asn Ala Ile Gly Arg Gly Lys Trp Trp Arg
1 5 10 15

Pro Ser Gly Pro
20

<210> SEQ ID NO 66
<211> LENGTH: 20
<212> TYPE: PRT
<213> ORGANISM: Homo sapiens

<400> SEQUENCE: 66

Ala Arg Leu Leu Pro Asn Ala Ile Gly Arg Gly Lys Trp Trp Arg Pro
1 5 10 15

Ser Gly Pro Asp
20

<210> SEQ ID NO 67
<211> LENGTH: 20
<212> TYPE: PRT
<213> ORGANISM: Homo sapiens

<400> SEQUENCE: 67

Arg Leu Leu Pro Asn Ala Ile Gly Arg Gly Lys Trp Trp Arg Pro Ser
1 5 10 15

Gly Pro Asp Phe
20

<210> SEQ ID NO 68
<211> LENGTH: 20
<212> TYPE: PRT
<213> ORGANISM: Homo sapiens

<400> SEQUENCE: 68

Leu Leu Pro Asn Ala Ile Gly Arg Gly Lys Trp Trp Arg Pro Ser Gly
1 5 10 15

Pro Asp Phe Arg
20

<210> SEQ ID NO 69
<211> LENGTH: 20
<212> TYPE: PRT
<213> ORGANISM: Homo sapiens

<400> SEQUENCE: 69

Leu Pro Asn Ala Ile Gly Arg Gly Lys Trp Trp Arg Pro Ser Gly Pro
1 5 10 15

Asp Phe Arg Cys
20

<210> SEQ ID NO 70
<211> LENGTH: 14
<212> TYPE: PRT
<213> ORGANISM: Homo sapiens

<400> SEQUENCE: 70

Ser Ala Lys Pro Val Thr Glu Leu Val Cys Ser Gly Gln Cys
1 5 10

<210> SEQ ID NO 71
<211> LENGTH: 7
<212> TYPE: PRT
<213> ORGANISM: Homo sapiens

<400> SEQUENCE: 71

Leu Val Ala Ser Cys Lys Cys
1 5

<210> SEQ ID NO 72
<211> LENGTH: 8
<212> TYPE: PRT
<213> ORGANISM: Homo sapiens

<400> SEQUENCE: 72

Cys Arg Glu Leu His Phe Thr Arg
1               5

<210> SEQ ID NO 73
<211> LENGTH: 7
<212> TYPE: PRT
<213> ORGANISM: Homo sapiens

<400> SEQUENCE: 73

Cys Ile Pro Asp Arg Tyr Arg
1               5

<210> SEQ ID NO 74
<211> LENGTH: 399
<212> TYPE: DNA
<213> ORGANISM: Artificial Sequence
<220> FEATURE:
<223> OTHER INFORMATION: Humanized antibody sequence

<400> SEQUENCE: 74
atggacacga gggcccccac tcagctgctg gggctcctgc tgctctggct cccaggtgcc     60
acatttgctc aagttctgac ccagagtcca agcagtctct ccgccagcgt aggcgatcgt    120
gtgactatta cctgtcaatc tagtcagagc gtgtatgata acaattggct ggcgtggtac    180
cagcaaaaac cgggcaaagc ccccgaagctg ctcatctatg acgcgtccga tctggctagc    240
ggtgtgccaa gccgtttcag tggcagtggc agcggtactg actttaccct cacaatttcg    300
tctctccagc cggaagattt cgccacttac tattgtcaag gtgcttacaa cgatgtgatt    360
tatgccttcg gtcagggcac taaagtagaa atcaaacgt                           399

<210> SEQ ID NO 75
<211> LENGTH: 133
<212> TYPE: PRT
<213> ORGANISM: Artificial Sequence
<220> FEATURE:
<223> OTHER INFORMATION: Humanized antibody sequence

<400> SEQUENCE: 75

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Ser Pro Ser Ser
            20                  25                  30

Leu Ser Ala Ser Val Gly Asp Arg Val Thr Ile Thr Cys Gln Ser Ser
        35                  40                  45

Gln Ser Val Tyr Asp Asn Asn Trp Leu Ala Trp Tyr Gln Gln Lys Pro
    50                  55                  60

Gly Lys Ala Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gly Ala Tyr Asn Asp Val Ile Tyr Ala Phe Gly Gln Gly Thr Lys
        115                 120                 125

```
Val Glu Ile Lys Arg
    130


<210> SEQ ID NO 76
<211> LENGTH: 393
<212> TYPE: DNA
<213> ORGANISM: Artificial Sequence
<220> FEATURE:
<223> OTHER INFORMATION: Humanized antibody sequence

<400> SEQUENCE: 76

atggagactg ggctgcgctg gcttctcctg gtcgctgtgc tcaaaggtgt ccactgtgag     60

gtgcagctgt tggagtctgg aggcgggctt gtccagcctg gagggagcct gcgtctctct    120

tgtgcagcaa gcggcttcag cttatcctct tactggatga attgggtgcg gcaggcacct    180

gggaagggcc tggagtgggt gggcaccatt gattccggag gccgtacaga ctacgcgtct    240

tgggcaaagg gccgtttcac catttcccgc gacaactcca aaaataccat gtacctccag    300

atgaactctc tccgcgcaga ggacacagca cgttattact gtgcacgcaa ctggaatctg    360

tggggtcaag gtactcttgt aacagtctcg agc                                 393


<210> SEQ ID NO 77
<211> LENGTH: 131
<212> TYPE: PRT
<213> ORGANISM: Artificial Sequence
<220> FEATURE:
<223> OTHER INFORMATION: Humanized antibody sequence

<400> SEQUENCE: 77

Met Glu Thr Gly Leu Arg Trp Leu Leu Leu Val Ala Val Leu Lys Gly
1               5                   10                  15

Val His Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Ser Ser Tyr Trp Met Asn Trp Val Arg Gln Ala Pro Gly Lys Gly Leu
    50                  55                  60

Glu Trp Val Gly Thr Ile Asp Ser Gly Gly Arg Thr Asp Tyr Ala Ser
65                  70                  75                  80

Trp Ala Lys Gly Arg Phe Thr Ile Ser Arg Asp Asn Ser Lys Asn Thr
                85                  90                  95

Met Tyr Leu Gln Met Asn Ser Leu Arg Ala Glu Asp Thr Ala Arg Tyr
            100                 105                 110

Tyr Cys Ala Arg Asn Trp Asn Leu Trp Gly Gln Gly Thr Leu Val Thr
        115                 120                 125

Val Ser Ser
    130


<210> SEQ ID NO 78
<211> LENGTH: 11
<212> TYPE: PRT
<213> ORGANISM: Mus musculus

<400> SEQUENCE: 78

Arg Ala Ser Gln Asp Ile Ser Asn Tyr Leu Asn
1               5                   10


<210> SEQ ID NO 79
<211> LENGTH: 7
<212> TYPE: PRT
```

<213> ORGANISM: Mus musculus

<400> SEQUENCE: 79

Tyr Thr Ser Arg Leu Leu Ser
1               5

<210> SEQ ID NO 80
<211> LENGTH: 9
<212> TYPE: PRT
<213> ORGANISM: Mus musculus

<400> SEQUENCE: 80

Gln Gln Gly Asp Thr Leu Pro Tyr Thr
1               5

<210> SEQ ID NO 81
<211> LENGTH: 11
<212> TYPE: PRT
<213> ORGANISM: Mus musculus

<400> SEQUENCE: 81

Arg Ala Ser Gln Asp Ile Ser Asn Tyr Leu Asn
1               5                   10

<210> SEQ ID NO 82
<211> LENGTH: 24
<212> TYPE: PRT
<213> ORGANISM: Rattus norvegicus

<400> SEQUENCE: 82

Gln Gly Trp Gln Ala Phe Lys Asn Asp Ala Thr Glu Ile Ile Pro Gly
1               5                   10                  15

Leu Arg Glu Tyr Pro Glu Pro Pro
            20

<210> SEQ ID NO 83
<211> LENGTH: 20
<212> TYPE: PRT
<213> ORGANISM: Rattus norvegicus

<400> SEQUENCE: 83

Thr Glu Ile Ile Pro Gly Leu Arg Glu Tyr Pro Glu Pro Pro Gln Glu
1               5                   10                  15

Leu Glu Asn Asn
            20

<210> SEQ ID NO 84
<211> LENGTH: 20
<212> TYPE: PRT
<213> ORGANISM: Rattus norvegicus

<400> SEQUENCE: 84

Pro Glu Pro Pro Gln Glu Leu Glu Asn Asn Gln Thr Met Asn Arg Ala
1               5                   10                  15

Glu Asn Gly Gly
            20

<210> SEQ ID NO 85
<211> LENGTH: 20
<212> TYPE: PRT
<213> ORGANISM: Rattus norvegicus

<400> SEQUENCE: 85

```
Glu Asn Gly Gly Arg Pro Pro His His Pro Tyr Asp Thr Lys Asp Val
1               5                   10                  15

Ser Glu Tyr Ser
            20


<210> SEQ ID NO 86
<211> LENGTH: 14
<212> TYPE: PRT
<213> ORGANISM: Rattus norvegicus

<400> SEQUENCE: 86

Cys Arg Glu Leu His Tyr Thr Arg Phe Val Thr Asp Gly Pro
1               5                   10


<210> SEQ ID NO 87
<211> LENGTH: 25
<212> TYPE: PRT
<213> ORGANISM: Rattus norvegicus

<400> SEQUENCE: 87

Cys Arg Glu Leu His Tyr Thr Arg Phe Val Thr Asp Gly Pro Ser Arg
1               5                   10                  15

Ser Ala Lys Pro Val Thr Glu Leu Val
            20                  25


<210> SEQ ID NO 88
<211> LENGTH: 23
<212> TYPE: PRT
<213> ORGANISM: Rattus norvegicus

<400> SEQUENCE: 88

Cys Arg Ser Ala Lys Pro Val Thr Glu Leu Val Ser Ser Gly Gln Ser
1               5                   10                  15

Gly Pro Arg Ala Arg Leu Leu
            20


<210> SEQ ID NO 89
<211> LENGTH: 25
<212> TYPE: PRT
<213> ORGANISM: Rattus norvegicus

<400> SEQUENCE: 89

Cys Gly Pro Ala Arg Leu Leu Pro Asn Ala Ile Gly Arg Val Lys Trp
1               5                   10                  15

Trp Arg Pro Asn Gly Pro Asp Phe Arg
            20                  25


<210> SEQ ID NO 90
<211> LENGTH: 20
<212> TYPE: PRT
<213> ORGANISM: Rattus norvegicus

<400> SEQUENCE: 90

Arg Ala Gln Arg Val Gln Leu Leu Cys Pro Gly Gly Ala Ala Pro Arg
1               5                   10                  15

Ser Arg Lys Val
            20


<210> SEQ ID NO 91
<211> LENGTH: 16
<212> TYPE: PRT
<213> ORGANISM: Rattus norvegicus
```

<400> SEQUENCE: 91

Pro Gly Gly Ala Ala Pro Arg Ser Arg Lys Val Arg Leu Val Ala Ser
1 5 10 15

<210> SEQ ID NO 92
<211> LENGTH: 23
<212> TYPE: PRT
<213> ORGANISM: Rattus norvegicus

<400> SEQUENCE: 92

Lys Arg Leu Thr Arg Phe His Asn Gln Ser Glu Leu Lys Asp Phe Gly
1 5 10 15

Pro Glu Thr Ala Arg Pro Gln
20

<210> SEQ ID NO 93
<211> LENGTH: 16
<212> TYPE: PRT
<213> ORGANISM: Rattus norvegicus

<400> SEQUENCE: 93

Ile Pro Asp Arg Tyr Ala Gln Arg Val Gln Leu Leu Ser Pro Gly Gly
1 5 10 15

<210> SEQ ID NO 94
<211> LENGTH: 24
<212> TYPE: PRT
<213> ORGANISM: Rattus norvegicus

<400> SEQUENCE: 94

Ser Glu Leu Lys Asp Phe Gly Pro Glu Thr Ala Arg Pro Gln Lys Gly
1 5 10 15

Arg Lys Pro Arg Pro Arg Ala Arg
20

<210> SEQ ID NO 95
<211> LENGTH: 23
<212> TYPE: PRT
<213> ORGANISM: Rattus norvegicus

<400> SEQUENCE: 95

Lys Gly Arg Lys Pro Arg Pro Arg Ala Arg Gly Ala Lys Ala Asn Gln
1 5 10 15

Ala Glu Leu Glu Asn Ala Tyr
20

<210> SEQ ID NO 96
<211> LENGTH: 18
<212> TYPE: PRT
<213> ORGANISM: Rattus norvegicus

<400> SEQUENCE: 96

Pro Asn Ala Ile Gly Arg Val Lys Trp Trp Arg Pro Asn Gly Pro Asp
1 5 10 15

Phe Arg

<210> SEQ ID NO 97
<211> LENGTH: 22
<212> TYPE: PRT
<213> ORGANISM: Rattus norvegicus

<400> SEQUENCE: 97

```
Lys Trp Trp Arg Pro Asn Gly Pro Asp Phe Arg Cys Ile Pro Asp Arg
1               5                   10                  15

Tyr Arg Ala Gln Arg Val
            20


<210> SEQ ID NO 98
<211> LENGTH: 213
<212> TYPE: PRT
<213> ORGANISM: Rattus norvegicus

<400> SEQUENCE: 98

Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210


<210> SEQ ID NO 99
<211> LENGTH: 7
<212> TYPE: PRT
<213> ORGANISM: Mus musculus

<400> SEQUENCE: 99

Tyr Thr Ser Arg Leu His Ser
1               5


<210> SEQ ID NO 100
<211> LENGTH: 9
<212> TYPE: PRT
<213> ORGANISM: Mus musculus

<400> SEQUENCE: 100

Gln Gln Gly Asp Thr Leu Pro Tyr Thr
1               5
```

<210> SEQ ID NO 101
<211> LENGTH: 11
<212> TYPE: PRT
<213> ORGANISM: Mus musculus

<400> SEQUENCE: 101

Arg Ala Ser Gln Val Ile Thr Asn Tyr Leu Tyr
1 5 10

<210> SEQ ID NO 102
<211> LENGTH: 7
<212> TYPE: PRT
<213> ORGANISM: Mus musculus

<400> SEQUENCE: 102

Tyr Thr Ser Arg Leu His Ser
1 5

<210> SEQ ID NO 103
<211> LENGTH: 9
<212> TYPE: PRT
<213> ORGANISM: Mus musculus

<400> SEQUENCE: 103

Gln Gln Gly Asp Thr Leu Pro Tyr Thr
1 5

<210> SEQ ID NO 104
<211> LENGTH: 11
<212> TYPE: PRT
<213> ORGANISM: Mus musculus

<400> SEQUENCE: 104

Arg Ala Ser Gln Asp Ile Ser Asn Tyr Leu Asn
1 5 10

<210> SEQ ID NO 105
<211> LENGTH: 7
<212> TYPE: PRT
<213> ORGANISM: Mus musculus

<400> SEQUENCE: 105

Tyr Thr Ser Arg Leu Leu Ser
1 5

<210> SEQ ID NO 106
<211> LENGTH: 9
<212> TYPE: PRT
<213> ORGANISM: Mus musculus

<400> SEQUENCE: 106

Gln Gln Gly Asp Thr Leu Pro Tyr Thr
1 5

<210> SEQ ID NO 107
<211> LENGTH: 11
<212> TYPE: PRT
<213> ORGANISM: Mus musculus

<400> SEQUENCE: 107

Arg Ala Ser Gln Asp Ile Ser Asn Tyr Leu Asn
1 5 10

<210> SEQ ID NO 108
<211> LENGTH: 7

```
<212> TYPE: PRT
<213> ORGANISM: Mus musculus

<400> SEQUENCE: 108

Tyr Thr Ser Arg Leu Phe Ser
1               5


<210> SEQ ID NO 109
<211> LENGTH: 9
<212> TYPE: PRT
<213> ORGANISM: Mus musculus

<400> SEQUENCE: 109

Gln Gln Gly Asp Thr Leu Pro Tyr Thr
1               5


<210> SEQ ID NO 110
<211> LENGTH: 11
<212> TYPE: PRT
<213> ORGANISM: Mus musculus

<400> SEQUENCE: 110

Arg Ala Ser Gln Asp Ile Ser Asn Tyr Leu Asn
1               5                   10


<210> SEQ ID NO 111
<211> LENGTH: 7
<212> TYPE: PRT
<213> ORGANISM: Mus musculus

<400> SEQUENCE: 111

Tyr Thr Ser Arg Leu Leu Ser
1               5


<210> SEQ ID NO 112
<211> LENGTH: 9
<212> TYPE: PRT
<213> ORGANISM: Mus musculus

<400> SEQUENCE: 112

Gln Gln Gly Asp Thr Leu Pro Tyr Thr
1               5


<210> SEQ ID NO 113
<211> LENGTH: 11
<212> TYPE: PRT
<213> ORGANISM: Mus musculus

<400> SEQUENCE: 113

Arg Ala Ser Gln Asp Ile Ser Asn Tyr Leu Asn
1               5                   10


<210> SEQ ID NO 114
<211> LENGTH: 7
<212> TYPE: PRT
<213> ORGANISM: Mus musculus

<400> SEQUENCE: 114

Tyr Thr Ser Thr Leu Gln Ser
1               5


<210> SEQ ID NO 115
<211> LENGTH: 9
<212> TYPE: PRT
<213> ORGANISM: Mus musculus
```

<400> SEQUENCE: 115

Gln Gln Gly Asp Thr Leu Pro Tyr Thr
1 5

<210> SEQ ID NO 116
<211> LENGTH: 12
<212> TYPE: PRT
<213> ORGANISM: Mus musculus

<400> SEQUENCE: 116

Ser Val Ser Ser Ser Ile Ser Ser Ser Asn Leu His
1 5 10

<210> SEQ ID NO 117
<211> LENGTH: 213
<212> TYPE: PRT
<213> ORGANISM: Mus musculus

<400> SEQUENCE: 117

Gln Ile Val Leu Ser Gln Ser Pro Ala Ile Leu Ser Thr Ser Pro Gly
1 5 10 15

Glu Lys Val Thr Met Thr Cys Arg Ala Ser Ser Ser Val Tyr Tyr Met
20 25 30

His Trp Tyr Gln Gln Lys Pro Gly Ser Ser Pro Lys Pro Trp Ile Tyr
35 40 45

Ala Thr Ser Asn Leu Ala Ser Gly Val Pro Val Arg Phe Ser Gly Ser
50 55 60

Gly Ser Gly Thr Ser Tyr Ser Leu Thr Ile Thr Arg Val Glu Ala Glu
65 70 75 80

Asp Ala Ala Thr Tyr Tyr Cys Gln Gln Trp Ser Ser Asp Pro Leu Thr
85 90 95

Phe Gly Ala Gly Thr Lys Leu Glu Leu Lys Arg Ala Asp Ala Ala Pro
100 105 110

Thr Val Ser Ile Phe Pro Pro Ser Ser Glu Gln Leu Thr Ser Gly Gly
115 120 125

Ala Ser Val Val Cys Phe Leu Asn Asn Phe Tyr Pro Lys Asp Ile Asn
130 135 140

Val Lys Trp Lys Ile Asp Gly Ser Glu Arg Gln Asn Gly Val Leu Asn
145 150 155 160

Ser Trp Thr Asp Gln Asp Ser Lys Asp Ser Thr Tyr Ser Met Ser Ser
165 170 175

Thr Leu Thr Leu Thr Lys Asp Glu Tyr Glu Arg His Asn Ser Tyr Thr
180 185 190

Cys Glu Ala Thr His Lys Thr Ser Thr Ser Pro Ile Val Lys Ser Phe
195 200 205

Asn Arg Asn Glu Cys
210

<210> SEQ ID NO 118
<211> LENGTH: 642
<212> TYPE: DNA
<213> ORGANISM: Mus musculus

<400> SEQUENCE: 118
caaattgttc tctcccagtc tccagcaatc ctgtctacat ctccagggga gaaggtcaca 60
atgacttgca gggccagctc aagtgtatat tacatgcact ggtaccagca gaagccagga 120

```
tcctccccca aaccctggat ttatgccaca tccaacctgg cttctggagt ccctgttcgc    180

ttcagtggca gtgggtctgg gacctcttac tctctcacaa tcaccagagt ggaggctgaa    240

gatgctgcca cttattactg ccagcagtgg agtagtgacc cactcacgtt cggtgctggg    300

accaagctgg agctgaaacg ggctgatgct gcaccaactg tatccatctt cccaccatcc    360

agtgagcagt taacatctgg aggtgcctca gtcgtgtgct tcttgaacaa cttctacccc    420

aaagacatca atgtcaagtg gaagattgat ggcagtgaac gacaaaatgg cgtcctgaac    480

agttggactg atcaggacag caaagacagc acctacagca tgagcagcac cctcacgttg    540

accaaggacg agtatgaacg acataacagc tatacctgtg aggccactca caagacatca    600

acttcaccca ttgtcaagag cttcaacagg aatgagtgtt ag                       642


<210> SEQ ID NO 119
<211> LENGTH: 235
<212> TYPE: PRT
<213> ORGANISM: Mus musculus

<400> SEQUENCE: 119

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Thr Ser Pro Gly Glu Lys Val Thr Met Thr Cys Arg Ala Ser
        35                  40                  45

Ser Ser Val Tyr Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Thr Arg Val Glu Ala Glu Asp Ala Ala Thr Tyr Tyr Cys Gln Gln Trp
            100                 105                 110

Ser Ser Asp Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 120
<211> LENGTH: 708
<212> TYPE: DNA
<213> ORGANISM: Mus musculus

<400> SEQUENCE: 120
```

```
atggatttc aagtgcagat tttcagcttc ctgctaatca gtgcttcagt cattatgtcc     60

aggggacaaa ttgttctctc ccagtctcca gcaatcctgt ctacatctcc aggggagaag    120

gtcacaatga cttgcagggc cagctcaagt gtatattaca tgcactggta ccagcagaag    180

ccaggatcct cccccaaacc ctggatttat gccacatcca acctggcttc tggagtccct    240

gttcgcttca gtggcagtgg gtctgggacc tcttactctc tcacaatcac cagagtggag    300

gctgaagatg ctgccactta ttactgccag cagtggagta gtgacccact cacgttcggt    360

gctgggacca agctggagct gaaacgggct gatgctgcac caactgtatc catcttccca    420

ccatccagtg agcagttaac atctggaggt gcctcagtcg tgtgcttctt gaacaacttc    480

taccccaaag acatcaatgt caagtggaag attgatggca gtgaacgaca aaatggcgtc    540

ctgaacagtt ggactgatca ggacagcaaa gacagcacct acagcatgag cagcaccctc    600

acgttgacca aggacgagta tgaacgacat aacagctata cctgtgaggc cactcacaag    660

acatcaactt cacccattgt caagagcttc aacaggaatg agtgttag                708
```

```
<210> SEQ ID NO 121
<211> LENGTH: 445
<212> TYPE: PRT
<213> ORGANISM: Mus musculus

<400> SEQUENCE: 121

Glu Val Gln Val Gln Gln Ser Gly Pro Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Arg Leu Asp Pro Glu Asp Gly Glu Ser Asp Tyr Ala Pro Lys Phe
    50                  55                  60

Gln Asp Lys Ala Ile Met Thr Ala Asp Thr Ser Ser Asn Thr Ala Tyr
65                  70                  75                  80

Leu Gln Leu Arg Ser Leu Thr Ser Glu Asp Thr Ala Ile Tyr Tyr Cys
                85                  90                  95

Glu Arg Glu Asp Tyr Asp Gly Thr Tyr Thr Phe Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255
```

```
Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 122
<211> LENGTH: 1338
<212> TYPE: DNA
<213> ORGANISM: Mus musculus

<400> SEQUENCE: 122

gaggttcagg tgcagcagtc tgggccagaa cttgtgaagc caggggcctc agtcaagttg      60

tcctgcacag cttctggctt caacattaaa gactacttta tacactgggt gaagcagagg     120

cctgaacagg gcctggagtg gattggaagg cttgatcctg aggatggtga aagtgattat     180

gccccgaagt tccaggacaa ggccattatg acagcagaca catcatccaa cacagcctat     240

cttcagctca gaagcctgac atctgaggac actgccatct attattgtga gagagaggac     300

tacgatggta cctacacctt ttttccttac tggggccaag ggactctggt cactgtctct     360

gcagccaaaa cgacaccccc atctgtctat ccactggccc ctggatctgc tgcccaaact     420

aactccatgg tgaccctggg atgcctggtc aagggctatt tccctgagcc agtgacagtg     480

acctggaact ctggatccct gtccagcggt gtgcacacct tcccagctgt cctgcagtct     540

gacctctaca ctctgagcag ctcagtgact gtcccctcca gcacctggcc cagcgagacc     600

gtcacctgca acgttgccca cccggccagc agcaccaagg tggacaagaa aattgtgccc     660

agggattgtg gttgtaagcc ttgcatatgt acagtcccag aagtatcatc tgtcttcatc     720

ttccccccaa agcccaagga tgtgctcacc attactctga ctcctaaggt cacgtgtgtt     780

gtggtagaca tcagcaagga tgatcccgag gtccagttca gctggtttgt agatgatgtg     840

gaggtgcaca cagctcagac gcaaccccgg gaggagcagt tcaacagcac tttccgctca     900

gtcagtgaac ttcccatcat gcaccaggac tggctcaatg gcaaggagtt caaatgcagg     960

gtcaacagtg cagctttccc tgcccccatc gagaaaacca tctccaaaac caaaggcaga    1020
```

```
ccgaaggctc cacaggtgta caccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200

tcttacttca tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaatga                                                 1338


<210> SEQ ID NO 123
<211> LENGTH: 464
<212> TYPE: PRT
<213> ORGANISM: Mus musculus

<400> SEQUENCE: 123

Met Lys Cys Ser Trp Val Ile Phe Phe Leu Met Ala Val Val Thr Gly
1               5                   10                  15

Val Asn Ser Glu Val Gln Val Gln Gln Ser Gly Pro Glu Leu Val Lys
            20                  25                  30

Pro Gly Ala Ser Val Lys Leu Ser Cys Thr Ala Ser Gly Phe Asn Ile
        35                  40                  45

Lys Asp Tyr Phe Ile His Trp Val Lys Gln Arg Pro Glu Gln Gly Leu
    50                  55                  60

Glu Trp Ile Gly Arg Leu Asp Pro Glu Asp Gly Glu Ser Asp Tyr Ala
65                  70                  75                  80

Pro Lys Phe Gln Asp Lys Ala Ile Met Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Glu Arg Glu Asp Tyr Asp Gly Thr Tyr Thr Phe Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320
```

```
Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 124
<211> LENGTH: 1395
<212> TYPE: DNA
<213> ORGANISM: Mus musculus

<400> SEQUENCE: 124

atgaaatgca gctgggtcat cttcttcctg atggcagtgg ttacaggggt caattcagag      60

gttcaggtgc agcagtctgg gccagaactt gtgaagccag gggcctcagt caagttgtcc     120

tgcacagctt ctggcttcaa cattaaagac tactttatac actgggtgaa gcagaggcct     180

gaacagggcc tggagtggat tggaaggctt gatcctgagg atggtgaaag tgattatgcc     240

ccgaagttcc aggacaaggc cattatgaca gcagacacat catccaacac agcctatctt     300

cagctcagaa gcctgacatc tgaggacact gccatctatt attgtgagag agaggactac     360

gatggtacct acaccttttt tccttactgg ggccaaggga ctctggtcac tgtctctgca     420

gccaaaacga cacccccatc tgtctatcca ctggcccctg gatctgctgc ccaaactaac     480

tccatggtga ccctgggatg cctggtcaag ggctatttcc ctgagccagt gacagtgacc     540

tggaactctg gatccctgtc cagcggtgtg cacaccttcc cagctgtcct gcagtctgac     600

ctctacactc tgagcagctc agtgactgtc ccctccagca cctggcccag cgagaccgtc     660

acctgcaacg ttgcccaccc ggccagcagc accaaggtgg acaagaaaat tgtgcccagg     720

gattgtggtt gtaagccttg catatgtaca gtcccagaag tatcatctgt cttcatcttc     780

cccccaaagc ccaaggatgt gctcaccatt actctgactc ctaaggtcac gtgtgttgtg     840

gtagacatca gcaaggatga tcccgaggtc cagttcagct ggtttgtaga tgatgtggag     900

gtgcacacag ctcagacgca accccgggag gagcagttca acagcacttt ccgctcagtc     960

agtgaacttc ccatcatgca ccaggactgg ctcaatggca aggagttcaa atgcagggtc    1020

aacagtgcag ctttccctgc ccccatcgag aaaaccatct ccaaaaccaa aggcagaccg    1080

aaggctccac aggtgtacac cattccacct cccaaggagc agatggccaa ggataaagtc    1140

agtctgacct gcatgataac agacttcttc cctgaagaca ttactgtgga gtggcagtgg    1200

aatgggcagc cagcggagaa ctacaagaac actcagccca tcatggacac agatggctct    1260

tacttcatct acagcaagct caatgtgcag aagagcaact gggaggcagg aaatactttc    1320
```

```
acctgctctg tgttacatga gggcctgcac aaccaccata ctgagaagag cctctcccac   1380

tctcctggta aatga                                                     1395
```

<210> SEQ ID NO 125
<211> LENGTH: 215
<212> TYPE: PRT
<213> ORGANISM: Mus musculus

<400> SEQUENCE: 125

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Thr Ile Ser Ser Asn
            20                  25                  30

His Leu His Trp Phe Gln Gln Lys Ser Asp Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Arg Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 126
<211> LENGTH: 648
<212> TYPE: DNA
<213> ORGANISM: Mus musculus

<400> SEQUENCE: 126

```
gaaattgtgc tcacccagtc tccagcactc atggctgcat ctccggggga gaaggtcacc     60

atcacctgca gtgtcagttc aactataagt tccaaccact tgcactggtt ccagcagaag    120

tcagacacct cccccaaacc ctggatttat ggcacatcca acctggcttc tggagtccct    180

gttcgcttca gtggcagtgg atctgggacc tcttattctc tcacaatcag cagcatggag    240

gctgaggatg ctgccactta ttactgtcaa cagtggagta gttacccact cacgttcggc    300

gctgggacca agctggagct gagacgggct gatgctgcac caactgtatc catcttccca    360

ccatccagtg agcagttaac atctggaggt gcctcagtcg tgtgcttctt gaacaacttc    420

taccccaaag acatcaatgt caagtggaag attgatggca gtgaacgaca aaatggcgtc    480
```

```
ctgaacagtt ggactgatca ggacagcaaa gacagcacct acagcatgag cagcaccctc    540

acgttgacca aggacgagta tgaacgacat aacagctata cctgtgaggc cactcacaag    600

acatcaactt cacccattgt caagagcttc aacaggaatg agtgttag                 648


<210> SEQ ID NO 127
<211> LENGTH: 237
<212> TYPE: PRT
<213> ORGANISM: Mus musculus

<400> SEQUENCE: 127

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Thr Ile Ser Ser Asn His Leu His Trp Phe Gln Gln Lys Ser Asp
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Arg Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235


<210> SEQ ID NO 128
<211> LENGTH: 714
<212> TYPE: DNA
<213> ORGANISM: Mus musculus

<400> SEQUENCE: 128

atggattttc atgtgcagat tttcagcttc atgctaatca gtgtcacagt cattttgtcc     60

agtggagaaa ttgtgctcac ccagtctcca gcactcatgg ctgcatctcc gggggagaag    120

gtcaccatca cctgcagtgt cagttcaact ataagttcca accacttgca ctggttccag    180

cagaagtcag acacctcccc caaaccctgg atttatggca catccaacct ggcttctgga    240

gtccctgttc gcttcagtgg cagtggatct gggacctctt attctctcac aatcagcagc    300

atggaggctg aggatgctgc cacttattac tgtcaacagt ggagtagtta cccactcacg    360
```

```
ttcggcgctg ggaccaagct ggagctgaga cgggctgatg ctgcaccaac tgtatccatc    420

ttcccaccat ccagtgagca gttaacatct ggaggtgcct cagtcgtgtg cttcttgaac    480

aacttctacc ccaaagacat caatgtcaag tggaagattg atggcagtga acgacaaaat    540

ggcgtcctga acagttggac tgatcaggac agcaaagaca gcacctacag catgagcagc    600

accctcacgt tgaccaagga cgagtatgaa cgacataaca gctatacctg tgaggccact    660

cacaagacat caacttcacc cattgtcaag agcttcaaca ggaatgagtg ttag          714
```

<210> SEQ ID NO 129
<211> LENGTH: 449
<212> TYPE: PRT
<213> ORGANISM: Mus musculus

<400> SEQUENCE: 129

```
Glu Val Gln Leu Gln Gln Ser Gly Ala Glu Leu Val Arg Pro Gly Ala
1               5                   10                  15

Leu Val Lys Leu Ser Cys Thr Ala Ser Asp Phe Asn Ile Lys Asp Phe
            20                  25                  30

Tyr Leu His Trp Met Arg Gln Arg Pro Glu Gln Gly Leu Asp Trp Ile
        35                  40                  45

Gly Arg Ile Asp Pro Glu Asn Gly Asp Thr Leu Tyr Asp Pro Lys Phe
    50                  55                  60

Gln Asp Lys Ala Thr Leu Thr Thr Asp Thr Ser Ser Asn Thr Ala Tyr
65                  70                  75                  80

Leu Gln Leu Ser Gly Leu Thr Ser Glu Thr Thr Ala Val Tyr Tyr Cys
                85                  90                  95

Ser Arg Glu Ala Asp Tyr Phe His Asp Gly Thr Ser Tyr Trp Tyr Phe
            100                 105                 110

Asp Val Trp Gly Ala Gly Thr Thr Ile Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320
```

```
Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys

<210> SEQ ID NO 130
<211> LENGTH: 1350
<212> TYPE: DNA
<213> ORGANISM: Mus musculus

<400> SEQUENCE: 130

gaggttcagc tgcagcagtc tggggctgaa cttgtgaggc caggggcctt agtcaagttg     60

tcctgcacag cttctgactt caacattaaa gacttctatc tacactggat gaggcagcgg    120

cctgaacagg gcctggactg gattggaagg attgatcctg agaatggtga tactttatat    180

gacccgaagt tccaggacaa ggccactctt acaacagaca catcctccaa cacagcctac    240

ctgcagctca gcggcctgac atctgagacc actgccgtct attactgttc tagagaggcg    300

gattatttcc acgatggtac ctcctactgg tacttcgatg tctggggcgc agggaccaca    360

atcaccgtct cctcagccaa aacgacaccc ccatctgtct atccactggc ccctggatct    420

gctgcccaaa ctaactccat ggtgaccctg ggatgcctgg tcaagggcta tttccctgag    480

ccagtgacag tgacctggaa ctctggatcc ctgtccagcg gtgtgcacac cttcccagct    540

gtcctgcagt ctgacctcta cactctgagc agctcagtga ctgtcccctc cagcacctgg    600

cccagcgaga ccgtcacctg caacgttgcc cacccggcca gcagcaccaa ggtggacaag    660

aaaattgtgc ccagggattg tggttgtaag ccttgcatat gtacagtccc agaagtatca    720

tctgtcttca tcttcccccc aaagcccaag gatgtgctca ccattactct gactcctaag    780

gtcacgtgtg ttgtggtaga catcagcaag gatgatcccg aggtccagtt cagctggttt    840

gtagatgatg tggaggtgca cacagctcag acgcaacccc gggaggagca gttcaacagc    900

actttccgct cagtcagtga acttcccatc atgcaccagg actggctcaa tggcaaggag    960

ttcaaatgca gggtcaacag tgcagctttc cctgccccca tcgagaaaac catctccaaa   1020

accaaaggca gaccgaaggc tccacaggtg tacaccattc cacctcccaa ggagcagatg   1080

gccaaggata aagtcagtct gacctgcatg ataacagact tcttccctga agacattact   1140

gtggagtggc agtggaatgg gcagccagcg gagaactaca agaacactca gcccatcatg   1200

gacacagatg gctcttactt catctacagc aagctcaatg tgcagaagag caactgggag   1260

gcaggaaata ctttcacctg ctctgtgtta catgagggcc tgcacaacca ccatactgag   1320
```

```
aagagcctct cccactctcc tggtaaatga                                    1350


<210> SEQ ID NO 131
<211> LENGTH: 468
<212> TYPE: PRT
<213> ORGANISM: Mus musculus

<400> SEQUENCE: 131

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Thr Ala Ser Asp Phe Asn Ile
        35                  40                  45

Lys Asp Phe Tyr Leu His Trp Met Arg Gln Arg Pro Glu Gln Gly Leu
    50                  55                  60

Asp Trp Ile Gly Arg Ile Asp Pro Glu Asn Gly Asp Thr Leu Tyr Asp
65                  70                  75                  80

Pro Lys Phe Gln Asp Lys Ala Thr Leu Thr Thr Asp Thr Ser Ser Asn
                85                  90                  95

Thr Ala Tyr Leu Gln Leu Ser Gly Leu Thr Ser Glu Thr Thr Ala Val
            100                 105                 110

Tyr Tyr Cys Ser Arg Glu Ala Asp Tyr Phe His Asp Gly Thr Ser Tyr
        115                 120                 125

Trp Tyr Phe Asp Val Trp Gly Ala Gly Thr Thr Ile Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365
```

```
Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465


<210> SEQ ID NO 132
<211> LENGTH: 1407
<212> TYPE: DNA
<213> ORGANISM: Mus musculus

<400> SEQUENCE: 132

atgaaatgca gctgggtcat cttcttcctg atggcagtgg ttacaggggt caattcagag      60

gttcagctgc agcagtctgg ggctgaactt gtgaggccag gggccttagt caagttgtcc     120

tgcacagctt ctgacttcaa cattaaagac ttctatctac actggatgag gcagcggcct     180

gaacagggcc tggactggat tggaaggatt gatcctgaga atggtgatac tttatatgac     240

ccgaagttcc aggacaaggc cactcttaca acagacacat cctccaacac agcctacctg     300

cagctcagcg gcctgacatc tgagaccact gccgtctatt actgttctag agaggcggat     360

tatttccacg atggtacctc ctactggtac ttcgatgtct ggggcgcagg gaccacaatc     420

accgtctcct cagccaaaac gacaccccca tctgtctatc cactggcccc tggatctgct     480

gcccaaacta actccatggt gaccctggga tgcctggtca agggctattt ccctgagcca     540

gtgacagtga cctggaactc tggatccctg tccagcggtg tgcacacctt cccagctgtc     600

ctgcagtctg acctctacac tctgagcagc tcagtgactg tcccctccag cacctggccc     660

agcgagaccg tcacctgcaa cgttgcccac ccggccagca gcaccaaggt ggacaagaaa     720

attgtgccca gggattgtgg ttgtaagcct tgcatatgta cagtcccaga agtatcatct     780

gtcttcatct tccccccaaa gcccaaggat gtgctcacca ttactctgac tcctaaggtc     840

acgtgtgttg tggtagacat cagcaaggat gatcccgagg tccagttcag ctggtttgta     900

gatgatgtgg aggtgcacac agctcagacg caaccccggg aggagcagtt caacagcact     960

ttccgctcag tcagtgaact tcccatcatg caccaggact ggctcaatgg caaggagttc    1020

aaatgcaggg tcaacagtgc agctttccct gcccccatcg agaaaaccat ctccaaaacc    1080

aaaggcagac cgaaggctcc acaggtgtac accattccac ctcccaagga gcagatggcc    1140

aaggataaag tcagtctgac ctgcatgata acagacttct tccctgaaga cattactgtg    1200

gagtggcagt ggaatgggca gccagcggag aactacaaga acactcagcc catcatggac    1260

acagatggct cttacttcat ctacagcaag ctcaatgtgc agaagagcaa ctgggaggca    1320

ggaaatactt tcacctgctc tgtgttacat gagggcctgc acaaccacca tactgagaag    1380

agcctctccc actctcctgg taaatga                                        1407


<210> SEQ ID NO 133
```

<211> LENGTH: 214
<212> TYPE: PRT
<213> ORGANISM: Mus musculus

<400> SEQUENCE: 133

```
Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 134
<211> LENGTH: 645
<212> TYPE: DNA
<213> ORGANISM: Mus musculus

<400> SEQUENCE: 134

```
gatatccaga tgacacagat tacatcctcc ctgtctgcct ctctgggaga cagggtctcc     60

atcagttgca gggcaagtca agacattagc aattatttaa actggtatca gcagaaacca    120

gatggaactt ttaaactcct tatcttctac acatcaagat tactctcagg agtcccatca    180

aggttcagtg gcagtgggtc tggaacagat tattctctca ccatttacaa cctggagcaa    240

gaagattttg ccacttactt ttgccaacag ggagatacgc ttccgtacac tttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 135
<211> LENGTH: 234
<212> TYPE: PRT
<213> ORGANISM: Mus musculus

<400> SEQUENCE: 135

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 136
<211> LENGTH: 705
<212> TYPE: DNA
<213> ORGANISM: Mus musculus

<400> SEQUENCE: 136

```
atgatgtcct ctgctcagtt ccttggtctc ctgttgctct gttttcaagg taccagatgt      60

gatatccaga tgacacagat tacatcctcc ctgtctgcct ctctgggaga cagggtctcc     120

atcagttgca gggcaagtca agacattagc aattatttaa actggtatca gcagaaacca     180

gatggaactt ttaaactcct tatcttctac acatcaagat tactctcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaagc tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600
```

```
ttgaccaagg acgagtatga acgacataac agctatacct gtgaggccac tcacaagaca    660

tcaacttcac ccattgtcaa gagcttcaac aggaatgagt gttag                    705


<210> SEQ ID NO 137
<211> LENGTH: 447
<212> TYPE: PRT
<213> ORGANISM: Mus musculus

<400> SEQUENCE: 137

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350
```

```
Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
            405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 138
<211> LENGTH: 1344
<212> TYPE: DNA
<213> ORGANISM: Mus musculus

<400> SEQUENCE: 138

gaggtccaac tgcaacagtc tggacctgaa ctaatgaagc ctggggcttc agtgaagatg     60

tcctgcaagg cttctggata tacattcact gactacaaca tgcactgggt gaagcagaac    120

caaggaaaga ccctagagtg gataggagaa attaatccta acagtggtgg tgctggctac    180

aaccagaagt tcaagggcaa ggccacattg actgtagaca agtcctccac cacagcctac    240

atggagctcc gcagcctgac atctgaggac tctgcagtct attactgtgc aagattgggc    300

tacgatgata tctacgacga ctggtacttc gatgtctggg gcgcagggac cacggtcacc    360

gtctcctcag ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900

cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                           1344


<210> SEQ ID NO 139
<211> LENGTH: 466
<212> TYPE: PRT
<213> ORGANISM: Mus musculus

<400> SEQUENCE: 139
```

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415
```

```
Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 140
<211> LENGTH: 1401
<212> TYPE: DNA
<213> ORGANISM: Mus musculus

<400> SEQUENCE: 140

```
atgggatgga gctggacctt tctcttcctc ctgtcaggaa ctgcaggtgt cctctctgag      60

gtccaactgc aacagtctgg acctgaacta atgaagcctg ggcttcagt gaagatgtcc     120

tgcaaggctt ctggatatac attcactgac tacaacatgc actgggtgaa gcagaaccaa     180

ggaaagaccc tagagtggat aggagaaatt aatcctaaca gtggtggtgc tggctacaac     240

cagaagttca agggcaaggc cacattgact gtagacaagt cctccaccac agcctacatg     300

gagctccgca gcctgacatc tgaggactct gcagtctatt actgtgcaag attgggctac     360

gatgatatct acgacgactg gtacttcgat gtctggggcg cagggaccac ggtcaccgtc     420

tcctcagcca aaacgacacc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900

gtggaggtgc acacagctca gacgcaaccc cgggaggagc agttcaacag cactttccgc     960

tcagtcagtg aacttcccat catgcaccag gactggctca atggcaagga gttcaaatgc    1020

agggtcaaca gtgcagcttt ccctgccccc atcgagaaaa ccatctccaa aaccaaaggc    1080

agaccgaagg ctccacaggt gtacaccatt ccacctccca aggagcagat ggccaaggat    1140

aaagtcagtc tgacctgcat gataacagac ttcttccctg aagacattac tgtggagtgg    1200

cagtggaatg gcagccagc ggagaactac aagaacactc agcccatcat ggacacagat    1260

ggctcttact tcatctacag caagctcaat gtgcagaaga gcaactggga ggcaggaaat    1320

actttcacct gctctgtgtt acatgagggc ctgcacaacc accatactga gaagagcctc    1380

tcccactctc ctggtaaatg a                                              1401
```

<210> SEQ ID NO 141
<211> LENGTH: 214
<212> TYPE: PRT
<213> ORGANISM: Artificial Sequence
<220> FEATURE:
<223> OTHER INFORMATION: Humanized antibody sequence

<400> SEQUENCE: 141

```
Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 642
<212> TYPE: DNA
<213> ORGANISM: Artificial Sequence
<220> FEATURE:
<223> OTHER INFORMATION: Humanized antibody sequence

<400> SEQUENCE: 142

```
gacatccaga tgacccagtc tccatcctcc ctctccgcat ccgtaggcga ccgcgtaacc      60

ataacatgta gagcatctca agatatttcc aactatttga attggtacca acaaaaaccc     120

ggcaaagcac ctaaactcct catttactat acatcaagac tcctctccgg cgttccatca     180

cgattctcag gctccggctc cggcacagat ttcacactca ctatttcctc cctccaacca     240

gaagattttg caacctatta ctgtcaacaa ggcgatacac tcccatacac attcggcggc     300

ggcacaaaag ttgaaattaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642
```

<210> SEQ ID NO 143
<211> LENGTH: 236
<212> TYPE: PRT
<213> ORGANISM: Artificial Sequence
<220> FEATURE:

<223> OTHER INFORMATION: Humanized antibody sequence

<400> SEQUENCE: 143

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Tyr Thr Ser Arg Leu Leu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Gly Asp Thr Leu Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 144
<211> LENGTH: 708
<212> TYPE: DNA
<213> ORGANISM: Artificial Sequence
<220> FEATURE:
<223> OTHER INFORMATION: Humanized antibody sequence

<400> SEQUENCE: 144

```
atggacatga gggtccccgc tcagctcctg gggctcctgc tactctggct ccgaggtgcc     60

agatgtgaca tccagatgac ccagtctcca tcctccctct ccgcatccgt aggcgaccgc    120

gtaaccataa catgtagagc atctcaagat atttccaact atttgaattg gtaccaacaa    180

aaacccggca aagcacctaa actcctcatt tactatacat caagactcct ctccggcgtt    240

ccatcacgat tctcaggctc cggctccggc acagatttca cactcactat ttcctccctc    300

caaccagaag attttgcaac ctattactgt caacaaggcg atacactccc atacacattc    360

ggcggcggca caaaagttga aattaaacgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600
```

```
ctgacgctga gcaaagcaga ctacgagaaa cacaaagtct acgcctgcga agtcacccat    660

cagggcctga gctcgcccgt cacaaagagc ttcaacaggg gagagtgt                 708


<210> SEQ ID NO 145
<211> LENGTH: 449
<212> TYPE: PRT
<213> ORGANISM: Artificial Sequence
<220> FEATURE:
<223> OTHER INFORMATION: Humanized antibody sequence

<400> SEQUENCE: 145

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 146
<211> LENGTH: 1347
<212> TYPE: DNA
<213> ORGANISM: Artificial Sequence
<220> FEATURE:
<223> OTHER INFORMATION: Humanized antibody sequence

<400> SEQUENCE: 146

gaggtgcagc tggtgcagag cggcgccgag gtaaaaaaac caggagcaag cgttaaagtt      60

tcttgtaaag caagcggata tacatttaca gattacaaca tgcattgggt aagacaagcg     120

ccaggacaag gattggaatg gatgggcgaa attaacccta atagtggagg agcaggctac     180

aatcaaaaat tcaaagggag agttacaatg acaacagaca caagcacttc aacagcatat     240

atggaactgc gatcacttag aagcgacgat acagctgtat actattgcgc acgacttggg     300

tatgatgata tatatgatga ctggtatttc gatgtttggg gccagggaac aacagttacc     360

gtctctagtg cctccaccaa gggcccatcg gtcttccccc tggcgccctg ctccaggagc     420

acctccgaga gcacagcggc cctgggctgc ctggtcaagg actacttccc cgaaccggtg     480

acggtgtcgt ggaactcagg cgctctgacc agcggcgtgc acaccttccc agctgtccta     540

cagtcctcag gactctactc cctcagcagc gtggtgaccg tgccctccag caacttcggc     600

acccagacct acacctgcaa cgtagatcac aagcccagca acaccaaggt ggacaagaca     660

gttgagcgca aatgttgtgt cgagtgccca ccgtgcccag caccacctgt ggcaggaccg     720

tcagtcttcc tcttcccccc aaaacccaag gacaccctca tgatctcccg gacccctgag     780

gtcacgtgcg tggtggtgga cgtgagccac gaagaccccg aggtccagtt caactggtac     840

gtggacggcg tggaggtgca taatgccaag acaaagccac gggaggagca gttcaacagc     900

acgttccgtg tggtcagcgt cctcaccgtt gtgcaccagg actggctgaa cggcaaggag     960

tacaagtgca aggtctccaa caaaggcctc ccagccccca tcgagaaaac catctccaaa    1020

accaaagggc agccccgaga accacaggtg tacaccctgc ccccatcccg ggaggagatg    1080

accaagaacc aggtcagcct gacctgcctg gtcaaaggct tctaccccag cgacatcgcc    1140

gtggagtggg agagcaatgg gcagccggag aacaactaca agaccacacc tcccatgctg    1200

gactccgacg gctccttctt cctctacagc aagctcaccg tggacaagag caggtggcag    1260

caggggaacg tcttctcatg ctccgtgatg catgaggctc tgcacaacca ctacacgcag    1320

aagagcctct ccctgtctcc gggtaaa                                        1347


<210> SEQ ID NO 147
```

```
<211> LENGTH: 468
<212> TYPE: PRT
<213> ORGANISM: Artificial Sequence
<220> FEATURE:
<223> OTHER INFORMATION: Humanized antibody sequence

<400> SEQUENCE: 147

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
    50                  55                  60

Glu Trp Met Gly Glu Ile Asn Pro Asn Ser Gly Gly Ala Gly Tyr Asn
65                  70                  75                  80

Gln Lys Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 148
<211> LENGTH: 1404
<212> TYPE: DNA
<213> ORGANISM: Mus musculus

<400> SEQUENCE: 148

```
atggactgga cctggaggat cctcttcttg gtggcagcag ccacaggagc ccactccgag     60

gtgcagctgg tgcagagcgg cgccgaggta aaaaaaccag gagcaagcgt taaagtttct    120

tgtaaagcaa gcggatatac atttacagat tacaacatgc attgggtaag acaagcgcca    180

ggacaaggat tggaatggat gggcgaaatt aaccctaata gtggaggagc aggctacaat    240

caaaaattca aagggagagt tacaatgaca acagacacaa gcacttcaac agcatatatg    300

gaactgcgat cacttagaag cgacgataca gctgtatact attgcgcacg acttgggtat    360

gatgatatat atgatgactg gtatttcgat gtttggggcc agggaacaac agttaccgtc    420

tctagtgcct ccaccaaggg cccatcggtc ttccccctgg cgccctgctc caggagcacc    480

tccgagagca cagcggccct gggctgcctg gtcaaggact acttccccga accggtgacg    540

gtgtcgtgga actcaggcgc tctgaccagc ggcgtgcaca ccttcccagc tgtcctacag    600

tcctcaggac tctactccct cagcagcgtg gtgaccgtgc cctccagcaa cttcggcacc    660

cagacctaca cctgcaacgt agatcacaag cccagcaaca ccaaggtgga caagacagtt    720

gagcgcaaat gttgtgtcga gtgcccaccg tgcccagcac cacctgtggc aggaccgtca    780

gtcttcctct tccccccaaa acccaaggac accctcatga tctcccggac ccctgaggtc    840

acgtgcgtgg tggtggacgt gagccacgaa gaccccgagg tccagttcaa ctggtacgtg    900

gacggcgtgg aggtgcataa tgccaagaca aagccacggg aggagcagtt caacagcacg    960

ttccgtgtgg tcagcgtcct caccgttgtg caccaggact ggctgaacgg caaggagtac   1020

aagtgcaagg tctccaacaa aggcctccca gcccccatcg agaaaaccat ctccaaaacc   1080

aaagggcagc cccgagaacc acaggtgtac accctgcccc catcccggga ggagatgacc   1140

aagaaccagg tcagcctgac ctgcctggtc aaaggcttct accccagcga catcgccgtg   1200

gagtgggaga gcaatgggca gccggagaac aactacaaga ccacacctcc catgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaa                                          1404
```

<210> SEQ ID NO 149
<211> LENGTH: 214
<212> TYPE: PRT

<213> ORGANISM: Mus musculus

<400> SEQUENCE: 149

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Phe Gln Gln Lys Pro Asp Gly Thr Leu Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Arg Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 150
<211> LENGTH: 645
<212> TYPE: DNA
<213> ORGANISM: Mus musculus

<400> SEQUENCE: 150

```
gatatccaga tgacacagac tacatcctcc ctgtctgcct ctctgggaga cagagtcacc     60

atcagttgca gggcaagtca ggacattagc aattatttaa actggtttca gcagaaacca    120

gatggaactc ttaaactcct gatcttctac acatcaagat tacactcagg agttccatca    180

aggttcagtg gcagtgggtc tggaacagat tattctctca ccattagcaa cctggagcaa    240

gaagatattg ccacttactt ttgccaacag ggtgatacgc ttccgtacac gttcgggggg    300

gggaccaagc tggaaataag acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 151
<211> LENGTH: 234

<212> TYPE: PRT
<213> ORGANISM: Mus musculus

<400> SEQUENCE: 151

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Phe Gln Gln Lys Pro Asp Gly Thr Leu
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Arg Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 152
<211> LENGTH: 705
<212> TYPE: DNA
<213> ORGANISM: Mus musculus

<400> SEQUENCE: 152

```
atgatgtcct ctgctcagtt ccttggtctc ctgttgctct gttttcaagg taccagatgt     60

gatatccaga tgacacagac tacatcctcc ctgtctgcct ctctgggaga cagagtcacc    120

atcagttgca gggcaagtca ggacattagc aattatttaa actggtttca gcagaaacca    180

gatggaactc ttaaactcct gatcttctac acatcaagat tacactcagg agttccatca    240

aggttcagtg gcagtgggtc tggaacagat tattctctca ccattagcaa cctggagcaa    300

gaagatattg ccacttactt ttgccaacag ggtgatacgc ttccgtacac gttcgggggg    360

gggaccaagc tggaaataag acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660
```

tcaacttcac ccattgtcaa gagcttcaac aggaatgagt gttag 705

<210> SEQ ID NO 153
<211> LENGTH: 447
<212> TYPE: PRT
<213> ORGANISM: Mus musculus

<400> SEQUENCE: 153

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Ser Leu Glu Trp Ile
        35                  40                  45

Gly Glu Ile Asn Pro Asn Ser Gly Gly Ser Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Val Tyr Asp Gly Ser Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365
```

```
Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 154
<211> LENGTH: 1344
<212> TYPE: DNA
<213> ORGANISM: Mus musculus

<400> SEQUENCE: 154

gaggtccagc tgcaacagtc tggacctgaa ctaatgaagc ctggggcttc agtgaagatg      60

tcctgcaagg cttctggata cacattcact gactacaaca tgcactgggt gaaacagaac     120

caaggaaaga gcctagagtg gataggagaa attaatccta acagtggtgg tagtggctac     180

aaccaaaagt tcaaaggcaa ggccacattg actgtagaca agtcttccag cacagcctac     240

atggagctcc gcagcctgac atctgaggac tctgcagtct attactgtgc aagattggtc     300

tacgatggca gctacgagga ctggtacttc gatgtctggg gcgcagggac cacggtcacc     360

gtctcctcag ccaaaacgac acccccatct gtctatccac tggcccctgg atctgctgcc     420

caaactaact ccatggtgac cctgggatgc ctggtcaagg gctatttccc tgagccagtg     480

acagtgacct ggaactctgg atccctgtcc agcggtgtgc acaccttccc agctgtcctg     540

cagtctgacc tctacactct gagcagctca gtgactgtcc cctccagcac ctggcccagc     600

gagaccgtca cctgcaacgt tgcccacccg gccagcagca ccaaggtgga caagaaaatt     660

gtgcccaggg attgtggttg taagccttgc atatgtacag tcccagaagt atcatctgtc     720

ttcatcttcc ccccaaagcc caaggatgtg ctcaccatta ctctgactcc taaggtcacg     780

tgtgttgtgg tagacatcag caaggatgat cccgaggtcc agttcagctg gtttgtagat     840

gatgtggagg tgcacacagc tcagacgcaa ccccgggagg agcagttcaa cagcactttc     900

cgctcagtca gtgaacttcc catcatgcac caggactggc tcaatggcaa ggagttcaaa     960

tgcagggtca acagtgcagc tttccctgcc cccatcgaga aaaccatctc caaaaccaaa    1020

ggcagaccga aggctccaca ggtgtacacc attccacctc ccaaggagca gatggccaag    1080

gataaagtca gtctgacctg catgataaca gacttcttcc ctgaagacat tactgtggag    1140

tggcagtgga atgggcagcc agcggagaac tacaagaaca ctcagcccat catggacaca    1200

gatggctctt acttcatcta cagcaagctc aatgtgcaga agagcaactg ggaggcagga    1260

aatactttca cctgctctgt gttacatgag ggcctgcaca accaccatac tgagaagagc    1320

ctctcccact ctcctggtaa atga                                           1344


<210> SEQ ID NO 155
<211> LENGTH: 466
<212> TYPE: PRT
<213> ORGANISM: Mus musculus

<400> SEQUENCE: 155

Met Gly Trp Ser Trp Thr Phe Leu Phe Leu Leu Ser Gly Thr Ala Gly
```

```
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Ser Leu
    50                  55                  60

Glu Trp Ile Gly Glu Ile Asn Pro Asn Ser Gly Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Val Tyr Asp Gly Ser Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430
```

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 156
<211> LENGTH: 1401
<212> TYPE: DNA
<213> ORGANISM: Mus musculus

<400> SEQUENCE: 156
atgggatgga gctggacctt tctcttcctc ctgtcaggaa ctgcaggtgt cctctctgag 60
gtccagctgc aacagtctgg acctgaacta atgaagcctg gggcttcagt gaagatgtcc 120
tgcaaggctt ctggatacac attcactgac tacaacatgc actgggtgaa acagaaccaa 180
ggaaagagcc tagagtggat aggagaaatt aatcctaaca gtggtggtag tggctacaac 240
caaaagttca aggcaaggc cacattgact gtagacaagt cttccagcac agcctacatg 300
gagctccgca gcctgacatc tgaggactct gcagtctatt actgtgcaag attggtctac 360
gatggcagct acgaggactg gtacttcgat gtctggggcg cagggaccac ggtcaccgtc 420
tcctcagcca aaacgacacc cccatctgtc tatccactgg cccctggatc tgctgcccaa 480
actaactcca tggtgaccct gggatgcctg gtcaagggct atttccctga gccagtgaca 540
gtgacctgga actctggatc cctgtccagc ggtgtgcaca ccttcccagc tgtcctgcag 600
tctgacctct acactctgag cagctcagtg actgtcccct ccagcacctg gcccagcgag 660
accgtcacct gcaacgttgc ccacccggcc agcagcacca aggtggacaa gaaaattgtg 720
cccagggatt gtggttgtaa gccttgcata tgtacagtcc cagaagtatc atctgtcttc 780
atcttccccc caaagcccaa ggatgtgctc accattactc tgactcctaa ggtcacgtgt 840
gttgtggtag acatcagcaa ggatgatccc gaggtccagt tcagctggtt tgtagatgat 900
gtggaggtgc acacagctca gacgcaaccc cgggaggagc agttcaacag cactttccgc 960
tcagtcagtg aacttcccat catgcaccag gactggctca atggcaagga gttcaaatgc 1020
agggtcaaca gtgcagcttt ccctgccccc atcgagaaaa ccatctccaa aaccaaaggc 1080
agaccgaagg ctccacaggt gtacaccatt ccacctccca aggagcagat ggccaaggat 1140
aaagtcagtc tgacctgcat gataacagac ttcttccctg aagacattac tgtggagtgg 1200
cagtggaatg ggcagccagc ggagaactac aagaacactc agcccatcat ggacacagat 1260
ggctcttact tcatctacag caagctcaat gtgcagaaga gcaactggga ggcaggaaat 1320
actttcacct gctctgtgtt acatgagggc ctgcacaacc accatactga gaagagcctc 1380
tcccactctc ctggtaaatg a 1401

<210> SEQ ID NO 157
<211> LENGTH: 214
<212> TYPE: PRT
<213> ORGANISM: Mus musculus

<400> SEQUENCE: 157

Asp Ile Gln Met Thr Gln Thr Thr Ser Ser Leu Ser Ala Ser Leu Gly
1               5                   10                  15

Asp Arg Val Thr Ile Cys Cys Arg Ala Ser Gln Val Ile Thr Asn Tyr
            20                  25                  30

```
Leu Tyr Trp Tyr Gln Gln Lys Pro Asp Gly Thr Phe Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 158
<211> LENGTH: 642
<212> TYPE: DNA
<213> ORGANISM: Mus musculus

<400> SEQUENCE: 158

gatatccaga tgacacagac tacatcctcc ctgtctgcct ctctgggaga cagagtcacc      60

atctgttgca gggcaagtca ggtcattacc aattatttat actggtatca gcagaaacca     120

gatggaactt ttaaactcct gatctactac acatcaagat tacactcagg agtcccatca     180

aggttcagtg gcagtgggtc tggaacagat tattctctca ccattagcaa cctggaacag     240

gaagatattg ccacttactt ttgccaacag ggtgatacgc ttccgtacac gttcggaggg     300

gggaccaagc tggaaataaa acgggctgat gctgcaccaa ctgtatccat cttcccacca     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gt                        642


<210> SEQ ID NO 159
<211> LENGTH: 234
<212> TYPE: PRT
<213> ORGANISM: Mus musculus

<400> SEQUENCE: 159

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
```

```
            20                  25                  30

Ala Ser Leu Gly Asp Arg Val Thr Ile Cys Cys Arg Ala Ser Gln Val
        35                  40                  45

Ile Thr Asn Tyr Leu Tyr Trp Tyr Gln Gln Lys Pro Asp Gly Thr Phe
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 160
<211> LENGTH: 702
<212> TYPE: DNA
<213> ORGANISM: Mus musculus

<400> SEQUENCE: 160

atgatgtcct ctgctcagtt ccttggtctc ctgttgctct gttttcaagg taccagatgt      60

gatatccaga tgacacagac tacatcctcc ctgtctgcct ctctgggaga cagagtcacc     120

atctgttgca gggcaagtca ggtcattacc aattatttat actggtatca gcagaaacca     180

gatggaactt ttaaactcct gatctactac acatcaagat tacactcagg agtcccatca     240

aggttcagtg gcagtgggtc tggaacagat tattctctca ccattagcaa cctggaacag     300

gaagatattg ccacttactt ttgccaacag ggtgatacgc ttccgtacac gttcggaggg     360

gggaccaagc tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gt                         702

<210> SEQ ID NO 161
<211> LENGTH: 447
<212> TYPE: PRT
<213> ORGANISM: Mus musculus
```

<400> SEQUENCE: 161

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Met Lys Gln Asn Gln Gly Lys Ser Leu Glu Trp Ile
        35                  40                  45

Gly Glu Ile Asn Pro Asn Ser Gly Gly Ala Gly Tyr Asn Gln Gln Phe
    50                  55                  60

Lys Gly Lys Ala Thr Leu Thr Val Asp Lys Ser Ser Arg Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Val Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415
```

```
Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 162
<211> LENGTH: 1341
<212> TYPE: DNA
<213> ORGANISM: Mus musculus

<400> SEQUENCE: 162

gaggtccagc tgcaacagtc tggacctgaa ctaatgaagc ctggggcttc agtgaagatg     60

tcctgcaagg cttctggata cacattcact gactacaaca tgcactggat gaagcagaac    120

caaggaaaga gcctagaatg gataggagaa attaatccta acagtggtgg tgctggctac    180

aaccagcagt tcaaaggcaa ggccacattg actgtagaca agtcctccag gacagcctac    240

atggagctcc gcagcctgac atctgaggac tctgcagtct attactgtgc aagattgggc    300

tacgttggta attacgagga ctggtacttc gatgtctggg gcgcagggac cacggtcacc    360

gtctcctcag ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900

cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa a                                              1341


<210> SEQ ID NO 163
<211> LENGTH: 466
<212> TYPE: PRT
<213> ORGANISM: Mus musculus

<400> SEQUENCE: 163

Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Met Lys Gln Asn Gln Gly Lys Ser Leu
```

```
    50                  55                  60

Glu Trp Ile Gly Glu Ile Asn Pro Asn Ser Gly Gly Ala Gly Tyr Asn
65                  70                  75                  80

Gln Gln Phe Lys Gly Lys Ala Thr Leu Thr Val Asp Lys Ser Ser Arg
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Val Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 164
<211> LENGTH: 1398
<212> TYPE: DNA
<213> ORGANISM: Mus musculus

<400> SEQUENCE: 164

```
atgggatgga gctggacctt tctcttcctc ctgtcaggaa ctgcaggtgt cctctctgag      60

gtccagctgc aacagtctgg acctgaacta atgaagcctg gggcttcagt gaagatgtcc     120

tgcaaggctt ctggatacac attcactgac tacaacatgc actggatgaa gcagaaccaa     180

ggaaagagcc tagaatggat aggagaaatt aatcctaaca gtggtggtgc tggctacaac     240

cagcagttca aaggcaaggc cacattgact gtagacaagt cctccaggac agcctacatg     300

gagctccgca gcctgacatc tgaggactct gcagtctatt actgtgcaag attgggctac     360

gttggtaatt acgaggactg gtacttcgat gtctggggcg cagggaccac ggtcaccgtc     420

tcctcagcca aaacgacacc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900

gtggaggtgc acacagctca gacgcaaccc cgggaggagc agttcaacag cactttccgc     960

tcagtcagtg aacttcccat catgcaccag gactggctca atggcaagga gttcaaatgc    1020

agggtcaaca gtgcagcttt ccctgccccc atcgagaaaa ccatctccaa aaccaaaggc    1080

agaccgaagg ctccacaggt gtacaccatt ccacctccca aggagcagat ggccaaggat    1140

aaagtcagtc tgacctgcat gataacagac ttcttccctg aagacattac tgtggagtgg    1200

cagtggaatg ggcagccagc ggagaactac aagaacactc agcccatcat ggacacagat    1260

ggctcttact tcatctacag caagctcaat gtgcagaaga gcaactggga ggcaggaaat    1320

actttcacct gctctgtgtt acatgagggc ctgcacaacc accatactga gaagagcctc    1380

tcccactctc ctggtaaa                                                  1398
```

<210> SEQ ID NO 165
<211> LENGTH: 214
<212> TYPE: PRT
<213> ORGANISM: Mus musculus

<400> SEQUENCE: 165

```
Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80
```

```
Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 166
<211> LENGTH: 645
<212> TYPE: DNA
<213> ORGANISM: Mus musculus

<400> SEQUENCE: 166

```
gatatccaga tgacacagac tacatcctcc ctgtctgcct ctctgggaga cagggtctcc     60

atcagttgca gggcaagtca agacattagc aattatttaa actggtatca gcagaaacca    120

gatggaactt ttaaactcct tatcttctac acatcaagat tactctcagg agtcccatca    180

aggttcagtg gcagtgggtc tggaacagat tattctctca ccatttacaa cctggagcaa    240

gaagattttg ccacttactt ttgccaacag ggagatacgc ttccgtacac tttcggaggg    300

gggaccaaac tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 167
<211> LENGTH: 234
<212> TYPE: PRT
<213> ORGANISM: Mus musculus

<400> SEQUENCE: 167

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
```

```
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 168
<211> LENGTH: 705
<212> TYPE: DNA
<213> ORGANISM: Mus musculus

<400> SEQUENCE: 168

atgatgtcct ctgctcagtt ccttggtctc ctgttgctct gttttcaagg taccagatgt      60

gatatccaga tgacacagac tacatcctcc ctgtctgcct ctctgggaga cagggtctcc     120

atcagttgca gggcaagtca agacattagc aattatttaa actggtatca gcagaaacca     180

gatggaactt ttaaactcct tatcttctac acatcaagat tactctcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaaac tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttag                     705


<210> SEQ ID NO 169
<211> LENGTH: 447
<212> TYPE: PRT
<213> ORGANISM: Mus musculus

<400> SEQUENCE: 169

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Asp Trp Ile
```

```
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445
```

<210> SEQ ID NO 170

<211> LENGTH: 1344
<212> TYPE: DNA
<213> ORGANISM: Mus musculus

<400> SEQUENCE: 170

```
gaggtccaac tgcaacagtc tggacctgaa ctaatgaagc ctggggcttc agtgaagatg     60
tcctgcaagg cttctggata tacattcact gactacaaca tgcactgggt gaagcagaac    120
caaggaaaga ccctagactg gataggagaa attaatccta acagtggtgg tgctggctac    180
aaccagaagt tcaagggcaa ggccacattg actgtagaca agtcctccac cacagcctac    240
atggagctcc gcagcctgac atctgaggac tctgcagtct attactgtgc aagattgggc    300
tacgatgata tctacgacga ctggtacttc gatgtctggg gcgcagggac cacggtcacc    360
gtctcctcag ccaaaacgac acccccatct gtctatccac tggcccctgg atctgctgcc    420
caaactaact ccatggtgac cctgggatgc ctggtcaagg gctatttccc tgagccagtg    480
acagtgacct ggaactctgg atccctgtcc agcggtgtgc acaccttccc agctgtcctg    540
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc ccaaggagca gatggccaag   1080
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga agagcaactg ggaggcagga   1260
aatactttca cctgctctgt gttacatgag ggcctgcaca accaccatac tgagaagagc   1320
ctctcccact ctcctggtaa atga                                          1344
```

<210> SEQ ID NO 171
<211> LENGTH: 466
<212> TYPE: PRT
<213> ORGANISM: Mus musculus

<400> SEQUENCE: 171

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

Asp Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
```

```
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465


<210> SEQ ID NO 172
<211> LENGTH: 1401
<212> TYPE: DNA
<213> ORGANISM: Mus musculus

<400> SEQUENCE: 172
```

```
atgggatgga gctggacctt tctcttcctc ctgtcaggaa ctgcaggtgt cctctctgag     60

gtccaactgc aacagtctgg acctgaacta atgaagcctg gggcttcagt gaagatgtcc    120

tgcaaggctt ctggatatac attcactgac tacaacatgc actgggtgaa gcagaaccaa    180

ggaaagaccc tagactggat aggagaaatt aatcctaaca gtggtggtgc tggctacaac    240

cagaagttca agggcaaggc cacattgact gtagacaagt cctccaccac agcctacatg    300

gagctccgca gcctgacatc tgaggactct gcagtctatt actgtgcaag attgggctac    360

gatgatatct acgacgactg gtacttcgat gtctggggcg cagggaccac ggtcaccgtc    420

tcctcagcca aaacgacacc cccatctgtc tatccactgg cccctggatc tgctgcccaa    480

actaactcca tggtgaccct gggatgcctg gtcaagggct atttccctga gccagtgaca    540

gtgacctgga actctggatc cctgtccagc ggtgtgcaca ccttcccagc tgtcctgcag    600

tctgacctct acactctgag cagctcagtg actgtcccct ccagcacctg gcccagcgag    660

accgtcacct gcaacgttgc ccacccggcc agcagcacca aggtggacaa gaaaattgtg    720

cccagggatt gtggttgtaa gccttgcata tgtacagtcc cagaagtatc atctgtcttc    780

atcttccccc caaagcccaa ggatgtgctc accattactc tgactcctaa ggtcacgtgt    840

gttgtggtag acatcagcaa ggatgatccc gaggtccagt tcagctggtt tgtagatgat    900

gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacagat   1260

ggctcttact tcatctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                              1401
```

<210> SEQ ID NO 173
<211> LENGTH: 214
<212> TYPE: PRT
<213> ORGANISM: Mus musculus

<400> SEQUENCE: 173

```
Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Phe Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125
```

```
Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 174
<211> LENGTH: 642
<212> TYPE: DNA
<213> ORGANISM: Mus musculus

<400> SEQUENCE: 174

gatatccaga tgacacagat tacatcctcc ctgtctgcct ctctgggaga cagggtctcc      60

atcagttgca gggcaagtca agacattagc aattatttaa attggtatca gcagaaacca     120

gatggaactt ttaaactcct tatcttctac acatcaagat tattttcagg agtcccatca     180

aggttcagtg gcagtgggtc tggaacagat tattctctca ccatttacaa cctggagcaa     240

gaagattttg ccacttactt ttgccaacag ggagatacgc ttccgtacac tttcggaggg     300

gggaccaagg tggaaataaa acgggctgat gctgcaccaa ctgtatccat cttcccacca     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gt                        642


<210> SEQ ID NO 175
<211> LENGTH: 234
<212> TYPE: PRT
<213> ORGANISM: Mus musculus

<400> SEQUENCE: 175

Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Phe Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Val Glu Ile Lys Arg
```

```
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 176
<211> LENGTH: 702
<212> TYPE: DNA
<213> ORGANISM: Mus musculus

<400> SEQUENCE: 176

atgatgtcct ctgctcagtt ccttggtctc ctgttgctct gttttcaagg taccagatgt     60

gatatccaga tgacacagat tacatcctcc ctgtctgcct ctctgggaga cagggtctcc    120

atcagttgca gggcaagtca agacattagc aattatttaa attggtatca gcagaaacca    180

gatggaactt ttaaactcct tatcttctac acatcaagat tattttcagg agtcccatca    240

aggttcagtg gcagtgggtc tggaacagat tattctctca ccatttacaa cctggagcaa    300

gaagattttg ccacttactt ttgccaacag ggagatacgc ttccgtacac tttcggaggg    360

gggaccaagg tggaaataaa acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gt                       702


<210> SEQ ID NO 177
<211> LENGTH: 450
<212> TYPE: PRT
<213> ORGANISM: Mus musculus

<400> SEQUENCE: 177

Glu Val Gln Leu Gln Gln Ser Gly Pro Glu Leu Met Lys Pro Gly Thr
1               5                   10                  15

Ser Val Lys Met Ser Cys Lys Ala Ser Gly Tyr Thr Phe Thr Asp Tyr
            20                  25                  30

Asn Met His Trp Val Lys Gln Thr Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
```

```
                85                  90                  95

Ala Lys Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Ala
        115                 120                 125

Pro Ser Val Tyr Pro Leu Ala Pro Val Cys Gly Asp Thr Thr Gly Ser
    130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Asp Val His Thr Phe
                165                 170                 175

Pro Ala Leu Leu Gln Ser Gly Leu Tyr Thr Leu Ser Ser Ser Val Thr
            180                 185                 190

Val Thr Thr Trp Pro Ser Gln Thr Ile Thr Cys Asn Val Ala His Pro
        195                 200                 205

Ala Ser Ser Thr Lys Val Asp Lys Lys Ile Glu Pro Arg Gly Ser Pro
    210                 215                 220

Thr His Lys Pro Cys Pro Pro Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Met Val Thr Cys Val Val Val Asp Val Ser Glu Asp
            260                 265                 270

Asp Pro Asp Val His Val Ser Trp Phe Val Asn Asn Val Glu Val His
        275                 280                 285

Thr Ala Gln Thr Gln Thr His Arg Glu Asp Tyr Asn Ser Thr Ile Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Ala Leu Pro Ala Pro Ile Glu
                325                 330                 335

Arg Thr Ile Ser Lys Pro Lys Gly Pro Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Ile Thr Asp Phe Met Pro Glu Asp Ile Tyr Val Glu Trp
    370                 375                 380

Thr Asn Asn Gly Gln Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 178
<211> LENGTH: 1350
<212> TYPE: DNA
<213> ORGANISM: Mus musculus

<400> SEQUENCE: 178

```
gaggtccaac tgcaacagtc tggacctgaa ctaatgaagc ctgggacttc agtgaagatg     60

tcctgcaagg cttctggata tacattcact gactacaaca tgcactgggt gaagcagacc    120

caaggaaaga ccctagagtg gataggagaa attaatccta acagtggtgg tgctggctac    180

aaccagaagt tcaagggcaa ggccacattg actgtagaca agtcctccac cacagcctac    240

atggagctcc gcagcctgac atctgaggac tctgcagtct attactgtgc aaaattgggc    300

tacgatgata tctacgacga ctggtatttc gatgtctggg gcgcagggac cacggtcacc    360

gtctcctcag ccaaaacaac agccccatcg gtctatccac tggcccctgt gtgtggagat    420

acaactggct cctcggtgac tctaggatgc ctggtcaagg gttatttccc tgagccagtg    480

accttgacct ggaactctgg atccctgtcc agtgatgtgc acaccttccc agctctcctg    540

cagtctggcc tctacaccct cagcagctca gtgactgtaa ccacctggcc cagccagacc    600

atcacctgca atgtggccca cccggcaagc agcaccaaag tggacaagaa aattgagccc    660

agagggtccc caacacataa accctgtcct ccatgcccag ctcctaacct cttgggtgga    720

ccatccgtct tcatcttccc tccaaagatc aaggatgtac tcatgatctc cctgagcccc    780

atggtcacgt gtgtggtggt ggatgtgagc gaggatgacc cagatgtcca tgtcagctgg    840

ttcgtgaaca acgtggaagt acacacagct cagacacaaa cccatagaga ggattacaac    900

agtactatcc gggtggtcag tgccctcccc atccagcacc aggactggat gagtggcaag    960

gagttcaaat gcaaggtcaa caacaaagcc ctcccagcgc ccatcgagag aaccatctca   1020

aaacccaaag ggccagtaag agctccacag gtatatgtct tgcctccacc agaagaagag   1080

atgactaaga aacaggtcac tctgacctgc atgatcacag acttcatgcc tgaagacatt   1140

tacgtggagt ggaccaacaa cgggcaaaca gagctaaact acaagaacac tgaaccagtc   1200

ctggactctg atggttctta cttcatgtac agcaagctga gagtggaaaa gaagaactgg   1260

gtggaaagaa atagctactc ctgttcagtg gtccacgagg gtctgcacaa tcaccacacg   1320

actaagagct tctcccggac tccgggtaaa                                    1350
```

<210> SEQ ID NO 179
<211> LENGTH: 469
<212> TYPE: PRT
<213> ORGANISM: Mus musculus

<400> SEQUENCE: 179

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Thr Ser Val Lys Met Ser Cys Lys Ala Ser Gly Tyr Thr Phe
        35                  40                  45

Thr Asp Tyr Asn Met His Trp Val Lys Gln Thr Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Lys Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
```

```
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Asp Val
            180                 185                 190

His Thr Phe Pro Ala Leu Leu Gln Ser Gly Leu Tyr Thr Leu Ser Ser
        195                 200                 205

Ser Val Thr Val Thr Thr Trp Pro Ser Gln Thr Ile Thr Cys Asn Val
    210                 215                 220

Ala His Pro Ala Ser Ser Thr Lys Val Asp Lys Lys Ile Glu Pro Arg
225                 230                 235                 240

Gly Ser Pro Thr His Lys Pro Cys Pro Pro Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Met Val Thr Cys Val Val Val Asp Val
        275                 280                 285

Ser Glu Asp Asp Pro Asp Val His Val Ser Trp Phe Val Asn Asn Val
    290                 295                 300

Glu Val His Thr Ala Gln Thr Gln Thr His Arg Glu Asp Tyr Asn Ser
305                 310                 315                 320

Thr Ile Arg Val Val Ser Ala Leu Pro Ile Gln His Gln Asp Trp Met
                325                 330                 335

Ser Gly Lys Glu Phe Lys Cys Lys Val Asn Asn Lys Ala Leu Pro Ala
            340                 345                 350

Pro Ile Glu Arg Thr Ile Ser Lys Pro Lys Gly Pro Val Arg Ala Pro
        355                 360                 365

Gln Val Tyr Val Leu Pro Pro Pro Glu Glu Glu Met Thr Lys Lys Gln
    370                 375                 380

Val Thr Leu Thr Cys Met Ile Thr Asp Phe Met Pro Glu Asp Ile Tyr
385                 390                 395                 400

Val Glu Trp Thr Asn Asn Gly Gln Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465


<210> SEQ ID NO 180
<211> LENGTH: 1407
<212> TYPE: DNA
<213> ORGANISM: Mus musculus

<400> SEQUENCE: 180

atgggatgga gctggacctt tctcttcctc ctgtcaggaa ctgcaggtgt cctctctgag      60

gtccaactgc aacagtctgg acctgaacta atgaagcctg ggacttcagt gaagatgtcc     120

tgcaaggctt ctggatatac attcactgac tacaacatgc actgggtgaa gcagacccaa     180
```

```
ggaaagaccc tagagtggat aggagaaatt aatcctaaca gtggtggtgc tggctacaac    240

cagaagttca agggcaaggc cacattgact gtagacaagt cctccaccac agcctacatg    300

gagctccgca gcctgacatc tgaggactct gcagtctatt actgtgcaaa attgggctac    360

gatgatatct acgacgactg gtatttcgat gtctggggcg cagggaccac ggtcaccgtc    420

tcctcagcca aaacaacagc cccatcggtc tatccactgg cccctgtgtg tggagataca    480

actggctcct cggtgactct aggatgcctg gtcaagggtt atttccctga gccagtgacc    540

ttgacctgga actctggatc cctgtccagt gatgtgcaca ccttcccagc tctcctgcag    600

tctggcctct acaccctcag cagctcagtg actgtaacca cctggcccag ccagaccatc    660

acctgcaatg tggcccaccc ggcaagcagc accaaagtgg acaagaaaat tgagcccaga    720

gggtccccaa cacataaacc ctgtcctcca tgcccagctc ctaacctctt gggtggacca    780

tccgtcttca tcttccctcc aaagatcaag gatgtactca tgatctccct gagccccatg    840

gtcacgtgtg tggtggtgga tgtgagcgag gatgacccag atgtccatgt cagctggttc    900

gtgaacaacg tggaagtaca cacagctcag acacaaaccc atagagagga ttacaacagt    960

actatccggg tggtcagtgc cctccccatc cagcaccagg actggatgag tggcaaggag   1020

ttcaaatgca aggtcaacaa caaagccctc ccagcgccca tcgagagaac catctcaaaa   1080

cccaaagggc cagtaagagc tccacaggta tatgtcttgc ctccaccaga agaagagatg   1140

actaagaaac aggtcactct gacctgcatg atcacagact tcatgcctga agacatttac   1200

gtggagtgga ccaacaacgg gcaaacagag ctaaactaca agaacactga accagtcctg   1260

gactctgatg gttcttactt catgtacagc aagctgagag tggaaaagaa gaactgggtg   1320

gaaagaaata gctactcctg ttcagtggtc cacgagggtc tgcacaatca ccacacgact   1380

aagagcttct cccggactcc gggtaaa                                       1407
```

```
<210> SEQ ID NO 181
<211> LENGTH: 214
<212> TYPE: PRT
<213> ORGANISM: Mus musculus

<400> SEQUENCE: 181

Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Leu Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

```
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 182
<211> LENGTH: 645
<212> TYPE: DNA
<213> ORGANISM: Mus musculus

<400> SEQUENCE: 182

gatatccaga tgacacagac tacatcctcc ctgtctgcct ctctgggaga cagggtctcc      60

atcagttgca gggcaagtca agacattagc aattatttaa actggtatca gcagaaacca     120

gatggaactt ttaaactcct tatcttctac acatcaagat tactctcagg agtcccatca     180

aggttcagtg gcagtgggtc tggaacagat tattctctca ccatttacaa cctggagcaa     240

gaagattttg ccacttactt ttgccaacag ggagatacgc ttccgtacac tttcggaggg     300

gggaccaaac tggaaataaa acgggctgat gctgcaccaa ctgtatccat cttcccacta     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gttag                     645


<210> SEQ ID NO 183
<211> LENGTH: 234
<212> TYPE: PRT
<213> ORGANISM: Mus musculus

<400> SEQUENCE: 183

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Leu Ser Ser Glu Gln
    130                 135                 140

Leu Thr Ser Gly Gly Ala Ser Val Val Cys Phe Leu Asn Asn Phe Tyr
```

```
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 184
<211> LENGTH: 705
<212> TYPE: DNA
<213> ORGANISM: Mus musculus

<400> SEQUENCE: 184

```
atgatgtcct ctgctcagtt ccttggtctc ctgttgctct gttttcaagg taccagatgt     60

gatatccaga tgacacagac tacatcctcc ctgtctgcct ctctgggaga cagggtctcc    120

atcagttgca gggcaagtca agacattagc aattatttaa actggtatca gcagaaacca    180

gatggaactt ttaaactcct tatcttctac acatcaagat tactctcagg agtcccatca    240

aggttcagtg gcagtgggtc tggaacagat tattctctca ccatttacaa cctggagcaa    300

gaagattttg ccacttactt ttgccaacag ggagatacgc ttccgtacac tttcggaggg    360

gggaccaaac tggaaataaa acgggctgat gctgcaccaa ctgtatccat cttcccacta    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gttag                    705
```

<210> SEQ ID NO 185
<211> LENGTH: 447
<212> TYPE: PRT
<213> ORGANISM: Mus musculus

<400> SEQUENCE: 185

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
```

```
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 186
<211> LENGTH: 1344
<212> TYPE: DNA
<213> ORGANISM: Mus musculus

<400> SEQUENCE: 186

gaggtccaac tgcaacagtc tggacctgaa ctaatgaagc ctggggcttc agtgaagatg      60

tcctgcaagg cttctggata tacattcact gactacaaca tgcactgggt gaagcagaac     120

caaggaaaga ccctagaatg gataggagaa attaatccta acagtggtgg tgctggctac     180

aaccagaagt tcaagggcaa ggccacattg actgtagaca agtcctccac cacagcctac     240

atggagctcc gcagcctgac atctgaggac tctgcagtct attactgtgc aagattgggc     300
```

```
tacgatgata tctacgacga ctggtacttc gatgtctggg gcgcagggac cacggtcacc    360

gtctcctcag ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900

cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                           1344
```

<210> SEQ ID NO 187
<211> LENGTH: 466
<212> TYPE: PRT
<213> ORGANISM: Mus musculus

<400> SEQUENCE: 187

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
```

```
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 188
<211> LENGTH: 1401
<212> TYPE: DNA
<213> ORGANISM: Mus musculus

<400> SEQUENCE: 188

```
atgggatgga gctggacctt tctcttcctc ctgtcaggaa ctgcaggtgt cctctctgag      60

gtccaactgc aacagtctgg acctgaacta atgaagcctg gggcttcagt gaagatgtcc     120

tgcaaggctt ctggatatac attcactgac tacaacatgc actgggtgaa gcagaaccaa     180

ggaaagaccc tagaatggat aggagaaatt aatcctaaca gtggtggtgc tggctacaac     240

cagaagttca agggcaaggc cacattgact gtagacaagt cctccaccac agcctacatg     300

gagctccgca gcctgacatc tgaggactct gcagtctatt actgtgcaag attgggctac     360

gatgatatct acgacgactg gtacttcgat gtctggggcg cagggaccac ggtcaccgtc     420

tcctcagcca aaacgacacc cccatctgtc tatccactgg cccctggatc tgctgcccaa     480
```

```
actaactcca tggtgaccct gggatgcctg gtcaagggct atttccctga gccagtgaca    540

gtgacctgga actctggatc cctgtccagc ggtgtgcaca ccttcccagc tgtcctgcag    600

tctgacctct acactctgag cagctcagtg actgtcccct ccagcacctg gcccagcgag    660

accgtcacct gcaacgttgc ccacccggcc agcagcacca aggtggacaa gaaaattgtg    720

cccagggatt gtggttgtaa gccttgcata tgtacagtcc cagaagtatc atctgtcttc    780

atcttccccc caaagcccaa ggatgtgctc accattactc tgactcctaa ggtcacgtgt    840

gttgtggtag acatcagcaa ggatgatccc gaggtccagt tcagctggtt tgtagatgat    900

gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacagat   1260

ggctcttact tcatctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                             1401
```

<210> SEQ ID NO 189
<211> LENGTH: 213
<212> TYPE: PRT
<213> ORGANISM: Mus musculus

<400> SEQUENCE: 189

```
Gln Ile Val Leu Ser Gln Ser Pro Ala Phe Leu Ser Val Ser Pro Gly
1               5                   10                  15

Asp Lys Val Thr Met Thr Cys Arg Ala Ser Ser Ser Ile Ser Tyr Ile
            20                  25                  30

His Trp Phe Gln Gln Lys Pro Gly Ser Ser Pro Arg Ser Trp Ile Tyr
        35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205
```

```
Asn Arg Asn Glu Cys
    210


<210> SEQ ID NO 190
<211> LENGTH: 642
<212> TYPE: DNA
<213> ORGANISM: Mus musculus

<400> SEQUENCE: 190

caaattgttc tctcccagtc tccagcattc ctgtctgtat ctccagggga taaggtcaca      60

atgacttgca gggccagctc aagtataagt tacatacact ggtttcagca gaagccagga     120

tcctccccca gatcctggat ttatgccaca tccaacctgg cttctggagt ccctggtcgc     180

ttcagtggca gtgggtctgg gacctcttac tctctcacaa tcagcagagt ggaggctgag     240

gatgctgcca cttattactg ccagcagtgg agtagtgacc cactcacgtt cggtgctggg     300

accaagctgg agctgaaacg ggctgatgct gcaccaactg tatccatctt cccaccatcc     360

agtgagcagt taacatctgg aggtgcctca gtcgtgtgct tcttgaacaa cttctacccc     420

aaagacatca atgtcaagtg gaagattgat ggcagtgaac gacaaaatgg cgtcctgaac     480

agttggactg atcaggacag caaagacagc acctacagca tgagcagcac cctcacgttg     540

accaaggacg agtatgaacg acataacagc tatacctgtg aggccactca caagacatca     600

acttcaccca ttgtcaagag cttcaacagg aatgagtgtt ag                        642


<210> SEQ ID NO 191
<211> LENGTH: 235
<212> TYPE: PRT
<213> ORGANISM: Mus musculus

<400> SEQUENCE: 191

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Phe
            20                  25                  30

Leu Ser Val Ser Pro Gly Asp Lys Val Thr Met Thr Cys Arg Ala Ser
        35                  40                  45

Ser Ser Ile Ser Tyr Ile His Trp Phe Gln Gln Lys Pro Gly Ser Ser
    50                  55                  60

Pro Arg Ser Trp Ile Tyr Ala Thr Ser Asn Leu Ala Ser Gly Val Pro
65                  70                  75                  80

Gly Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asp Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
```

```
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 192
<211> LENGTH: 708
<212> TYPE: DNA
<213> ORGANISM: Mus musculus

<400> SEQUENCE: 192

atggattttc aagtgcagat tttcagcttc ctgctaatca gtgcttcagt cataatgtcc      60

agaggacaaa ttgttctctc ccagtctcca gcattcctgt ctgtatctcc aggggataag     120

gtcacaatga cttgcagggc cagctcaagt ataagttaca tacactggtt tcagcagaag     180

ccaggatcct cccccagatc ctggatttat gccacatcca acctggcttc tggagtccct     240

ggtcgcttca gtggcagtgg gtctgggacc tcttactctc tcacaatcag cagagtggag     300

gctgaggatg ctgccactta ttactgccag cagtggagta gtgacccact cacgttcggt     360

gctgggacca agctggagct gaaacgggct gatgctgcac caactgtatc catcttccca     420

ccatccagtg agcagttaac atctggaggt gcctcagtcg tgtgcttctt gaacaacttc     480

taccccaaag acatcaatgt caagtggaag attgatggca gtgaacgaca aaatggcgtc     540

ctgaacagtt ggactgatca ggacagcaaa gacagcacct acagcatgag cagcaccctc     600

acgttgacca aggacgagta tgaacgacat aacagctata cctgtgaggc cactcacaag     660

acatcaactt cacccattgt caagagcttc aacaggaatg agtgttag                  708


<210> SEQ ID NO 193
<211> LENGTH: 445
<212> TYPE: PRT
<213> ORGANISM: Mus musculus

<400> SEQUENCE: 193

Glu Val Gln Leu Gln Gln Ser Gly Ala Asp Leu Val Gln Pro Gly Ala
1               5                   10                  15

Ser Val Lys Val Ser Cys Thr Ala Ser Gly Phe Asp Ile Lys Asp Tyr
            20                  25                  30

Tyr Ile His Trp Met Lys Gln Arg Pro Asp Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Ala Thr Phe Thr Thr Asp Thr Ser Ser Asn Thr Ala Tyr
65                  70                  75                  80

Leu Gln Leu Arg Gly Leu Thr Ser Glu Asp Thr Ala Ile Tyr Tyr Cys
                85                  90                  95

Gly Arg Glu Asp Tyr Asp Gly Thr Tyr Thr Trp Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
```

```
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 194
<211> LENGTH: 1338
<212> TYPE: DNA
<213> ORGANISM: Mus musculus

<400> SEQUENCE: 194

gaagttcagc tgcaacagtc tggggcagac cttgtgcagc caggggcctc agtcaaggtg     60

tcctgcacag cttctggctt cgacattaag gactactata tacactggat gaaacagagg    120

cctgaccagg gcctggagtg gattggaagg gttgatcctg acaatggtga gactgaattt    180

gccccgaagt tcccgggcaa ggccactttt acaacagaca catcctccaa cacagcctac    240

ctacaactca gaggcctgac atctgaggac actgccatct attactgtgg gagagaagac    300

tacgatggta cctacacctg gtttccttat tggggccaag ggactctggt cactgtctct    360

gcagccaaaa cgacaccccc atctgtctat ccactggccc ctggatctgc tgcccaaact    420

aactccatgg tgaccctggg atgcctggtc aagggctatt tccctgagcc agtgacagtg    480

acctggaact ctggatccct gtccagcggt gtgcacacct tcccagctgt cctgcagtct    540
```

```
gacctctaca ctctgagcag ctcagtgact gtcccctcca gcacctggcc cagcgagacc    600

gtcacctgca acgttgccca cccggccagc agcaccaagg tggacaagaa aattgtgccc    660

agggattgtg gttgtaagcc ttgcatatgt acagtcccag aagtatcatc tgtcttcatc    720

ttccccccaa agcccaagga tgtgctcacc attactctga ctcctaaggt cacgtgtgtt    780

gtggtagaca tcagcaagga tgatcccgag gtccagttca gctggtttgt agatgatgtg    840

gaggtgcaca cagctcagac gcaaccccgg gaggagcagt tcaacagcac tttccgctca    900

gtcagtgaac ttcccatcat gcaccaggac tggctcaatg gcaaggagtt caaatgcagg    960

gtcaacagtg cagctttccc tgcccccatc gagaaaacca tctccaaaac caaaggcaga   1020

ccgaaggctc cacaggtgta caccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200

tcttacttca tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaatga                                                1338


<210> SEQ ID NO 195
<211> LENGTH: 464
<212> TYPE: PRT
<213> ORGANISM: Mus musculus

<400> SEQUENCE: 195

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Asp Leu Val Gln
            20                  25                  30

Pro Gly Ala Ser Val Lys Val Ser Cys Thr Ala Ser Gly Phe Asp Ile
        35                  40                  45

Lys Asp Tyr Tyr Ile His Trp Met Lys Gln Arg Pro Asp Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Ala Thr Phe Thr Thr Asp Thr Ser Ser Asn
                85                  90                  95

Thr Ala Tyr Leu Gln Leu Arg Gly Leu Thr Ser Glu Asp Thr Ala Ile
            100                 105                 110

Tyr Tyr Cys Gly Arg Glu Asp Tyr Asp Gly Thr Tyr Thr Trp Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
```

```
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460
```

```
<210> SEQ ID NO 196
<211> LENGTH: 1395
<212> TYPE: DNA
<213> ORGANISM: Mus musculus

<400> SEQUENCE: 196

atgaaatgca gctgggtcat cttcttcctg atggcagtgg ttacaggggt caattcagaa     60

gttcagctgc aacagtctgg ggcagacctt gtgcagccag gggcctcagt caaggtgtcc    120

tgcacagctt ctggcttcga cattaaggac tactatatac actggatgaa acagaggcct    180

gaccagggcc tggagtggat tggaagggtt gatcctgaca atggtgagac tgaatttgcc    240

ccgaagttcc cgggcaaggc cacttttaca acagacacat cctccaacac agcctaccta    300

caactcagag gcctgacatc tgaggacact gccatctatt actgtgggag agaagactac    360

gatggtacct acacctggtt tccttattgg ggccaaggga ctctggtcac tgtctctgca    420

gccaaaacga cacccccatc tgtctatcca ctggcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840
```

```
gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcatct acagcaagct caatgtgcag aagagcaact gggaggcagg aaatactttc   1320

acctgctctg tgttacatga gggcctgcac aaccaccata ctgagaagag cctctcccac   1380

tctcctggta aatga                                                    1395
```

<210> SEQ ID NO 197
<211> LENGTH: 214
<212> TYPE: PRT
<213> ORGANISM: Mus musculus

<400> SEQUENCE: 197

```
Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Thr Leu Gln Ser Gly Val Pro Ser Arg Phe Ser Gly
    50                  55                  60

Ser Gly Ser Gly Thr Asn Tyr Ser Leu Thr Ile Thr Asn Leu Glu Gln
65                  70                  75                  80

Asp Asp Ala Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 198
<211> LENGTH: 645
<212> TYPE: DNA
<213> ORGANISM: Mus musculus

<400> SEQUENCE: 198

```
gatctccaga tgacacagac tacttcctcc ctgtctgcct ctctgggaga cagagtcacc     60

atcagttgca gggcaagtca ggacattagc aattatttaa actggtatca gcagaaacca    120

gatggaactg ttaagctcct gatcttctac acatcaacat tacagtcagg agtcccatcg    180

aggttcagtg gcagtgggtc tggaacaaat tattctctca ccattaccaa cctggagcaa    240

gatgatgctg ccacttactt ttgccaacag ggtgatacgc ttccgtacac gttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645


<210> SEQ ID NO 199
<211> LENGTH: 234
<212> TYPE: PRT
<213> ORGANISM: Mus musculus

<400> SEQUENCE: 199

Met Met Ser Ser Ala Gln Phe Leu Gly Leu Leu Leu Leu Cys Phe Gln
1               5                   10                  15

Gly Ser Arg Cys Asp Leu Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Phe Tyr Thr Ser Thr Leu Gln Ser Gly Val Pro Ser
65                  70                  75                  80

Arg Phe Ser Gly Ser Gly Ser Gly Thr Asn Tyr Ser Leu Thr Ile Thr
                85                  90                  95

Asn Leu Glu Gln Asp Asp Ala Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 200
<211> LENGTH: 705
<212> TYPE: DNA
```

<213> ORGANISM: Mus musculus

<400> SEQUENCE: 200

```
atgatgtcct ctgctcagtt ccttggtctc ctgttgctct gttttcaagg ttccagatgt     60

gatctccaga tgacacagac tacttcctcc ctgtctgcct ctctgggaga cagagtcacc    120

atcagttgca gggcaagtca ggacattagc aattatttaa actggtatca gcagaaacca    180

gatggaactg ttaagctcct gatcttctac acatcaacat tacagtcagg agtcccatcg    240

aggttcagtg gcagtgggtc tggaacaaat tattctctca ccattaccaa cctggagcaa    300

gatgatgctg ccacttactt ttgccaacag ggtgatacgc ttccgtacac gttcggaggg    360

gggaccaagc tggaaataaa acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gttag                    705
```

<210> SEQ ID NO 201
<211> LENGTH: 447
<212> TYPE: PRT
<213> ORGANISM: Mus musculus

<400> SEQUENCE: 201

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Met Lys Gln Asn Gln Gly Lys Ser Leu Glu Trp Ile
        35                  40                  45

Gly Glu Ile Asn Pro Asn Ser Gly Gly Ser Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Tyr Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
```

```
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 202
<211> LENGTH: 1344
<212> TYPE: DNA
<213> ORGANISM: Mus musculus

<400> SEQUENCE: 202

gaggtccagt tgcaacagtc tggacctgaa ctaatgaagc ctggggcttc agtgaagatg     60

tcctgcaagg cttctggata cacattcact gactacaaca tgcactggat gaagcagaac    120

caaggaaaga gcctagagtg gataggagag attaatccta acagtggtgg ttctggttac    180

aaccagaagt tcaaaggcaa ggccacattg actgtagaca agtcctccag cacagcctac    240

atggagctcc gcagcctgac atctgaggac tctgcagtct attactgtgc aagattgggc    300

tactatggta actacgagga ctggtatttc gatgtctggg gcgcagggac cacggtcacc    360

gtctcctctg ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900
```

```
cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                          1344


<210> SEQ ID NO 203
<211> LENGTH: 466
<212> TYPE: PRT
<213> ORGANISM: Mus musculus

<400> SEQUENCE: 203

Met Gly Trp Ser Trp Thr Phe Leu Phe Leu Leu Ser Gly Thr Ser Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Met Lys Gln Asn Gln Gly Lys Ser Leu
    50                  55                  60

Glu Trp Ile Gly Glu Ile Asn Pro Asn Ser Gly Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Tyr Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
```

```
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465


<210> SEQ ID NO 204
<211> LENGTH: 1401
<212> TYPE: DNA
<213> ORGANISM: Mus musculus

<400> SEQUENCE: 204

atgggatgga gctggacctt tctcttcctc ctgtcaggaa cttcgggtgt cctctctgag      60

gtccagttgc aacagtctgg acctgaacta atgaagcctg gggcttcagt gaagatgtcc     120

tgcaaggctt ctggatacac attcactgac tacaacatgc actggatgaa gcagaaccaa     180

ggaaagagcc tagagtggat aggagagatt aatcctaaca gtggtggttc tggttacaac     240

cagaagttca aggcaaggc cacattgact gtagacaagt cctccagcac agcctacatg      300

gagctccgca gcctgacatc tgaggactct gcagtctatt actgtgcaag attgggctac     360

tatggtaact acgaggactg gtatttcgat gtctggggcg cagggaccac ggtcaccgtc     420

tcctctgcca aaacgacacc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900

gtggaggtgc acacagctca gacgcaaccc cgggaggagc agttcaacag cactttccgc     960

tcagtcagtg aacttcccat catgcaccag gactggctca atggcaagga gttcaaatgc    1020

agggtcaaca gtgcagcttt ccctgccccc atcgagaaaa ccatctccaa aaccaaaggc    1080
```

```
agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacagat   1260

ggctcttact tcatctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                               1401
```

<210> SEQ ID NO 205
<211> LENGTH: 215
<212> TYPE: PRT
<213> ORGANISM: Mus musculus

<400> SEQUENCE: 205

```
Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Thr Ser Ser
            20                  25                  30

Tyr Leu Asn Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Phe Phe Pro
                85                  90                  95

Ser Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 206
<211> LENGTH: 645
<212> TYPE: DNA
<213> ORGANISM: Mus musculus

<400> SEQUENCE: 206

```
cagattgttc tcacccagtc tccagcaatc atgtctgcat ctccagggga gaaggtcacc     60

atgacctgca gggccagctc aagtgtaact tccagttact tgaactggta ccagcagaag    120

ccaggatctt cccccaaact ctggatttat agcacatcca acctggcttc aggagtccca    180

gctcgcttca gtggcagtgg gtctgggacc tcttactctc tcacaatcag cagtgtggag    240

gctgaggatg ctgccactta ttactgccag cagtatgatt ttttcccatc gacgttcggt    300
```

```
ggaggcacca agctggaaat caagcgggct gatgctgcac caactgtatc catcttccca    360

ccatccagtg agcagttaac atctggaggt gcctcagtcg tgtgcttctt gaacaacttc    420

taccccaaag acatcaatgt caagtggaag attgatggca gtgaacgaca aaatggcgtc    480

ctgaacagtt ggactgatca ggacagcaaa gacagcacct acagcatgag cagcaccctc    540

acgttgacca aggacgagta tgaacgacat aacagctata cctgtgaggc cactcacaag    600

acatcaactt cacccatcgt caagagcttc aacaggaatg agtgt                    645
```

<210> SEQ ID NO 207
<211> LENGTH: 237
<212> TYPE: PRT
<213> ORGANISM: Mus musculus

<400> SEQUENCE: 207

```
Met Asp Ser Gln Val Gln Ile Phe Ser Phe Leu Leu Ile Ser Ala Leu
1               5                   10                  15

Val Lys Met Ser Arg Gly Gln Ile Val Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Thr Ser Ser Tyr Leu Asn Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Asp Phe Phe Pro Ser Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

<210> SEQ ID NO 208
<211> LENGTH: 711
<212> TYPE: DNA
<213> ORGANISM: Mus musculus

<400> SEQUENCE: 208

```
atggattctc aagtgcagat tttcagcttc cttctaatca gtgccttagt caaaatgtcc     60

agaggacaga ttgttctcac ccagtctcca gcaatcatgt ctgcatctcc aggggagaag    120

gtcaccatga cctgcagggc cagctcaagt gtaacttcca gttacttgaa ctggtaccag    180
```

```
cagaagccag gatcttcccc caaactctgg atttatagca catccaacct ggcttcagga    240

gtcccagctc gcttcagtgg cagtgggtct gggacctctt actctctcac aatcagcagt    300

gtggaggctg aggatgctgc cacttattac tgccagcagt atgatttttt cccatcgacg    360

ttcggtggag gcaccaagct ggaaatcaag cgggctgatg ctgcaccaac tgtatccatc    420

ttcccaccat ccagtgagca gttaacatct ggaggtgcct cagtcgtgtg cttcttgaac    480

aacttctacc ccaaagacat caatgtcaag tggaagattg atggcagtga acgacaaaat    540

ggcgtcctga acagttggac tgatcaggac agcaaagaca gcacctacag catgagcagc    600

accctcacgt tgaccaagga cgagtatgaa cgacataaca gctatacctg tgaggccact    660

cacaagacat caacttcacc catcgtcaag agcttcaaca ggaatgagtg t             711
```

```
<210> SEQ ID NO 209
<211> LENGTH: 445
<212> TYPE: PRT
<213> ORGANISM: Mus musculus

<400> SEQUENCE: 209

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Glu Ser Leu Glu Trp Ile
        35                  40                  45

Gly Asp Ile Asn Pro Tyr Asn Asp Asp Thr Thr Tyr Asn His Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
```

```
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 210
<211> LENGTH: 1335
<212> TYPE: DNA
<213> ORGANISM: Mus musculus

<400> SEQUENCE: 210

gaggtccagc tgcaacaatc tggacctgag ctggtgaagc ctggggcttc agtgaagatg     60

tcctgtaagg cttctggata cacattcact gactactaca tgaactgggt gaagcagagc    120

catggagaga gccttgagtg gattggagat attaatcctt acaacgatga tactacctac    180

aaccacaagt tcaagggcaa ggccacattg actgtagaca aatcctccaa cacagcctac    240

atgcagctca acagcctgac atctgaggac tctgcagtct attactgtgc aagagagacg    300

gccgttatta ctacgaatgc tatggactac tggggtcaag gaacctcagt caccgtctcc    360

tcagccaaaa cgacaccccc atctgtctat ccactggccc ctggatctgc tgcccaaact    420

aactccatgg tgaccctggg atgcctggtc aagggctatt tccctgagcc agtgacagtg    480

acctggaact ctggatccct gtccagcggt gtgcacacct tcccagctgt cctgcagtct    540

gacctctaca ctctgagcag ctcagtgact gtcccctcca gcacctggcc cagcgagacc    600

gtcacctgca acgttgccca cccggccagc agcaccaagg tggacaagaa aattgtgccc    660

agggattgtg gttgtaagcc ttgcatatgt acagtcccag aagtatcatc tgtcttcatc    720

ttccccccaa agcccaagga tgtgctcacc attactctga ctcctaaggt cacgtgtgtt    780

gtggtagaca tcagcaagga tgatcccgag gtccagttca gctggtttgt agatgatgtg    840

gaggtgcaca cagctcagac gcaaccccgg gaggagcagt tcaacagcac tttccgctca    900

gtcagtgaac ttcccatcat gcaccaggac tggctcaatg gcaaggagtt caaatgcagg    960

gtcaacagtg cagctttccc tgcccccatc gagaaaacca tctccaaaac caaaggcaga   1020

ccgaaggctc cacaggtgta caccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200
```

```
tcttacttca tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaa                                                    1335


<210> SEQ ID NO 211
<211> LENGTH: 464
<212> TYPE: PRT
<213> ORGANISM: Mus musculus

<400> SEQUENCE: 211

Met Gly Trp Asn Trp Ile Phe Leu Phe Leu Leu Ser Gly Thr Ala Gly
1               5                   10                  15

Val Tyr Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Glu Ser Leu
    50                  55                  60

Glu Trp Ile Gly Asp Ile Asn Pro Tyr Asn Asp Asp Thr Thr Tyr Asn
65                  70                  75                  80

His Lys Phe Lys Gly Lys Ala Thr Leu Thr Val Asp Lys Ser Ser Asn
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
```

```
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 212
<211> LENGTH: 1392
<212> TYPE: DNA
<213> ORGANISM: Mus musculus

<400> SEQUENCE: 212

atgggatgga actggatctt tctcttcctc ttgtcaggaa ctgcaggtgt ctactctgag      60

gtccagctgc aacaatctgg acctgagctg gtgaagcctg gggcttcagt gaagatgtcc     120

tgtaaggctt ctggatacac attcactgac tactacatga actgggtgaa gcagagccat     180

ggagagagcc ttgagtggat tggagatatt aatccttaca acgatgatac tacctacaac     240

cacaagttca agggcaaggc cacattgact gtagacaaat cctccaacac agcctacatg     300

cagctcaaca gcctgacatc tgaggactct gcagtctatt actgtgcaag agagacggcc     360

gttattacta cgaatgctat ggactactgg ggtcaaggaa cctcagtcac cgtctcctca     420

gccaaaacga cacccccatc tgtctatcca ctggcccctg gatctgctgc ccaaactaac     480

tccatggtga ccctgggatg cctggtcaag ggctatttcc ctgagccagt gacagtgacc     540

tggaactctg gatccctgtc cagcggtgtg cacaccttcc cagctgtcct gcagtctgac     600

ctctacactc tgagcagctc agtgactgtc ccctccagca cctggcccag cgagaccgtc     660

acctgcaacg ttgcccaccc ggccagcagc accaaggtgg acaagaaaat tgtgcccagg     720

gattgtggtt gtaagccttg catatgtaca gtcccagaag tatcatctgt cttcatcttc     780

cccccaaagc ccaaggatgt gctcaccatt actctgactc ctaaggtcac gtgtgttgtg     840

gtagacatca gcaaggatga tcccgaggtc cagttcagct ggtttgtaga tgatgtggag     900

gtgcacacag ctcagacgca accccgggag gagcagttca acagcacttt ccgctcagtc     960

agtgaacttc ccatcatgca ccaggactgg ctcaatggca aggagttcaa atgcagggtc    1020

aacagtgcag ctttccctgc ccccatcgag aaaaccatct ccaaaaccaa aggcagaccg    1080

aaggctccac aggtgtacac cattccacct cccaaggagc agatggccaa ggataaagtc    1140

agtctgacct gcatgataac agacttcttc cctgaagaca ttactgtgga gtggcagtgg    1200

aatgggcagc cagcggagaa ctacaagaac actcagccca tcatggacac agatggctct    1260

tacttcatct acagcaagct caatgtgcag aagagcaact gggaggcagg aaatactttc    1320

acctgctctg tgttacatga gggcctgcac aaccaccata ctgagaagag cctctcccac    1380

tctcctggta aa                                                        1392
```

<210> SEQ ID NO 213
<211> LENGTH: 215
<212> TYPE: PRT
<213> ORGANISM: Artificial Sequence
<220> FEATURE:
<223> OTHER INFORMATION: Humanized antibody sequence

<400> SEQUENCE: 213

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 214
<211> LENGTH: 645
<212> TYPE: DNA
<213> ORGANISM: Artificial Sequence
<220> FEATURE:
<223> OTHER INFORMATION: Humanized antibody sequence

<400> SEQUENCE: 214

```
gacatccagc tgacccagag ccccagcttc ctttccgcat ccgttggtga ccgagtaaca     60

atcacatgcc gcgcctcatc ttcagttaca tcttcttatc ttaattggta tcaacaaaaa    120

ccaggaaaag cacctaaact tcttatatac tctacatcta atctcgcatc aggagttccc    180

tctcgatttt caggatctgg atcaggcaca gaatttacac ttactatatc atcactccaa    240

ccagaagact tcgccactta ttactgccaa caatacgatt tttttccaag cacattcgga    300

ggaggtacaa aagtagaaat caagcgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540
```

```
acgctgagca aagcagacta cgagaaacac aaagtctacg cctgcgaagt cacccatcag    600

ggcctgagct cgcccgtcac aaagagcttc aacaggggag agtgt                    645


<210> SEQ ID NO 215
<211> LENGTH: 237
<212> TYPE: PRT
<213> ORGANISM: Artificial Sequence
<220> FEATURE:
<223> OTHER INFORMATION: Humanized antibody sequence

<400> SEQUENCE: 215

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Val Thr Ser Ser Tyr Leu Asn Trp Tyr Gln Gln Lys Pro Gly
    50                  55                  60

Lys Ala Pro Lys Leu Leu Ile Tyr Ser Thr Ser Asn Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Tyr Asp Phe Phe Pro Ser Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 216
<211> LENGTH: 711
<212> TYPE: DNA
<213> ORGANISM: Artificial Sequence
<220> FEATURE:
<223> OTHER INFORMATION: Humanized antibody sequence

<400> SEQUENCE: 216

atggacatga gggtccccgc tcagctcctg gggctcctgc tactctggct cccaggtgcc     60

agatgtgaca tccagctgac ccagagcccc agcttccttt ccgcatccgt tggtgaccga    120

gtaacaatca catgccgcgc ctcatcttca gttacatctt cttatcttaa ttggtatcaa    180

caaaaaccag gaaaagcacc taaacttctt atatactcta catctaatct cgcatcagga    240

gttccctctc gattttcagg atctggatca ggcacagaat ttacacttac tatatcatca    300
```

```
ctccaaccag aagacttcgc cacttattac tgccaacaat acgatttttt tccaagcaca    360

ttcggaggag gtacaaaagt agaaatcaag cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg t             711
```

```
<210> SEQ ID NO 217
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 217

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 218
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 218

gaggtgcagc tggtgcagag cggcgccgag gtcaagaaac ctggagcaag cgtaaaggtt     60

agttgcaaag catctggata cacatttacc gactactaca tgaattgggt acgacaagcc    120

cctggacaaa gacttgaatg gatgggagac attaaccctt ataacgacga cactacatac    180

aatcataaat ttaaaggaag agttacaatt acaagagata catccgcatc aaccgcctat    240

atggaacttt cctcattgag atctgaagac actgctgttt attactgtgc aagagaaact    300

gccgttatta ctactaacgc tatggattac tggggtcaag gaaccactgt taccgtctct    360

agtgcctcca ccaagggccc atcggtcttc cccctggcgc cctgctccag gagcacctcc    420

gagagcacag cggccctggg ctgcctggtc aaggactact tccccgaacc ggtgacggtg    480

tcgtggaact caggcgctct gaccagcggc gtgcacacct tcccagctgt cctacagtcc    540

tcaggactct actccctcag cagcgtggtg accgtgccct ccagcaactt cggcacccag    600

acctacacct gcaacgtaga tcacaagccc agcaacacca aggtggacaa gacagttgag    660

cgcaaatgtt gtgtcgagtg cccaccgtgc ccagcaccac ctgtggcagg accgtcagtc    720

ttcctcttcc ccccaaaacc caaggacacc ctcatgatct cccggacccc tgaggtcacg    780

tgcgtggtgg tggacgtgag ccacgaagac cccgaggtcc agttcaactg gtacgtggac    840

ggcgtggagg tgcataatgc caagacaaag ccacgggagg agcagttcaa cagcacgttc    900

cgtgtggtca gcgtcctcac cgttgtgcac caggactggc tgaacggcaa ggagtacaag    960

tgcaaggtct ccaacaaagg cctcccagcc cccatcgaga aaaccatctc caaaaccaaa   1020

gggcagcccc gagaaccaca ggtgtacacc ctgcccccat cccgggagga gatgaccaag   1080

aaccaggtca gcctgacctg cctggtcaaa ggcttctacc ccagcgacat cgccgtggag   1140

tgggagagca atgggcagcc ggagaacaac tacaagacca cacctcccat gctggactcc   1200
```

```
gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                              1341


<210> SEQ ID NO 219
<211> LENGTH: 466
<212> TYPE: PRT
<213> ORGANISM: Artificial Sequence
<220> FEATURE:
<223> OTHER INFORMATION: Humanized antibody sequence

<400> SEQUENCE: 219

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Met Asn Trp Val Arg Gln Ala Pro Gly Gln Arg Leu
    50                  55                  60

Glu Trp Met Gly Asp Ile Asn Pro Tyr Asn Asp Asp Thr Thr Tyr Asn
65                  70                  75                  80

His Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335
```

```
Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 220
<211> LENGTH: 1398
<212> TYPE: DNA
<213> ORGANISM: Artificial Sequence
<220> FEATURE:
<223> OTHER INFORMATION: Humanized antibody sequence

<400> SEQUENCE: 220

```
atggactgga cctggaggat cctcttcttg gtggcagcag ccacaggagc ccactccgag     60
gtgcagctgg tgcagagcgg cgccgaggtc aagaaacctg gagcaagcgt aaaggttagt    120
tgcaaagcat ctggatacac atttaccgac tactacatga attgggtacg acaagcccct    180
ggacaaagac ttgaatggat gggagacatt aacccttata acgacgacac tacatacaat    240
cataaattta aggaagagt tacaattaca agagatacat ccgcatcaac cgcctatatg    300
gaactttcct cattgagatc tgaagacact gctgtttatt actgtgcaag agaaactgcc    360
gttattacta ctaacgctat ggattactgg ggtcaaggaa ccactgttac cgtctctagt    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
```

```
ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaa                                                 1398


<210> SEQ ID NO 221
<211> LENGTH: 215
<212> TYPE: PRT
<213> ORGANISM: Artificial Sequence
<220> FEATURE:
<223> OTHER INFORMATION: Humanized antibody sequence

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 222
<211> LENGTH: 645
<212> TYPE: DNA
<213> ORGANISM: Artificial Sequence
<220> FEATURE:
<223> OTHER INFORMATION: Humanized antibody sequence

<400> SEQUENCE: 222

gacatccaga tgacccagtc tccatcctcc ctctcagcat ccgtaggcga tagagttaca     60

ataacatgca gcgtatcatc aactatatca tcaaatcatc ttcattggtt ccaacagaaa    120

cccggcaaag cacctaaatc acttatatac ggcacatcaa atctcgcatc aggcgttcct    180

tcaagatttt caggctctgg ctcaggcacc gactttactc ttacaatatc ctccctccaa    240

cccgaagact tcgcaaccta ttactgtcaa caatggtcct catatccact cacatttggc    300
```

```
ggcggcacaa aagtagaaat taaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 223
<211> LENGTH: 237
<212> TYPE: PRT
<213> ORGANISM: Artificial Sequence
<220> FEATURE:
<223> OTHER INFORMATION: Humanized antibody sequence

<400> SEQUENCE: 223

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Ser Val Ser
        35                  40                  45

Ser Thr Ile Ser Ser Asn His Leu His Trp Phe Gln Gln Lys Pro Gly
    50                  55                  60

Lys Ala Pro Lys Ser Leu Ile Tyr Gly Thr Ser Asn Leu Ala Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Trp Ser Ser Tyr Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 224
<211> LENGTH: 711
<212> TYPE: DNA
<213> ORGANISM: Artificial Sequence
<220> FEATURE:
<223> OTHER INFORMATION: Humanized antibody sequence

<400> SEQUENCE: 224

```
atggacatga gggtccccgc tcagctcctg gggctcctgc tactctggct ccgaggtgcc     60
```

```
agatgtgaca tccagatgac ccagtctcca tcctccctct cagcatccgt aggcgataga    120

gttacaataa catgcagcgt atcatcaact atatcatcaa atcatcttca ttggttccaa    180

cagaaacccg gcaaagcacc taaatcactt atatacggca catcaaatct cgcatcaggc    240

gttccttcaa gattttcagg ctctggctca ggcaccgact ttactcttac aatatcctcc    300

ctccaacccg aagacttcgc aacctattac tgtcaacaat ggtcctcata tccactcaca    360

tttggcggcg gcacaaaagt agaaattaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg t             711
```

```
<210> SEQ ID NO 225
<211> LENGTH: 451
<212> TYPE: PRT
<213> ORGANISM: Artificial Sequence
<220> FEATURE:
<223> OTHER INFORMATION: Humanized antibody sequence

<400> SEQUENCE: 225

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 226
<211> LENGTH: 1353
<212> TYPE: DNA
<213> ORGANISM: Artificial Sequence
<220> FEATURE:
<223> OTHER INFORMATION: Humanized antibody sequence

<400> SEQUENCE: 226

```
gaggtgcagc tggtgcagtc tggggctgag gtgaagaagc ctggggcctc agtgaaggtc      60

tcctgcaagg cttctgactt caacattaaa gacttctatc tacactgggt gcgacaggcc     120

cctggacaag ggcttgagtg gattggaagg attgatcctg agaatggtga tactttatat     180

gacccgaagt tccaggacaa ggtcaccatg accacagaca cgtccaccag cacagcctac     240

atggagctga ggagcctgag atctgacgac acggccgtgt attactgtgc gagagaggcg     300

gattatttcc acgatggtac ctcctactgg tacttcgatg tctggggccg tggcaccctg     360

gtcaccgtct ctagtgcctc caccaagggc ccatcggtct tccccctggc gccctgctcc     420

aggagcacct ccgagagcac agcggccctg ggctgcctgg tcaaggacta cttccccgaa     480

ccggtgacgg tgtcgtggaa ctcaggcgct ctgaccagcg gcgtgcacac cttcccagct     540

gtcctacagt cctcaggact ctactccctc agcagcgtgg tgaccgtgcc ctccagcaac     600

ttcggcaccc agacctacac ctgcaacgta gatcacaagc ccagcaacac caaggtggac     660

aagacagttg agcgcaaatg ttgtgtcgag tgcccaccgt gcccagcacc acctgtggca     720

ggaccgtcag tcttcctctt ccccccaaaa cccaaggaca ccctcatgat ctcccggacc     780

cctgaggtca cgtgcgtggt ggtggacgtg agccacgaag accccgaggt ccagttcaac     840

tggtacgtgg acggcgtgga ggtgcataat gccaagacaa agccacggga ggagcagttc     900
```

```
aacagcacgt tccgtgtggt cagcgtcctc accgttgtgc accaggactg gctgaacggc    960

aaggagtaca agtgcaaggt ctccaacaaa ggcctcccag cccccatcga gaaaaccatc   1020

tccaaaacca aagggcagcc ccgagaacca caggtgtaca ccctgccccc atcccgggag   1080

gagatgacca agaaccaggt cagcctgacc tgcctggtca aaggcttcta ccccagcgac   1140

atcgccgtgg agtgggagag caatgggcag ccggagaaca actacaagac cacacctccc   1200

atgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

```
<210> SEQ ID NO 227
<211> LENGTH: 470
<212> TYPE: PRT
<213> ORGANISM: Artificial Sequence
<220> FEATURE:
<223> OTHER INFORMATION: Humanized antibody sequence

<400> SEQUENCE: 227

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Asp Phe Asn Ile
        35                  40                  45

Lys Asp Phe Tyr Leu His Trp Val Arg Gln Ala Pro Gly Gln Gly Leu
    50                  55                  60

Glu Trp Ile Gly Arg Ile Asp Pro Glu Asn Gly Asp Thr Leu Tyr Asp
65                  70                  75                  80

Pro Lys Phe Gln Asp Lys Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ala Asp Tyr Phe His Asp Gly Thr Ser Tyr
        115                 120                 125

Trp Tyr Phe Asp Val Trp Gly Arg Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 228
<211> LENGTH: 1410
<212> TYPE: DNA
<213> ORGANISM: Artificial Sequence
<220> FEATURE:
<223> OTHER INFORMATION: Humanized antibody sequence

<400> SEQUENCE: 228

atggactgga cctggaggat cctcttcttg gtggcagcag ccacaggagc ccactccgag      60

gtgcagctgg tgcagtctgg ggctgaggtg aagaagcctg gggcctcagt gaaggtctcc     120

tgcaaggctt ctgacttcaa cattaaagac ttctatctac actgggtgcg acaggcccct     180

ggacaagggc ttgagtggat tggaaggatt gatcctgaga atggtgatac tttatatgac     240

ccgaagttcc aggacaaggt caccatgacc acagacacgt ccaccagcac agcctacatg     300

gagctgagga gcctgagatc tgacgacacg gccgtgtatt actgtgcgag agaggcggat     360

tatttccacg atggtacctc ctactggtac ttcgatgtct ggggccgtgg caccctggtc     420

accgtctcta gtgcctccac caagggccca tcggtcttcc ccctggcgcc ctgctccagg     480

agcacctccg agagcacagc ggccctgggc tgcctggtca aggactactt ccccgaaccg     540

gtgacggtgt cgtggaactc aggcgctctg accagcggcg tgcacacctt cccagctgtc     600

ctacagtcct caggactcta ctccctcagc agcgtggtga ccgtgccctc cagcaacttc     660

ggcacccaga cctacacctg caacgtagat cacaagccca gcaacaccaa ggtggacaag     720

acagttgagc gcaaatgttg tgtcgagtgc ccaccgtgcc cagcaccacc tgtggcagga     780

ccgtcagtct tcctcttccc cccaaaaccc aaggacaccc tcatgatctc ccggacccct     840

gaggtcacgt gcgtggtggt ggacgtgagc cacgaagacc ccgaggtcca gttcaactgg     900

tacgtggacg gcgtggaggt gcataatgcc aagacaaagc cacgggagga gcagttcaac     960
```

```
agcacgttcc gtgtggtcag cgtcctcacc gttgtgcacc aggactggct gaacggcaag   1020

gagtacaagt gcaaggtctc caacaaaggc ctcccagccc ccatcgagaa aaccatctcc   1080

aaaaccaaag ggcagccccg agaaccacag gtgtacaccc tgcccccatc ccgggaggag   1140

atgaccaaga accaggtcag cctgacctgc ctggtcaaag gcttctaccc cagcgacatc   1200

gccgtggagt gggagagcaa tgggcagccg gagaacaact acaagaccac acctcccatg   1260

ctggactccg acggctcctt cttcctctac agcaagctca ccgtggacaa gagcaggtgg   1320

cagcagggga acgtcttctc atgctccgtg atgcatgagg ctctgcacaa ccactacacg   1380

cagaagagcc tctccctgtc tccgggtaaa                                    1410
```

<210> SEQ ID NO 229
<211> LENGTH: 213
<212> TYPE: PRT
<213> ORGANISM: Artificial Sequence
<220> FEATURE:
<223> OTHER INFORMATION: Humanized antibody sequence

<400> SEQUENCE: 229

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 230
<211> LENGTH: 639
<212> TYPE: DNA
<213> ORGANISM: Artificial Sequence
<220> FEATURE:
<223> OTHER INFORMATION: Humanized antibody sequence

<400> SEQUENCE: 230

```
gacatccagt tgacccagtc tccatccttc ctgtctgcat ctgtaggaga cagagtcacc     60

atcacttgca gggccagctc aagtataagt tacatacact ggtatcagca aaaaccaggg    120

aaagccccta agctcctgat ctatgccaca tccaacctgg cttctggggt cccatcaagg    180

ttcagcggca gtggatctgg gacagaattc actctcacaa tcagcagcct gcagcctgaa    240

gattttgcaa cttattactg tcagcagtgg agtagtgacc cactcacgtt cggcggaggg    300

accaaggtgg agatcaaacg tacggtggct gcaccatctg tcttcatctt cccgccatct    360

gatgagcagt tgaaatctgg aactgcctct gttgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaagtc tacgcctgcg aagtcaccca tcagggcctg    600

agctcgcccg tcacaaagag cttcaacagg ggagagtgt                           639


<210> SEQ ID NO 231
<211> LENGTH: 235
<212> TYPE: PRT
<213> ORGANISM: Artificial Sequence
<220> FEATURE:
<223> OTHER INFORMATION: Humanized antibody sequence

<400> SEQUENCE: 231

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Ile Ser Tyr Ile His Trp Tyr Gln Gln Lys Pro Gly Lys Ala
    50                  55                  60

Pro Lys Leu Leu Ile Tyr Ala Thr Ser Asn Leu Ala Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Trp
            100                 105                 110

Ser Ser Asp Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 232
```

<211> LENGTH: 705
<212> TYPE: DNA
<213> ORGANISM: Artificial Sequence
<220> FEATURE:
<223> OTHER INFORMATION: Humanized antibody sequence

<400> SEQUENCE: 232

```
atggacatga gggtccccgc tcagctcctg gggctcctgc tgctctggct cccaggtgcc     60

agatgtgaca tccagttgac ccagtctcca tccttcctgt ctgcatctgt aggagacaga    120

gtcaccatca cttgcagggc cagctcaagt ataagttaca tacactggta tcagcaaaaa    180

ccagggaaag cccctaagct cctgatctat gccacatcca acctggcttc tggggtccca    240

tcaaggttca gcggcagtgg atctgggaca gaattcactc tcacaatcag cagcctgcag    300

cctgaagatt ttgcaactta ttactgtcag cagtggagta gtgacccact cacgttcggc    360

ggagggacca aggtggagat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705
```

<210> SEQ ID NO 233
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 233

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
```

```
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

```
<210> SEQ ID NO 234
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 234

gaggtgcagc tggtgcagtc tggggctgag gtgaagaagc ctggggcctc agtgaaggtc     60

tcctgcaagg cttctggatt cgacattaag gactactata tacactgggt gcgacaggcc    120

cctggacaag ggcttgagtg gatcggaagg gttgatcctg acaatggtga gactgaattt    180

gccccgaagt tcccgggcaa ggtcaccatg accacagaca cgtccatcag cacagcctac    240

atggagctga gcaggctgag atctgacgac acggccgtgt attactgtgc gagagaagac    300

tacgatggta cctacacctg gtttccttat tggggccaag gactctggt caccgtctct     360

agtgcctcca ccaagggccc atcggtcttc cccctggcgc cctgctccag gagcacctcc    420

gagagcacag cggccctggg ctgcctggtc aaggactact tccccgaacc ggtgacggtg    480

tcgtggaact caggcgctct gaccagcggc gtgcacacct tcccagctgt cctacagtcc    540

tcaggactct actccctcag cagcgtggtg accgtgccct ccagcaactt cggcacccag    600

acctacacct gcaacgtaga tcacaagccc agcaacacca aggtggacaa gacagttgag    660
```

```
cgcaaatgtt gtgtcgagtg cccaccgtgc ccagcaccac ctgtggcagg accgtcagtc    720

ttcctcttcc ccccaaaacc caaggacacc ctcatgatct cccggacccc tgaggtcacg    780

tgcgtggtgg tggacgtgag ccacgaagac cccgaggtcc agttcaactg gtacgtggac    840

ggcgtggagg tgcataatgc caagacaaag ccacgggagg agcagttcaa cagcacgttc    900

cgtgtggtca gcgtcctcac cgttgtgcac caggactggc tgaacggcaa ggagtacaag    960

tgcaaggtct ccaacaaagg cctcccagcc cccatcgaga aaaccatctc caaaaccaaa   1020

gggcagcccc gagaaccaca ggtgtacacc ctgcccccat cccgggagga gatgaccaag   1080

aaccaggtca gcctgacctg cctggtcaaa ggcttctacc ccagcgacat cgccgtggag   1140

tgggagagca atgggcagcc ggagaacaac tacaagacca cacctcccat gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                              1341
```

<210> SEQ ID NO 235
<211> LENGTH: 466
<212> TYPE: PRT
<213> ORGANISM: Artificial Sequence
<220> FEATURE:
<223> OTHER INFORMATION: Humanized antibody sequence

<400> SEQUENCE: 235

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asp Ile
        35                  40                  45

Lys Asp Tyr Tyr Ile His Trp Val Arg Gln Ala Pro Gly Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Val Thr Met Thr Thr Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Glu Asp Tyr Asp Gly Thr Tyr Thr Trp Phe Pro
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240
```

```
Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 236
<211> LENGTH: 1398
<212> TYPE: DNA
<213> ORGANISM: Artificial Sequence
<220> FEATURE:
<223> OTHER INFORMATION: Humanized antibody sequence

<400> SEQUENCE: 236

atggactgga cctggaggat cctcttcttg gtggcagcag ccacaggagc ccactccgag     60

gtgcagctgg tgcagtctgg ggctgaggtg aagaagcctg gggcctcagt gaaggtctcc    120

tgcaaggctt ctggattcga cattaaggac tactatatac actgggtgcg acaggcccct    180

ggacaagggc ttgagtggat cggaagggtt gatcctgaca atggtgagac tgaatttgcc    240

ccgaagttcc cgggcaaggt caccatgacc acagacacgt ccatcagcac agcctacatg    300

gagctgagca ggctgagatc tgacgacacg gccgtgtatt actgtgcgag agaagactac    360

gatggtacct acacctggtt tccttattgg ggccaaggga ctctggtcac cgtctctagt    420

gcctccacca agggcccatc ggtcttcccc ctggcgccct gctccaggag cacctccgag    480

agcacagcgg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720
```

-continued

```
aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080

cagccccgag aaccacaggt gtacaccctg cccccatccc gggaggagat gaccaagaac   1140

caggtcagcc tgacctgcct ggtcaaaggc ttctacccca gcgacatcgc cgtggagtgg   1200

gagagcaatg ggcagccgga gaacaactac aagaccacac ctcccatgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaa                                                 1398
```

<210> SEQ ID NO 237
<211> LENGTH: 7
<212> TYPE: PRT
<213> ORGANISM: Mus musculus

<400> SEQUENCE: 237

```
Gly Thr Ser Asn Leu Ala Ser
1               5
```

<210> SEQ ID NO 238
<211> LENGTH: 8
<212> TYPE: PRT
<213> ORGANISM: Mus musculus

<400> SEQUENCE: 238

```
Gln Gln Trp Thr Thr Thr Tyr Thr
1               5
```

<210> SEQ ID NO 239
<211> LENGTH: 11
<212> TYPE: PRT
<213> ORGANISM: Mus musculus

<400> SEQUENCE: 239

```
Arg Ala Ser Gln Asp Ile Ser Ser Tyr Leu Asn
1               5                   10
```

<210> SEQ ID NO 240
<211> LENGTH: 7
<212> TYPE: PRT
<213> ORGANISM: Mus musculus

<400> SEQUENCE: 240

```
Ser Thr Ser Arg Leu Asn Ser
1               5
```

<210> SEQ ID NO 241
<211> LENGTH: 8
<212> TYPE: PRT
<213> ORGANISM: Mus musculus

<400> SEQUENCE: 241

```
Gln Gln Asp Ile Lys His Pro Thr
1               5
```

<210> SEQ ID NO 242
<211> LENGTH: 11
<212> TYPE: PRT
<213> ORGANISM: Mus musculus

<400> SEQUENCE: 242

Lys Ala Ser Gln Asp Val Phe Thr Ala Val Ala
1 5 10

<210> SEQ ID NO 243
<211> LENGTH: 7
<212> TYPE: PRT
<213> ORGANISM: Mus musculus

<400> SEQUENCE: 243

Trp Ala Ser Thr Arg His Thr
1 5

<210> SEQ ID NO 244
<211> LENGTH: 9
<212> TYPE: PRT
<213> ORGANISM: Mus musculus

<400> SEQUENCE: 244

Gln Gln Tyr Ser Ser Tyr Pro Leu Thr
1 5

<210> SEQ ID NO 245
<211> LENGTH: 5
<212> TYPE: PRT
<213> ORGANISM: Mus musculus

<400> SEQUENCE: 245

Asp Tyr Asn Met His
1 5

<210> SEQ ID NO 246
<211> LENGTH: 17
<212> TYPE: PRT
<213> ORGANISM: Mus musculus

<400> SEQUENCE: 246

Glu Ile Asn Pro Asn Ser Gly Gly Ala Gly Tyr Asn Gln Lys Phe Lys
1 5 10 15

Gly

<210> SEQ ID NO 247
<211> LENGTH: 14
<212> TYPE: PRT
<213> ORGANISM: Mus musculus

<400> SEQUENCE: 247

Leu Gly Tyr Asp Asp Ile Tyr Asp Asp Trp Tyr Phe Asp Val
1 5 10

<210> SEQ ID NO 248
<211> LENGTH: 5
<212> TYPE: PRT
<213> ORGANISM: Mus musculus

<400> SEQUENCE: 248

Asp Tyr Asn Met His
1 5

<210> SEQ ID NO 249
<211> LENGTH: 17
<212> TYPE: PRT
<213> ORGANISM: Mus musculus

<400> SEQUENCE: 249

Glu Ile Asn Pro Asn Ser Gly Gly Ser Gly Tyr Asn Gln Lys Phe Lys
1 5 10 15

Gly

<210> SEQ ID NO 250
<211> LENGTH: 14
<212> TYPE: PRT
<213> ORGANISM: Mus musculus

<400> SEQUENCE: 250

Leu Val Tyr Asp Gly Ser Tyr Glu Asp Trp Tyr Phe Asp Val
1 5 10

<210> SEQ ID NO 251
<211> LENGTH: 5
<212> TYPE: PRT
<213> ORGANISM: Mus musculus

<400> SEQUENCE: 251

Asp Tyr Asn Met His
1 5

<210> SEQ ID NO 252
<211> LENGTH: 17
<212> TYPE: PRT
<213> ORGANISM: Mus musculus

<400> SEQUENCE: 252

Glu Ile Asn Pro Asn Ser Gly Gly Ala Gly Tyr Asn Gln Gln Phe Lys
1 5 10 15

Gly

<210> SEQ ID NO 253
<211> LENGTH: 14
<212> TYPE: PRT
<213> ORGANISM: Mus musculus

<400> SEQUENCE: 253

Leu Gly Tyr Val Gly Asn Tyr Glu Asp Trp Tyr Phe Asp Val
1 5 10

<210> SEQ ID NO 254
<211> LENGTH: 5
<212> TYPE: PRT
<213> ORGANISM: Mus musculus

<400> SEQUENCE: 254

Asp Tyr Asn Met His
1 5

<210> SEQ ID NO 255
<211> LENGTH: 17
<212> TYPE: PRT
<213> ORGANISM: Mus musculus

<400> SEQUENCE: 255

Glu Ile Asn Pro Asn Ser Gly Gly Ala Gly Tyr Asn Gln Lys Phe Lys 1 5 10 15

Gly

<210> SEQ ID NO 256
<211> LENGTH: 14
<212> TYPE: PRT
<213> ORGANISM: Mus musculus

<400> SEQUENCE: 256

Leu Gly Tyr Asp Asp Ile Tyr Asp Asp Trp Tyr Phe Asp Val
1 5 10

<210> SEQ ID NO 257
<211> LENGTH: 5
<212> TYPE: PRT
<213> ORGANISM: Mus musculus

<400> SEQUENCE: 257

Asp Tyr Asn Met His
1 5

<210> SEQ ID NO 258
<211> LENGTH: 17
<212> TYPE: PRT
<213> ORGANISM: Mus musculus

<400> SEQUENCE: 258

Glu Ile Asn Pro Asn Ser Gly Gly Ala Gly Tyr Asn Gln Lys Phe Lys
1 5 10 15

Gly

<210> SEQ ID NO 259
<211> LENGTH: 14
<212> TYPE: PRT
<213> ORGANISM: Mus musculus

<400> SEQUENCE: 259

Leu Gly Tyr Asp Asp Ile Tyr Asp Asp Trp Tyr Phe Asp Val
1 5 10

<210> SEQ ID NO 260
<211> LENGTH: 5
<212> TYPE: PRT
<213> ORGANISM: Mus musculus

<400> SEQUENCE: 260

Asp Tyr Asn Met His
1 5

<210> SEQ ID NO 261
<211> LENGTH: 17
<212> TYPE: PRT
<213> ORGANISM: Mus musculus

<400> SEQUENCE: 261

Glu Ile Asn Pro Asn Ser Gly Gly Ala Gly Tyr Asn Gln Lys Phe Lys
1 5 10 15

Gly

<210> SEQ ID NO 262
<211> LENGTH: 14
<212> TYPE: PRT
<213> ORGANISM: Mus musculus

<400> SEQUENCE: 262

Leu Gly Tyr Asp Asp Ile Tyr Asp Asp Trp Tyr Phe Asp Val
1               5                   10

<210> SEQ ID NO 263
<211> LENGTH: 5
<212> TYPE: PRT
<213> ORGANISM: Mus musculus

<400> SEQUENCE: 263

Asp Tyr Asn Met His
1               5

<210> SEQ ID NO 264
<211> LENGTH: 17
<212> TYPE: PRT
<213> ORGANISM: Mus musculus

<400> SEQUENCE: 264

Glu Ile Asn Pro Asn Ser Gly Gly Ser Gly Tyr Asn Gln Lys Phe Lys
1               5                   10                  15

Gly

<210> SEQ ID NO 265
<211> LENGTH: 14
<212> TYPE: PRT
<213> ORGANISM: Mus musculus

<400> SEQUENCE: 265

Leu Gly Tyr Tyr Gly Asn Tyr Glu Asp Trp Tyr Phe Asp Val
1               5                   10

<210> SEQ ID NO 266
<211> LENGTH: 5
<212> TYPE: PRT
<213> ORGANISM: Mus musculus

<400> SEQUENCE: 266

Asp Tyr Tyr Ile His
1               5

<210> SEQ ID NO 267
<211> LENGTH: 17
<212> TYPE: PRT
<213> ORGANISM: Mus musculus

<400> SEQUENCE: 267

Arg Ile Asp Pro Asp Asn Gly Glu Ser Thr Tyr Val Pro Lys Phe Gln
1               5                   10                  15

Gly

<210> SEQ ID NO 268
<211> LENGTH: 13
<212> TYPE: PRT
<213> ORGANISM: Mus musculus

<400> SEQUENCE: 268

Glu Gly Leu Asp Tyr Gly Asp Tyr Tyr Ala Val Asp Tyr
1               5                   10

<210> SEQ ID NO 269
<211> LENGTH: 5

<212> TYPE: PRT
<213> ORGANISM: Mus musculus

<400> SEQUENCE: 269

Asp Tyr Ile Met His
1               5

<210> SEQ ID NO 270
<211> LENGTH: 17
<212> TYPE: PRT
<213> ORGANISM: Mus musculus

<400> SEQUENCE: 270

Tyr Ile Asn Pro Tyr Asn Asp Asp Thr Glu Tyr Asn Glu Lys Phe Lys
1               5                   10                  15

Gly

<210> SEQ ID NO 271
<211> LENGTH: 11
<212> TYPE: PRT
<213> ORGANISM: Mus musculus

<400> SEQUENCE: 271

Ser Ile Tyr Tyr Tyr Asp Ala Pro Phe Ala Tyr
1               5                   10

<210> SEQ ID NO 272
<211> LENGTH: 5
<212> TYPE: PRT
<213> ORGANISM: Mus musculus

<400> SEQUENCE: 272

Asp Tyr Tyr Met His
1               5

<210> SEQ ID NO 273
<211> LENGTH: 17
<212> TYPE: PRT
<213> ORGANISM: Mus musculus

<400> SEQUENCE: 273

Arg Ile Asp Pro Glu Asn Gly Asp Ile Ile Tyr Asp Pro Lys Phe Gln
1               5                   10                  15

Gly

<210> SEQ ID NO 274
<211> LENGTH: 10
<212> TYPE: PRT
<213> ORGANISM: Mus musculus

<400> SEQUENCE: 274

Asp Ala Gly Asp Pro Ala Trp Phe Thr Tyr
1               5                   10

<210> SEQ ID NO 275
<211> LENGTH: 10
<212> TYPE: PRT
<213> ORGANISM: Mus musculus

<400> SEQUENCE: 275

Arg Ala Ser Ser Ser Val Tyr Tyr Met His
1               5                   10

<210> SEQ ID NO 276
<211> LENGTH: 7
<212> TYPE: PRT
<213> ORGANISM: Mus musculus

<400> SEQUENCE: 276

Ala Thr Ser Asn Leu Ala Ser
1               5

<210> SEQ ID NO 277
<211> LENGTH: 9
<212> TYPE: PRT
<213> ORGANISM: Mus musculus

<400> SEQUENCE: 277

Gln Gln Trp Ser Ser Asp Pro Leu Thr
1               5

<210> SEQ ID NO 278
<211> LENGTH: 12
<212> TYPE: PRT
<213> ORGANISM: Mus musculus

<400> SEQUENCE: 278

Ser Val Ser Ser Thr Ile Ser Ser Asn His Leu His
1               5                   10

<210> SEQ ID NO 279
<211> LENGTH: 7
<212> TYPE: PRT
<213> ORGANISM: Mus musculus

<400> SEQUENCE: 279

Gly Thr Ser Asn Leu Ala Ser
1               5

<210> SEQ ID NO 280
<211> LENGTH: 9
<212> TYPE: PRT
<213> ORGANISM: Mus musculus

<400> SEQUENCE: 280

Gln Gln Trp Ser Ser Tyr Pro Leu Thr
1               5

<210> SEQ ID NO 281
<211> LENGTH: 10
<212> TYPE: PRT
<213> ORGANISM: Mus musculus

<400> SEQUENCE: 281

Arg Ala Ser Ser Ser Ile Ser Tyr Ile His
1               5                   10

<210> SEQ ID NO 282
<211> LENGTH: 7
<212> TYPE: PRT
<213> ORGANISM: Mus musculus

<400> SEQUENCE: 282

Ala Thr Ser Asn Leu Ala Ser
1               5

<210> SEQ ID NO 283
<211> LENGTH: 9

<212> TYPE: PRT
<213> ORGANISM: Mus musculus

<400> SEQUENCE: 283

Gln Gln Trp Ser Ser Asp Pro Leu Thr
1 5

<210> SEQ ID NO 284
<211> LENGTH: 12
<212> TYPE: PRT
<213> ORGANISM: Mus musculus

<400> SEQUENCE: 284

Arg Ala Ser Ser Ser Val Thr Ser Ser Tyr Leu Asn
1 5 10

<210> SEQ ID NO 285
<211> LENGTH: 7
<212> TYPE: PRT
<213> ORGANISM: Mus musculus

<400> SEQUENCE: 285

Ser Thr Ser Asn Leu Ala Ser
1 5

<210> SEQ ID NO 286
<211> LENGTH: 9
<212> TYPE: PRT
<213> ORGANISM: Mus musculus

<400> SEQUENCE: 286

Gln Gln Tyr Asp Phe Phe Pro Ser Thr
1 5

<210> SEQ ID NO 287
<211> LENGTH: 5
<212> TYPE: PRT
<213> ORGANISM: Mus musculus

<400> SEQUENCE: 287

Asp Tyr Phe Ile His
1 5

<210> SEQ ID NO 288
<211> LENGTH: 17
<212> TYPE: PRT
<213> ORGANISM: Mus musculus

<400> SEQUENCE: 288

Arg Leu Asp Pro Glu Asp Gly Glu Ser Asp Tyr Ala Pro Lys Phe Gln
1 5 10 15

Asp

<210> SEQ ID NO 289
<211> LENGTH: 12
<212> TYPE: PRT
<213> ORGANISM: Mus musculus

<400> SEQUENCE: 289

Glu Asp Tyr Asp Gly Thr Tyr Thr Phe Phe Pro Tyr
1 5 10

<210> SEQ ID NO 290
<211> LENGTH: 5

<212> TYPE: PRT
<213> ORGANISM: Mus musculus

<400> SEQUENCE: 290

Asp Phe Tyr Leu His
1 5

<210> SEQ ID NO 291
<211> LENGTH: 17
<212> TYPE: PRT
<213> ORGANISM: Mus musculus

<400> SEQUENCE: 291

Arg Ile Asp Pro Glu Asn Gly Asp Thr Leu Tyr Asp Pro Lys Phe Gln
1 5 10 15

Asp

<210> SEQ ID NO 292
<211> LENGTH: 16
<212> TYPE: PRT
<213> ORGANISM: Mus musculus

<400> SEQUENCE: 292

Glu Ala Asp Tyr Phe His Asp Gly Thr Ser Tyr Trp Tyr Phe Asp Val
1 5 10 15

<210> SEQ ID NO 293
<211> LENGTH: 5
<212> TYPE: PRT
<213> ORGANISM: Mus musculus

<400> SEQUENCE: 293

Asp Tyr Tyr Ile His
1 5

<210> SEQ ID NO 294
<211> LENGTH: 17
<212> TYPE: PRT
<213> ORGANISM: Mus musculus

<400> SEQUENCE: 294

Arg Val Asp Pro Asp Asn Gly Glu Thr Glu Phe Ala Pro Lys Phe Pro
1 5 10 15

Gly

<210> SEQ ID NO 295
<211> LENGTH: 12
<212> TYPE: PRT
<213> ORGANISM: Mus musculus

<400> SEQUENCE: 295

Glu Asp Tyr Asp Gly Thr Tyr Thr Trp Phe Pro Tyr
1 5 10

<210> SEQ ID NO 296
<211> LENGTH: 5
<212> TYPE: PRT
<213> ORGANISM: Mus musculus

<400> SEQUENCE: 296

Asp Tyr Tyr Met Asn
1 5

<210> SEQ ID NO 297
<211> LENGTH: 17
<212> TYPE: PRT
<213> ORGANISM: Mus musculus

<400> SEQUENCE: 297

```
Asp Ile Asn Pro Tyr Asn Asp Asp Thr Thr Tyr Asn His Lys Phe Lys
1               5                   10                  15

Gly
```

<210> SEQ ID NO 298
<211> LENGTH: 11
<212> TYPE: PRT
<213> ORGANISM: Mus musculus

<400> SEQUENCE: 298

```
Glu Thr Ala Val Ile Thr Thr Asn Ala Met Asp
1               5                   10
```

<210> SEQ ID NO 299
<211> LENGTH: 130
<212> TYPE: PRT
<213> ORGANISM: Mus musculus

<400> SEQUENCE: 299

```
Met Asp Phe Gln Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Ser Gln Gln Lys Ser Gly
    50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Thr Thr Thr Tyr Thr Phe Gly Ser Gly Thr Lys Leu Glu Leu
        115                 120                 125

Lys Arg
    130
```

<210> SEQ ID NO 300
<211> LENGTH: 390
<212> TYPE: DNA
<213> ORGANISM: Mus musculus

<400> SEQUENCE: 300

```
atggattttc aggtgcagat tttcagcttc atgctaatca gtgtcacagt catattgtcc      60

agtggagaaa ttgtgctcac ccagtctcca gcactcatgg ctgcatctcc aggggagaag     120

gtcaccatca cctgcagtgt cagctcgagt ataagttcca gcaacttaca ctggtcccag     180

cagaagtcag gaacctcccc caaactctgg atttatggca catccaacct tgcttctgga     240

gtccctgttc gcttcagtgg cagtggatct gggacctctt attctctcac aatcagcagc     300

atggaggctg aagatgctgc cacttattac tgtcaacagt ggactactac gtatacgttc     360

ggatcgggga ccaagctgga gctgaaacgt                                      390
```

<210> SEQ ID NO 301
<211> LENGTH: 141
<212> TYPE: PRT
<213> ORGANISM: Mus musculus

<400> SEQUENCE: 301

```
Met Gly Trp Asn Trp Ile Ile Phe Phe Leu Met Ala Val Val Thr Gly
1               5                   10                  15

Val Asn Ser Glu Val Gln Leu Arg Gln Ser Gly Ala Asp Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Arg Ile Asp Pro Asp Asn Gly Glu Ser Thr Tyr Val
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Gly Arg Glu Gly Leu Asp Tyr Gly Asp Tyr Tyr Ala Val
        115                 120                 125

Asp Tyr Trp Gly Gln Gly Thr Ser Val Thr Val Ser Ser
    130                 135                 140
```

<210> SEQ ID NO 302
<211> LENGTH: 423
<212> TYPE: DNA
<213> ORGANISM: Mus musculus

<400> SEQUENCE: 302

```
atgggatgga actggatcat cttcttcctg atggcagtgg ttacaggggt caattcagag      60

gtgcagttgc ggcagtctgg ggcagacctt gtgaagccag gggcctcagt caagttgtcc     120

tgcacagctt ctggcttcaa cattaaagac tactatatac actgggtgaa gcagaggcct     180

gaacagggcc tggagtggat tggaaggatt gatcctgata atggtgaaag tacatatgtc     240

ccgaagttcc agggcaaggc cactataaca gcagacacat catccaacac agcctaccta     300

caactcagaa gcctgacatc tgaggacact gccatctatt attgtgggag agaggggctc     360

gactatggtg actactatgc tgtggactac tggggtcaag gaacctcggt cacagtctcg     420

agc                                                                   423
```

<210> SEQ ID NO 303
<211> LENGTH: 130
<212> TYPE: PRT
<213> ORGANISM: Artificial Sequence
<220> FEATURE:
<223> OTHER INFORMATION: Humanized antibody sequence

<400> SEQUENCE: 303

```
Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Ser Val Ser
        35                  40                  45
```

```
Ser Ser Ile Ser Ser Ser Asn Leu His Trp Tyr Gln Gln Lys Pro Gly
    50                  55                  60

Lys Ala Pro Lys Leu Leu Ile Tyr Gly Thr Ser Asn Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Trp Thr Thr Thr Tyr Thr Phe Gly Gln Gly Thr Lys Leu Glu Ile
        115                 120                 125

Lys Arg
    130


<210> SEQ ID NO 304
<211> LENGTH: 390
<212> TYPE: DNA
<213> ORGANISM: Artificial Sequence
<220> FEATURE:
<223> OTHER INFORMATION: Humanized antibody sequence

<400> SEQUENCE: 304

atggatatgc gcgtgccggc gcagctgctg ggcctgctgc tgctgtggct gccgggcgcg      60

cgctgcgata ttcagctgac ccagagcccg agctttctga gcgcgagcgt gggcgatcgc     120

gtgaccatta cctgcagcgt gagcagcagc attagcagca gcaacctgca ttggtatcag     180

cagaaaccgg gcaaagcgcc gaaactgctg atttatggca ccagcaacct ggcgagcggc     240

gtgccgagcc gctttagcgg cagcggcagc ggcaccgaat ttaccctgac cattagcagc     300

ctgcagccgg aagatttgc gacctattat tgccagcagt ggaccaccac ctatacccttt     360

ggccagggca ccaaactgga aattaaacgt                                      390


<210> SEQ ID NO 305
<211> LENGTH: 141
<212> TYPE: PRT
<213> ORGANISM: Artificial Sequence
<220> FEATURE:
<223> OTHER INFORMATION: Humanized antibody sequence

<400> SEQUENCE: 305

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Ile His Trp Val Arg Gln Ala Pro Gly Gln Gly Leu
    50                  55                  60

Glu Trp Met Gly Arg Ile Asp Pro Asp Asn Gly Glu Ser Thr Tyr Val
65                  70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Gly Leu Asp Tyr Gly Asp Tyr Tyr Ala Val
        115                 120                 125

Asp Tyr Trp Gly Gln Gly Thr Leu Val Thr Val Ser Ser
    130                 135                 140
```

<210> SEQ ID NO 306
<211> LENGTH: 423
<212> TYPE: DNA
<213> ORGANISM: Artificial Sequence
<220> FEATURE:
<223> OTHER INFORMATION: Humanized antibody sequence

<400> SEQUENCE: 306

```
atggattgga cctggagcat tctgtttctg gtggcggcgc cgaccggcgc gcatagcgaa     60

gtgcagctgg tgcagagcgg cgcggaagtg aaaaaaccgg gcgcgagcgt gaaagtgagc    120

tgcaaagcga gcggctttaa cattaaagat tattatattc attgggtgcg ccaggcgccg    180

ggccagggcc tggaatggat gggccgcatt gatccggata acggcgaaag cacctatgtg    240

ccgaaatttc agggccgcgt gaccatgacc accgatacca gcaccagcac cgcgtatatg    300

gaactgcgca gcctgcgcag cgatgatacc gcggtgtatt attgcgcgcg cgaaggcctg    360

gattatggcg attattatgc ggtggattat tggggccagg gcaccctggt gaccgtctcg    420

agc                                                                  423
```

<210> SEQ ID NO 307
<211> LENGTH: 127
<212> TYPE: PRT
<213> ORGANISM: Mus musculus

<400> SEQUENCE: 307

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Asn Ile Ser Cys Arg Ala Ser Gln Asp
        35                  40                  45

Ile Ser Ser Tyr Leu Asn Trp Tyr Gln Gln Lys Pro Asp Gly Thr Val
    50                  55                  60

Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Ala Gln Glu Asp Ile Ala Thr Tyr Phe Cys Gln Gln Asp Ile
            100                 105                 110

Lys His Pro Thr Phe Gly Gly Gly Thr Lys Leu Glu Leu Lys Arg
        115                 120                 125
```

<210> SEQ ID NO 308
<211> LENGTH: 381
<212> TYPE: DNA
<213> ORGANISM: Mus musculus

<400> SEQUENCE: 308

```
atgatgtcct ctgctcagtt ccttggtctc ctgttgctct gttttcaagg taccagatgt     60

gatatccaga tgacacagac tacatcctcc ctgtctgcct ctctgggaga cagagtcaac    120

atcagctgca gggcaagtca ggacattagc agttatttaa actggtatca gcagaaacca    180

gatggaactg ttaaactcct gatctactcc acatcaagat taaactcagg agtcccatca    240

aggttcagtg gcagtgggtc tgggacagat tattctctca ctattagcaa cctggcacaa    300

gaagatattg ccacttactt ttgccaacag gatattaagc atccgacgtt cggtggaggc    360

accaagttgg agctgaaacg t                                              381
```

<210> SEQ ID NO 309
<211> LENGTH: 139
<212> TYPE: PRT
<213> ORGANISM: Mus musculus

<400> SEQUENCE: 309

```
Met Glu Trp Ile Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Phe Thr Phe
        35                  40                  45

Thr Asp Tyr Ile Met His Trp Val Lys Gln Lys Pro Gly Gln Gly Leu
    50                  55                  60

Glu Trp Ile Gly Tyr Ile Asn Pro Tyr Asn Asp Asp Thr Glu Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Gly Ser Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135
```

<210> SEQ ID NO 310
<211> LENGTH: 417
<212> TYPE: DNA
<213> ORGANISM: Mus musculus

<400> SEQUENCE: 310

```
atggaatgga tctggatatt tctcttcctc ctgtcaggaa ctgcaggtgt ccactctgag     60

gtccagctgc agcagtctgg acctgagctg gtaaagcctg gggcttcagt gaagatgtcc    120

tgcaaggctt ctgggttcac attcactgac tacattatgc actgggtgaa gcagaagcct    180

gggcagggcc ttgagtggat tggatatatt aatccttaca atgatgatac tgaatacaat    240

gagaagttca aaggcaaggc cacactgact tcagacaaat cctccagcac agcctacatg    300

gatctcagca gtctgacctc tgagggctct gcggtctatt actgtgcaag atcgatttat    360

tactacgatg ccccgtttgc ttactggggc caagggactc tggtcacagt ctcgagc       417
```

<210> SEQ ID NO 311
<211> LENGTH: 127
<212> TYPE: PRT
<213> ORGANISM: Artificial Sequence
<220> FEATURE:
<223> OTHER INFORMATION: Humanized antibody sequence

<400> SEQUENCE: 311

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Ser Tyr Leu Asn Trp Tyr Gln Gln Lys Pro Gly Lys Ala Pro
    50                  55                  60
```

```
Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Asp Ile
            100                 105                 110

Lys His Pro Thr Phe Gly Gln Gly Thr Lys Val Glu Ile Lys Arg
        115                 120                 125


<210> SEQ ID NO 312
<211> LENGTH: 381
<212> TYPE: DNA
<213> ORGANISM: Artificial Sequence
<220> FEATURE:
<223> OTHER INFORMATION: Humanized antibody sequence

<400> SEQUENCE: 312

atgatgtcct ctgctcagtt ccttggtctc ctgttgctct gttttcaagg taccagatgt      60

gatatccaga tgacccagtc tccatcctcc ctgtctgcat ctgtaggtga ccgtgtcacc     120

atcacttgcc gcgcaagtca ggatattagc agctatttaa attggtatca gcagaaacca     180

gggaaagccc ctaagctcct gatctattct acttcccgtt tgaatagtgg ggtcccatca     240

cgcttcagtg gcagtggctc tgggacagat ttcactctca ccatcagcag tctgcaacct     300

gaagattttg caacttacta ctgtcaacag gatattaaac accctacgtt cggtcaaggc     360

accaaggtgg agatcaaacg t                                               381


<210> SEQ ID NO 313
<211> LENGTH: 139
<212> TYPE: PRT
<213> ORGANISM: Artificial Sequence
<220> FEATURE:
<223> OTHER INFORMATION: Humanized antibody sequence

<400> SEQUENCE: 313

Met Glu Trp Ile Trp Ile Phe Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135


<210> SEQ ID NO 314
<211> LENGTH: 107
<212> TYPE: PRT
<213> ORGANISM: Mus musculus
```

<400> SEQUENCE: 314

```
Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg
            100                 105
```

<210> SEQ ID NO 315
<211> LENGTH: 128
<212> TYPE: PRT
<213> ORGANISM: Mus musculus

<400> SEQUENCE: 315

```
Met Lys Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Thr Ile Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys Arg
        115                 120                 125
```

<210> SEQ ID NO 316
<211> LENGTH: 381
<212> TYPE: DNA
<213> ORGANISM: Mus musculus

<400> SEQUENCE: 316

```
atgaagtcac agacccaggt ctttgtatac atgttgctgt ggttgtctgg tgttgaagga     60

gacattgtga tgacccagtc tcacaaattc atgtccacgt cagtaggaga cagggtcacc    120

atcacctgca aggccagtca ggatgtcttt actgctgtag cctggtatca acagaaacca    180

ggacaatctc ctaaactact gatttactgg gcatccaccc ggcacactgg agtccctgat    240

cgcttcacag gcagtggatc tgggacagat ttcactctca ccattagcaa tgtgcagtct    300

gaagacttgg cagattattt ctgtcaacaa tatagcagct atcctctcac gttcggtgct    360

gggaccaagt tggagctgaa a                                              381
```

<210> SEQ ID NO 317
<211> LENGTH: 138
<212> TYPE: PRT
<213> ORGANISM: Mus musculus

<400> SEQUENCE: 317

```
Met Gly Trp Asn Trp Ile Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Lys Gln Arg Pro Glu Gln Gly Leu
    50                  55                  60

Glu Trp Ile Gly Arg Ile Asp Pro Glu Asn Gly Asp Ile Ile Tyr Asp
65                  70                  75                  80

Pro Lys Phe Gln Gly Lys Ala Ser Ile Thr Thr Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135
```

<210> SEQ ID NO 318
<211> LENGTH: 411
<212> TYPE: DNA
<213> ORGANISM: Mus musculus

<400> SEQUENCE: 318

```
atgggatgga actggatcat cttcttcctg atggcagtgg ttacaggggt caattcagag      60

gttcagctgc agcagtctgg ggctgagctt gtgaggccag gggccttagt caagttgtcc     120

tgcaaagctt ctggcttcaa tattaaagac tactatatgc actgggtgaa gcagaggcct     180

gaacagggcc tggagtggat tggaaggatt gatcctgaga atggtgatat tatatatgac     240

ccgaagttcc agggcaaggc cagtataaca acagacacat cctccaacac agcctacctg     300

cagctcagca gcctgacgtc tgaggacact gccgtctatt actgtgctta cgatgctggt     360

gaccccgcct ggtttactta ctggggccaa gggactctgg tcaccgtctc g              411
```

<210> SEQ ID NO 319
<211> LENGTH: 130
<212> TYPE: PRT
<213> ORGANISM: Artificial Sequence
<220> FEATURE:
<223> OTHER INFORMATION: Humanized antibody sequence

<400> SEQUENCE: 319

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Phe Thr Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
```

```
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Ser Tyr Pro Leu Thr Phe Gly Gly Gly Thr Lys Val Glu Ile
        115                 120                 125

Lys Arg
    130


<210> SEQ ID NO 320
<211> LENGTH: 390
<212> TYPE: DNA
<213> ORGANISM: Artificial Sequence
<220> FEATURE:
<223> OTHER INFORMATION: Humanized antibody sequence

<400> SEQUENCE: 320

atggatatgc gcgtgccggc gcagctgctg ggcctgctgc tgctgtggct gcgcggcgcg      60

cgctgcgata tccagatgac ccagagcccg agcagcctga gcgcgagcgt gggcgatcgc     120

gtgaccatta cctgcaaagc gagccaggat gtgtttaccg cggtggcgtg gtatcagcag     180

aaaccgggca aagcgccgaa actgctgatt tattgggcga gcacccgcca taccggcgtg     240

ccgagtcgct ttagcggcag cggcagcggc accgatttta ccctgaccat tagcagcctg     300

cagccggaag attttgcgac ctattattgc cagcagtata gcagctatcc gctgaccttt     360

ggcggcggca ccaaagtgga aattaaacgt                                      390


<210> SEQ ID NO 321
<211> LENGTH: 138
<212> TYPE: PRT
<213> ORGANISM: Artificial Sequence
<220> FEATURE:
<223> OTHER INFORMATION: Humanized antibody sequence

<400> SEQUENCE: 321

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Met His Trp Val Arg Gln Ala Pro Gly Gln Gly Leu
    50                  55                  60

Glu Trp Ile Gly Arg Ile Asp Pro Glu Asn Gly Asp Ile Ile Tyr Asp
65                  70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135


<210> SEQ ID NO 322
<211> LENGTH: 414
<212> TYPE: DNA
```

<213> ORGANISM: Artificial Sequence
<220> FEATURE:
<223> OTHER INFORMATION: Humanized antibody sequence

<400> SEQUENCE: 322

```
atggattgga cctggagcat tctgtttctg gtggcggcgc cgaccggcgc gcatagcgaa     60

gtgcagctgg tgcagagcgg cgcggaagtg aaaaaaccgg gcgcgagcgt gaaagtgagc    120

tgcaaagcga gcggctttaa cattaaagat tattatatgc attgggtgcg ccaggcgccg    180

ggccagggcc tggaatggat cggccgcatt gatccggaaa acggcgatat tatttatgat    240

ccgaaatttc agggccgcgt gaccatgacc accgatacca gcaccagcac cgcgtatatg    300

gaactgcgca gcctgcgcag cgatgatacc gcggtgtatt attgcgcgta tgatgcgggc    360

gatccggcgt ggtttaccta ttggggccag ggcaccctgg tgaccgtctc gagc          414
```

<210> SEQ ID NO 323
<211> LENGTH: 106
<212> TYPE: PRT
<213> ORGANISM: Mus musculus

<400> SEQUENCE: 323

```
Thr Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

<210> SEQ ID NO 324
<211> LENGTH: 324
<212> TYPE: PRT
<213> ORGANISM: Mus musculus

<400> SEQUENCE: 324

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
```

```
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 325
<211> LENGTH: 106
<212> TYPE: PRT
<213> ORGANISM: Homo sapiens

<400> SEQUENCE: 325

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 326
<211> LENGTH: 327
<212> TYPE: PRT
<213> ORGANISM: Homo sapiens

<400> SEQUENCE: 326

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 327
<211> LENGTH: 120
<212> TYPE: PRT
<213> ORGANISM: Mus musculus

<400> SEQUENCE: 327

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
```

```
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120


<210> SEQ ID NO 328
<211> LENGTH: 120
<212> TYPE: PRT
<213> ORGANISM: Mus musculus

<400> SEQUENCE: 328

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120


<210> SEQ ID NO 329
<211> LENGTH: 120
<212> TYPE: PRT
<213> ORGANISM: Mus musculus

<400> SEQUENCE: 329

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120
```

<210> SEQ ID NO 330
<211> LENGTH: 226
<212> TYPE: PRT
<213> ORGANISM: Mus musculus

<400> SEQUENCE: 330

```
Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225
```

<210> SEQ ID NO 331
<211> LENGTH: 447
<212> TYPE: PRT
<213> ORGANISM: Mus musculus

<400> SEQUENCE: 331

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
```

```
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 332
<211> LENGTH: 107
<212> TYPE: PRT
<213> ORGANISM: Mus musculus

<400> SEQUENCE: 332

```
Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30
```

```
Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys
            100                 105


<210> SEQ ID NO 333
<211> LENGTH: 324
<212> TYPE: PRT
<213> ORGANISM: Mus musculus

<400> SEQUENCE: 333

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Ile Tyr Ser Lys Leu Asn
        275                 280                 285

Val Gln Lys Ser Asn Trp Glu Ala Gly Asn Thr Phe Thr Cys Ser Val
    290                 295                 300
```

Leu His Glu Gly Leu His Asn His His Thr Glu Lys Ser Leu Ser His
305 310 315 320

Ser Pro Gly Lys

<210> SEQ ID NO 334
<211> LENGTH: 213
<212> TYPE: PRT
<213> ORGANISM: Mus musculus

<400> SEQUENCE: 334

Asp Ile Gln Met Thr Gln Thr Thr Ser Ser Leu Ser Ala Ser Leu Gly
1 5 10 15

Asp Arg Val Asn Ile Ser Cys Arg Ala Ser Gln Asp Ile Ser Ser Tyr
20 25 30

Leu Asn Trp Tyr Gln Gln Lys Pro Asp Gly Thr Val Lys Leu Leu Ile
35 40 45

Tyr Ser Thr Ser Arg Leu Asn Ser Gly Val Pro Ser Arg Phe Ser Gly
50 55 60

Ser Gly Ser Gly Thr Asp Tyr Ser Leu Thr Ile Ser Asn Leu Ala Gln
65 70 75 80

Glu Asp Ile Ala Thr Tyr Phe Cys Gln Gln Asp Ile Lys His Pro Thr
85 90 95

Phe Gly Gly Gly Thr Lys Leu Glu Leu Lys Arg Thr Asp Ala Ala Pro
100 105 110

Thr Val Ser Ile Phe Pro Pro Ser Ser Glu Gln Leu Thr Ser Gly Gly
115 120 125

Ala Ser Val Val Cys Phe Leu Asn Asn Phe Tyr Pro Lys Asp Ile Asn
130 135 140

Val Lys Trp Lys Ile Asp Gly Ser Glu Arg Gln Asn Gly Val Leu Asn
145 150 155 160

Ser Trp Thr Asp Gln Asp Ser Lys Asp Ser Thr Tyr Ser Met Ser Ser
165 170 175

Thr Leu Thr Leu Thr Lys Asp Glu Tyr Glu Arg His Asn Ser Tyr Thr
180 185 190

Cys Glu Ala Thr His Lys Thr Ser Thr Ser Pro Ile Val Lys Ser Phe
195 200 205

Asn Arg Asn Glu Cys
210

<210> SEQ ID NO 335
<211> LENGTH: 444
<212> TYPE: PRT
<213> ORGANISM: Mus musculus

<400> SEQUENCE: 335

Glu Val Gln Leu Gln Gln Ser Gly Pro Glu Leu Val Lys Pro Gly Ala
1 5 10 15

Ser Val Lys Met Ser Cys Lys Ala Ser Gly Phe Thr Phe Thr Asp Tyr
20 25 30

Ile Met His Trp Val Lys Gln Lys Pro Gly Gln Gly Leu Glu Trp Ile
35 40 45

Gly Tyr Ile Asn Pro Tyr Asn Asp Asp Thr Glu Tyr Asn Glu Lys Phe
50 55 60

Lys Gly Lys Ala Thr Leu Thr Ser Asp Lys Ser Ser Ser Thr Ala Tyr
65 70 75 80

```
Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 336
<211> LENGTH: 108
<212> TYPE: PRT
<213> ORGANISM: Mus musculus

<400> SEQUENCE: 336

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105


<210> SEQ ID NO 337
<211> LENGTH: 324
<212> TYPE: DNA
<213> ORGANISM: Mus musculus

<400> SEQUENCE: 337

gatatccaga tgacccagag cccgagcagc ctgagcgcga gcgtgggcga tcgcgtgacc      60

attacctgca aagcgagcca ggatgtgttt accgcggtgg cgtggtatca gcagaaaccg     120

ggcaaagcgc cgaaactgct gatttattgg gcgagcaccc gccataccgg cgtgccgagt     180

cgctttagcg gcagcggcag cggcaccgat tttaccctga ccattagcag cctgcagccg     240

gaagattttg cgacctatta ttgccagcag tatagcagct atccgctgac ctttggcggc     300

ggcaccaaag tggaaattaa acgt                                            324


<210> SEQ ID NO 338
<211> LENGTH: 119
<212> TYPE: PRT
<213> ORGANISM: Mus musculus

<400> SEQUENCE: 338

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115


<210> SEQ ID NO 339
<211> LENGTH: 357
<212> TYPE: DNA
<213> ORGANISM: Mus musculus

<400> SEQUENCE: 339
```

```
gaagtgcagc tggtgcagag cggcgcggaa gtgaaaaaac cgggcgcgag cgtgaaagtg     60

agctgcaaag cgagcggctt taacattaaa gattattata tgcattgggt gcgccaggcg    120

ccgggccagg gcctggaatg gatcggccgc attgatccgg aaaacggcga tattatttat    180

gatccgaaat ttcagggccg cgtgaccatg accaccgata ccagcaccag caccgcgtat    240

atggaactgc gcagcctgcg cagcgatgat accgcggtgt attattgcgc gtatgatgcg    300

ggcgatccgg cgtggtttac ctattggggc cagggcaccc tggtgaccgt ctcgagc       357
```

<210> SEQ ID NO 340
<211> LENGTH: 1395
<212> TYPE: DNA
<213> ORGANISM: Mus musculus

<400> SEQUENCE: 340

```
atggactgga cctggaggat cctcttcttg gtggcagcag ccacaggagc ccactccgag     60

gtgcagctgg tgcagtctgg ggctgaggtg aagaagcctg ggtcctcggt gaaggtctcc    120

tgcaaggctt ctggttttac cttcaccgac tatattatgc actgggtgcg tcaggcccct    180

ggtcaagggc ttgagtggat gggctatatc aacccttata atgatgacac cgaatacaac    240

gagaagttca agggccgtgt cacgattacc gcggacaaat ccacgagcac agcctacatg    300

gagctgagca gcctgcgctc tgaggacacg gccgtgtatt actgtgcgcg ttcgatttat    360

tactacgatg ccccgtttgc ttactggggc caagggactc tggtcaccgt ctctagtgcc    420

tccaccaagg gcccatcggt cttccccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900

gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140

gtcagcctga cctgcctggt caaaggcttc taccccagcg acatcgccgt ggagtgggag   1200

agcaatgggc agccggagaa caactacaag accacacctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaa                                                    1395
```

<210> SEQ ID NO 341
<211> LENGTH: 213
<212> TYPE: PRT
<213> ORGANISM: Mus musculus

<400> SEQUENCE: 341

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 342
<211> LENGTH: 639
<212> TYPE: DNA
<213> ORGANISM: Mus musculus

<400> SEQUENCE: 342

gacatccaga tgacccagtc tccatcctcc ctgtctgcat ctgtaggtga ccgtgtcacc      60

atcacttgcc gcgcaagtca ggatattagc agctatttaa attggtatca gcagaaacca     120

gggaaagccc ctaagctcct gatctattct acttcccgtt tgaatagtgg ggtcccatca     180

cgcttcagtg gcagtggctc tgggacagat ttcactctca ccatcagcag tctgcaacct     240

gaagattttg caacttacta ctgtcaacag gatattaaac accctacgtt cggtcaaggc     300

accaaggtgg agatcaaacg tacggtggct gcaccatctg tcttcatctt cccgccatct     360

gatgagcagt tgaaatctgg aactgcctct gttgtgtgcc tgctgaataa cttctatccc     420

agagaggcca aagtacagtg gaaggtggat aacgccctcc aatcgggtaa ctcccaggag     480

agtgtcacag agcaggacag caaggacagc acctacagcc tcagcagcac cctgacgctg     540

agcaaagcag actacgagaa acacaaagtc tacgcctgcg aagtcaccca tcagggcctg     600

agctcgcccg tcacaaagag cttcaacagg ggagagtgt                            639


<210> SEQ ID NO 343
<211> LENGTH: 235
<212> TYPE: PRT
<213> ORGANISM: Mus musculus

<400> SEQUENCE: 343

Met Asp Met Arg Val Pro Ala Gln Leu Leu Gly Leu Leu Leu Leu Trp
1               5                   10                  15
```

```
Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Ser Tyr Leu Asn Trp Tyr Gln Gln Lys Pro Gly Lys
    50                  55                  60

Ala Pro Lys Leu Leu Ile Tyr Ser Thr Ser Arg Leu Asn Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Asp Ile Lys His Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 344
<211> LENGTH: 705
<212> TYPE: DNA
<213> ORGANISM: Mus musculus

<400> SEQUENCE: 344

atggacatga gggtgcccgc tcagctcctg gggctcctgc tgctgtggct gagaggtgcc      60

agatgtgaca tccagatgac ccagtctcca tcctccctgt ctgcatctgt aggtgaccgt     120

gtcaccatca cttgccgcgc aagtcaggat attagcagct atttaaattg gtatcagcag     180

aaaccaggga aagcccctaa gctcctgatc tattctactt cccgtttgaa tagtggggtc     240

ccatcacgct tcagtggcag tggctctggg acagatttca ctctcaccat cagcagtctg     300

caacctgaag attttgcaac ttactactgt caacaggata ttaaacaccc tacgttcggt     360

caaggcacca aggtggagat caaacgtacg gtggctgcac catctgtctt catcttcccg     420

ccatctgatg agcagttgaa atctggaact gcctctgttg tgtgcctgct gaataacttc     480

tatcccagag aggccaaagt acagtggaag gtggataacg ccctccaatc gggtaactcc     540

caggagagtg tcacagagca ggacagcaag gacagcacct acagcctcag cagcaccctg     600

acgctgagca aagcagacta cgagaaacac aaagtctacg cctgcgaagt cacccatcag     660

ggcctgagct cgcccgtcac aaagagcttc aacaggggag agtgt                     705


<210> SEQ ID NO 345
<211> LENGTH: 446
<212> TYPE: PRT
```

<213> ORGANISM: Mus musculus

<400> SEQUENCE: 345

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 346
<211> LENGTH: 1338
<212> TYPE: DNA
<213> ORGANISM: Mus musculus

<400> SEQUENCE: 346

gaggtgcagc tggtgcagtc tggggctgag gtgaagaagc ctgggtcctc ggtgaaggtc      60

tcctgcaagg cttctggttt taccttcacc gactatatta tgcactgggt gcgtcaggcc     120

cctggtcaag ggcttgagtg gatgggctat atcaaccctt ataatgatga caccgaatac     180

aacgagaagt tcaagggccg tgtcacgatt accgcggaca aatccacgag cacagcctac     240

atggagctga gcagcctgcg ctctgaggac acggccgtgt attactgtgc gcgttcgatt     300

tattactacg atgccccgtt tgcttactgg ggccaaggga ctctggtcac cgtctctagt     360

gcctccacca agggcccatc ggtcttcccc ctggcgccct gctccaggag cacctccgag     420

agcacagcgg ccctgggctg cctggtcaag gactacttcc ccgaaccggt gacggtgtcg     480

tggaactcag gcgctctgac cagcggcgtg cacaccttcc cagctgtcct acagtcctca     540

ggactctact ccctcagcag cgtggtgacc gtgccctcca gcaacttcgg cacccagacc     600

tacacctgca acgtagatca caagcccagc aacaccaagg tggacaagac agttgagcgc     660

aaatgttgtg tcgagtgccc accgtgccca gcaccacctg tggcaggacc gtcagtcttc     720

ctcttccccc caaaacccaa ggacaccctc atgatctccc ggacccctga ggtcacgtgc     780

gtggtggtgg acgtgagcca cgaagacccc gaggtccagt tcaactggta cgtggacggc     840

gtggaggtgc ataatgccaa gacaaagcca cgggaggagc agttcaacag cacgttccgt     900

gtggtcagcg tcctcaccgt tgtgcaccag gactggctga acggcaagga gtacaagtgc     960

aaggtctcca acaaaggcct cccagccccc atcgagaaaa ccatctccaa aaccaaaggg    1020

cagccccgag aaccacaggt gtacaccctg cccccatccc gggaggagat gaccaagaac    1080

caggtcagcc tgacctgcct ggtcaaaggc ttctacccca gcgacatcgc cgtggagtgg    1140

gagagcaatg ggcagccgga gaacaactac aagaccacac ctcccatgct ggactccgac    1200

ggctccttct tcctctacag caagctcacc gtggacaaga gcaggtggca gcaggggaac    1260

gtcttctcat gctccgtgat gcatgaggct ctgcacaacc actacacgca gaagagcctc    1320

tccctgtctc cgggtaaa                                                   1338


<210> SEQ ID NO 347
<211> LENGTH: 465
<212> TYPE: PRT
<213> ORGANISM: Mus musculus

<400> SEQUENCE: 347

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45
```

```
Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460
```

Lys
465

<210> SEQ ID NO 348
<211> LENGTH: 1395
<212> TYPE: DNA
<213> ORGANISM: Mus musculus

<400> SEQUENCE: 348
atggactgga cctggaggat cctcttcttg gtggcagcag ccacaggagc ccactccgag 60
gtgcagctgg tgcagtctgg ggctgaggtg aagaagcctg ggtcctcggt gaaggtctcc 120
tgcaaggctt ctggttttac cttcaccgac tatattatgc actgggtgcg tcaggcccct 180
ggtcaagggc ttgagtggat gggctatatc aacccttata atgatgacac cgaatacaac 240
gagaagttca agggccgtgt cacgattacc gcggacaaat ccacgagcac agcctacatg 300
gagctgagca gcctgcgctc tgaggacacg gccgtgtatt actgtgcgcg ttcgatttat 360
tactacgatg ccccgtttgc ttactggggc caagggactc tggtcaccgt ctctagtgcc 420
tccaccaagg gcccatcggt cttccccctg gcgccctgct ccaggagcac ctccgagagc 480
acagcggccc tgggctgcct ggtcaaggac tacttccccg aaccggtgac ggtgtcgtgg 540
aactcaggcg ctctgaccag cggcgtgcac accttcccag ctgtcctaca gtcctcagga 600
ctctactccc tcagcagcgt ggtgaccgtg ccctccagca acttcggcac ccagacctac 660
acctgcaacg tagatcacaa gcccagcaac accaaggtgg acaagacagt tgagcgcaaa 720
tgttgtgtcg agtgcccacc gtgcccagca ccacctgtgg caggaccgtc agtcttcctc 780
ttccccccaa aacccaagga caccctcatg atctcccgga cccctgaggt cacgtgcgtg 840
gtggtggacg tgagccacga agaccccgag gtccagttca actggtacgt ggacggcgtg 900
gaggtgcata atgccaagac aaagccacgg gaggagcagt tcaacagcac gttccgtgtg 960
gtcagcgtcc tcaccgttgt gcaccaggac tggctgaacg gcaaggagta caagtgcaag 1020
gtctccaaca aaggcctccc agcccccatc gagaaaacca tctccaaaac caaagggcag 1080
ccccgagaac cacaggtgta caccctgccc ccatcccggg aggagatgac caagaaccag 1140
gtcagcctga cctgcctggt caaaggcttc taccccagcg acatcgccgt ggagtgggag 1200
agcaatgggc agccggagaa caactacaag accacacctc ccatgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaa 1395

<210> SEQ ID NO 349
<211> LENGTH: 417
<212> TYPE: DNA
<213> ORGANISM: Mus musculus

<400> SEQUENCE: 349
atggaatgga tctggatatt tctcttcctc ctgtcaggaa ctgcaggtgt ccactctgag 60
gtgcagctgg tgcagtctgg ggctgaggtg aagaagcctg ggtcctcggt gaaggtctcc 120
tgcaaggctt ctggttttac cttcaccgac tatattatgc actgggtgcg tcaggcccct 180
ggtcaagggc ttgagtggat gggctatatc aacccttata atgatgacac cgaatacaac 240
gagaagttca agggccgtgt cacgattacc gcggacaaat ccacgagcac agcctacatg 300
gagctgagca gcctgcgctc tgaggacacg gccgtgtatt actgtgcgcg ttcgatttat 360

```
tactacgatg ccccgtttgc ttactggggc caagggactc tggtcacagt ctcgagc       417


<210> SEQ ID NO 350
<211> LENGTH: 218
<212> TYPE: PRT
<213> ORGANISM: Mus musculus

<400> SEQUENCE: 350

Asp Ile Val Leu Thr Gln Ser Pro Ala Ser Leu Ala Val Ser Leu Gly
1               5                   10                  15

Gln Arg Ala Thr Ile Ala Cys Lys Ala Ser Gln Ser Val Asp Tyr Asp
            20                  25                  30

Gly Thr Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Glu Ile Pro Ala
    50                  55                  60

Arg Phe Ser Gly Thr Gly Ser Gly Thr Asp Phe Thr Leu Asn Ile His
65                  70                  75                  80

Pro Val Glu Glu Glu Asp Ile Thr Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 351
<211> LENGTH: 15
<212> TYPE: PRT
<213> ORGANISM: Mus musculus

<400> SEQUENCE: 351

Lys Ala Ser Gln Ser Val Asp Tyr Asp Gly Thr Ser Tyr Met Asn
1               5                   10                  15


<210> SEQ ID NO 352
<211> LENGTH: 7
<212> TYPE: PRT
<213> ORGANISM: Mus musculus

<400> SEQUENCE: 352

Ala Ala Ser Asn Leu Glu Ser
1               5


<210> SEQ ID NO 353
<211> LENGTH: 9
<212> TYPE: PRT
<213> ORGANISM: Mus musculus
```

<400> SEQUENCE: 353

Gln Gln Ser Asn Glu Asp Pro Phe Thr
1               5

<210> SEQ ID NO 354
<211> LENGTH: 657
<212> TYPE: DNA
<213> ORGANISM: Mus musculus

<400> SEQUENCE: 354
gacattgtgt tgacccagtc tccagcttct ttggctgtgt ctctagggca gagggccacc 60
atcgcctgca aggccagcca aagtgttgat tatgatggta ctagttatat gaattggtac 120
caacagaaac caggacagcc acccaaactc ctcatctatg ctgcatccaa tctagaatct 180
gagatcccag ccaggtttag tggcactggg tctgggacag acttcaccct caacatccat 240
cctgtggagg aggaggatat cacaacctat tactgtcagc aaagtaatga ggatccgttc 300
acgttcggag gggggaccaa gttggaaata aaacgggctg atgctgcacc aactgtatcc 360
atcttcccac catccagtga gcagttaaca tctggaggtg cctcagtcgt gtgcttcttg 420
aacaacttct accccaaaga catcaatgtc aagtggaaga ttgatggcag tgaacgacaa 480
aatggcgtcc tgaacagttg gactgatcag gacagcaaag acagcaccta cagcatgagc 540
agcaccctca cgttgaccaa ggacgagtat gaacgacata acagctatac ctgtgaggcc 600
actcacaaga catcaacttc acccattgtc aagagcttca acaggaatga gtgttag 657

<210> SEQ ID NO 355
<211> LENGTH: 238
<212> TYPE: PRT
<213> ORGANISM: Mus musculus

<400> SEQUENCE: 355

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ala Cys Lys Ala Ser Gln Ser
        35                  40                  45

Val Asp Tyr Asp Gly Thr Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Glu Ile Pro Ala Arg Phe Ser Gly Thr Gly Ser Gly Thr Asp Phe Thr
                85                  90                  95

Leu Asn Ile His Pro Val Glu Glu Glu Asp Ile Thr Thr Tyr Tyr Cys
            100                 105                 110

Gln Gln Ser Asn Glu Asp Pro Phe Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

```
Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 356
<211> LENGTH: 717
<212> TYPE: DNA
<213> ORGANISM: Mus musculus

<400> SEQUENCE: 356

atggagacag acacaatcct gctatgggtg ctgctgctct gggttccagg ctccactggt      60

gacattgtgt tgacccagtc tccagcttct ttggctgtgt ctctagggca gagggccacc     120

atcgcctgca aggccagcca aagtgttgat tatgatggta ctagttatat gaattggtac     180

caacagaaac caggacagcc acccaaactc ctcatctatg ctgcatccaa tctagaatct     240

gagatcccag ccaggtttag tggcactggg tctgggacag acttcaccct caacatccat     300

cctgtggagg aggaggatat cacaacctat tactgtcagc aaagtaatga ggatccgttc     360

acgttcggag gggggaccaa gttggaaata aaacgggctg atgctgcacc aactgtatcc     420

atcttcccac catccagtga gcagttaaca tctggaggtg cctcagtcgt gtgcttcttg     480

aacaacttct accccaaaga catcaatgtc aagtggaaga ttgatggcag tgaacgacaa     540

aatggcgtcc tgaacagttg gactgatcag gacagcaaag acagcaccta cagcatgagc     600

agcaccctca cgttgaccaa ggacgagtat gaacgacata acagctatac ctgtgaggcc     660

actcacaaga catcaacttc acccattgtc aagagcttca acaggaatga gtgttag        717


<210> SEQ ID NO 357
<211> LENGTH: 442
<212> TYPE: PRT
<213> ORGANISM: Mus musculus

<400> SEQUENCE: 357

Gln Val Gln Leu Gln Gln Pro Gly Thr Glu Leu Val Arg Pro Gly Thr
1               5                   10                  15

Ser Val Lys Leu Ser Cys Lys Ala Ser Gly Tyr Ile Phe Thr Thr Tyr
            20                  25                  30

Trp Met Asn Trp Val Lys Gln Arg Pro Gly Gln Gly Leu Glu Trp Ile
        35                  40                  45

Gly Met Ile His Pro Ser Ala Ser Glu Ile Arg Leu Asp Gln Lys Phe
    50                  55                  60

Lys Asp Lys Ala Thr Leu Thr Leu Asp Lys Ser Ser Ser Thr Ala Tyr
65                  70                  75                  80

Met His Leu Ser Gly Pro Thr Ser Val Asp Ser Ala Val Tyr Tyr Cys
                85                  90                  95

Ala Arg Ser Gly Glu Trp Gly Ser Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160
```

```
Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Ile Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 358
<211> LENGTH: 5
<212> TYPE: PRT
<213> ORGANISM: Mus musculus

<400> SEQUENCE: 358

```
Thr Tyr Trp Met Asn
1               5
```

<210> SEQ ID NO 359
<211> LENGTH: 17
<212> TYPE: PRT
<213> ORGANISM: Mus musculus

<400> SEQUENCE: 359

```
Met Ile His Pro Ser Ala Ser Glu Ile Arg Leu Asp Gln Lys Phe Lys
1               5                   10                  15

Asp
```

<210> SEQ ID NO 360
<211> LENGTH: 9
<212> TYPE: PRT
<213> ORGANISM: Mus musculus

<400> SEQUENCE: 360

Ser Gly Glu Trp Gly Ser Met Asp Tyr
1               5

<210> SEQ ID NO 361
<211> LENGTH: 1329
<212> TYPE: DNA
<213> ORGANISM: Mus musculus

<400> SEQUENCE: 361
caggtccaac tacagcagcc tgggactgag ctggtgaggc ctggaacttc agtgaagttg 60
tcctgtaagg cttctggcta catcttcacc acctactgga tgaactgggt gaaacagagg 120
cctggacaag gccttgagtg gattggcatg attcatcctt ccgcaagtga aattaggttg 180
gatcagaaat tcaaggacaa ggccacattg actcttgaca aatcctccag cacagcctat 240
atgcacctca gcggcccgac atctgtggat tctgcggtct attactgtgc aagatcaggg 300
gaatgggggt ctatggacta ctggggtcaa ggaacctcag tcaccgtctc ctcagccaaa 360
acgacacccc catctgtcta tccactggcc cctggatctg ctgcccaaac taactccatg 420
gtgaccctgg gatgcctggt caagggctat ttccctgagc cagtgacagt gacctggaac 480
tctggatccc tgtccagcgg tgtgcacacc ttcccagctg tcctgcagtc tgacctctac 540
actctgagca gctcagtgac tgtcccctcc agcacctggc ccagcgagac cgtcacctgc 600
aacgttgccc acccggccag cagcaccaag gtggacaaga aaattgtgcc cagggattgt 660
ggttgtaagc cttgcatatg tacagtccca gaagtatcat ctgtcttcat cttcccccca 720
aagcccaagg atgtgctcac cattactctg actcctaagg tcacgtgtgt tgtggtagac 780
atcagcaagg atgatcccga ggtccagttc agctggtttg tagatgatgt ggaggtgcac 840
acagctcaga cgcaaccccg ggaggagcag ttcaacagca ctttccgctc agtcagtgaa 900
cttcccatca tgcaccagga ctggctcaat ggcaaggagt tcaaatgcag ggtcaacagt 960
gcagctttcc ctgcccccat cgagaaaacc atctccaaaa ccaaaggcag accgaaggct 1020
ccacaggtgt acaccattcc acctcccaag gagcagatgg ccaaggataa agtcagtctg 1080
acctgcatga taacagactt cttccctgaa gacattactg tggagtggca gtggaatggg 1140
cagccagcgg agaactacaa gaacactcag cccatcatgg acacagatgg ctcttacttc 1200
atctacagca agctcaatgt gcagaagagc aactgggagg caggaaatac tttcacctgc 1260
tctgtgttac atgagggcct gcacaaccac catactgaga agagcctctc ccactctcct 1320
ggtaaatga 1329

<210> SEQ ID NO 362
<211> LENGTH: 461
<212> TYPE: PRT
<213> ORGANISM: Mus musculus

<400> SEQUENCE: 362

Met Gly Trp Ser Ser Ile Ile Leu Phe Leu Val Ala Thr Ala Thr Gly
1               5                   10                  15

Val His Ser Gln Val Gln Leu Gln Gln Pro Gly Thr Glu Leu Val Arg
            20                  25                  30

```
Pro Gly Thr Ser Val Lys Leu Ser Cys Lys Ala Ser Gly Tyr Ile Phe
        35                  40                  45

Thr Thr Tyr Trp Met Asn Trp Val Lys Gln Arg Pro Gly Gln Gly Leu
    50                  55                  60

Glu Trp Ile Gly Met Ile His Pro Ser Ala Ser Glu Ile Arg Leu Asp
65                  70                  75                  80

Gln Lys Phe Lys Asp Lys Ala Thr Leu Thr Leu Asp Lys Ser Ser Ser
                85                  90                  95

Thr Ala Tyr Met His Leu Ser Gly Pro Thr Ser Val Asp Ser Ala Val
            100                 105                 110

Tyr Tyr Cys Ala Arg Ser Gly Glu Trp Gly Ser Met Asp Tyr Trp Gly
        115                 120                 125

Gln Gly Thr Ser Val Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
    370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Ile Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
```

```
    450                 455                 460

<210> SEQ ID NO 363
<211> LENGTH: 1386
<212> TYPE: DNA
<213> ORGANISM: Mus musculus

<400> SEQUENCE: 363

atgggatgga gctctatcat cctcttcttg gtagcaacag ctacaggtgt ccactcccag      60

gtccaactac agcagcctgg gactgagctg gtgaggcctg gaacttcagt gaagttgtcc     120

tgtaaggctt ctggctacat cttcaccacc tactggatga actgggtgaa acagaggcct     180

ggacaaggcc ttgagtggat tggcatgatt catccttccg caagtgaaat taggttggat     240

cagaaattca aggacaaggc cacattgact cttgacaaat cctccagcac agcctatatg     300

cacctcagcg gcccgacatc tgtggattct gcggtctatt actgtgcaag atcaggggaa     360

tgggggtcta tggactactg gggtcaagga acctcagtca ccgtctcctc agccaaaacg     420

acacccccat ctgtctatcc actggcccct ggatctgctg cccaaactaa ctccatggtg     480

accctgggat gcctggtcaa gggctatttc cctgagccag tgacagtgac ctggaactct     540

ggatccctgt ccagcggtgt gcacaccttc ccagctgtcc tgcagtctga cctctacact     600

ctgagcagct cagtgactgt cccctccagc acctggccca gcgagaccgt cacctgcaac     660

gttgcccacc cggccagcag caccaaggtg gacaagaaaa ttgtgcccag ggattgtggt     720

tgtaagcctt gcatatgtac agtcccagaa gtatcatctg tcttcatctt ccccccaaag     780

cccaaggatg tgctcaccat tactctgact cctaaggtca cgtgtgttgt ggtagacatc     840

agcaaggatg atcccgaggt ccagttcagc tggtttgtag atgatgtgga ggtgcacaca     900

gctcagacgc aaccccggga ggagcagttc aacagcactt tccgctcagt cagtgaactt     960

cccatcatgc accaggactg gctcaatggc aaggagttca aatgcagggt caacagtgca    1020

gctttccctg cccccatcga gaaaaccatc tccaaaacca aaggcagacc gaaggctcca    1080

caggtgtaca ccattccacc tcccaaggag cagatggcca aggataaagt cagtctgacc    1140

tgcatgataa cagacttctt ccctgaagac attactgtgg agtggcagtg gaatgggcag    1200

ccagcggaga actacaagaa cactcagccc atcatggaca cagatggctc ttacttcatc    1260

tacagcaagc tcaatgtgca gaagagcaac tgggaggcag gaaatacttt cacctgctct    1320

gtgttacatg agggcctgca caaccaccat actgagaaga gcctctccca ctctcctggt    1380

aaatga                                                               1386

<210> SEQ ID NO 364
<211> LENGTH: 106
<212> TYPE: PRT
<213> ORGANISM: Mus musculus

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys
            100                 105


<210> SEQ ID NO 365
<211> LENGTH: 318
<212> TYPE: DNA
<213> ORGANISM: Mus musculus

<400> SEQUENCE: 365

gacatccaga tgacccagtc tccatcctcc ctgtctgcat ctgtaggtga ccgtgtcacc      60

atcacttgcc gcgcaagtca ggatattagc agctatttaa attggtatca gcagaaacca     120

gggaaagccc ctaagctcct gatctattct acttcccgtt tgaatagtgg ggtcccatca     180

cgcttcagtg gcagtggctc tgggacagat ttcactctca ccatcagcag tctgcaacct     240

gaagattttg caacttacta ctgtcaacag gatattaaac accctacgtt cggtcaaggc     300

accaaggtgg agatcaaa                                                   318


<210> SEQ ID NO 366
<211> LENGTH: 120
<212> TYPE: PRT
<213> ORGANISM: Mus musculus

<400> SEQUENCE: 366

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120


<210> SEQ ID NO 367
<211> LENGTH: 360
<212> TYPE: DNA
<213> ORGANISM: Mus musculus

<400> SEQUENCE: 367

gaggtgcagc tggtgcagtc tggggctgag gtgaagaagc ctgggtcctc ggtgaaggtc      60

tcctgcaagg cttctggttt taccttcacc gactatatta tgcactgggt gcgtcaggcc     120

cctggtcaag gcttgagtg gatgggctat atcaaccctt ataatgatga caccgaatac     180

aacgagaagt tcaagggccg tgtcacgatt accgcggaca aatccacgag cacagcctac     240

atggagctga gcagcctgcg ctctgaggac acggccgtgt attactgtgc gcgttcgatt     300

tattactacg atgccccgtt tgcttactgg ggccaaggga ctctggtcac cgtctctagt     360
```

<210> SEQ ID NO 368
<211> LENGTH: 108
<212> TYPE: PRT
<213> ORGANISM: Mus musculus

<400> SEQUENCE: 368

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105
```

<210> SEQ ID NO 369
<211> LENGTH: 324
<212> TYPE: DNA
<213> ORGANISM: Mus musculus

<400> SEQUENCE: 369

```
gatatccaga tgacccagag cccgagcagc ctgagcgcga gcgtgggcga tcgcgtgacc      60

attacctgca aagcgagcca ggatgtgttt accgcggtgg cgtggtatca gcagaaaccg     120

ggcaaagcgc cgaaactgct gatttattgg gcgagcaccc gccataccgg cgtgccgagt     180

cgctttagcg gcagcggcag cggcaccgat tttaccctga ccattagcag cctgcagccg     240

gaagattttg cgacctatta ttgccagcag tatagcagct atccgctgac ctttggcggc     300

ggcaccaaag tggaaattaa acgt                                            324
```

<210> SEQ ID NO 370
<211> LENGTH: 119
<212> TYPE: PRT
<213> ORGANISM: Mus musculus

<400> SEQUENCE: 370

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110
```

Thr Leu Val Thr Val Ser Ser
115

<210> SEQ ID NO 371
<211> LENGTH: 357
<212> TYPE: DNA
<213> ORGANISM: Mus musculus

<400> SEQUENCE: 371
gaagtgcagc tggtgcagag cggcgcggaa gtgaaaaaac cgggcgcgag cgtgaaagtg 60
agctgcaaag cgagcggctt taacattaaa gattattata tgcattgggt gcgccaggcg 120
ccgggccagg gcctggaatg gatcggccgc attgatccgg aaaacggcga tattatttat 180
gatccgaaat ttcagggccg cgtgaccatg accaccgata ccagcaccag caccgcgtat 240
atggaactgc gcagcctgcg cagcgatgat accgcggtgt attattgcgc gtatgatgcg 300
ggcgatccgg cgtggtttac ctattggggc cagggcaccc tggtgaccgt ctcgagc 357

<210> SEQ ID NO 372
<211> LENGTH: 108
<212> TYPE: PRT
<213> ORGANISM: Mus musculus

<400> SEQUENCE: 372

Asp Ile Gln Leu Thr Gln Ser Pro Ser Phe Leu Ser Ala Ser Val Gly
1 5 10 15

Asp Arg Val Thr Ile Thr Cys Ser Val Ser Ser Ser Ile Ser Ser Ser
20 25 30

Asn Leu His Trp Tyr Gln Gln Lys Pro Gly Lys Ala Pro Lys Leu Leu
35 40 45

Ile Tyr Gly Thr Ser Asn Leu Ala Ser Gly Val Pro Ser Arg Phe Ser
50 55 60

Gly Ser Gly Ser Gly Thr Glu Phe Thr Leu Thr Ile Ser Ser Leu Gln
65 70 75 80

Pro Glu Asp Phe Ala Thr Tyr Tyr Cys Gln Gln Trp Thr Thr Thr Tyr
85 90 95

Thr Phe Gly Gln Gly Thr Lys Leu Glu Ile Lys Arg
100 105

<210> SEQ ID NO 373
<211> LENGTH: 324
<212> TYPE: DNA
<213> ORGANISM: Mus musculus

<400> SEQUENCE: 373
gatattcagc tgacccagag cccgagcttt ctgagcgcga gcgtgggcga tcgcgtgacc 60
attacctgca gcgtgagcag cagcattagc agcagcaacc tgcattggta tcagcagaaa 120
ccgggcaaag cgccgaaact gctgatttat ggcaccagca acctggcgag cggcgtgccg 180
agccgcttta gcggcagcgg cagcggcacc gaatttaccc tgaccattag cagcctgcag 240
ccggaagatt ttgcgaccta ttattgccag cagtggacca ccacctatac ctttggccag 300
ggcaccaaac tggaaattaa acgt 324

<210> SEQ ID NO 374
<211> LENGTH: 122
<212> TYPE: PRT
<213> ORGANISM: Mus musculus

<400> SEQUENCE: 374

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Asp Asn Gly Glu Ser Thr Tyr Val Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Leu Asp Tyr Gly Asp Tyr Tyr Ala Val Asp Tyr Trp
            100                 105                 110

Gly Gln Gly Thr Leu Val Thr Val Ser Ser
        115                 120
```

<210> SEQ ID NO 375
<211> LENGTH: 366
<212> TYPE: DNA
<213> ORGANISM: Mus musculus

<400> SEQUENCE: 375

```
gaagtgcagc tggtgcagag cggcgcggaa gtgaaaaaac cgggcgcgag cgtgaaagtg     60

agctgcaaag cgagcggctt taacattaaa gattattata ttcattgggt gcgccaggcg    120

ccgggccagg gcctggaatg gatgggccgc attgatccgg ataacggcga aagcacctat    180

gtgccgaaat ttcagggccg cgtgaccatg accaccgata ccagcaccag caccgcgtat    240

atggaactgc gcagcctgcg cagcgatgat accgcggtgt attattgcgc gcgcgaaggc    300

ctggattatg gcgattatta tgcggtggat tattggggcc agggcaccct ggtgaccgtc    360

tcgagc                                                               366
```

<210> SEQ ID NO 376
<211> LENGTH: 107
<212> TYPE: PRT
<213> ORGANISM: Mus musculus

<400> SEQUENCE: 376

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105
```

<210> SEQ ID NO 377
<211> LENGTH: 321

<212> TYPE: DNA
<213> ORGANISM: Mus musculus

<400> SEQUENCE: 377
gacatccaga tgacccagtc tccatcctcc ctctccgcat ccgtaggcga ccgcgtaacc 60
ataacatgta gagcatctca agatatttcc aactatttga attggtacca acaaaaaccc 120
ggcaaagcac ctaaactcct catttactat acatcaagac tcctctccgg cgttccatca 180
cgattctcag gctccggctc cggcacagat ttcacactca ctatttcctc cctccaacca 240
gaagattttg caacctatta ctgtcaacaa ggcgatacac tcccatacac attcggcggc 300
ggcacaaaag ttgaaattaa a 321

<210> SEQ ID NO 378
<211> LENGTH: 123
<212> TYPE: PRT
<213> ORGANISM: Mus musculus

<400> SEQUENCE: 378

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Asn Met His Trp Val Arg Gln Ala Pro Gly Gln Gly Leu Glu Trp Met
35 40 45

Gly Glu Ile Asn Pro Asn Ser Gly Gly Ala Gly Tyr Asn Gln Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Leu Gly Tyr Asp Asp Ile Tyr Asp Asp Trp Tyr Phe Asp Val
100 105 110

Trp Gly Gln Gly Thr Thr Val Thr Val Ser Ser
115 120

<210> SEQ ID NO 379
<211> LENGTH: 369
<212> TYPE: DNA
<213> ORGANISM: Mus musculus

<400> SEQUENCE: 379
gaggtgcagc tggtgcagag cggcgccgag gtaaaaaaac caggagcaag cgttaaagtt 60
tcttgtaaag caagcggata tacatttaca gattacaaca tgcattgggt aagacaagcg 120
ccaggacaag gattggaatg gatgggcgaa attaacccta atagtggagg agcaggctac 180
aatcaaaaat tcaaagggag agttacaatg acaacagaca caagcacttc aacagcatat 240
atggaactgc gatcacttag aagcgacgat acagctgtat actattgcgc acgacttggg 300
tatgatgata tatatgatga ctggtatttc gatgtttggg gccagggaac aacagttacc 360
gtctctagt 369

<210> SEQ ID NO 380
<211> LENGTH: 108
<212> TYPE: PRT
<213> ORGANISM: Mus musculus

<400> SEQUENCE: 380

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys
            100                 105
```

<210> SEQ ID NO 381
<211> LENGTH: 324
<212> TYPE: DNA
<213> ORGANISM: Mus musculus

<400> SEQUENCE: 381

```
gacatccagc tgacccagag ccccagcttc ctttccgcat ccgttggtga ccgagtaaca     60

atcacatgcc gcgcctcatc ttcagttaca tcttcttatc ttaattggta tcaacaaaaa    120

ccaggaaaag cacctaaact tcttatatac tctacatcta atctcgcatc aggagttccc    180

tctcgatttt caggatctgg atcaggcaca gaatttacac ttactatatc atcactccaa    240

ccagaagact tcgccactta ttactgccaa caatacgatt tttttccaag cacattcgga    300

ggaggtacaa aagtagaaat caag                                           324
```

<210> SEQ ID NO 382
<211> LENGTH: 121
<212> TYPE: PRT
<213> ORGANISM: Mus musculus

<400> SEQUENCE: 382

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser
        115                 120
```

<210> SEQ ID NO 383
<211> LENGTH: 363
<212> TYPE: DNA
<213> ORGANISM: Mus musculus

<400> SEQUENCE: 383
gaggtgcagc tggtgcagag cggcgccgag gtcaagaaac ctggagcaag cgtaaaggtt 60
agttgcaaag catctggata cacatttacc gactactaca tgaattgggt acgacaagcc 120
cctggacaaa gacttgaatg gatgggagac attaaccctt ataacgacga cactacatac 180
aatcataaat ttaaaggaag agttacaatt acaagagata catccgcatc aaccgcctat 240
atggaacttt cctcattgag atctgaagac actgctgttt attactgtgc aagagaaact 300
gccgttatta ctactaacgc tatggattac tggggtcaag gaaccactgt taccgtctct 360
agt 363

<210> SEQ ID NO 384
<211> LENGTH: 108
<212> TYPE: PRT
<213> ORGANISM: Mus musculus

<400> SEQUENCE: 384

Asp Ile Gln Met Thr Gln Ser Pro Ser Ser Leu Ser Ala Ser Val Gly
1 5 10 15

Asp Arg Val Thr Ile Thr Cys Ser Val Ser Ser Thr Ile Ser Ser Asn
20 25 30

His Leu His Trp Phe Gln Gln Lys Pro Gly Lys Ala Pro Lys Ser Leu
35 40 45

Ile Tyr Gly Thr Ser Asn Leu Ala Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys Gln Gln Trp Ser Ser Tyr Pro
85 90 95

Leu Thr Phe Gly Gly Gly Thr Lys Val Glu Ile Lys
100 105

<210> SEQ ID NO 385
<211> LENGTH: 324
<212> TYPE: DNA
<213> ORGANISM: Mus musculus

<400> SEQUENCE: 385
gacatccaga tgacccagtc tccatcctcc ctctcagcat ccgtaggcga tagagttaca 60
ataacatgca gcgtatcatc aactatatca tcaaatcatc ttcattggtt ccaacagaaa 120
cccggcaaag cacctaaatc acttatatac ggcacatcaa atctcgcatc aggcgttcct 180
tcaagatttt caggctctgg ctcaggcacc gactttactc ttacaatatc ctccctccaa 240
cccgaagact tcgcaaccta ttactgtcaa caatggtcct catatccact cacatttggc 300
ggcggcacaa aagtagaaat taaa 324

<210> SEQ ID NO 386
<211> LENGTH: 125
<212> TYPE: PRT
<213> ORGANISM: Mus musculus

<400> SEQUENCE: 386

Glu Val Gln Leu Val Gln Ser Gly Ala Glu Val Lys Lys Pro Gly Ala
1 5 10 15

Ser Val Lys Val Ser Cys Lys Ala Ser Asp Phe Asn Ile Lys Asp Phe
20 25 30

```
Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser
        115                 120                 125


<210> SEQ ID NO 387
<211> LENGTH: 375
<212> TYPE: DNA
<213> ORGANISM: Mus musculus

<400> SEQUENCE: 387

gaggtgcagc tggtgcagtc tggggctgag gtgaagaagc ctggggcctc agtgaaggtc     60

tcctgcaagg cttctgactt caacattaaa gacttctatc tacactgggt gcgacaggcc    120

cctggacaag ggcttgagtg gattggaagg attgatcctg agaatggtga tactttatat    180

gacccgaagt tccaggacaa ggtcaccatg accacagaca cgtccaccag cacagcctac    240

atggagctga ggagcctgag atctgacgac acggccgtgt attactgtgc gagagaggcg    300

gattatttcc acgatggtac ctcctactgg tacttcgatg tctggggccg tggcaccctg    360

gtcaccgtct ctagt                                                     375


<210> SEQ ID NO 388
<211> LENGTH: 106
<212> TYPE: PRT
<213> ORGANISM: Mus musculus

<400> SEQUENCE: 388

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys
            100                 105


<210> SEQ ID NO 389
<211> LENGTH: 318
<212> TYPE: DNA
<213> ORGANISM: Mus musculus

<400> SEQUENCE: 389

gacatccagt tgacccagtc tccatccttc ctgtctgcat ctgtaggaga cagagtcacc     60
```

```
atcacttgca gggccagctc aagtataagt tacatacact ggtatcagca aaaaccaggg    120

aaagccccta agctcctgat ctatgccaca tccaacctgg cttctggggt cccatcaagg    180

ttcagcggca gtggatctgg gacagaattc actctcacaa tcagcagcct gcagcctgaa    240

gattttgcaa cttattactg tcagcagtgg agtagtgacc cactcacgtt cggcggaggg    300

accaaggtgg agatcaaa                                                  318


<210> SEQ ID NO 390
<211> LENGTH: 121
<212> TYPE: PRT
<213> ORGANISM: Mus musculus

<400> SEQUENCE: 390

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser
        115                 120


<210> SEQ ID NO 391
<211> LENGTH: 363
<212> TYPE: DNA
<213> ORGANISM: Mus musculus

<400> SEQUENCE: 391

gaggtgcagc tggtgcagtc tggggctgag gtgaagaagc ctggggcctc agtgaaggtc     60

tcctgcaagg cttctggatt cgacattaag gactactata tacactgggt gcgacaggcc    120

cctggacaag ggcttgagtg gatcggaagg gttgatcctg acaatggtga gactgaattt    180

gccccgaagt tcccgggcaa ggtcaccatg accacagaca cgtccatcag cacagcctac    240

atggagctga gcaggctgag atctgacgac acggccgtgt attactgtgc gagagaagac    300

tacgatggta cctacacctg gtttccttat tggggccaag ggactctggt caccgtctct    360

agt                                                                  363


<210> SEQ ID NO 392
<211> LENGTH: 448
<212> TYPE: PRT
<213> ORGANISM: Artificial Sequence
<220> FEATURE:
<223> OTHER INFORMATION: Humanized antibody sequence

<400> SEQUENCE: 392

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 393
<211> LENGTH: 446
<212> TYPE: PRT
<213> ORGANISM: Artificial Sequence
<220> FEATURE:
<223> OTHER INFORMATION: Humanized antibody sequence

<400> SEQUENCE: 393

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 394
<211> LENGTH: 450
<212> TYPE: PRT
<213> ORGANISM: Artificial Sequence
<220> FEATURE:
<223> OTHER INFORMATION: Humanized antibody sequence

<400> SEQUENCE: 394

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285
```

```
His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 395
<211> LENGTH: 446
<212> TYPE: PRT
<213> ORGANISM: Artificial Sequence
<220> FEATURE:
<223> OTHER INFORMATION: Humanized antibody sequence

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 396
<211> LENGTH: 445
<212> TYPE: PRT
<213> ORGANISM: Artificial Sequence
<220> FEATURE:
<223> OTHER INFORMATION: Humanized antibody sequence

<400> SEQUENCE: 396

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110
```

-continued

```
Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```